United States Patent
Turner, Jr. et al.

(10) Patent No.: US 10,183,936 B2
(45) Date of Patent: Jan. 22, 2019

(54) HEPATITIS B CORE PROTEIN ALLOSTERIC MODULATORS

(71) Applicants: Indiana University Research and Technology Corporation, Indianapolis, IN (US); Assembly Biosciences, Inc., Carmel, IN (US)

(72) Inventors: William W. Turner, Jr., Bloomington, IN (US); Lee Daniel Arnold, Bloomington, IN (US); Hans Maag, Kleines Wiesental (DE); Adam Zlotnick, Bloomington, IN (US)

(73) Assignees: Indiana University Research and Technology Corporation, Indianapolis, IN (US); Assembly Biosciences, Inc., Indianapolis, IN (US)

( * ) Notice: Subject to any disclaimer, the term of this patent is extended or adjusted under 35 U.S.C. 154(b) by 0 days.

(21) Appl. No.: 15/125,911

(22) PCT Filed: Mar. 13, 2015

(86) PCT No.: PCT/US2015/020444
§ 371 (c)(1),
(2) Date: Sep. 13, 2016

(87) PCT Pub. No.: WO2015/138895
PCT Pub. Date: Sep. 17, 2015

(65) Prior Publication Data
US 2017/0015658 A1    Jan. 19, 2017

Related U.S. Application Data

(60) Provisional application No. 62/010,025, filed on Jun. 10, 2014, provisional application No. 61/952,467, filed on Mar. 13, 2014.

(51) Int. Cl.

| | |
|---|---|
| C07D 417/12 | (2006.01) |
| C07D 403/12 | (2006.01) |
| C07D 223/20 | (2006.01) |
| C07D 401/12 | (2006.01) |
| C07D 413/12 | (2006.01) |
| C07D 243/38 | (2006.01) |
| C07D 281/14 | (2006.01) |
| A61K 31/55 | (2006.01) |
| A61K 31/5513 | (2006.01) |
| A61K 31/553 | (2006.01) |
| A61K 31/554 | (2006.01) |
| A61K 45/06 | (2006.01) |
| C07D 281/16 | (2006.01) |

(52) U.S. Cl.
CPC ............ *C07D 417/12* (2013.01); *A61K 31/55* (2013.01); *A61K 31/553* (2013.01); *A61K 31/554* (2013.01); *A61K 31/5513* (2013.01); *A61K 45/06* (2013.01); *C07D 223/20* (2013.01); *C07D 243/38* (2013.01); *C07D 281/14* (2013.01); *C07D 281/16* (2013.01); *C07D 401/12* (2013.01); *C07D 403/12* (2013.01); *C07D 413/12* (2013.01)

(58) Field of Classification Search
CPC .................................................. C07D 417/12
See application file for complete search history.

(56) References Cited

U.S. PATENT DOCUMENTS

| | | |
|---|---|---|
| 5,512,563 A | 4/1996 | Albright et al. |
| 8,618,090 B2 | 12/2013 | Desai et al. |
| 9,399,619 B2 | 7/2016 | Guo et al. |
| 9,873,684 B2 | 1/2018 | Kahraman et al. |
| 2007/0105819 A1 | 5/2007 | Olsson et al. |
| 2015/0368261 A1 | 12/2015 | Demin et al. |
| 2017/0107185 A1 | 4/2017 | Grammneos et al. |
| 2017/0267685 A1 | 9/2017 | D'Agostino et al. |

FOREIGN PATENT DOCUMENTS

| | | |
|---|---|---|
| CL | 2015002706 A1 | 4/2016 |
| CL | 2015003456 A1 | 7/2016 |
| CL | 20105002628 A1 | 8/2016 |
| CL | 2016003175 A1 | 8/2017 |
| GB | 1480553 | 7/1977 |
| JP | 58225074 A | 12/1983 |
| WO | WO 92/19277 | 11/1992 |
| WO | WO 2005072741 A1 | 8/2005 |
| WO | WO 2008/036139 A2 | 3/2008 |
| WO | WO 2008/118141 A2 | 10/2008 |
| WO | WO 2010/011537 A1 | 1/2010 |
| WO | WO 2012/045194 A1 | 4/2012 |
| WO | WO 2013/006394 A1 | 1/2013 |
| WO | WO2015/017412 * | 2/2015 |
| WO | WO 2015017412 A1 | 2/2015 |
| WO | WO2015138895 A1 | 9/2015 |

OTHER PUBLICATIONS

International Search Report and Written Opinion issued by the ISA/US, Commissioner for Patents, dated Jul. 6, 2015, for International Application No. PCT/US2015/020444; 10 pages.

National Center for Biotechnology Information. PubChem Compound Database; CID=20885151; available at https://pubchem.ncbi.nlm.nih.gov/compound/20885151 (accessed Sep. 13, 2016; deposit date Dec. 5, 2007); 10 pages.

(Continued)

*Primary Examiner* — Brian E McDowell
(74) *Attorney, Agent, or Firm* — Faegre Baker Daniels LLP

(57) ABSTRACT

The present disclosure provides, in part, compounds having allosteric effector properties against Hepatitis B virus Cp. Also provided herein are methods of treating viral infections, such as hepatitis B, comprising administering to a patient in need thereof a disclosed compound.

11 Claims, 2 Drawing Sheets
Specification includes a Sequence Listing.

(56) References Cited

OTHER PUBLICATIONS

National Center for Biotechnology Information. PubChem Compound Database; CID=4119171, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID=4167865, https://pubchem.ncbi.nlm.nih.gov/compound/4167865 (accessed Sep. 13, 2016; deposit date Sep. 13, 2005); 12 pages.
Xiao, Jingbo, et al., "Discovery, Optimization, and Characterization of Novel $D_2$ Dopamine Receptor Selective Antagonists," Journal of Medicinal Chemistry, Mar. 25, 2014, vol. 57, pp. 3450-3463.
International Preliminary Report on Patentability issued by the International Bureau of WIPO, dated Sep. 13, 2016, for International Application No. PCT/US2015/020444; 6 pages.
Hall, Pamela R., et al., "*Small molecule inhibitors of hantavirus infection*," Bioorganic & Medicinal Chemistry Letters, vol. 20, (2010), pp. 7085-7091.
Supplemental European Search Report issued by the European Patent Office (Munich), dated Apr. 11, 2018, for related Application No. EP 15761201; 21 pages.
Supplemental Partial European Search Report issued by the European Patent Office (Munich), dated Nov. 23, 2017, for related Application No. EP 15761201; 14 pages.
Takeda, M., et al., "Synthesis of Dibenzo [b,e) [1,4] Diazepine Derivatives as Anti-depressants," Yakugaku Zahhi, vol. 89, No. 2, (1969), 6 pages.
National Center for Biotechnology Information, PubChem Compound Database; CID-4152425, XP-002779931, modified Apr. 7, 2017, created Sep. 13, 2005; 3 pages.
National Center for Biotechnology Information, PubChem Compound Database; CID-46260649, XP-002779932, modified Apr. 7, 2017, created Jul. 21, 2010; 3 pages.
National Center for Biotechnology Information, PubChem Compound Database; CID-4163919, XP-002779933, modified Apr. 7, 2018, created Sep. 13, 2005; 3 pages.
National Center for Biotechnology Information, PubChem Compound Database; CID-4167865, XP-002779934, modified Apr. 7, 2018, created Sep. 13, 2005; 3 pages.
National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.
National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-23734106, XP-002779939, modified Apr. 7, 2018, created Feb. 20, 2008; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified Nov. 18, 20187, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report issued by The Patent Office of the People's Republic of China (translated in English language), dated Jun. 29, 2018, for Chinese Application No. 201580024580.0; 3 pages.
Letter Exam Report issued by the Chilean Patent Office, dated Jun. 12, 2018, for Chilean Application No. 2269-2016; 15 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.
English translation of the First Official Action issued by the Mexican Patent Office for Mexican Patent Application No. MX/a/2016/011800, dated Jul. 4, 2018; 3 pages.
Letter dated Jun. 27, 2018 regarding Examination Report issued by the National Office of Industrial Property for Dominican Republic Patent Application No. P2016-0233; 2 pages.

* cited by examiner

SEQUENCE LISTING

```
<160> NUMBER OF SEQ ID NOS: 3

<210> SEQ ID NO 1
<211> LENGTH: 19
<212> TYPE: DNA
<213> ORGANISM: artificial
<220> FEATURE:
<223> OTHER INFORMATION: HBV forward primer

<400> SEQUENCE: 1
ctgtgccttg ggtggcttt                                              19

<210> SEQ ID NO 2
<211> LENGTH: 24
<212> TYPE: DNA
<213> ORGANISM: artificial
<220> FEATURE:
<223> OTHER INFORMATION: HBV reverse primer

<400> SEQUENCE: 2
aaggaaagaa gtcagaaggc aaaa                                        24

<210> SEQ ID NO 3
<211> LENGTH: 34
<212> TYPE: DNA
<213> ORGANISM: artificial
<220> FEATURE:
<223> OTHER INFORMATION: Fluorescent TaqManTM Probes HBV-probe
<220> FEATURE:
<221> NAME/KEY: misc_binding
<222> LOCATION: (1)..(1)
<223> OTHER INFORMATION: FAM
<220> FEATURE:
<221> NAME/KEY: misc_binding
<222> LOCATION: (10)..(10)
<223> OTHER INFORMATION: ZEN
<220> FEATURE:
<221> NAME/KEY: misc_binding
<222> LOCATION: (34)..(34)
<223> OTHER INFORMATION: 3IABkFQ quencher

<400> SEQUENCE: 3
agctccaaat tctttataag ggtcgatgtc catg                             34
```

HEPATITIS B CORE PROTEIN ALLOSTERIC MODULATORS

RELATED APPLICATIONS

This application is a National Phase entry of International Patent Application No. PCT/US2015/020444, filed Mar. 13, 2015, which claims the benefit of and priority to United States Provisional Patent Applications No. 61/952,467, filed Mar. 13, 2014, and U.S. Provisional Patent Application No. 62/010,025, filed Jun. 10, 2014, the contents of each of which are hereby incorporated by reference in their entireties.

SEQUENCE LISTING

The instant application contains a Sequence Listing which has been submitted via EFS-web and is hereby incorporated by reference in its entirety. The ASCII copy, created on Apr. 24, 2015, is named 12141_WO_SEQ_ST25, and is 1,117 bytes in size.

STATEMENT OF GOVERNMENT SUPPORT

This invention was made with government support under AI067417 awarded by the National Institutes of Health. The government has certain rights in the invention.

BACKGROUND

Hepatitis B (HBV) causes viral Hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths (2009; WHO, 2009). HBV can be spread by body fluids: from mother to child, by sex, and via blood products. Children born to HBV-positive mothers may also be infected, unless vaccinated at birth.

The virus particle is composed of a lipid enveloped studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core. For convenience, we divide the assembly process at the point of capsid assembly and pgRNA-packaging. Steps preceding this event are "upstream"; steps following RNA-packaging are "downstream".

At present, chronic HBV is primarily treated with nucleos(t)ide analogs (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, nucleos(t)ide therapy may lead to the emergence of antiviral drug resistance (Deres and Rubsamen-Waigmann, 1999; Tennant et al., 1998; Zhang et al., 2003) and—in rare patients—adverse events have been reported (Ayoub and Keeffe, 2011).

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon based therapies are used in only a small percentage of all diagnosed patients who elect for treatment.

Thus, current HBV treatments can range from palliative to watchful waiting. Nucleos(t)ide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

Provided herein are compounds that can have properties such as those described below, where the compounds in some embodiments may be represented by:

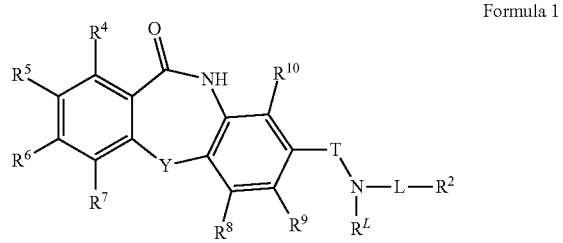

Formula 1

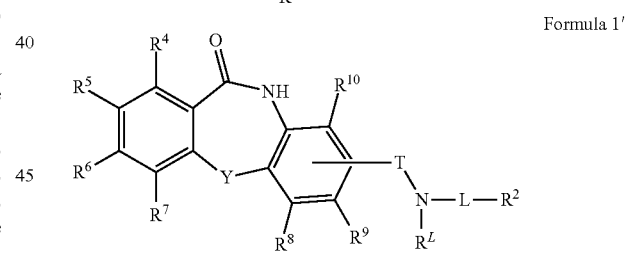

Formula 1' wherein $R^2$, $R^4$, $R^5$, $R^6$, $R^7$, $R^8$, $R^9$, $R^{10}$, $R^L$, Y, T, and L are defined herein. Also provided herein are methods of treating viral infections, such as hepatitis B, comprising administering to patient a disclosed compound.

For example, the present disclosure is directed in part to compounds having allosteric effector properties against Hepatitis B virus Cp, a protein found as a dimer, a multimer, and as the protein shell of the HBV core. Without being bound by theory, disclosed compounds may ultimately target multimerization of viral core proteins, which is central to HBV infection, where the core protein multimerizes into shell, or capsid, and/or disclosed compounds may for example, ultimately target interaction of viral core proteins with other macromolecules, such as host or viral nucleic acid, host proteins, or other viral proteins. For example, disclosed compounds may be considered in some embodiments CpAM—core protein allosteric modifiers. CpAM interaction with core protein can allosterically favor an assembly-active form of Cp dimer and lead to viral capsid assembly at an inappropriate time or place or lead to non-standard intersubunit interactions, all resulting in defective capsids. CpAMs may additionally or alternatively affect steps of "upstream" of capsid assembly by altering the concentrations or nature of Cp available as dimer as compared to capsid or other multimeric forms. Disclosed compounds or CpAMs may, in some embodiments, noticeably affect functions upstream of viral assembly such as modulation of cccDNA transcription, RNA stability and/or protein-protein interactions.

DETAILED DESCRIPTION

Figure 1:
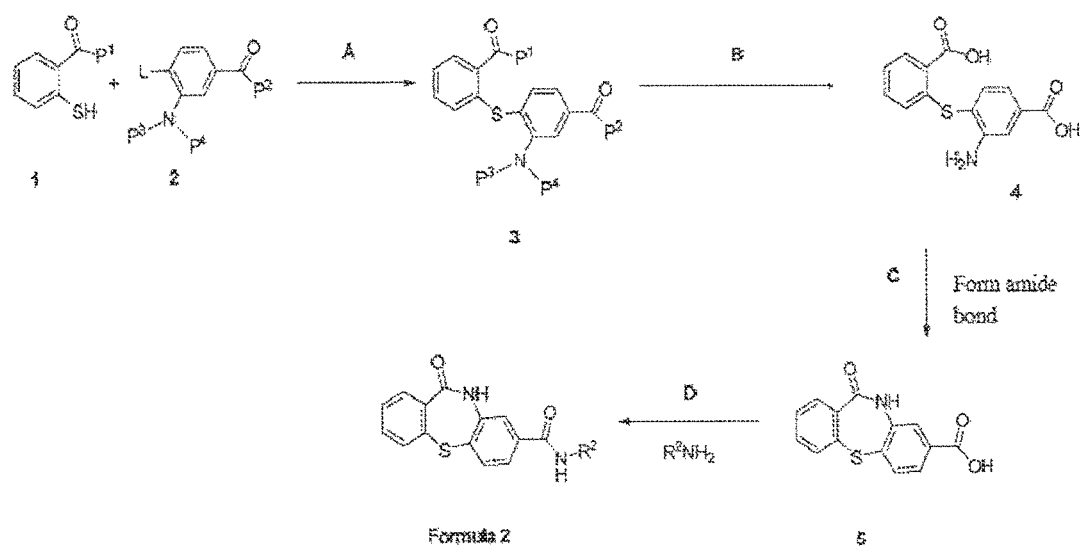
FIG. 1 illustrates synthetic scheme 1.

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As intended herein, the terms "a" and "an" include singular as well as plural references unless the context clearly dictates otherwise. For example, the term "an assembly effector" can include one or more such effectors.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc The terms "hydroxy" and "hydroxyl" as used herein refers to the radical —OH.

"Treatment" as used herein includes the alleviation, prevention, reversal, amelioration or control of a pathology, disease, disorder, process, condition or event, including viral infection. In this context, the term "treatment" is further to be understood as embracing the use of a drug to inhibit, block, reverse, restrict or control progression of viral infection.

As used herein, the term "pharmaceutical composition" refers to compositions of matter comprising at least one pharmaceutical compound and optionally a pharmaceutically acceptable carrier.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaemo, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, form ate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen. US2011/0144086 describes the use of some diabenzothiazepine molecules (DBTs) as anti-malarial "inhibitors of the plasmodial surface anion channel." However, no study of DBT molecules as anti-virals has yet been reported.

1. Disclosed compounds contemplated herein may in some embodiments be represented by Formula 1:

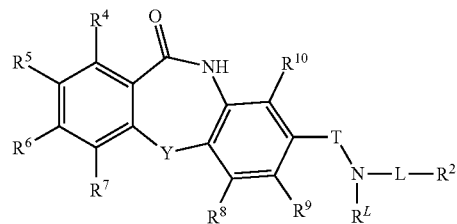

Formula 1 wherein:
T is selected from the group consisting of —C(O)—, —CH$_2$—C(O)—, —N(C(O)—CH$_3$)—, —NH—, —O—, and —S(O)$_z$—, where z is 0, 1 or 2;
Y is C(R$^{11}$)$_2$, S(O)$_y$, NR$_Y$ and O wherein y is 0, 1, or 2;
R$_Y$ is selected from the group consisting of H, methyl, ethyl, propyl, phenyl and benzyl;

R$_L$ is selected from the group consisting of H, methyl, and —C(O)—C$_{1-3}$alkyl;
L is a bond or C$_{1-4}$ straight chain alkylene optionally substituted by one or two substituents each independently selected from the group consisting of methyl (optionally substituted by halogen or hydroxyl), ethenyl, hydroxyl, NR'R", phenyl, heterocycle, and halogen and wherein the C$_{1-4}$ straight chain alkylene may be interrupted by an —O—;
R$^2$ is selected from the group consisting of H,
phenyl or naphthyl (wherein the phenyl or naphthyl may be optionally substituted with one, two, three or more substituents selected from the group consisting of halogen, hydroxyl, nitro, cyano, carboxy, C$_{1-6}$alkyl, C$_{2-6}$alkenyl, C$_{2-6}$alkynyl, C$_{1-6}$alkoxy, NR'R", —C(O)— NR'R", —C(O)—C$_{1-6}$alkyl, —C(O)—C$_{1-6}$alkoxy, phenyl (optionally substituted by one, two or three substituents each independently selected from the group consisting of halogen, hydroxyl, cyano, C$_{1-6}$alkyl, C$_{2-6}$alkenyl, C$_{2-6}$alkynyl, C$_{1-6}$alkoxy, NR'R", C(O)—NR'R", —C(O)—C$_{1-6}$alkyl, —C(O)—C$_{1-6}$alkoxy, —S(O)$_w$—C$_{1-6}$alkyl (where w is 1, 2 or 3), S(O)$_w$—NR'R" (where w is 1, 2 or 3), —NR'—S(O)$_w$, and —S(O)$_w$—NR'R" (where w is 1, 2 or 3)), heteroaryl (optionally substituted by one, two or three substituents each independently selected from the group consisting of halogen, hydroxyl, C$_{1-6}$alkyl, C$_{2-6}$alkenyl, C$_{2-6}$alkynyl, C$_{1-6}$alkoxy, NR'R", C(O)—NR'R", —C(O)—C$_{1-6}$alkyl, —C(O)—C$_{1-6}$alkoxy, —S(O)$_w$—C$_{1-6}$alkyl (where w is 1, 2 or 3), NR'—S(O)$_w$, and —S(O)$_w$—NR'R" (where w is 1, 2 or 3)), C$_{3-6}$cycloalkyl, —S(O)$_w$—C$_{1-6}$alkyl (where w is 1, 2 or 3), —S(O)$_w$—NR'R" (where w is 1, 2 or 3), and —NR'—S(O)$_w$, (where w is 1, 2 or 3)),
5-6 membered heteroaryl having one, two, or three heteroatoms each independently selected from O, N and S (wherein the 5-6 membered heteroaryl may be optionally substituted on a carbon with one, two, three or more substituents selected from the group consisting of halogen, hydroxyl, nitro, cyano, carboxy, C$_{1-6}$alkyl, C$_{2-6}$alkenyl, C$_{2-6}$alkynyl, C$_{1-6}$alkoxy, phenyl (optionally substituted by one, two or three substituents each independently selected from the group consisting of halogen, hydroxyl, C$_{1-6}$alkyl, C$_{2-6}$alkenyl, C$_{2-6}$alkynyl, C$_{1-6}$alkoxy, NR'R", C(O)—NR'R", —C(O)—C$_{1-6}$alkyl, —C(O)—OH, —C(O)—C$_{1-6}$alkoxy, —S(O)$_w$—C$_{1-6}$alkyl (where w is 1, 2 or 3), —NR'—S(O)$_w$, and —S(O)$_w$—NR'R" (where w is 1, 2 or 3)), heteroaryl, heterocycle, NR'R", —C(O)—NR'R", —C(O)—C$_{1-6}$alkyl, —C(O)—C$_{1-6}$alkoxy, —S(O)$_w$—C$_{1-6}$alkyl (where w is 1, 2 or 3), —NR'—S(O)$_w$, and —S(O)$_w$—NR'R" (where w is 1, 2 or 3), and on a nitrogen by R'), C$_{1-6}$alkyl, C$_{1-6}$alkoxy, C$_{2-6}$alkenyl, C$_{3-10}$cycloalkyl (optionally substituted with one, two, three or more substituents selected from the group consisting of halogen, hydroxyl, nitro, cyano, carboxy, NR'R", —C(O)—NR'R", =CNR', C$_{1-6}$alkyl, C$_{1-6}$alkoxy, —C(O)—C$_{1-6}$alkyl, and —C(O)—C$_{1-6}$alkoxy, and wherein the C$_{3-10}$cycloalkyl may optionally be a bridged cycloalkyl)), and a 4-6 membered heterocycloalkyl having one or two heteroatoms each independently selected from O, N and S (wherein the 4-6 membered heterocycloalkyl may be optionally substituted with one, two, three or more substituents selected from the group consisting of halogen, hydroxyl, nitro, cyano, carboxy, NR'R", —C(O)—NR'R", C$_{1-6}$alkyl, C$_{1-6}$alkoxy, —C(O)—C$_{1-6}$alkyl, and —C(O)—C$_{1-6}$alkoxy);
R' is selected, independently for each occurrence, from H, methyl, ethyl, propyl, phenyl, and benzyl;

R″ is selected, independently for each occurrence, from H, methyl, ethyl, propyl, butyl, carboxybenzyl, —C(O)-methyl and —C(O)-ethyl, or R′ and R″ taken together may form a 4-6 membered heterocycle;

each of moieties $R^4$, $R^5$, $R^6$, $R^7$, $R^8$, $R^9$, $R^{10}$, and $R^{11}$ are independently selected for each occurrence from the group consisting of hydrogen, $C_{1-6}$alkyl, $C_{2-6}$alkenyl, $C_{2-6}$alkynyl, halogen, hydroxyl, nitro, cyano, NR′R″, —C(O)—NR′R″, —S(O)$_w$—$C_{1-6}$alkyl (where w is 1, 2 or 3), —NR′—S(O)$_w$, and —S(O)$_w$—NR′R″ (where w is 0, 1 or 2), $C_{1-6}$alkoxy, —C(O)—OH, —C(O)—$C_{1-6}$alkyl, and —C(O)—$C_{1-6}$alkoxy;

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, phenyl, NR′R″, —C(O)—NR′R″, S(O)$_w$-methyl (where w is 1, 2 or 3), —NR′—S(O)$_w$, and S(O)$_w$—NR′R″ (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, phenyl, NR′R″, —C(O)—NR′R″, S(O)$_w$—$C_{1-6}$alkyl (where w is 1, 2 or 3), —NR′—S(O)$_w$, and S(O)$_w$—NR′R″ (where w is 0, 1 or 2); and $C_{3-6}$cycloalkyl may be optionally substituted with one, two, three or more substituents selected from the group consisting of halogen, hydroxyl, nitro, cyano, carboxy, $C_{1-6}$alkyl, $C_{1-6}$alkoxy, —C(O)—$C_{1-6}$alkyl, —C(O)—$C_{1-6}$alkoxy, and NR′R″; and pharmaceutically acceptable salts thereof.

For example, in certain embodiments, L may be selected from the group consisting of a bond, —CH$_2$—, —CH$_2$—CH$_2$—, or CH$_2$(CH$_2$)—CH$_2$—. For example, in certain embodiments, L is $C_{2-3}$alkylene, or in other embodiments, L is selected from the group consisting of —CH$_2$—CH$_2$—, —CH$_2$(CH$_2$)—CH$_2$—, —CH$_2$—CH$_2$(OH)—, —CH$_2$—CH$_2$(CH$_3$OH)—, and —CH$_2$—CH$_2$(OH)—CH$_2$—. L may be a bond, or for example, L may be $C_{2-3}$alkylene-O—. For example, L may be —O—CH$_2$—CH$_2$(OH)—, —CH$_2$—CH$_2$(CH$_3$OH)—, or —CH$_2$—CH$_2$(OH)—C—H$_2$—. In other embodiments, L is —O—.

Y, in certain embodiments, may be S(O)$_y$ (where y is 0, 1 or 2), or NR$_Y$. In certain embodiments y is 0 or 2, for example, Y may be S.

In certain other embodiments, $R^2$ is phenyl, for example, $R^2$ may be phenyl substituted by $C_{1-6}$alkyl or $C_{1-6}$alkoxy. In other embodiments, $R^2$ is phenyl substituted by one or two substituents each selected from the group consisting of fluorine, chlorine, $C_{1-6}$alkyl (optionally substituted by one, two or three fluorines), $C_{1-6}$alkoxy (optionally substituted by one, two or three fluorines), hydroxyl, NR′R″, —S(O)$_2$—NR′R″, heteroaryl, and phenyl (optionally substituted by halogen or hydroxyl). For example, $R^2$ may be phenyl substituted by an 5-6 membered heteroaryl selected from the group consisting of:

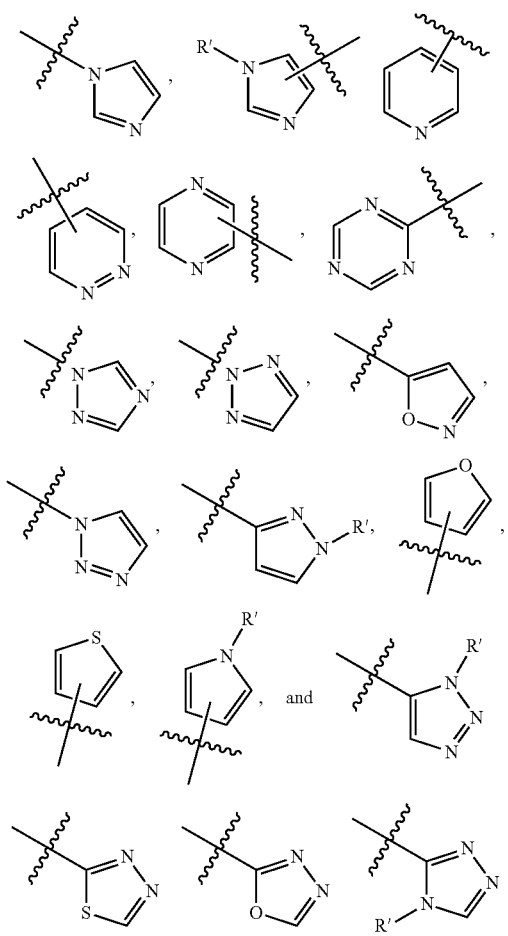

In an exemplary embodiment $R^2$ is phenyl substituted by

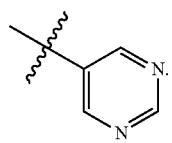 [SMILES: *c1cncnc1]

In other embodiments, $R^2$ may be a 5-6 membered heteroaryl, for example, $R^2$ may be selected from the group consisting of:

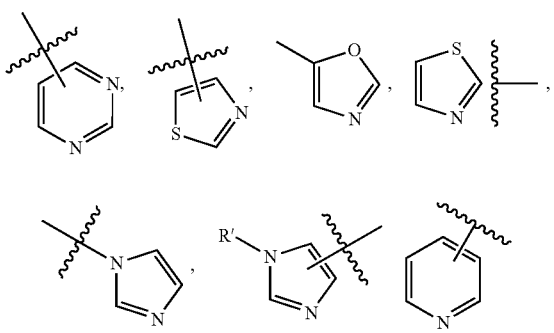

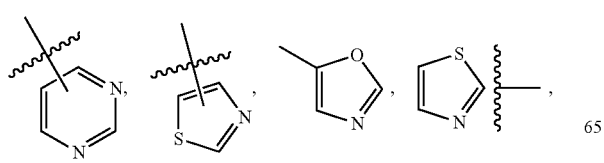

-continued

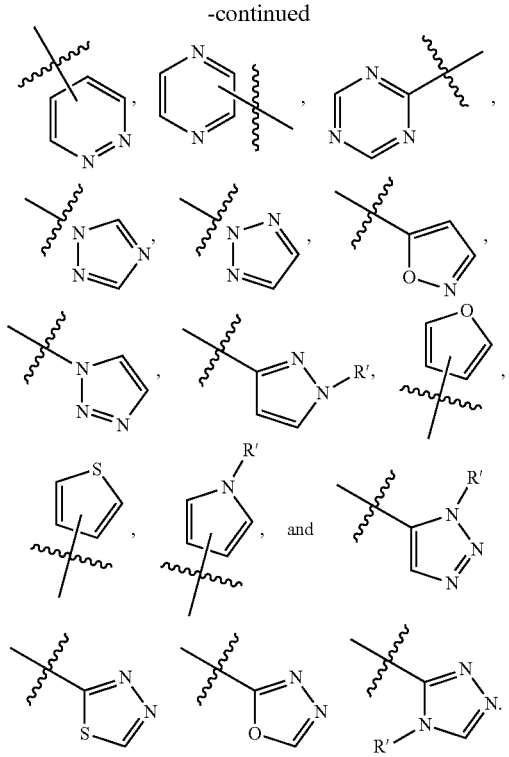

In another embodiment, $R^2$ may be a 4-6 membered heterocycloalkyl, which may be optionally substituted as described above. For example, $R^2$ may be selected from the group consisting of:

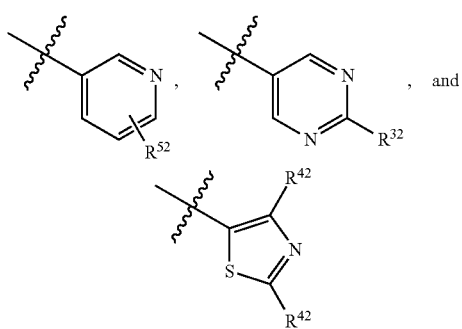

wherein $R^{32}$ is selected from the group consisting of H, halogen, phenyl, and $C_{1-6}$alkyl (optionally substituted by one, two or three halogens); $R^{52}$ is selected from the group consisting of H, halogen, phenyl, and $C_{1-6}$alkyl (optionally substituted by one, two or three halogens); and $R^{42}$ is selected from the group consisting of H, halogen, phenyl, $C_{1-6}$alkyl (optionally substituted by one, two or three halogens), $C_{1-6}$alkoxy (optionally substituted by one, two or three halogens), $NH_2$, —$OCH_3$, $NHCH_3$, and $N(CH_3)_2$.

$R^{42}$, in some embodiments, may be independently selected for each occurrence from the group consisting of H, methyl, ethyl, propyl, —$CF_3$, —$CH_2CH_3$, Cl, F, phenyl, —$NH_2$, —$OCH_3$, $NHCH_3$, and $N(CH_3)_2$.

In other embodiments, e.g. when $R^2$ is a heteroaryl, $R^2$ may be optionally substituted on a carbon by one or two substituents each selected from the group consisting of fluorine, chlorine, phenyl, —$NH_2$, $NH$ $C_{1-6}$alkyl, and $N(C_{1-6}$alkyl$)_2$, $C_{1-6}$alkyl, and $C_{1-6}$alkoxy. In certain embodiments, $R^{11}$ is $CH_2$ or —$CH_2(CH_3)$—

Also contemplated herein is a compound of formula 1 or 1' wherein $R^2$ is a 4-6 membered heterocycloalkyl or $C_{4-6}$cycloalkyl, for example, $R^2$ is selected from the group of: tetrahydropyranyl, tetrahydrofuran, cyclopentane, cyclohexane, and cyclobutane. In an embodiment, $R^2$ is selected from the group consisting of:

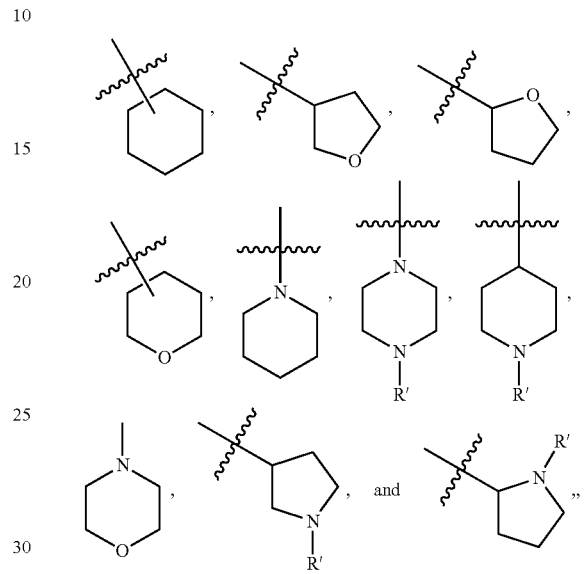

A compound represented by:

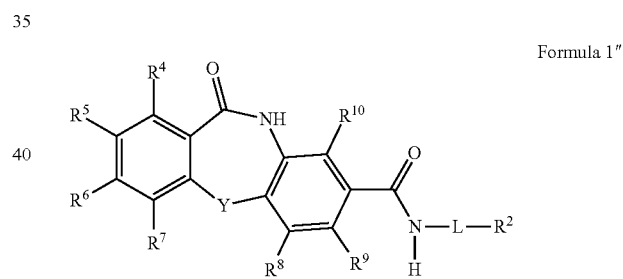

Formula 1″ is also contemplated herein, wherein

Y is $S(O)_y$, wherein y is 0, 1, 2;

L is a bond or $C_{1-4}$ straight chain alkylene optionally substituted by one or two substituents each independently selected from the group consisting of methyl (optionally substituted by halogen or hydroxyl), hydroxyl and halogen;

$R^2$ is selected from phenyl optionally substituted with one, two, three or more substituents selected from the group consisting of halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—NR'R", —C(O)—$C_{1-6}$alkyl, —C(O)—$C_{1-6}$alkoxy, phenyl (optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3)), 5-6 membered heteroaryl having one, two, or three heteroatoms each independently selected from O, N and S (optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), —NR'—S(O)$_w$, and —S(O)$_w$—NR'R" (where w is 1, 2 or 3)), $C_{3-6}$cycloalkyl, —S(O)$_w$—$C_{1-6}$alkyl (where w is 1, 2 or 3), S(O)$_w$—NR'R" (where w is 1, 2 or 3), and —NR'—S(O)$_w$, (where w is 1, 2 or 3)), and a 5-6 membered heteroaryl having one, two, or three heteroatoms each independently selected from O, N and S (wherein the 5-6 membered heteroaryl may be optionally substituted on a carbon with one, two, three or more substituents selected from the group consisting of halogen, hydroxyl, nitro, cyano, carboxy, $C_{1-6}$alkyl, $C_{2-6}$alkenyl, $C_{2-6}$alkynyl, $C_{1-6}$alkoxy, phenyl (optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), S(O)$_w$—NR'R" (where w is 1, 2 or 3), —NR'—S(O)$_w$, and —S(O)$_w$—NR'R" (where w is 1, 2 or 3)), heteroaryl, heterocycle, NR'R", —C(O)—NR'R", —C(O)—$C_{1-6}$alkyl, —C(O)—$C_{1-6}$alkoxy, —S(O)$_w$—$C_{1-6}$alkyl (where w is 1, 2 or 3), —NR'—S(O)$_w$, and —S(O)$_w$—NR'R" (where w is 1, 2 or 3), and on a nitrogen by R');

R' is selected, independently for each occurrence, from H, methyl, ethyl, and propyl, R" is selected, independently for each occurrence, from H, methyl, ethyl, propyl, butyl, —C(O)-methyl and —C(O)-ethyl, or R' and R" taken together may form a 4-6 membered heterocycle;

each of moieties $R^4$, $R^5$, $R^6$, $R^7$, $R^8$, $R^9$, $R^{10}$, and $R^{11}$ are independently selected for each occurrence from the group consisting of hydrogen, $C_{1-6}$alkyl, $C_{2-6}$alkenyl, $C_{2-6}$alkynyl, halogen, hydroxyl, nitro, cyano, NR'R", —C(O)—NR'R", —S(O)$_w$—$C_{1-6}$alkyl (where w is 1, 2 or 3), NR'—S(O)$_w$, and S(O)$_w$—NR'R" (where w is 0, 1 or 2), $C_{1-6}$alkoxy, —C(O)—OH, —C(O)—$C_{1-6}$alkyl, and —C(O)—$C_{1-6}$alkoxy;

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, phenyl, NR'R", —C(O)—NR'R", S(O)$_w$-methyl (where w is 1, 2 or 3), —NR'—S(O)$_w$, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, phenyl, NR'R", —C(O)—NR'R", S(O)$_w$—$C_{1-6}$alkyl (where w is 1, 2 or 3), —NR'—S(O)$_w$, and S(O)$_w$—NR'R" (where w is 0, 1 or 2); and $C_{3-6}$cycloalkyl may be optionally substituted with one, two, three or more substituents selected from the group consisting of halogen, hydroxyl, nitro, cyano, carboxy, $C_{1-6}$alkyl, $C_{1-6}$alkoxy, —C(O)—$C_{1-6}$alkyl, —C(O)—$C_{1-6}$alkoxy, and NR'R" and pharmaceutically acceptable salts thereof.

In some embodiments, compounds of Formula 1, 1' and/or 1" may have $R^7$ selected from H and F; and/or $R^6$ is selected from H and F; and/or $R^5$ is selected from H and F. In some embodiments, compounds of Formula 1, 1' and/or 1" may have $R^{10}$ selected from the group consisting of H, methyl and F and/or $R^4$, $R^5$, $R^6$, $R^7$, $R^8$, $R^9$, $R^{10}$, and/or $R^{11}$ may be H.

In another embodiment, a compound represented by Formula 2 is provided:

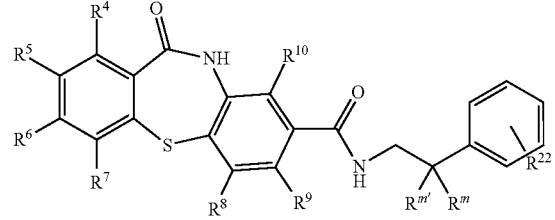

wherein $R^{m'}$ and $R^m$ are each independently selected from the group consisting of H, halogen, $C_{1-6}$alkyl (optionally substituted by one, two or three substituents each independently selected from halogen and hydroxyl), NR'R", and hydroxyl;

$R^{22}$ is selected for each occurrence from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, phenyl, heteroaryl, $C_{3-6}$cycloalkyl, —S(O)$_w$—$C_{1-6}$alkyl (where w is 1, 2 or 3), —S(O)$_w$—NR'R" (where w is 1, 2 or 3), and —NR'—S(O)$_w$, (where w is 1, 2 or 3));

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$, and S(O)$_w$—NR'R"; $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$, and S(O)$_w$—NR'R"; $C_{3-6}$cycloalkyl may be optionally substituted with one, two, three or more substituents selected from the group consisting of halogen, hydroxyl, nitro, cyano, carboxy, $C_{1-6}$alkyl, $C_{1-6}$alkoxy, —C(O)—$C_{1-6}$alkyl, —C(O)—$C_{1-6}$alkoxy, and NR'R"; phenyl may be optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3), and heteroaryl may be optionally substituted by one, two or three substituents each independently selected from the group consisting of halogen, hydroxyl, $C_{1-6}$alkyl, $C_{2-6}$alkenyl, $C_{3-6}$cycloalkyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3)), $C_{3-6}$cycloalkyl; and pharmaceutically acceptable salts thereof.

For example, a compound of Formula 2 may have $R^7$ is selected from H and F; and/or $R^6$ is selected from H and F; and/or $R^5$ is selected from H and F; and/or $R^{10}$ is selected from the group consisting of H, methyl and F; and/or each of $R^4$, $R^5$, $R^6$, $R^7$, $R^8$, $R^9$, $R^{10}$, and $R^{11}$ may be H.

For example, provided herein is a compound represented by

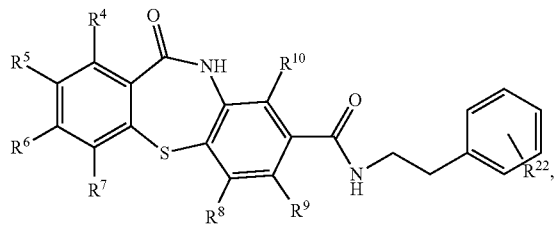

wherein the R moieties are described above. For example, in an embodiment, provided herein is a compound represented by:

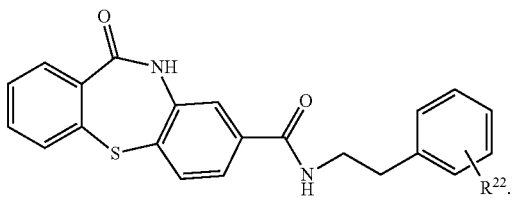

wherein $R^{22}$ for example, is selected from the group consisting of:

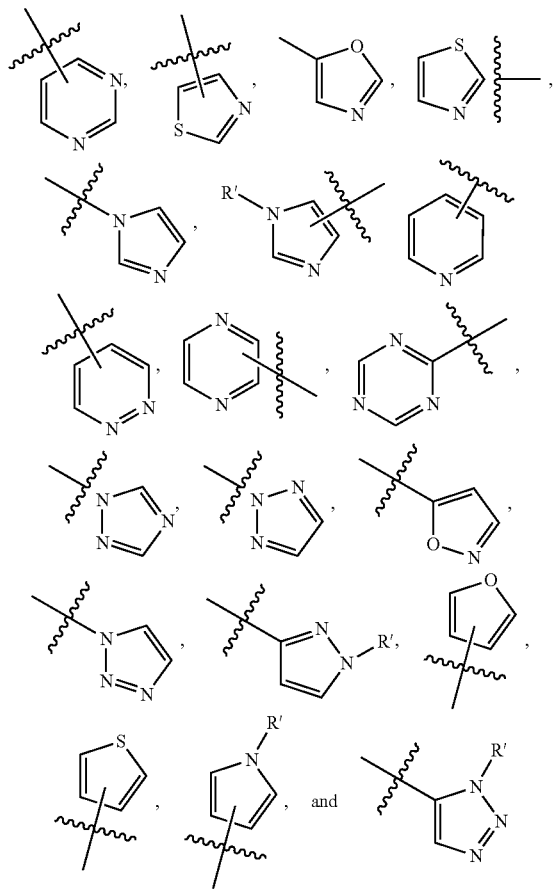

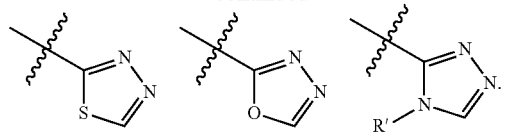

Also provided are compounds of Formula 3:

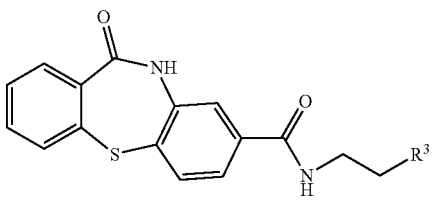

Formula 3 wherein the moiety $R^3$ is selected from the group consisting of phenyl and naphthyl. $R^3$ is optionally substituted with one or more substituents selected from the group consisting of halogen, hydroxyl, cyano, carboxy, alkoxy, amino-cycloalkyl, phenyl, carbonyl-alkoxy, sulfonyl-alkyl, sulfonyl-amino, and sulfonyl-amino-alkyl.

In addition, compounds of Formula 4 are provided:

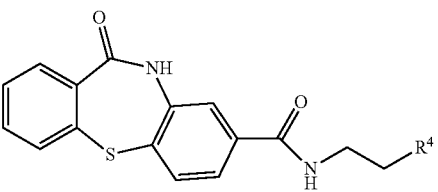

Formula 4 wherein moiety $R^4$ is selected from the group consisting of pyridinyl, pyrimidinyl, thiazolyl, oxazolyl, piperidinyl, and piperazinyl. $R^4$ may be optionally substituted with one or more substituents selected from the group consisting of halogen, hydroxyl, cyano, carboxy, alkoxy, amino-cycloalkyl, phenyl, carbonyl-alkoxy, sulfonyl-alkyl, sulfonyl-amino, and sulfonylamino-alkyl.

In another embodiment, a compound represented by:

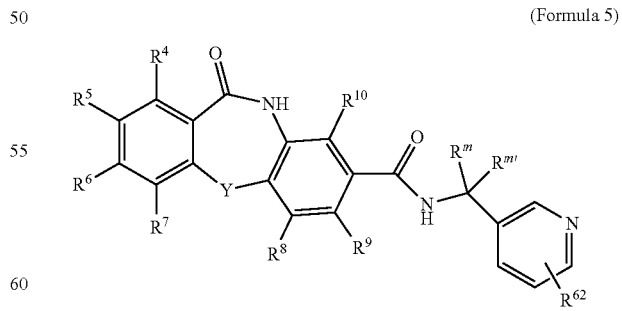

(Formula 5)

is provided
wherein
Y is $C(R^{11})_2$, $S(O)_y$, $NR_Y$ and O wherein y is 0, 1, or 2;
$R_Y$ is selected from the group consisting of H, methyl, ethyl, propyl, phenyl and benzyl;

$R^{m'}$ and $R^{m}$ are each independently selected from the group consisting of H, halogen, $C_{1-6}$alkyl (optionally substituted by one, two or three substituents each independently selected from halogen and hydroxyl), $C_{2-6}$alkenyl (optionally substituted by one, two or three substituents each independently selected from halogen and hydroxyl), NR'R", and hydroxyl (e.g., $R^{m'}$ and $R^{m}$ may each be H in certain embodiments);

$R^{62}$ is selected for each occurrence from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, phenyl, heteroaryl, $C_{3-6}$cycloalkyl, —S(O)$_w$—$C_{1-6}$alkyl (where w is 1, 2 or 3), —S(O)$_w$—NR'R" (where w is 1, 2 or 3), and —NR'—S(O)$_w$, (where w is 1, 2 or 3));

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$, and S(O)$_w$—NR'R"; $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$, and S(O)$_w$—NR'R"; $C_{3-6}$cycloalkyl may be optionally substituted with one, two, three or more substituents selected from the group consisting of halogen, hydroxyl, nitro, cyano, carboxy, $C_{1-6}$alkyl, $C_{1-6}$alkoxy, —C(O)—$C_{1-6}$alkyl, —C(O)—$C_{1-6}$alkoxy, and NR'R"; phenyl may be optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3), and heteroaryl may be optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3)), and $C_{3-6}$cycloalkyl; and pharmaceutically acceptable salts thereof.

In an embodiment, a compound of Formula 5 may have $R^7$ selected from H and F and/or $R^6$ is selected from H and F and/or $R^5$ may be selected from H and F; and/or $R^{10}$ may be selected from the group consisting of H, methyl and F; and/or $R^4$, $R^5$, $R^6$, $R^7$, $R^8$, $R^9$, $R^{10}$, and $R^{11}$ may be H.

In some embodiments, Y of Formula 5 may be S.

A compound represented by:

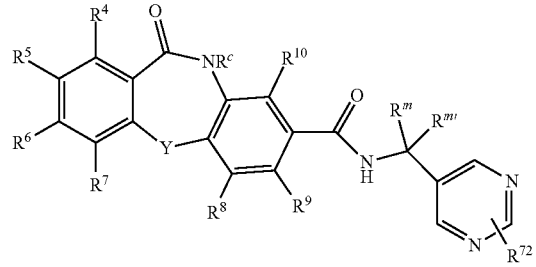

(Formula 6)

is also provided
wherein
Y is $C(R^{11})_2$, $S(O)_y$, $NR_Y$ and O wherein y is 0, 1, or 2;

$R_Y$ is selected from the group consisting of H, methyl, ethyl, propyl, phenyl and benzyl;

$R^{m'}$ and $R^{m}$ are each independently selected from the group consisting of H, halogen, $C_{1-6}$alkyl (optionally substituted by one, two or three substituents each independently selected from halogen and hydroxyl), $C_{2-6}$alkenyl (optionally substituted by one, two or three substituents each independently selected from halogen and hydroxyl), NR'R", and hydroxyl (e.g., $R^{m'}$ and $R^{m}$ may each be H in certain embodiments);

$R^c$ is H or $C_{1-6}$alkyl;

$R^{72}$ is selected for each occurrence from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, phenyl, heteroaryl, $C_{3-6}$cycloalkyl, —S(O)$_w$—$C_{1-6}$alkyl (where w is 1, 2 or 3), —S(O)$_w$—NR'R" (where w is 1, 2 or 3), and —NR'—S(O)$_w$, (where w is 1, 2 or 3));

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$, and S(O)$_w$—NR'R"; $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$, and S(O)$_w$—NR'R"; $C_{3-6}$cycloalkyl may be optionally substituted with one, two, three or more substituents selected from the group consisting of halogen, hydroxyl, nitro, cyano, carboxy, $C_{1-6}$alkyl, $C_{1-6}$alkoxy, —C(O)—$C_{1-6}$alkyl, —C(O)—$C_{1-6}$alkoxy, and NR'R"; phenyl may be optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3), and heteroaryl may be optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, —S(O)$_w$—NR'R" (where w is 1, 2 or 3)), and $C_{3-6}$cycloalkyl, and pharmaceutically acceptable salts thereof.

In some embodiments, Re of a compound of formula 6 may be H or methyl, e.g., H; and/or $R^7$ may be selected from H and F; and/or $R^6$ may be selected from H and F; and/or $R^5$ may be selected from H and F; and/or $R^{10}$ may be selected from the group consisting of H, methyl and F; and/or $R^4$, $R^5$, $R^6$, $R^7$, $R^8$, $R^9$, $R^{10}$, and $R^{11}$ may be H.

In certain embodiments, the Y moiety of Formula 6 is S.

Provided herein, in certain embodiments, is a compound represented by:

Formula 7

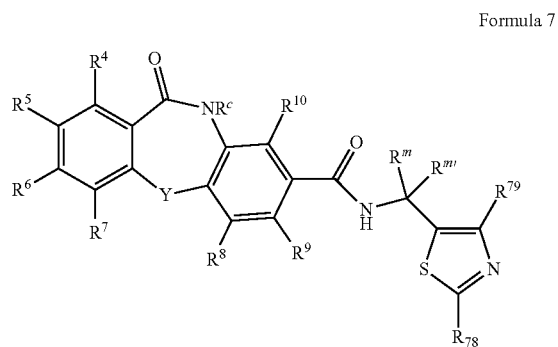

wherein

Y is $C(R^{11})_2$, S(O)$_y$, NR$_Y$ and O wherein y is 0, 1, or 2;

R$_Y$ is selected from the group consisting of H, methyl, ethyl, propyl, phenyl and benzyl;

$R^{m'}$ and $R^m$ are each independently selected from the group consisting of H, halogen, $C_{1-6}$alkyl (optionally substituted by one, two or three substituents each independently selected from halogen and hydroxyl), $C_{2-6}$alkenyl (optionally substituted by one, two or three substituents each independently selected from halogen and hydroxyl), NR'R", and hydroxyl(e.g., $R^{m'}$ and $R^m$ may each be H in certain embodiments);

$R^c$ is H or $C_{1-6}$alkyl;

$R^{78}$ is selected from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, phenyl, heteroaryl, $C_{3-6}$cycloalkyl, —S(O)$_w$—$C_{1-6}$alkyl (where w is 1, 2 or 3), —S(O)$_w$—NR'R" (where w is 1, 2 or 3), and —NR'—S(O)$_w$, (where w is 1, 2 or 3));

$R^{79}$ is selected from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, phenyl, heteroaryl, $C_{3-6}$cycloalkyl, —S(O)$_w$—$C_{1-6}$alkyl (where w is 1, 2 or 3), —S(O)$_w$—NR'R" (where w is 1, 2 or 3), and —NR'—S(O)$_w$, (where w is 1, 2 or 3));

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$, and S(O)$_w$—NR'R"; $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$, and S(O)$_w$—NR'R"; $C_{3-6}$cycloalkyl may be optionally substituted with one, two, three or more substituents selected from the group consisting of halogen, hydroxyl, nitro, cyano, carboxy, $C_{1-6}$alkyl, $C_{1-6}$alkoxy, —C(O)—$C_{1-6}$alkyl, —C(O)—$C_{1-6}$alkoxy, and NR'R"; phenyl may be optionally substituted by one, two or three substituents each independently selected from the group consisting of halogen, hydroxyl, $C_{1-6}$alkyl, $C_{2-6}$alkenyl, $C_{2-6}$alkynyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3), and heteroaryl may be optionally substituted by one, two or three substituents each independently selected from the group consisting of halogen, hydroxyl, $C_{1-6}$alkyl, $C_{2-6}$alkenyl, $C_{2-6}$alkynyl, $C_{3-6}$cycloalkyl, $C_{1-6}$alkoxy, NR'R", C(O)—NR'R", —C(O)—$C_{1-6}$alkyl, —C(O)—$C_{1-6}$alkoxy, —S(O)$_w$—$C_{1-6}$alkyl (where w is 1, 2 or 3), NR'—S(O)$_w$, and —S(O)$_w$—NR'R" (where w is 1, 2 or 3), and pharmaceutically acceptable salts thereof.

$R^c$ is H or methyl.

In certain embodiments, compound of formula 7 may have Re as H; and/or $R^7$ may be selected from H and F; and/or $R^6$ may be selected from H and F; and/or $R^5$ may be selected from H and F; and/or $R^{10}$ may be selected from the group consisting of H, methyl and F; and/or each of $R^4$, $R^5$, $R^6$, $R^7$, $R^8$, $R^9$, $R^{10}$, and $R^{11}$ may be H.

For example, the present disclosure also provides, in part, a compound selected from the group consisting a compound of Table 1, 2, 3, 4, 5, 6 and 7. Also contemplated herein are compounds: N-((2-methylthiazol-5-yl)methyl)-11-oxo-10, 11-dihydrodibenzo[b,f][1,4]thiazepine-8-carboxamide 5-oxide, N-((2-aminothiazol-5-yl)methyl)-11-oxo-10,11-dihydrodibenzo[b,f][1,4]thiazepine-8-carboxamide 5-oxide, N-((2-methylthiazol-5-yl)methyl)-11-oxo-10,11-dihydrodibenz[b,f][1,4]thiazepine-8-carboxamide 5,5-dioxide, N-((2-aminothiazol-5-yl)methyl)-11-oxo-10,11-dihydrodibenzo[b,f][1,4]thiazepine-8-carboxamide 5,5-dioxide, 11-oxo-N-(2-phenylbutyl)-10,11-dihydrodibenz[b,f][1,4]thiazepine-8-carboxamide 5,5-dioxide, N-(2-(4,4-difluorocyclohexyl)ethyl)-11-oxo-10,11-dihydrodibenz[b,f][1,4]thiazepine-8-carboxamide 5,5-dioxide, 3'-(5,5-dioxido-11-oxo-10,11-dihydrodibenz[b,f][1,4]thiazepine-8-carboxamido)-[1,1'-biphenyl]-2-carboxylic acid, 9-methyl-N-((2-methylthiazol-5-yl)methyl)-11-oxo-10,11-dihydrodibenz[b,f][1,4]thiazepine-8-carboxamide, N-(2-(4'-fluoro-[1,1'-biphenyl]-4-yl)ethyl)-11-oxo-10,11-dihydrodibenz[b,f][1,4]thiazepine-8-carboxamide 5,5-dioxide, N-((2-aminothiazol-5-yl)methyl)-9-methyl-11-oxo-10,11-dihydrodibenz[b,f][1,4]thiazepine-8-carboxamide, 11-oxo-N-(pyrimidin-5-ylmethyl)-10,11-dihydro-5H-dibenzo[b,e][1,4]diazepine-8-carboxamide, 11-oxo-N-(2-(pyridin-2-yl)ethyl)-10,11-dihydro-5H-dibenzo[b,e][1,4]diazepine-8-carboxamide, 11-oxo-N-(2-(pyridin-3-yl)ethyl)-10,11-dihydro-5H-dibenzo[b,e][1,4]diazepine-8-carboxamide, 11-oxo-N-(pyridin-3-ylmethyl)-10,11-dihydro-5H-dibenzo[b,e][1,4]diazepine-8-carboxamide, N-(2-([1,1'-biphenyl]-4-yl)ethyl)-11-oxo-10,11-dihydro- 5H-dibenz[b,e][1,4]diazepine-8-carboxamide, 11-oxo-N-(pyridin-4-yl)-10,11-dihydro-5H-dibenzo[b,e][1,4]diazepine-8-carboxamide, N-(4-(N,N-dimethylsulfamoyl)phenethyl)-11-oxo-10,11-dihydro-5H-dibenzo[b,e][1,4]diazepine-8-carboxamide, N-([1,1'-biphenyl]-3-yl)-11-oxo-10,11-dihydro-5H-dibenzo[b,e][1,4]diazepine-8-carboxamide, (Z)—N-((3-(methylimino)prop-1-en-2-yl)oxy)-11-oxo-10,11-dihydrodibenzo[b,f][1,4]thiazepine-8-carboxamide, 11-oxo-N-(pyrimidin-5-yloxy)-10,11-dihydrodibenzo[b,f][1,4]thiazepine-8-carboxamide, 11-oxo-N-(4-(pyrimidin-5-yl)benzyl)-10,11-dihydrodibenzo[b,f][1,4]thiazepine-8-carboxamide, N-(2-(4'-fluoro-[1,1'-biphenyl]-4-yl)ethyl)-11-oxo-10,11-dihydrodibenzo[b,f][1,4]thiazepine-8-carboxamide, 2-chloro-N-((2-methylthiazol-5-yl)methyl)-11-oxo-10,11-dihydrodibenzo[b,f][1,4]thiazepine-8-carboxamide, 2-chloro-11-oxo-N-(pyridin-3-ylmethyl)-10,11-dihydrodibenzo[b,f][1,4]thiazepine-8-carboxamide, 2-chloro-11-oxo-N-(pyrimidin-5-ylmethyl)-10,11-dihydrodibenzo[b,f][1,4]thiazepine-8-carboxamide, 3-chloro-N-((2-methylthiazol-5-yl)methyl)-11-oxo-10,11-dihydrodibenzo[b,f][1,4]thiazepine-8-carboxamide, 3-chloro-11-oxo-N-(pyridin-3-ylmethyl)-10,11-dihydrodibenz[b,f][1,4]thiazepine-8-carboxamide, 3-chloro-11-oxo-N-(pyrimidin-5-ylmethyl)-10,11-dihydrodibenzo[b,f][1,4]thiazepine-8-carboxamide, 11-methyl-N-((2-methylthiazol-5-yl)methyl)-6-oxo-6,11-dihydro-5H-dibenz[b,e]azepine-3-carboxamide, 11-methyl-6-oxo-N-(pyridin-3-ylmethyl)-6,11-dihydro-5H-dibenz[b,e]azepine-3-carboxamide, 11-methyl-6-oxo-N-(pyrimidin-5-ylmethyl)-6,11-dihydro-5H-dibenzo[b,e]azepine-3-carboxamide, 2-chloro-11-oxo-N-(thiazol-5-ylmethyl)-10,11-dihydrodibenzo[b,f][1,4]thiazepine-8-carboxamide, 3-chloro-11-oxo-N-(thiazol-5-ylmethyl)-10,11-dihydrodibenzo[b,f][1,4]thiazepine-8-carboxamide, 11-methyl-6-oxo-N-(thiazol-5-ylmethyl)-6,11-dihydro-5H-dibenzo[b,e]azepine-3-carboxamide, and 11-oxo-N-(2-(thiazol-5-yl)propan-2-yl)-10,11-dihydrodibenz[b,f][1,4]thiazepine-8-carboxamide;
or a pharmaceutically acceptable salt thereof.

In a second aspect, a method for the synthesis of disclosed compounds is provided. The method follows Synthetic Scheme 1, as illustrated in FIG. 1. A first mixture comprising reagents 1 and 2 is formed for synthetic step A to yield synthetic intermediate 3. Synthetic step A may be conducted in an organic solvent, for instance a polar aprotic solvent such as dimethyl sulfoxide (DMSO), dimethylformamide (DMF), dioxane, hexamethylphosphorotriamide, and tetrahydrofuran. The reaction may be conducted in the presence of a base, for example a carbonate such as $Li_2CO_3$, $Na_2CO_3$, $K_2CO_3$, $Rb_2CO_3$, $Cs_2CO_3$, $MgCO_3$, $CaCO_3$, $SrCO_3$, and $BaCO_3$.

In reagent 1, moiety —YH is selected from the group consisting of —SH, —OH, and —N($R^{12}$)H, wherein $R^{12}$ is selected from the group consisting of hydrogen and alkyl. In intermediates 3, 4, 5, and in product 6, moiety —Y— is selected from the group consisting of —S—, —O—, and —N($R^{12}$)—. Moieties $P^1$ and $P^2$ are independently selected carboxyl protecting groups, such as methoxyl or ethoxyl groups. In some cases, at least one of $P^3$ and $P^4$ is an amino protecting group, for example selected from the group consisting of carbobenzyloxy (Cbz), p-methoxybenzyl-carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate group, p-Methoxybenzyl (PMB), 3,4-dimethoxybenzyl (DMPM), p-methoxyphenyl (PMP), tosyl (Ts), sulfonamides (Nosyl and Nps). Alternatively, moiety —N($P^3$)($P^4$) may be a group that can be transformed in an amino group by appropriate chemical reactions. By way of example, moiety —N($P^3$)($P^4$) may be an —$NO_2$ group that is transformed into an amino (—$NH_2$) moiety by reaction with a reductant.

In synthetic step B, protecting groups $P^1$ and $P^2$ are removed to yield carboxyl moieties. In instances where $P^1$ and $P^2$ are alkoxy groups, this may be achieved by hydrolysis, for example in the presence of a base or acid. Group —N($P^3$)($P^4$) is transformed into an amino moiety, as exemplified above, to yield intermediate 4. In synthetic step C, the amino group of intermediate 4 is reacted with the carboxy group on the other phenyl moiety, forming the 1,4-thiazepan-5-one moiety of intermediate 5. The formation of this amide bond may be speeded up by the addition of activators. Example activators include carbodiimides, such as N,N'-dicyclohexylcarbodiimide (DCC), N,N'-diisopropylcarbodiimide (DIC), and carbonyl diimidazole (CDI); and triazololols, such as 1-hydroxy-benzotriazole (HOBt) and 1-hydroxy-7-aza-benzotriazole (HOAt). Other activators include HBTU, HATU, HCTU, TBTU, and PyBOP.

Figure 2:
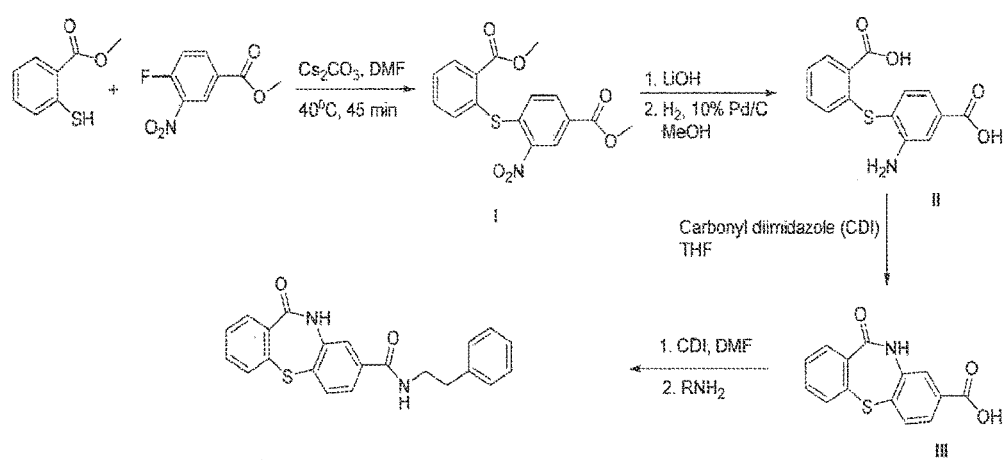
FIG. 2 illustrates synthetic scheme 2.

In synthetic step D, intermediate 5 is reacted with a molecule of formula $R^2NH_2$ to create an amide bond and yield products of Formula 6. As with synthetic step C, the formation of the amide bond may be speeded up with an activator. An exemplary Synthetic Scheme is illustrated in FIG. 2.

In a further aspect, a method for treating a hepatitis B infection in a patient in need thereof is provided, comprising administering to a subject or patient an effective amount of a disclosed compound, and/or administering a first disclosed compound and optionally, and additional, different disclosed compound(s). In another embodiment, a method for treating a hepatitis B infection in a patient in need thereof is provided, comprising administering to a subject or patient a therapeutically effective amount of a pharmaceutical composition comprising a disclosed compound, or two or more disclosed compounds.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 g/kg body weight. In some cases, the administration dose of the compound may be less than 400 g/kg body weight. In other cases, the administration dose may be less than 200 g/kg body weight. In yet other cases, the administration dose may be in the range between about 0.1 to about 100 g/kg body weight. The dose may be conveniently administered once daily, or in divided doses up to, for example, four times a day or in sustained release form.

A compound may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multidose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating patient suffering from hepatitis B comprising administering to a subject a first amount of a disclosed compound and a second amount of an antiviral, or other anti HBV agent, for example a second amount of a second compound selected from the group consisting of: another HBV caspid assembly promoter (such as certain compounds disclosed herein or for example, GLS4, BAY 41-4109, AT-130, DVR-23 (e.g., as depicted below),

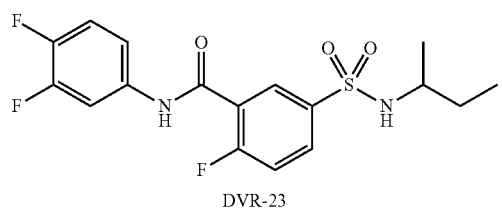
DVR-23

NVR 3-778, NVR1221 (by code), and N890 (as depicted below):

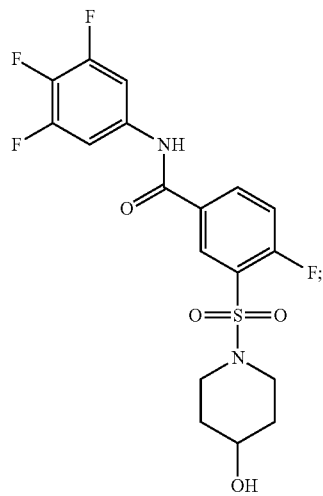 [SMILES: O=C(Nc1cc(F)c(F)c(F)c1)c1ccc(F)c(S(=O)(=O)N2CCC(O)CC2)c1]

other CpAMs such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleoside analogs interfering with viral polymerase, such as entecavir (Baraclude), Lamiv-udine, (Epivir-HBV), Telbivudine (Tyzeka, Sebivo), Adefovir dipivoxil (Hepsera), Tenofovir (Viread), Tenofovir alafenarnide fumarate (TAF), prodrugs of tenofavir (e.g. AGX-1009), L-FMAU (Clevudine), LB80380 (Besifovir) and:

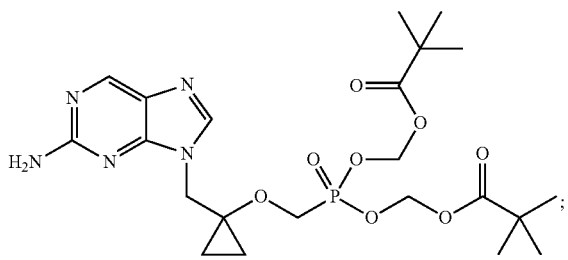 [SMILES: CC(C)(C)C(=O)OCOP(=O)(COC1(Cn2cnc3cnc(N)nc32)CC1)OCOC(=O)C(C)(C)C]

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

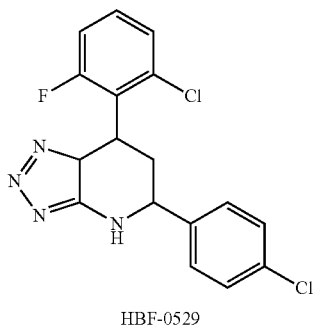

HBF-0529

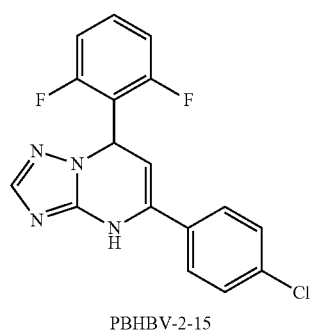

PBHBV-2-15 and BM601 as depicted below:

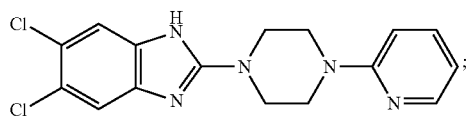

disruptors of nucleocapsid formation or integrity such as NZ-4/W28F:

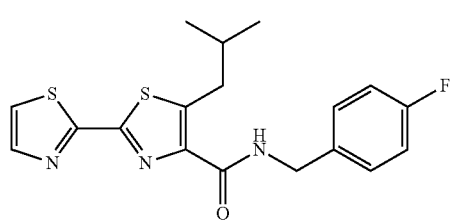

NZ-4 cccDNA formation inhibitors: such as BSBI-25, CCC-0346, CCC-0975 (as depicted below):

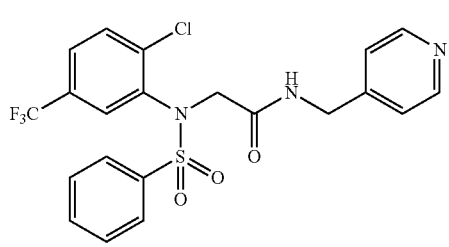

A

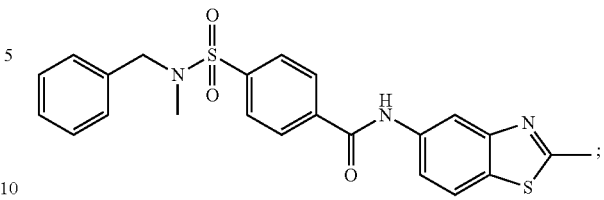

B

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906 each incorporated by reference); inhibitors of HBx-interactions such as RNAi, antisense and nucleic acid based polymers targeting HBV RNA, e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin Inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, e.g. a fluorophore moiety (such a moiety may for example re-emit a certain light frequency upon binding to a virus and/or upon photon excitation. Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydrooxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Example 1: Synthesis of 11-oxo-10, 11-dihydrodibenzo [b,f] [1,4] thiazepine-8-carboxylic acid (6)—a Common Intermediate

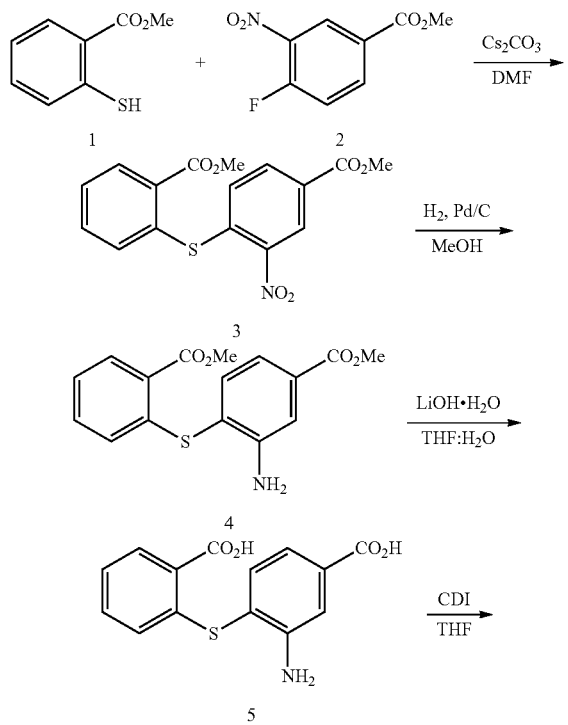

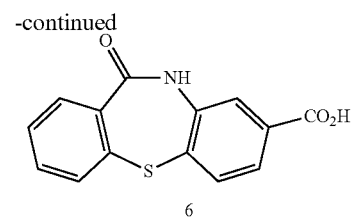

Synthesis of Methyl 4-((2-(methoxycarbonyl) phenyl) thio)-3-nitrobenzoate (3)

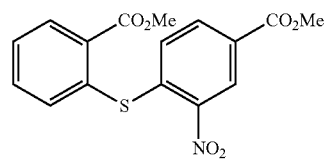

To a stirred solution of methyl 4-fluoro-3-nitrobenzoate 2 (30 g, 150.67 mmol) in DMF (300 mL) under inert atmosphere were added cesium carbonate (58.76 g, 180.8 mmol) and methyl 2-mercaptobenzoate 1 (22.6 mL, 165.47 mmol) at RT; heated to 55-60° C. and stirred for 2 h. The reaction was monitored by TLC; after completion of the reaction, the reaction mixture was diluted with water (1500 mL) and the precipitated solid was filtered to obtain the crude. The crude was washed with water (500 mL), hexane (200 mL) and dried in vacuo to afford compound 3 (48.8 g, 93%) as yellow solid. TLC: 20% EtOAc/hexanes ($R_f$: 0.4); $^1$H NMR (CDCl$_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H).

Synthesis of Methyl 3-amino-4-((2-(methoxycarbonyl) phenyl) thio) benzoate (4)

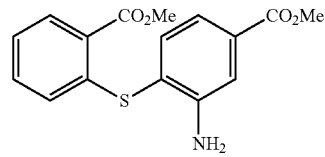

To a stirred solution of compound 3 (48 g, 138.32 mmol) in MeOH (1000 mL) under inert atmosphere was added 10% Pd/C (20 g, wet) at RT under hydrogen atmosphere in an autoclave (100 psi pressure) and stirred for 24 h. The reaction was monitored by TLC; after completion of the reaction, the reaction mixture was filtered through celite, washed with 50% MeOH/CH$_2$Cl$_2$ (500 mL). The filtrate was removed in vacuo to obtain the crude which as triturated with diethyl ether (200 mL), washed with hexane (200 mL) and dried in vacuo to afford compound 4 (40 g, 91%) as yellow solid. TLC: 10% EtOAc/hexanes ($R_f$: 0.3); $^1$H NMR (DMSO-d$_6$, 400 MHz): δ 7.95 (dd, J=7.8, 1.4 Hz, 1H), 7.48-7.35 (m, 3H), 7.23 (td, J=7.5, 1.1 Hz, 1H), 7.15 (dd, J=8.0, 1.8 Hz, 1H), 6.66 (dd, J=8.2, 0.8 Hz, 1H), 5.67 (br s, 2H), 3.88 (s, 3H), 3.84 (s, 3H).

Synthesis of 3-amino-4-((2-carboxyphenyl) thio) benzoic acid (5)

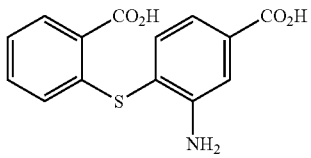

To a stirred solution of compound 4 (40 g, 126.18 mmol) in THF:H$_2$O (5:1, 400 mL) was added lithium hydroxide monohydrate (26 g, 619.0 mmol) at 0° C.; warmed to RT and stirred for 48 h. The reaction was monitored by TLC; after completion of the reaction, the volatiles were removed in vacuo. The pH of the residue was acidified with 2 N HCl to ~2. The precipitated solid was filtered and dried in vacuo to afford compound 5 (34.6 g, 95%) as an off-white solid. TLC: 30% EtOAc/hexanes (R$_f$: 0.1); $^1$H NMR (DMSO-d$_6$, 500 MHz): δ 13.00 (br s, 2H), 7.93 (dd, J=7.7, 1.0 Hz, 1H), 7.42 (s, 1H), 7.40-7.31 (m, 2H), 7.18 (t, J=7.4 Hz, 1H), 7.13 (dd, J=8.0, 1.6 Hz, 1H), 6.61 (d, J=7.8 Hz, 1H), 5.55 (br s, 2H).

Synthesis of 11-oxo-10, 11-dihydrodibenzo [b,f] [1,4] thiazepine-8-carboxylic acid (6)

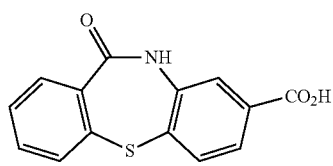

To a stirred solution of compound 5 (31 g, 107.26 mmol) in THF (600 mL) under inert atmosphere was added CDI (86.88 g, 536.29 mmol) at 0° C.; warmed to RT and stirred for 16 h. The reaction was monitored by TLC; after completion of the reaction, the reaction mixture was acidified with 2 N HCl to pH-4. The obtained solid was filtered and further dried by using toluene (2×200 mL) to afford compound 6 (26 g, 90%) as white solid. TLC: 10% MeOH/CH$_2$Cl$_2$ (R$_f$: 0.3); 1H NMR (DMSO-d$_6$, 400 MHz): δ 13.22 (br s, 1H), 10.81 (s, 1H), 7.78 (s, 1H), 7.72-7.64 (m, 3H), 7.57-7.44 (m, 3H).

Example 2: Synthesis of 2-chloro-11-oxo-10, 11-dihydrodibenzo [b,f] [1,4] thiazepine-8-carboxylic acid (14)—a Common Intermediate

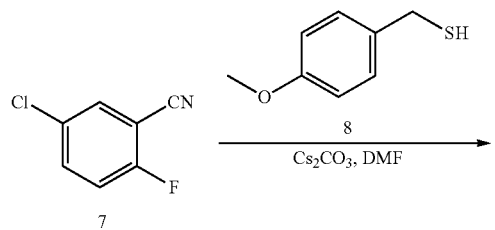

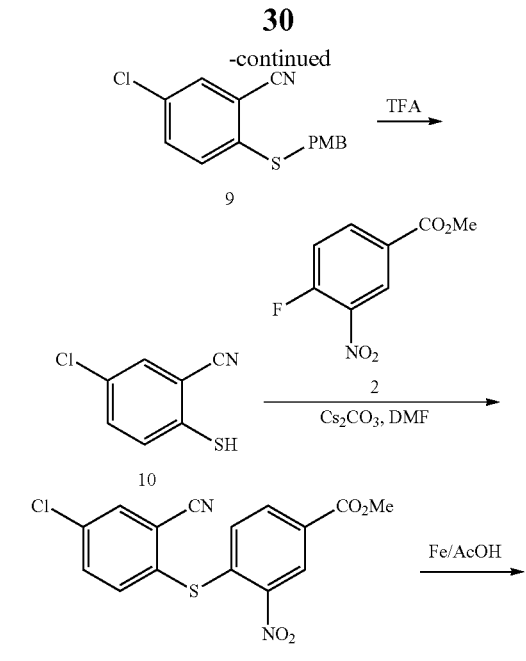

Synthesis of 5-chloro-2-((4-methoxybenzyl) thio) benzonitrile (9)

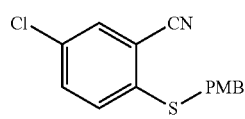

To a stirred solution of 5-chloro-2-fluorobenzonitrile 7 (1 g, 6.41 mmol) in DMF (10 mL) under inert atmosphere was added cesium carbonate (2.30 g, 7.05 mmol) at RT; heated to 40° C. and to this was added (4-methoxyphenyl) methanethiol 8 (1.08 g, 7.05 mmol); heated to 60° C. and stirred for 2 h. The reaction was monitored by TLC; after completion of the reaction, the reaction mixture was diluted with

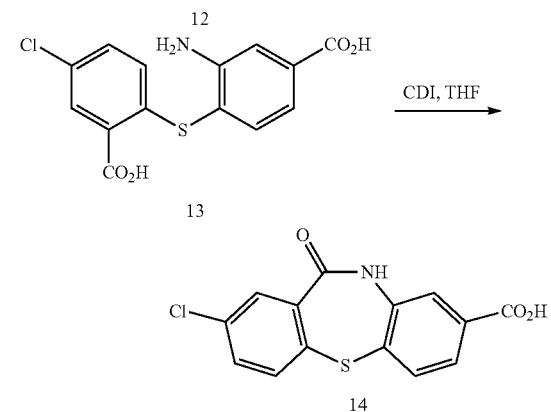

water (20 mL) and extracted with EtOAc (2×25 mL). The combined organic extracts were dried over sodium sulfate, filtered and concentrated in vacuo to obtain the crude. The crude was purified through silica gel column chromatography using 3-5% EtOAc/hexanes to afford compound 9 (1 g, 54%) as white solid. TLC: 10% EtOAc/hexanes (R$_f$: 0.6); $^1$H-NMR (CDCl$_3$, 500 MHz): δ 7.57 (s, 1H), 7.39 (d, J=8.0 Hz, 1H), 7.28-7.27 (m, 1H), 7.20 (d, J=9.0 Hz, 2H), 6.81 (d, J=9.0 Hz, 2H), 4.15 (s, 2H), 3.78 (s, 3H).

Synthesis of 5-chloro-2-mercaptobenzonitrile (10)

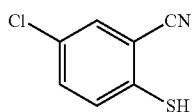

A stirred solution of compound 9 (1 g, 3.47 mmol) in trifluoro acetic acid (10 mL) under inert atmosphere was stirred at 70° C. for 5 h. The reaction was monitored by TLC; after completion of the reaction, the volatiles were removed in vacuo to obtain the crude compound 10 (590 mg) which was carried to the next step without further purification. TLC: 30% EtOAc/hexanes (R$_f$: 0.2); $^1$H-NMR (CDCl$_3$, 500 MHz): δ 7.57 (s, 1H), 7.41 (d, J=9.0 Hz, 1H), 7.34 (d, J=9.0 Hz, 1H), 4.08 (s, 1H).

Synthesis of Methyl 4-((4-chloro-2-cyanophenyl) thio)-3-nitrobenzoate (11)

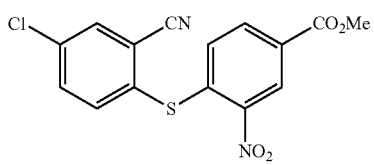

To a stirred solution of compound 10 (620 mg, 3.11 mmol) in DMF (10 mL) under inert atmosphere was added cesium carbonate (1.1 g, 3.42 mmol) at RT; heated to 40° C. and stirred for 10 min. To this was added methyl 4-fluoro-3-nitrobenzoate 2 (582 mg, 3.42 mmol) at 60° C. and stirred for 3 h. The reaction was monitored by TLC; after completion of the reaction, the reaction mixture was diluted with water (20 mL) and extracted with EtOAc (2×20 mL). The combined organic extracts were dried over sodium sulfate, filtered and concentrated in vacuo to obtain the crude. The crude was purified through silica gel column chromatography using 25% EtOAc/hexanes to afford compound 11 (600 mg, 55%) as pale yellow solid. TLC: 30% EtOAc/hexanes (R$_f$: 0.4); $^1$H-NMR (DMSO-d$_6$, 400 MHz): δ 8.66 (s, 1H), 8.33 (s, 1H), 8.05-8.03 (m, 1H), 7.98-7.92 (m, 2H), 7.02 (d, J=8.4 Hz, 1H), 3.86 (s, 3H).

Synthesis of Methyl 3-amino-4-((4-chloro-2-cyanophenyl) thio) benzoate (12)

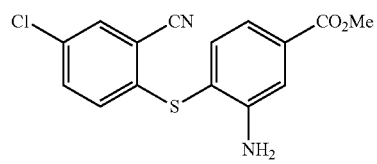

To a stirred solution of compound 11 (450 mg, 1.29 mmol) in acetic acid (15 mL) under inert atmosphere was added iron powder (724 mg, 12.9 mmol) at RT; heated to 90° C. and stirred for 3 h. The reaction was monitored by TLC; after completion of the reaction, the volatiles were removed in vacuo. The residue was basified with saturated NaHCO$_3$ solution (15 mL) and extracted with CH$_2$Cl$_2$ (2×20 mL). The combined organic extracts were dried over sodium sulfate, filtered and concentrated in vacuo to obtain the crude. The crude was triturated with 3% EtOAc/hexanes (2×5 mL) to afford compound 12 (290 mg, 70%) as pale yellow solid. TLC: 20% MeOH/CH$_2$Cl$_2$ (R$_f$: 0.7); $^1$H-NMR (DMSO-d$_6$, 400 MHz): δ 8.05 (s, 1H), 7.63-7.60 (m, 1H), 7.48 (s, 1H), 7.43 (d, J=8.0 Hz, 1H), 7.14 (d, J=8.8 Hz, 1H), 6.75 (d, J=8.8 Hz, 1H), 5.88 (s, 2H), 3.84 (s, 3H).

Synthesis of 2-((2-amino-4-carboxyphenyl) thio)-5-chlorobenzoic acid (13)

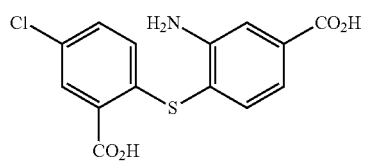

To a stirred solution of compound 12 (450 mg, 1.41 mmol) in MeOH (10 mL) was added potassium hydroxide (792 mg, 14.1 mmol) in water (3 mL) at 0° C.; heated to 90° C. and stirred for 9 h. The reaction was monitored by TLC; after completion of the reaction, the volatiles were removed in vacuo. The residue was acidified with 1 N HCl to pH-4.0. The obtained solid was filtered, washed with ether (2×5 mL) and dried in vacuo to afford compound 13 (350 mg, 76%) as an off-white solid. TLC: 20% MeOH/CH$_2$Cl$_2$ (R$_f$: 0.3); $^1$H-NMR (DMSO-d$_6$, 400 MHz): δ 12.92 (br s, 2H), 7.89 (s, 1H), 7.44-7.38 (m, 3H), 7.14 (d, J=8.8 Hz, 1H), 6.60 (d, J=8.8 Hz, 1H), 5.64 (br s, 2H).

Synthesis of 2-chloro-11-oxo-10, 11-dihydrodibenzo [b,f] [1,4] thiazepine-8-carboxylic acid (14)

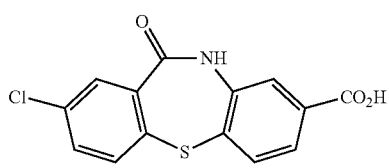

To a stirred solution of compound 13 (30 mg, 0.09 mmol) in THF (2 mL) under inert atmosphere was added CDI (45 mg, 0.27 mmol) at RT and stirred for 7 h. The reaction was monitored by TLC; after completion of the reaction, the volatiles were removed in vacuo. The residue was acidified with 2 N HCl to pH-4.0. The obtained solid was filtered, washed with ether (2×3 mL) and dried in vacuo to afford compound 14 (15 mg, 53%) as an off-white solid. TLC: 15% MeOH/CH$_2$Cl$_2$ (R$_f$: 0.5); $^1$H-NMR (DMSO-d$_6$, 400 MHz): δ 13.05 (br s, 1H), 10.98 (s, 1H), 7.80 (s, 1H), 7.72-7.70 (m, 3H), 7.64 (s, 2H).

Example 3: Synthesis of 3-chloro-11-oxo-10, 11-dihydrodibenzo [b,f] [1,4] thiazepine-8-carboxylic acid (21)—a Common Intermediate

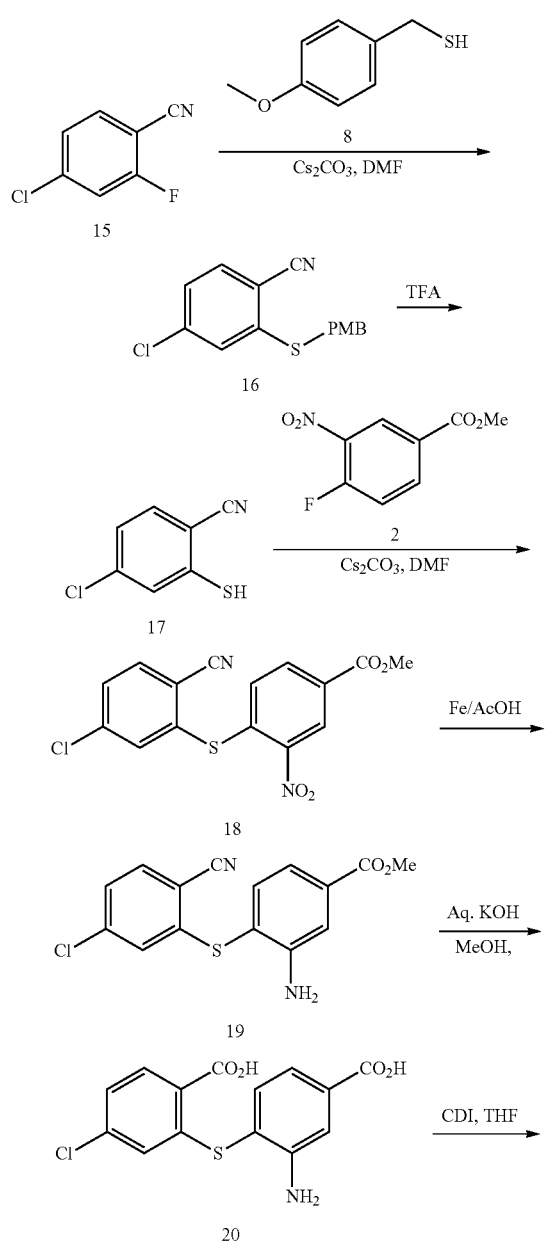

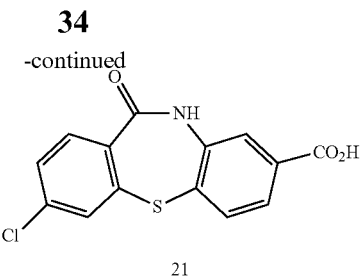

Synthesis of 4-chloro-2-((4-methoxybenzyl) thio) benzonitrile (16)

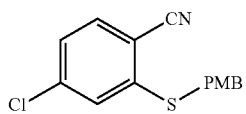

To a stirred solution of 4-chloro-2-fluorobenzonitrile 15 (1 g, 6.41 mmol) in DMF (25 mL) under inert atmosphere was added cesium carbonate (2.30 g, 7.05 mmol) at RT; heated to 40° C. and to this was added (4-methoxyphenyl) methanethiol 8 (1.08 g, 7.05 mmol); heated to 60° C. and stirred for 2 h. The reaction was monitored by TLC; after completion of the reaction, the reaction mixture was diluted with water (20 mL) and extracted with EtOAc (2×25 mL). The combined organic extracts were dried over sodium sulfate, filtered and concentrated in vacuo to obtain the crude. The crude was purified through silica gel column chromatography using 4% EtOAc/hexanes to afford compound 16 (900 mg, 48%) as white solid. TLC: 10% EtOAc/hexanes (R$_f$: 0.6); $^1$H-NMR (CDCl$_3$, 400 MHz): δ 7.51 (d, J=8.4 Hz, 1H), 7.33 (s, 1H), 7.23-7.20 (m, 3H), 6.84 (d, J=8.4 Hz, 2H), 4.19 (s, 2H), 3.79 (s, 3H).

Synthesis of 4-chloro-2-mercaptobenzonitrile (17)

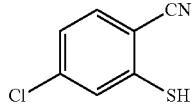

A stirred solution of compound 16 (900 mg, 3.11 mmol) in trifluoro acetic acid (10 mL) under inert atmosphere at RT was heated to 70° C. and stirred for 4 h. The reaction was monitored by TLC; after completion of the reaction, the volatiles were removed in vacuo to obtain the crude compound 17 (527 mg) as brown solid. The crude was carried to the next step without further purification. TLC: 5% MeOH/CH$_2$Cl$_2$ (R$_f$: 0.1); $^1$H-NMR (CDCl$_3$, 400 MHz): δ 7.52 (d, J=8.4 Hz, 1H), 7.41 (s, 1H), 7.22-7.19 (m, 1H), 4.13 (s, 1H).

Synthesis of Methyl 4-((5-chloro-2-cyanophenyl)thio)-3-nitrobenzoate (18)

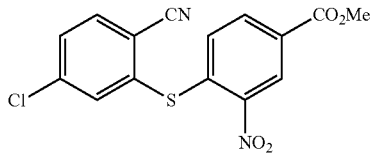

18

To a stirred solution of compound 17 (550 mg, 2.76 mmol) in DMF (15 mL) under inert atmosphere was added cesium carbonate (988 mg, 3.04 mmol) at RT; heated to 40° C. and stirred for 10 min. To this was added methyl 4-fluoro-3-nitrobenzoate 2 (515 mg, 3.04 mmol) at 60° C. and stirred for 3 h. The reaction was monitored by TLC; after completion of the reaction, the reaction mixture was diluted with water (20 mL). The obtained solid was filtered, washed with 15% EtOAc/hexanes (2×5 mL) and dried in vacuo to afford compound 18 (700 mg, 73%) as yellow solid. TLC: 20% EtOAc/hexanes ($R_f$: 0.3); $^1$H-NMR (DMSO-$d_6$, 500 MHz): δ 8.69 (s, 1H), 8.18-8.15 (m, 2H), 8.10 (d, J=8.5 Hz, 1H), 7.92 (d, J=8.5 Hz, 1H), 7.10 (d, J=9.0 Hz, 1H), 3.90 (s, 3H).

Synthesis of Methyl 3-amino-4-((5-chloro-2-cyanophenyl) thio) benzoate (19)

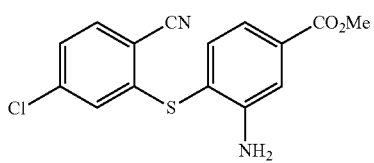

19

To a stirred solution of compound 18 (700 mg, 2.01 mmol) in acetic acid (15 mL) under inert atmosphere was added iron powder (1.12 g, 20.11 mmol) at RT; heated to 90° C. and stirred for 5 h. The reaction was monitored by TLC; after completion of the reaction, the volatiles were removed in vacuo. The residue was basified with 10% NaHCO$_3$ solution (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 20% EtOAc/hexanes to afford compound 19 (500 mg, 78%) as yellow solid. TLC: 30% EtOAc/hexanes ($R_f$: 0.8); $^1$H-NMR (DMSO-$d_6$, 500 MHz): δ 7.92 (d, J=7.5 Hz, 1H), 7.51-7.43 (m, 3H), 7.17 (d, J=8.0 Hz, 1H), 6.66 (s, 1H), 5.96 (s, 2H), 3.86 (s, 3H).

Synthesis of 2-((2-amino-4-carboxyphenyl) thio)-4-chlorobenzoic acid (20)

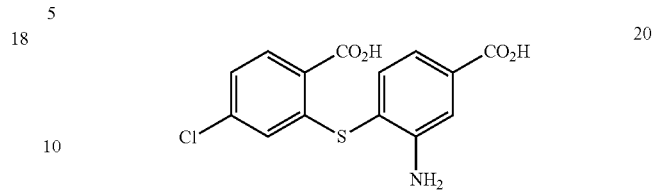

20

To a stirred solution of compound 19 (500 mg, 1.57 mmol) in MeOH (6 mL) was added potassium hydroxide (1.32 mg, 23.5 mmol) in water (6 mL) at 0° C.; heated to 90° C. and stirred for 24 h. The reaction was monitored by TLC; after completion of the reaction, the volatiles were removed in vacuo. The residue was diluted with water (20 mL) and extracted with EtOAc (2×25 mL). The aqueous layer was acidified with 1 N HCl to pH-6.0. The obtained solid was filtered, washed with ether (2×7 mL) and dried in vacuo to afford compound 20 (375 mg, 74%) as an off-white solid. TLC: 20% MeOH/CH$_2$Cl$_2$ ($R_f$: 0.2); $^1$H-NMR (CDCl$_3$, 400 MHz): δ 8.05 (d, J=8.4 Hz, 1H), 7.55-7.47 (m, 3H), 7.17-7.14 (m, 1H), 6.67 (s, 1H).

Synthesis of 3-chloro-11-oxo-10, 11-dihydrodibenzo [b,f] [1,4] thiazepine-8-carboxylic acid (21)

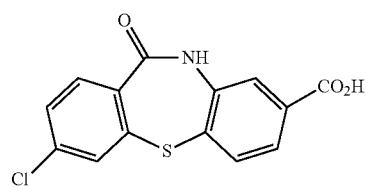

21

To a stirred solution of compound 20 (375 mg, 1.16 mmol) in THF (10 mL) under inert atmosphere was added CDI (564 mg, 3.48 mmol) at RT and stirred for 16 h. The reaction was monitored by TLC; after completion of the reaction, the volatiles were removed in vacuo. The residue was diluted with water (15 mL) and acidified with 6 N HCl to pH-1.0. The obtained solid was filtered, washed with ether (2×5 mL) and dried in vacuo to afford compound 21 (285 mg, 81%) as an off-white solid. TLC: 20% MeOH/CH$_2$Cl$_2$ ($R_f$: 0.4); $^1$H-NMR (DMSO-$d_6$, 400 MHz): δ 14.56 (br s, 2H), 10.90 (s, 1H), 9.11 (s, 1H), 7.71-7.65 (m, 4H).

Example 4: Synthesis of 1-fluoro-11-oxo-10, 11-dihydrodibenzo [b,f] [1,4] thiazepine-8-carboxylic acid (28)—a Common Intermediate

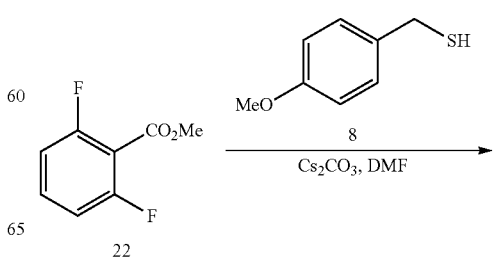

22

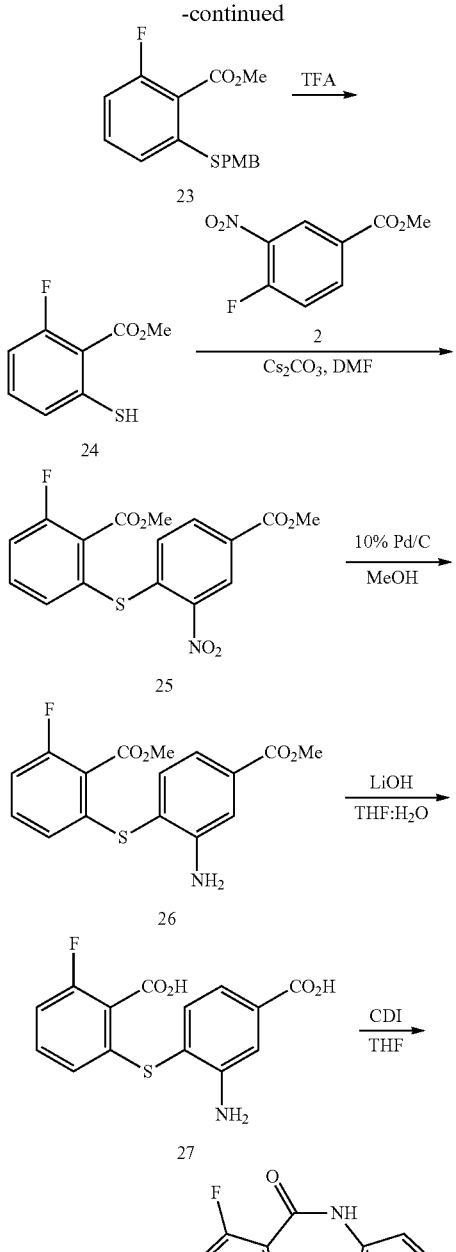

To a stirred solution of methyl 2, 6-difluorobenzoate 22 (10 g, 58.13 mmol) in DMF (100 mL) under inert atmosphere were added (4-methoxyphenyl) methanethiol 8 (8.96 g, 58.13 mmol), cesium carbonate (20.8 g, 63.95 mmol) at 0° C.; warmed to 10° C. and stirred for 2 h. The reaction was monitored by TLC; after completion of the reaction, the reaction mixture was diluted with water (200 mL) and extracted with EtOAc (2×800 mL). The combined organic extracts were dried over sodium sulfate, filtered and concentrated in vacuo to obtain the crude. The crude was purified through silica gel column chromatography using 10-15% EtOAc/hexanes to afford compound 23 (7.5 g, 42%) as white solid. TLC: 10% EtOAc/hexanes ($R_f$: 0.3); $^1$H NMR (DMSO-$d_6$, 400 MHz) δ 7.53-7.44 (m, 1H), 7.35 (d, J=8.0 Hz, 1H), 7.26 (d, J=8.6 Hz, 2H), 7.15 (t, J=9.0 Hz, 1H), 6.86 (d, J=8.7 Hz, 2H), 4.22 (s, 2H), 3.72 (s, 3H), 3.33 (s, 3H).

Synthesis of Methyl 2-fluoro-6-mercaptobenzoate (24)

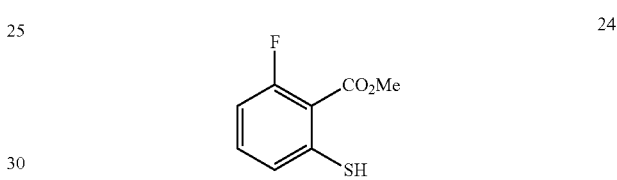

A stirred solution of compound 23 (7.5 g, 24.5 mmol) in trifluoro acetic acid (100 mL) at RT under inert atmosphere was heated to 60-65° C. and stirred for 5 h. The reaction was monitored by TLC; after completion of the reaction, the volatiles were removed and dried in vacuo to obtain compound 24 (4.6 g) as brown syrup. The crude was carried forward for next step without further purification. TLC: 10% EtOAc/hexanes ($R_f$: 0.7).

Synthesis of Methyl 2-fluoro-6-((4-(methoxycarbonyl)-2-nitrophenyl) thio) benzoate (25)

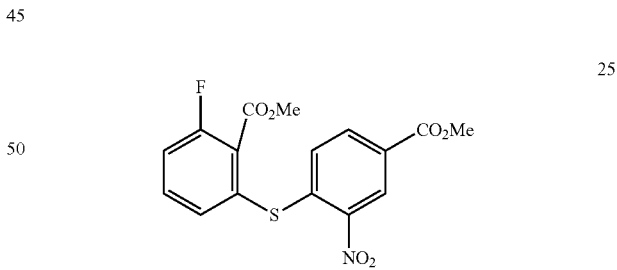

To a stirred solution of methyl 4-fluoro-3-nitrobenzoate 2 (4.5 g, 22.61 mmol) in DMF (100 mL) under inert atmosphere were added compound 24 (4.6 g, crude), cesium carbonate (11 g, 33.91 mmol) at RT; heated to 60-65° C. and stirred for 2 h. The reaction was monitored by TLC; after completion of the reaction, the reaction mixture was diluted with water (600 mL) and stirred for 1 h. The precipitated solid was filtered, titurated with 10% EtOAc/hexanes (2×20 mL) and dried in vacuo to afford compound 25 (7 g, 85%) as yellow solid. TLC: 20% EtOAc/hexanes ($R_f$: 0.3); 1H NMR (DMSO-$d_6$, 400 MHz): δ 8.65 (s, 1H), 8.08 (dd, J=8.6, Synthesis of Methyl 2-fluoro-6-((4-methoxybenzyl) thio) benzoate (23)

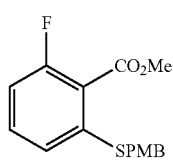

1.9 Hz, 1H), 7.79-7.72 (m, 1H), 7.67-7.61 (m, 2H), 7.01 (d, J=8.6 Hz, 1H), 3.88 (s, 3H), 3.72 (s, 3H).

Synthesis of Methyl 2-((2-amino-4-(methoxycarbonyl) phenyl) thio)-6-fluorobenzoate (26)

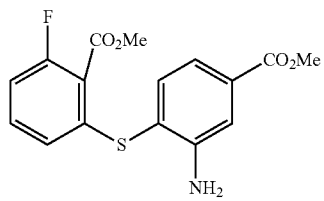

To a stirred solution of compound 25 (7.09 g, 19.17 mmol) in MeOH (200 mL) under inert atmosphere was added 10% Pd/C (3.5 g) at RT and stirred under hydrogen at 80 psi for 16 h in an autoclave. The reaction was monitored by TLC; after completion of the reaction, the reaction mixture was filtered through celite and washed with 40% MeOH/CH$_2$Cl$_2$ (3×500 mL). The combined organic extracts were dried over sodium sulfate, filtered and concentrated in vacuo to obtain the crude. The crude compound was triturated with 20% EtOAc/hexanes (200 mL) and dried in vacuo to afford compound 26 (5 g, 78%) as an off-white solid. TLC: 20% EtOAc/hexanes (R$_f$: 0.4); $^1$H NMR (DMSO-d$_6$, 400 MHz): δ 7.45-7.36 (m, 3H), 7.19-7.11 (m, 2H), 6.68 (d, J=7.7 Hz, 1H), 5.71 (s, 2H), 3.90 (s, 3H), 3.83 (s, 3H).

Synthesis of 2-((2-amino-4-carboxyphenyl) thio)-6-fluorobenzoic acid (27)

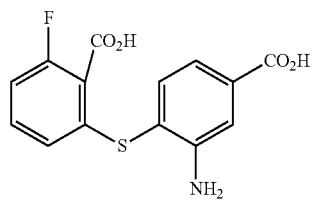

To a stirred solution of compound 26 (5 g, 14.92 mmol) in THF:H$_2$O (5:1, 90 mL) was added lithium hydroxide monohydrate (3.13 g, 74.62 mmol) at RT and stirred for 16 h and heated to 80° C. for 5 h. The reaction was monitored by TLC; after completion of the reaction, the volatiles were removed in vacuo. The residue was diluted with water (200 mL) and acidified with 2 N HCl to pH-4. The precipitated solid was filtered and dried in vacuo to afford compound 27 (4 g, 87%) as an off-white solid. TLC: 30% EtOAc/hexanes (R$_f$: 0.1); $^1$H NMR (DMSO-d$_6$, 400 MHz): δ 12.89 (br s, 1H), 7.42-7.36 (m, 2H), 7.35-7.31 (m, 1H), 7.14-7.08 (m, 2H), 6.63 (d, J=8.0 Hz, 1H), 5.75 (br s, 2H).

Synthesis of 1-fluoro-11-oxo-10, 11-dihydrodibenzo [b,f] [1,4] thiazepine-8-carboxylic acid (28)

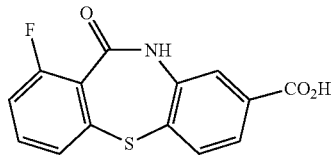

To a stirred solution of compound 27 (4 g, 13.02 mmol) in THF (100 mL) under inert atmosphere was added CDI (10.56 g, 65.1 mmol) at RT and stirred for 26 h. The reaction was monitored by TLC; after completion of the reaction, the volatiles were removed in vacuo. The residue was diluted with ice cold water (80 mL) and acidified with 2 N HCl to pH-4. The precipitated solid was filtered and dried in vacuo to afford compound 28 (3.3 g, 88%) as an off-white solid. TLC: 15% MeOH/CH$_2$Cl$_2$ (R$_f$: 0.2); 1H NMR (DMSO-d$_6$, 400 MHz): δ 13.33 (br s, 2H), 11.00 (s, 1H), 7.77 (s, 1H), 7.69-7.67 (m, 2H), 7.53-7.47 (m, 1H), 7.42-7.39 (m, 1H), 7.35-7.29 (m, 1H).

Example 5: Synthesis of 2-fluoro-11-oxo-10, 11-dihydrodibenzo [b,f] [1,4] thiazepine-8-carboxylic acid (35)—a Common Intermediate

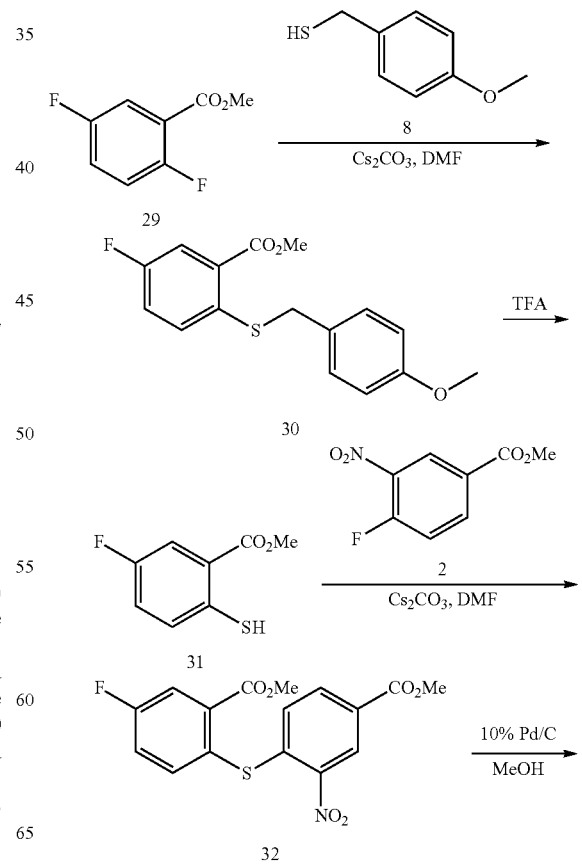

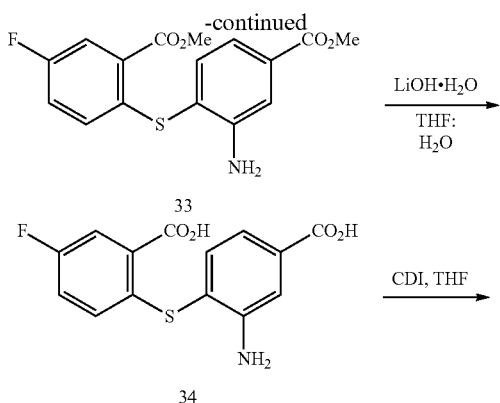

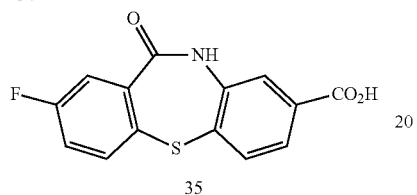

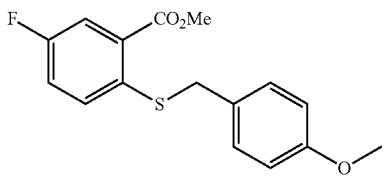

Synthesis of methyl-5-fluoro-2-((4-methoxybenzyl)thio) benzoate (30)

To a stirred solution of methyl 2, 5-difluorobenzoate 29 (1 g, 5.80 mmol) in DMF (20 mL) under argon atmosphere were added (4-methoxyphenyl) methanethiol 8 (985 mg, 6.39 mmol), cesium carbonate (2.07 g, 6.39 mmol) at RT and stirred for 3 h. The reaction was monitored by TLC; after completion of the reaction, the reaction mixture was diluted with water (30 mL) and extracted with $CH_2Cl_2$ (2×30 mL). The combined organic extracts were dried over sodium sulfate, filtered and concentrated in vacuo to obtain the crude. The crude was purified through silica gel column chromatography using 5-7% EtOAc/hexanes to afford compound 30 (700 mg, 40%) as white solid. TLC: 10% EtOAc/hexanes ($R_f$: 0.3); $^1$H-NMR ($CDCl_3$, 400 MHz): δ 7.64-7.61 (m, 1H), 7.32-7.29 (m, 3H), 7.17-7.09 (m, 1H), 6.86-6.82 (m, 2H), 4.09 (s, 2H), 3.90 (s, 3H), 3.79 (s, 3H).

Synthesis of Methyl 5-fluoro-2-mercaptobenzoate (31)

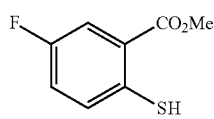

A stirred solution of compound 30 (700 mg, 2.28 mmol) in trifluoro acetic acid (7 mL) at RT under argon atmosphere was heated to 60-65° C. and stirred for 5 h. The reaction was monitored by TLC; after completion of the reaction, the volatiles were removed and dried in vacuo to obtain compound 31 (380 mg, 89%) as brown syrup. TLC: 10% EtOAc/hexanes ($R_f$: 0.7); $^1$H-NMR (DMSO-$d_6$, 400 MHz): δ 7.70-7.58 (m, 2H), 7.42-7.35 (m, 1H), 5.42 (s, 1H), 3.86 (s, 3H).

Synthesis of Methyl 5-fluoro-2-((4-(methoxycarbonyl)-2-nitrophenyl) thio) benzoate (32)

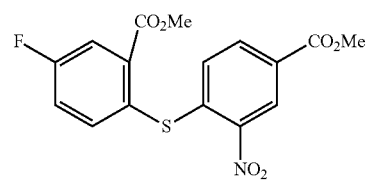

To a stirred solution of methyl 4-fluoro-3-nitrobenzoate 2 (350 mg, 1.75 mmol) in DMF (10 mL) under argon atmosphere were added compound 31 (360 mg, 1.93 mmol), cesium carbonate (1.14 g, 3.51 mmol) at RT; heated to 60-65° C. and stirred for 2 h. The reaction was monitored by TLC; after completion of the reaction, the reaction mixture was diluted with water (30 mL) and extracted with $CH_2Cl_2$ (2×40 mL). The combined organic extracts were dried over sodium sulfate, filtered and concentrated in vacuo to obtain the crude. The crude was purified through silica gel column chromatography using 7-10% EtOAc/hexanes to afford compound 32 (500 mg, 78%) as yellow solid. TLC: 10% EtOAc/hexanes ($R_f$: 0.3); $^1$H-NMR (DMSO-$d_6$, 400 MHz): δ 8.64 (s, 1H), 8.04-8.02 (m, 1H), 7.83-7.79 (m, 2H), 7.64-7.59 (m, 1H), 7.01 (d, J=8.4 Hz, 1H), 3.88 (s, 3H), 3.71 (s, 3H).

Synthesis of Methyl 2-((2-amino-4-(methoxycarbonyl) phenyl) thio)-5-fluorobenzoate (33)

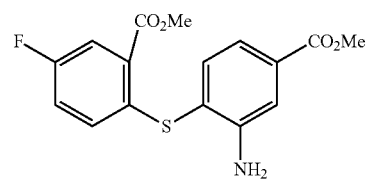

To a stirred solution of compound 32 (500 mg, 1.36 mmol) in MeOH (10 mL) under argon atmosphere was added 10% Pd/C (300 mg) at RT and stirred under hydrogen atmosphere (balloon pressure) for 16 h. The reaction was monitored by TLC; after completion of the reaction, the reaction mixture was filtered through celite and washed with 20% MeOH/$CH_2Cl_2$ (2×30 mL). The combined organic extracts were dried over sodium sulfate, filtered and concentrated in vacuo to obtain the crude. The crude was purified through silica gel column chromatography using 8-10% EtOAc/hexanes to afford compound 33 (300 mg, 66%) as pale yellow solid. TLC: 30% EtOAc/hexanes ($R_f$:

0.5); ¹H-NMR (DMSO-d₆, 400 MHz): δ 7.78 (d, J=9.6 Hz, 1H), 7.45-7.41 (m, 2H), 7.35-7.30 (m, 1H), 7.14 (d, J=9.6 Hz, 1H), 6.68-6.65 (m, 1H), 5.70 (s, 2H), 3.89 (s, 3H), 3.83 (s, 3H).

Synthesis of 2-((2-amino-4-carboxyphenyl) thio)-5-fluorobenzoic acid (34)

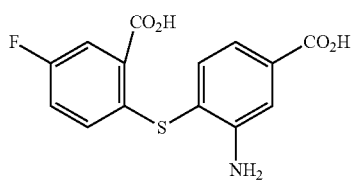

34

To a stirred solution of compound 33 (300 mg, 0.89 mmol) in THF:H₂O (5:1, 6 mL) under argon atmosphere was added lithium hydroxide monohydrate (188 mg, 4.47 mmol) at RT and stirred for 16 h. The reaction was monitored by TLC; after completion of the reaction, the volatiles were removed in vacuo. The residue was diluted with water (15 mL) and acidified with 6 N HCl to pH-4. The precipitated solid was filtered and dried in vacuo to afford compound 34 (180 mg, 66%) as white solid. TLC: 50% EtOAc/hexanes (R_f: 0.2); ¹H-NMR (DMSO-d₆, 400 MHz): δ 12.99-12.96 (m, 2H), 7.69 (d, J=6.8 Hz, 1H), 7.40 (t, J=7.2 Hz, 2H), 7.29 (t, J=7.2 Hz, 1H), 7.13 (d, J=7.2 Hz, 1H), 6.64-6.61 (m, 1H), 5.64-5.61 (m, 2H).

Synthesis of 2-fluoro-11-oxo-10, 11-dihydrodibenzo [b,f] [1,4] thiazepine-8-carboxylic acid (35)

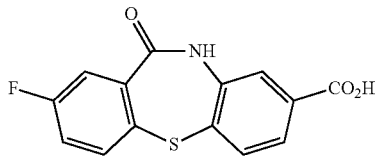

35

To a stirred solution of compound 34 (180 mg, 0.58 mmol) in THF (10 mL) under argon atmosphere was added CDI (284 mg, 1.75 mmol) at RT and stirred for 16 h. The reaction was monitored by TLC; after completion of the reaction, the volatiles were removed in vacuo. The residue was diluted with ice cold water (10 mL) and acidified with 6 N HCl to pH-4. The precipitated solid was filtered and dried in vacuo to afford compound 35 (80 mg, 47%) as an off-white solid. TLC: 10% MeOH/CH₂Cl₂ (R_f: 0.2); ¹H-NMR (DMSO-d₆, 400 MHz): δ 13.30 (br s, 1H), 10.93 (s, 1H), 7.70 (s, 1H), 7.67 (d, J=7.6 Hz, 2H), 7.59 (t, J=7.6 Hz, 1H), 7.48 (t, J=7.6 Hz, 1H), 7.40-7.35 (m, 1H).

Example 6: Synthesis of 3-fluoro-11-oxo-10, 11-dihydrodibenzo [b,f] [1,4] thiazepine-8-carboxylic acid (42)—a Common Intermediate

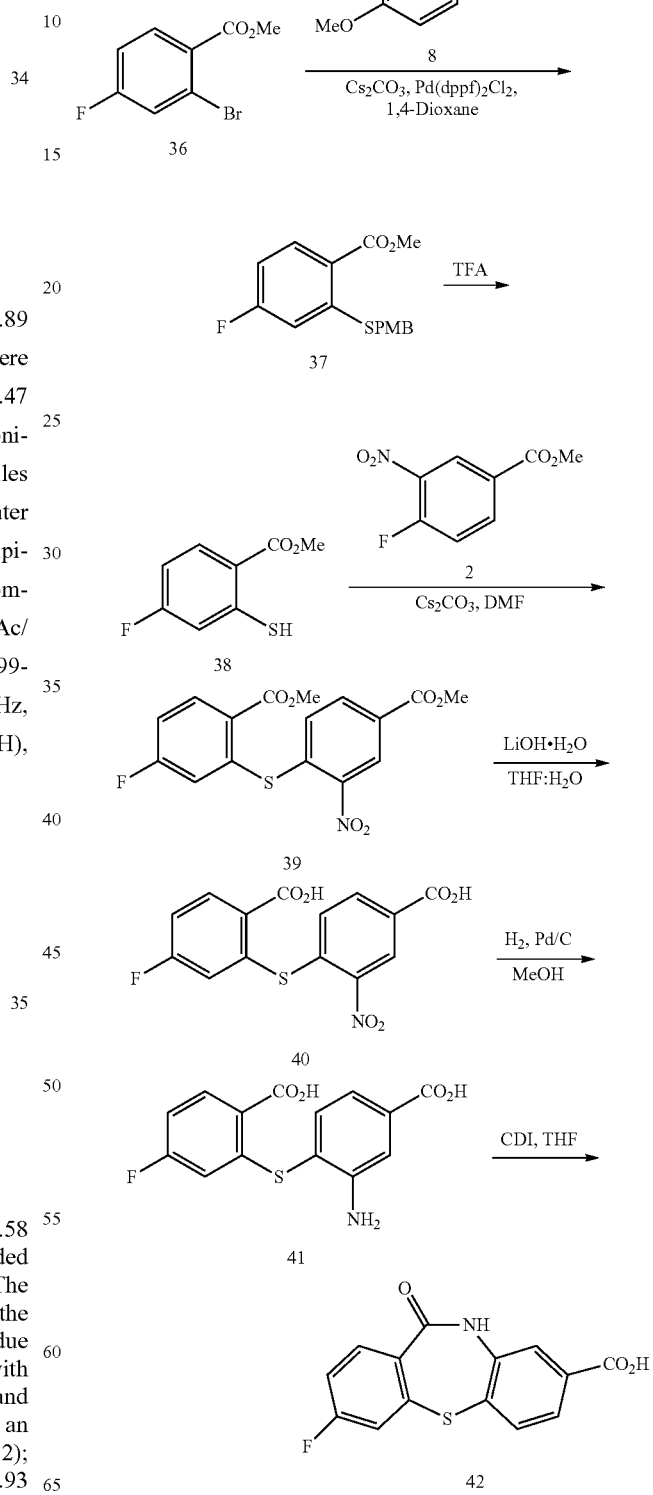

Synthesis of Methyl 4-fluoro-2-((4-methoxybenzyl)thio) benzoate (37)

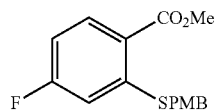

To a stirred solution of methyl 2-bromo-4-fluorobenzoate 36 (2 g, 8.58 mmol) in 1,4-dioxane (50 mL) under inert atmosphere were added (4-methoxyphenyl) methanethiol 8 (1.58 g, 10.25 mmol), cesium carbonate (4.18 g, 12.80 mmol) at RT and purged under argon atmosphere for 30 min. To this was added Pd(dppf)$_2$Cl$_2$ (306 mg, 0.42 mmol); heated to 120° C. and stirred for 16 h. The reaction was monitored by TLC; after completion of the reaction, the reaction mixture was diluted with water (20 mL) and extracted with EtOAc (2×250 mL). The combined organic extracts were dried over sodium sulfate, filtered and concentrated in vacuo to obtain the crude. The crude was purified through silica gel column chromatography using 7% EtOAc/hexanes to afford compound 37 (1.6 g, 61%) as an off-white solid. TLC: 10% EtOAc/hexanes (R$_f$: 0.4); $^1$H NMR (CDCl$_3$, 400 MHz): δ 8.01 (dd, J=8.7, 6.2 Hz, 1H), 7.34 (d, J=7.9 Hz, 2H), 7.04 (dd, J=10.3, 2.4 Hz, 1H), 6.88-6.80 (m, 3H), 4.09 (s, 2H), 3.88 (s, 3H), 3.80 (s, 3H).

Synthesis of Methyl 4-fluoro-2-mercaptobenzoate (38)

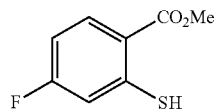

A stirred solution of compound 37 (2.2 g, 7.18 mmol) in trifluoro acetic acid (30 mL) at RT under inert atmosphere was heated to 90° C. and stirred for 3 h. The reaction was monitored by TLC; after completion of the reaction, the volatiles were removed in vacuo to obtain compound 38 (1.33 g, crude) as brown syrup. The crude was carried forward for next step without further purification. TLC: 10% EtOAc/hexanes (R$_f$: 0.8).

Synthesis of Methyl 4-fluoro-2-((4-(methoxycarbonyl)-2-nitrophenyl) thio) benzoate (39)

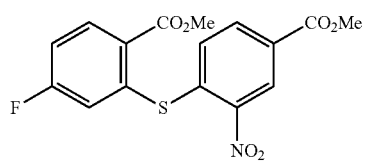

To a stirred solution of methyl 4-fluoro-3-nitrobenzoate 2 (1.29 g, 6.93 mmol) in DMF (50 mL) under inert atmosphere were added cesium carbonate (2.93 g, 9.01 mmol) and compound 38 (1.2 g, 6.03 mmol) at RT; heated to 55-60° C. and stirred for 2 h. The reaction was monitored by TLC; after completion of the reaction, the reaction mixture was diluted with water (20 mL), the precipitated solid was filtered to obtain the crude. The crude was washed with pentane (2×20 mL) and dried in vacuo to afford compound 39 (1.5 g, 68%) as yellow solid. TLC: 10% EtOAc/hexanes (R$_f$: 0.3); $^1$H-NMR (DMSO-d$_6$, 400 MHz): δ 8.63 (s, 1H), 8.13-8.04 (m, 2H), 7.53-7.46 (m, 2H), 7.24 (d, J=8.4 Hz, 1H), 3.89 (s, 3H), 3.72 (s, 3H).

Synthesis of 2-((4-carboxy-2-nitrophenyl) thio)-4-fluorobenzoic acid (40)

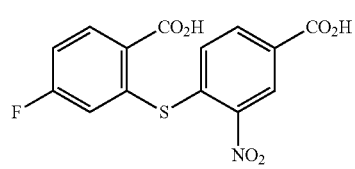

To a stirred solution of compound 39 (1.5 g, 4.10 mmol) in THF:H$_2$O (4:1, 20 mL) was added lithium hydroxide monohydrate (690 mg, 16.4 mmol) at RT, heated to 80° C. and stirred for 2 h. The reaction was monitored by TLC; after completion of the reaction, the volatiles were removed in vacuo. The pH of the residue was acidified with 2 N HCl to ~6. The precipitated solid was filtered and dried in vacuo to afford compound 40 (1.2 g, 86%) as an off-white solid. TLC: 5% MeOH/CH$_2$Cl$_2$ (R$_f$: 0.2); $^1$H-NMR (DMSO-d$_6$, 400 MHz): δ 13.46 (br s, 2H), 8.58 (s, 1H), 8.08-8.01 (m, 2H), 7.45-7.40 (m, 1H), 7.38-7.35 (m, 1H), 7.29 (d, J=8.4 Hz, 1H).

Synthesis of 2-((2-amino-4-carboxyphenyl) thio)-4-fluorobenzoic acid (41)

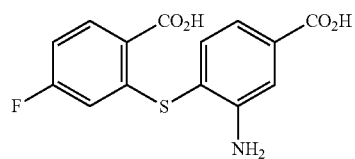

To a stirred solution of compound 40 (1.2 g, 3.56 mmol) in MeOH (50 mL) under inert atmosphere was added 10% Pd/C (300 mg) at RT and stirred under hydrogen atmosphere (balloon pressure) for 16 h. The reaction was monitored by TLC; after completion of the reaction, the reaction mixture was filtered through celite, washed with MeOH (20 mL). The filtrate was removed in vacuo to obtain the crude which as triturated with 10% EtOAc/n-pentane (50 mL) to afford compound 41 (1 g, 91%) as an off-white solid. TLC: 10% MeOH/CH$_2$Cl$_2$ (R$_f$: 0.3); $^1$H-NMR (DMSO-d$_6$, 400 MHz): δ 12.96 (br s, 2H), 8.06-8.02 (m, 1H), 7.46 (s, 1H), 7.40 (d, J=8.0 Hz, 1H), 7.16 (d, J=8.0 Hz, 1H), 7.07-7.02 (m, 1H), 6.24 (d, J=8.0 Hz, 1H), 5.67 (br s, 2H).

47

Synthesis of 3-fluoro-11-oxo-10, 11-dihydrodibenzo [b,f] [1,4] thiazepine-8-carboxylic acid (42)

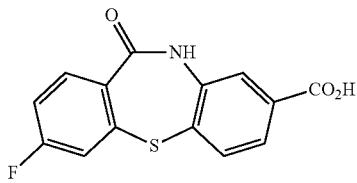

To a stirred solution of compound 41 (1 g, 3.25 mmol) in THF (30 mL) under inert atmosphere was added CDI (1.61 g, 9.77 mmol) at RT and stirred for 16 h. The reaction was monitored by TLC; after completion of the reaction, the reaction mixture was acidified with 2 N HCl to pH-4. The obtained solid was filtered, washed with water (20 mL), ether (2×5 mL) and dried in vacuo to afford compound 42 (760 mg, 80%) as white solid. TLC: 10% MeOH/CH$_2$Cl$_2$ (R$_f$: 0.3); $^1$H-NMR (DMSO-d$_6$, 400 MHz): δ 13.24 (br s, 1H), 10.83 (s, 1H), 7.78-7.74 (m, 2H), 7.69-7.66 (m, 2H), 7.47-7.44 (m, 1H), 7.35-7.30 (m, 1H).

Example 7: Synthesis of 4-fluoro-11-oxo-10, 11-dihydrodibenzo [b,f] [1,4] thiazepine-8-carboxylic acid (50)—a Common Intermediate

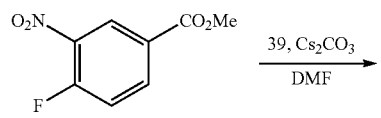

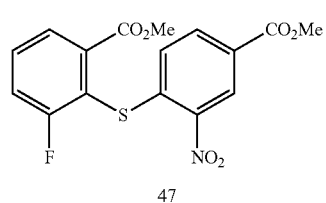

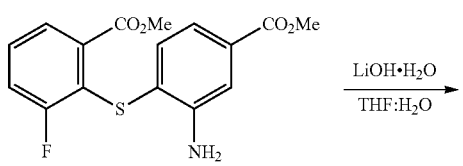

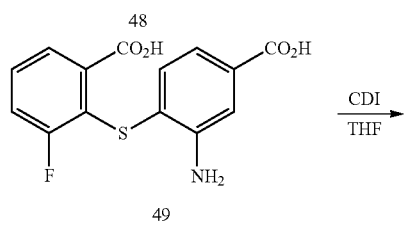

48

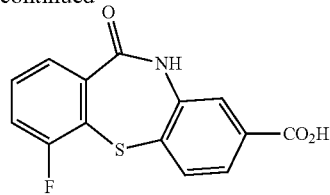

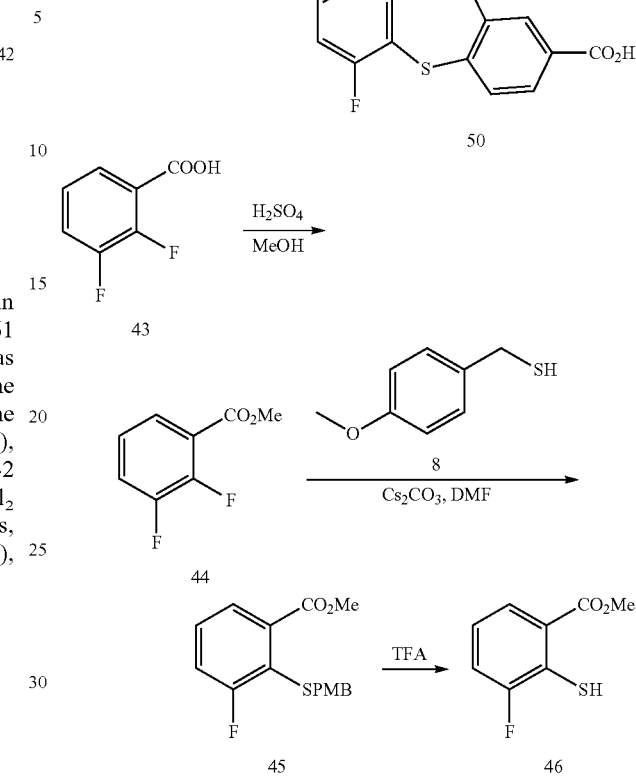

Synthesis of Methyl 2, 3-difluorobenzoate (44)

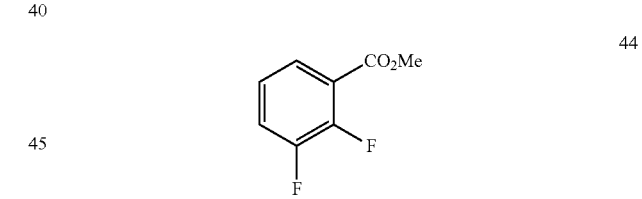

To a stirred solution of 2, 3-difluorobenzoic acid 43 (1 g, 6.28 mmol) in MeOH (10 mL) under inert atmosphere was added Conc. H$_2$SO$_4$ (5 mL) at 0° C. and heated to reflux for 36 h. The reaction was monitored by TLC; after completion of the reaction, the volatiles were removed in vacuo. The residue was diluted with water (25 mL) and pH adjusted to ~8 with saturated sodium bicarbonate solution (20 mL) and extracted with EtOAc (2×20 mL). The combined organic extracts were dried over sodium sulfate, filtered and concentrated in vacuo to obtain the crude. The crude was purified through silica gel column chromatography using 20% EtOAc/hexanes to afford compound 44 (800 mg, 74%) as an off-white solid. TLC: 40% EtOAc/hexanes (R$_f$: 0.8); $^1$H NMR (DMSO-d$_6$, 500 MHz) δ 7.80-7.65 (m, 2H), 7.41-7.23 (m, 1H), 3.88 (s, 3H).

Synthesis of Methyl 3-fluoro-2-((4-methoxybenzyl)thio) benzoate (45)

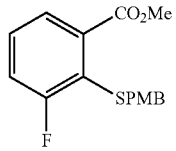

To a stirred solution of compound 44 (800 mg, 4.65 mmol) in DMF (10 mL) under inert atmosphere were added (4-methoxyphenyl) methanethiol 8 (282 mg, 5.11 mmol), cesium carbonate (1.66 g, 5.11 mmol) at RT and stirred for 6 h. The reaction was monitored by TLC; after completion of the reaction, the reaction mixture was diluted water (25 mL) and extracted with ether (2×40 mL). The combined organic extracts were dried over sodium sulfate, filtered and concentrated in vacuo to obtain the crude. The crude was purified through silica gel column chromatography using 20% EtOAc/hexanes to afford compound 45 (750 mg, 53%) as an off-white solid. TLC: 20% EtOAc/hexanes ($R_f$: 0.4); 1H NMR (DMSO-$d_6$, 500 MHz): δ 7.49-7.36 (m, 3H), 7.10 (d, J=8.9 Hz, 2H), 6.79 (d, J=8.9 Hz, 2H), 4.06 (s, 2H), 3.81 (s, 3H), 3.70 (s, 3H);

Synthesis of Methyl 3-fluoro-2-mercaptobenzoate (46)

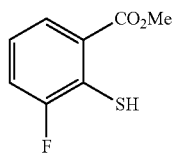

A stirred solution of compound 45 (750 mg, 2.45 mmol) in trifluoro acetic acid (7 mL) at RT under inert atmosphere was heated to 70° C. and stirred for 2 h. The reaction was monitored by TLC; after completion of the reaction, the volatiles were removed in vacuo to obtain compound 46 (1.1 g, crude) as colorless liquid. The crude was carried forward for next step. TLC: 30% EtOAc/hexanes ($R_f$: 0.8).

Synthesis of Methyl 3-fluoro-2-((4-(methoxycarbonyl)-2-nitrophenyl) thio) benzoate (47)

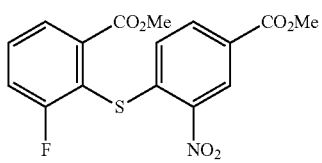

To a stirred solution of compound 46 (5.96 g, 3.20 mmol) in DMF (100 mL) under inert atmosphere were added methyl 4-fluoro-3-nitrobenzoate 2 (5.8 g, 2.91 mmol), cesium carbonate (10.41 g, 3.20 mmol) at RT; heated to 80° C. and stirred for 4 h. The reaction was monitored by TLC; after completion of the reaction, the reaction mixture was diluted with ice cold water (25 mL). The obtained solid was filtered, washed with hexane (2×10 mL) and dried in vacuo to afford compound 47 (7.8 g, 73%) as an pale yellow solid. TLC: 30% EtOAc/hexanes ($R_f$: 0.5); $^1$H NMR (DMSO-$d_6$, 500 MHz): δ 8.67 (s, 1H), 8.05 (dd, J=8.7, 1.7 Hz, 1H), 7.94-7.75 (m, 2H), 7.73-7.67 (m, 1H), 7.00 (d, J=8.4 Hz, 1H), 3.88 (s, 3H), 3.77-3.64 (m, 3H).

Synthesis of Methyl 2-((2-amino-4-(methoxycarbonyl) phenyl) thio)-3-fluorobenzoate (48)

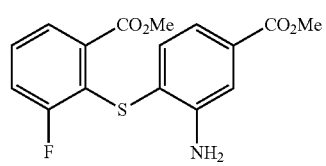

To a stirred solution of compound 47 (670 mg, 1.83 mmol) in MeOH (10 mL) under inert atmosphere was added 10% Pd/C (150 mg) at RT and stirred under hydrogen atmosphere (balloon pressure) for 12 h. The reaction was monitored by TLC; after completion of the reaction, the reaction mixture was filtered through celite and the filtrate was concentrated in vacuo to afford compound 48 (500 mg, 81%) as an off-white solid. TLC: 30% EtOAc/hexanes ($R_f$: 0.4); $^1$H NMR (DMSO-$d_6$, 400 MHz): δ 7.58-7.50 (m, 2H), 7.48-7.41 (m, 1H), 7.33 (s, 1H), 7.04 (s, 2H), 5.59 (br s, 2H), 3.82 (s, 3H), 3.79 (s, 3H).

Synthesis of 2-((2-amino-4-carboxyphenyl) thio)-3-fluorobenzoic acid (49)

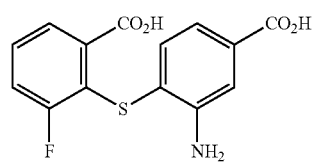

To a stirred solution of compound 48 (500 mg, 1.49 mmol) in THF:H$_2$O (4:1, 20 mL) was added lithium hydroxide monohydrate (376 mg, 8.95 mmol) at RT; heated to 80° C. and stirred for 3 h. The reaction was monitored by TLC; after completion of the reaction, the volatiles were removed in vacuo. The residue was diluted with water (25 mL) and washed with diethyl ether (2×25 mL). The aqueous layer was acidified with 2 N HCl to pH-4 and extracted with EtOAc (2×20 mL). The combined organic extracts were dried over sodium sulfate, filtered and concentrated in vacuo to obtain the crude which was washed with diethyl ether (2×5 mL) and dried in vacuo to afford compound 49 (300 mg, 65%) as an off-white solid. TLC: 10% MeOH/CH$_2$Cl$_2$ ($R_f$: 0.2); 1H NMR (DMSO-$d_6$, 500 MHz): δ 12.68 (br s, 2H), 7.54-7.45 (m, 2H), 7.39-7.32 (m, 1H), 7.28 (s, 1H), 7.09-7.06 (m, 1H), 7.02-6.96 (m, 1H), 5.56 (br s, 2H);

Synthesis of 4-fluoro-11-oxo-10, 11-dihydrodibenzo [b,f] [1,4] thiazepine-8-carboxylic acid (50)

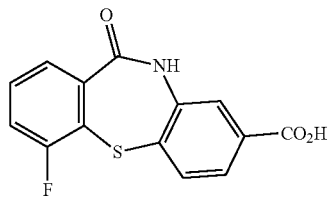

To a stirred solution of compound 49 (300 mg, 0.97 mmol) in THF (15 mL) under inert atmosphere was added CDI (474 mg, 2.92 mmol) at RT and stirred for 16 h. The reaction was monitored by TLC; after completion of the reaction, the volatiles were removed in vacuo. The pH of the residue was acidified with 4 N HCl to ~2. The obtained solid was filtered, washed with diethyl ether (2×5 mL) and dried in vacuo to afford compound 50 (150 mg, 53%) as an off-white solid. TLC: 15% MeOH/CH$_2$Cl$_2$ (R$_f$: 0.5); 1H NMR (DMSO-d$_6$, 400 MHz): δ 13.38 (br s, 1H), 10.92 (s, 1H), 7.79 (s, 1H), 7.75-7.66 (m, 2H), 7.55-7.46 (m, 3H).

Example 8: Synthesis of 7-fluoro-11-oxo-10, 11-dihydrodibenzo [b,f] [1,4] thiazepine-8-carboxylic acid (55)—a Common Intermediate

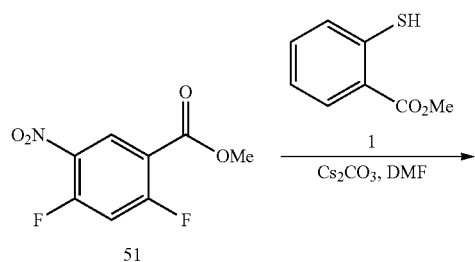

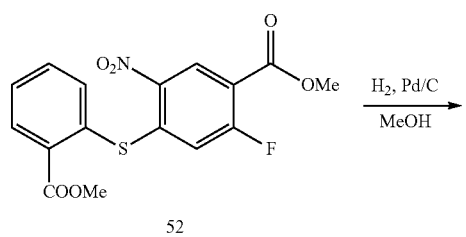

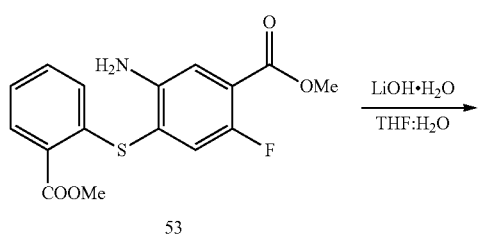

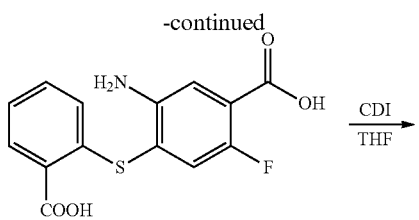

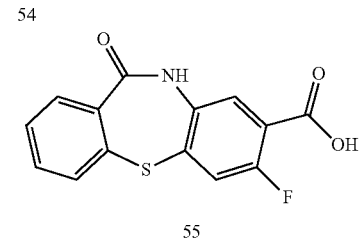

Synthesis of Methyl 2-fluoro-4-((2-(methoxycarbonyl) phenyl) thio)-5-nitrobenzoate (52)

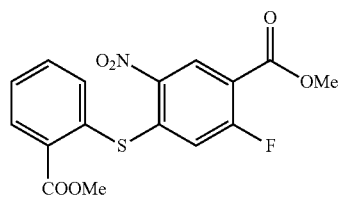

To a stirred solution of methyl 2, 4-difluoro-5-nitrobenzoate 51 (9.0 g, 41.45 mmol) in DMF (100 mL) under inert atmosphere were added methyl 2-mercaptobenzoate 1 (6.97 g, 41.45 mmol), cesium carbonate (14.82 g, 45.60 mmol) at 0° C.; warmed to 10° C. and stirred for 2 h. The reaction was monitored by TLC; after completion of the reaction, the reaction mixture was diluted with water (800 mL) and extracted with EtOAc (2×500 mL). The combined organic extracts were dried under sodium sulfate, filtered and concentrated in vacuo to obtain the crude. The crude was purified through silica gel column chromatography using 10% EtOAc/hexanes to afford compound 52 (11 g, 73%) as an off-white solid. TLC: 10% EtOAc/hexanes (R$_f$: 0.4); $^1$H NMR (DMSO-d$_6$, 400 MHz): δ 8.69 (d, J=6.8 Hz, 1H), 8.04-7.92 (m, 1H), 7.81-7.69 (m, 3H), 6.60 (d, J=11.5 Hz, 1H), 3.88 (s, 3H), 3.73 (s, 3H).

Synthesis of Methyl 5-amino-2-fluoro-4-((2-(methoxycarbonyl) phenyl) thio) benzoate (53)

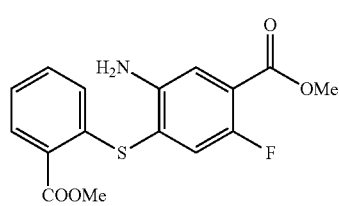

To a stirred solution of compound 52 (11 g, 30.13 mmol) in MeOH (400 mL) under inert atmosphere was added 10% Pd/C (5 g) at RT and stirred under hydrogen atmosphere (balloon pressure) for 24 h. The reaction was monitored by TLC; after completion of the reaction, the reaction mixture was filtered through celite, washed with 30% MeOH/CH$_2$Cl$_2$ (3×60 mL). The filtrate was removed in vacuo to afford compound 53 (6.5 g, 64%) as an off-white solid. TLC: 20% EtOAc/hexanes (R$_f$: 0.4); 1H NMR (DMSO-d$_6$, 400 MHz): δ 8.01-7.88 (m, 1H), 7.45-7.40 (m, 1H), 7.34-7.24 (m, 3H), 6.72 (dd, J=8.2, 0.8 Hz, 1H), 5.51 (s, 2H), 3.88 (s, 3H), 3.85 (s, 3H).

Synthesis of 5-amino-4-((2-carboxyphenyl) thio)-2-fluorobenzoic acid (54)

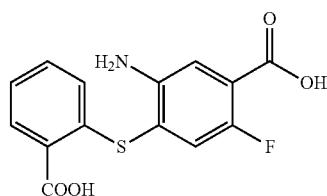

54

To a stirred solution of compound 53 (6.5 g, 19.4 mmol) in THF:H$_2$O (4:1, 90 mL) was added lithium hydroxide monohydrate (4 g, 97.01 mmol) at RT and stirred for 16 h. The reaction was monitored by TLC; after completion of the reaction, the volatiles were removed in vacuo. The pH of the residue was acidified with 2 N HCl to ~4. The precipitated solid was filtered and dried in vacuo to afford compound 54 (4.5 g, 75.6%) as an off-white solid. TLC: 30% EtOAc/hexane (R$_f$: 0.2); 1H NMR (DMSO-d$_6$, 400 MHz): δ 13.19 (br s, 2H), 7.96 (dd, J=7.7, 1.5 Hz, 1H), 7.39 (t, J=7.3 Hz, 1H), 7.30 (d, J=6.6 Hz, 1H), 7.27-7.20 (m, 2H), 6.68 (dd, J=8.2, 0.7 Hz, 1H), 5.42 (br s, 2H).

Synthesis of 7-fluoro-11-oxo-10, 11-dihydrodibenzo [b,f] [1,4] thiazepine-8-carboxylic acid (55)

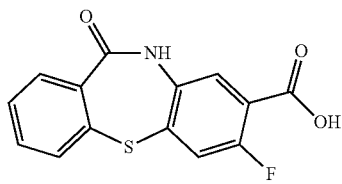

55

To a stirred solution of compound 54 (4.5 g, 14.65 mmol) in THF (100 mL) under inert atmosphere was added CDI (11.88 g, 73.28 mmol) at 0° C.; warmed to RT and stirred for 16 h. The reaction was monitored by TLC; after completion of the reaction, the reaction mixture was quenched with 2 N HCl to pH-4; the precipitated solid was filtered, dried in vacuo to afford compound 55 (3.5 g, 83%) as an off-white solid. TLC: 15% MeOH/CH$_2$Cl$_2$ (R$_f$: 0.2); 1H NMR (DMSO-d$_6$, 400 MHz): δ 13.61 (br s, 1H), 10.75 (s, 1H), 7.74-7.65 (m, 2H), 7.59-7.45 (m, 4H).

Example 9: Synthesis of 7, 9-difluoro-11-oxo-10, 11-dihydrodibenzo [b,f] [1,4] thiazepine-8-carboxylic acid (62)—a Common Intermediate

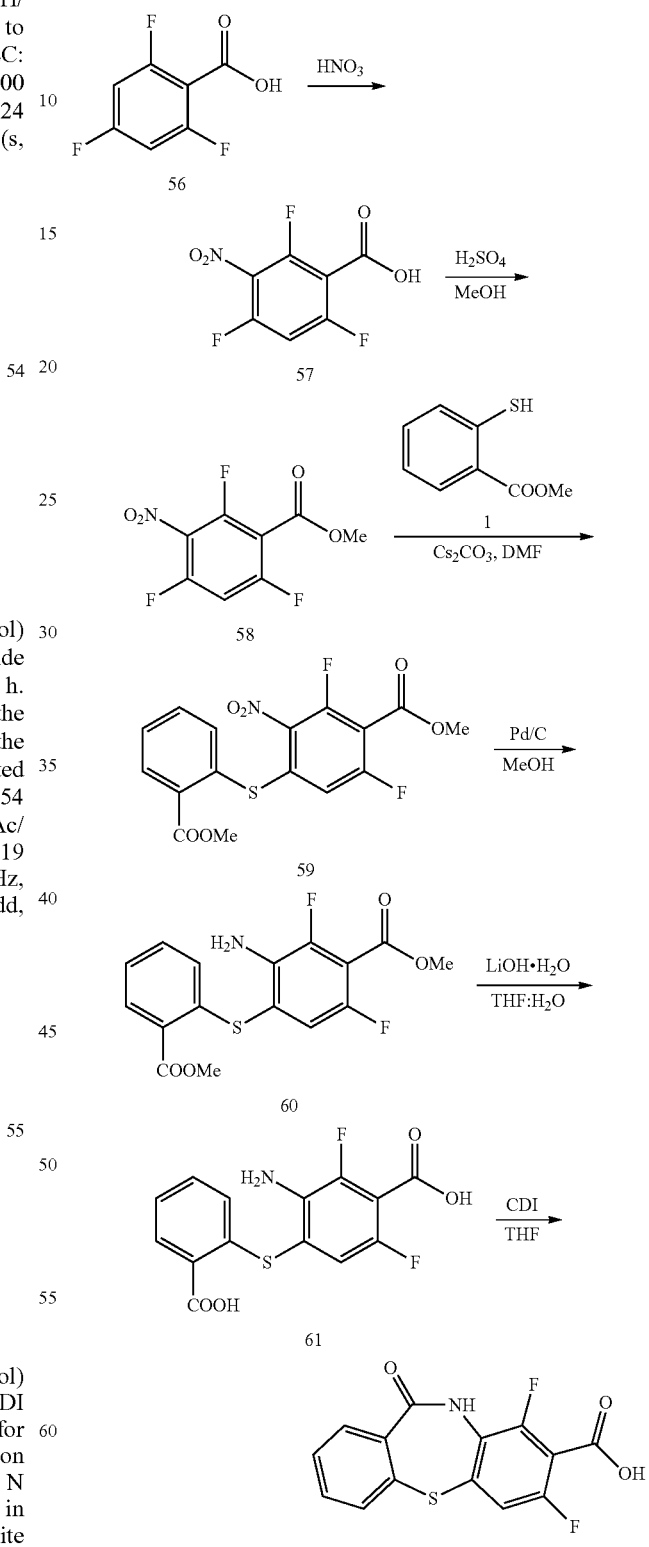

Synthesis of 2, 4, 6-trifluoro-3-nitrobenzoic acid (57)

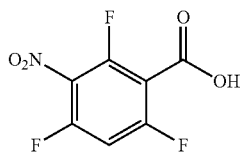

To 2, 4, 6-trifluorobenzoic acid 56 (15 g, 85.22 mmol) at 0° C., fuming nitric acid (20 mL) was added dropwise for 10 min; warmed to RT and stirred for 16 h. The reaction was monitored by TLC; after completion of the reaction, the reaction mixture was diluted with ice cold water (500 mL) and extracted with EtOAc (2×200 mL). The combined organic extracts were dried over sodium sulfate, filtered and concentrated in vacuo to afford compound 57 (20 g) as pale yellow liquid. TLC: 5% MeOH/CH$_2$Cl$_2$+0.05 mL CH$_3$COOH (R$_f$: 0.2); 1H NMR (DMSO-d$_6$, 400 MHz): δ 14.12 (br s, 1H), 7.83 (td, J=10.5, 2.1 Hz, 1H).

Synthesis of Methyl 2, 4, 6-trifluoro-3-nitrobenzoate (58)

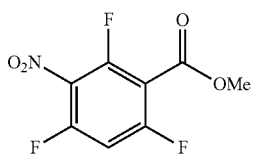

To a stirred solution of compound 57 (20 g) in MeOH (200 mL) under argon atmosphere was added concentrated sulfuric acid (20 mL) dropwise for 20 min at 0° C. and heated to reflux for 48 h. The reaction was monitored by TLC; after completion of the reaction, the volatiles were removed in vacuo. The residue was diluted with water (500 mL) and extracted with EtOAc (4×200 mL). The combined organic extracts were dried over sodium sulfate, filtered and concentrated in vacuo to obtain the crude. The crude was purified through silica gel column chromatography using 5-8% EtOAc/hexanes to afford compound 58 (14 g, 70% for 2 steps) as pale yellow syrup. TLC: 20% EtOAc/hexane (R$_f$: 0.8); 1H NMR (DMSO-d$_6$, 400 MHz): δ 7.88 (td, J=10.6, 2.2 Hz, 1H), 3.93 (s, 3H).

Synthesis of Methyl 2, 6-difluoro-4-((2-(methoxycarbonyl) phenyl) thio)-3-nitrobenzoate (59)

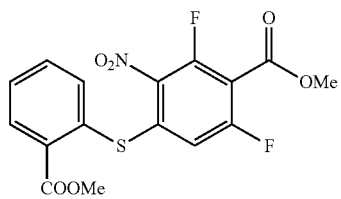

To a stirred solution of compounds 58 (14 g, 59.57 mmol) in DMF (300 mL) under inert atmosphere were added methyl 2-mercaptobenzoate 1 (11.1 g, 66.07 mmol), cesium carbonate (38.77 g, 119.14 mmol) at 0° C.; warmed to RT and stirred for 2 h. The reaction was monitored by TLC; after completion of the reaction, the reaction mixture was diluted with ice cold water (200 mL) and extracted with EtOAc (3×300 mL). The combined organic extracts were washed with water (200 mL), brine (200 mL), dried over sodium sulfate, filtered and concentrated in vacuo to obtain the crude. The crude was purified through silica gel column chromatography to afford compound 59 (14.5 g, 64%) as yellow syrup. TLC: 10% EtOAc/hexanes (R$_f$: 0.2); $^1$H NMR (DMSO-d$_6$, 500 MHz): δ 7.98 (dd, J=7.7, 1.3 Hz, 1H), 7.66-7.61 (m, 1H), 7.59-7.55 (m, 1H), 7.46 (d, J=7.8 Hz, 1H), 7.19 (d, J=9.3 Hz, 1H), 3.93 (s, 3H), 3.81 (s, 3H).

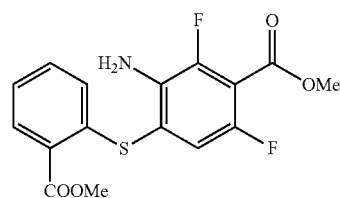

Synthesis of Methyl 3-amino-2, 6-difluoro-4-((2-(methoxycarbonyl) phenyl) thio) benzoate To a stirred solution of compound 59 (18 g, 46.99) in MeOH (400 mL) under inert atmosphere was added Pd/C (9 g, 50% wet) at RT and stirred under hydrogen atmosphere in an autoclave (5 kg/cm$^2$ pressure) for 16 h. The reaction was monitored by TLC; after completion of the reaction, the reaction mixture was filtered through celite, washed with MeOH (500 mL). The filtrate was concentrated in vacuo to afford compound 60 (15.1 g, 91%) as colorless semi solid. TLC: 20% EtOAc/hexanes (R$_f$: 0.5); $^1$H NMR (DMSO-d$_6$, 500 MHz): δ 8.00-7.93 (m, 1H), 7.48-7.42 (m, 1H), 7.31-7.21 (m, 2H), 6.76-6.64 (m, 1H), 5.54-5.47 (m, 2H), 3.91 (s, 3H), 3.89 (s, 3H).

Synthesis of 3-amino-4-((2-carboxyphenyl) thio)-2, 6-difluorobenzoic acid (61)

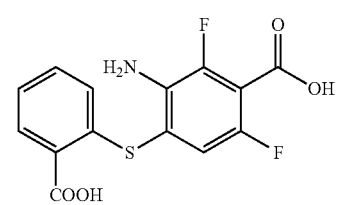

To a stirred solution of compound 60 (15.1 g, 39.42 mmol) in THF:H$_2$O (4:1, 250 mL) was added lithium hydroxide monohydrate (8.3 g, 197.61 mmol) at RT and stirred for 16 h. The reaction was monitored by TLC; after completion of the reaction, the volatiles were removed in vacuo, diluted with water (100 mL) and washed with EtOAc (2×100 mL). The pH of the aqueous layer was acidified with 4 N HCl to ~4. The precipitated solid was filtered, washed with water (100 mL), pentane (100 mL). The obtained solid was further dried using toluene (150 mL) to afford compound 61 (11 g, 79%) as an off-white solid. TLC: 20% EtOAc/hexanes ($R_f$: 0.2); $^1$H NMR (DMSO-$d_6$, 400 MHz): δ 13.24 (br s, 1H), 7.97 (dd, J=7.7, 1.4 Hz, 1H), 7.46-7.39 (m, 1H), 7.28-7.19 (m, 2H), 6.66 (d, J=8.2 Hz, 1H), 5.39 (br s, 2H).

Synthesis of 7, 9-difluoro-11-oxo-10, 11-dihydrodibenzo [b,f] [1,4] thiazepine-8-carboxylic acid (62)

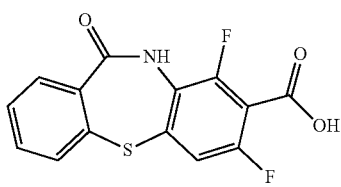

To a stirred solution of compound 61 (10 g, 30.76 mmol) in THF (200 mL) under argon atmosphere was added CDI (14.9 g, 81.97 mmol) at RT and stirred for 24 h. The reaction was monitored by TLC; after completion of the reaction, the volatiles were removed in vacuo. The residue was diluted with water (300 mL) and the pH was adjusted to ~3 with 2 N HCl. The obtained solid was filtered, washed with water (100 mL), pentane (50 mL) and diethyl ether (150 mL) and dried in vacuo to obtain compound 62 (2.83 g, 30%) as brick red solid. TLC: 15% MeOH/CH$_2$Cl$_2$ ($R_f$: 0.3); $^1$H NMR (DMSO-$d_6$, 500 MHz): δ 14.19 (br s, 1H), 10.64 (s, 1H), 7.73-7.66 (m, 2H), 7.58-7.48 (m, 3H).

Example 10: 2-methoxy-11-oxo-10, 11-dihydrodibenzo [b,f] [1,4] thiazepine-8-carboxylic acid (70)—a Common Intermediate

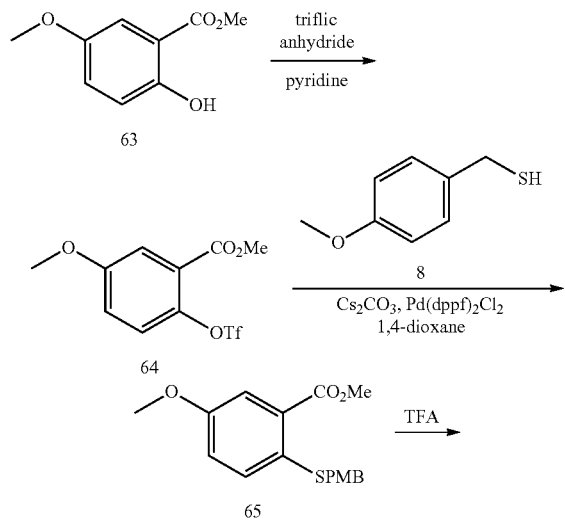

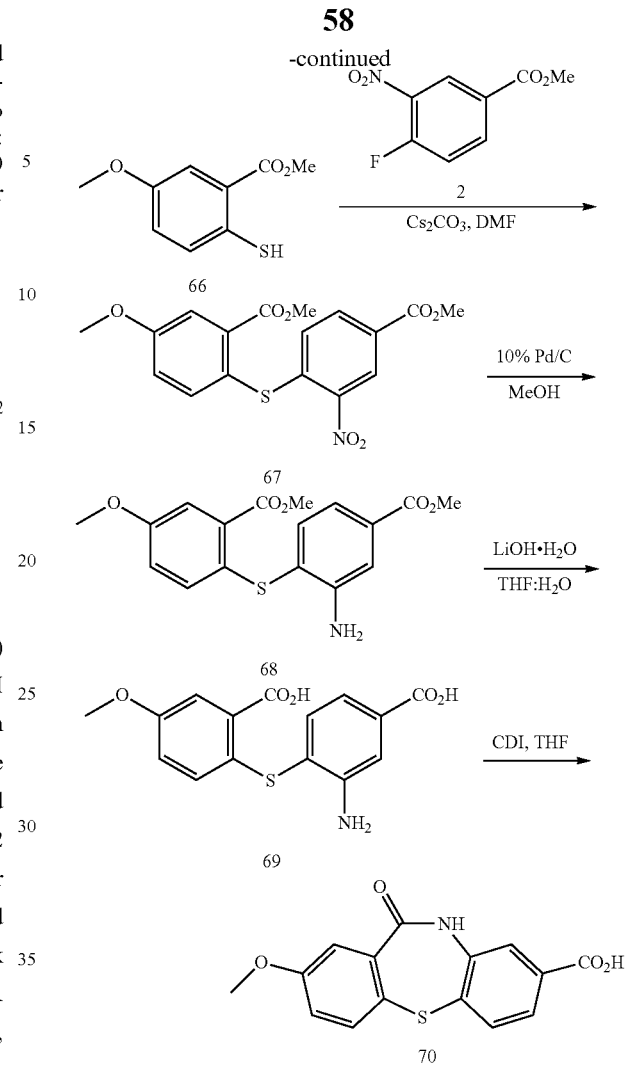

Synthesis of Methyl 5-methoxy-2-(((trifluoromethyl) sulfonyl) oxy) benzoate (64)

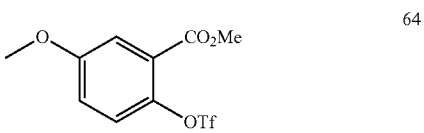 [SMILES: COC(=O)c1cc(OC)ccc1OS(=O)(=O)C(F)(F)F]

To a stirred solution of methyl 2-hydroxy-5-methoxybenzoate 63 (2 g, 10.97 mmol) in pyridine (8 mL) under inert atmosphere was added triflic anhydride (3.56 g, 12.62 mmol) at 0° C.; warmed to RT and stirred for 2 h; heated to 40° C. and stirred for 16 h. The reaction was monitored by TLC; after completion of the reaction, the volatiles were removed in vacuo. The residue was diluted with water (40 mL) and extracted with ether (3×40 mL). The combined organic extracts were washed with 1 N HCl (40 mL), water (40 mL), brine (40 mL), dried over sodium sulfate, filtered and concentrated in vacuo to obtain the crude. The crude was purified through silica gel column chromatography using 5-10% EtOAc/hexanes to afford compound 64 (2.9 g, 85%) as colorless liquid. TLC: 10% EtOAc/hexanes ($R_f$: 0.6);

$^1$H-NMR (CDCl$_3$, 500 MHz): δ 7.50 (s, 1H), 7.09 (d, J=7.5 Hz, 1H), 7.03 (d, J=7.5 Hz, 1H), 3.94 (s, 3H), 3.84 (s, 3H).

Synthesis of methyl-5-methoxy-2-((4-methoxybenzyl) thio) benzoate (65)

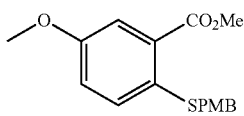

To a stirred solution of compound 64 (500 mg, 1.59 mmol) in 1, 4-dioxane (10 mL) under inert atmosphere were added (4-methoxyphenyl) methanethiol 8 (270 mg, 1.75 mmol), cesium carbonate (1.035 g, 3.18 mmol) at RT and degassed for 20 min. To this was added Pd(dppf)$_2$Cl$_2$ (29.1 mg, 0.039 mmol); heated to 110° C. and stirred for 10 h. The reaction was monitored by TLC; after completion of the reaction, the reaction mixture was diluted with water (20 mL) and extracted with EtOAc (2×30 mL). The combined organic extracts were dried over sodium sulfate, filtered and concentrated in vacuo to obtain the crude. The crude was purified through silica gel column chromatography using 10-15% EtOAc/hexanes to afford compound 65 (280 mg, 55%) as pale yellow solid. TLC: 10% EtOAc/hexanes (R$_f$: 0.4); $^1$H-NMR (CDCl$_3$, 500 MHz): δ 7.42 (s, 1H), 7.28-7.25 (m, 3H), 6.98 (d, J=8.5 Hz, 1H), 6.84 (d, J=8.5 Hz, 2H), 4.08 (s, 2H), 3.93 (s, 3H), 3.83 (s, 3H), 3.81 (s, 3H).

Synthesis of Methyl 2-mercapto-5-methoxybenzoate (66)

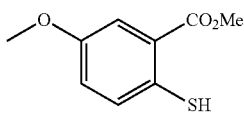

A stirred solution of compound 65 (280 mg, 0.88 mmol) in trifluoro acetic acid (10 mL) at RT under inert atmosphere was heated to 70° C. and stirred for 4 h. The reaction was monitored by TLC; after completion of the reaction, the volatiles were removed in vacuo to obtain compound 66 (170 mg, crude) as brown syrup. TLC: 10% MeOH/CH$_2$Cl$_2$ (R$_f$: 0.8); $^1$H-NMR (DMSO-d$_6$, 400 MHz): δ 7.68 (d, J=8.0 Hz, 1H), 7.48 (d, J=7.2 Hz, 1H), 7.39 (s, 1H), 5.13 (s, 1H), 3.88 (s, 3H), 3.84 (s, 3H).

Synthesis of Methyl 5-methoxy-2-((4-(methoxycarbonyl)-2-nitrophenyl) thio) benzoate (67)

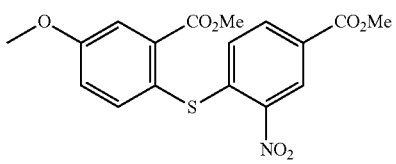

To a stirred solution of compound 66 (150 mg, 0.75 mmol) in DMF (5 mL) under inert atmosphere were added methyl 4-fluoro-3-nitrobenzoate 2 (164 mg, 0.82 mmol), cesium carbonate (490 mg, 1.50 mmol) at RT; heated to 55-60° C. and stirred for 2 h. The reaction was monitored by TLC; after completion of the reaction, the reaction mixture was diluted with water (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 15-25% EtOAc/hexanes to afford compound 67 (200 mg, 70%) as yellow solid. TLC: 10% EtOAc/hexanes (R$_f$: 0.3); $^1$H-NMR (DMSO-d$_6$, 400 MHz): δ 8.64 (s, 1H), 8.02 (d, J=8.4 Hz, 1H), 7.69 (d, J=8.8 Hz, 1H), 7.59-7.54 (m, 1H), 7.31 (d, J=8.8 Hz, 1H), 6.94 (d, J=8.8 Hz, 1H), 3.88 (s, 3H), 3.87 (s, 3H), 3.68 (s, 3H).

Synthesis of Methyl 2-((2-amino-4-(methoxycarbonyl) phenyl) thio)-5-methoxybenzoate (68)

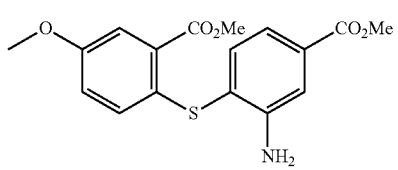

To a stirred solution of compound 67 (200 mg, 0.53 mmol) in MeOH (10 mL) under inert atmosphere was added 10% Pd/C (100 mg) at RT and stirred under hydrogen atmosphere (balloon pressure) for 26 h. The reaction was monitored by TLC; after completion of the reaction, the reaction mixture was filtered through celite and washed with 50% CH$_2$Cl$_2$/MeOH (2×25 mL). The combined organic extracts were dried over sodium sulfate, filtered and concentrated in vacuo to obtain the crude. The crude was purified through silica gel column chromatography using 15-20% EtOAc/hexanes to afford compound 68 (120 mg, 65%) as yellow solid. TLC: 30% EtOAc/hexanes (R$_f$: 0.6); $^1$H-NMR (DMSO-d$_6$, 400 MHz): δ 7.42 (s, 2H), 7.36 (d, J=8.0 Hz, 1H), 7.12 (d, J=8.0 Hz, 1H), 7.05 (d, J=8.4 Hz, 1H), 6.66 (d, J=8.8 Hz, 1H), 5.61 (s, 2H), 3.87 (s, 3H), 3.83 (s, 3H), 3.75 (s, 3H).

Synthesis of 2-((2-amino-4-carboxyphenyl) thio)-5-methoxybenzoic acid (69)

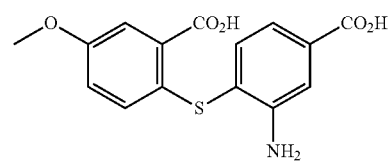

To a stirred solution of compound 68 (120 mg, 0.34 mmol) in THF:H$_2$O (4:1, 5 mL) was added lithium hydroxide monohydrate (72.5 mg, 1.72 mmol) at RT and stirred for 16 h. The reaction was monitored by TLC; after completion of the reaction, the volatiles were removed in vacuo. The residue was diluted with water (10 mL) and acidified with 6 N HCl to pH-4. The precipitated solid was filtered and dried in vacuo to afford compound 69 (80 mg, 73%) as an off-white solid. TLC: 40% EtOAc/hexanes (R$_f$: 0.2); $^1$H-NMR (DMSO-d$_6$, 400 MHz): δ 12.99 (br s, 2H), 7.41 (d, J=8.4 Hz, 2H), 7.35 (d, J=7.6 Hz, 1H), 7.12 (d, J=7.6 Hz, 1H), 7.01 (d, J=8.8 Hz, 1H), 6.61 (d, J=8.8 Hz, 1H), 5.54 (br s, 2H), 3.74 (s, 3H).

Synthesis of 2-methoxy-11-oxo-10, 11-dihydrodibenzo [b,f] [1,4] thiazepine-8-carboxylic acid (70)

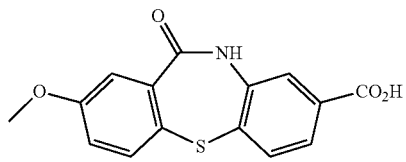

To a stirred solution of compound 69 (80 mg, 0.25 mmol) in THF (5 mL) under inert atmosphere was added CDI (122 mg, 0.75 mmol) at RT and stirred for 16 h. The reaction was monitored by TLC; after completion of the reaction, the volatiles were removed in vacuo. The residue was diluted with water (10 mL) and acidified with 6 N HCl to pH-4. The precipitated solid was filtered and dried in vacuo to afford compound 70 (40 mg, 53%) as an off-white solid. TLC: 10% MeOH/CH$_2$Cl$_2$ (R$_f$: 0.4); $^1$H-NMR (DMSO-d$_6$, 400 MHz): δ 13.15 (br s, 1H), 10.79 (s, 1H), 7.78 (s, 1H), 7.69-7.66 (m, 2H), 7.44-7.42 (m, 1H), 7.20-7.19 (m, 1H), 7.08-7.05 (m, 1H), 3.77 (s, 3H).

Example 11: 7-methoxy-11-oxo-10, 11-dihydrodibenzo [b,f] [1,4] thiazepine-8-carboxylic acid (76)—a Common Intermediate

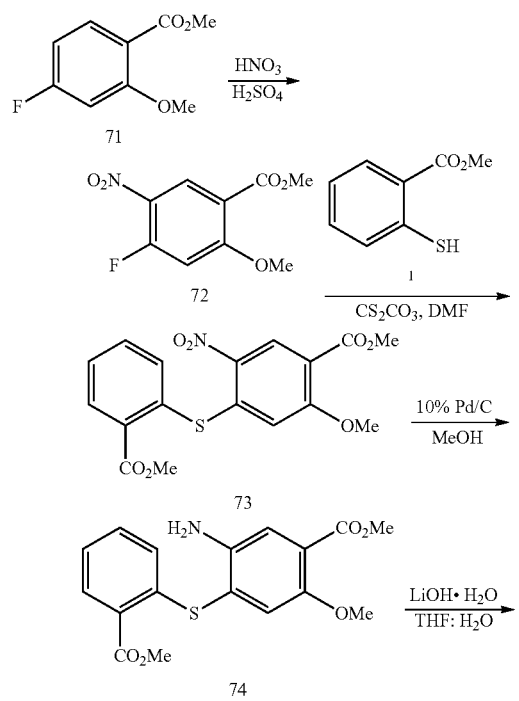

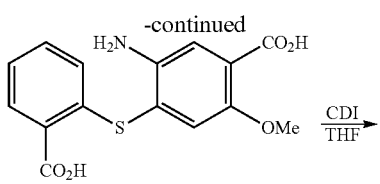

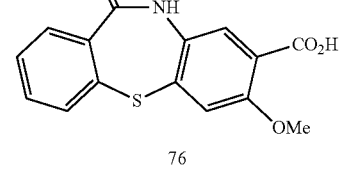

Synthesis of Methyl 4-fluoro-2-methoxy-5-nitrobenzoate (72)

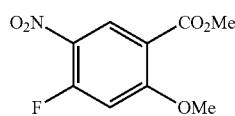

To a stirred solution of methyl 4-fluoro-2-methoxybenzoate 71 (500 mg, 2.50 mmol) in sulfuric acid (1 mL) under inert atmosphere was added the mixture of nitric acid (0.125 mL), sulfuric acid (0.5 mL) at −5° C. and stirred for 10 min. The reaction was monitored by TLC; after completion of the reaction, the reaction mixture was diluted with water (25 mL) and extracted with CH$_2$Cl$_2$ (2×30 mL). The combined organic extracts were washed with 10% NaHCO$_3$ solution (20 mL), dried over sodium sulfate, filtered and concentrated in vacuo to obtain the crude. The crude was triturated with diethyl ether (2×5 mL) to afford compound 72 (200 mg, 33%) as an off-white solid. TLC: 20% EtOAc/hexanes (R$_f$: 0.4); $^1$H-NMR (CDCl$_3$, 400 MHz): δ 8.69 (d, J=8.8 Hz, 1H), 6.83 (d, J=12.8 Hz, 1H), 4.01 (s, 3H), 3.92 (s, 3H).

Synthesis of Methyl 2-methoxy-4-((2-(methoxycarbonyl) phenyl) thio)-5-nitrobenzoate (73)

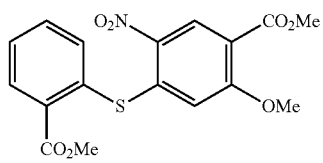

To a stirred solution of compound 72 (200 mg, 0.81 mmol) in DMF (4 mL) under inert atmosphere were added methyl 2-mercaptobenzoate 1 (151 mg, 0.89 mmol), cesium carbonate (318 mg, 0.97 mmol) at RT; heated to 80° C. and stirred for 2 h. The reaction was monitored by TLC; after completion of the reaction, the reaction mixture was diluted with ice water (20 mL) and extracted with EtOAc (2×35 mL). The combined organic extracts were dried over sodium sulfate, filtered and concentrated in vacuo to obtain the crude. The crude was purified through silica gel column chromatography using 15% EtOAc/hexanes to afford compound 73 (200 mg, 61%) as yellow solid. TLC: 20% EtOAc/hexanes ($R_f$: 0.4); $^1$H-NMR (CDCl$_3$, 400 MHz): δ 8.80 (s, 1H), 7.94-7.92 (m, 1H), 7.70 (t, J=8.0 Hz, 1H), 7.61-7.59 (m, 2H), 6.30 (s, 1H), 3.90 (s, 3H), 3.82 (s, 3H), 3.52 (s, 3H).

Synthesis of Methyl 5-amino-2-methoxy-4-((2-(methoxycarbonyl) phenyl) thio) benzoate (74)

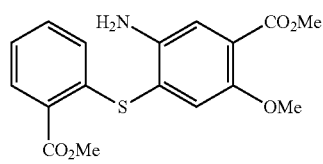

To a stirred solution of compound 73 (200 mg, 0.53 mmol) in MeOH (15 mL) under inert atmosphere was added 10% Pd/C (100 mg) at RT and stirred under hydrogen atmosphere (balloon pressure) for 16 h. The reaction was monitored by TLC; after completion of the reaction, the reaction mixture was filtered through celite and the filtrate was concentrated in vacuo to obtain the crude. The crude was purified through silica gel column chromatography using 15% EtOAc/hexanes to afford compound 74 (110 mg, 60%) as yellow sticky solid. TLC: 20% EtOAc/hexanes ($R_f$: 0.6); $^1$H-NMR (CDCl$_3$, 400 MHz): δ 7.99 (d, J=8.0 Hz, 1H), 7.54 (s, 1H), 7.34-7.31 (m, 1H), 7.20 (t, J=8.0 Hz, 1H), 7.12 (s, 1H), 6.80 (d, J=8.4 Hz, 1H), 3.96 (s, 3H), 3.88 (s, 3H), 3.80 (s, 3H).

Synthesis of 5-amino-4-((2-carboxyphenyl) thio)-2-methoxybenzoic acid (75)

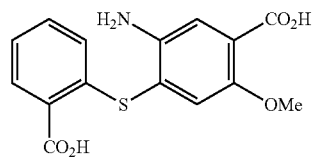

To a stirred solution of compound 74 (110 mg, 0.31 mmol) in THF:H$_2$O (5:1, 3 mL) was added lithium hydroxide monohydrate (66 mg, 1.58 mmol) at RT; heated to 70° C. and stirred for 2 h. The reaction was monitored by TLC; after completion of the reaction, the reaction mixture was diluted with water (15 mL) and extracted with EtOAc (2×25 mL). The aqueous layer was acidified to pH-2 with 6 N HCl, the obtained solid was filtered, washed with n-hexane (2×5 mL) and dried in vacuo to afford compound 75 (70 mg, 70%) as an off-white solid. TLC: 10% MeOH/CH$_2$Cl$_2$ ($R_f$: 0.2); $^1$H-NMR (DMSO-d$_6$, 500 MHz): δ 12.78 (br s, 2H), 7.94 (d, J=7.5 Hz, 1H), 7.36 (t, J=7.5 Hz, 1H), 7.20 (t, J=7.5 Hz, 1H), 7.13 (s, 1H), 7.05 (s, 1H), 6.67 (d, J=8.5 Hz, 1H), 5.11 (br s, 2H), 3.68 (s, 3H).

Synthesis of 7-methoxy-11-oxo-10, 11-dihydrodibenzo [b,f] [1,4] thiazepine-8-carboxylic acid (76)

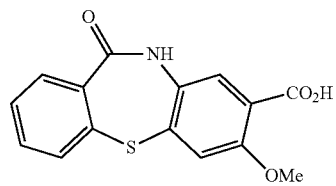

To a stirred solution of compound 75 (70 mg, 0.21 mmol) in THF (2 mL) under inert atmosphere was added CDI (106 mg, 0.65 mmol) at RT and stirred for 16 h. The reaction was monitored by TLC; after completion of the reaction, the volatiles were removed in vacuo, diluted with ice water (15 mL), acidified with 6 N HCl, the obtained solid was filtered, washed with 20% EtOAc/hexanes and dried in vacuo to afford compound 76 (40 mg, 61%) as an off-white solid. TLC: 5% MeOH/CH$_2$Cl$_2$ ($R_f$: 0.3); $^1$H-NMR (DMSO-d$_6$, 400 MHz): δ 12.88 (br s, 1H), 10.64 (s, 1H), 7.71-7.69 (m, 1H), 7.58-7.42 (m, 4H), 7.28 (s, 1H), 3.81 (s, 3H).

Example 12: Synthesis of 6-methyl-11-oxo-10, 11-dihydrodibenzo [b,f] [1,4] thiazepine-8-carboxylic acid (82)—a Common Intermediate

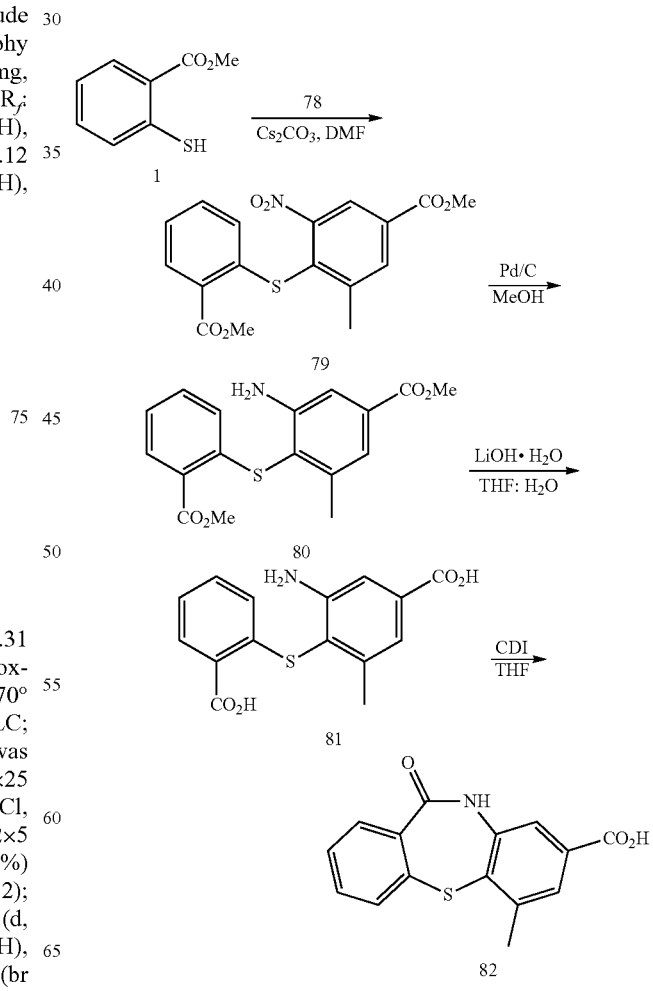

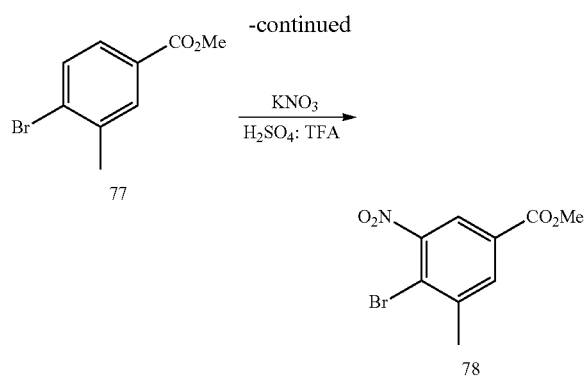

Synthesis of Methyl 4-bromo-3-methyl-5-nitrobenzoate (78)

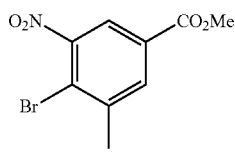

To a stirred solution of methyl 4-bromo-3-methylbenzoate 77 (500 mg, 2.18 mmol) in sulfuric acid: trifluoro acetic acid (1:0.1, 6.6 mL) under inert atmosphere was added potassium nitrate (231 mg, 2.29 mmol) at 0° C.; warmed to RT and stirred for 4 h. The reaction was monitored by TLC; after completion of the reaction, the reaction mixture was quenched with ice water (20 mL) and extracted with EtOAc (2×20 mL). The combined organic extracts were dried over sodium sulfate, filtered and concentrated in vacuo to afford crude compound 78 (540 mg, 95%) as yellow oil. TLC: 10% EtOAc/hexanes ($R_f$: 0.4); $^1$H-NMR (DMSO-$d_6$, 400 MHz): δ 8.25 (s, 1H), 8.17 (s, 1H), 3.89 (s, 3H), 2.53 (s, 3H).

Synthesis of Methyl 4-((2-(methoxycarbonyl) phenyl) thio)-3-methyl-5-nitrobenzoate (79)

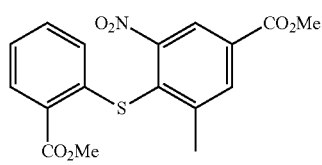

To a stirred solution of methyl 2-mercaptobenzoate 1 (575 mg, 2.18 mmol) in DMF (6 mL) under inert atmosphere were added cesium carbonate (1.42 g, 4.37 mmol), compound 78 (385 mg, 2.29 mmol) at RT; heated to 65° C. and stirred for 4 h. The reaction was monitored by TLC; after completion of the reaction, the reaction mixture was diluted with water (20 mL) and extracted with EtOAc (2×25 mL). The combined organic extracts were washed with water (15 mL), brine (15 mL), dried over sodium sulfate, filtered and concentrated in vacuo to afford the crude. The crude was recrystallized using CH$_2$Cl$_2$: n-pentane (1:4, 5 mL) to afford compound 79 (120 mg, 16%) as yellow solid. TLC: 20% EtOAc/hexanes ($R_f$: 0.4); $^1$H-NMR (DMSO-$d_6$, 400 MHz): δ 8.32 (s, 1H), 8.24 (s, 1H), 7.63-7.59 (m, 1H), 7.49-7.45 (m, 1H), 7.23 (t, J=8.0 Hz, 1H), 6.61 (d, J=8.0 Hz, 1H), 3.92 (s, 3H), 3.89 (s, 3H), 2.35 (s, 3H).

Synthesis of Methyl 3-amino-4-((2-(methoxycarbonyl) phenyl) thio)-5-methylbenzoate (80)

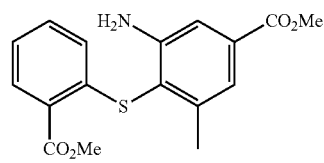

To a stirred solution of compound 79 (200 mg, 0.55 mmol) in MeOH (5 mL) under inert atmosphere was added Pd/C (70 mg) at RT and stirred under hydrogen atmosphere for 6 h. The reaction was monitored by TLC; after completion of the reaction, the volatiles were removed in vacuo to obtain the crude compound 80 (175 mg, 96%) as yellow solid. TLC: 30% EtOAc/hexanes ($R_f$: 0.7); $^1$H-NMR (DMSO-$d_6$, 400 MHz): δ 7.96 (d, J=7.6 Hz, 1H), 7.38-7.31 (m, 2H), 7.24-7.20 (m, 1H), 7.14 (s, 1H), 6.56 (d, J=8.0 Hz, 1H), 5.67 (s, 2H), 3.89 (s, 3H), 3.83 (s, 3H), 2.25 (s, 3H).

Synthesis of 3-amino-4-((2-carboxyphenyl) thio)-5-methylbenzoic acid (81)

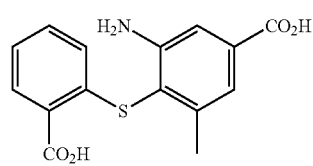

To a stirred solution of compound 80 (160 mg, 0.48 mmol) in THF:H$_2$O (3:1.5, 4.5 mL) was added lithium hydroxide (118 mg, 2.90 mmol) at RT and stirred for 24 h; heated to reflux and stirred for 12 h. The reaction was monitored by TLC; after completion of the reaction, the volatiles were removed in vacuo. The residue was diluted with water (15 mL), filtered the precipitated solid and dried in vacuo to afford the crude compound 81 (140 mg, 96%) as an off-white solid. TLC: 30% EtOAc/hexanes ($R_f$: 0.2); $^1$H-NMR (DMSO-$d_6$, 400 MHz): δ 13.00 (br s, 2H), 7.95 (d, J=8.0 Hz, 1H), 7.35-7.29 (m, 2H), 7.19 (t, J=7.6 Hz, 1H), 7.13 (s, 1H), 6.54 (d, J=8.0 Hz, 1H), 5.30 (br s, 2H), 2.25 (s, 3H).

67

Synthesis of 6-methyl-11-oxo-10, 11-dihydrodibenzo [b,f] [1,4] thiazepine-8-carboxylic acid (82)

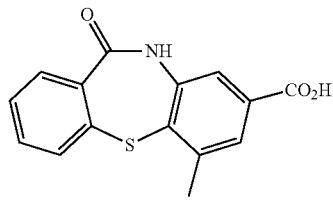

To a stirred solution of compound 81 (140 mg, 0.46 mmol) in THF (5 mL) under inert atmosphere was added CDI (375 mg, 2.31 mmol) at RT and stirred for 24 h. The reaction was monitored by TLC; after completion of the reaction, the volatiles were removed in vacuo and neutralized with 1 N HCl, filtered the precipitated solid and dried in vacuo to afford the crude compound 82 (120 mg, 91%) as an off-white solid. TLC: 10% MeOH/CH$_2$Cl$_2$ (R$_f$: 0.4); $^1$H-NMR (DMSO-d$_6$, 400 MHz): δ 13.05 (br s, 1H), 10.73 (s, 1H), 7.69-7.58 (m, 4H), 7.51-7.44 (m, 2H), 2.56 (s, 3H).

Example 13: Synthesis of 7-methyl-11-oxo-10, 11-dihydrodibenzo [b,f] [1,4] thiazepine-8-carboxylic acid (88)—a Common Intermediate

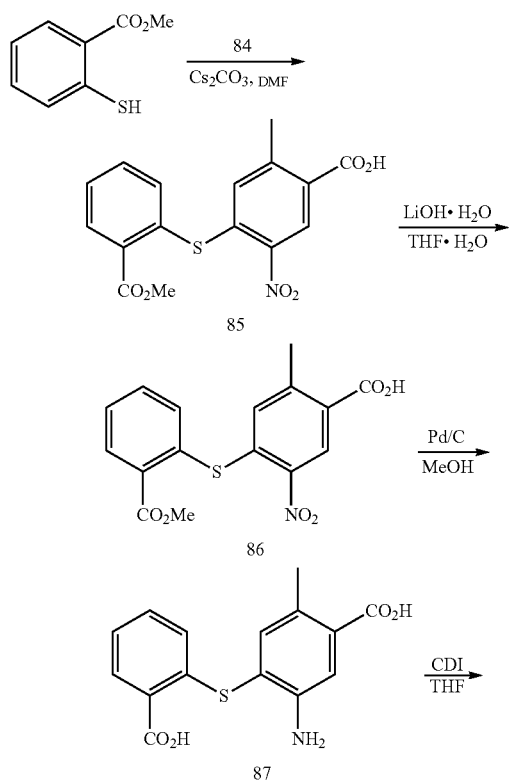

68

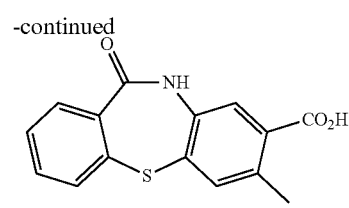

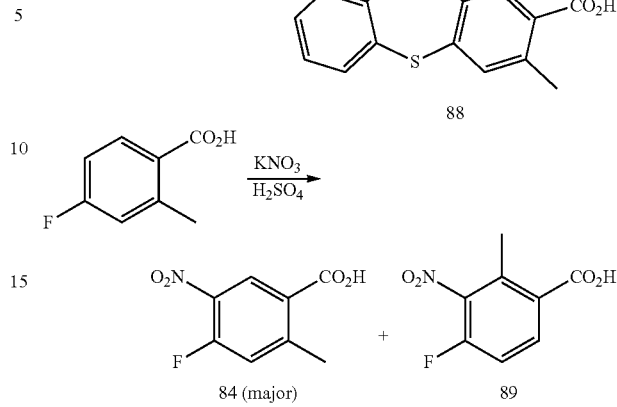

Synthesis of 4-fluoro-2-methyl-5-nitrobenzoic acid (84)

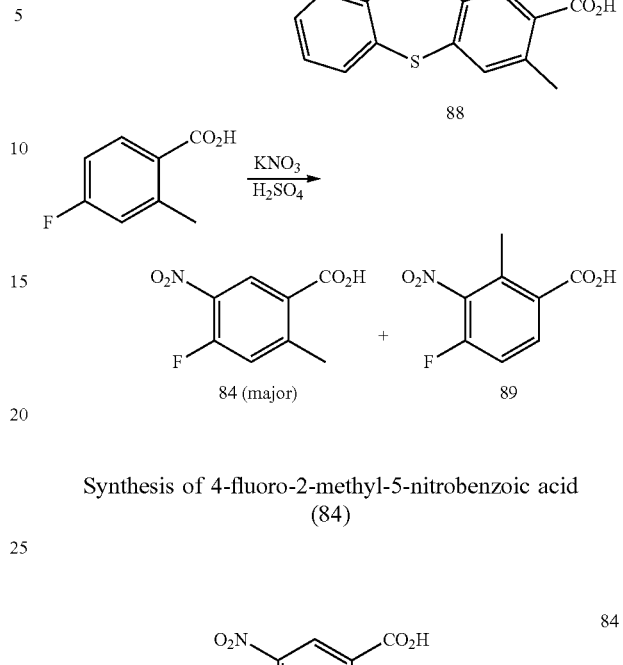

To a stirred solution of 4-fluoro-2-methylbenzoic acid 83 (500 mg, 3.24 mmol) in concentrated sulfuric acid (2.5 mL) under inert atmosphere was added potassium nitrate (655 mg, 6.49 mmol) at 0° C.; warmed to RT and stirred for 6 h. The reaction was monitored by TLC; after completion of the reaction, the reaction mixture was quenched with ice water (20 mL), filtered the precipitated solid and dried in vacuo to obtain the crude. The crude was purified through silica gel column chromatography using 5% MeOH/CH$_2$Cl$_2$ to afford compound 84 (300 mg, 60%) as brown syrup. TLC: 10% MeOH/CH$_2$Cl$_2$ (R$_f$: 0.3); $^1$H-NMR (DMSO-d$_6$, 500 MHz): δ 13.56 (br s, 1H), 8.52 (d, J=8.0 Hz, 1H), 7.61 (d, J=12.5 Hz, 1H), 2.63 (s, 3H).

Synthesis of 4-((2-(methoxycarbonyl) phenyl) thio)-2-methyl-5-nitrobenzoic acid (85)

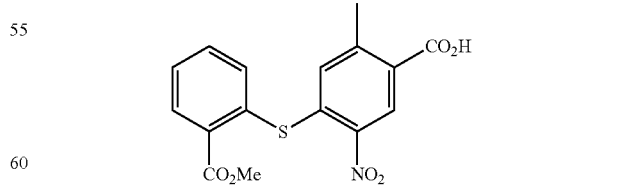

To a stirred solution of methyl 2-mercaptobenzoate 1 (514 mg, 3.08 mmol) in DMF (10 mL) under inert atmosphere were added cesium carbonate (1.81 g, 5.57 mmol), compound 84 (560 mg, 2.78 mmol) at RT; heated to 60° C. and stirred for 4 h. The reaction was monitored by TLC; after completion of the reaction, the volatiles were removed under reduced pressure. The residue was diluted with water (20 mL) and pH was adjusted to ~2 with 1 N HCl, filtered the precipitated solid and dried in vacuo to afford compound 85 (500 mg, 52%) as an off-white solid. TLC: 5% MeOH/CH$_2$Cl$_2$ (R! 0.4); $^1$H-NMR (DMSO-d$_6$, 400 MHz): δ 13.47 (br s, 1H), 8.59 (s, 1H), 7.94 (d, J=7.2 Hz, 1H), 7.68-7.60 (m, 3H), 6.83 (s, 1H), 3.72 (s, 3H), 2.40 (s, 3H).

Synthesis of 4-((2 carboxyphenyl)thio)-2-methyl-5-nitrobenzoic acid (86)

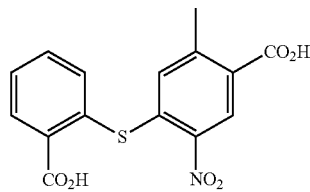

To a stirred solution of compound 85 (500 mg, 1.45 mmol) in THF:H$_2$O (2:1, 15 mL) was added lithium hydroxide monohydrate (300 mg, 7.31 mmol) at RT and stirred for 8 h. The reaction was monitored by TLC; after completion of the reaction, the volatiles were removed in vacuo. The residue was diluted with water (15 mL), and pH was adjusted to ~2 with 1 N HCl, filtered the precipitated solid and dried in vacuo to afford crude compound 86 (500 mg) as an off-white solid. TLC: 5% MeOH/CH$_2$Cl$_2$ (R$_f$: 0.1); $^1$H-NMR (DMSO-d$_6$, 400 MHz): δ 13.51 (br s, 2H), 8.57 (s, 1H), 7.92 (d, J=7.2 Hz, 1H), 7.64-7.58 (m, 2H), 7.53 (t, J=8.0 Hz, 1H), 6.89 (s, 1H), 2.41 (s, 3H).

Synthesis of 5-amino-4-((2-carboxyphenyl) thio)-2-methylbenzoic acid (87)

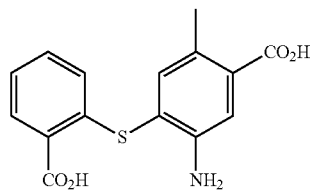

To a stirred solution of compound 86 (500 mg) in MeOH (15 mL) under inert atmosphere was added Pd/C (250 mg) at RT and stirred under hydrogen atmosphere for 16 h. The reaction was monitored by TLC; after completion of the reaction, the volatiles were removed in vacuo to afford crude compound 87 (430 mg) as an off-white solid. TLC: MeOH/CH$_2$Cl$_2$ (R$_f$: 0.1); LC-MS: 84.24%; 304.5 (M$^+$+1); (column; X-Select CSH C-18, (50×3.0 mm, 3.5 μm); RT 3.75 min. 0.05% TFA (Aq): ACN; 0.8 mL/min).

Synthesis of 7-methyl-11-oxo-10, 11-dihydrodibenzo [b,f] [1,4] thiazepine-8-carboxylic acid (88)

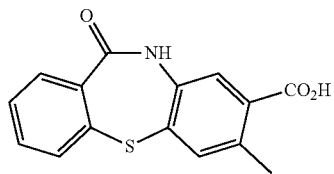

To a stirred solution of compound 87 (430 mg) in THF (20 mL) under inert atmosphere was added CDI (1.15 g, 7.09 mmol) at RT and stirred for 18 h. The reaction was monitored by TLC; after completion of the reaction, the volatiles were removed in vacuo and neutralized with 1 N HCl, filtered the precipitated solid and dried in vacuo to afford the crude compound 88 (290 mg) as an off-white solid. TLC: 10% MeOH/CH$_2$Cl$_2$ (R$_f$: 0.5); $^1$H-NMR (DMSO-d$_6$, 500 MHz): δ 13.15 (br s, 1H), 10.68 (s, 1H), 7.69-7.68 (m, 2H), 7.67-7.44 (m, 4H), 2.44 (s, 3H).

Example 14: 9-methyl-11-oxo-10, 11-dihydrodibenzo [b, f][1, 4] thiazepine-8-carboxylic acid (97)—a common intermediate and Synthesis of 7-methyl-11-oxo-10, 11-dihydrodibenzo [b, f] [1, 4] thiazepine-8-carboxylic acid (88) a common intermediate—Alternate Approach

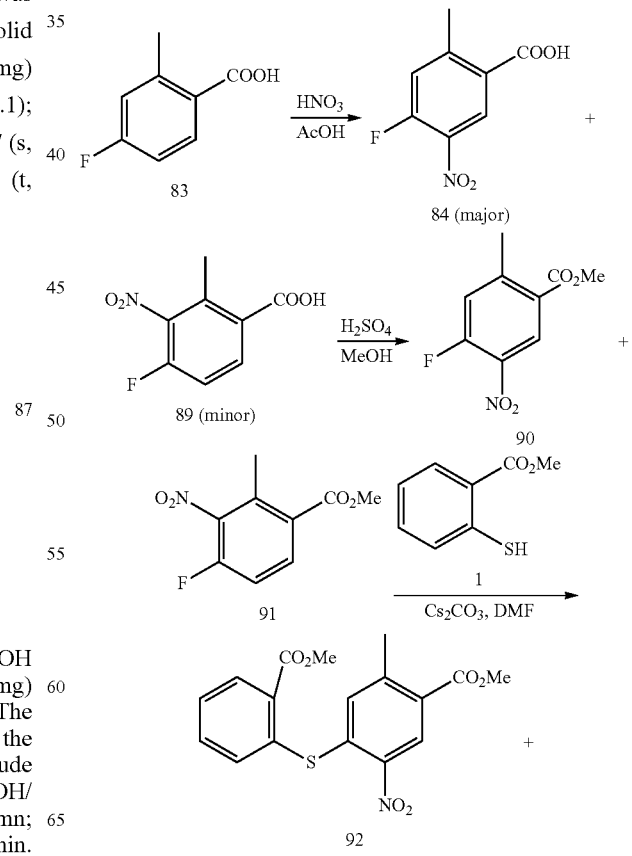

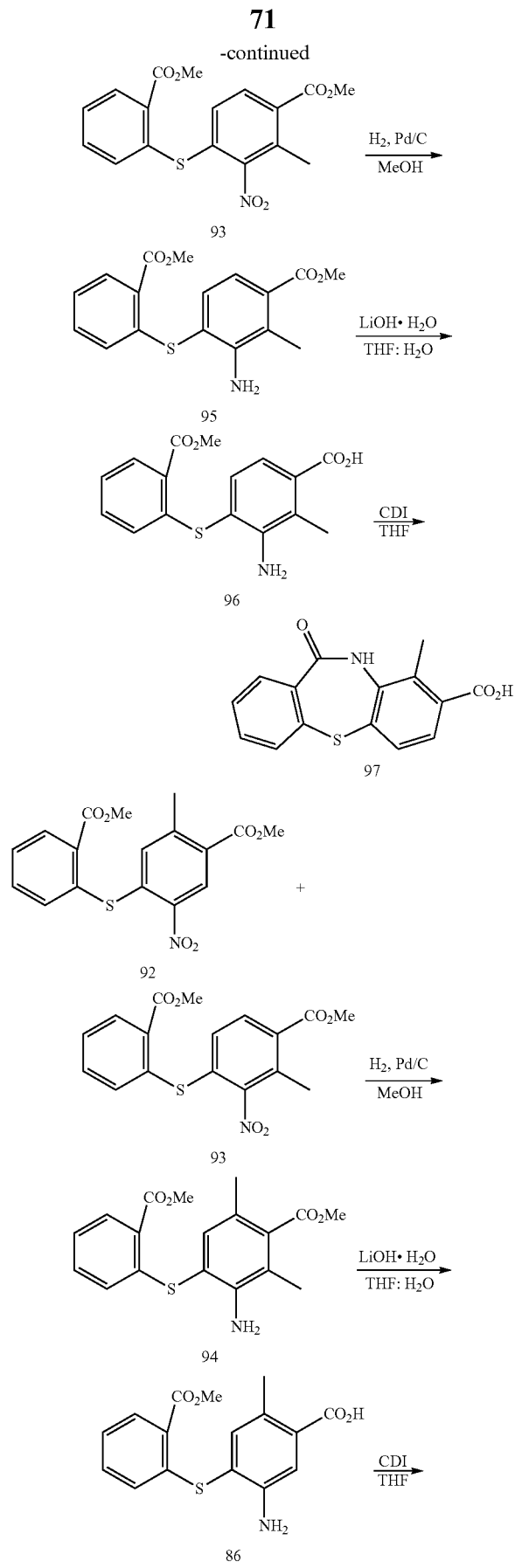

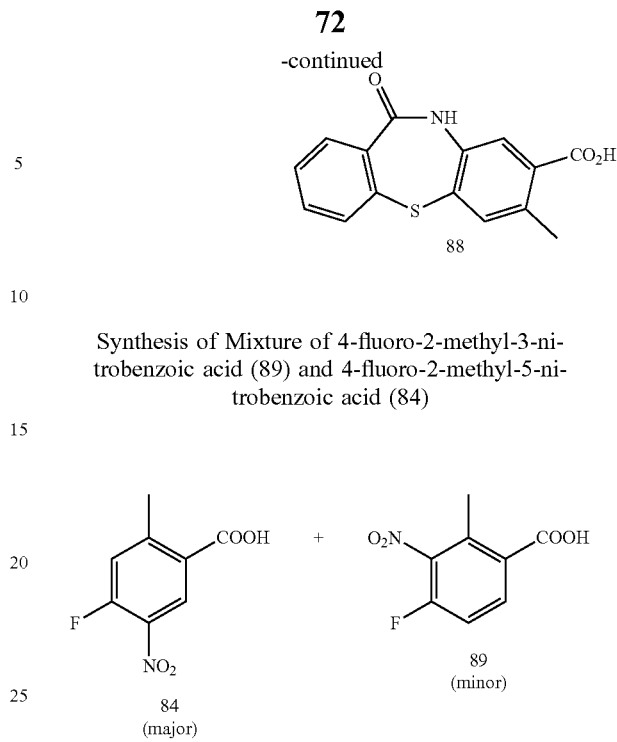

Synthesis of Mixture of 4-fluoro-2-methyl-3-nitrobenzoic acid (89) and 4-fluoro-2-methyl-5-nitrobenzoic acid (84)

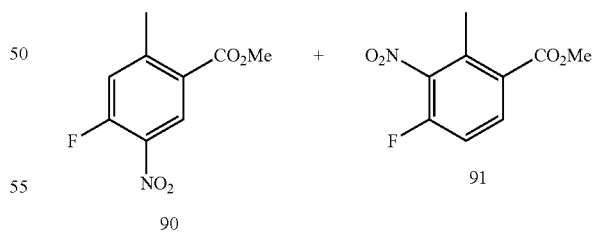

To a stirred solution of 4-fluoro-2-methylbenzoic acid 83 (10 g, 64.51 mmol) in acetic acid (50 mL) under inert atmosphere was added fuming nitric acid (50 mL) at RT and heated to 80° C. for 6 h. The reaction was monitored by TLC; after completion of the reaction, the reaction mixture was diluted with ice cold water (100 mL). The precipitate was filtered and dried in vacuo to afford mixture of compounds 84 and 89 (5.3 g, 40%) as white solid. TLC: 70% EtOAc/hexanes ($R_f$: 0.4); 1H NMR (DMSO-$d_6$, 400 MHz): δ 13.30 (br s, 2H), 8.52 (d, J=8.0 Hz, 2H), 8.10 (dd, J=8.9 5.9, Hz, 1H), 7.60 (d, J=12.5 Hz, 2H), 7.56 (t, J=9.3 Hz, 1H), 2.63 (s, 6H), 2.48 (s, 3H); ($^1$H NMR showed mixture of compounds 84 and 89 in the ratio of 2:1).

Synthesis of Methyl 4-fluoro-2-methyl-3-nitrobenzoate (91) and methyl 4-fluoro-2-methyl-5-nitrobenzoate (90)

To a stirred solution of compound 84 and 89 (10 g) in MeOH (100 mL) under argon atmosphere was conc. sulfuric acid (20 mL) at 0° C. and heated to reflux for 48 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to afford mixture of compounds 90 & 91 (6 g) as colorless thick syrup. TLC: 30% EtOAc/hexane ($R_f$: 0.5); 1H NMR (DMSO-$d_6$, 500 MHz): δ 8.51 (d, J=7.8 Hz, 1H), 8.09 (dd, J=8.8, 5.6 Hz, 0.5H), 7.63 (d, J=12.4 Hz, 1H), 7.58 (t, J=9.1 Hz, 0.5H), 3.87 (s, 4.5H), 2.62 (s, 3H), 2.45 (s, 1.5H); ($^1$H NMR showed mixture of compounds 90:91 in the ratio of 2:1).

Synthesis of Methyl 4-((2-(methoxycarbonyl) phenyl) thio)-2-methyl-3-nitrobenzoate (93) and methyl 4-((2-(methoxycarbonyl) phenyl) thio)-2-methyl-5-nitrobenzoate (92)

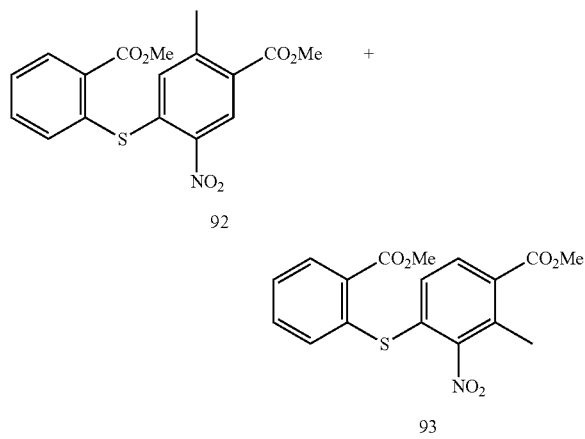

To a stirred solution of compounds 90 and 91 (11 g) in DMF (100 mL) under inert atmosphere were added methyl 2-mercaptobenzoate 1 (10.4 g, 61.97 mmol), cesium carbonate (18.5 g, 56.81 mmol) at 0° C.; heated to 80° C. and stirred for 4 h. The reaction was monitored by TLC; after completion of the reaction, the reaction mixture was diluted with ice cold water (100 mL) and extracted with EtOAc (2×100 mL). The combined organic extracts were washed with water (200 mL), brine (200 mL), dried over sodium sulfate, filtered and concentrated in vacuo to afford a mixture of compounds 93 and 92 (12 g) as a yellow solid. TLC: 20% EtOAc/hexanes ($R_f$: 0.2); LC-MS: 12.57%+81.14%; 370.8 (M$^+$+1); (column; X-Select CSH C18, (50×3.0 mm, 3.5 μm); RT 2.77 min. 0.05% Aq. TFA: ACN; 0.8 mL/min); RT 4.05, 4.14 min.

Synthesis of Methyl 3-amino-4-((2-(methoxycarbonyl) phenyl) thio)-2-methylbenzoate (95) and Synthesis of methyl 5-amino-4-((2-(methoxycarbonyl) phenyl) thio)-2-methylbenzoate (94)

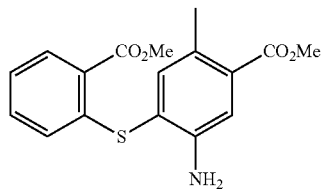

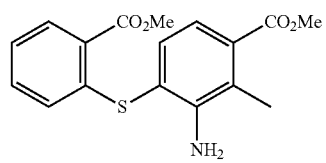

To a stirred solution of compound 93 and 92 (14 g, crude) in MeOH (500 mL) under inert atmosphere was added Pd/C (1.4 g, 50% wet) at RT and stirred under hydrogen atmosphere in an autoclave (6 kg/cm$^2$ pressure) for 18 h. The reaction was monitored by TLC; after completion of the reaction, the reaction mixture was filtered through celite, washed with MeOH (100 mL). The filtrate was concentrated in vacuo to obtain the crude. The crude was recrystallized with EtOH (20 mL) and further purified through silica gel column chromatography column chromatography using 10% EtOAc/hexanes to afford compound 95 (3 g, 30%) and 94 (8 g, 63%) as sticky off-white solids. TLC: 30% EtOAc/hexanes ($R_f$: 0.4); $^1$H NMR (DMSO-$d_6$, 400 MHz) (95): δ 7.94 (d, J=7.1 Hz, 1H), 7.40 (t, J=7.3 Hz, 1H), 7.33-7.26 (m, 2H), 7.22 (dt, J=7.6, 1.1 Hz, 1H), 6.67 (dd, J=8.2, 0.8 Hz, 1H), 5.41 (s, 2H), 3.89 (s, 3H), 3.83 (s, 3H), 2.33 (s, 3H). $^1$H NMR (DMSO-$d_6$, 400 MHz) (94): δ 7.94 (dd, J=7.8, 1.4 Hz, 1H), 7.42-7.38 (m, 1H), 7.32 (s, 1H), 7.26 (s, 1H), 7.22 (td, J=7.5, 1.0 Hz, 1H), 6.67 (dd, J=8.1, 0.8 Hz, 1H), 5.41 (s, 2H), 3.88 (s, 2H), 3.82 (s, 3H), 2.33 (s, 3H).

Synthesis of 3-amino-4-((2-carboxyphenyl) thio)-2-methylbenzoic acid (96)

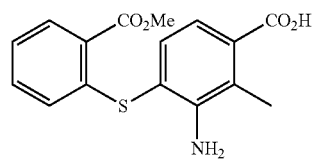

To a stirred solution of compound 95 (2 g, 6.04 mmol) in THF:H$_2$O (4:1, 50 mL) was added lithium hydroxide monohydrate (2.5 g, 10.0 mmol) at 0° C.; warmed to RT and stirred for 48 h. The reaction was monitored by TLC; after completion of the reaction, the volatiles were removed in vacuo. The residue was diluted with water (10 mL) and washed with diethyl ether (2×50 mL). The pH of the aqueous layer was acidified with 4 N HCl to ~1. The precipitated solid was filtered and dried in vacuo to afford compound 96 (1.2 g, 66%) as white solid. TLC: 20% MeOH/CH$_2$Cl$_2$ ($R_f$: 0.2); 1H NMR (DMSO-$d_6$, 400 MHz): δ 13.01 (br s, 2H), 7.94 (d, J=7.4 Hz, 1H), 7.36 (t, J=7.8 Hz, 1H), 7.28 (d, J=8.0 Hz, 1H), 7.20 (dt, J=7.4, 6.3 Hz, 1H), 6.95 (d, J=8.0 Hz, 1H), 6.61 (d, J=7.4 Hz, 1H), 5.25 (br s, 2H), 2.27 (s, 3H).

Synthesis of 9-methyl-11-oxo-10, 11-dihydrodibenzo [b,f] [1,4] thiazepine-8-carboxylic acid (97)

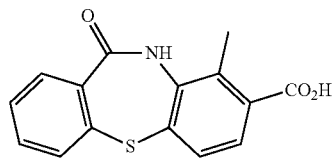

To a stirred solution of compound 96 (2.6 g, 4.30 mmol) in THF (30 mL) under argon atmosphere was added CDI (3.5 g, 21.50 mmol) at RT; heated to 80° C. and stirred for 16 h. The reaction was monitored by TLC; after completion of the reaction, the volatiles were removed in vacuo. The residue was diluted with water (20 mL) and pH was adjusted with 4 N HCl to ~2. The obtained solid was filtered, washed with diethyl ether and dried in vacuo to obtain compound 97 (1.6 g, 67%) as an off white solid. TLC: 15% MeOH/CH$_2$Cl$_2$ (R$_f$: 0.2); 1H NMR (DMSO-d$_6$, 400 MHz): δ 13.20 (br s, 1H), 10.23 (s, 1H), 7.74-7.60 (m, 1H), 7.56-7.51 (m, 2H), 7.50-7.42 (m, 3H), 2.47 (s, 3H).

Example 15: Synthesis of 3-carbamoyl-11-oxo-10, 11-dihydrodibenzo [b,f] [1,4] thiazepine-8-carboxylic acid (135)—a Common Intermediate

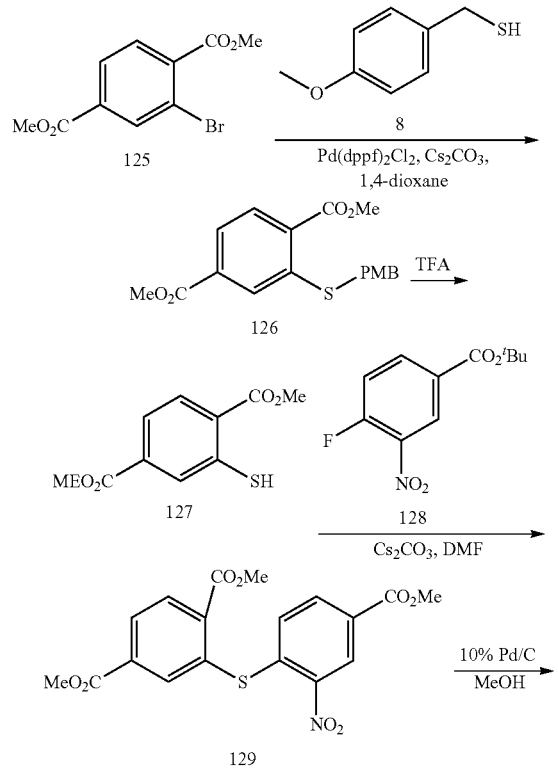

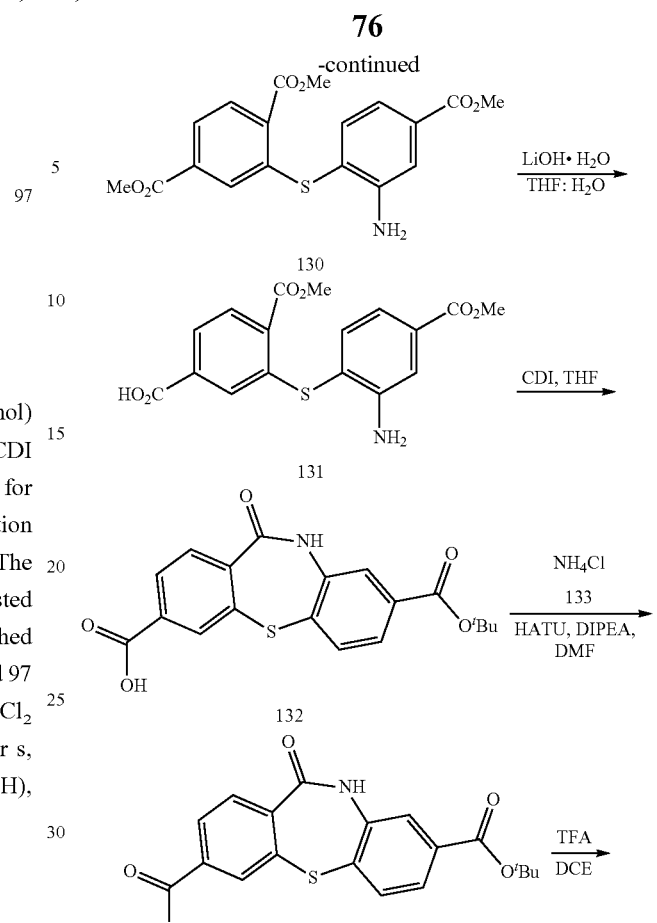

Synthesis of Dimethyl 2-((4-methoxybenzyl) thio) terephthalate (126)

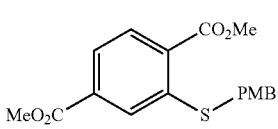

To a stirred solution of dimethyl 2-bromoterephthalate 125 (1 g, 3.66 mmol) in 1, 4-dioxane (50 mL) under inert atmosphere were added (4-methoxyphenyl) methanethiol 8 (620 mg, 4.02 mmol), cesium carbonate (2.38 g, 7.32 mmol), Pd(dppf)$_2$Cl$_2$ (67 mg, 0.09 mmol) at RT and stirred under argon for 30 min; heated to 110° C. and stirred for 20 h in a sealed tube. The reaction was monitored by TLC; after completion of the reaction, the reaction mixture was diluted with water (50 mL) and extracted with EtOAc (2×75 mL).

The combined organic extracts were dried over sodium sulfate, filtered and concentrated in vacuo to obtain the crude. The crude was purified through silica gel column chromatography using 10% EtOAc/hexanes to afford compound 126 (680 mg, 54%) as an off-white solid. TLC: 10% EtOAc/hexanes ($R_f$: 0.3); $^1$H-NMR (CDCl$_3$, 500 MHz): δ 8.06 (s, 1H), 7.99 (d, J=8.5 Hz, 1H), 7.77 (d, J=8.0 Hz, 1H), 7.34 (d, J=8.5 Hz, 2H), 6.85 (d, J=8.5 Hz, 2H), 4.18 (s, 2H), 3.93 (s, 3H), 3.91 (s, 3H), 3.79 (s, 3H).

Synthesis of Dimethyl 2-mercaptoterephthalate (127)

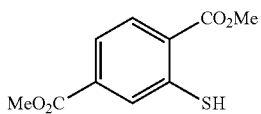

A stirred solution of compound 126 (1.47 g, 4.24 mmol) in trifluoro acetic acid (25 mL) under inert atmosphere at RT was heated to 80° C. and stirred for 5 h. The reaction was monitored by TLC; after completion of the reaction, the volatiles were removed in vacuo to obtain the crude compound 127 (950 mg) as pale green semi-solid which was carried to the next step without any purification. TLC: 15% EtOAc/hexanes ($R_f$: 0.7).

Synthesis of Dimethyl 2-((4-(tert-butoxycarbonyl)-2-nitrophenyl) thio) terephthalate (129)

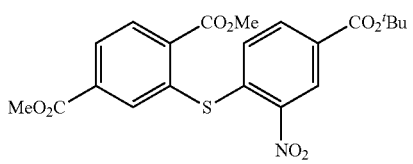

To a stirred solution of tert-butyl 4-fluoro-3-nitrobenzoate 128 (400 mg, 1.65 mmol) in DMF (20 mL) under inert atmosphere were added compound 127 (525 mg, crude), cesium carbonate (1.07 g, 3.31 mmol) at RT; heated to 60° C. and stirred for 1 h. The reaction was monitored by TLC; after completion of the reaction, the reaction mixture was diluted water (25 mL) and extracted with EtOAc (2×40 mL). The combined organic extracts were dried over sodium sulfate, filtered and concentrated in vacuo to obtain the crude. The crude was purified through silica gel column chromatography using 5-7% EtOAc/hexanes to afford compound 129 (400 mg, 54%) as yellow solid. TLC: 10% EtOAc/hexanes ($R_f$: 0.4); $^1$H-NMR (CDCl$_3$, 400 MHz): δ 8.76 (s, 1H), 8.25 (s, 1H), 8.20-8.17 (m, 1H), 7.98 (d, J=8.4 Hz, 1H), 7.92 (d, J=8.4 Hz, 1H), 6.91 (d, J=8.4 Hz, 1H), 3.93 (s, 3H), 3.82 (s, 3H), 1.58 (s, 9H).

Synthesis of Dimethyl 2-((2-amino-4-(tert-butoxycarbonyl) phenyl) thio) terephthalate (130)

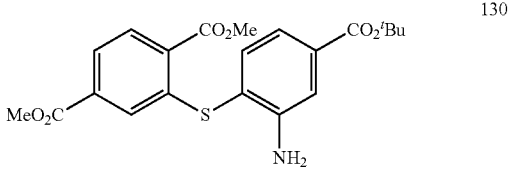 [SMILES: COC(=O)c1ccc(C(=O)OC)c(Sc2ccc(C(=O)OC(C)(C)C)cc2N)c1]

To a stirred solution of compound 129 (1 g, 2.23 mmol) in MeOH (50 mL) under inert atmosphere was added 10% Pd/C (500 mg) at RT and stirred under hydrogen atmosphere (balloon pressure) for 24 h. The reaction was monitored by TLC; after completion of the reaction, the reaction mixture was filtered through celite and the filtrate was concentrated in vacuo to obtain the crude. The crude was triturated with 2% EtOAc/n-pentane (2×5 mL) and dried in vacuo to afford compound 130 (800 mg, 86%) as an off-white solid. TLC: 15% EtOAc/hexanes ($R_f$: 0.4); $^1$H-NMR (DMSO-d$_6$, 400 MHz): δ 8.05 (d, J=8.0 Hz, 1H), 7.76-7.73 (m, 1H), 7.43-7.40 (m, 2H), 7.27 (s, 1H), 7.13-7.10 (m, 1H), 5.68 (br s, 2H), 3.91 (s, 3H), 3.75 (s, 3H), 1.55 (s, 9H).

Synthesis of 2-((2-amino-4-(tert-butoxycarbonyl) phenyl) thio) terephthalic acid (131)

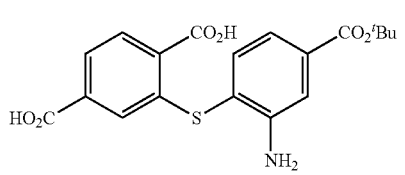

To a stirred solution of compound 130 (250 mg, 0.59 mmol) in THF:H$_2$O (4:1, 10 mL) under inert atmosphere was added lithium hydroxide monohydrate (123 mg, 2.99 mmol) at RT and stirred for 5 h. The reaction was monitored by TLC; after completion of the reaction, the volatiles were removed in vacuo. The residue was diluted with water (25 mL) and extracted with diethyl ether (2×25 mL). The aqueous layer was acidified with 2 N HCl to pH-6. The obtained solid was filtered and dried in vacuo to afford compound 131 (180 mg, 77%) as yellow solid. TLC: 10% MeOH/CH$_2$Cl$_2$ ($R_f$: 0.2); $^1$H-NMR (DMSO-d$_6$, 400 MHz): δ 13.16 (br s, 2H), 8.02 (d, J=8.0 Hz, 1H), 7.70 (d, J=8.4 Hz, 1H), 7.44-7.40 (m, 2H), 7.16 (s, 1H), 7.13-7.09 (m, 1H), 5.64 (br s, 2H), 1.55 (s, 9H).

Synthesis of 8-(tert-butoxycarbonyl)-11-oxo-10, 11-dihydrodibenzo [b,f] [1,4] thiazepine-3-carboxylic acid (132)

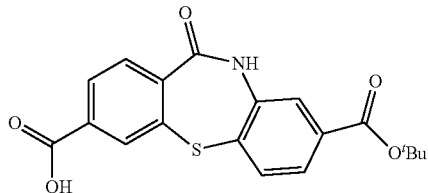

To a stirred solution of compound 131 (180 mg, 0.46 mmol) in THF (9 mL) under inert atmosphere was added CDI (225 mg, 1.39 mmol) at RT and stirred for 16 h. The reaction was monitored by TLC; after completion of the reaction, the volatiles were removed in vacuo. The residue was diluted with water (15 mL) and acidified with HCl. The obtained solid was filtered and dried in vacuo to afford compound 132 (150 mg, 87%) as an off-white solid. TLC: 7% MeOH/CH$_2$Cl$_2$ (R$_f$: 0.2); $^1$H-NMR (DMSO-d$_6$, 400 MHz): δ 13.32 (br s, 1H), 10.93 (s, 1H), 8.02 (d, J=8.4 Hz, 1H), 7.97-7.94 (m, 1H), 7.81-7.77 (m, 2H), 7.71-7.62 (m, 1H), 7.43-7.42 (m, 1H), 1.55-1.51 (m, 9H).

Synthesis of Tert-Butyl 3-carbamoyl-11-oxo-10, 11-dihydrodibenzo [b,f] [1,4] thiazepine-8-carboxylate (134)

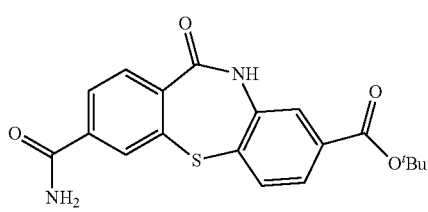

To a stirred solution of compound 132 (150 mg, 0.40 mmol) in DMF (9 mL) under inert atmosphere were added HATU (307 mg, 0.80 mmol), ammonium chloride 133 (43 mg, 0.80 mmol), diisopropyl ethyl amine (0.3 mL, 1.60 mmol) at 0° C.; warmed to RT and stirred for 16 h. The reaction was monitored by TLC; after completion of the reaction, the reaction mixture was diluted with water (20 mL). The obtained solid was filtered, triturated with 10% EtOAc/hexanes (2×5 mL) and dried in vacuo to afford compound 134 (95 mg, 63%) as white solid. TLC: 7% MeOH/CH$_2$Cl$_2$ (R$_f$: 0.6); $^1$H-NMR (DMSO-d$_6$, 400 MHz): δ 10.89 (s, 1H), 8.15 (s, 1H), 8.00 (s, 1H), 7.89 (d, J=8.0 Hz, 1H), 7.77-7.76 (m, 2H), 7.74-7.69 (m, 1H), 7.64 (d, J=8.0 Hz, 1H), 7.58 (br s, 1H), 1.52 (s, 9H).

Synthesis of 3-carbamoyl-11-oxo-10, 11-dihydrodibenzo [b,f] [1,4] thiazepine-8-carboxylic acid (135)

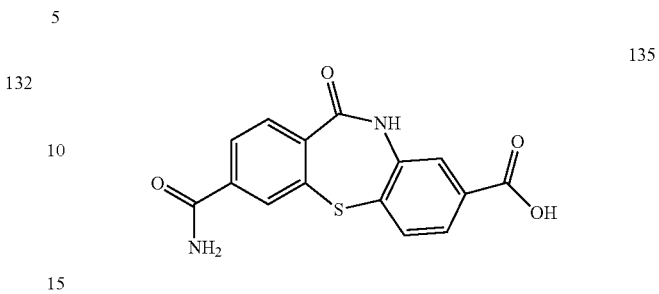

To a stirred solution of compound 134 (95 mg, 0.25 mmol) in EDC (10 mL) under inert atmosphere was added trifluoroacetic acid (293 mg, 2.56 mmol) at RT; heated to 80° C. and stirred for 5 h. The reaction was monitored by TLC; after completion of the reaction, the reaction mixture was filtered. The obtained solid was triturated with 5% CH$_2$Cl$_2$ (2×5 mL) and dried in vacuo to afford compound 135 (70 mg, 87%) as white solid. TLC: 10% MeOH/CH$_2$Cl$_2$ (R$_f$: 0.2); $^1$H-NMR (DMSO-d$_6$, 500 MHz): δ 10.93 (s, 1H), 8.16 (s, 1H), 8.01 (s, 1H), 7.90 (d, J=8.5 Hz, 1H), 7.81-7.76 (m, 2H), 7.72-7.68 (m, 2H), 7.59 (s, 1H).

Example 16: 11-oxo-10, 11-dihydrodibenzo [b,f] [1,4] thiazepine-7-carboxylic acid (140)—a Common Intermediate

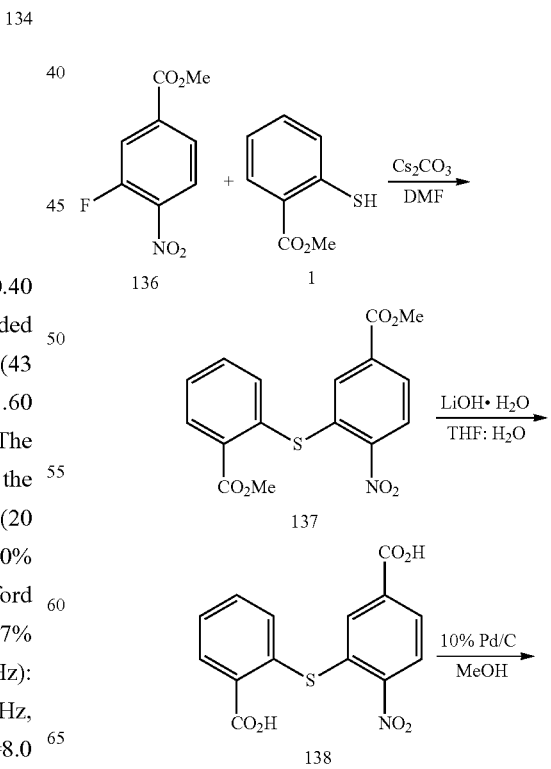

-continued

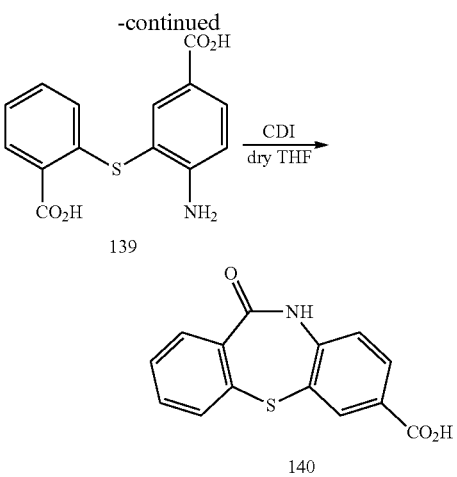

Synthesis of Methyl 3-((2-(methoxycarbonyl) phenyl) thio)-4-nitrobenzoate (137)

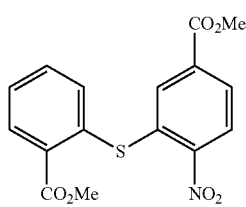

137

To a stirred solution of methyl 3-fluoro-4-nitrobenzoate 136 (100 mg, 0.50 mmol) in DMF (3 mL) under argon atmosphere was added cesium carbonate (180 mg, 0.55 mmol) at RT and heated to 40° C. To this was added methyl 2-mercaptobenzoate 1 (93 mg, 0.55 mmol) in DMF (1 mL) drop wise for 3 min and stirred for 2 h. The reaction was monitored by TLC; after completion of the reaction, the volatiles were removed in vacuo to obtain the crude. The crude was diluted with water (30 mL) and extracted with $CH_2Cl_2$ (2×30 mL). The combined organic extracts were dried over sodium sulfate, filtered and concentrated in vacuo to afford compound 137 (120 mg, 69%) as yellow crystalline solid. TLC: 20% EtOAc/hexanes ($R_f$: 0.3); $^1$H-NMR (DMSO-$d_6$, 400 MHz): δ 8.30 (d, J=8.4 Hz, 1H), 7.99-7.93 (m, 2H), 7.65-7.60 (m, 3H), 7.49 (d, J=7.6 Hz, 1H), 3.80 (s, 3H), 3.74 (s, 3H).

Synthesis of 3-((2-carboxyphenyl) thio)-4-nitrobenzoic acid (138)

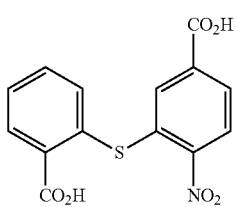

138

To a stirred solution of compound 137 (100 mg, 0.26 mmol) in THF (7 mL) under argon atmosphere was added lithium hydroxide monohydrate (28 mg, 0.66 mmol) in water (3 mL) at RT; heated to reflux and stirred for 2 h. The reaction was monitored by TLC; after completion of the reaction, the volatiles were removed in vacuo, diluted with water (20 mL) and pH was adjusted to ~2 with 1 N HCl. The obtained solid was filtered and dried in vacuo to afford compound 138 (72 mg, 85%) as yellow solid. TLC: 10% MeOH/$CH_2Cl_2$ ($R_f$: 0.2); $^1$H-NMR (DMSO-$d_6$, 400 MHz): δ 13.49 (br s, 2H), 8.25 (d, J=8.4 Hz, 1H), 7.96-7.91 (m, 2H), 7.66 (s, 1H), 7.60-7.54 (m, 2H), 7.40 (d, J=7.6 Hz, 1H).

Synthesis of 4-amino-3-((2-carboxyphenyl) thio) benzoic acid (139)

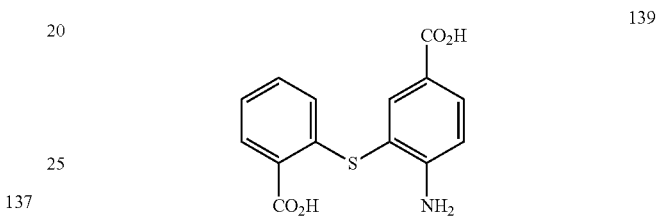

To a stirred solution of compound 138 (70 mg, 0.20 mmol) in MeOH (5 mL) under argon atmosphere was added 10% Pd/C (10 mg) and stirred under hydrogen atmosphere (balloon pressure) for 24 h. The reaction was monitored by TLC; after completion of the reaction, the reaction mixture was filtered through celite, washed with MeOH (2×5 mL) and the filtrate was concentrated in vacuo to afford compound 139 (53 mg, 90%) as an off-white solid. TLC: 20% MeOH/$CH_2Cl_2$ ($R_f$: 0.3); $^1$H-NMR (DMSO-$d_6$, 400 MHz): δ 12.91 (br s, 2H), 7.94 (d, J=6.4 Hz, 1H), 7.86 (s, 1H), 7.76 (d, J=8.4 Hz, 1H), 7.37 (t, J=8.0 Hz, 1H), 7.19 (t, J=7.6 Hz, 1H), 6.83 (d, J=8.8 Hz, 1H), 6.63 (d, J=8.0 Hz, 1H), 6.14 (br s, 2H).

Synthesis of 11-oxo-10, 11-dihydrodibenzo [b,f] [1,4] thiazepine-7-carboxylic acid (140)

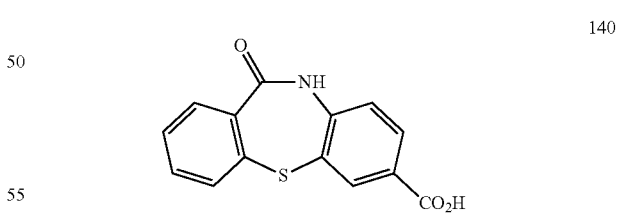

To a stirred solution of compound 139 (50 mg, 0.17 mmol) in dry THF (3 mL) under argon atmosphere was added CDI (84 mg, 0.51 mmol) at 0° C.; warmed to RT and stirred for 12 h. The reaction was monitored by TLC; after completion of the reaction, the reaction mixture was quenched with 1 N HCl (3 mL), water (10 mL). The obtained solid was filtered, washed with ether (2×5 mL) and dried in vacuo to afford compound 140 (28 mg, 61%) as white solid. TLC: 20% MeOH/$CH_2Cl_2$ ($R_f$: 0.5); $^1$H-NMR (DMSO-$d_6$, 400 MHz): δ 13.10 (br s, 1H), 10.97 (s, 1H), 8.05 (s, 1H), 7.89 (d, J=8.4 Hz, 1H), 7.69 (d, J=7.6 Hz, 1H), 7.57 (d, J=7.6 Hz, 1H), 7.53-7.44 (m, 2H), 7.31 (d, J=8.4 Hz, 1H).

Example 17: Synthesis of 8-aminodibenzo [b,f] [1,4] thiazepin-11 (10H)-one (145)—a Common Intermediate

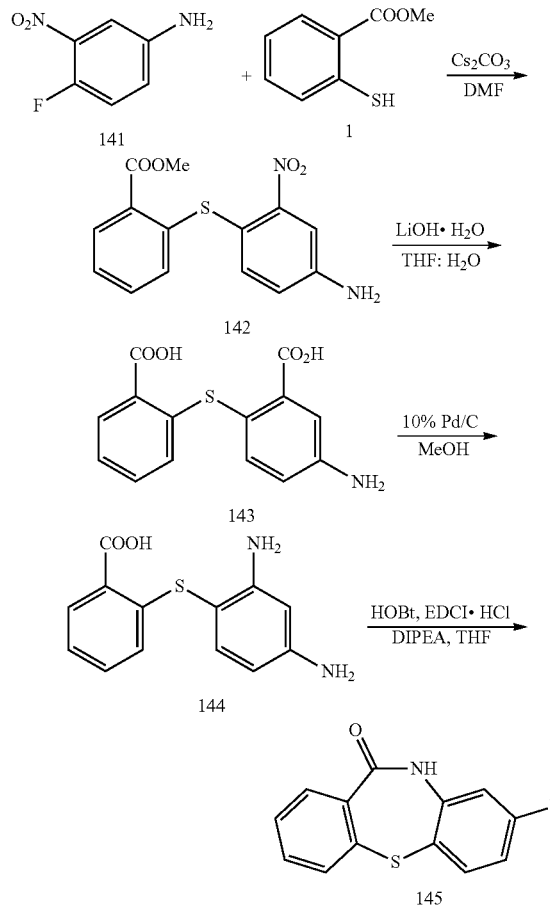

Synthesis of Methyl 2-((4-amino-2-nitrophenyl) thio) benzoate (142)

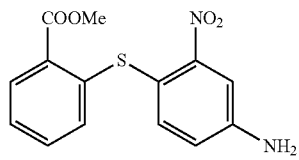

To a stirred solution of 4-fluoro-3-nitroaniline 141 (500 mg, 3.20 mmol) in DMF (6 mL) under inert atmosphere was added cesium carbonate (1.14 g, 3.50 mmol) at RT and heated to 40° C. To this was added methyl 2-mercaptobenzoate 1 (592 mg, 3.50 mmol) in DMF (1 mL) drop wise for 3 min and stirred for 3 h. The reaction was monitored by TLC; after completion of the reaction, the reaction mixture was diluted with water (35 mL) and extracted with CH₂Cl₂ (2×35 mL). The combined organic extracts were dried over sodium sulfate, filtered and concentrated in vacuo to obtain the crude. The crude was purified through silica gel column chromatography using 15% EtOAc/hexanes to afford compound 142 (600 mg, 62%) as brown syrup. TLC: 30% EtOAc/hexanes ($R_f$: 0.5); $^1$H-NMR (DMSO-$d_6$, 400 MHz): δ 7.91 (d, J=8.0 Hz, 1H), 7.44 (t, J=8.0 Hz, 1H), 7.30-7.20 (m, 2H), 7.10 (s, 1H), 6.87-6.84 (m, 1H), 6.79 (d, J=8.0 Hz, 1H), 6.24 (s, 2H), 3.84 (s, 3H).

Synthesis of 2-((4-amino-2-nitrophenyl) thio) benzoic acid (143)

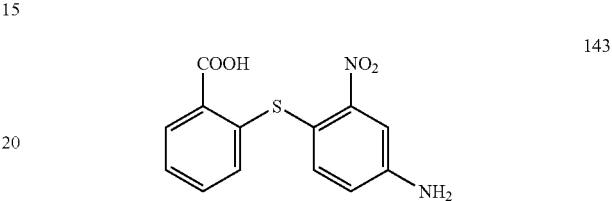

To a stirred solution of compound 142 (600 mg, 1.98 mmol) in THF:H₂O (10:3, 13 mL) under inert atmosphere was added lithium hydroxide monohydrate (406 mg, 9.90 mmol) at RT; heated to 60° C. and stirred for 5 h. The reaction was monitored by TLC; after completion of the reaction, the volatiles were removed in vacuo. The residue was diluted with water (50 mL) and extracted with EtOAc (2×50 mL). The aqueous layer was acidified with HCl to pH-2. The obtained solid was filtered and dried in vacuo to afford compound 143 (350 mg, 61%) as orange solid. TLC: 10% MeOH/CH₂Cl₂ ($R_f$: 0.3); $^1$H-NMR (DMSO-$d_6$, 500 MHz): δ 13.18 (s, 1H), 7.89 (d, J=7.5 Hz, 1H), 7.38 (t, J=7.0 Hz, 1H), 7.28 (d, J=9.0 Hz, 1H), 7.19 (t, J=8.0 Hz, 1H), 7.07 (s, 1H), 6.84 (d, J=8.5 Hz, 1H), 6.71 (d, J=8.5 Hz, 1H), 6.23 (s, 2H).

Synthesis of 2-((2, 4-diaminophenyl) thio) benzoic acid (144)

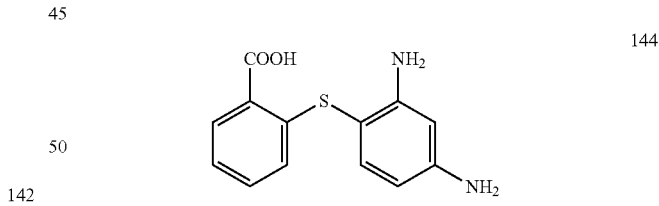

To a stirred solution of compound 143 (350 mg, 1.20 mmol) in MeOH (10 mL) under inert atmosphere was added 10% Pd/C (100 mg) at RT and stirred under hydrogen atmosphere (balloon pressure) for 16 h. The reaction was monitored by TLC; after completion of the reaction, the reaction mixture was filtered and the filtrate was concentrated in vacuo to obtain the crude. The crude was washed with n-pentane (2×10 mL) and dried in vacuo to afford compound 144 (250 mg, 80%) as white solid. TLC: 10% MeOH/CH₂Cl₂ ($R_f$: 0.3); $^1$H-NMR (DMSO-$d_6$, 400 MHz): δ 12.60 (br s, 1H), 7.87 (d, J=7.6 Hz, 1H), 7.32 (t, J=8.4 Hz, 1H), 7.12 (t, J=6.8 Hz, 1H), 6.90 (d, J=8.0 Hz, 1H), 6.72 (d, J=8.0 Hz, 1H), 6.02 (s, 1H), 5.93 (d, J=8.4 Hz, 1H), 5.02-4.98 (m, 4H).

Synthesis of 8-aminodibenzo [b,f] [1,4] thiazepin-11 (10H)-one (145)

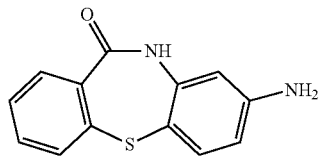

145

To a stirred solution of compound 144 (150 mg, 0.57 mmol) in DMF (4 mL) under inert atmosphere were added HOBt (233 mg, 1.73 mmol), EDCI.HCl (330 mg, 5.19 mmol), diisopropyl ethyl amine (0.5 mL, 2.87 mmol) at 0° C.; warmed to RT and stirred for 6 h. The reaction was monitored by TLC; after completion of the reaction, the reaction mixture was diluted with ice cold water (30 mL). The obtained solid was filtered, washed with hexanes (2×10 mL) and dried in vacuo to afford compound 145 (80 mg, 57%) as an off-white solid. TLC: 5% MeOH/CH$_2$Cl$_2$ (R$_f$: 0.5); $^1$H-NMR (DMSO-d$_6$, 400 MHz): δ 10.40 (s, 1H), 7.63 (d, J=6.8 Hz, 1H), 7.45-7.37 (m, 3H), 7.12 (d, J=8.4 Hz, 1H), 6.39 (s, 1H), 6.31 (d, J=8.4 Hz, 1H), 5.46 (s, 2H).

Example 18: Synthesis of 11-oxo-10, 11-dihydrodibenzo [b,f] [1,4] thiazepine-8-carboxylic acid 5-oxide (156)—a Common Intermediate

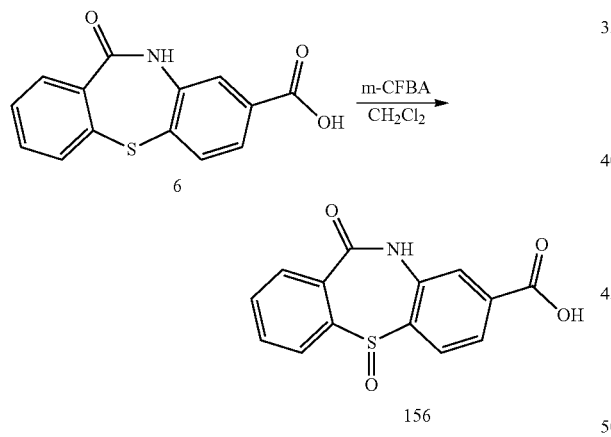

Synthesis of 11-oxo-10, 11-dihydrodibenzo [b,f] [1,4] thiazepine-8-carboxylic acid 5-oxide

156

To a stirred solution of 6 (2.5 g, 9.21 mmol) in CH$_2$Cl$_2$ (50 mL) under inert atmosphere was added m-chloro perbenzoic acid (1.59 g, 9.21 mmol) at RT and stirred for 48 h. The reaction was monitored by TLC; after completion of the reaction, the reaction mixture was the volatiles were removed in vacuo to obtain the crude. The crude was triturated with 10% MeOH/CH$_2$Cl$_2$ (2×5 mL), isopropanol (10 mL) to afford compound 156 (2.3 g, 87%) as white solid. TLC: 10% MeOH/CH$_2$Cl$_2$+0.05 mL CH$_3$COOH (R$_f$: 0.4); 1H NMR (DMSO-d$_6$, 500 MHz): δ 13.36 (br s, 1H), 11.08 (s, 1H), 7.96 (d, J=7.8 Hz, 1H), 7.92-7.87 (m, 1H), 7.85-7.66 (m, 3H), 7.63 (t, J=7.8 Hz, 1H), 7.53 (t, J=7.8 Hz, 1H);

Example 19: Synthesis of 11-oxo-10, 11-dihydrodibenzo [b,f] [1,4] thiazepine-8-carboxylic acid 5, 5-dioxide (159)—a Common Intermediate

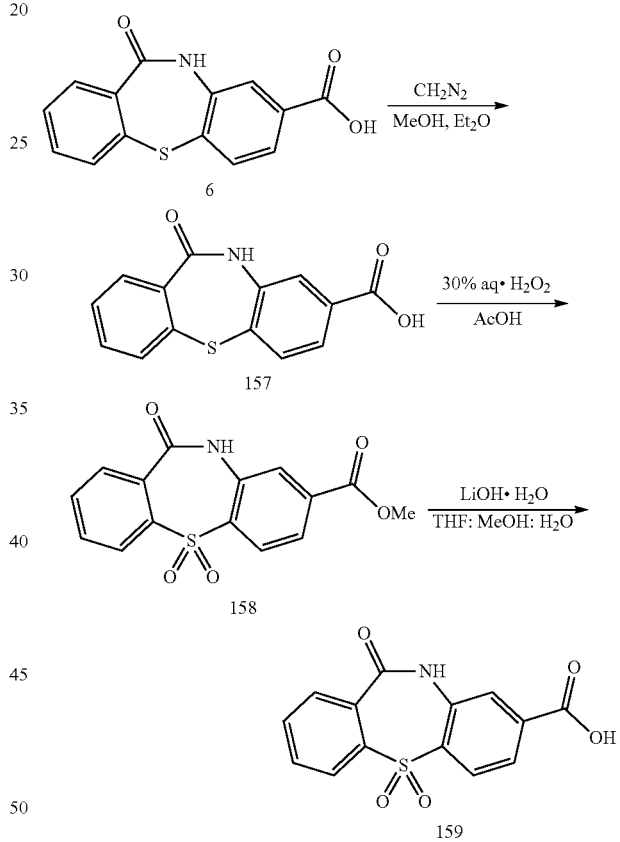

Synthesis of Methyl 11-oxo-10, 11-dihydrodibenzo [b,f] [1,4] thiazepine-8-carboxylate

157

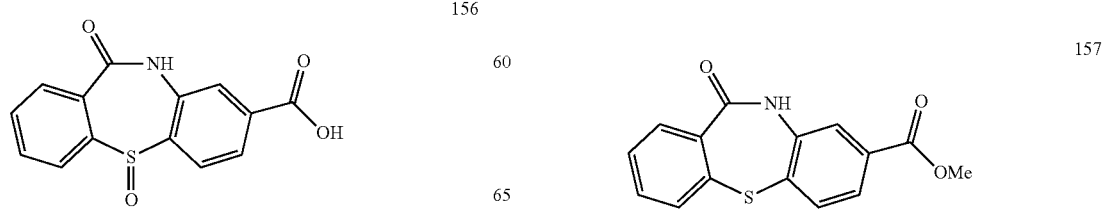

To a stirred solution of 6 (500 mg, 1.84 mmol) in MeOH:CH₂Cl₂ (1:1, 20 mL) under argon atmosphere was added CH₂N₂ (prepared in situ using N-nitrosomethyl urea (0.95 g, 9.2 mmol)+KOH (0.51 g, 9.22 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 157 (450 mg, 86%) as white solid. TLC: 30% EtOAc/hexanes ($R_f$: 0.5); ¹H-NMR (DMSO-$d_6$, 500 MHz): δ 10.82 (s, 1H), 7.82 (s, 1H), 7.75-7.69 (m, 3H), 7.58-7.63 (m, 3H), 3.82 (s, 3H).

Synthesis of Methyl 11-oxo-10, 11-dihydrodibenzo [b,f] [1,4] thiazepine-8-carboxylate 5, 5-dioxide (158)

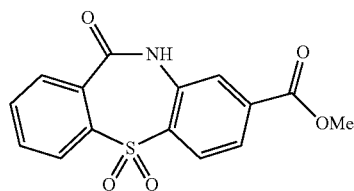

To a stirred solution of 157 (5 g, 17.54 mmol) in acetic acid (25 mL) was added 30% aqueous hydrogen peroxide (100 mL) at 0° C.; warmed to 50° C. and stirred for 72 h. The reaction was monitored by TLC; after completion of the reaction, the obtained solid was filtered, washed with water (100 mL), 10% EtOAc/hexanes (100 mL) and dried in vacuo to afford compound 158 (3.5 g, 64%) as white solid. TLC: 5% MeOH/CH₂Cl₂ ($R_f$: 0.3); 1H NMR (DMSO-$d_6$, 500 MHz): δ 11.58 (s, 1H), 8.09 (d, J=8.4 Hz, 1H), 8.01-7.95 (m, 3H), 7.93-7.83 (m, 3H), 3.88 (s, 3H).

Synthesis of 11-oxo-10, 11-dihydrodibenzo [b,f] [1,4] thiazepine-8-carboxylic acid 5, 5-dioxide (159)

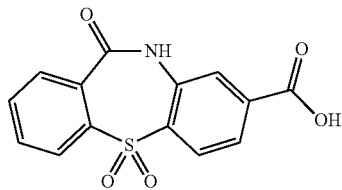

To a stirred solution of compound 158 (3.5 g, 11.04 mmol) in a mixture of THF:MeOH:H₂O (2:2:1, 25 mL) was added lithium hydroxide monohydrate (1.3 g, 33.12 mmol) portion wise for 10 min at 0° C.; warmed to RT and stirred for 3 h. The reaction was monitored by TLC; after completion of the reaction, the volatiles were removed in vacuo. The residue was diluted with water (20 mL) and acidified with 1 N HCl to pH-2. The obtained solid was filtered, washed with isopropyl alcohol (15 mL) and dried in vacuo to obtain compound 159 (2.8 g, 84%) as white solid. TLC: 5% MeOH/CH₂Cl₂ ($R_f$: 0.1); 1H NMR (DMSO-$d_6$, 400 MHz): δ 13.65 (br s, 1H), 11.55 (s, 1H), 8.07 (d, J=8.3 Hz, 1H), 8.03-7.82 (m, 6H).

Example 20: Synthesis of 5-methyl-11-oxo-10, 11-dihydro-5H-dibenzo [b,f] [1,4] diazepine-8-carboxylic acid (164)—a Common Intermediate

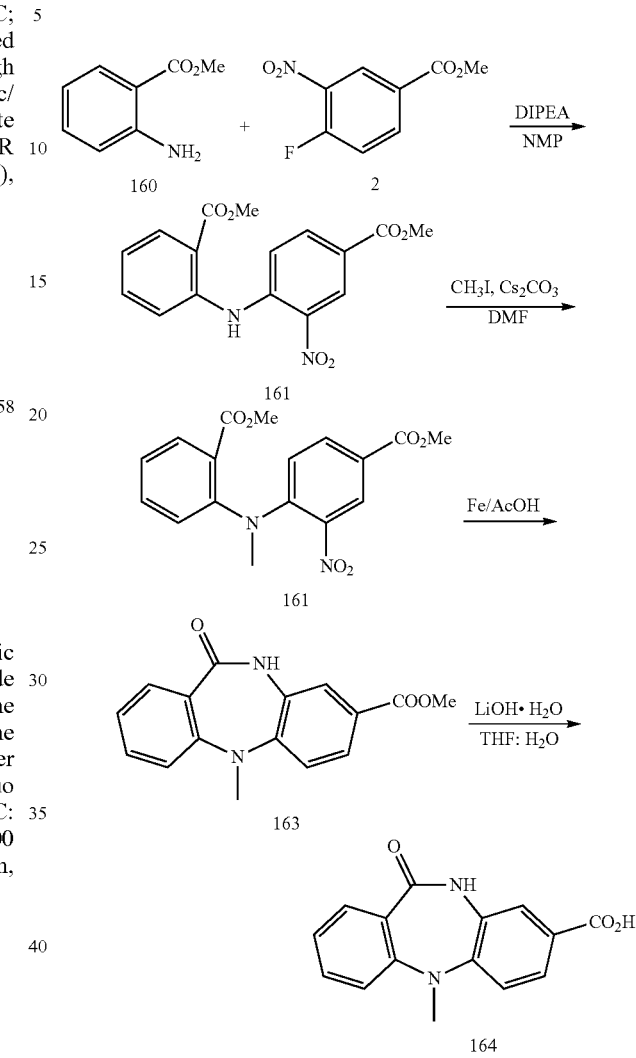

Synthesis of Methyl 4-((2-(methoxycarbonyl) phenyl) amino)-3-nitrobenzoate (161)

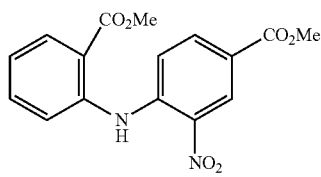

To a stirred solution of methyl 2-aminobenzoate 160 (5 g, 33.07 mmol) in NMP (13 mL) under inert atmosphere were added diisopropylethylamine (18 mL, 103.46 mmol), methyl 4-fluoro-3-nitrobenzoate 2 (9.87 g, 49.61 mmol) at RT; heated to 120° C. in a sealed tube and stirred for 24 h. The reaction was monitored by TLC; after completion of the reaction, the reaction mixture was diluted with diethyl ether (50 mL) and stirred for 1 h. The obtained solid was filtered, washed with diethyl ether (10 mL) and dried in vacuo to afford compound 161 (3.2 g, 29%) as yellow solid. TLC: 20% EtOAc/hexanes ($R_f$: 0.4); 1H NMR (DMSO-$d_6$, 400 MHz): δ 11.13 (s, 1H), 8.67 (s, 1H), 8.11-7.94 (m, 2H), 7.70-7.62 (m, 2H), 7.58 (d, J=9.0 Hz, 1H), 7.32-7.27 (m, 1H), 3.87 (s, 6H).

Synthesis of Methyl 4-((2-(methoxycarbonyl) phenyl)(methyl) amino)-3-nitrobenzoate (162)

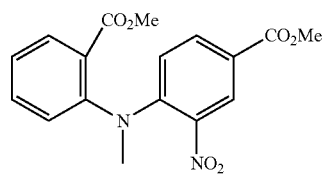

162

To a stirred solution of compound 161 (3 g, 9.09 mmol) in DMF (30 mL) under inert atmosphere were added cesium carbonate (5.9 g, 18.15 mmol), methyl iodide (0.84 mL, 13.59 mmol) at RT and stirred for 6 h. The reaction was monitored by TLC; after completion of the reaction, the reaction mixture was diluted with ice-cold water (60 mL) and extracted with EtOAc (2×100 mL). The combined organic extracts were dried over sodium sulfate, filtered and concentrated in vacuo to obtain the crude. The crude was purified through silica gel column chromatography using 20% EtOAc/hexanes to afford compound 162 (2.73 g, 88%) as yellow solid. TLC: 30% EtOAc/hexanes ($R_f$: 0.4); 1H NMR (DMSO-$d_6$, 400 MHz): δ 8.07 (s, 1H), 8.06 (d, J=7.8 Hz, 1H), 7.71 (dd, J=7.8, 1.5 Hz, 1H), 7.62 (t, J=7.3 Hz, 1H), 7.40-7.26 (m, 3H), 3.84 (s, 3H), 3.53 (s, 3H), 3.38 (s, 3H).

Synthesis of Methyl 5-methyl-11-oxo-10, 11-dihydro-5H-dibenzo [b,e] [1,4] diazepine-8-carboxylate (163)

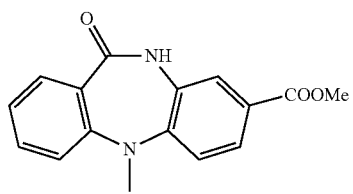

163

To a stirred solution of compound 162 (2.73 g, 7.93 mmol) in acetic acid (36 mL) under inert atmosphere was added iron powder (7 g, 127.2 mmol) at RT; heated to 80° C. and stirred for 4 h. The reaction was monitored by TLC; after completion of the reaction, the reaction mixture was diluted with CH$_2$Cl$_2$ (50 mL), stirred for 2 h and filtered through celite and the filtrate was concentrated in vacuo to obtain the crude. The crude was dissolved in CH$_2$Cl$_2$ (200 mL), washed with saturated aqueous NaHCO$_3$ solution (100 mL), brine (100 mL). The organic extract was dried over sodium sulfate, filtered and concentrated in vacuo to afford compound 163 (2 g, 91%) as an off-white solid. TLC: 30% EtOAc/hexanes ($R_f$: 0.4); $^1$H NMR (DMSO-$d_6$, 500 MHz): δ 10.33 (s, 1H), 7.68 (dd, J=8.5, 1.9 Hz, 1H), 7.65-7.61 (m, 2H), 7.50 (t, J=7.8 Hz, 1H), 7.28 (d, J=8.4 Hz, 1H), 7.21 (d, J=8.1 Hz, 1H), 7.10 (t, J=7.4 Hz, 1H), 3.80 (s, 3H), 3.33 (s, 3H).

Synthesis of 5-methyl-11-oxo-10, 11-dihydro-5H-dibenzo [b,e] [1,4] diazepine-8-carboxylic acid (164)

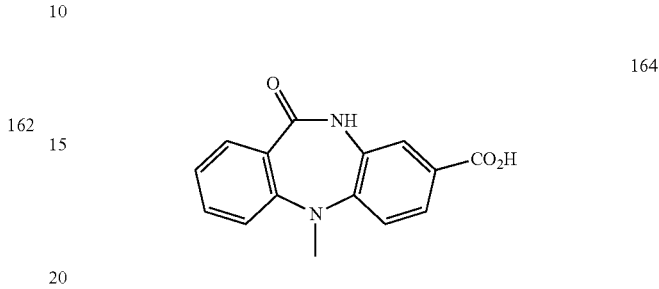

164

To a stirred solution of compound 163 (2 g, 7.09 mmol) in THF:H$_2$O (1:1, 80 mL) was added lithium hydroxide monohydrate (900 mg, 21.42 mmol) at RT and stirred for 12 h. The reaction was monitored by TLC; after completion of the reaction, the volatiles were removed in vacuo. The pH of the residue was adjusted to ~2 with 2 N HCl. The precipitated solid was filtered and dried in vacuo to afford compound 164 (1.7 g, 89%) as an off-white solid. TLC: 40% EtOAc/hexanes ($R_f$: 0.2); 1H NMR (DMSO-$d_6$, 400 MHz): δ 12.82 (br s, 1H), 10.33 (s, 1H), 7.70-7.60 (m, 3H), 7.51 (t, J=7.8 Hz, 1H), 7.27 (d, J=8.5 Hz, 1H), 7.21 (d, J=7.8 Hz, 1H), 7.11 (t, J=7.2 Hz, 1H), 3.32 (s, 3H).

Example 21: Synthesis of 5-ethyl-11-oxo-10, 11-dihydro-5H-dibenzo [b,f] [1,4] diazepine-8-carboxylic acid (167)—a Common Intermediate

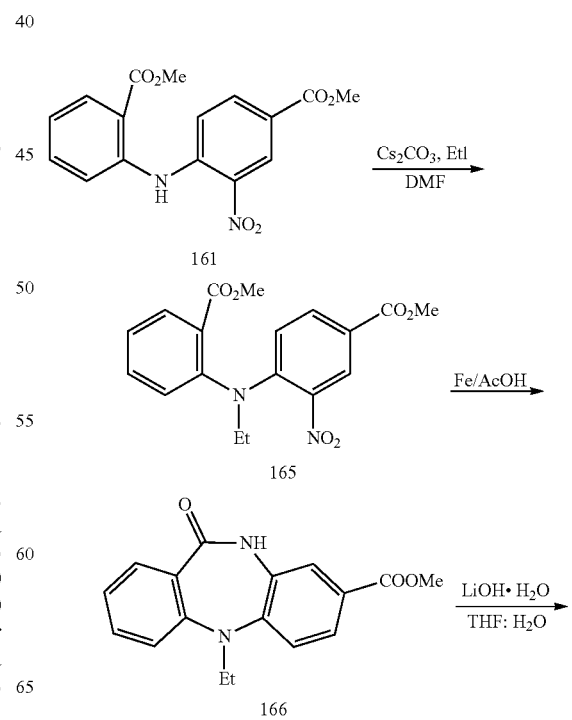

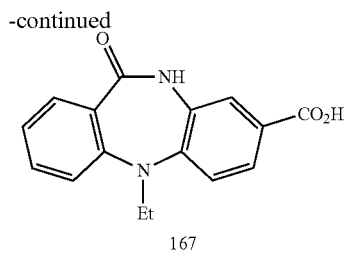

167

Synthesis of Methyl 4-(ethyl (2-(methoxycarbonyl) phenyl) amino)-3-nitrobenzoate (165)

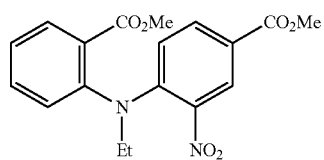

165

To a stirred solution of compound 161 (2.9 g, 8.78 mmol) in DMF (40 mL) under inert atmosphere were added cesium carbonate (6 g, 18.46 mmol), ethyl iodide (1.06 mL, 12.82 mmol) at RT and stirred for 5 h. The reaction was monitored by TLC; after completion of the reaction, the reaction mixture was diluted with ice-cold water (60 mL), extracted with EtOAc (2×100 mL). The combined organic extracts were dried over sodium sulfate, filtered and concentrated in vacuo to obtain the crude which was titurated with n-pentane (20 mL) to afford compound 165 (2.8 g, 89%) as pale yellow solid. TLC: 30% EtOAc/hexanes ($R_f$: 0.5); $^1$H NMR (DMSO-$d_6$, 500 MHz): δ 8.05 (dd, J=9.0, 2.0 Hz, 1H), 8.02 (s, 1H), 7.62-7.57 (m, 2H), 7.45 (d, J=9.0 Hz, 1H), 7.33 (d, J=8.1 Hz, 1H), 7.28 (t, J=7.5 Hz, 1H), 3.94 (q, J=7.1 Hz, 2H), 3.82 (s, 3H), 3.44 (s, 3H), 1.20 (t, J=7.1 Hz, 3H).

Synthesis of Methyl 5-ethyl-11-oxo-10, 11-dihydro-5H-dibenzo [b,e] [1,4] diazepine-8-carboxylate (166)

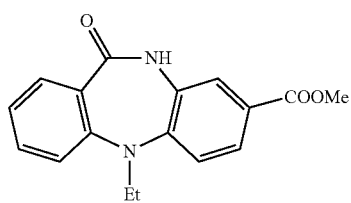

166

To a stirred solution of compound 165 (2.8 g, 7.82 mmol) in acetic acid (40 mL) under inert atmosphere was added iron powder (6.8 g, 125.1 mmol) at RT; heated to 80° C. and stirred for 4 h. The reaction was monitored by TLC; after completion of the reaction, the reaction mixture was diluted with CH$_2$Cl$_2$ (50 mL), stirred for 2 h and filtered through celite. The filtrate was concentrated in vacuo to obtain the crude. The crude was diluted with CH$_2$Cl$_2$ (200 mL), washed with saturated aqueous sodium bicarbonate solution (100 mL) and brine (100 mL). The organic extract was dried over sodium sulfate, filtered and concentrated in vacuo to afford compound 166 (2.2 g, 96%) as an off-white solid. TLC: 30% EtOAc/hexanes ($R_f$: 0.3); $^1$H NMR (DMSO-$d_6$, 500 MHz): δ 10.35 (br s, 1H), 7.70 (dd, J=8.5, 1.9 Hz, 1H), 7.67 (s, 1H), 7.62 (d, J=7.5 Hz, 1H), 7.51 (t, J=8.1 Hz, 1H), 7.29 (d, J=8.4 Hz, 1H), 7.22 (d, J=8.1 Hz, 1H), 7.12 (t, J=7.4 Hz, 1H), 3.31 (s, 5H), 1.11 (t, J=6.9 Hz, 3H).

Synthesis of 5-ethyl-11-oxo-10, 11-dihydro-5H-dibenzo [b,e] [1,4] diazepine-8-carboxylic acid (167)

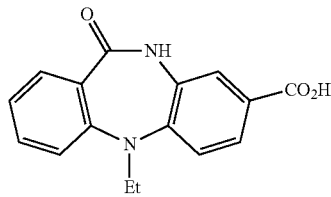

167

To a stirred solution of compound 166 (2.1 g, 7.09 mmol) in THF:H$_2$O (1:1, 60 mL) was added lithium hydroxide monohydrate (890 mg, 21.26 mmol) at RT and stirred for 12 h. The reaction was monitored by TLC; after completion of the reaction, the volatiles were removed in vacuo. The pH of the residue was acidified to ~2 with 2 N HCl. The precipitated solid was filtered, washed with water (50 mL) and dried in vacuo to afford compound 167 (1.6 g, 80%) as an off-white solid. TLC: 30% EtOAc/hexanes ($R_f$: 0.2); $^1$H NMR (DMSO-$d_6$, 400 MHz): δ 12.82 (br s, 1H), 10.33 (s, 1H), 7.69-7.59 (m, 3H), 7.53-7.48 (m, 1H), 7.24 (dd, J=19.7, 8.2 Hz, 2H), 7.12 (t, J=7.5 Hz, 1H), 3.79 (br s, 2H), 1.12 (t, J=7.0 Hz, 3H).

Example 22: Synthesis of 5-benzyl-11-oxo-10, 11-dihydro-5H-dibenzo [b,f] [1,4] diazepine-8-carboxylic acid (170)—a Common Intermediate

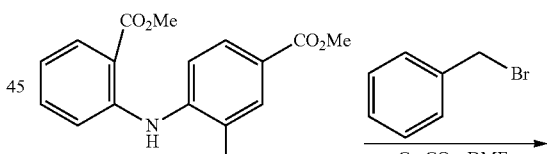

161

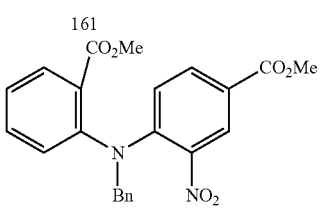

168

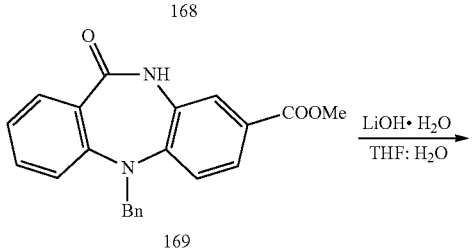

169

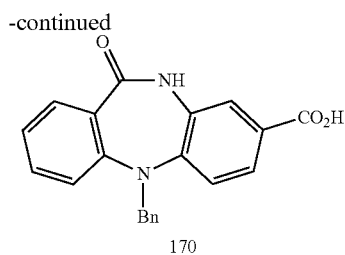

170

Synthesis of Methyl 4-(benzyl (2-(methoxycarbonyl) phenyl) amino)-3-nitrobenzoate (168)

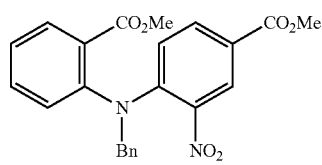

168

To a stirred solution of compound 161 (2.5 g, 7.57 mmol) in DMF (40 mL) under inert atmosphere were added cesium carbonate (4.92 g, 15.15 mmol), benzyl bromide (1.34 mL, 11.36 mmol) at RT and stirred for 16 h. The reaction was monitored by TLC; after completion of the reaction, the reaction mixture was diluted with ice-cold water (60 mL) and extracted with EtOAc (2×100 mL). The combined organic extracts were dried over sodium sulfate, filtered and concentrated in vacuo to obtain the crude. The crude was purified through silica gel column chromatography using 10% EtOAc/hexanes to afford compound 168 (3 g, 91%) as colorless thick syrup. TLC: 20% EtOAc/hexanes ($R_f$: 0.4); 1H NMR (DMSO-$d_6$, 500 MHz): δ 8.04 (s, 1H), 7.97 (dd, J=8.8, 1.9 Hz, 1H), 7.61-7.57 (m, 1H), 7.56-7.50 (m, 3H), 7.40 (t, J=8.2 Hz, 2H), 7.34 (t, J=7.7 Hz, 2H), 7.28-7.23 (m, 2H), 5.20 (s, 2H), 3.81 (s, 3H), 3.39 (s, 3H).

Synthesis of Methyl 5-benzyl-11-oxo-10, 11-dihydro-5H-dibenzo [b,e] [1,4] diazepine-8-carboxylate (169)

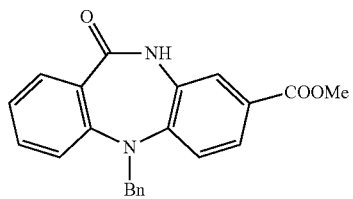

169

To a stirred solution of compound 168 (950 mg, 2.26 mmol) in acetic acid (10 mL) under inert atmosphere was added iron powder (2 g, 36.36 mmol) at RT; heated to 80° C. and stirred for 4 h. The reaction was monitored by TLC; after completion of the reaction, the reaction mixture was diluted with $CH_2Cl_2$ (50 mL), filtered through celite and the filtrate was concentrated in vacuo to obtain the crude. The crude was dissolved in $CH_2Cl_2$ (200 mL), washed with saturated aqueous sodium bicarbonate solution (100 mL) and brine (100 mL). The organic extract was dried over sodium sulfate, filtered and concentrated in vacuo to afford compound 169 (800 mg, 98%) as an off-white solid. TLC: 20% EtOAc/hexanes ($R_f$: 0.4); 1H NMR (DMSO-$d_6$, 500 MHz): δ 10.42 (s, 1H), 7.66 (s, 1H), 7.62 (d, J=8.1 Hz, 2H), 7.48-7.34 (m, 4H), 7.33-7.21 (m, 3H), 7.15 (t, J=7.2 Hz, 1H), 7.09 (t, J=7.4 Hz, 1H), 5.04 (br s, 2H), 3.79 (s, 3H).

Synthesis of 5-benzyl-11-oxo-10, 11-dihydro-5H-dibenzo [b,e] [1,4] diazepine-8-carboxylic acid (170)

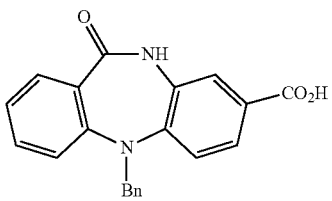

170

To a stirred solution of compound 169 (2 g, 5.58 mmol) in THF:$H_2O$ (1:1, 80 mL) was added lithium hydroxide monohydrate (703 mg, 16.73 mmol) at RT and stirred for 16 h. The reaction was monitored by TLC; after completion of the reaction, the volatiles were removed in vacuo. The pH of the residue was acidified with 6 N HCl to pH~2 and stirred for 1 h. The precipitated solid was filtered and dried in vacuo to afford compound 170 (1.5 g, 78%) as an off-white solid. TLC: 50% EtOAc/hexanes ($R_f$: 0.2); 1H NMR (DMSO-$d_6$, 500 MHz): δ 12.87 (br s, 1H), 10.39 (s, 1H), 7.65-7.55 (m, 3H), 7.47-7.21 (m, 7H), 7.16-7.04 (m, 2H), 5.02 (br s, 2H).

Example 23: Synthesis of 3-methoxy-1-oxo-10, 11-dihydrodibenzo [b,f] [1,4] thiazepine-8-carboxylic acid (P-42

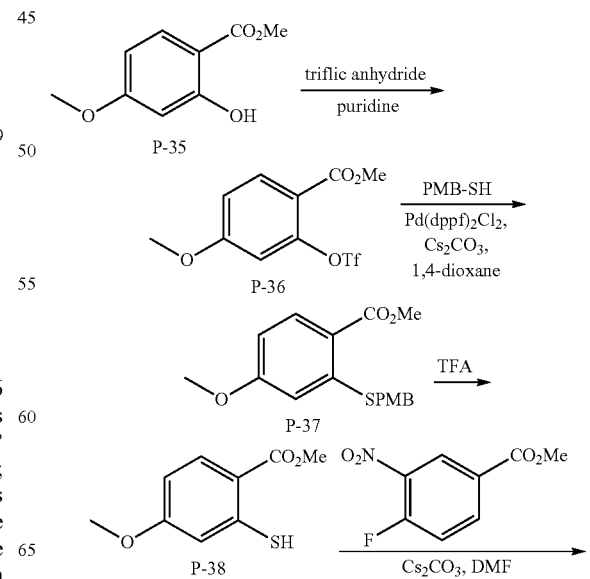

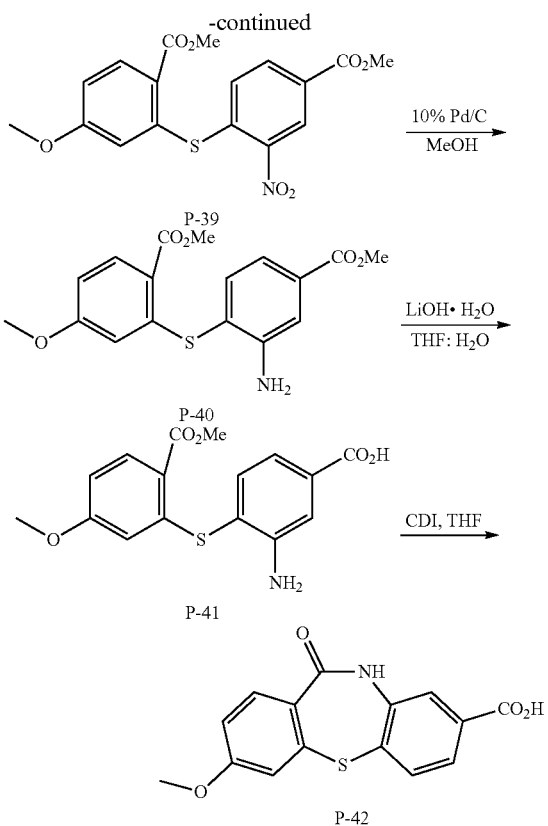

Synthesis of Methyl 4-methoxy-2-(((trifluoromethyl) sulfonyl) oxy) benzoate (P-36)

To a stirred solution of methyl 2-hydroxy-4-methoxybenzoate P-35 (1 g, 5.49 mmol) in pyridine (5 mL) under argon atmosphere was added triflic anhydride (1 mL, 6.31 mmol) drop wise at 0° C.; warmed to RT and stirred for 2 h; heated to 40° C. and stirred for 16 h. The reaction was monitored by TLC; after completion of the reaction, the volatiles were removed in vacuo. The residue was diluted with water (25 mL) and extracted with diethyl ether (2×30 mL). The combined organic extracts were washed with 1 N HCl (15 mL), water (15 mL), dried over sodium sulfate, filtered and concentrated in vacuo to obtain the crude. The crude was purified through silica gel column chromatography using 10% EtOAc/hexanes to afford compound P-36 (1.58 g, 92%) as colorless syrup. TLC: 10% EtOAc/hexanes ($R_f$: 0.6); $^1$H-NMR (CDCl$_3$, 500 MHz): δ 8.06 (d, J=9.0 Hz, 1H), 6.95 (d, J=8.5 Hz, 1H), 6.78 (s, 1H), 3.93 (s, 3H), 3.88 (s, 3H).

Synthesis of methyl-4-methoxy-2-((4-methoxybenzyl) thio) benzoate (P-37)

To a stirred solution of compound P-36 (1 g, 3.18 mmol) in 1, 4-dioxane (15 mL) under argon atmosphere were added (4-methoxyphenyl) methanethiol (539 mg, 3.50 mmol), cesium carbonate (2 g, 6.36 mmol) at RT and degassed under argon for 20 min. To this was added Pd(dppf)$_2$Cl$_2$ (233 mg, 0.31 mmol); heated to 80° C. and stirred for 8 h. The reaction was monitored by TLC; after completion of the reaction, the reaction mixture was diluted with water (20 mL) and extracted with EtOAc (2×35 mL). The combined organic extracts were dried over sodium sulfate, filtered and concentrated in vacuo to obtain the crude. The crude was purified through silica gel column chromatography using 5-7% EtOAc/hexanes to afford compound P-37 (340 mg, 30%) as an off-white solid. TLC: 10% EtOAc/hexanes ($R_f$: 0.4); $^1$H-NMR (CDCl$_3$, 500 MHz): δ 7.96 (d, J=8.5 Hz, 1H), 7.38-7.37 (m, 1H), 7.35 (d, J=9.0 Hz, 1H), 6.85 (d, J=8.0 Hz, 2H), 6.82 (s, 1H), 6.64 (d, J=8.5 Hz, 1H), 4.10 (s, 2H), 3.86 (s, 3H), 3.79 (s, 6H).

Synthesis of Methyl 2-mercapto-4-methoxybenzoate (P-38)

A stirred solution of compound P-37 (330 mg, 1.03 mmol) in trifluoroacetic acid (5 mL) under argon atmosphere was heated to reflux and stirred for 6 h. The reaction was monitored by TLC; after completion of the reaction, the volatiles were removed in vacuo to obtain the crude compound P-38 (340 mg) as brown syrup which was carried to the next step without any further purification. TLC: 10% EtOAc/hexanes ($R_f$: 0.7).

Synthesis of Methyl 4-methoxy-2-((4-(methoxycarbonyl)-2-nitrophenyl) thio) benzoate (P-39)

To a stirred solution of compound P-38 (200 mg, 1.01 mmol) in DMF (5 mL) under argon atmosphere were added methyl 4-fluoro-3-nitrobenzoate (201 mg, 1.01 mmol), cesium carbonate (656 mg, 2.02 mmol) at RT; heated to 40° C. and stirred for 2 h. The reaction was monitored by TLC; after completion of the reaction, the volatiles were removed in vacuo. The residue was diluted with water (20 mL) and extracted with EtOAc (2×25 mL). The combined organic extracts were washed with water (20 mL), dried over sodium sulfate, filtered and concentrated in vacuo to obtain the crude. The crude was purified through silica gel column chromatography using 15% EtOAc/hexanes to afford compound P-39 (280 mg, 74%) as yellow solid. TLC: 20% EtOAc/hexanes ($R_f$: 0.4); $^1$H-NMR (CDCl$_3$, 400 MHz): δ 8.84 (d, J=7.2 Hz, 1H), 8.03 (d, J=8.8 Hz, 1H), 7.96-7.92 (m, 1H), 7.78 (s, 1H), 7.17-7.12 (m, 1H), 7.08-6.93 (m, 1H), 3.96-3.93 (m, 3H), 3.85 (s, 3H), 3.80-3.74 (m, 3H).

Synthesis of Methyl 2-((2-amino-4-(methoxycarbonyl) phenyl) thio)-4-methoxybenzoate (P-40)

To a stirred solution of compound P-39 (270 mg, 0.71 mmol) in MeOH (10 mL) under argon atmosphere was added 10% Pd/C (80 mg) at RT and stirred under hydrogen atmosphere (balloon pressure) for 16 h. The reaction was monitored by TLC; after completion of the reaction, the reaction mixture was filtered through celite, washed with CH$_2$Cl$_2$ (2×25 mL) and the filtrate was concentrated in vacuo to obtain the crude. The crude was purified through silica gel column chromatography using 15% EtOAc/hexanes to afford compound P-40 (180 mg, 79%) as colorless syrup. TLC: 20% EtOAc/hexanes ($R_f$: 0.5); $^1$H-NMR (CDCl$_3$, 400 MHz): δ 8.03 (d, J=8.8 Hz, 1H), 7.54-7.40 (m, 1H), 7.08 (d, J=8.8 Hz, 1H), 6.79-6.72 (m, 1H), 6.66-6.63 (m, 1H), 6.21-6.14 (m, 1H), 3.95-3.88 (m, 5H), 3.85 (s, 3H), 3.65 (s, 3H).

Synthesis of 2-((2-amino-4-carboxyphenyl) thio)-4-methoxybenzoic acid (P-41)

To a stirred solution of compound P-40 (160 mg, 0.46 mmol) in THF:H$_2$O (2:1, 6 mL) under argon atmosphere was added lithium hydroxide monohydrate (96 mg, 2.30 mmol) at RT and stirred for 16 h. The reaction was monitored by TLC; after completion of the reaction, the volatiles were removed in vacuo, diluted with water (20 mL), acidified with 1 N HCl to pH-6. The obtained precipitate was filtered and dried in vacuo to afford compound P-41 (85 mg, crude) as an off-white solid. TLC: 50% EtOAc/hexanes (R$_f$: 0.2); $^1$H-NMR (DMSO-d$_6$, 400 MHz): δ 12.84 (br s, 2H), 7.95 (d, J=8.8 Hz, 1H), 7.44 (s, 1H), 7.40 (d, J=8.0 Hz, 1H), 6.13 (s, 1H), 5.58 (br s, 2H), 3.80-3.69 (m, 2H), 3.60 (s, 3H).

Synthesis of 3-methoxy-11-oxo-10, 11-dihydrodibenzo [b,f] [1,4] thiazepine-8-carboxylic acid (P-42)

To a stirred solution of compound 41 (80 mg, 0.25 mmol) in THF (8 mL) under argon atmosphere was added CDI (203 mg, 1.25 mmol) at 0° C.; warmed to RT and stirred for 16 h. The reaction was monitored by TLC; after completion of the reaction, the volatiles were removed in vacuo, diluted with water (20 mL), acidified with dilute HCl. The obtained precipitate was filtered and dried in vacuo to afford compound P-42 (50 mg, crude) as an off-white solid. TLC: 5% MeOH/CH$_2$Cl$_2$ (R$_f$: 0.3); $^1$H-NMR (DMSO-d$_6$, 400 MHz): δ 13.18 (br s, 1H), 10.64 (s, 1H), 7.77 (s, 1H), 7.66 (s, 2H), 7.16-7.07 (m, 1H), 7.01 (d, J=8.8 Hz, 1H), 6.82-6.79 (m, 1H), 3.80 (s, 3H).

Example 24: Synthesis of 2-methyl-11-oxo-10, 11-dihydrodibenzo [b,f] [1,4] thiazepine-8-carboxylic acid (P-51)

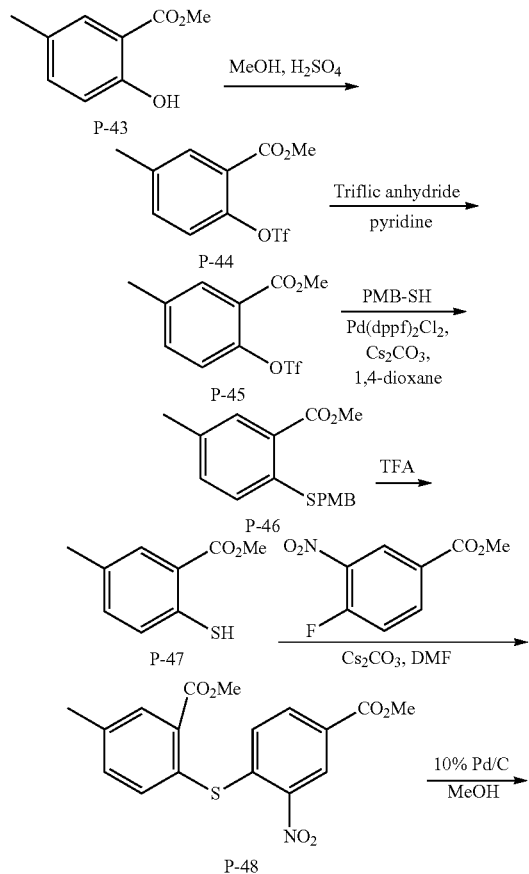

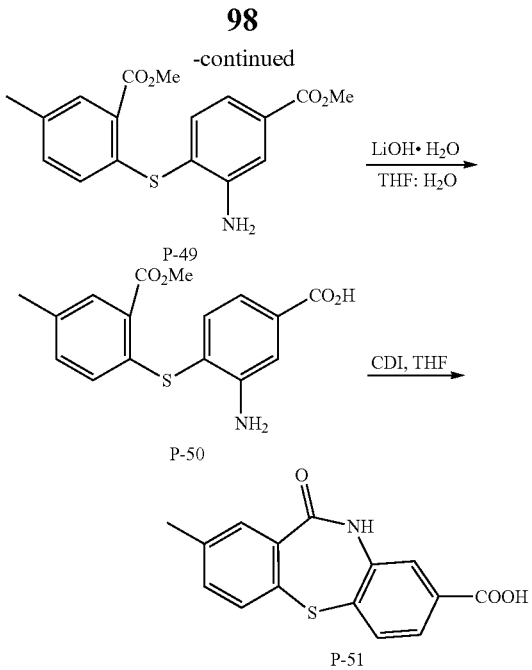

Synthesis of Methyl 2-hydroxy-5-methylbenzoate (P-44)

To a stirred solution of 2-hydroxy-5-methylbenzoic acid P-43 (2 g, 13.15 mmol) in MeOH (65 mL) under argon atmosphere was added sulphuric acid (0.65 mL) at RT; heated to reflux and stirred for 20 h. The reaction was monitored by TLC; after completion of the reaction, the volatiles were removed in vacuo. The residue was diluted with ice water (50 mL) and extracted with ether (3×40 mL). The combined organic extracts were washed with 10% aqueous NaHCO$_3$ solution (until the pH becomes neutral), dried over sodium sulfate, filtered and concentrated in vacuo to obtain compound P-44 (2 g, 92%) as colorless liquid. TLC: 10% EtOAc/hexanes (R$_f$: 0.7); $^1$H-NMR (CDCl$_3$, 500 MHz): δ 10.57 (s, 1H), 7.65 (s, 1H), 7.29 (d, J=7.5 Hz, 1H), 6.90 (d, J=8.0 Hz, 1H), 3.96 (s, 3H), 2.30 (s, 3H).

Synthesis of Methyl 5-methyl-2-(((trifluoromethyl) sulfonyl) oxy) benzoate (P-45)

To a stirred solution of compound P-44 (2 g, 12.04 mmol) in pyridine (8 mL) under argon atmosphere was added trifluoro methane sulfonic anhydride (2.3 mL, 13.85 mmol) at 0° C.; warmed to RT and stirred for 2 h; heated to 40° C. and stirred for 8 h. The reaction was monitored by TLC; after completion of the reaction, the volatiles were removed in vacuo. The residue was diluted with water (50 mL) and extracted with ether (3×50 mL). The combined organic extracts were washed with water (50 mL), brine (50 mL), 1 N HCl (40 mL), dried over sodium sulfate, filtered and concentrated in vacuo to obtain the crude. The crude was purified through silica gel column chromatography using 3-5% EtOAc/hexanes to afford compound P-45 (2.6 g, 72%) as colorless liquid. TLC: 7% EtOAc/hexanes (R$_f$: 0.6); $^1$H-NMR (CDCl$_3$, 500 MHz): δ 7.88 (s, 1H), 7.40 (d, J=8.5 Hz, 1H), 7.17 (d, J=8.0 Hz, 1H), 3.96 (s, 3H), 2.42 (s, 3H).

Synthesis of Methyl 2-((4-methoxybenzyl) thio)-5-methylbenzoate (P-46)

To a stirred solution of compound P-45 (1 g, 3.35 mmol) in 1, 4-dioxane (15 mL) under argon atmosphere were added (4-methoxyphenyl) methanethiol (568 mg, 3.69 mmol), cesium carbonate (2.18 g, 6.71 mmol) at RT and degassed for 20 min. To this was added Pd(dppf)$_2$Cl$_2$ (61.4 mg, 0.083 mmol); heated to 110° C. and stirred for 16 h. The reaction was monitored by TLC; after completion of the reaction, the reaction mixture was diluted with water (30 mL) and extracted with EtOAc (2×40 mL). The combined organic extracts were dried over sodium sulfate, filtered and concentrated in vacuo to obtain the crude. The crude was purified through silica gel column chromatography using 3-5% EtOAc/hexanes to afford compound P-46 (290 mg, 29%) as yellow solid. TLC: 10% EtOAc/hexanes (R$_f$: 0.5); $^1$H-NMR (CDCl$_3$, 400 MHz): δ 7.75 (s, 1H), 7.30 (d, J=8.8 Hz, 2H), 7.22-7.21 (m, 2H), 6.83 (d, J=8.8 Hz, 2H), 4.09 (s, 2H), 3.89 (s, 3H), 3.79 (s, 3H), 2.32 (s, 3H).

Synthesis of Methyl 2-mercapto-5-methylbenzoate (P-47)

A stirred solution of compound P-46 (200 mg, 0.66 mmol) in trifluoro acetic acid (10 mL) at RT under argon atmosphere was heated to 70-75° C. and stirred for 4 h. The reaction was monitored by TLC; after completion of the reaction, the volatiles were removed in vacuo to afford compound P-47 (100 mg, crude) as yellow syrup. TLC: 10% EtOAc/hexanes (R$_f$: 0.7); $^1$H-NMR (DMSO-d$_6$, 500 MHz): δ 7.74 (s, 1H), 7.44 (d, J=8.0 Hz, 1H), 7.26 (d, J=7.5 Hz, 1H), 5.20 (s, 1H), 3.82 (s, 3H), 2.28 (s, 3H).

Synthesis of Methyl 2-((4-(methoxycarbonyl)-2-nitrophenyl) thio)-5-methylbenzoate (P-48)

To a stirred solution of compound P-47 (100 mg, 0.50 mmol) in DMF (5 mL) under argon atmosphere were added methyl 4-fluoro-3-nitrobenzoate (100 mg, 0.55 mmol), cesium carbonate (326 mg, 1.00 mmol) at RT; heated to 60° C. and stirred for 2 h. The reaction was monitored by TLC; after completion of the reaction, the volatiles were removed in vacuo. The residue was diluted with water (30 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 10% EtOAc/hexanes to afford compound P-48 (100 mg, 55%) as yellow solid. TLC: 10% EtOAc/hexanes (R$_f$: 0.3); $^1$H-NMR (DMSO-d$_6$, 400 MHz): δ 8.63 (s, 1H), 8.03 (d, J=8.8 Hz, 1H), 7.78 (s, 1H), 7.61 (d, J=7.6 Hz, 1H), 7.55-7.53 (m, 1H), 6.99 (d, J=8.4 Hz, 1H), 3.87 (s, 3H), 3.68 (s, 3H), 2.43 (s, 3H).

Synthesis of Methyl 2-((2-amino-4-(methoxycarbonyl) phenyl) thio)-5-methylbenzoate (P-49)

To a stirred solution of compound P-48 (400 mg, 1.10 mmol) in MeOH (20 mL) under argon atmosphere was added 10% Pd/C (200 mg) at RT and stirred under hydrogen atmosphere (balloon pressure) for 24 h. The reaction was monitored by TLC; after completion of the reaction, the reaction mixture was filtered through celite and washed with 50% MeOH/CH$_2$Cl$_2$ (2×25 mL). The combined organic extracts were dried over sodium sulfate, filtered and concentrated in vacuo to obtain the crude. The crude was purified through silica gel column chromatography using 7-10% EtOAc/hexanes to afford compound P-49 (220 mg, 60%) as pale yellow solid. TLC: 20% EtOAc/hexanes (R$_f$: 0.5); $^1$H-NMR (DMSO-d$_6$, 500 MHz): δ 7.77 (s, 1H), 7.44 (s, 1H), 7.40 (d, J=7.5 Hz, 1H), 7.21 (d, J=8.0 Hz, 1H), 7.16-7.14 (m, 1H), 6.57 (d, J=8.5 Hz, 1H), 5.63 (br s, 2H), 3.87 (s, 3H), 3.84 (s, 3H), 2.27 (s, 3H).

Synthesis of 2-((2-amino-4-carboxyphenyl) thio)-5-methylbenzoic acid (P-50)

To a stirred solution of compound P-49 (220 mg, 0.66 mmol) in THF:H$_2$O (5:1, 6 mL) under argon atmosphere was added lithium hydroxide monohydrate (139 mg, 3.32 mmol) at RT and stirred for 20 h. The reaction was monitored by TLC; after completion of the reaction, the volatiles were removed in vacuo. The residue was diluted with water (15 mL) and acidified with 6 N HCl to pH-4. The precipitated solid was filtered and dried in vacuo to afford compound P-50 (110 mg, 55%) as an off-white solid. TLC: 20% EtOAc/hexanes (R$_f$: 0.2); $^1$H-NMR (DMSO-d$_6$, 500 MHz): δ 12.96 (br s, 2H), 7.76 (s, 1H), 7.42 (s, 1H), 7.37 (d, J=8.0 Hz, 1H), 7.18 (d, J=8.0 Hz, 1H), 7.15-7.13 (m, 1H), 6.54 (d, J=8.0 Hz, 1H), 5.54 (br s, 2H), 2.26 (s, 3H).

Synthesis of 2-methyl-11-oxo-10, 11-dihydrodibenzo [b,f] [1,4] thiazepine-8-carboxylic acid (P-51)

To a stirred solution of compound P-50 (110 mg, 0.36 mmol) in THF (10 mL) under argon atmosphere was added CDI (176 mg, 1.08 mmol) at RT and stirred for 16 h. The reaction was monitored by TLC; after completion of the reaction, the volatiles were removed in vacuo. The residue was diluted with ice cold water (20 mL) and acidified with 6 N HCl to pH-4. The precipitated solid was filtered and dried in vacuo to afford compound P-51 (60 mg, 58%) as white solid. TLC: 10% MeOH/CH$_2$Cl$_2$ (R$_f$: 0.6); $^1$H-NMR (DMSO-d$_6$, 400 MHz): δ 13.21 (br s, 1H), 10.76 (s, 1H), 7.76 (s, 1H), 7.65 (s, 2H), 7.50 (s, 1H), 7.41 (d, J=8.0 Hz, 1H), 7.30 (d, J=8.0 Hz, 1H), 2.29 (s, 3H).

Example 25: Synthesis of 3-methyl-11-oxo-10, 11-dihydrodibenzo [b,f] [1,4] thiazepine-8-carboxylic acid (P-8)

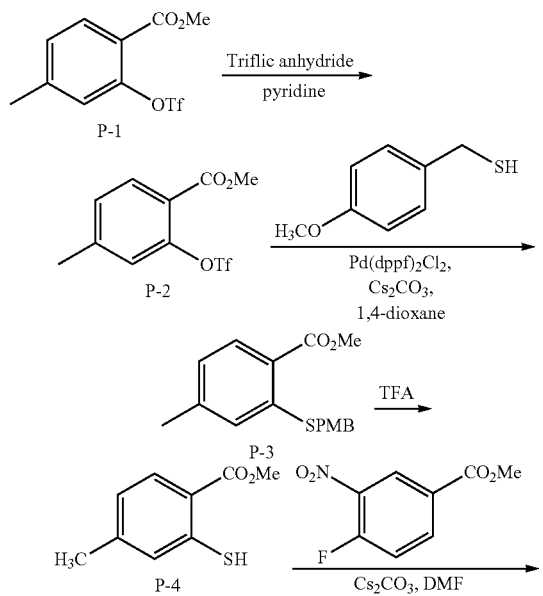

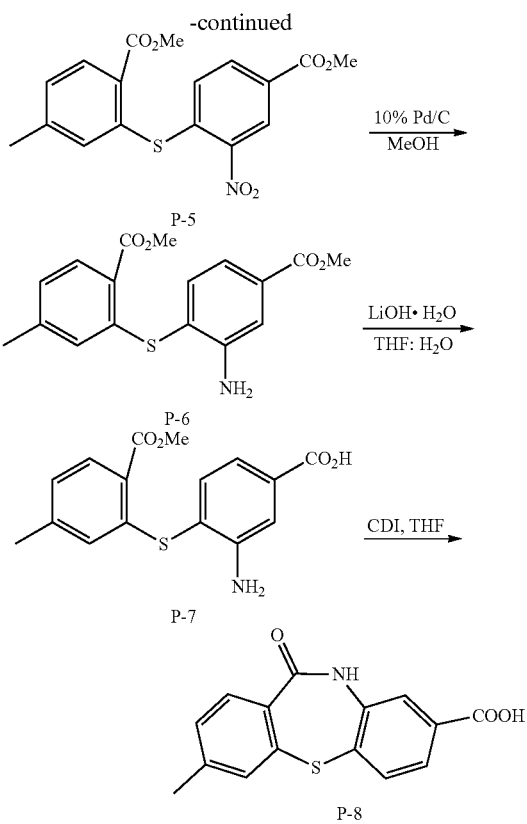

Synthesis of Methyl 4-methyl-2-(((trifluoromethyl)sulfonyl) oxy) benzoate (P-2)

To a stirred solution of methyl 2-hydroxy-4-methylbenzoate P-1 (950 mg, 5.70 mmol) in pyridine (9.5 mL) under argon atmosphere was added triflic anhydride (1.05 mL, 6.20 mmol) drop wise at 0° C.; warmed to RT and stirred for 16 h. The reaction was monitored by TLC; after completion of the reaction, the reaction mixture was acidified with 6 N HCl and extracted with diethyl ether (2×50 mL). The combined organic extracts were dried over sodium sulfate, filtered and concentrated in vacuo to obtain the crude. The crude was purified through silica gel column chromatography using 2% EtOAc/hexanes to afford compound P-2 (1.2 g, 71%) as colorless liquid. TLC: 10% EtOAc/hexanes ($R_f$: 0.7); $^1$H-NMR (CDCl$_3$, 400 MHz): δ 7.98 (d, J=8.0 Hz, 1H), 7.28 (d, J=8.0 Hz, 1H), 7.09 (s, 1H), 3.94 (s, 3H), 2.45 (s, 3H).

Synthesis of Methyl 2-((4-methoxybenzyl) thio)-4-methylbenzoate (P-3)

To a stirred solution of compound 2 (600 mg, 2.01 mmol) in 1,4-dioxane (12 mL) under argon atmosphere were added (4-methoxyphenyl) methanethiol (341 mg, 2.21 mmol), cesium carbonate (1.3 g, 4.02 mmol) at RT and degassed under argon for 20 min. To this was added Pd(dppf)$_2$Cl$_2$ (36.8 mg, 0.05 mmol); heated to 100° C. and stirred for 48 h. The reaction was monitored by TLC; after completion of the reaction, the reaction mixture was diluted with water (25 mL) and extracted with EtOAc (2×35 mL). The combined organic extracts were dried over sodium sulfate, filtered and concentrated in vacuo to obtain the crude. The crude was purified through silica gel column chromatography using 3% EtOAc/hexanes to afford compound 3 (200 mg, 33%) as sticky solid. TLC: 10% EtOAc/hexanes ($R_f$: 0.4); $^1$H-NMR (CDCl$_3$, 500 MHz): δ 7.85 (d, J=8.5 Hz, 1H), 7.32 (d, J=8.0 Hz, 2H), 7.14 (s, 1H), 6.94 (d, J=8.5 Hz, 1H), 6.84 (d, J=8.0 Hz, 2H), 4.10 (s, 2H), 3.86 (s, 3H), 3.78 (s, 3H), 2.34 (s, 3H).

Synthesis of Methyl 2-mercapto-4-methylbenzoate (P-4)

A stirred solution of compound P-3 (200 mg, 0.65 mmol) in trifluoro acetic acid (4 mL) under argon atmosphere at RT was heated to 80° C. and stirred for 4 h. The reaction was monitored by TLC; after completion of the reaction, the volatiles were removed in vacuo to obtain the crude compound P-4 (115 mg) which was carried to the next step without any further purification. TLC: 10% EtOAc/hexanes ($R_f$: 0.8).

Synthesis of Methyl 2-((4-(methoxycarbonyl)-2-nitrophenyl) thio)-4-methylbenzoate (P-5)

To a stirred solution of methyl 4-fluoro-3-nitrobenzoate (120 mg, 0.60 mmol) in DMF (4 mL) under argon atmosphere were added compound P-4 (115 mg, crude), cesium carbonate (392 mg, 1.20 mmol) at RT; heated to 60° C. and stirred for 2 h. The reaction was monitored by TLC; after completion of the reaction, the reaction mixture was diluted with water (20 mL) and extracted with EtOAc (2×35 mL). The combined organic extracts were dried over sodium sulfate, filtered and concentrated in vacuo to obtain the crude. The crude was purified through silica gel column chromatography using 10% EtOAc/hexanes to afford compound P-5 (120 mg, 55%) as yellow solid. TLC: 15% EtOAc/hexanes ($R_f$: 0.7); $^1$H-NMR (CDCl$_3$, 400 MHz): δ 8.85 (s, 1H), 7.95-7.89 (m, 2H), 7.46 (s, 1H), 7.38 (d, J=8.8 Hz, 1H), 6.93 (d, J=8.4 Hz, 1H), 3.93 (s, 3H), 3.76 (s, 3H), 2.42 (s, 3H).

Synthesis of Methyl 2-((2-amino-4-(methoxycarbonyl) phenyl) thio)-4-methylbenzoate (P-6)

To a stirred solution of compound P-5 (120 mg, 0.33 mmol) in MeOH (10 mL) under argon atmosphere was added 10% Pd/C (60 mg) at RT and stirred under hydrogen atmosphere (balloon pressure) for 16 h. The reaction was monitored by TLC; after completion of the reaction, the reaction mixture was filtered through celite, washed with n-pentane (2×5 mL) and dried in vacuo to afford compound P-6 (90 mg, 82%) as yellow sticky solid. TLC: 15% EtOAc/hexanes ($R_f$: 0.5); $^1$H-NMR (DMSO-d$_6$, 400 MHz): δ 7.86 (d, J=8.0 Hz, 1H), 7.45 (s, 1H), 7.40 (d, J=8.0 Hz, 1H), 7.15 (d, J=8.0 Hz, 1H), 7.05 (d, J=8.0 Hz, 1H), 6.44 (s, 1H), 5.65 (br s, 2H), 3.85-3.84 (m, 6H), 2.13 (s, 3H).

Synthesis of 2-((2-amino-4-carboxyphenyl) thio)-4-methylbenzoic acid (P-7)

To a stirred solution of compound P-6 (90 mg, 0.27 mmol) in THF:H$_2$O (2:1, 3 mL) under argon atmosphere was added lithium hydroxide monohydrate (56 mg, 1.35 mmol) at RT and stirred for 5 h. The reaction was monitored by TLC; after completion of the reaction, the reaction mixture was diluted with water (15 mL) and extracted with EtOAc (2×20 mL). The aqueous layer was acidified with 2 N HCl, the obtained solid was filtered, washed with n-hexane (2×5 mL) and dried in vacuo to afford compound P-7 (60 mg, 73%) as an off-white solid. TLC: 10% MeOH/CH$_2$Cl$_2$ (R$_f$: 0.2); $^1$H-NMR (DMSO-d$_6$, 500 MHz): δ 12.95 (br s, 2H), 7.85 (d, J=8.0 Hz, 1H), 7.44 (s, 1H), 7.38 (d, J=8.0 Hz, 1H), 7.15 (d, J=7.5 Hz, 1H), 7.02 (d, J=8.0 Hz, 1H), 6.42 (s, 1H), 5.57 (br s, 2H), 2.13 (s, 3H).

Synthesis of 3-methyl-11-oxo-10, 11-dihydrodibenzo [b,f] [1,4] thiazepine-8-carboxylic acid (P-8)

To a stirred solution of compound P-7 (60 mg, 0.19 mmol) in THF (4 mL) under argon atmosphere was added CDI (96 mg, 0.59 mmol) at RT and stirred for 16 h. The reaction was monitored by TLC; after completion of the reaction, the volatiles were removed in vacuo, diluted with water (20 mL), acidified with dil. HCl to pH-3. The obtained precipitate was filtered and dried in vacuo to afford compound P-8 (45 mg, 80%) as an off-white solid. TLC: 10% MeOH/CH$_2$Cl$_2$ (R$_f$: 0.3); $^1$H-NMR (DMSO-d$_6$, 400 MHz): δ 13.12 (br s, 1H), 10.72 (s, 1H), 7.76 (d, J=8.0 Hz, 2H), 7.59 (d, J=8.0 Hz, 2H), 7.37 (s, 1H), 7.26 (s, 1H), 2.30 (s, 3H).

Example 26: Preparation of Compounds

Acids similar to compound 6 (compounds 14, 21, 28, 35, 42, 50, 55, 62, 70, 76, 82, 88, 97, 135, 140, 145, 150, 155, 156, 159, 164, 167, 170, P-8, P-42, P-51) were synthesized as mentioned above and converted to final products either using commercially available amines or by using prepared amines employing Procedures A, B, C, D, E, F, G, H and the results are captured in Table 1.
Procedure A:

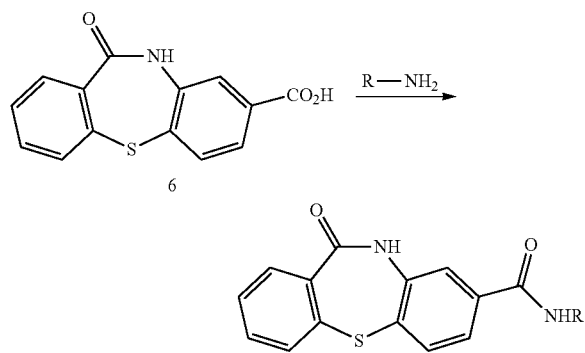

To a stirred solution of 6 (50 mg, 0.18 mmol) in DMF (3 mL) under argon atmosphere were added EDCI.HCl (50 mg, 0.22 mmol), HOBt (35 mg, 0.22 mmol), 2-(5-methyl-1, 3, 4-thiadiazol-2-yl) ethan-1-amine hydrochloride 187 (50 mg, 0.22 mmol) and diisopropyl ethyl amine (0.1 mL, 0.55 mmol) at 0° C.; warmed to RT and stirred for 16 h. The reaction was monitored by TLC; after completion of the reaction, the reaction mixture was diluted with water (20 mL) and stirred for 1 h. The crude was extracted with EtOAc or the precipitated material was either directly dried in vacuo or triturated or purified through silica gel column chromatography to afford the desired compound.
Procedure B:

To a stirred solution of 6 (40 mg, 0.14 mmol) in DMF (4 mL) under argon atmosphere were added pyridin-3-amine 182 (15 mg, 0.16 mmol), HATU (84 mg, 0.22 mmol), diisopropyl ethyl amine (0.05 mL, 0.29 mmol) at 0° C.; warmed to RT and stirred for 16 h. The reaction was monitored by TLC; after completion of the reaction, the reaction mixture was diluted with ice cold water (15 mL), the obtained precipitate was filtered, or extracted with EtOAc (2×30 mL). The combined organic extracts were dried over sodium sulfate, filtered, concentrated in vacuo to obtain the crude. The crude was extracted with EtOAc or the precipitated material was directly dried in vacuo, triturated or purified through silica gel column chromatography to afford the desired compound.
Procedure C:

To a stirred solution of compound 35 (50 mg, 0.17 mmol) in CH$_2$Cl$_2$ (5 mL) were added oxalyl chloride (0.03 mL, 0.34 mmol) or (0.06 mL, 0.69 mmol), DMF (0.01 mL) under argon atmosphere at 0° C.; warmed to 10° C. and stirred for 2-3 h. After completion of the reaction, the volatiles were removed in vacuo to obtain the crude. The crude was carried to the next step without further purification.

To a stirred solution of crude acid chloride (70 mg, crude) in CH$_2$Cl$_2$ (5 mL) under argon atmosphere were added 2-chloro-4-fluoroaniline 184 (25 mg, 0.17 mmol) and pyridine (0.07 mL, 0.86 mmol) at 0° C.; warmed to RT and stirred for 16 h. The reaction was monitored by TLC; after completion of the reaction, the reaction mixture was diluted with water (20 mL) and extracted with CH$_2$Cl$_2$ (2×30 mL). The combined organic extracts were washed with 1 N HCl (20 mL), 10% NaHCO$_3$ solution (30 mL), brine (15 mL) dried over sodium sulfate, filtered and concentrated in vacuo to obtain crude. The precipitated material was either directly dried in vacuo or triturated or purified through silica gel column chromatography/preparative HPLC or by acid-base treatment to afford the desired compound.
Procedure D:

To a stirred solution of 6 (40 mg, 0.14 mmol) in DMF (3 mL) under argon atmosphere was added CDI (71.7 mg, 0.17 mmol) at 0° C.; warmed to RT and stirred for 2 h. To this were added (4-(trifluoromethoxy) phenyl) methanamine 172 (33.8 mg, 0.17 mmol), and diisopropyl ethyl amine (0.05 mL, 0.29 mmol) and stirred for 16 h. The reaction was monitored by TLC; after completion of the reaction, the reaction mass was diluted with water (15 mL) and stirred for 1 h. The precipitate was filtered or extracted with EtOAc or CH$_2$Cl$_2$ and the obtained solid was dried in vacuo or purified by column chromatography or triturated to afford the desired product.
Procedure E:

A stirred solution of 6 (40 mg, 0.14 mmol) in thionyl chloride (1 mL) under argon atmosphere was heated to 90° C. and stirred for 1 h. The reaction was monitored by TLC; after completion of the reaction, the volatiles were removed in vacuo to obtain acid chloride (50 mg, crude) which was carried to the next step without further purification. To a stirred solution of 2-amino pyridine 181 (15 mg, 0.16 mmol) in CH$_2$Cl$_2$ (5 mL) under argon atmosphere were added pyridine (0.035 mL), acid chloride (50 mg, crude) at 0° C.; warmed to RT and stirred for 16 h. The reaction was monitored by TLC; after completion of the reaction, the volatiles were removed in vacuo to obtain the crude which was purified through silica gel column chromatography using 2% MeOH/CH$_2$Cl$_2$ to afford the desired product.
Procedure F:

To a stirred solution of compound 35 (50 mg, 0.17 mmol) in CH$_2$Cl$_2$ (5 mL) under argon atmosphere were added ethyl 2-amino-2-(pyridin-2-yl) acetate hydrochloride 249 (26 mg, 0.17 mmol), propylphosphonic anhydride (~50% solution in EtOAc, 0.22 mL, 0.34 mmol), NMM (0.037 mL, 0.34 mmol) at 0° C.; warmed to RT and stirred for 16 h. The reaction was monitored by TLC; after completion of the reaction, the volatiles were removed in vacuo and diluted with water (20 mL) or the pH of the reaction mixture was adjusted to ~8 and extracted with $CH_2Cl_2$ (2×30 mL). The combined organic extracts were dried over sodium sulfate, filtered and concentrated in vacuo to obtain the crude. The crude was purified either through silica gel column chromatography or triturated to afford the desired product.

Procedure G:

To a stirred solution of compound 159 (100 mg, 0.33 mmol) in $CH_3CN$ (2 mL) under argon atmosphere was added thiazol-2-amine 231 (36 mg, 0.36 mmol), propylphosphonic anhydride (~50% solution in EtOAc, 0.8 mL, 1.32 mmol) and NMM (0.14 mL, 1.32 mmol) at RT in a microwave vial and heated at 100° C. and stirred for 1 h. The reaction was monitored by TLC; after completion of the reaction, the volatiles were removed in vacuo and diluted with water (20 mL) and the precipitated solid was filtered. The obtained solid was either directly dried in vacuo or titurated or purified by column chromatography to afford the desired product.

Procedure H:

To a stirred solution of compound 159 (100 mg, 0.33 mmol) in $CH_2Cl_2$ (12 mL) under argon atmosphere were added EDCI.HCl (188.8 mg, 0.98 mmol), 6-fluorobenzo[d]thiazol-2-amine 241 (61 mg, 0.36 mmol) and DMAP (120.7 mg, 0.98 mmol) at RT and stirred for 16 h. The reaction was monitored by TLC; after completion of the reaction, the precipitated solid was filtered washed with water and titurated to afford the desired product.

Representative Commercially Available Amines Used for Synthesis

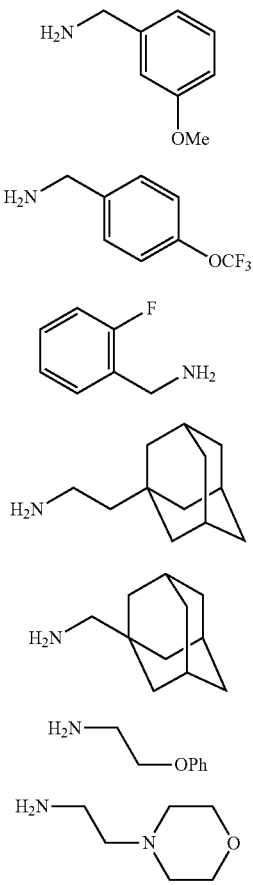

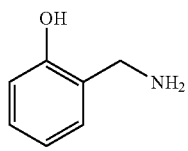
178

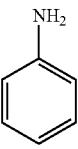
179

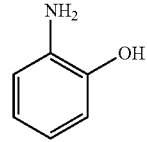
180

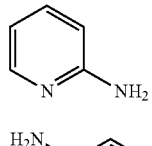
181

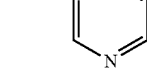
182

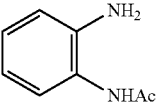
183

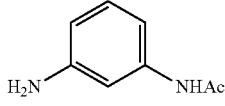
184

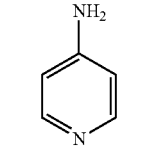
185

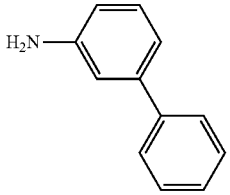
186

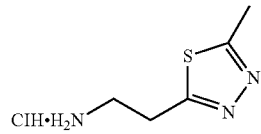
187

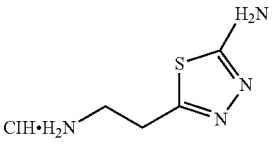
188

-continued

| | No. |
|---|---|
| (structure: 2-(5-(2-aminoethyl)-1,3,4-oxadiazol-2-ylthio)acetamide · HCl) | 189 |
| (structure: 2-(pyridazin-3-yl)ethanamine) | 190 |
| (structure: 2-(4H-1,2,4-triazol-3-yl)ethanamine · HCl) | 191 |
| (structure: 2-(5-methyl-4H-1,2,4-triazol-3-yl)ethanamine) | 192 |
| (structure: 2-(5-(furan-2-yl)-4H-1,2,4-triazol-3-yl)ethanamine) | 193 |
| (structure: 1-phenyl-2-(4H-1,2,4-triazol-3-yl)ethanamine) | 194 |
| (structure: (1,3,4-thiadiazol-2-yl)methanamine · HCl) | 195 |
| (structure: thiazol-4-ylmethanamine) | 196 |
| (structure: (4H-1,2,4-triazol-3-yl)methanamine) | 197 |
| (structure: pyridin-4-ylmethanamine) | 198 |

-continued

| | No. |
|---|---|
| (structure: pyrimidin-4-ylmethanamine) | 199 |
| (structure: pyrazin-2-ylmethanamine) | 200 |
| (structure: pyrimidin-2-ylmethanamine) | 201 |
| (structure: (2-methylthiazol-5-yl)methanamine) | 202 |
| (structure: (2-chlorothiazol-5-yl)methanamine) | 203 |
| (structure: (2-phenylthiazol-5-yl)methanamine) | 204 |
| (structure: (4-methylthiazol-5-yl)methanamine) | 205 |
| (structure: (4-phenylthiazol-5-yl)methanamine) | 206 |
| NH₄Cl | 133 |
| (structure: (tetrahydrofuran-2-yl)methanamine) | 207 |
| (structure: (tetrahydrofuran-3-yl)methanamine) | 208 |

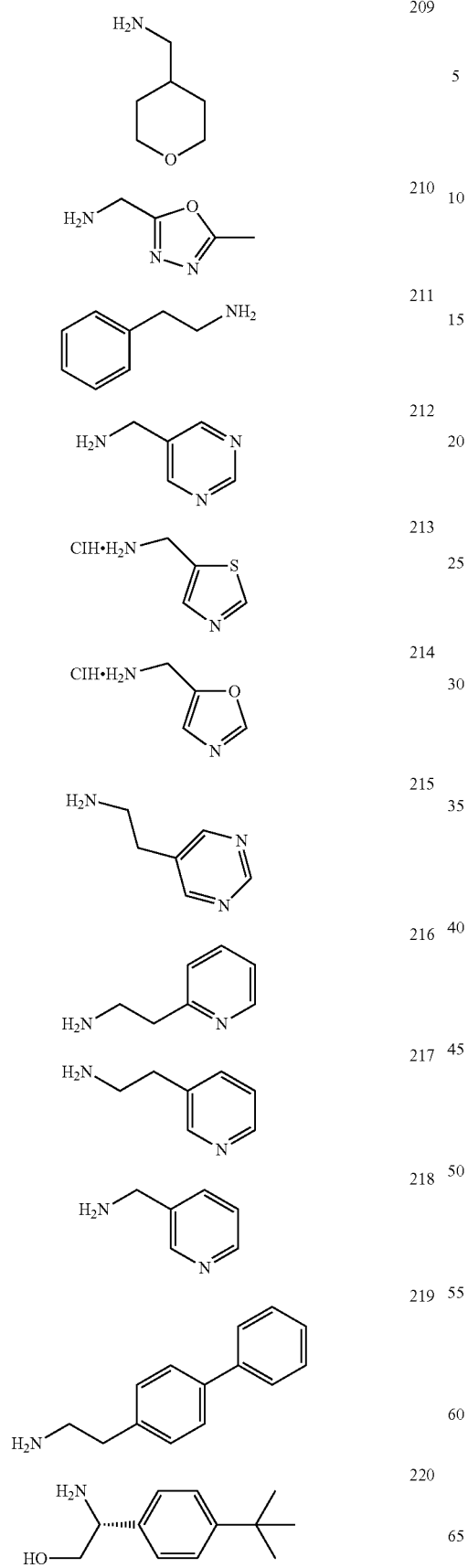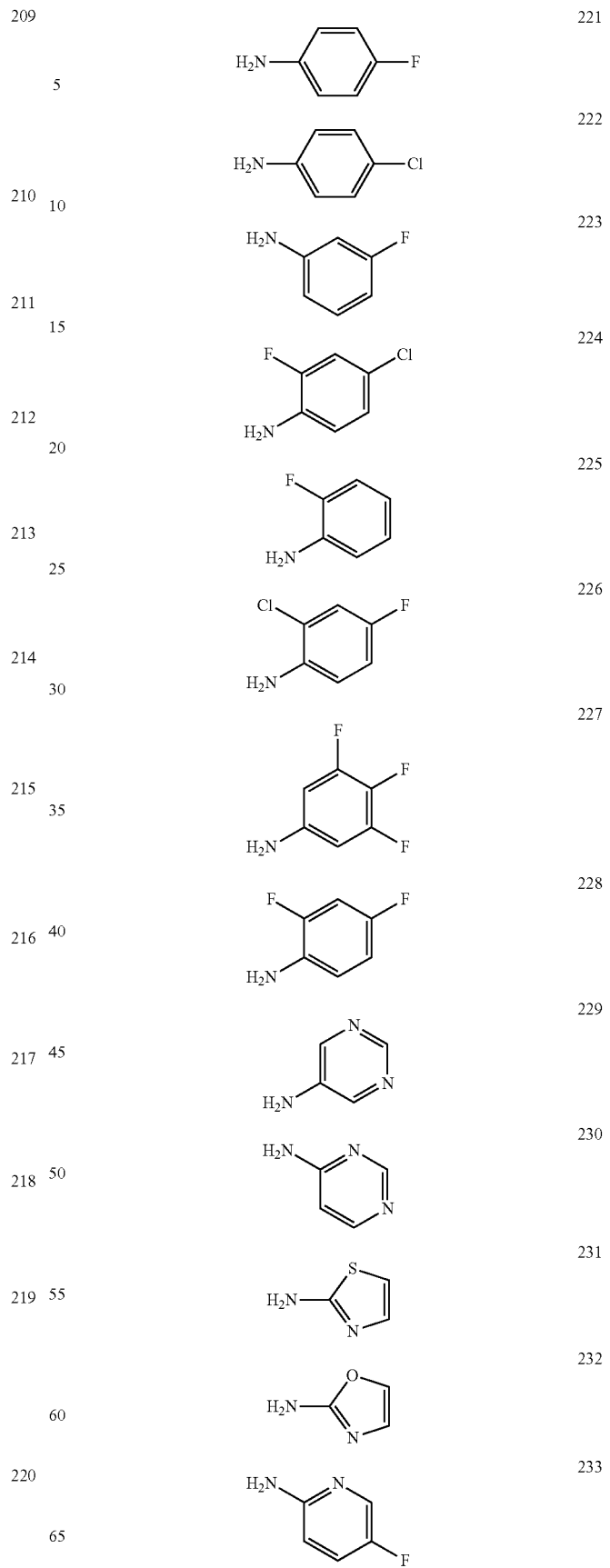

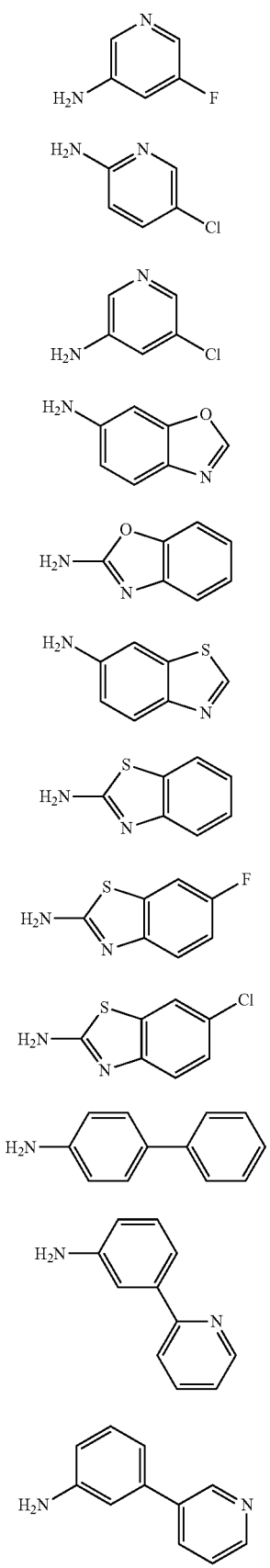
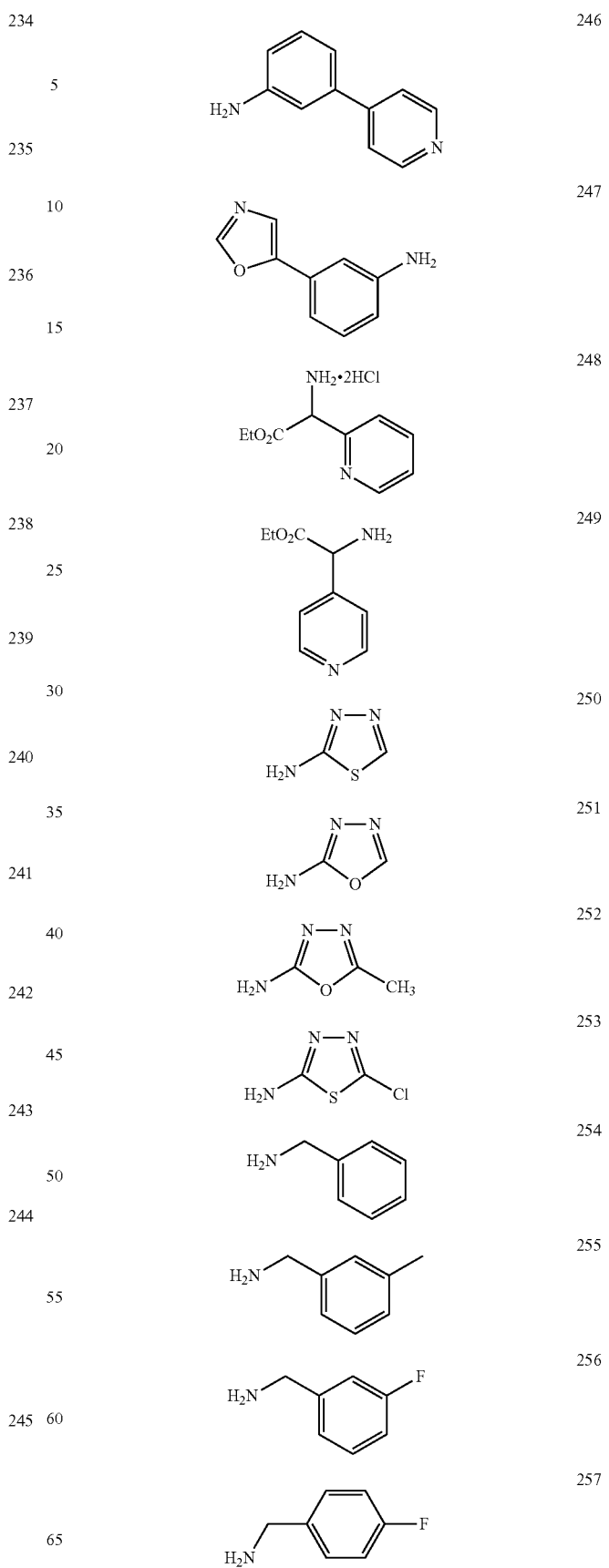

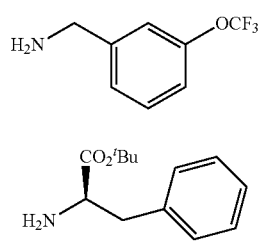

258

259

Preparation of Amines for Compound Synthesis

Synthesis of 2-cyclohexylethanamine hydrochloride (261)

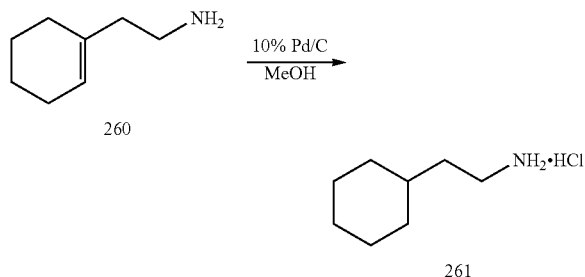

To a stirred solution of 2-(cyclohex-1-en-1-yl) ethanamine 260 (500 mg, 4.00 mmol) in MeOH (10 mL) under argon atmosphere was added 10% Pd/C (50 mg) at RT and stirred under hydrogen atmosphere (balloon pressure) for 16 h. The reaction was monitored by TLC; after completion of the reaction, the reaction mixture was filtered through celite, washed with MeOH (2×5 mL) and the filtrate was concentrated in vacuo. The residue was triturated with $CH_2Cl_2$: EtOAc (1:1, 2 mL), diethyl ether in 1 N HCl (4 mL) to afford compound 261 (250 mg, 38%) as white solid. TLC: 20% EtOAc/hexanes ($R_f$: 0.3); $^1$H-NMR (DMSO-$d_6$, 500 MHz): δ 7.79 (br s, 2H), 2.77 (t, J=7.5 Hz, 2H), 1.66-1.59 (m, 5H), 1.45-1.41 (m, 2H), 1.32-1.28 (m, 1H), 1.23-1.11 (m, 3H), 0.91-0.84 (m, 2H).

Synthesis of 2-(4-fluorophenoxy) ethan-1-amine hydrochloride (265)

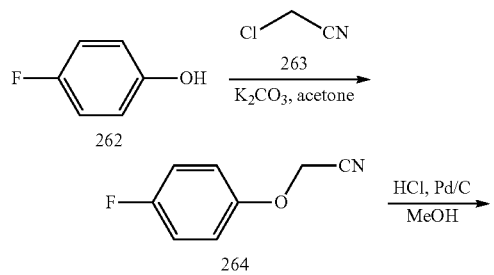

265

Synthesis of 2-(4-fluorophenoxy) acetonitrile (264)

To a stirred solution of 4-fluorophenol 262 (1.74 mL, 18.96 mmol) in acetone (50 mL) under argon atmosphere were added potassium carbonate (6.5 g, 47.40 mmol), chloro acetonitrile 263 (1 mL, 15.80 mmol) at RT; heated to reflux and stirred for 16 h. The reaction was monitored by TLC; after completion of the reaction, the reaction mixture was filtered and the filtrate was concentrated in vacuo. The residue was extracted with diethyl ether (3×40 mL). The combined organic extracts were washed with NaOH solution (30 mL), water (30 mL), dried over sodium sulfate, filtered and concentrated in vacuo to afford compound 264 (2.4 g, 90%) as brown syrup. TLC: 10% EtOAc/hexanes ($R_f$: 0.3); $^1$H-NMR (CDCl$_3$, 400 MHz): δ 7.06-7.01 (m, 2H), 6.98-6.89 (m, 2H), 4.73 (s, 2H).

Synthesis of 2-(4-fluorophenoxy) ethan-1-amine hydrochloride (265)

To a stirred solution of compound 264 (200 mg, 1.32 mmol) in MeOH (10 mL) under argon atmosphere were added HCl (0.3 mL), Pd/C (90 mg) and stirred under hydrogen atmosphere (balloon pressure) at RT and stirred for 16 h. The reaction was monitored by TLC; after completion of the reaction, the reaction mixture was diluted with saturated sodium potassium tartrate solution (20 mL) and extracted with diethyl ether (2×20 mL). The combined organic extracts were dried over sodium sulfate, filtered and concentrated in vacuo to afford compound 265 (130 mg, 65%) as an off-white solid. TLC: 10% EtOAc/hexanes ($R_f$: 0.2); $^1$H-NMR (DMSO-$d_6$, 400 MHz): δ 8.31-8.28 (m, 2H), 7.17-7.12 (m, 2H), 7.02-6.98 (m, 2H), 4.16 (t, J=5.2 Hz, 2H), 3.17 (t, J=5.2 Hz, 2H).

Synthesis of 2-(4-fluorocyclohexyl) ethan-1-amine hydrochloride (269)

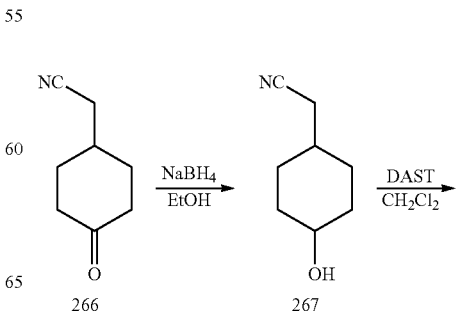

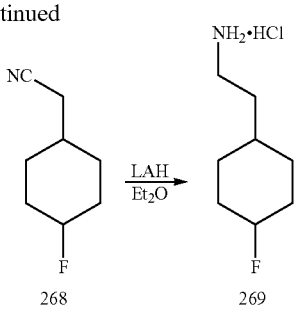

Synthesis of 2-(4-hydroxycyclohexyl) acetonitrile (267)

To a stirred solution of 2-(4-oxocyclohexyl) acetonitrile 266 (200 mg, 1.45 mmol) in EtOH (10 mL) under argon atmosphere was added sodium borohydride (82.7 mg, 2.18 mmol) at 0° C.; warmed to 10-15° C. and stirred for 1 h. The reaction was monitored by TLC; after completion of the reaction, the reaction mixture was quenched with ice cold water (2 mL) and the volatiles were removed in vacuo. The residue was diluted with water (20 mL) and extracted with $CH_2Cl_2$ (2×25 mL). The combined organic extracts were dried over sodium sulfate, filtered and concentrated in vacuo to afford compound 267 (180 mg, 89%) as colorless syrup. TLC: 50% EtOAc/hexanes ($R_f$: 0.4); $^1$H-NMR ($CDCl_3$, 400 MHz): δ 3.62-3.55 (m, 1H), 2.30-2.24 (m, 2H), 2.06-2.01 (m, 2H), 1.92-1.88 (m, 2H), 1.80-1.78 (m, 1H), 1.70-1.63 (m, 2H), 1.59-1.56 (m, 1H), 1.40-1.16 (m, 2H).

Synthesis of 2-(4-fluorocyclohexyl) acetonitrile (268)

To a stirred solution of compound 267 (180 mg, 1.29 mmol) in $CH_2Cl_2$ (5 mL) under argon atmosphere was added DAST (313 mg, 1.94 mmol) at −20° C.; warmed to RT and stirred for 6 h. The reaction was monitored by TLC; after completion of the reaction, the reaction mixture was quenched with ice cold water (20 mL) and extracted with $CH_2Cl_2$ (2×30 mL). The combined organic extracts were dried over sodium sulfate, filtered and concentrated in vacuo to obtain the crude. The crude was purified through silica gel column chromatography using 5-7% EtOAc/hexanes to afford compound 268 (35 mg, 19%) as colorless syrup. TLC: 20% EtOAc/hexanes ($R_f$: 0.4); $^1$H-NMR ($CDCl_3$, 500 MHz): δ 4.88-4.79 (m, 1H), 2.27 (d, J=7.0 Hz, 2H), 2.10-2.08 (m, 2H), 1.77-1.70 (m, 3H), 1.57-1.33 (m, 4H).

Synthesis of 2-(4-fluorocyclohexyl) ethan-1-amine hydrochloride (269)

To a stirred solution of compound 268 (35 mg, 0.24 mmol) in ether (5 mL) under argon atmosphere was added lithium aluminium hydride (18.8 mg, 0.49 mmol) at 0° C.; warmed to RT and stirred for 16 h. The reaction was monitored by TLC; after completion of the reaction, the reaction mixture was quenched with saturated sodium potassium tartrate solution (10 mL) at 0-5° C. and extracted with ether (2×20 mL). The combined organic extracts were dried over sodium sulfate, filtered and concentrated in vacuo to obtain the crude. The crude was dissolved in ether (3 mL), slowly added 2 N HCl in ether (10 mL) and stirred for 1 h. The precipitated solid was filtered and dried in vacuo to afford compound 269 (12 mg, 33%) as pale yellow solid. TLC: 30% EtOAc/hexanes ($R_f$: 0.2); $^1$H-NMR (DMSO-$d_6$, 400 MHz): δ 7.81 (br s, 2H), 4.87 (br s, 1H), 4.75 (br s, 1H), 2.82-2.77 (m, 2H), 1.89-1.84 (m, 2H), 1.59-1.40 (m, 6H), 1.20 (t, J=10.0 Hz, 2H).

Synthesis of 3-methoxy-3-methylbutan-1-amine (273)

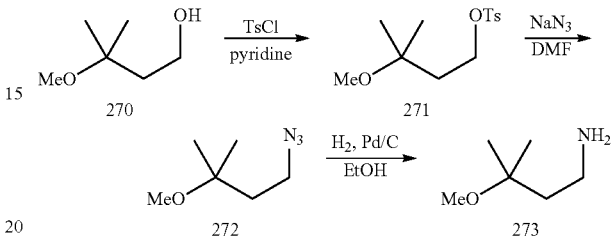

Synthesis of 3-methoxy-3-methylbutyl 4-methylbenzenesulfonate (271)

To a stirred solution of 3-methoxy-3-methylbutan-1-ol 270 (1 g, 8.46 mmol) in pyridine (15 mL) under argon atmosphere was added tosyl chloride (1.6 g, 8.46 mmol) at 0° C.; warmed to RT and stirred for 16 h. The reaction was monitored by TLC; after completion of the reaction, the volatiles were removed in vacuo. The residue was quenched with saturated $NaHCO_3$ solution (20 mL) and extracted with EtOAc (2×10 mL). The combined organic extracts were dried over sodium sulphate, filtered and concentrated in vacuo to afford compound 271 (1.8 g, 78%) as colorless syrup. TLC: 30% EtOAc/hexanes ($R_f$: 0.7); $^1$H-NMR ($CDCl_3$, 400 MHz): δ 7.79 (d, J=8.4 Hz, 2H), 7.34 (d, J=7.6 Hz, 2H), 4.13 (t, J=7.2 Hz, 2H), 3.10 (s, 3H), 2.45 (s, 3H), 1.87 (t, J=7.6 Hz, 2H), 1.12 (s, 6H).

Synthesis of 1-azido-3-methoxy-3-methylbutane (272)

To a stirred solution of compound 271 (1 g, 3.67 mmol) in DMF (10 mL) under argon atmosphere was added sodium azide (478 mg, 7.34 mmol) at 0° C.; warmed to RT and stirred for 16 h. The reaction was monitored by TLC; after completion of the reaction, the reaction mixture was diluted with water (30 mL) and extracted with EtOAc (2×20 mL). The combined organic extracts were dried over sodium sulphate, filtered and concentrated in vacuo to afford compound 272 (525 mg, 76%) as white solid. TLC: 30% EtOAc/hexanes ($R_f$: 0.7); $^1$H-NMR ($CDCl_3$, 400 MHz): δ 3.34 (t, J=7.6 Hz, 2H), 3.18 (s, 3H), 1.78 (t, J=8.0 Hz, 2H), 1.18 (s, 6H).

Synthesis of 3-methoxy-3-methylbutan-1-amine (273): To a stirred solution of compound 272 (400 mg, 2.79 mmol) in EtOH (5 mL) under argon atmosphere was added 10% Pd/C (250 mg) at RT and stirred under hydrogen atmosphere (balloon pressure) for 16 h. The reaction was monitored by TLC; after completion of the reaction, the reaction mixture was filtered through celite and the filtrate was concentrated in vacuo to obtain the crude. The crude was purified through silica gel column chromatography using 80% EtOAc/hexanes to afford compound 273 (320 mg, 33%) as colorless syrup. TLC: 70% EtOAc/hexanes ($R_f$: 0.3); $^1$H-NMR (CDCl$_3$, 400 MHz): δ 3.18 (s, 3H), 2.80 (t, J=8.0 Hz, 0.5H), 2.70 (t, J=7.6 Hz, 1H), 2.49 (t, J=8.0 Hz, 0.5H), 1.71 (t, J=7.6 Hz, 2H), 1.56 (s, 6H).

Synthesis of 3-phenyl-3-(pyrrolidin-1-yl) propan-1-amine (277)

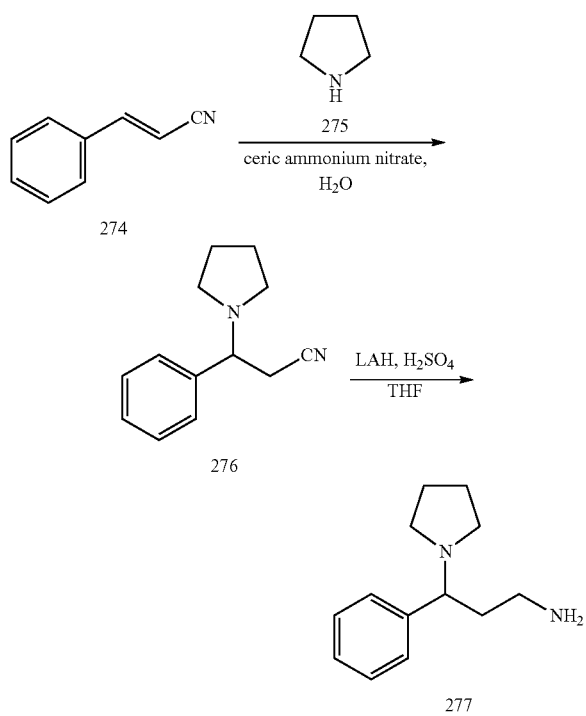

Synthesis of 3-phenyl-3-(pyrrolidin-1-yl) propanenitrile (276)

To a stirred solution of cinnamonitrile 274 (500 mg, 3.87 mmol) in H$_2$O (15 mL) were added pyrrolidine 275 (412 mg, 5.80 mmol), ceric ammonium nitrate (2.1 g, 3.87 mmol) at RT, heated to 60° C. and stirred for 4 h. The reaction was monitored by TLC; after completion of the reaction, the reaction mixture was diluted with water (20 mL) and extracted with EtOAc (2×30 mL). The combined organic extracts were dried over sodium sulphate, filtered and concentrated in vacuo to obtain the crude. The crude was purified through silica gel column chromatography using 25% EtOAc/hexanes to afford compound 276 (300 mg, 39%) as colorless syrup. TLC: 30% EtOAc/hexanes (R$_f$: 0.5); $^1$H-NMR (CDCl$_3$, 400 MHz): δ 7.39-7.31 (m, 5H), 3.50-3.35 (m, 1H), 2.80-2.70 (m, 2H), 2.60-2.45 (m, 4H), 1.89-1.72 (m, 4H).

Synthesis of 3-phenyl-3-(pyrrolidin-1-yl) propan-1-amine (277)

To a stirred solution of compound 276 (150 mg, 0.75 mmol) in THF (10 mL) under argon atmosphere were added lithium aluminium hydride (57 mg, 1.50 mmol), H$_2$SO$_4$ (0.04 mL, 0.75 mmol) at 0° C.; warmed to RT and stirred for 5 h. The reaction was monitored by TLC; after completion of the reaction, the reaction mixture was quenched with saturated sodium sulphate and the reaction mixture was filtered through celite, washed with EtOAc (2×5 mL). The volatiles were removed in vacuo to afford compound 277 (100 mg, 65%) as an off-white solid. TLC: 10% MeOH/EtOAc (R$_f$: 0.3); $^1$H-NMR (CDCl$_3$, 400 MHz): δ 7.31-7.30 (m, 5H), 3.26-3.22 (m, 1H), 2.59-2.40 (m, 4H), 2.39-2.37 (m, 2H), 2.14-2.10 (m, 1H), 2.10-2.04 (m, 1H), 1.98-1.72 (m, 6H).

Synthesis of 2-(5-methyl-1, 3, 4-oxadiazol-2-yl) ethan-1-amine hydrochloride (283)

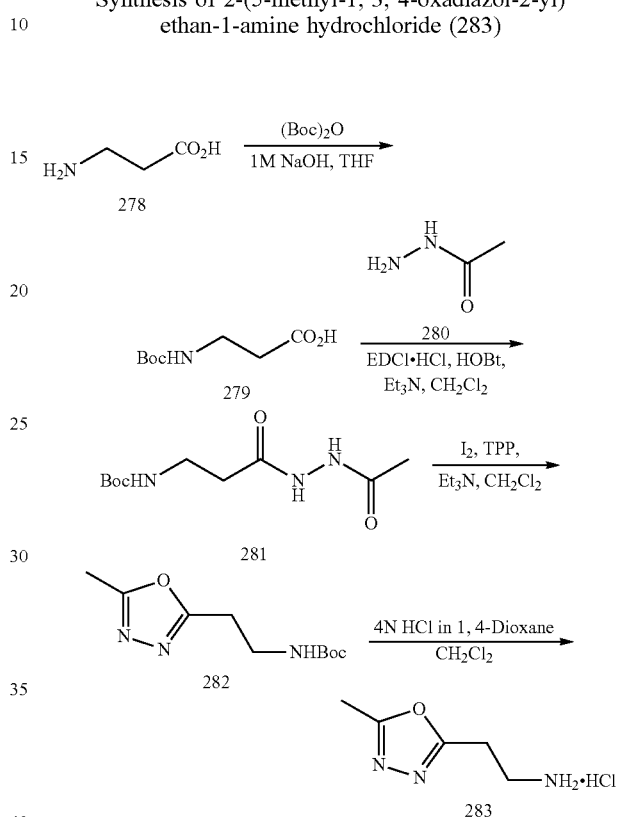

Synthesis of 3-((tert-butoxycarbonyl) amino) propanoic acid (279)

To a stirred solution of 3-aminopropanoic acid 278 (5 g, 51.02 mmol) in THF (50 mL) were added 1 M aqueous sodium hydroxide solution (25 mL) and Boc-anhydride (11.3 mL, 51.02 mmol) at 0° C.; warmed to RT and stirred for 12 h. The reaction was monitored by TLC; after completion of the reaction, the volatiles were removed in vacuo. The aqueous layer was washed with diethyl ether (2×50 mL) and the pH was adjusted to ~6 with 4 M HCl and extracted with diethyl ether (4×50 mL). The combined organic extracts were washed with brine (100 mL), dried over sodium sulphate, filtered and concentrated in vacuo to obtain compound 279 (8 g, 79%) as an off-white solid. TLC: 50% EtOAc/hexanes (R$_f$: 0.3); $^1$H-NMR (DMSO-d$_6$, 500 MHz): δ 12.18 (br s, 1H), 6.81 (t, J=4.8 Hz, 1H), 3.11 (q, J=6.9 Hz, 2H), 2.34 (t, J=7.1 Hz, 2H), 1.36 (s, 9H).

Synthesis of Tert-Butyl (3-(2-acetylhydrazinyl)-3-oxopropyl) carbamate (281)

To a stirred solution of compound 279 (1 g, 5.29 mmol) in CH$_2$Cl$_2$ (15 ML) under argon atmosphere were added EDCI.HCl (1.3 g, 6.87 mmol), HOBt (714 mg, 5.29 mmol), triethyl amine (0.99 ML, 6.87 mmol), acetic acid hydrazide 280 (430 mg, 5.82 mmol) at 0° C.; warmed to RT and stirred for 1.5 h. The reaction was monitored by TLC; after completion of the reaction, the reaction mixture was diluted with ice cold water (5 mL) and extracted with CH$_2$Cl$_2$ (4×20 mL). The combined organic extracts were dried over sodium sulphate, filtered and concentrated in vacuo to obtain crude. The crude was purified through silica gel column chromatography using 10% EtOAc/hexanes to afford compound 281 (610 mg, 50%) as an off white solid. TLC: 10% EtOAc/hexanes (R$_f$: 0.3); $^1$H-NMR (DMSO-d$_6$, 400 MHz): δ 9.70 (s, 2H), 6.73 (t, J=4.7 Hz, 1H), 3.13 (q, J=6.6 Hz, 2H), 2.27 (t, J=7.4 Hz, 2H), 1.83 (s, 3H), 1.37 (s, 9H).

Synthesis of Tert-Butyl (2-(5-methyl-1, 3, 4-oxadiazol-2-yl) ethyl) carbamate (282)

To a stirred solution of triphenyl phosphine (428 mg, 1.63 mmol) in CH$_2$Cl$_2$ (5 mL) under argon atmosphere were added iodine (414 mg, 1.63 mmol) and stirred for 15 min. To this were added triethyl amine (0.47 mL, 3.26 mmol), compound 281 (200 mg, 0.81 mmol) at RT and stirred for 16 h. The reaction was monitored by TLC; after completion of the reaction, the volatiles were removed in vacuo to obtain the crude. The crude was purified through silica gel column chromatography using 4% EtOAc/hexanes to afford crude compound 282 (360 mg) as an off-white solid. TLC: 10% EtOAc/hexanes (R$_f$: 0.7); 1H NMR shows mixture of compound and TPPO as major impurity. $^1$H-NMR (DMSO-d$_6$, 400 MHz): δ 7.68-7.49 (m, 48H-TPPO as impurity), 6.97 (t, J=5.0 Hz, 1H), 3.27 (q, J=6.5 Hz, 2H), 2.89 (t, J=6.7 Hz, 2H), 2.43 (s, 3H), 1.35 (s, 9H).

Synthesis of 2-(5-methyl-1, 3, 4-oxadiazol-2-yl) ethan-1-amine hydrochloride (283)

To a stirred solution of compound 282 (350 mg) in CH$_2$Cl$_2$ (5 mL) under argon atmosphere was added 4 N HCl in 1, 4-dioxane (4 mL) at 0° C.; warmed to RT and stirred for 4 h. The reaction was monitored by TLC; after completion of the reaction, the volatiles were removed in vacuo to obtain the crude. The crude was titurated with CH$_2$Cl$_2$ (2 mL), diethyl ether (5 mL) and n-pentane (5 mL) and dried in vacuo to afford crude compound 283 (60 mg) as brown solid. TLC: 10% EtOAc/hexanes (R$_f$: 0.1).

Synthesis of (2-ethylthiazol-5-yl) methanamine hydrochloride (292)

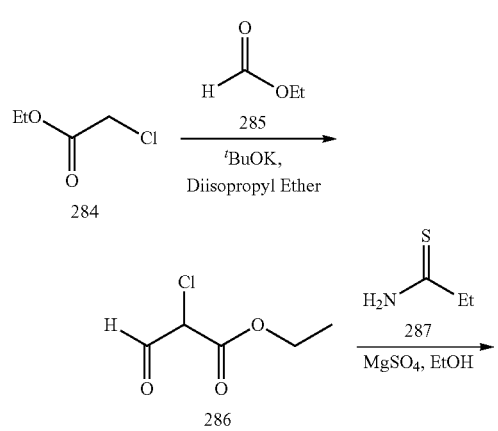

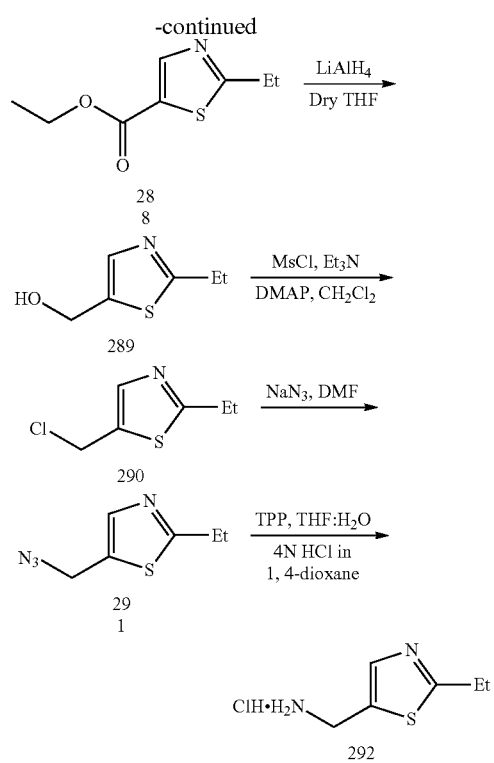

Synthesis of Ethyl 2-chloro-3-oxopropanoate (286)

To a stirred solution of ethyl 2-chloroacetate 284 (5 g, 40.98 mmol) and 285 (3.03 g, 40.98 mmol) in diisopropyl ether (100 mL) under argon atmosphere was added potassium tert-butoxide (5.49 g, 45.08 mmol) portion wise for 10 min at 0° C.; warmed to RT and stirred for 24 h. The reaction was monitored by TLC; after completion of the reaction, the pH of the reaction mixture was adjusted to ~6 using 5 N HCl. The obtained solid was filtered, washed with diethyl ether (200 mL) and dried in vacuo to afford compound 286 (6 g) as pale brown syrup. TLC: 30% EtOAc/hexanes (R$_f$: 0.2); LC-MS: 21.49%+75.58%; 149.0 (M$^+$-1); (column; X-Select C-18, (50×3.0 mm, 3.5 μm); RT 0.56 min, 0.77 min. 5 Mm Aq.NH$_4$OAc: ACN 0.8 mL/min).

Synthesis of Ethyl 2-ethylthiazole-5-carboxylate (288)

To a stirred solution of compound 286 (1 g) in ethanol (25 mL) under argon atmosphere were added propanethioamide 287 (594 mg, 6.67 mmol), dry magnesium sulfate (4 g) at RT and heated to reflux for 24 h. The reaction was monitored by TLC; after completion of the reaction, the volatiles were removed in vacuo, diluted with EtOAc (2×100 mL). The combined organic extracts were washed with saturated sodium bicarbonate solution (2×100 mL), brine (50 mL), dried over sodium sulfate, filtered and concentrated in vacuo to obtain the crude. The crude was purified through flash column chromatography using 6% EtOAc/hexanes to afford compound 288 (330 mg, 27%) as brown syrup. TLC: 10% EtOAc/hexanes (R$_f$: 0.4); $^1$H-NMR (DMSO-d$_6$, 400 MHz): δ 8.29 (s, 1H), 4.30 (q, J=7.1 Hz, 2H), 3.04 (q, J=7.5 Hz, 2H), 1.31 (t, J=7.3 Hz, 3H), 1.29 (t, J=7.3 Hz, 3H).

Synthesis of (2-ethylthiazol-5-yl) methanol (289) (SAP-MA1426-31)

To a stirred suspension of lithium aluminium hydride (205 mg, 5.40 mmol) in dry THF (15 mL) under inert atmosphere was added compound 288 (500 mg, 2.70 mmol) at 0° C.; warmed to RT and stirred for 16 h. The reaction was monitored by TLC; after completion of the reaction, the reaction mixture was cooled to 0° C., quenched with 20% aqueous sodium hydroxide solution (3 mL), filtered through celite and washed with EtOAc (3×100 mL). The filtrate was dried over sodium sulfate, filtered and concentrated in vacuo to afford compound 289 (310 mg, 80%) as pale yellow solid. TLC: 50% EtOAc/hexanes ($R_f$: 0.4). $^1$H-NMR (CDCl$_3$, 400 MHz): δ 7.51 (s, 1H), 4.82 (s, 2H), 3.01 (q, J=7.5 Hz, 2H), 1.38 (t, J=7.6 Hz, 3H).

Synthesis of 5-(chloromethyl)-2-ethylthiazole (290) (SAP-MA1426-34)

To a stirred solution of compound 289 (300 mg, 2.09 mmol) in CH$_2$Cl$_2$ (15 ML) under inert atmosphere were added triethyl amine (0.6 mL, 4.20 mmol), DMAP (25.6 mg, 0.21 mmol) and mesyl chloride (0.19 mL, 2.51 mmol) at 0° C.; warmed to RT and stirred for 2 h. The reaction was monitored by TLC; after completion of the reaction, the reaction mixture was diluted with water (50 mL) and extracted with CH$_2$Cl$_2$ (3×100 mL). The combined organic extracts were dried over sodium sulfate, filtered and concentrated in vacuo to afford compound 290 (500 mg, crude) as pale yellow syrup. TLC: 30% EtOAc/hexanes ($R_f$: 0.8); LC-MS: 30.71%; 162.0 (M$^+$+1); (column; Ascentis Express C18, (50×3.0 mm, 2.7 μm); RT 2.14 min. 0.025% Aq. TFA+5% ACN: ACN+5% 0.025% Aq. TFA, 1.2 mL/min).

Synthesis of 5-(azidomethyl)-2-ethylthiazole (291) (SAP-MA1426-35)

To a stirred solution of compound 290 (500 mg, 2.26 mmol) in DMF (20 mL) under inert atmosphere was added sodium azide (294 mg, 4.52 mmol) at RT and heated to 80° C. for 16 h. The reaction was monitored by TLC; after completion of the reaction, the reaction mixture was diluted with ice cold water (50 mL) and extracted with EtOAc (3×100 mL). The combined organic extracts were dried over sodium sulfate, filtered and concentrated in vacuo to obtain the crude. The crude was purified through flash column chromatography using 15% EtOAc/hexanes to afford compound 291 (250 mg, 71%) as pale yellow syrup. TLC: 20% EtOAc/hexanes ($R_f$: 0.4); $^1$H-NMR (CDCl$_3$, 400 MHz): δ 7.56 (s, 1H), 4.49 (s, 2H), 3.03 (q, J=7.6 Hz, 2H), 1.40 (t, J=7.6 Hz, 3H);

Synthesis of (2-ethylthiazol-5-yl) methanamine hydrochloride (292)

To a stirred solution of compound 291 (250 mg, 1.48 mmol) in THF:H$_2$O (5:1, 12 mL) was added triphenyl phosphine (780 mg, 2.97 mmol) at RT and stirred for 2 h. The reaction was monitored by TLC; after completion of the reaction, the volatiles were removed in vacuo to obtain the crude. The obtained solid was further dried using toluene (2×5 mL) to obtain the crude amine.

The above compound was dissolved in CH$_2$Cl$_2$ (5 mL) added 4 N HCl in 1, 4-dioxane (4 mL) under inert atmosphere at 0° C. and stirred for 30 min. The volatiles were removed in vacuo to obtain the crude, which was titurated with EtOAc (2 mL), diethyl ether (2 mL) and pentane (5 mL) to afford compound 292 (180 mg, 68%) as an off-white solid. TLC: 5% MeOH/CH$_2$Cl$_2$ ($R_f$: 0.2); $^1$H NMR (DMSO-d$_6$, 500 MHz): δ 8.48 (br s, 3H), 7.74 (s, 1H), 4.25 (q, J=5.5 Hz, 2H), 2.98 (q, J=7.5 Hz, 2H), 1.28 (t, J=7.5 Hz, 3H);

Synthesis of (2-isopropylthiazol-5-yl) methanamine hydrochloride (298)

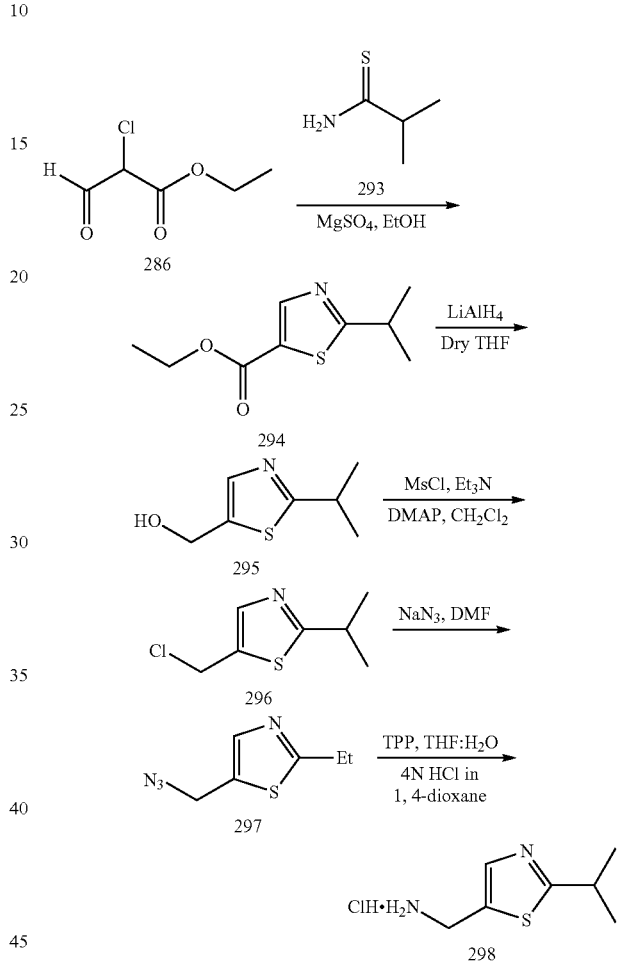

Synthesis of Ethyl 2-isopropylthiazole-5-carboxylate (294)

To a stirred solution of compound 286 (3.05 g) in ethanol (60 mL) under argon atmosphere were added 2-methylpropanethioamide 293 (1.5 g, 14.56 mmol), dry magnesium sulfate (5 g) at RT and heated to reflux for 24 h. The reaction was monitored by TLC; after completion of the reaction, the volatiles were removed in vacuo. The residue was diluted with saturated sodium bicarbonate solution (100 mL), extracted with EtOAc (3×100 mL). The combined organic extracts were dried over sodium sulfate, filtered and concentrated in vacuo to obtain the crude. The crude was purified through flash column chromatography using 2% EtOAc/hexanes to afford compound 294 (550 mg, 17%) as brown syrup. TLC: 10% EtOAc/hexanes ($R_f$: 0.5); $^1$H NMR (500 MHz, DMSO-d$_6$) δ 8.31 (s, 1H), 4.30 (q, J=7.0 Hz, 2H), 3.36-3.29 (m, 1H), 1.34 (d, J=6.9 Hz, 6H), 1.29 (t, J=7.1 Hz, 3H).

Synthesis of (2-isopropylthiazol-5-yl) methanol (295)

To a stirred solution of compound 294 (550 mg, 2.76 mmol) in dry THF (10 mL) under inert atmosphere was added lithium aluminium hydride (210 mg, 5.52 mmol) at 0° C.; warmed to RT and stirred for 16 h. The reaction was monitored by TLC; after completion of the reaction, the reaction mixture was cooled to 0° C., quenched with 15% aqueous sodium hydroxide solution (3 mL), filtered through celite and washed with EtOAc (100 mL). The filtrate was dried over sodium sulfate, filtered and concentrated in vacuo to afford compound 295 (360 mg, 83%) as pale yellow syrup. TLC: 50% EtOAc/hexanes ($R_f$: 0.3). 1H NMR (400 MHz, DMSO-$d_6$) δ 7.47 (s, 1H), 5.43 (t, J=5.7 Hz, 1H), 4.61 (dd, J=5.6, 0.6 Hz, 2H), 3.26-3.19 (m, 1H), 1.30 (d, J=6.9 Hz, 6H).

Synthesis of 5-(chloromethyl)-2-isopropylthiazole (296)

To a stirred solution of compound 295 (350 mg, 2.23 mmol) in $CH_2Cl_2$ (20 mL) under inert atmosphere were added triethyl amine (0.64 mL, 4.45 mmol), DMAP (27.2 mg, 0.22 mmol) and mesyl chloride (0.2 mL, 2.67 mmol) at 0° C.; warmed to RT and stirred for 3 h. The reaction was monitored by TLC; after completion of the reaction, the reaction mixture was diluted with water (50 mL) and extracted with $CH_2Cl_2$ (2×100 mL). The combined organic extracts were dried over sodium sulfate, filtered and concentrated in vacuo to afford compound 296 (500 mg, crude) as pale yellow syrup. TLC: 40% EtOAc/hexanes ($R_f$: 0.8); LC-MS: 70.54%; 175.8 ($M^+$+1); (column; Ascentis Express C18, (50×3.0 mm, 2.7 μm); RT 2.34 min. 0.025% Aq. TFA+5% ACN: ACN+5% 0.025% Aq. TFA, 1.2 mL/min).

Synthesis of 5-(azidomethyl)-2-isopropylthiazole (297)

To a stirred solution of compound 296 (500 mg, 2.26 mmol) in DMF (20 mL) under inert atmosphere was added sodium azide (445 mg, 6.85 mmol) at RT and heated to 80° C. for 16 h. The reaction was monitored by TLC; after completion of the reaction, the reaction mixture was diluted with ice cold water (100 mL) and extracted with EtOAc (2×100 mL). The combined organic extracts were dried over sodium sulfate, filtered and concentrated in vacuo to obtain the crude. The crude was purified through column chromatography using 8% EtOAc/hexanes to afford compound 297 (255 mg, 63%) as colorless liquid. TLC: 10% EtOAc/hexanes ($R_f$: 0.4); $^1$H NMR (500 MHz, DMSO-$d_6$): δ=7.67 (s, 1H), 4.69 (s, 2H), 3.29-3.24 (m, 1H), 1.32 (d, J=6.9 Hz, 8H).

Synthesis of (2-isopropylthiazol-5-yl) methanamine hydrochloride (298)

To a stirred solution of compound 297 (250 mg, 1.37 mmol) in THF:$H_2O$ (5:1, 12 mL) was added triphenyl phosphine (720 mg, 2.74 mmol) at RT and stirred for 2 h. The reaction was monitored by TLC; after completion of the reaction, the volatiles were removed in vacuo to obtain the crude. The obtained solid was further dried using toluene (2×5 mL) to obtain the crude amine.

The above crude compound was dissolved in $CH_2Cl_2$ (5 mL) added 4 N HCl in 1, 4-dioxane (10 mL) under inert atmosphere at 0° C. and stirred for 30 min. The volatiles were removed in vacuo to obtain the crude, which was titurated with EtOAc (2 mL), diethyl ether (2 mL) and pentane (5 mL) to afford compound 298 (170 mg, 65%) as low melting hygroscopic solid. TLC: 5% MeOH/$CH_2Cl_2$ ($R_f$: 0.2); 1H NMR (500 MHz, DMSO-$d_6$): δ 8.29 (br s, 2H), 7.72 (s, 1H), 4.25 (d, J=5.8 Hz, 2H), 3.29-3.24 (m, 1H), 1.30 (d, J=6.9 Hz, 6H)

Synthesis of (2-methoxythiazol-5-yl) methanamine (300)

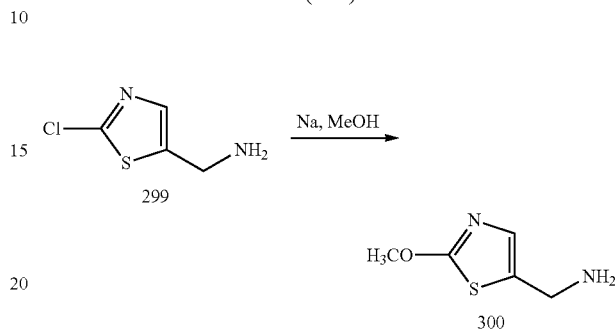

Synthesis of (2-methoxythiazol-5-yl) methanamine (300)

Sodium metal (46.6 mg, 2.02 mmol) was added slowly to MeOH (5 mL) under argon atmosphere and stirred for 15 min in a sealed tube. To this was added (2-chlorothiazol-5-yl) methanamine 299 (100 mg, 0.67 mmol) and the reaction mixture was heated to 80° C. for 3 h. The reaction was monitored by TLC; after completion the reaction, the reaction mixture was extracted with 20% MeOH/$CH_2Cl_2$ (3×50 mL). The combined organic extracts were dried over sodium sulfate, filtered and concentrated in vacuo to obtain the crude compound 300 (32 mg, 33%). The crude was carried forward for next step without purification. TLC: 5% MeOH/$CH_2Cl_2$ ($R_f$: 0.2); LC-MS: 90.34%; 145.0 ($M^+$+1); (column; X-Select CSH C18, (50×3.0 mm, 3.5 μm); RT 0.88 min. 2.5 mM Aq.$NH_4OOCH$+5% ACN: ACN+5% 2.5 mM Aq. $NH_4OOCH$; 1.2 mL/min).

Synthesis of 5-(aminomethyl) thiazol-2-amine dihydrochloride (303)

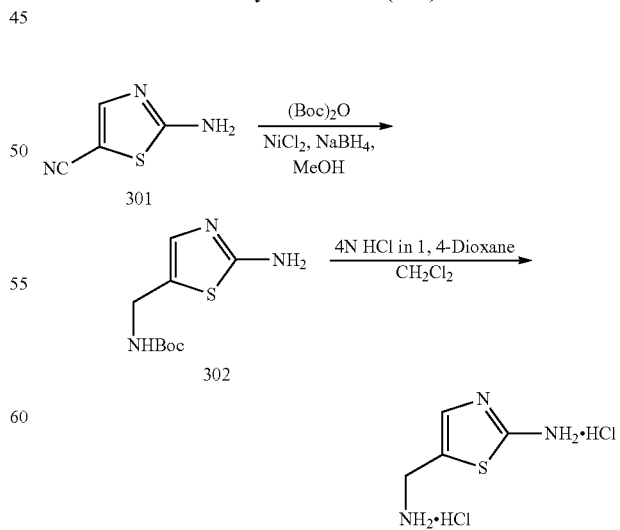

Synthesis of Tert-Butyl ((2-((tert-butoxycarbonyl) amino) thiazol-5-yl) methyl) carbamate (302)

To a stirred solution of 2-aminothiazole-5-carbonitrile 301 (300 mg, 2.40 mmol) in MeOH (50 mL) were added Boc-anhydride (1.5 mL, 7.20 mmol), nickel(II) chloride (571 mg, 2.40 mmol) at 0° C. To this was added sodium borohydride (638 mg, 16.80 mmol) portion wise for 10 min at 0° C.; warmed to RT and stirred for 18 h. The reaction was monitored by TLC; after completion of the reaction, the volatiles were removed in vacuo. The residue was diluted with EtOAc (100 mL) and water (75 mL), filtered through celite. The organic layer was dried over sodium sulphate, filtered and concentrated in vacuo to obtain compound 302 (300 mg) as colorless syrup. TLC: 10% MeOH/CH$_2$Cl$_2$ (R$_f$: 0.5); 1H NMR (DMSO-d$_6$, 500 MHz): δ 11.24 (br s, 1H), 7.38 (br s, 1H), 7.11 (s, 1H), 4.17 (d, J=5.5 Hz, 2H), 1.39 (s, 9H), 1.37 (s, 9H).

Synthesis of 5-(aminomethyl) thiazol-2-amine dihydrochloride (303)

To a stirred solution of compound 302 (300 mg) in CH$_2$Cl$_2$ (10 mL) was added 4 N HCl in 1, 4-dioxane (5 mL) under argon atmosphere at 0-5° C.; warmed to RT and stirred for 4 h. The reaction was monitored by TLC; after completion of the reaction, the volatiles were removed under reduced pressure. The obtained solid was washed with CH$_2$Cl$_2$ (5 mL), EtOAc (5 mL) and dried in vacuo to afford compound 303 (120 mg, HCl salt) as yellow solid. TLC: 10% MeOH/CH$_2$Cl$_2$ (R$_f$: 0.2); 1H NMR (DMSO-d$_6$, 500 MHz): δ 9.31 (br s, 1H), 8.53 (br s, 2H), 8.14 (br s, 1H), 7.37 (br s, 1H), 7.27 (br s, 1H), 7.17 (br s, 1H), 4.07 (d, J=5.5 Hz, 2H).

Synthesis of 4-(aminomethyl)-N-methylthiazol-2-amine hydrochloride (308)

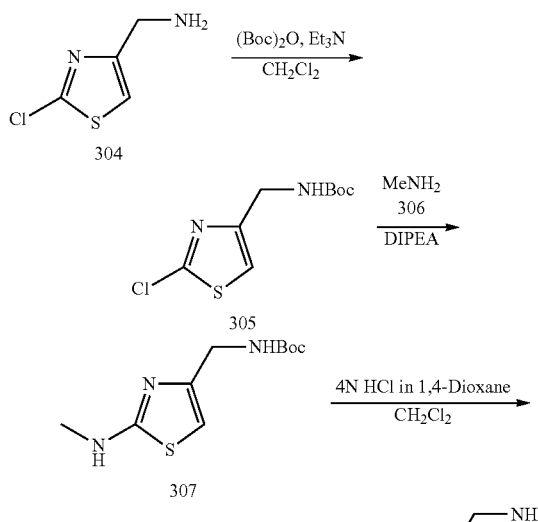

Synthesis of Tert-Butyl ((2-chlorothiazol-4-yl) methyl) carbamate (305)

To a stirred solution of (2-chlorothiazol-4-yl) methanamine 304 (200 mg, 1.35 mmol) in CH$_2$Cl$_2$ (10 mL) were added triethylamine (0.6 mL, 4.14 mmol) and Boc-anhydride (0.6 mL, 2.7 mmol) at 0° C.; warmed to RT and stirred for 16 h. The reaction was monitored by TLC; after completion of the reaction, the volatiles were removed in vacuo. The aqueous layer was washed with CH$_2$Cl$_2$ (50 mL), washed with water (50 mL). The organic extract was dried over sodium sulphate, filtered and concentrated in vacuo to obtain compound 305 (200 mg, 60%) as pale yellow sticky solid. TLC: 5% MeOH/CH$_2$Cl$_2$ (R$_f$: 0.4); 1H NMR (DMSO-d$_6$, 400 MHz): δ 7.56 (br s, 1H), 7.49 (s, 1H), 4.24 (d, J=5.9 Hz, 3H), 1.39 (s, 9H).

Synthesis of Tert-Butyl ((2-(methylamino) thiazol-4-yl) methyl) carbamate (307)

A mixture of compound 305 (100 mg, 0.41 mmol) and methyl amine 306 (5 mL, 33% solution in EtOH) in a sealed tube under argon atmosphere was added diisopropyl ethylamine (0.2 mL, 1.21 mmol) under argon atmosphere at RT and heated to 120° C. for 16 h. The reaction was monitored by TLC; after completion of the reaction, the volatiles were removed in vacuo. The crude was purified through silica gel column chromatography using 70% EtOAc/hexanes to afford compound 307 (90 mg, 92%) as colorless sticky solid. TLC: 50% EtOAc/hexanes (R$_f$: 0.2); 1H NMR (DMSO-d$_6$, 400 MHz): δ 7.26 (d, J=5.6 Hz, 2H), 6.77 (s, 1H), 4.05 (d, J=5.7 Hz, 2H), 2.76 (d, J=4.8 Hz, 3H), 1.38 (s, 9H).

Synthesis of 4-(aminomethyl)-N-methylthiazol-2-amine hydrochloride (308)

To a stirred solution of compound 307 (90 mg, 0.37 mmol) in CH$_2$Cl$_2$ (3 mL) under argon atmosphere was added 4 N HCl in 1, 4-dioxane (3 mL) at 0° C.; warmed to RT and stirred for 4 h. The reaction was monitored by TLC; after completion of the reaction, the volatiles were removed in vacuo. The crude was titurated with diethyl ether (5 mL) and dried in vacuo to afford compound 308 (70 mg, HCl salt) as brown solid. TLC: 30% EtOAc/hexanes (R$_f$: 0.1); $^1$H NMR (DMSO-d$_6$, 400 MHz): δ 9.73-9.27 (m, 1H), 8.39 (br s, 3H), 7.35 (s, 1H), 4.08 (q, J=5.3 Hz, 2H), 2.95 (s, 3H).

Synthesis of 4-(aminomethyl)-N, N-dimethylthiazol-2-amine hydrochloride (310)

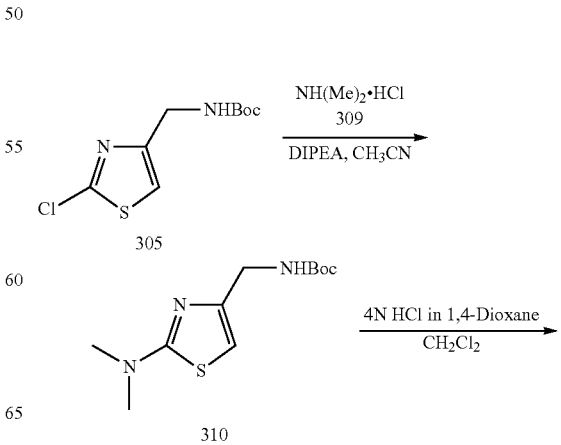

127

-continued

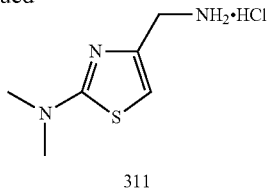

311

Synthesis of Tert-Butyl ((2-(dimethylamino) thiazol-4-yl) methyl) carbamate (310)

To a stirred solution of compound 305 (100 mg, 0.41 mmol) in CH$_3$CN (3 mL) under argon atmosphere were added dimethyl amine hydrochloride 310 (648 mg, 8.06 mmol) and diisopropyl ethylamine (0.2 mL, 1.21 mmol) in a sealed tube at RT and heated to 120° C. for 54 h. The reaction was monitored by TLC; after completion of the reaction, the reaction mixture was diluted with EtOAc (2×50 mL) washed with water (20 mL). The organic extract was dried over sodium sulphate, filtered and concentrated in vacuo to obtain the crude. The crude was purified through silica gel column chromatography using 20% EtOAc/hexanes to afford compound 310 (80 mg, 77%) as an off-white solid. TLC: 30% EtOAc/hexanes (R$_f$: 0.2); $^1$H NMR (DMSO-d$_6$, 400 MHz): δ 7.29 (t, J=4.8 Hz, 1H), 6.89 (s, 1H), 4.08 (d, J=5.9 Hz, 2H), 2.97 (s, 6H), 1.38 (s, 9H).

Synthesis of 4-(aminomethyl)-N,N-dimethylthiazol-2-amine hydrochloride (311)

To a stirred solution of compound 310 (100 mg, 0.38 mmol) in CH$_2$Cl$_2$ (3 mL) under argon atmosphere was added 4 N HCl in 1, 4-dioxane (3 mL) at 0° C.; warmed to RT and stirred for 4 h. The reaction was monitored by TLC; after completion of the reaction, the volatiles were removed in vacuo. The crude was titurated with diethyl ether (5 mL) and dried in vacuo to afford compound 311 (75 mg, HCl salt) as an off-white solid. TLC: 50% EtOAc/hexanes (R$_f$: 0.1); $^1$H NMR (DMSO-d$_6$, 400 MHz): δ 8.44 (br s, 3H), 7.38 (s, 1H), 4.10 (q, J=5.6 Hz, 2H), 3.14 (s, 6H).

Synthesis of (4-ethylthiazol-5-yl) methanamine hydrochloride (319)

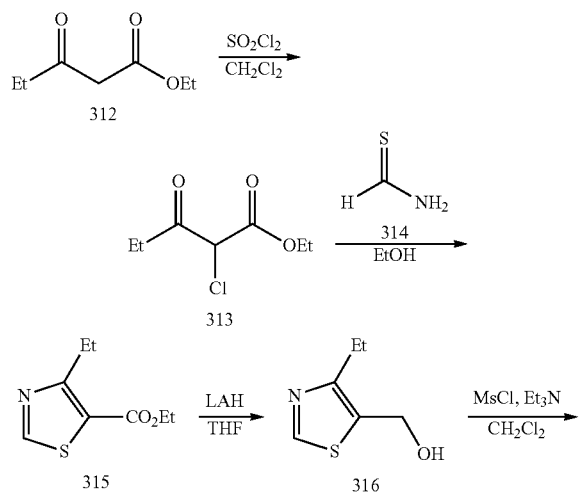

128

-continued

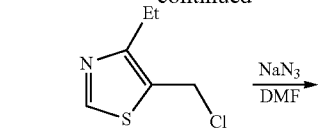

317

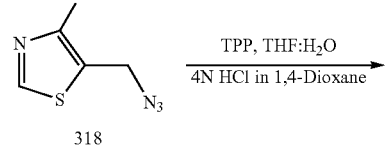

318

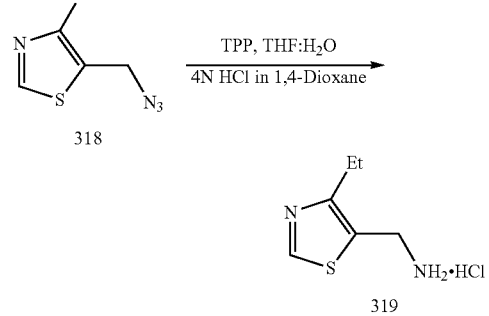

319

Synthesis of Ethyl 2-chloro-3-oxopentanoate (313)

To a stirred solution of ethyl 3-oxopentanoate 312 (1 g, 6.94 mmol) in CH$_2$Cl$_2$ (20 mL) under argon atmosphere was added sulfuryl chloride (0.56 ML, 6.94 mmol) at 0° C.; warmed to RT and stirred for 6 h. The reaction was monitored by TLC; after completion of the reaction, the volatiles were removed in vacuo to afford compound crude 313 (1 g) as colorless liquid. TLC: 10% EtOAc/hexanes (R$_f$: 0.5); $^1$H NMR (DMSO-d$_6$, 400 MHz): δ 5.66-5.55 (m, 1H), 5.66-5.55 (m, 1H), 4.22 (q, J=7.1 Hz, 3H), 2.73-2.67 (m, 2H), 1.22 (t, J=7.1 Hz, 3H), 0.99 (t, J=7.2 Hz, 3H).

Synthesis of Ethyl 4-ethylthiazole-5-carboxylate (315)

To a stirred solution of compound 313 (1 g, crude) in EtOH (10 mL) under inert atmosphere was added thioformamide 314 (3.3 g, 55.55 mmol) at RT; heated at 80° C. and stirred for 24 h. The reaction was monitored by TLC; after completion of the reaction, the volatiles were removed in vacuo to obtain the crude. The crude was purified through column chromatography using 40% EtOAc/hexanes to afford compound 315 (300 mg, 30%) as yellow solid. TLC: 20% EtOAc/hexanes (R$_f$: 0.4); LC-MS: 51.18%; 185.9 (M$^+$+1); (column; Ascentis Express C18, (50×3.0 mm, 2.7 μm); RT 2.24 min. 0.025% Aq. TFA+5% ACN: ACN+5% 0.025% Aq. TFA, 1.2 mL/min).

Synthesis of (4-ethylthiazol-5-yl) methanol (316)

To a stirred solution of compound 315 (300 mg, 1.62 mmol) in THF (10 mL) under inert atmosphere was added lithium aluminium hydride (123 mg, 3.24 mmol) at 0° C.; warmed to RT and stirred for 1 h. The reaction was monitored by TLC; after completion of the reaction, the reaction mixture was quenched with saturated 10% NaOH solution (1 mL), filtered through celite. The filtrate was concentrated in vacuo to obtain the crude. The crude was purified through column chromatography using 30% EtOAc/hexanes to afford compound 316 (200 mg, 86%) as yellow solid. TLC: 30% EtOAc/hexanes (R$_f$: 0.4); $^1$H NMR (DMSO-d$_6$, 400 MHz): δ 8.86 (s, 1H), 5.45 (t, J=5.5 Hz, 1H), 4.62 (d, J=5.5 Hz, 2H), 2.67 (q, J=7.5 Hz, 2H), 1.17 (t, J=7.5 Hz, 3H).

Synthesis of 5-(chloromethyl)-4-ethylthiazole (317)

To a stirred solution of compound 316 (200 mg, 1.39 mmol) in CH$_2$Cl$_2$ (10 mL) under inert atmosphere were added triethyl amine (0.4 mL, 4.17 mmol), mesyl chloride (0.3 mL, 2.79 mmol) at 0° C.; warmed to RT and stirred for 16 h. The reaction was monitored by TLC; after completion of the reaction, the reaction mixture was quenched with saturated NaHCO$_3$ solution (5 mL). The organic extract was dried over sodium sulphate, filtered and concentrated in vacuo to obtain compound 317 (200 mg, crude) as yellow solid. TLC: 30% EtOAc/hexanes (R$_f$: 0.7); $^1$H NMR (DMSO-d$_6$, 400 MHz): δ 9.01 (s, 1H), 5.08 (s, 2H), 2.76 (q, J=7.5 Hz, 2H), 1.20 (t, J=7.5 Hz, 3H).

Synthesis of 5-(azidomethyl)-4-ethylthiazole (318)

To a stirred solution of compound 317 (400 mg, 2.48 mmol) in DMF (10 mL) under argon atmosphere was added sodium azide (322 mg, 4.96 mmol) at RT; warmed to 80° C. and stirred for 16 h. The reaction was monitored by TLC; after completion of the reaction, the reaction mixture was quenched with ice-cold water (100 mL) and extracted with EtOAc (2×50 mL). The combined organic extracts were dried over sodium sulphate, filtered and concentrated in vacuo to afford crude compound 318 (350 mg) as yellow liquid. The crude was carried forward for next step without further purification. TLC: 20% EtOAc/hexanes (R$_f$: 0.5).

Synthesis of (4-ethylthiazol-5-yl) methanamine hydrochloride (319)

To a stirred solution of compound 318 (350 mg) in THF:H$_2$O (4:1, 20 mL) was added triphenyl phosphine (1.3 g, 5.20 mmol) at RT and stirred for 3 h. The reaction was monitored by TLC; after completion of the reaction, the volatiles were removed in vacuo to obtain the crude.

The crude was diluted with CH$_2$Cl$_2$ (2 mL) cooled to 0° C.; added 4 N HCl 1, 4-dioxane (5 mL) under argon atmosphere and stirred for 1 h. The reaction was monitored by TLC; after completion of the reaction, the volatiles were removed in vacuo to obtain the crude which was titurated with diethyl ether (2×5 mL) dried in vacuo to afford compound 319 (136 mg) as an off-white solid. TLC: 40% EtOAc/hexanes (R$_f$: 0.2); LC-MS: 89.95%; 142.9 (M$^+$+1); (column; Ascentis Express C18, (50×3.0 mm, 2.7 μm); RT 1.29 min. 0.025% Aq. TFA+5% ACN: ACN+5% 0.025% Aq. TFA, 1.2 mL/min).

Synthesis of (4-isopropylthiazol-5-yl) methanamine hydrochloride (327)

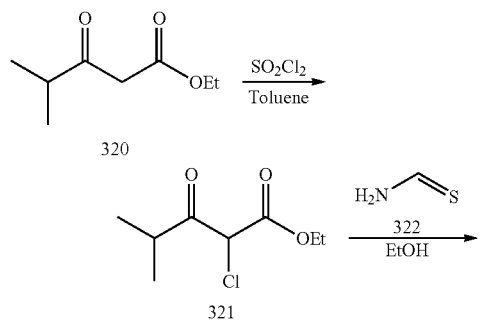

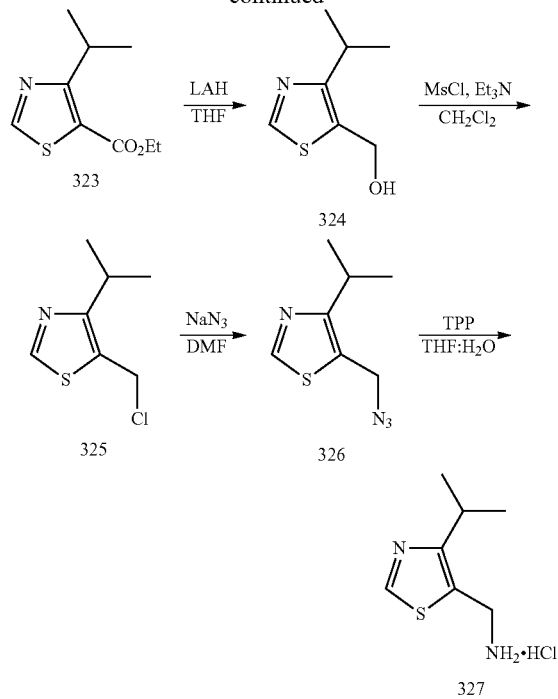

Synthesis of Ethyl 2-chloro-4-methyl-3-oxopentanoate (321)

To a stirred solution of ethyl 4-methyl-3-oxopentanoate 320 (5 g, 31.64 mmol) in Toluene (50 mL) under argon atmosphere was added sulfuryl chloride (4.26 g, 31.64 mmol) at 0° C.; warmed to RT and stirred for 24 h. The reaction was monitored by TLC; after completion of the reaction, the volatiles were removed in vacuo to afford compound crude 321 (6 g) as brown syrup. TLC: 10% EtOAc/hexanes (R$_f$: 0.8).

Synthesis of Ethyl 4-isopropylthiazole-5-carboxylate (323)

To a stirred solution of compound 321 (2.1 g) in ethanol (30 mL) under argon atmosphere was added thioformamide 322 (0.667 g, 10.93 mmol) at RT and heated to reflux for 30 h. The reaction was monitored by TLC; after completion of the reaction, the volatiles were removed in vacuo. The residue was diluted with EtOAc (200 mL), washed with saturated sodium bicarbonate solution (100 mL). The organic extract was dried over sodium sulfate, filtered and concentrated in vacuo to afford crude compound 323 (230 mg, 11%) as brown syrup. TLC: 10% EtOAc/hexanes (R$_f$: 0.5); LC-MS: 93.64%; 199.9 (M$^+$+1); (column; Ascentis Express C18, (50×3.0 mm, 2.7 μm); RT 2.49 min. 0.025% Aq. TFA+5% ACN: ACN+5% 0.025% Aq. TFA, 1.2 mL/min).

Synthesis of (4-isopropylthiazol-5-yl) methanol (324)

To a stirred solution of compound 323 (230 mg, 1.15 mmol) in THF (10 mL) under inert atmosphere was added lithium aluminium hydride (87 mg, 2.28 mmol) at 0° C.; warmed to RT and stirred for 4 h. The reaction was monitored by TLC; after completion of the reaction, the reaction mixture was cooled to 0° C., quenched with ice-cold water (10 mL), 15% aqueous sodium hydroxide solution (5 mL), filtered through celite and washed with EtOAc (100 mL). The filtrate was dried over sodium sulfate, filtered and concentrated in vacuo to afford crude compound 324 (112 mg) as an off-white solid. TLC: 20% EtOAc/hexanes (R$_f$: 0.2). $^1$H NMR (DMSO-d$_6$, 400 MHz): δ 8.85 (s, 1H), 5.45 (t, J=5.5 Hz, 1H), 4.64 (d, J=5.5 Hz, 2H), 3.14-3.07 (m, 1H), 1.19 (d, J=6.8 Hz, 6H).

Synthesis of 5-(chloromethyl)-4-isopropylthiazole (325)

To a stirred solution of compound 324 (112 mg) in CH$_2$Cl$_2$ (10 mL) under inert atmosphere were added triethyl amine (0.21 mL, 2.13 mmol), mesyl chloride (0.08 mL, 0.97 mmol) at 0° C.; warmed to RT and stirred for 5 h. The reaction was monitored by TLC; after completion of the reaction, the reaction mixture was diluted with CH$_2$Cl$_2$ (50 mL) washed with NaHCO$_3$ solution (50 mL), brine (50 mL). The organic extract was dried over sodium sulfate, filtered and concentrated in vacuo to afford compound 325 (126 mg) as brown thick syrup. TLC: 30% EtOAc/hexanes (R$_f$: 0.8); LC-MS: 87.83%; 175.8 (M$^+$+1); (column; Ascentis Express C18, (50×3.0 mm, 2.7 μm); RT 2.30 min. 0.025% Aq. TFA+5% ACN: ACN+5% 0.025% Aq. TFA, 1.2 mL/min).

Synthesis of 5-(azidomethyl)-4-isopropylthiazole (326)

To a stirred solution of compound 325 (126 mg, 0.53 mmol) in DMF (10 mL) under inert atmosphere was added sodium azide (70 mg, 1.07 mmol) at RT and heated to 80° C. for 4 h. The reaction was monitored by TLC; after completion of the reaction, the reaction mixture was diluted with EtOAc (75 mL) washed with water (50 mL). The organic extract were dried over sodium sulfate, filtered and concentrated in vacuo to afford crude compound 326 (82 mg, 63%) as thick syrup. TLC: 30% EtOAc/hexanes (R$_f$: 0.7); 1H NMR (DMSO-d$_6$, 500 MHz): δ 9.01 (s, 1H), 4.74 (s, 2H), 3.30-3.21 (m, 1H), 1.21 (d, J=6.8 Hz, 6H);

Synthesis of (4-isopropylthiazol-5-yl) methanamine hydrochloride (327)

To a stirred solution of compound 326 (80 mg, 0.43 mmol) in THF:H$_2$O (4:1, 10 mL) was added triphenyl phosphine (230 mg, 0.87 mmol) at RT and stirred for 4 h. The reaction was monitored by TLC; after completion of the reaction, the volatiles were removed in vacuo to obtain the crude. The obtained solid was further dried using toluene (2×5 mL) to obtain the crude.

The crude compound was dissolved in CH$_2$Cl$_2$ (3 mL) added 4 N HCl in 1, 4-dioxane (2 mL) under inert atmosphere at 0° C. and stirred for 1 h. The volatiles were removed in vacuo to obtain the crude, which was washed with diethyl ether (2 mL) to afford compound 327 (42 mg, 50%) as an off-white solid. TLC: 10% MeOH/CH$_2$Cl$_2$ (R$_f$: 0.2); $^1$H NMR (DMSO-d$_6$, 400 MHz): δ 9.02 (s, 1H), 8.26 (br s, 2H), 4.24 (q, J=5.6 Hz, 2H), 3.24-3.17 (m, 1H), 1.19 (d, J=6.8 Hz, 6H).

Synthesis of (4-chlorothiazol-5-yl) methanamine hydrochloride (337)

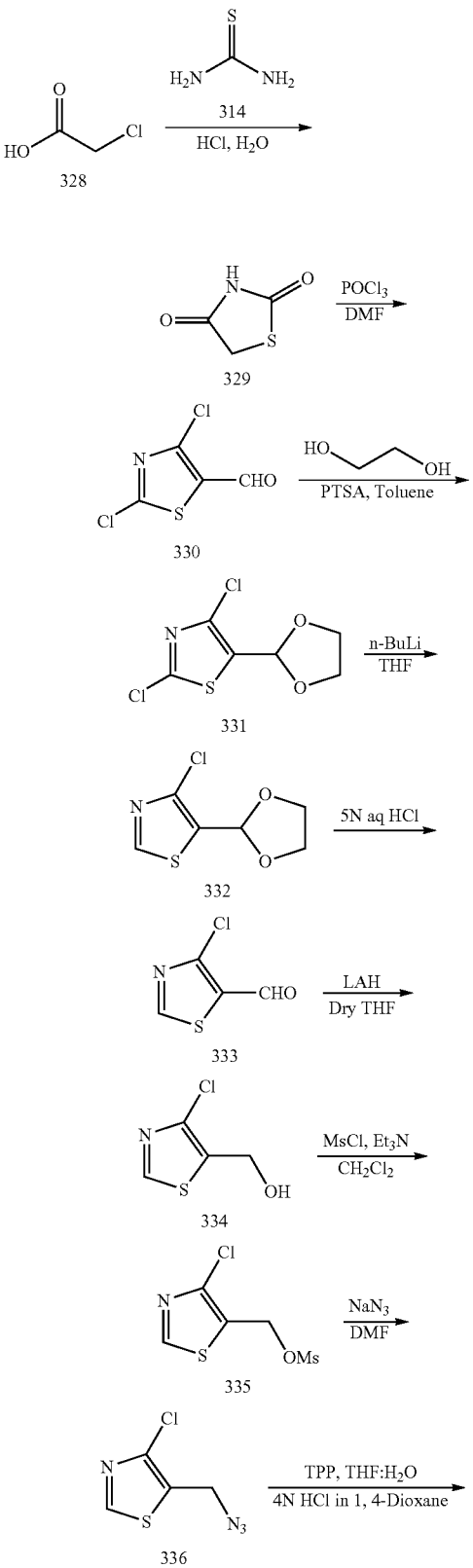

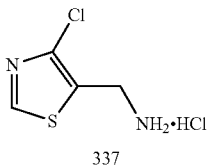

337

Synthesis of thiazolidine-2, 4-dione (329)

To a stirred solution of 2-chloroacetic acid 328 (5 g, 52.9 mmol) in H$_2$O (10 mL) was added thiourea 314 (3.80 g, 52.9 mmol) at 0° C. stirred for 30 min added concentrated HCl (6 mL) dropwise for 15 min; heated at 110° C. and stirred for 24 h. The reaction was monitored by TLC; after completion of the reaction, the reaction mixture was cooled to 0° C. and stirred for 30 min. The precipitated solid was filtered and dried in vacuo to afford compound 329 (3.2 g, 47%) as white solid. TLC: 30% EtOAc/hexanes (R$_f$: 0.2); $^1$H NMR (400 MHz, DMSO-d$_6$): δ 12.01 (br s, 1H), 4.15 (s, 2H).

Synthesis of 2, 4-dichlorothiazole-5-carbaldehyde (330)

A mixture of compound 329 (2.7 g, 23.07 mmol) in DMF (1.23 mL, 15.98 mmol) at 0° C. under argon atmosphere was added phosphorous oxychloride (8.15 mL, 87.17 mmol) dropwise for 15 min at 0° C.; warmed to RT and stirred for 1 h; heated to 120° C. and stirred for 4 h. The reaction was monitored by TLC; after completion of the reaction, the reaction mixture was poured into ice cold water slowly and extracted with CH$_2$Cl$_2$ (3×100 mL). The combined organic extracts were washed with saturated NaHCO$_3$ solution (100 mL), water (100 mL), dried over sodium sulfate, filtered and concentrated in vacuo to obtain the crude. The crude was purified through column chromatography using 5% EtOAc/hexanes to afford compound 330 (1.4 g, 33%) as brown color oil. TLC: 30% EtOAc/hexanes (R$_f$: 0.8); $^1$H NMR (500 MHz, DMSO-d$_6$): δ 9.87 (s, 1H).

Synthesis of 2,4-dichloro-5-(1, 3-dioxolan-2-yl) thiazole (331)

To a stirred solution of compound 330 (1.4 g, 7.73 mmol) in Toluene (20 mL) under argon atmosphere was added ethane-1, 2-diol (1.43 g, 23.20 mmol), p-toluenesulfonic acid (133 mg, 0.77 mmol) at 0° C.; heated at 110° C. and stirred for 5 h. The reaction was monitored by TLC; after completion of the reaction, the reaction mixture was quenched with 10% aqueous NaHCO$_3$ solution (50 mL) and extracted with EtOAc (2×100 mL). The combined organic extracts were dried over sodium sulfate, filtered and concentrated in vacuo to obtain the crude. The crude was purified through column chromatography using 10% EtOAc/hexanes to afford compound 331 (1.7 g, 98%) as yellow oil. TLC: 10% EtOAc/hexanes (R$_f$: 0.2); 1H NMR (400 MHz, CDCl$_3$): δ 6.04 (s, 1H), 4.14-4.07 (m, 2H), 4.06-4.00 (m, 2H).

Synthesis of 4-chloro-5-(1, 3-dioxolan-2-yl) thiazole (332)

To a stirred solution of compound 331 (1.7 g, 7.55 mmol) in THF (20 ML) under argon atmosphere was added n-butyl lithium (3.9 mL, 9.82 mmol, 2.5 M solution in THF) dropwise for 10 min at −78° C. and stirred for 2 h. The reaction was monitored by TLC; after completion of the reaction, the reaction mixture was quenched with ice cold water (50 mL) and extracted with EtOAc (2×100 mL). The combined organic extracts were dried over sodium sulfate, filtered and concentrated in vacuo to obtain the crude. The crude was purified through column chromatography using 5% EtOAc/hexanes to afford compound 332 (1.1 g, 76%) as yellow oil. TLC: 10% EtOAc/hexanes (R$_f$: 0.2); 1H NMR (CDCl$_3$, 500 MHz): δ 8.74 (s, 1H), 6.16 (s, 1H), 4.19-4.15 (m, 2H), 4.08-4.04 (m, 2H).

Synthesis of 4-chlorothiazole-5-carbaldehyde (333)

To a stirred solution of compound 332 (1.1 g, 5.75 mmol) in THF (10 mL) was added 5 N aqueous HCl in 1, 4-dioxane (6 mL) at 0° C.; warmed to RT and stirred for 3 h. The reaction was monitored by TLC; after completion of the reaction, the reaction mixture was poured into brine (20 mL) extracted with EtOAc (2×50 mL). The combined organic extracts were washed with saturated sodium bicarbonate (100 mL) dried over sodium sulfate, filtered and concentrated in vacuo to afford compound 333 (800 mg, 95%) as yellow oil. TLC: 10% EtOAc/hexanes (R$_f$: 0.3); $^1$H NMR (CDCl$_3$, 500 MHz): δ 10.11 (s, 1H), 9.00 (s, 1H).

Synthesis of (4-chlorothiazol-5-yl) methanol (334)

To a stirred solution of compound 333 (750 mg, 5.10 mmol) in dry THF (20 mL) under inert atmosphere was added lithium aluminium hydride (193 mg, 5.10 mmol) at 0° C.; warmed to RT and stirred for 3 h. The reaction was monitored by TLC; after completion of the reaction, the reaction mixture was cooled to 0° C., quenched with 30% aqueous sodium hydroxide solution (3 mL) extracted with EtOAc (2×100 mL). The combined organic extracts were dried over sodium sulfate, filtered and concentrated in vacuo to afford compound 334 (520 mg, 68%) as yellow oil. TLC: 10% EtOAc/hexanes (R$_f$: 0.3); $^1$H NMR (CDCl$_3$, 500 MHz): δ 8.69 (m, 1H), 4.88 (s, 2H).

Synthesis of (4-chlorothiazol-5-yl) methyl methanesulfonate (335)

To a stirred solution of compound 334 (520 mg, 3.48 mmol) in CH$_2$Cl$_2$ (15 mL) under inert atmosphere were added triethyl amine (1.23 mL, 8.71 mmol) and mesyl chloride (0.34 mL, 4.18 mmol) at 0° C.; warmed to RT and stirred for 16 h. The reaction was monitored by TLC; after completion of the reaction, the reaction mixture was diluted with water (50 mL) and extracted with CH$_2$Cl$_2$ (2×50 mL). The combined organic extracts were washed with saturated NaHCO$_3$ (50 mL) dried over sodium sulfate, filtered and concentrated in vacuo to afford compound 335 (600 mg, crude) as brown liquid. TLC: 10% EtOAc/hexanes (R$_f$: 0.8 $^1$H NMR (CDCl$_3$, 500 MHz): δ 8.74 (s, 1H), 4.79 (s, 2H), 1.44 (s, 3H).

Synthesis of 5-(azidomethyl)-4-chlorothiazole (336)

To a stirred solution of compound 335 (600 mg, 2.64 mmol) in DMF (10 mL) under inert atmosphere was added sodium azide (343 mg, 5.28 mmol) at RT and heated to 100° C. for 4 h. The reaction was monitored by TLC; after completion of the reaction, the reaction mixture was diluted with ice cold water (100 mL) and extracted with diethyl ether (2×50 mL). The combined organic extracts were dried over sodium sulfate, filtered and concentrated in vacuo to afford compound 336 (250 mg, 54%) as yellow oil. TLC: 8% EtOAc/hexanes ($R_f$: 0.5); 1H NMR (CDCl$_3$, 400 MHz) δ 8.74 (s, 1H), 4.58 (s, 2H).

Synthesis of (4-chlorothiazol-5-yl) methanamine hydrochloride (337)

To a stirred solution of compound 336 (250 mg, 1.43 mmol) in THF:H$_2$O (3:1, 13 ML) was added triphenyl phosphine (752 mg, 2.87 mmol) at RT and stirred for 4 h. The reaction was monitored by TLC; after completion of the reaction, the volatiles were removed in vacuo and the residue was acidified with 4 N HCl in 1, 4-dioxane (2 mL) at 0° C. The volatiles were removed in vacuo and the obtained solid was washed with EtOAc (2 mL), diethyl ether (2 mL) to afford compound 337 (110 mg) as yellow solid. TLC: 5% MeOH/CH$_2$Cl$_2$ ($R_f$: 0.2); $^1$H NMR (DMSO-d$_6$, 400 MHz): δ 9.19 (s, 1H), 8.52 (br s, 3H), 4.24 (q, J=5.6 Hz, 2H);

Synthesis of oxetan-3-ylmethanamine (341)

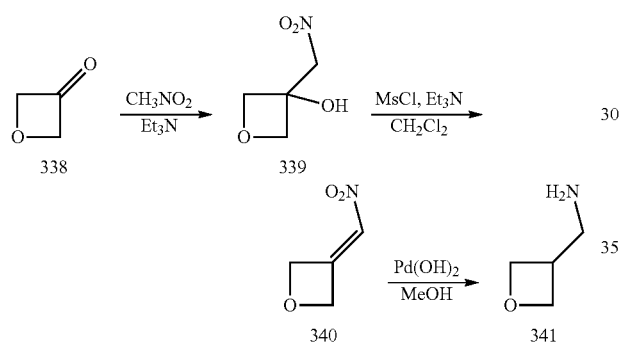

Synthesis of 3-(nitromethyl) oxetan-3-ol (339)

To a stirred solution of oxetan-3-one 338 (500 mg, 0.69 mmol) in nitromethane (1.25 mL) under argon atmosphere was added triethyl amine (0.25 mL) at RT and stirred for 12 h. The reaction was monitored by TLC; after completion of the reaction, the volatiles were removed in vacuo to obtain crude. The crude was purified through silica gel column chromatography using 25% EtOAc/hexanes to afford compound 339 (750 mg, 81%) as an off white solid. TLC: 30% EtOAc/hexanes ($R_f$: 0.3); $^1$H NMR (DMSO-d$_6$, 400 MHz): δ 6.47 (s, 1H), 4.93 (s, 2H), 4.64 (d, J=7.5 Hz, 2H), 4.49 (d, J=7.3 Hz, 2H).

Synthesis of 3-(nitromethylene) oxetane (340)

To a stirred solution of compound 339 (750 mg, 5.63 mmol) in CH$_2$Cl$_2$ (10 mL) under inert atmosphere were added triethyl amine (3.17 mL, 22.55 mmol), mesyl chloride (1.20 mL, 15.50 mmol), at 0° C.; cooled −78° C. and stirred for 1 h. The reaction was monitored by TLC; after completion of the reaction, the volatiles were removed in vacuo to obtain crude. The crude was purified through silica gel column chromatography using 25% EtOAc/hexanes to afford compound 340 (380 mg, 58%) as an off white solid.

TLC: 10% EtOAc/hexanes ($R_f$: 0.5 $^1$H NMR (CDCl$_3$, 400 MHz): δ 6.94-6.92 (m, 1H), 5.68-5.64 (m, 2H), 5.41-5.36 (m, 2H).

Synthesis of oxetan-3-ylmethanamine (341)

To a stirred solution of compound 340 (500 mg, 4.34 mmol) in MeOH (10 mL) under inert atmosphere was added Pd(OH)$_2$ (100 mg) at RT; heated at 45° C. stirred under hydrogen atmosphere (balloon pressure) for 5 h. The reaction was monitored by TLC; after completion of the reaction, the reaction mixture was filtered through celite and washed with MeOH (20 mL). The filtrate was evaporated in vacuo to obtain the crude which was triturated with diethyl ether (2×10 mL) to afford crude compound 341 (100 mg) as pale brown solid. TLC: 10% MeOH/CH$_2$Cl$_2$ ($R_f$: 0.2); Mass (m/z) (Agilent 6310 Ion Trap): 88.5 (M$^+$+1).

Synthesis of 2-(oxazol-5-yl)ethan-1-amine, TFA salt (347)

Synthesis of oxazol-5-ylmethanol (343)

To a stirred solution of ethyl oxazole-5-carboxylate 342 (2 g, 14.18 mmol) in EtOH (20 mL) under argon atmosphere was added sodium borohydride (1.07 g, 28.36 mmol) at 0° C.; warmed to RT and stirred for 16 h. The reaction was monitored by TLC; after completion of the reaction, the reaction mixture was quenched with saturated ammonium chloride solution (25 mL) and extracted with 5% MeOH/CH$_2$Cl$_2$ (2×20 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 343 (810 mg, 58%) as colorless syrup. TLC: 5% MeOH/CH$_2$Cl$_2$ (R$_f$: 0.3); $^1$H-NMR (DMSO-d$_6$, 500 MHz): δ 8.28 (s, 1H), 7.04 (s, 1H), 5.36 (t, J=6.0 Hz, 1H), 4.47 (d, J=6.0 Hz, 2H).

Synthesis of 5-(chloromethyl) oxazole (344)

To a stirred solution of compound 343 (800 mg, 8.08 mmol) in CH$_2$Cl$_2$: n-hexane (1:1, 10 mL) under argon atmosphere was added thionyl chloride (1.2 mL, 16.16 mmol) at 0° C.; heated to reflux and stirred for 3 h. The reaction was monitored by TLC; after completion of the reaction, the reaction mixture was neutralized with saturated NaHCO$_3$ solution (20 mL) and extracted with ether (2×20 mL). The combined organic extracts were dried over sodium sulfate, filtered and concentrated in vacuo to obtain the crude compound 344 (700 mg) as colorless syrup. TLC: 40% EtOAc/hexanes (R$_f$: 0.5); $^1$H-NMR (CDCl$_3$, 400 MHz): δ 7.89 (s, 1H), 7.10 (s, 1H), 4.62 (s, 2H).

Synthesis of 2-(oxazol-5-yl) acetonitrile (345)

To a stirred solution of compound 344 (700 mg, 5.95 mmol) in DMF (8 mL) under argon atmosphere was added sodium cyanide (1.02 g, 20.85 mmol) at RT; heated to 70° C. and stirred for 4 h. The reaction was monitored by TLC; after completion of the reaction, the reaction mixture was diluted with water (20 mL) and extracted with ether (2×20 mL). The combined organic extracts were dried over sodium sulfate, filtered and concentrated in vacuo to obtain the crude compound 345 (650 mg) as colorless syrup. TLC: 40% EtOAc/hexanes (R$_f$: 0.3); $^1$H-NMR (CDCl$_3$, 400 MHz): δ 7.89 (s, 1H), 7.10 (s, 1H), 3.84 (s, 2H).

Synthesis of Tert-Butyl (2-(oxazol-5-yl) ethyl) carbamate (346)

To a stirred solution of compound 345 (50 mg, 0.46 mmol) in MeOH (3 mL) under argon atmosphere were added Boc-anhydride (0.21 mL, 0.92 mmol), nickel chloride hexahydrate (11 mg, 0.04 mmol), sodium borohydride (122 mg, 3.24 mmol) portion wise for 5 min at 0° C.; warmed to RT and stirred for 6 h. The reaction was monitored by TLC; after completion of the reaction, the reaction mixture was diluted with MeOH (10 mL), filtered through celite and the filtrate was concentrated in vacuo to obtain the crude. The crude was purified through silica gel column chromatography using 30% EtOAc/hexanes to afford compound 346 (68 mg, 71%) as colorless syrup. TLC: 50% EtOAc/hexanes (R$_f$: 0.5); $^1$H-NMR (CDCl$_3$, 400 MHz): δ 7.82 (s, 1H), 6.85 (s, 1H), 4.64 (br s, 1H), 3.42-3.40 (m, 2H), 2.89 (t, J=6.4 Hz, 2H), 1.43 (s, 9H).

Synthesis of 2 oxazol-5-yl)ethan-1-amine, TFA salt (347)

To a stirred solution of compound 346 (65 mg, 0.30 mmol) in CH$_2$Cl$_2$ (3 mL) under argon atmosphere was added trifluoro acetic acid (0.14 mL, 1.83 mmol) at 0° C.; warmed to RT and stirred for 4 h. The reaction was monitored by TLC; after completion of the reaction, the volatiles were removed in vacuo to obtain the crude compound 347 (50 mg) as colorless syrup. TLC: 60% EtOAc/hexanes (R$_f$: 0.2); $^1$H-NMR (DMSO-d$_6$, 500 MHz): δ 8.30 (s, 1H), 7.85-7.79 (m, 2H), 7.02 (s, 1H), 3.10-3.05 (m, 2H), 2.98 (t, J=7.5 Hz, 2H).

Synthesis of 2 (thiazol-5-yl)ethan-1-amine, TFA salt (352)

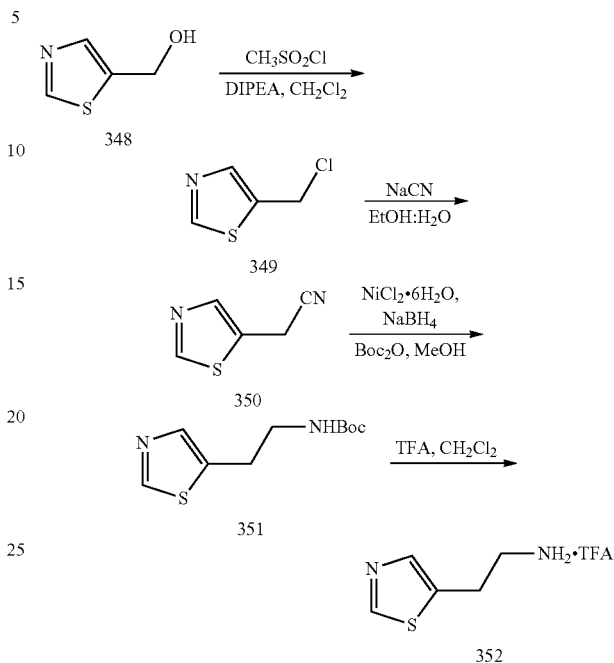

Synthesis of 5-(chloromethyl) thiazole (349)

To a stirred solution of thiazol-5-ylmethanol 348 (1 g, 8.69 mmol) in CH$_2$Cl$_2$ (50 mL) under argon atmosphere were added mesyl chloride (1.09 g, 9.56 mmol) drop wise for 15 min, diisopropyl ethyl amine (1.23 g, 9.56 mmol) at 0-5° C.; warmed to RT and stirred for 4 h. The reaction was monitored by TLC; after completion of the reaction, the volatiles were removed in vacuo to obtain the crude. The crude was washed with saturated NaHCO$_3$ solution (20 mL) and purified through silica gel column chromatography using 50% EtOAc/hexanes to afford compound 349 (650 mg, 57%) as yellow liquid. TLC: 5% MeOH/CH$_2$Cl$_2$ (R$_f$: 0.7); $^1$H-NMR (CDCl$_3$, 500 MHz): δ 8.84 (s, 1H), 7.86 (s, 1H), 4.84 (s, 2H).

Synthesis of 2-(thiazol-5-yl) acetonitrile (350)

To a stirred solution of compound 349 (650 mg, 4.92 mmol) in EtOH: H$_2$O (4:1, 10 mL) under argon atmosphere was added sodium cyanide (361 mg, 7.38 mmol) at RT; heated to 80° C. and stirred for 4 h. The reaction was monitored by TLC; after completion of the reaction, the volatiles were removed in vacuo. The residue was diluted with water (20 mL) and extracted with EtOAc (2×25 mL). The combined organic extracts were dried over sodium sulfate, filtered and concentrated in vacuo to obtain the crude. The crude was purified through silica gel column chromatography using 70% EtOAc/hexanes to afford compound 350 (250 mg, 41%) as colorless semi-solid. TLC: 70% EtOAc/hexanes (R$_f$: 0.4); $^1$H-NMR (CDCl$_3$, 500 MHz): δ 8.81 (s, 1H), 7.85 (s, 1H), 3.84 (s, 2H).

Synthesis of Tert-Butyl (2-(thiazol-5-yl) ethyl) carbamate (351)

To a stirred solution of compound 350 (50 mg, 0.40 mmol) in MeOH (3 mL) under argon atmosphere were added Boc-anhydride (175 mg, 0.80 mmol), nickel chloride hexahydrate (9.75 mg, 0.04 mmol), sodium borohydride (107 mg, 2.82 mmol) portion wise for 5 min at 0-5° C.; warmed to RT and stirred for 4 h. The reaction was monitored by TLC; after completion of the reaction, the reaction mixture was filtered, washed with EtOAc (2×10 mL) and the filtrate was concentrated in vacuo to obtain the crude. The crude was purified through silica gel column chromatography using 50% EtOAc/hexanes to afford compound 351 (20 mg, 22%) as brown solid. TLC: 70% EtOAc/hexanes ($R_f$: 0.6); $^1$H-NMR (DMSO-$d_6$, 400 MHz): δ 8.92 (s, 1H), 7.65 (s, 1H), 6.98-6.96 (m, 1H), 3.15 (q, 2H), 2.95 (t, J=6.8 Hz, 2H), 1.39 (s, 9H).

Synthesis of 2-(thiazol-5-yl) ethan-1-amine (352)

To a stirred solution of compound 351 (20 mg, 0.08 mmol) in $CH_2Cl_2$ (3 mL) under argon atmosphere was added trifluoro acetic acid (60 mg, 0.53 mmol) at 0-5° C.; warmed to RT and stirred for 4 h. The reaction was monitored by TLC; after completion of the reaction, the volatiles were removed in vacuo to obtain the crude compound 352 (10 mg) as colorless liquid. The crude was carried to the next step without any further purification. TLC: 70% EtOAc/hexanes ($R_f$: 0.2); $^1$H-NMR (DMSO-$d_6$, 400 MHz): δ 9.01 (s, 1H), 7.95-7.89 (m, 2H), 7.76 (s, 1H), 3.16-3.10 (m, 4H).

Synthesis of 2-(4-(pyrimidin-5-yl) phenyl) ethan-1-amine (359)

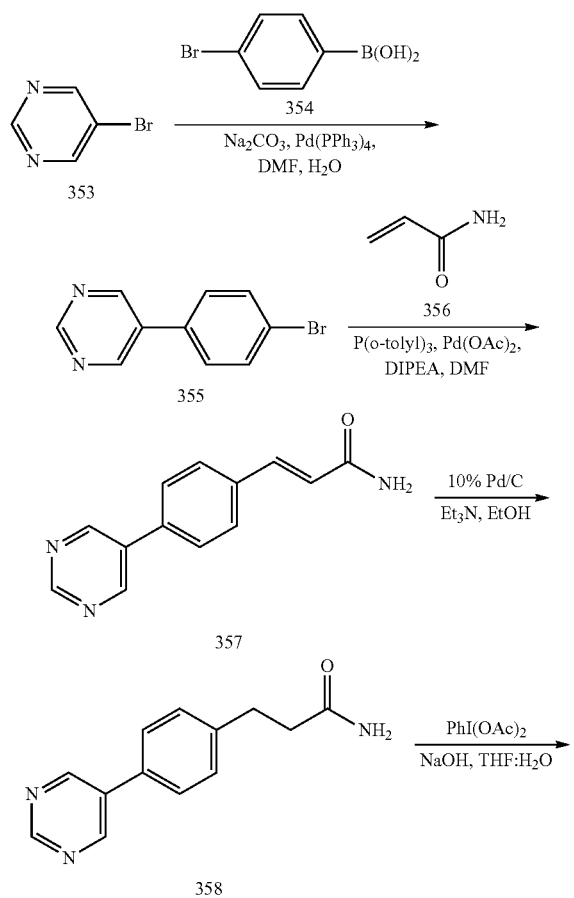

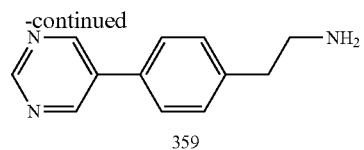

Synthesis of 5-(4-bromophenyl) pyrimidine (355)

To a stirred solution of 5-bromopyrimidine 353 (1 g, 6.32 mmol) in DMF: $H_2O$ (4:1, 25 mL) were added sodium carbonate (1 g, 9.43 mmol) and (4-bromophenyl) boronic acid 354 (1.26 g, 6.32 mmol), purged under argon atmosphere for 30 min. To this was added $Pd(PPh_3)_4$ (731 mg, 0.63 mmol) at RT; heated to 80° C. and stirred for 2.5 h. The reaction was monitored by TLC; after completion of the reaction, the reaction mass was filtered through celite; the filtrate was diluted with water (100 mL) and extracted with EtOAc (3×15 mL). The combined organic extracts were dried over sodium sulfate, filtered and concentrated in vacuo to obtain the crude. The crude was purified through silica gel column chromatography using 15% EtOAc/hexanes to afford compound 355 (1 g, 67%) as white solid. TLC: 30% EtOAc/hexanes ($R_f$: 0.3); $^1$H-NMR (DMSO-$d_6$, 500 MHz): δ 9.20 (s, 1H), 9.15 (s, 2H), 7.93 (d, J=8.5 Hz, 2H), 7.74 (d, J=9.0 Hz, 2H).

Synthesis of (E)-3-(4-(pyrimidin-5-yl) phenyl) acrylamide (357)

To a stirred solution of 5-(4-bromophenyl) pyrimidine 355 (1 g, 4.27 mmol) in DMF (10 mL) under inert atmosphere was added acrylamide 356 (364 mg, 5.12 mmol) at RT and purged under argon for 10 min. To this were added o-tolyl phosphine (142 mg, 0.47 mmol), $Pd(OAc)_2$ (4.78 mg, 0.021 mmol), and diisopropyl ethyl amine (0.9 mL, 7.32 mmol) at RT; heated to 130° C. and stirred for 5 h. The reaction was monitored by TLC; after completion of the reaction, the reaction mixture was filtered through celite washed with 50% MeOH/$CH_2Cl_2$ (2×10 mL), the filtrate was concentrated under reduced pressure to afford the crude. The crude was washed with 50% MeOH/$CH_2Cl_2$ (2×15 mL), dried in vacuo to afford compound 357 (600 mg, 62%) as white solid. TLC: 40% EtOAc/hexanes ($R_f$: 0.2); $^1$H NMR (400 MHz, DMSO-$d_6$) δ 9.23-9.16 (m, 3H), 7.88 (d, J=8.3 Hz, 2H), 7.72 (d, J=8.3 Hz, 2H), 7.56 (br s, 1H), 7.48 (d, J=15.9 Hz, 1H), 7.14 (br s, 1H), 6.70 (d, J=15.9 Hz, 1H).

Synthesis of 3-(4-(pyrimidin-5-yl) phenyl) propanamide (358)

To a stirred solution of compound 357 (150 mg, 0.64 mmol) in EtOH (4 mL) under inert atmosphere were added 10% Pd/C (50 mg) and triethylamine (0.092 mL, 0.64 mmol) at RT and stirred under $H_2$ (balloon pressure) for 4 h. The reaction was monitored by TLC; after completion of the reaction, the reaction mixture was filtered through celite. The filtrate was concentrated in vacuo to obtain the crude which was purified by silicagel column chromatography using 3% MeOH/$CH_2Cl_2$ to afford compound 358 (65 mg, 43%) as white solid. TLC: 30% EtOAc/hexanes ($R_f$: 0.2); $^1$H-NMR (DMSO-$d_6$, 400 MHz): δ 9.16 (s, 1H), 9.12 (s, 2H), 7.72 (d, J=8.0 Hz, 2H), 7.37 (d, J=8.0 Hz, 2H), 7.29 (br s, 1H), 6.76 (br s, 1H), 2.87 (t, J=8.0 Hz, 2H), 2.39 (t, J=8.0 Hz, 2H).

Synthesis of 2-(4-(pyrimidin-5-yl) phenyl) ethan-1-amine (359)

To a stirred solution of compound 358 (65 mg, 0.28 mmol) in THF:H$_2$O (1:1, 3 mL) were added NaOH (128 mg, 0.91 mmol), phenyl-λ$^3$-iodanediyl diacetate (92 mg, 0.28 mmol) at 0° C. and stirred for 1 h. The reaction was monitored by TLC; after completion of the reaction, the pH of the reaction mixture was adjusted to ~2 using 3 N HCl and extracted with CH$_2$Cl$_2$ (2×50 mL). The pH of the aqueous layer was basified to ~8 with 3 N NaOH, extracted with THF (2×100 mL). The combined organic extracts were dried over sodium sulphate, filtered and concentrated in vacuo to afford crude compound 359 (40 mg) as white solid. TLC: 10% MeOH/CH$_2$Cl$_2$ (R$_f$: 0.3); $^1$H-NMR (DMSO-d$_6$, 400 MHz): δ 9.16 (s, 1H), 9.11 (s, 2H), 7.72 (d, J=8.4 Hz, 2H), 7.37 (d, J=8.0 Hz, 2H), 2.81-2.66 (m, 2H), 1.78-1.69 (m, 2H).

Synthesis of 2-(2-phenylpyrimidin-5-yl) ethan-1-amine hydrochloride (366)

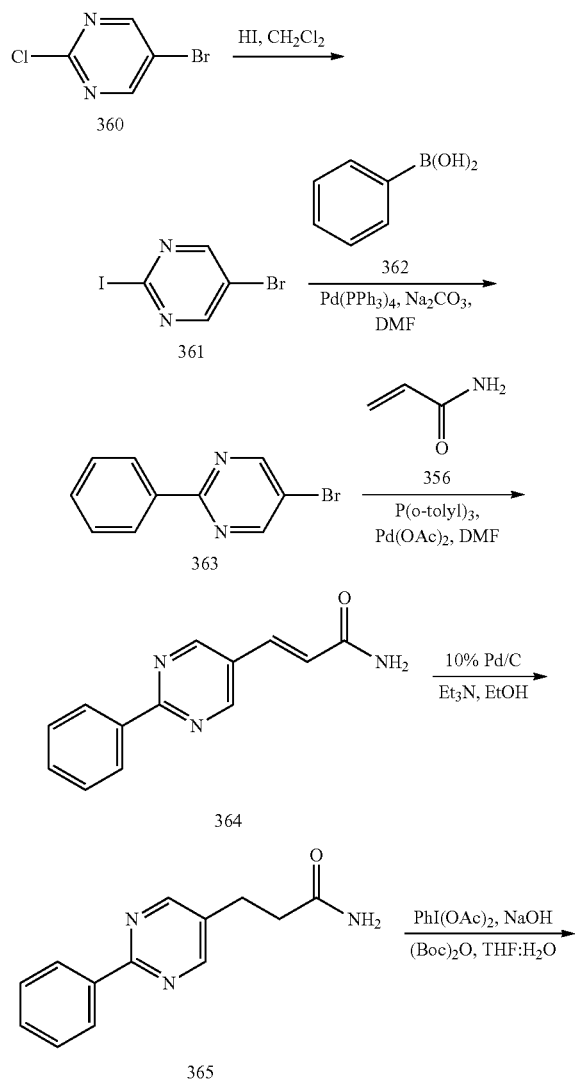

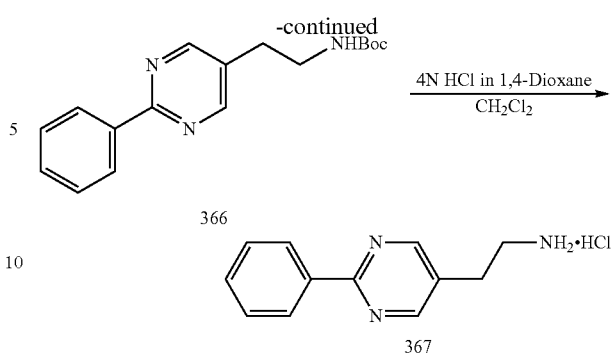

Synthesis of 5-bromo-2-iodopyrimidine (361)

To a stirred solution of 5-bromo-2-chloropyrimidine 360 (1 g, 5.16 mmol) in CH$_2$Cl$_2$ (10 mL) was added hydrogen iodide (5 mL, 57% aqueous solution) at −10° C.; warmed to 0° C. and stirred for 5 h. The reaction was monitored by TLC; after completion of the reaction, the reaction mixture was quenched with solid K$_2$CO$_3$ (2 g), diluted with water (100 mL) and extracted with CH$_2$Cl$_2$ (2×100 mL). The combined organic extracts were dried over sodium sulfate, filtered and concentrated in vacuo to obtain crude compound 361 (1.4 g, 94%) as yellow solid. TLC: 10% EtOAc/hexanes (R$_f$: 0.7); $^1$H-NMR (DMSO-d$_6$, 400 MHz): δ 8.55 (s, 2H).

Synthesis of 5-bromo-2-phenylpyrimidine (363)

To a stirred solution of compound 361 (1.4 g) in DMF:H$_2$O (4:1, 20 mL) were added sodium carbonate (783 mg, 7.39 mmol) and phenylboronic acid 362 (451 mg, 3.69 mmol), purged under argon for 30 min. To this was added Pd(PPh$_3$)$_4$ (570 mg, 0.49 mmol) at RT; heated to 80° C. and stirred for 2 h. The reaction was monitored by TLC; after completion of the reaction, the reaction mass was filtered through celite; the filtrate was diluted with water (100 mL) and extracted with EtOAc (2×100 mL). The combined organic extracts were dried over sodium sulfate, filtered, concentrated in vacuo to obtain the crude. The crude was purified through silica gel column chromatography using 2% EtOAc/hexanes to afford compound 363 (400 mg, 35%) as white solid. TLC: 10% EtOAc/hexanes (R$_f$: 0.9); $^1$H-NMR (DMSO-d$_6$, 400 MHz): δ 8.83 (s, 2H), 8.41-8.39 (m, 2H), 7.50-7.48 (m, 3H).

Synthesis of (E)-3-(2-phenylpyrimidin-5-yl) acrylamide (364)

To a stirred solution of compound 363 (300 mg, 1.28 mmol) in DMF (20 mL) under inert atmosphere was added acrylamide 356 (109 mg, 1.53 mmol) at RT and purged under argon for 10 min. To this were added o-tolyl phosphine (42 mg, 0.07 mmol), palladium acetate (15.7 mg, 0.07 mmol), and diisopropyl ethyl amine (0.28 mL, 1.53 mmol) at RT; heated to 140° C. and stirred for 16 h. The reaction was monitored by TLC; after completion of the reaction, the reaction mixture was diluted water (100 mL) and extracted with 10% MeOH/CH$_2$Cl$_2$ (2×50 mL). The combined organic extracts were dried over sodium sulphate, filtered and concentrated in vacuo to obtain the crude. The crude compound was triturated with 50% EtOAc/hexanes (10 mL) and dried in vacuo to afford compound 364 (50 mg, 17%) as an off-white solid. TLC: 70% EtOAc/hexanes (R$_f$: 0.2);

$^1$H-NMR (DMSO-d$_6$, 400 MHz): δ 9.10 (s, 2H), 8.43-8.41 (m, 2H), 7.64 (br s, 1H), 7.55-7.54 (m, 3H), 7.47 (d, J=16.0 Hz, 1H), 7.22 (br s, 1H), 6.85 (d, J=16.0 Hz, 1H).

Synthesis of 3-(2-phenylpyrimidin-5-yl) propanamide (365)

To a stirred solution of compound 364 (50 mg, 0.22 mmol) in EtOH (2 mL) under inert atmosphere were added triethyl amine (0.032 mL, 0.22 mmol), 10% Pd/C (17 mg, dry) at RT and stirred under hydrogen atmosphere (balloon pressure) for 4 h. The reaction was monitored by LC-MS; after completion of the reaction, the reaction mixture was filtered through celite and the filtrate was concentrated in vacuo to obtain the crude which was triturated with 10% EtOAc/n-pentane (2×5 mL) and dried in vacuo to afford compound 365 (30 mg, 60%) as an off-white solid. TLC: 5% MeOH/CH$_2$Cl$_2$ (R$_f$: 0.5); $^1$H-NMR (DMSO-d$_6$, 400 MHz): δ 8.76 (s, 2H), 8.37-8.35 (m, 2H), 7.52-7.50 (m, 3H), 7.31 (br s, 1H), 6.80 (br s, 1H), 2.85 (t, J=7.2 Hz, 2H), 2.46 (t, J=7.2 Hz, 2H).

Synthesis of Tert-Butyl (2-(2-phenylpyrimidin-5-yl) ethyl) carbamate (366)

To a stirred solution of compound 365 (15 mg, 0.06 mmol) in THF (2 mL) were added sodium hydroxide (8 mg, 0.2 mmol) in water (0.5 mL), phenyl-λ$^3$-iodanediyl diacetate (21 mg, 0.06 mmol) at 0° C. and stirred for 30 min. The reaction was monitored by TLC; after completion of the reaction, the volatiles were removed in vacuo. The residue was diluted with water (25 mL) and extracted with EtOAc (2×25 mL). The combined organic extracts were dried over sodium sulfate, filtered and concentrated in vacuo to obtain the crude. The crude was purified through silica gel column chromatography using 20% EtOAc/hexanes to afford compound 366 (10 mg, 51%) as sticky solid. TLC: 50% EtOAc/hexanes (R$_f$: 0.9); $^1$H-NMR (CDCl$_3$, 400 MHz): δ 8.65 (s, 2H), 8.42-8.40 (m, 2H), 7.49-7.47 (m, 3H), 4.62 (br s, 1H), 3.43-3.38 (m, 2H), 2.84 (t, J=7.2 Hz, 2H), 1.43 (s, 9H).

Synthesis of 2-(2-phenylpyrimidin-5-yl) ethan-1-amine hydrochloride (367)

To a stirred solution of compound 366 (80 mg, 0.35 mmol) in CH$_2$Cl$_2$ (3 ML) was added 4N HCl in 1, 4-Dioxane (0.7 mL) under argon atmosphere at 0° C.; warmed to RT and stirred for 2 h. The reaction was monitored by TLC; after completion of the reaction, the volatiles were removed in vacuo to obtain the crude and was washed with 20% CH$_2$Cl$_2$/n-pentane (2×5 mL) and dried in vacuo to afford compound 367 (50 mg, HCl salt) as white solid. TLC: 10% MeOH/CH$_2$Cl$_2$ (R$_f$: 0.1); $^1$H-NMR (DMSO-d$_6$, 400 MHz): δ 8.84 (s, 2H), 8.40-8.37 (m, 2H), 8.07 (br s, 2H), 7.54-7.52 (m, 3H), 3.19-3.14 (m, 2H), 2.97 (t, J=7.2 Hz, 2H).

Synthesis of (4-(pyrimidin-5-yl) phenyl) methanamine (372)

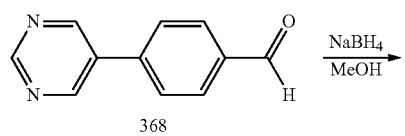

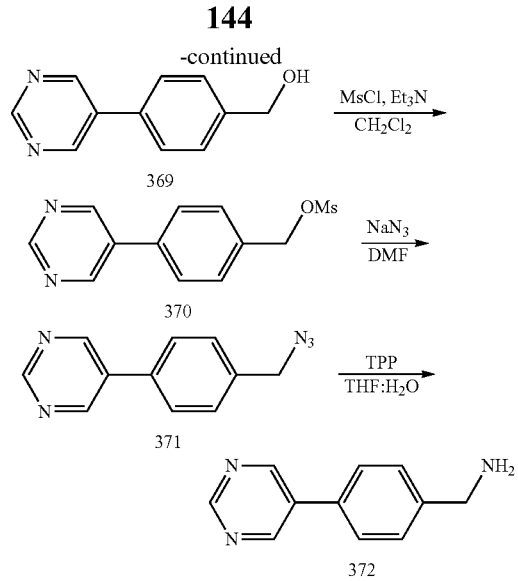

Synthesis of (4-(pyrimidin-5-yl) phenyl) methanol (369)

To a stirred solution of 4-(pyrimidin-5-yl) benzaldehyde 368 (500 mg, 2.71 mmol) in MeOH (20 mL) under argon atmosphere and sodium borohydride (155 mg, 39.99 mmol) at 0° C.; warmed to RT and stirred for 2 h. The reaction was monitored by TLC; after completion of the reaction, volatiles were removed in vacuo. The residue was diluted with brine solution (100 mL), extracted with EtOAc (2×50 mL). The combined organic extracts were dried over sodium sulphate, filtered and concentrated in vacuo to obtain the crude. The crude was purified through silica gel column chromatography using 5% MeOH/CH$_2$Cl$_2$ to afford compound 369 (260 mg, 51%) as white solid. TLC: 20% EtOAc/hexanes (R$_f$: 0.4); $^1$H-NMR (CDCl$_3$, 500 MHz): δ 9.20 (s, 1H), 8.93 (s, 2H), 7.58 (d, J=8.5 Hz, 2H), 7.53 (d, J=8.0 Hz, 2H), 4.79 (s, 2H).

Synthesis of 4-(pyrimidin-5-yl) benzyl methanesulfonate (370)

To a stirred solution of compound 369 (260 mg, 1.39 mmol) in CH$_2$Cl$_2$ (10 mL) under argon atmosphere were added triethyl amine (0.3 mL, 2.09 mmol), methane sulfonyl chloride (0.16 mL, 2.09 mmol) at 0° C.; warmed to RT and stirred for 14 h. The reaction was monitored by TLC; after completion of the reaction, the reaction mixture was diluted with water (20 mL), washed with 10% NaHCO$_3$ solution (30 mL), dried over sodium sulfate, filtered and concentrated in vacuo to obtain crude compound 370 (300 mg) as thick syrup. The crude was carried to the next step without further purification. TLC: 5% MeOH/CH$_2$Cl$_2$ (R$_f$: 0.4).

Synthesis of 5-(4-(azidomethyl) phenyl) pyrimidine (371)

To a stirred solution of compound 370 (300 mg, crude) in DMF (6 mL) under argon atmosphere was added sodium azide (74 mg, 1.13 mmol) at RT; heated to 60° C. and stirred for 2 h. The reaction was monitored by TLC; after completion of the reaction, the reaction mixture was diluted with ice water (20 mL) and extracted with EtOAc (2×50 mL). The combined organic extracts were dried over sodium sulfate, filtered and concentrated in vacuo to obtain crude. The crude was purified through silica gel column chromatography using 20% EtOAc/hexanes to afford compound 371 (45 mg) as colorless thick syrup. TLC: 30% EtOAc/hexanes ($R_f$: 0.6); $^1$H-NMR (CDCl$_3$, 400 MHz): δ 9.22 (s, 1H), 8.96 (s, 2H), 7.61 (d, J=8.4 Hz, 2H), 7.48 (d, J=8.0 Hz, 2H), 4.43 (s, 2H).

Synthesis of (4-(pyrimidin-5-yl) phenyl) methanamine (372)

To a stirred solution of compound 371 (40 mg, 0.18 mmol) in THF:H$_2$O (9:1, 2 mL) was added triphenyl phosphine (74 mg, 0.28 mmol) at RT and stirred for 16 h. The reaction was monitored by TLC; after completion of the reaction, the volatiles were removed in vacuo to obtain the crude. The crude was purified through silica gel column chromatography using 10% MeOH/CH$_2$Cl$_2$ to afford compound 372 (23 mg, 66%) as an off-white solid. TLC: 10% MeOH/CH$_2$Cl$_2$ ($R_f$: 0.2); $^1$H-NMR (DMSO-d$_6$, 400 MHz): δ 9.21 (s, 1H), 9.17 (s, 2H), 8.27 (br s, 2H), 7.87 (d, J=8.0 Hz, 2H), 7.64 (d, J=8.4 Hz, 2H), 4.07 (s, 2H).

Synthesis of (2-phenylpyrimidin-5-yl) methanamine (377)

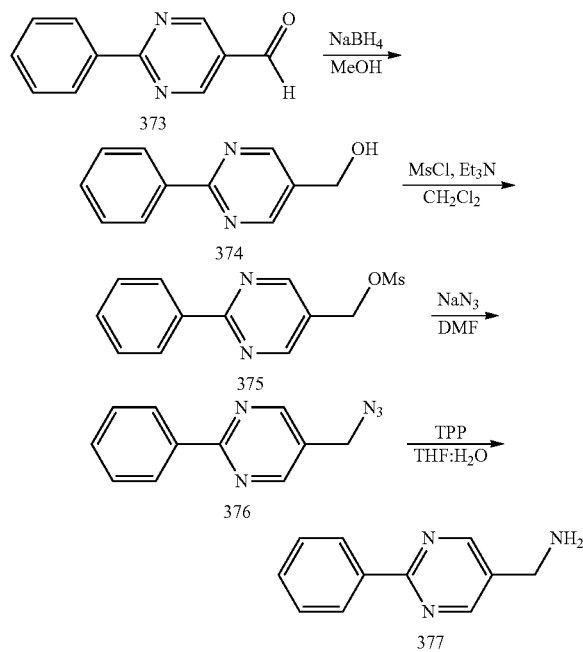

Synthesis of (2-phenylpyrimidin-5-yl) methanol (374)

To a stirred solution of 2-phenylpyrimidine-5-carbaldehyde 373 (200 mg, 1.08 mmol) in MeOH (20 mL) under argon atmosphere was added sodium borohydride (74 mg, 2.17 mmol) at 0° C.; warmed to RT and stirred for 2 h. The reaction was monitored by TLC; after completion of the reaction, the reaction mixture was diluted with ice cold water (50 mL), extracted with EtOAc (2×50 mL). The combined organic extracts were dried over sodium sulphate, filtered and concentrated in vacuo to obtain the crude. The crude was purified through silica gel column chromatography using 5% MeOH/CH$_2$Cl$_2$ to afford compound 374 (135 mg, 65%) as colorless solid. TLC: 40% EtOAc/MeOH ($R_f$: 0.3); $^1$H-NMR (DMSO-d$_6$, 500 MHz): δ 8.83 (s, 2H), 8.40-8.38 (m, 2H), 7.53-7.51 (m, 3H), 5.45 (t, J=5.5 Hz, 1H), 4.58 (d, J=5.5 Hz, 2H).

Synthesis of (2-phenylpyrimidin-5-yl) methyl methanesulfonate (375)

To a stirred solution of compound 374 (130 mg, 0.69 mmol) in CH$_2$Cl$_2$ (5 mL) under argon atmosphere were added triethyl amine (0.4 mL, 2.09 mmol) and methane sulfonyl chloride (0.07 mL, 0.84 mmol) at 0° C.; warmed to RT and stirred for 30 min. The reaction was monitored by TLC; after completion of the reaction, the reaction mixture was diluted CH$_2$Cl$_2$ (50 mL), washed with water (2×20 mL). The organic extract was dried over sodium sulfate, filtered and concentrated in vacuo to obtain crude compound 375 (150 mg) as yellow oil. The crude was carried to the next step without further purification. TLC: 50% EtOAc/hexanes ($R_f$: 0.5); $^1$H-NMR (DMSO-d$_6$, 500 MHz): 9.00 (t, J=10.0 Hz, 2H), 8.42-8.41 (m, 2H), 7.56-7.55 (m, 3H), 5.40 (s, 2H), 3.32 (s, 3H).

Synthesis of 5-(azidomethyl)-2-phenylpyrimidine (376)

To a stirred solution of compound 375 (150 mg) in DMF (6 mL) under argon atmosphere was added sodium azide (56 mg, 0.76 mmol) at RT; heated to 60° C. and stirred for 2 h. The reaction was monitored by TLC; after completion of the reaction, the reaction mixture was diluted with ice water (20 mL) and extracted with diethyl ether (2×50 mL). The combined organic extracts were dried over sodium sulfate, filtered and concentrated in vacuo to obtain crude. The crude was purified through silica gel column chromatography using 20% EtOAc/hexanes to afford compound 376 (60 mg, 49%) as colorless syrup. TLC: 40% EtOAc/hexanes ($R_f$: 0.9); $^1$H NMR (DMSO-d$_6$, 400 MHz): δ 8.94 (s, 2H), 8.41 (dd, J=6.8, 3.0 Hz, 2H), 7.56-7.53 (m, 3H), 4.63 (s, 2H).

Synthesis of (2-phenylpyrimidin-5-yl) methanamine (377)

To a stirred solution of compound 376 (90 mg, 0.42 mmol) in THF:H$_2$O (9:1, 4 mL) was added triphenyl phosphine (167 mg, 0.63 mmol) at RT and stirred for 16 h. The reaction was monitored by TLC; after completion of the reaction, the volatiles were removed in vacuo to obtain the crude. The crude was purified through silica gel column chromatography using 10% MeOH/CH$_2$Cl$_2$ to afford compound 377 (30 mg, 38%) as yellow solid. TLC: 10% MeOH/CH$_2$Cl$_2$ ($R_f$: 0.2); $^1$H NMR (DMSO-d$_6$ 500 MHz): δ 8.96 (s, 2H), 8.40 (d, J=3.9 Hz, 2H), 7.59-7.45 (m, 3H), 6.84 (br s, 2H), 4.01 (s, 2H).

Synthesis of thiazol-5-amine hydrochloride (380)

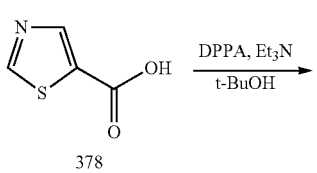

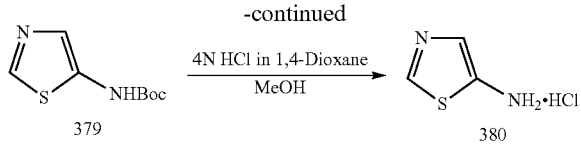

Synthesis of Tert-Butyl thiazol-5-ylcarbamate (379)

To a stirred solution of thiazole-5-carboxylic acid 378 (400 mg, 3.1 mmol) in t-butanol (6 mL) were added diphenylphosphonic azide (1.34 mL, 6.18 mmol) and triethyl amine (0.89 mL, 6.18 mmol) at RT and heated to 100° C. for 16 h. The reaction was monitored by TLC; after completion of the reaction, the volatiles were removed in vacuo to obtain the crude. The crude was purified through silica gel column chromatography using 30% EtOAc/hexanes to afford compound 379 (300 mg, 48%) as white solid. TLC: 50% EtOAc/hexanes ($R_f$: 0.8); $^1$H-NMR (DMSO-$d_6$, 400 MHz): δ 10.60 (br s, 1H), 8.51 (s, 1H), 8.40 (s, 1H), 1.49 (s, 9H).

Synthesis of thiazol-5-amine hydrochloride (380)

To a stirred solution of compound 379 (300 mg, 1.5 mmol) in MeOH (5 mL) was added 4 N HCl in 1, 4-Dioxane (5 mL) under argon atmosphere at 0° C.; warmed to RT and stirred for 3 h. The reaction was monitored by TLC; after completion of the reaction, the volatiles were removed in vacuo to obtain the crude. The crude was washed with n-pentane (2×5 mL) and dried in vacuo to afford compound 380 (150 mg, HCl salt) as pale yellow solid. TLC: 50% EtOAc/hexanes ($R_f$: 0.1); $^1$H-NMR (DMSO-$d_6$, 500 MHz): δ 9.10 (s, 1H), 7.22 (s, 1H).

Synthesis of 3-(pyrimidin-5-yl) aniline (383)

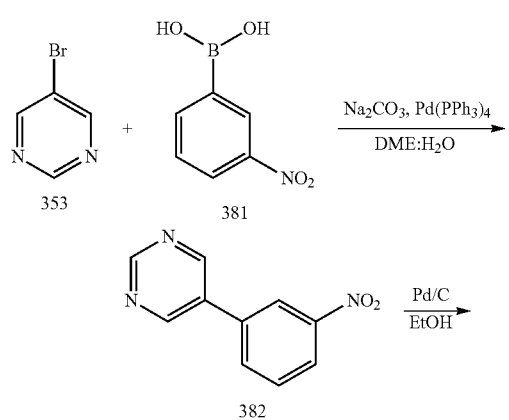

Synthesis of 5-(3-nitrophenyl) pyrimidine (382)

To a stirred solution of 5-bromopyrimidine 353 (2 g, 12.58 mmol) and (3-nitrophenyl) boronic acid 381 (2.3 g, 13.84 mmol) in 1, 2-dimethoxy ethane: $H_2O$ (4:1, 20 mL) under inert atmosphere were added sodium carbonate (2.66 g, 25.17 mmol) at RT and purged under argon atmosphere for 20 min. To this was added Pd(PPh$_3$)$_4$ (726 mg, 0.62 mmol) and heated to 110° C. for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude. The obtained solid was filtered, dried in vacuo to obtain the crude which was purified through silicagel column chromatography in 50% EtOAc/hexanes to afford compound 382 (2.5 g, 68%) as an off-white solid. TLC: 60% EtOAc/hexanes ($R_f$: 0.3); 1H NMR (DMSO-$d_6$, 400 MHz): δ 9.27 (s, 3H), 8.66-8.63 (m, 1H), 8.37-8.25 (m, 2H), 7.84 (t, J=8.0 Hz, 1H).

Synthesis of 3-(pyrimidin-5-yl) aniline (383)

To a stirred solution of compound 382 (1.7 g, 8.45 mmol) in EtOH (30 mL) under argon atmosphere was added 10% Pd/C (500 mg) under argon atmosphere and stirred under $H_2$ atmosphere (balloon pressure) for 5 h. After completion of the reaction, the reaction mixture was filtered through celite, washed with 5% MeOH/$CH_2Cl_2$ (50 mL). The filtrate was concentrated in vacuo to obtain the crude which was triturated with mixture of ether: pentane (1:1, 10 ML) and dried in vacuo to afford compound 383 (1.2 g, 86%) as an off-white solid. TLC: 70% % EtOAc/hexanes ($R_f$: 0.2); $^1$H NMR (DMSO-$d_6$, 400 MHz): δ 9.15 (s, 1H), 9.00 (s, 2H), 7.17 (t, J=7.8 Hz, 1H), 6.91-6.86 (m, 2H), 6.69-6.64 (m, 1H), 5.27 (s, 3H).

Synthesis of 3-(pyrimidin-4-yl) aniline (386)

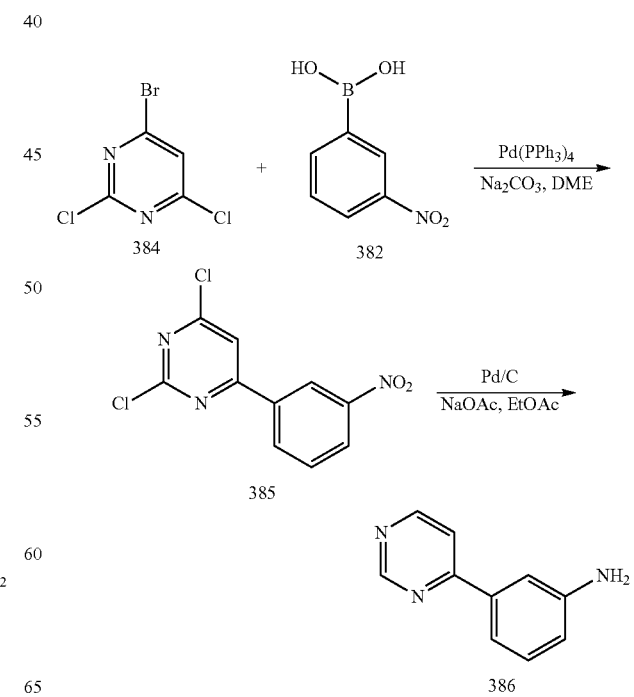

Synthesis of 2, 4-dichloro-6-(3-nitrophenyl) pyrimidine (385)

To a stirred solution of 2, 4, 6-trichloropyrimidine 384 (500 mg, 2.76 mmol) and (3-nitrophenyl) boronic acid 382 (594 mg, 2.76 mmol) in 1, 2-dimethoxy ethane (10 mL) under inert atmosphere were added sodium carbonate (878 mg, 8.28 mmol) at RT and purged under argon atmosphere for 20 min. To this was added Pd(PPh$_3$)$_4$ (159 mg, 0.13 mmol) and heated to 80° C. for 16 h. The reaction was monitored by TLC; after completion of the reaction, the reaction mixture was filtered through celite and the filtrate was concentrated in vacuo to obtain the crude. The crude was purified through silica gel column chromatography using 10% EtOAc/hexanes to afford crude compound 385 (200 mg) as yellow solid which was carried forward for next step. TLC: 10% EtOAc/hexanes (R$_f$: 0.7).

Synthesis of 3-(pyrimidin-4-yl) aniline (386)

To a stirred solution of compound 385 (200 mg, crude) in EtOAc (50 mL) under inert atmosphere were added sodium acetate (304 mg, 3.71 mmol), 10% Pd/C (100 mg, wet) under argon atmosphere and stirred under H$_2$ atmosphere (balloon pressure) for 6 h. After completion of the reaction, the reaction mixture was filtered through celite, washed with 50% MeOH/CH$_2$Cl$_2$ (50 mL). The filtrate was concentrated in vacuo to obtain the crude which was purified through silicagel column chromatography in 90% EtOAc/hexanes to afford compound 386 (100 mg, 78%) as an off-white solid. TLC: 70% % EtOAc/hexanes (R$_f$: 0.4); $^1$H NMR (400 MHz, DMSO-d$_6$): δ 9.19 (s, 1H), 8.80 (d, J=5.4 Hz, 1H), 7.91 (dd, J=5.4, 1.4 Hz, 1H), 7.45-7.43 (m, 1H), 7.30 (d, J=7.7 Hz, 1H), 7.18 (t, J=7.8 Hz, 1H), 6.74 (d, J=7.5 Hz, 1H), 5.31 (s, 2H).

Synthesis of 3-(thiazol-5-yl) aniline (389)

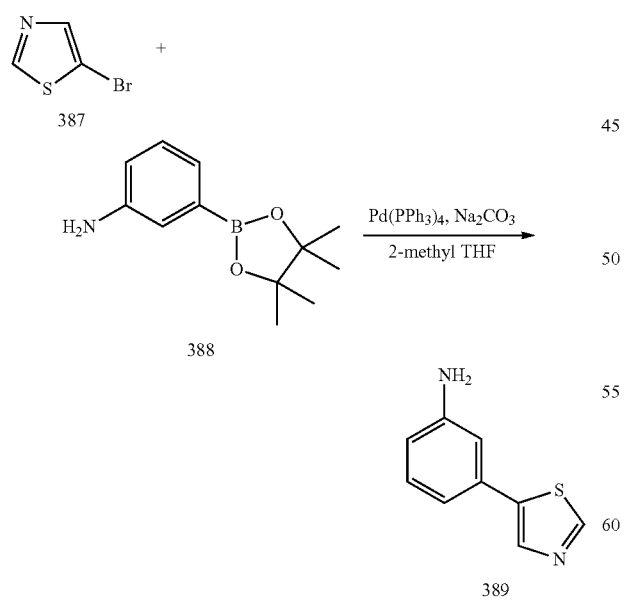

To a stirred solution of 5-bromothiazole 387 (350 mg, 2.13 mmol) in 2-methyl THF (5 mL) under inert atmosphere were added 3-aminophenylboronic acid pinacol ester 388 (600 mg, 2.35 mmol), sodium carbonate (565 mg, 5.33 mmol), at RT and stirred under argon atmosphere for 20 min. To this was added Pd(dppf)$_2$Cl$_2$ (78 mg, 0.106 mmol) and heated to 110° C. and stirred for 16 h. The reaction was monitored by TLC; after completion of the reaction, the reaction mixture was filtered through celite and the filtrate was concentrated in vacuo to obtain the crude. The crude was purified through silica gel column chromatography using 80% EtOAc/hexanes to afford compound 389 (200 mg, 52%) as yellow syrup. TLC: 70% EtOAc/hexanes (R$_f$: 0.4); LC-MS: 84.49%; 176.8 (M$^+$+1); (column; Ascentis Express C18, (50×3.0 mm, 2.7 μm); RT 1.40 min. 0.025% Aq. TFA+5% ACN: ACN+5% 0.025% Aq. TFA, 1.2 mL/min).

Synthesis of 3'-amino-[1, 1'-biphenyl]-4-ol (392)

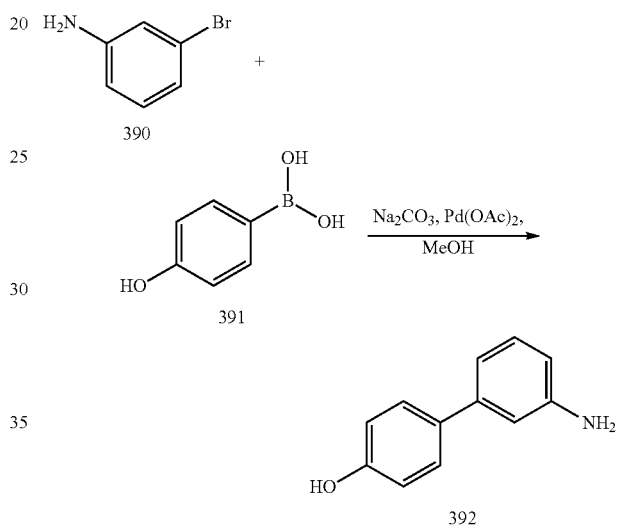

To a stirred solution of 3-bromoaniline 390 (400 mg, 2.32 mmol) and (4-hydroxyphenyl) boronic acid 391 (353 mg, 2.55 mmol) in MeOH (4 mL) under inert atmosphere were added sodium carbonate (493 mg, 4.65 mmol) at RT and purged under argon atmosphere for 20 min. To this was added Pd(OAc)$_2$ (156 mg, 0.23 mmol) and heated to 80° C. for 16 h. The reaction was monitored by TLC; after completion of the reaction, the reaction mixture was filtered through celite, washed with MeOH (20 mL). The filtrate was concentrated in vacuo to obtain the crude. The crude was purified through silica gel column chromatography in 20% EtOAc/hexanes to afford compound 392 (160 mg) as brick red solid. TLC: 30% EtOAc/hexanes (R$_f$: 0.4); LC-MS: 67.89%; 185.9 (M$^+$+1); (column; Ascentis Express C18, (50×3.0 mm, 2.7 μm); RT 2.10 min. 0.025% Aq. TFA+5% ACN: ACN+5% 0.025% Aq. TFA, 1.2 mL/min).

Synthesis of 5-phenyloxazol-2-amine (396)

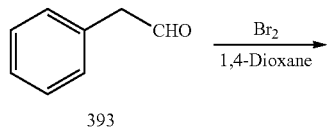

Synthesis of 2-bromo-2-phenylacetaldehyde (394)

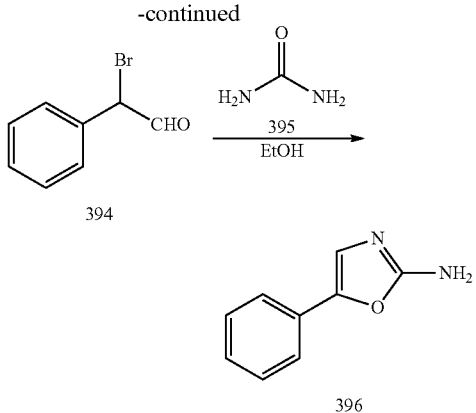

To a stirred solution of 2-phenylacetaldehyde 393 (500 mg, 4.16 mmol) in 1, 4-Dioxane (2 mL) under inert atmosphere was added bromine (0.27 mL, 4.99 mmol) at 0° C. and stirred for 20 min; warmed to RT and stirred for 1 h. The reaction was monitored by TLC; after completion of the reaction, the volatiles were removed in vacuo to afford crude compound 394 (800 mg) as green syrup. The crude was carried forward for next step without further purification. TLC: 10% EtOAc/hexanes ($R_f$: 0.7);

Synthesis of 5-phenyloxazol-2-amine (396)

To a stirred solution of compound 394 (800 mg, crude) in EtOH (10 mL) under inert atmosphere was added urea 395 (482 mg, 8.04 mmol) at RT; heated at 80° C. and stirred for 6 h. The reaction was monitored by TLC; after completion of the reaction, the volatiles were removed in vacuo and the residue was diluted with water (60 mL). The pH was neutralized with 10% aqueous NaHCO$_3$ solution (10 mL) and extracted with EtOAc (2×100 mL). The combined organic extracts were dried over sodium sulfate, filtered and concentrated in vacuo to obtain the crude. The crude was purified through flash column chromatography using 2-3% MeOH/CH$_2$Cl$_2$ to afford compound 396 (200 mg, 32%) as an off-white solid. TLC: 5% MeOH/CH$_2$Cl$_2$ ($R_f$: 0.5); 1H NMR (400 MHz, DMSO-d$_6$): δ 7.45 (d, J=7.2 Hz, 2H), 7.36 (t, J=7.8 Hz, 2H), 7.21-7.16 (m, 2H), 6.81 (s, 2H);

Synthesis of 5-phenylthiazol-2-amine (397)

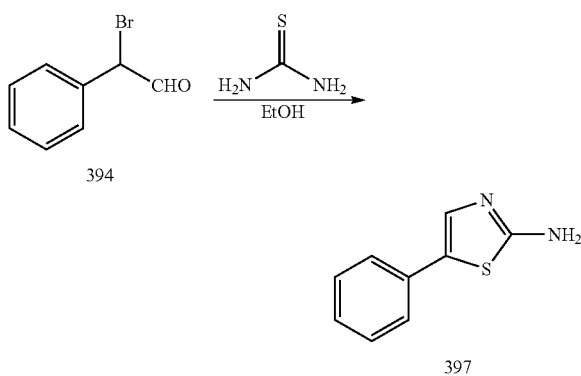

Synthesis of 5-phenylthiazol-2-amine (397)

To a stirred solution of 2-bromo-2-phenylacetaldehyde 394 (860 mg, crude) in EtOH (20 mL) under inert atmosphere was added thiourea (658 mg, 8.64 mmol) at RT; heated at 80° C. and stirred for 8 h. The reaction was monitored by TLC; after completion of the reaction, the volatiles were removed in vacuo to obtain the crude. The pH of the residue was neutralized with 10% aqueous NaHCO$_3$ solution (10 mL) and extracted with EtOAc (2×200 mL). The combined organic extracts were dried over sodium sulfate, filtered and concentrated in vacuo to obtain the crude. The crude was purified through flash column chromatography using 2-3% MeOH/CH$_2$Cl$_2$ to afford compound 397 (500 mg, 66%) as an off-white solid. TLC: 5% MeOH/CH$_2$Cl$_2$ ($R_f$: 0.6); $^1$H NMR (400 MHz, DMSO-d$_6$): δ 7.43-7.38 (m, 3H), 7.32 (t, J=7.8 Hz, 2H), 7.17 (tt, J=7.5, 0.9 Hz, 1H), 7.12 (s, 2H).

Synthesis of 1-methoxy-3-(pyrimidin-5-yl) propan-2-amine hydrochloride (401)

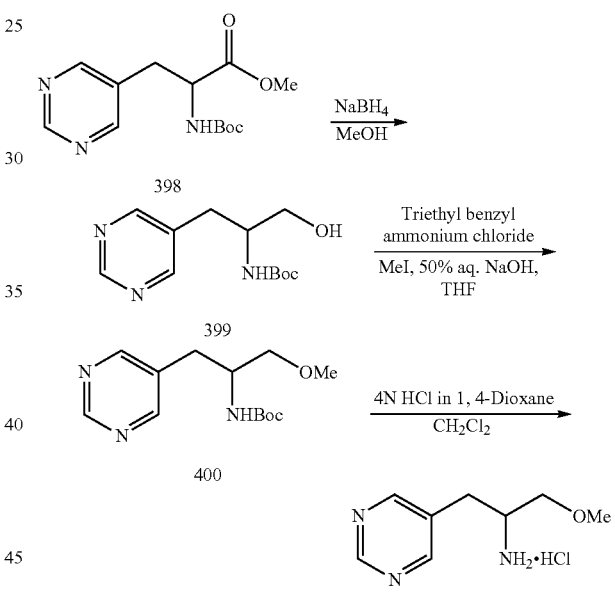

Synthesis of Tert-Butyl (1-hydroxy-3-(pyrimidin-5-yl) propan-2-yl) carbamate (399)

To a stirred solution of methyl 2-((tert-butoxycarbonyl) amino)-3-(pyrimidin-5-yl) propanoate 398 (200 mg, 0.71 mmol) in MeOH (5 mL) under inert atmosphere was added sodium borohydride (105 mg, 2.84 mmol) at 0° C.; warmed to RT and stirred for 16 h. The reaction was monitored by TLC; after completion of the reaction, the reaction mixture was diluted with water (25 mL) and extracted with 10% MeOH/CH$_2$Cl$_2$ (5×25 mL). The combined organic extracts were dried over sodium sulfate, filtered and concentrated in vacuo to obtain the crude. The crude was purified through silica gel column chromatography using 8% MeOH/CH$_2$Cl$_2$ to afford compound 399 (110 mg, 61%) as an off-white solid. TLC: 10% MeOH/CH$_2$Cl$_2$ ($R_f$: 0.4); $^1$H NMR (DMSO-d$_6$, 400 MHz): δ 8.99 (s, 1H), 8.61 (s, 2H), 6.70 (d, J=9.0 Hz, 1H), 4.82 (t, J=5.4 Hz, 1H), 3.61 (br s, 2H), 3.45-3.34 (m, 2H), 2.93-2.82 (m, 1H), 1.26 (s, 9H)

Synthesis of Tert-Butyl (1-methoxy-3-(pyrimidin-5-yl) propan-2-yl) carbamate (400)

To a stirred solution of compound 399 (100 mg, 0.39 mmol) in THF (10 mL) were added triethyl benzyl ammonium chloride (9 mg, 0.03 mmol), 50% aqueous sodium hydroxide solution (3.5 mL) and methyl iodide (0.02 mL, 0.39 mmol) at 0° C.; warmed to RT and stirred for 24 h. The reaction was monitored by TLC; after completion of the reaction, the reaction mixture was diluted with water (25 mL) and extracted with EtOAc (3×25 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 400 (70 mg, 67%) as colorless syrup. TLC: 5% MeOH/CH$_2$Cl$_2$ (R$_f$: 0.5); $^1$H NMR (DMSO-d$_6$, 400 MHz): δ 9.00 (s, 1H), 8.62 (s, 2H), 6.84 (d, J=8.8 Hz, 1H), 3.78 (brs, 2H), 3.29-3.23 (m, 5H), 2.85 (dd, J=13.8, 4.1 Hz, 1H), 1.28-1.21 (m, 9H).

Synthesis of 1-methoxy-3-(pyrimidin-5-yl) propan-2-amine hydrochloride (401)

To a stirred solution of compound 400 (60 mg, 0.22 mmol) in CH$_2$Cl$_2$ (3 mL) was added 4 N HCl in 1, 4-Dioxane (1 mL) under argon atmosphere at 0° C.; warmed to RT and stirred for 3 h. The reaction was monitored by TLC; after completion of the reaction, the volatiles were removed in vacuo to obtain the crude. The crude was washed with n-pentane (2×5 mL) and dried in vacuo to afford compound 401 (40 mg, HCl salt) as brown solid. TLC: 5% MeOH/CH$_2$Cl$_2$ (R$_f$: 0.1); 1H NMR (DMSO-d$_6$, 400 MHz): δ 9.11 (s, 1H), 8.75 (s, 2H), 8.24 (br s, 2H), 3.68-3.59 (m, 1H), 3.53-3.48 (m, 1H), 3.39 (dd, J=10.5, 5.7 Hz, 1H), 3.30 (s, 3H), 2.95 (t, J=7.3 Hz, 2H).

Synthesis of 4-(2-aminoethyl)-N,N-dimethylbenzenesulfonamide hydrochloride (406)

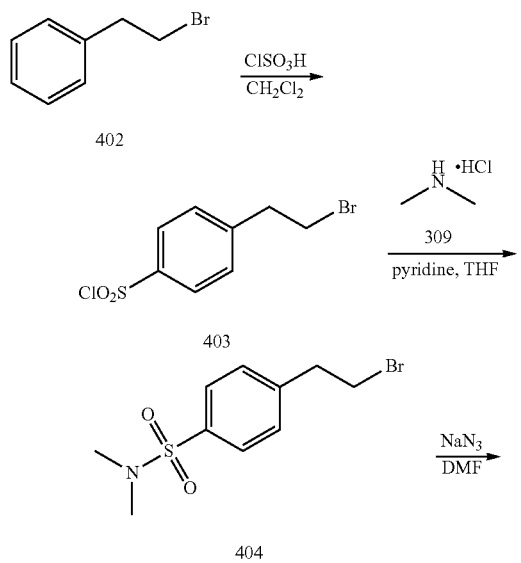

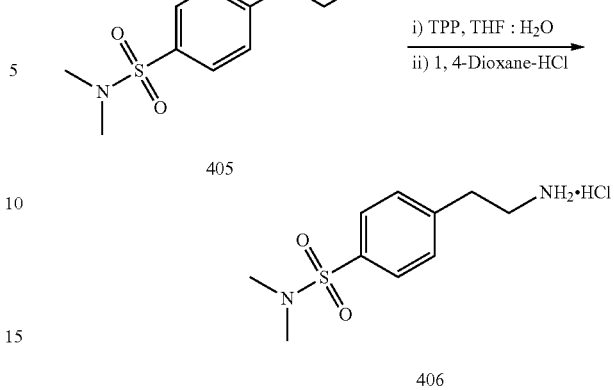

Synthesis of 4-(2-bromoethyl) benzenesulfonyl chloride (403)

To a stirred solution of (2-bromoethyl) benzene 402 (5 g, 27.02 mmol) in CH$_2$Cl$_2$ (15 mL) under argon atmosphere was added chlorosulfonic acid (5.4 mL, 81.08 mmol) at 0° C.; warmed to RT and stirred for 3 h. The reaction was monitored by TLC; after completion the reaction, the reaction mixture was poured into ice-cold water (100 mL) extracted with CH$_2$Cl$_2$ (2×150 mL). The combined organic extracts were washed with brine (100 mL), separated dried over sodium sulfate, filtered and concentrated in vacuo to afford crude compound 403 (5 g) as colorless thick syrup. TLC: 10% EtOAc/hexanes (R$_f$: 0.6); $^1$H-NMR (DMSO-d$_6$, 400 MHz): δ 8.00 (d, J=8.4 Hz, 2H), 7.47 (d, J=8.8 Hz, 2H), 3.62 (t, J=7.2 Hz, 2H), 3.30 (t, J=7.2 Hz, 2H).

Synthesis of 4-(2-bromoethyl)-N,N-dimethylbenzenesulfonamide (404)

To a stirred solution of compound 403 (5 g, crude) in THF (100 mL) under argon atmosphere were added pyridine (14.37 mL, 176.05 mmol), dimethylamine hydrochloride 309 (7.1 g, 88.02 mmol) at 0° C.; warmed to RT and stirred for 1 h. The reaction was monitored by TLC; after completion the reaction, the volatiles were removed in vacuo. The residue was diluted with CH$_2$Cl$_2$ (500 mL) and washed with 1 N HCl (15 mL). The organic layer was dried over sodium sulfate, filtered and concentrated in vacuo to obtain crude. The crude was titurated with pentane (30 mL) and dried in vacuo to afford compound 404 (3.5 g, 68%) as an off-white solid. TLC: 20% EtOAc/hexane (R$_f$: 0.5); 1H NMR (CDCl$_3$, 400 MHz): δ 7.74 (d, J=8.4 Hz, 2H), 7.39 (d, J=8.5 Hz, 2H), 3.60 (t, J=7.2 Hz, 2H), 3.25 (t, J=7.3 Hz, 2H), 2.72 (s, 6H).

Synthesis of 4-(2-azidoethyl)-N,N-dimethylbenzenesulfonamide (405)

To a stirred solution of compound 404 (500 mg, 1.71 mmol) in DMF (10 mL) under inert atmosphere was added sodium azide (335 mg, 5.15 mmol) at RT and heated to 80° C. for 2 h. The reaction was monitored by TLC; after completion of the reaction, the reaction mixture was diluted with ice-cold water (20 mL) and extracted with CH$_2$Cl$_2$ (2×200 mL). The combined organic extracts were dried under sodium sulfate, filtered and concentrated in vacuo to afford compound 405 (350 mg, 80%) as thick syrup. TLC: 20% EtOAc/hexane (R$_f$: 0.6); $^1$H-NMR (DMSO-d$_6$, 400

MHz): δ 7.73 (d, J=8.4 Hz, 2H), 7.40 (d, J=6.8 Hz, 2H), 3.56 (t, J=6.8 Hz, 2H), 2.97 (t, J=6.8 Hz, 2H), 2.71 (s, 6H).

Synthesis of 4-(2-aminoethyl)-N,N-dimethylbenzenesulfonamide hydrochloride (406)

To a stirred solution of compound 405 (350 mg, 1.37 mmol) in a mixture of THF:H$_2$O (4:1, 10 mL) was added triphenyl phosphine (1.08 g, 4.13 mmol) at RT and stirred for 16 h. The reaction was monitored by TLC; after completion of the reaction, the volatiles were removed in vacuo to obtain the crude. The crude was purified through silica gel column chromatography using 3-5% MeOH/CH$_2$Cl$_2$ to afford free amine (200 mg) as thick syrup.

To a stirred solution of the free amine (200 mg) in CH$_2$Cl$_2$ (2 mL) under argon atmosphere was added 4 N HCl in 1,4-dioxane (0.5 mL) at 0° C. and stirred for 10 min. The volatiles were removed in vacuo to obtain the crude which was washed with diethyl ether (2×5 mL) and dried in vacuo to afford compound 406 (125 mg, 35%) as white solid. TLC: 10% MeOH/CH$_2$Cl$_2$ (R$_f$: 0.2); $^1$H-NMR (DMSO-d$_6$, 400 MHz): δ 8.04 (br s, 2H), 7.70 (d, J=8.4 Hz, 2H), 7.54 (d, J=8.4 Hz, 2H), 3.15-3.05 (m, 2H), 3.01-2.98 (m, 2H), 2.60 (s, 6H).

Synthesis of 4-(3-aminopropyl)-N,N-dimethylbenzenesulfonamide hydrochloride (410)

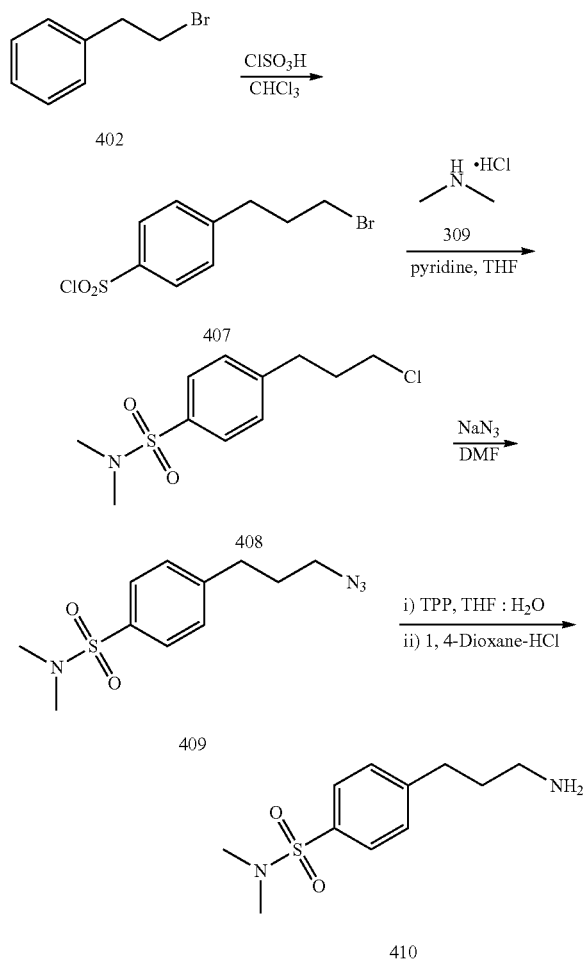

Synthesis of 4-(3-bromopropyl) benzenesulfonyl chloride (407)

To a stirred solution of (2-bromoethyl) benzene 402 (5 g, 27.02 mmol) in CHCl$_3$ (15 mL) under argon atmosphere was added chlorosulfonic acid (5.4 mL, 81.08 mmol) at 0° C.; warmed to RT and stirred for 3 h. The reaction was monitored by TLC; after completion the reaction, the reaction mixture was poured into ice-cold water (100 mL) extracted with CH$_2$Cl$_2$ (2×100 mL). The combined organic extracts were dried over sodium sulfate, filtered and concentrated in vacuo to afford crude compound 407 (5 g) as colorless thick syrup. TLC: 10% EtOAc/hexanes (R$_f$: 0.4); $^1$H NMR (CDCl$_3$, 400 MHz): δ 7.97 (d, J=8.8 Hz, 2H), 7.45 (d, J=8.8 Hz, 2H), 3.40 (t, J=6.4 Hz, 2H), 2.93 (t, J=7.2 Hz, 2H), 2.24-2.17 (m, 2H).

Synthesis of 4-(3-chloropropyl)-N,N-dimethylbenzenesulfonamide (408)

To a stirred solution of compound 407 (5 g, crude) in THF (100 mL) under argon atmosphere were added pyridine (14.42 mL, 176.6 mmol), dimethylamine hydrochloride 309 (7.2 g, 88.33 mmol) at 0° C.; warmed to RT and stirred for 1 h. The reaction was monitored by TLC; after completion the reaction, the volatiles were removed the in vacuo. The residue was diluted with water (100 mL) and extracted with CH$_2$Cl$_2$ (2×100 mL). The combined organic extracts were dried over sodium sulfate, filtered and concentrated in vacuo to obtain the crude. The crude was purified through silica gel column chromatography using 20% EtOAc/hexanes to afford compound 408 (3 g) as white sticky solid. TLC: 20% EtOAc/hexanes (R$_f$: 0.5); 1H NMR (CDCl$_3$, 400 MHz): δ 7.71 (d, J=8.4 Hz, 2H), 7.37 (d, J=8.0 Hz, 2H), 3.53 (t, J=6.4 Hz, 1H), 3.40 (t, J=6.4 Hz, 1H), 2.87 (t, J=7.2 Hz, 2H), 2.71 (s, 6H), 2.23-2.08 (m, 2H).

Synthesis of 4-(3-azidopropyl)-N,N-dimethylbenzenesulfonamide (409)

To a stirred solution of compound 408 (3 g, 9.83 mmol) in DMF (50 mL) under inert atmosphere was added sodium azide (1.91 g, 29.50 mmol) at RT and heated to 70-80° C. for 2 h. The reaction was monitored by TLC; after completion of the reaction, the reaction mixture was diluted with ice-cold water (20 mL) and extracted with EtOAc (2×150 mL). The combined organic extracts were dried under sodium sulfate, filtered and concentrated in vacuo to afford compound 409 (2 g, 76%) as colorless thick syrup. TLC: 20% EtOAc/hexane (R$_f$: 0.6); 1H NMR (CDCl$_3$, 500 MHz): δ 7.71 (d, J=8.1 Hz, 2H), 7.36 (d, J=8.1 Hz, 2H), 3.32 (t, J=6.7 Hz, 2H), 2.82-2.77 (m, 2H), 2.71 (s, 6H), 1.98-1.91 (m, 2H).

Synthesis of 4-(3-aminopropyl)-N,N-dimethylbenzenesulfonamide hydrochloride (410)

To a stirred solution of compound 409 (2.35 g, 8.76 mmol) in a mixture of THF:H$_2$O (4:1, 100 mL) was added triphenyl phosphine (6.89 g, 26.30 mmol) at RT and stirred for 16 h. The reaction was monitored by TLC; after completion of the reaction, the volatiles were removed in vacuo to obtain the crude. The crude was purified through silica gel column chromatography using 15% MeOH/CH$_2$Cl$_2$ to afford free amine (2 g) as thick syrup.

To a stirred solution of the above compound (2 g) in CH$_2$Cl$_2$ (20 mL) under argon atmosphere was added 4 N HCl in 1,4-dioxane (10 mL) at 0° C. and stirred for 10 min.

The solvent was decanted and the obtained solid was dried in vacuo to afford compound 410 (1.5 g, 70%) as white solid. TLC: 10% MeOH/CH$_2$Cl$_2$ (R$_f$: 0.2); $^1$H-NMR (DMSO-d$_6$, 400 MHz): δ 8.08 (br s, 3H), 7.68 (d, J=8.4 Hz, 2H), 7.50 (d, J=8.4 Hz, 2H), 2.81-2.75 (m, 4H), 2.59 (s, 6H), 1.94-1.86 (m, 2H).

Synthesis of 3'-methoxy-[1, 1'-biphenyl]-3-amine (412)

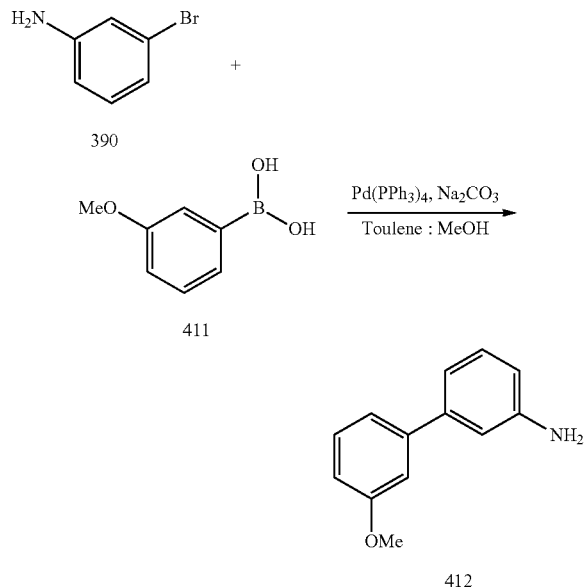

To a stirred solution of 3-bromoaniline 390 (1 g, 5.81 mmol) and (3-methoxyphenyl) boronic acid 411 (883 mg, 5.81 mmol) in Toluene: MeOH (1:1, 20 mL) under inert atmosphere were added sodium carbonate (2.15 g, 20.34 mmol) in 10 mL of H$_2$O) at RT and purged under argon atmosphere for 20 min. To this was added Pd(PPh$_3$)$_4$ (335 mg, 0.28 mmol) and heated to 100° C. for 16 h. The reaction was monitored by TLC; after completion of the reaction, the reaction mixture was filtered through celite, washed with 50% MeOH/CH$_2$Cl$_2$ (150 mL). The filtrate was evaporated in vacuo to obtain the crude which was purified through silica gel column chromatography in 70% EtOAc/hexanes to afford compound 412 (500 mg, 54%) as yellow thick syrup. TLC: 70% EtOAc/hexanes (R$_f$: 0.5); $^1$H NMR (400 MHz, CDCl$_3$): δ 7.35-7.30 (m, 1H), 7.25-7.19 (m, 1H), 7.17-7.13 (m, 1H), 7.10-7.08 (m, 1H), 7.00-6.96 (m, 1H), 6.92-6.85 (m, 2H), 6.68-6.65 (m, 1H), 3.85 (s, 3H), 3.72 (br s, 2H);

Synthesis of 3'-amino-[1, 1'-biphenyl]-3-ol (413)

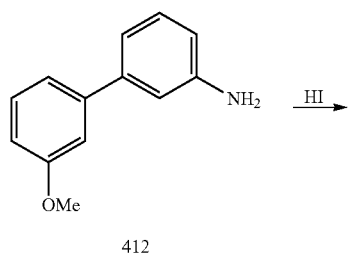

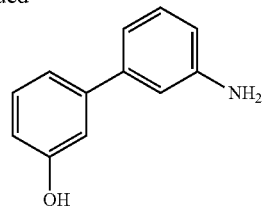

A mixture of compound 412 (400 mg, 2.01 mmol) in hydrogen iodide (5 mL, 57% aqueous solution) was refluxed for 5 h. The reaction was monitored by TLC; after completion of the reaction, the reaction mixture was quenched with ice-cold water and the pH was neutralized with 10% sodium bicarbonate solution (5 mL) and extracted with EtOAc (2×50 mL). The combined organic extracts were dried over sodium sulfate, filtered and concentrated in vacuo to obtain the crude. The obtained solid was filtered, dried in vacuo to obtain the crude which was purified through silicagel column chromatography in 80% EtOAc/hexanes to afford compound 413 (200 mg, 54%) as an off-white solid. TLC: 50% EtOAc/hexanes (R$_f$: 0.4); $^1$H NMR (400 MHz, DMSO-d$_6$): δ 9.41 (s, 1H), 7.20 (t, J=7.8 Hz, 1H), 7.06 (t, J=7.8 Hz, 1H), 6.99-6.88 (m, 2H), 6.78-6.76 (m, 1H), 6.73-6.68 (m, 2H), 6.55-6.52 (m, 1H), 5.12 (s, 2H).

Synthesis of 2-(tetrahydrofuran-2-yl) ethan-1-amine hydrochloride (415)

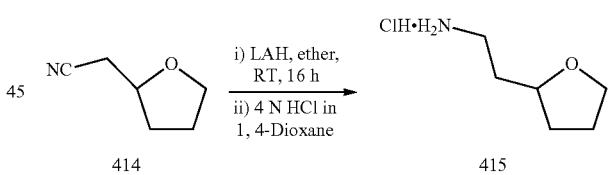

To a stirred solution of 2-(tetrahydrofuran-2-yl) acetonitrile 414 (2 g, 17.99 mmol) in ether (20 mL) under argon atmosphere was added lithium aluminium hydride (1.36 g, 35.83 mmol) at 0° C.; warmed to RT and stirred for 16 h. The reaction was monitored by TLC; after completion of the reaction, the reaction mixture was quenched with saturated sodium potassium tartrate solution (30 mL) at 0-5° C. and extracted with ether (2×50 mL). The combined organic extracts were dried over sodium sulfate, filtered and concentrated in vacuo to obtain the crude.

The crude was dissolved in CH$_2$Cl$_2$ (5 mL) cooled to 0° C. and added 4 N HCl in 1, 4-dioxane (10 mL) under argon atmosphere and stirred at the same temperature for 30 min. The volatiles were removed in vacuo. The obtained solid was titurated with CH$_2$Cl$_2$ (2×5 mL) and in vacuo to afford compound 415 (500 mg, HCl salt) as sticky solid. TLC: 10% MeOH/CH$_2$Cl$_2$ (R$_f$: 0.2).

Synthesis of 2-(4-(2H-1, 2, 3-triazol-2-yl) phenyl) ethan-1-amine hydrochloride (421)

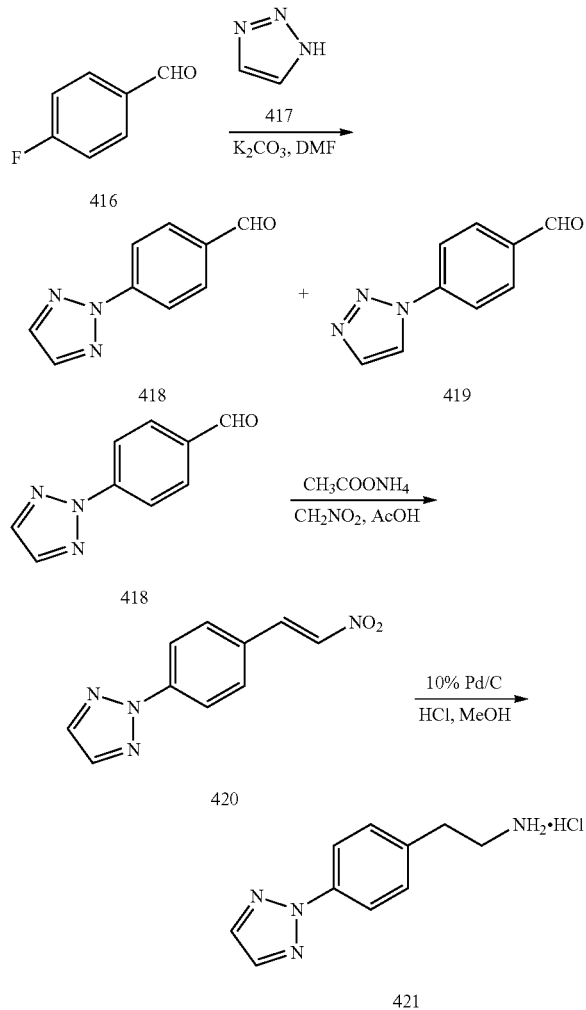

Synthesis of 4-(2H-1, 2, 3-triazol-2-yl) benzaldehyde & 4-(1H-1, 2, 3-triazol-1-yl) benzaldehyde (418 & 419)

To a stirred solution of 4-fluorobenzaldehyde 417 (2 g, 16 mmol) in DMF (50 mL) under argon atmosphere were added 1H-1, 2, 3-triazole 417 (1.32 g, 19.2 mmol), potassium carbonate (3.3 g, 24 mmol) at RT; heated to 100° C. and stirred for 5 h. The reaction was monitored by TLC; after completion of the reaction, the reaction mixture was diluted with ice cold water (35 mL) and extracted with EtOAc (2×40 mL). The combined organic extracts were dried over sodium sulfate, filtered and concentrated in vacuo to obtain the crude. The crude was purified through silica gel column chromatography using 20% EtOAc/hexanes to afford compound 418 (800 mg, 29%) and using 40% EtOAc/hexanes to afford compound 419 (1 g, 36%) as yellow solids.

Compound 418 Analytical Data:
TLC: 20% EtOAc/hexanes ($R_f$: 0.8); $^1$H-NMR (DMSO-$d_6$, 400 MHz): δ 10.05 (s, 1H), 8.27 (s, 2H), 8.25 (d, J=8.8 Hz, 2H), 8.11 (d, J=8.8 Hz, 2H).

Compound 419 Analytical Data:
TLC: 20% EtOAc/hexanes ($R_f$: 0.3); $^1$H-NMR (DMSO-$d_6$, 400 MHz): δ 10.07 (s, 1H), 8.98 (s, 1H), 8.19 (d, J=8.8 Hz, 2H), 8.13 (d, J=8.8 Hz, 2H), 8.04 (s, 1H).

Synthesis of (E)-2-(4-(2-nitrovinyl) phenyl)-2H-1, 2, 3-triazole (420)

To a stirred solution of compound 418 (400 mg, 2.31 mmol) in AcOH (10 mL) under argon atmosphere were added nitromethane (1.41 mL, 23.12 mmol), ammonium acetate (267 mg, 3.46 mmol) at RT; heated to 100° C. and stirred for 16 h. The reaction was monitored by TLC; after completion of the reaction, the volatiles were removed in vacuo and diluted with water (20 mL). The obtained solid was filtered, washed with n-hexane and dried in vacuo to afford compound 420 (400 mg, 80%) as yellow solid. TLC: 20% EtOAc/hexanes ($R_f$: 0.3); $^1$H-NMR (DMSO-$d_6$, 400 MHz): δ 8.29-8.18 (m, 4H), 8.13-8.05 (m, 4H).

Synthesis of 2-(4-(2H-1, 2, 3-triazol-2-yl) phenyl) ethan-1-amine hydrochloride (421)

To a stirred solution of compound 420 (200 mg, 0.92 mmol) in MeOH (10 mL) under argon atmosphere were added 10% Pd/C (100 mg), HCl (0.2 mL) at RT and stirred under hydrogen atmosphere (balloon pressure) for 16 h. The reaction was monitored by TLC; after completion of the reaction, the reaction mixture was filtered through celite and the filtrate was concentrated in vacuo to obtain the crude. The crude was triturated with 2 M HCl in Et$_2$O (2×5 mL) and dried in vacuo to afford compound 421 (100 mg, 48%) as an off-white solid. TLC: 30% EtOAc/hexanes ($R_f$: 0.2); $^1$H-NMR (DMSO-$d_6$, 400 MHz): δ 8.16 (s, 2H), 8.12 (br s, 2H), 7.98 (d, J=8.4 Hz, 2H), 7.46 (d, J=8.4 Hz, 2H), 3.10-3.05 (m, 2H), 2.96 (t, J=8.4 Hz, 2H).

Synthesis of Benzyl (4-(4-(2-aminoethyl) phenoxy) butyl) carbamate hydrochloride (427)

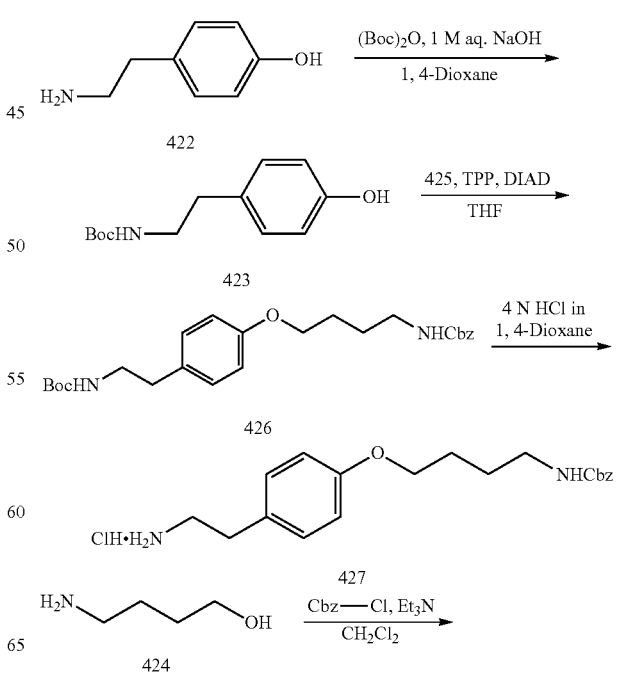

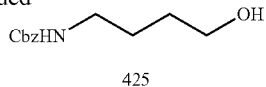

Synthesis of Tert-Butyl (4-hydroxyphenethyl) carbamate (423)

To a stirred solution of 4-(2-aminoethyl) phenol 422 (1 g, 7.29 mmol) in 1, 4-dioxane: $H_2O$ (1:1, 30 mL) were added 2 M aqueous sodium hydroxide solution (2 mL) and Boc-anhydride (1.9 mL, 8.25 mmol) at 0° C.; warmed to RT and stirred for 3 h. The reaction was monitored by TLC; after completion of the reaction, the pH of the reaction mixture cooled to 0° C., acidified with 1 M HCl to ~3 and extracted with EtOAc (2×50 mL). The combined organic extracts were dried over sodium sulphate, filtered and concentrated in vacuo to afford compound 423 (1.5 g, 87%) as an off-white solid. TLC: 50% EtOAc/hexanes ($R_f$: 0.8); $^1$H NMR (DMSO-$d_6$, 500 MHz): δ 9.15 (s, 1H), 6.95 (d, J=8.4 Hz, 2H), 6.83 (t, J=5.4 Hz, 1H), 6.64 (d, J=8.1 Hz, 2H), 3.09-3.00 (m, 2H), 2.56-2.51 (m, 2H), 1.35 (s, 9H).

Synthesis of Benzyl (4-hydroxybutyl) carbamate (425)

To a stirred solution of 4-aminobutan-1-ol 424 (1.0 g, 11.23 mmol) in $CH_2Cl_2$ (15 mL) under argon atmosphere were added triethyl amine (1.78 mL, 12.35 mmol) and benzyl chloroformate (1.76 mL, 12.35 mmol, 50% solution in toluene) at 0° C.; warmed to RT and stirred for 6 h. The reaction was monitored by TLC; after completion of the reaction, the reaction mixture was diluted with saturated ammonium chloride (50 mL) at 0° C. The organic layer was washed with brine (50 mL), dried over sodium sulfate, filtered and concentrated in vacuo to afford compound 425 (2.1 g, 84%) as colorless liquid. TLC: 50% EtOAc/hexanes ($R_f$: 0.5); $^1$H NMR (DMSO-$d_6$, 500 MHz): δ 7.40-7.22 (m, 6H), 4.98 (s, 2H), 4.37 (t, J=5.1 Hz, 1H), 3.36 (q, J=5.8 Hz, 2H), 2.97 (q, J=6.3 Hz, 2H), 1.51-1.28 (m, 4H).

Synthesis of Tert-Butyl (4-(4-(((benzyloxy) carbonyl) amino) butoxy) phenethyl) carbamate (426)

To a stirred solution of compound 423 (1.5 g, 6.32 mmol) and compound 425 (1.4 g, 6.32 mmol) in THF (50 mL) under argon atmosphere at 0° C. were added triphenyl phosphine (1.65 g, 6.32 mmol), diisopropyl azodicarboxylate (1.4 mL, 6.96 mmol) at 0° C.; warmed to RT and stirred for 2 h. The reaction was monitored by TLC; after completion of the reaction, the volatiles were removed in vacuo to obtain the crude. The crude was dissolved in 10% EtOAc/hexanes (5 mL) and the precipitated solid was filtered, washed with hexane (20 mL), dried in vacuo to afford compound 426 (1.9 g, 68%) as an off-white solid. TLC: 5% MeOH/$CH_2Cl_2$ ($R_f$: 0.7); 1H NMR (DMSO-$d_6$, 500 MHz): δ 8.89 (s, 1H), 7.68-7.51 (m, 5H), 7.40-7.24 (m, 2H), 7.07 (d, J=8.4 Hz, 1H), 6.88-6.78 (m, 2H), 5.00 (s, 2H), 4.80-4.73 (m, 2H), 3.91 (t, J=6.4 Hz, 2H), 3.11-3.02 (m, 2H), 2.60 (t, J=7.5 Hz, 2H), 1.72-1.64 (m, 2H), 1.56-1.52 (m, 2H), 1.18 (d, J=6.1 Hz, 9H).

Synthesis of Benzyl (4-(4-(2-aminoethyl) phenoxy) butyl) carbamate hydrochloride (427)

To a stirred solution of compound 426 (500 mg, 1.13 mmol) in $CH_2Cl_2$ (5 mL) was added 4 N HCl in 1, 4-dioxane (3 mL) under argon atmosphere at 0-5° C.; warmed to RT and stirred for 3 h. The reaction was monitored by TLC; after completion of the reaction, the volatiles were removed under reduced pressure. The obtained solid was washed with diethyl ether (10 mL), n-pentane (10 mL) and dried in vacuo to afford compound 427 (200 mg, 47%) as white solid. TLC: 5% MeOH/$CH_2Cl_2$ ($R_f$: 0.4); 1H NMR (DMSO-$d_6$, 500 MHz): δ 7.88 (br s, 3H), 7.39-7.28 (m, 5H), 7.15 (d, J=8.7 Hz, 2H), 6.88 (d, J=8.7 Hz, 2H), 5.00 (s, 2H), 3.93 (t, J=6.4 Hz, 2H), 3.04 (q, J=6.7 Hz, 2H), 2.97 (d, J=6.4 Hz, 2H), 2.81-2.76 (m, 2H), 1.73-1.65 (m, 2H), 1.57-1.51 (m, 2H).

Synthesis of 4-phenyloxazol-2-amine (429)

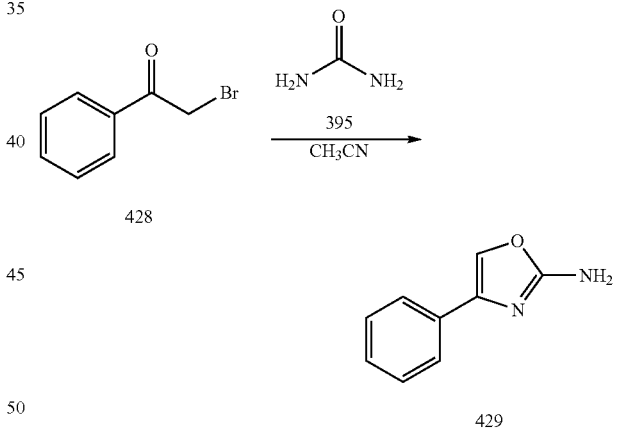

Synthesis of 4-phenyloxazol-2-amine (429)

To a stirred solution of 2-bromo-1-phenylethan-1-one 428 (100 mg, 0.50 mmol) in $CH_3CN$ (5 ml) under inert atmosphere was added urea 395 (301 mg, 5.02 mmol) at RT; heated at 80° C. and stirred for 16 h. The reaction was monitored by TLC; after completion of the reaction, the volatiles were removed in vacuo to obtain the crude. The crude was purified through flash column chromatography using 30% EtOAc/hexanes to afford compound 429 (50 mg, 63%) as an off-white solid. TLC: 50% EtOAc/hexanes ($R_f$: 0.6); $^1$H NMR (400 MHz, DMSO-$d_6$): δ 7.86 (s, 1H), 7.63 (d, J=7.0 Hz, 2H), 7.35 (t, 7.6 Hz, 2H), 7.26-7.22 (m, 1H), 6.70 (s, 2H).

TABLE 1

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1101 | 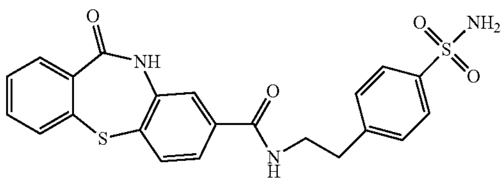 [SMILES: NS(=O)(=O)c1ccc(CCNC(=O)c2ccc3c(c2)NC(=O)c2ccccc2S3)cc1] | D, 6 | 52 | 476.0701 | 476.0715 for $C_{22}H_{19}N_3O_4S_2Na$ $(M + Na)^+$ | $^1$H NMR (400 MHz, DMSO-$d_6$) δ 10.78 (s, 1H), 8.62 (t, J = 5.6 Hz, 1H), 7.76-7.59 (m, 5H), 7.57-7.35 (m, 6H), 7.26 (s, 2H), 3.47 (t, J = 6.6 Hz, 2H), 2.88 (t, J = 7.1 Hz, 2H). |
| 1102 | 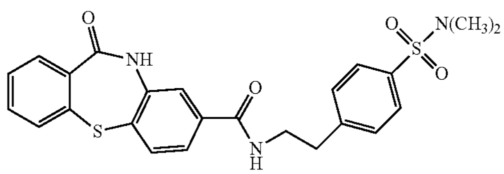 [SMILES: CN(C)S(=O)(=O)c1ccc(CCNC(=O)c2ccc3c(c2)NC(=O)c2ccccc2S3)cc1] | D, 6 | 51 | 504.1048 | 504.1028 for $C_{24}H_{23}N_3O_4S_2Na$ $(M + Na)^+$ | $^1$H NMR (400 MHz, DMSO-$d_6$) δ 10.78 (s, 1H), 8.60 (t, J = 5.6 Hz, 1H), 7.71-7.57 (m, 5H), 7.55-7.40 (m, 6H), 3.50 (q, J = 6.8 Hz, 2H), 2.91 (t, J = 7.1 Hz, 2H), 2.52 (s, 6H). |
| 1103 | 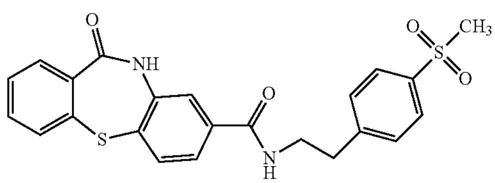 [SMILES: CS(=O)(=O)c1ccc(CCNC(=O)c2ccc3c(c2)NC(=O)c2ccccc2S3)cc1] | D, 6 | 83 | 453.0936 | 453.0943 for $C_{23}H_{21}N_2O_4S_2$ $(M + H)^+$ | $^1$H NMR (400 MHz, DMSO-$d_6$) δ 10.78 (s, 1H), 8.60 (t, J = 5.5 Hz, 1H), 7.71-7.59 (m, 3H), 7.53 (d, J = 8.3 Hz, 1H), 7.51-7.42 (m, 2H), 7.27 (t, J = 7.3 Hz, 2H), 7.18 (dd, J = 15.9, 7.3 Hz, 3H), 3.44 (q, J = 6.9 Hz, 2H), 2.80 (t, J = 7.4 Hz, 2H). |
| 1104 | 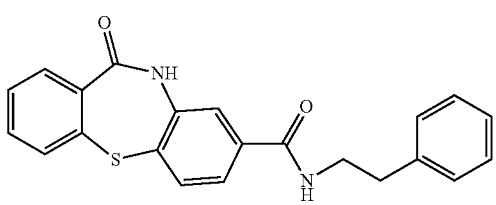 [SMILES: O=C(NCCc1ccccc1)c1ccc2c(c1)NC(=O)c1ccccc1S2] | D, 6 | 63 | 373.0999 | 373.1016 for $C_{22}H_{17}N_2O_2S$ $(M - H)^-$ | $^1$H NMR (400 MHz, DMSO-$d_6$) δ 10.78 (s, 1H), 8.60 (t, J = 5.5 Hz, 1H), 7.71-7.59 (m, 3H), 7.53 (d, J = 8.3 Hz, 1H), 7.51-7.42 (m, 2H), 7.27 (t, J = 7.3 Hz, 2H), 7.18 (dd, J = 15.9, 7.3 Hz, 3H), 3.44 (q, J = 6.9 Hz, 2H), 2.80 (t, J = 7.4 Hz, 2H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1105 | 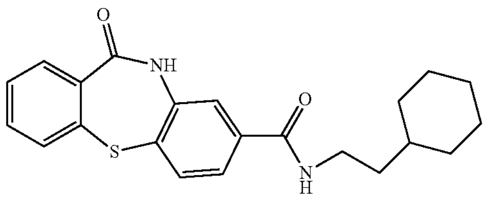 [SMILES: O=C(NCCC1CCCCC1)c1ccc2c(c1)NC(=O)c1ccccc1S2] | D, 6 | 80 | 381.1633 | 381.1637 for $C_{22}H_{25}N_2O_2S$ $(M + H)^+$ | $^1$H NMR (400 MHz, DMSO-$d_6$) δ 10.76 (s, 1H), 8.43 (t, J = 5.6 Hz, 1H), 7.71-7.59 (m, 3H), 7.58-7.40 (m, 4H), 3.28-3.17 (m, 2H), 1.73-1.53 (m, 6H), 1.37 (q, J = 7.0 Hz, 2H), 1.32-1.03 (m, 3H), 0.87 (tt, J = 11.5, 6.1 Hz, 2H). |
| 1107 | 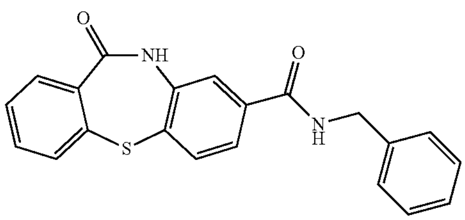 [SMILES: O=C(NCc1ccccc1)c1ccc2c(c1)NC(=O)c1ccccc1S2] | D, 6 | 79 | 361.1001 | 361.1011 for $C_{21}H_{17}N_2O_2S$ $(M + H)^+$ | $^1$H NMR (400 MHz, DMSO-$d_6$) δ 10.77 (s, 1H), 9.08 (t, J = 6.0 Hz, 1H), 7.74-7.58 (m, 4H), 7.57-7.40 (m, 3H), 7.35-7.19 (m, 5H), 4.43 (d, J = 6.0 Hz, 2H). |
| 1108 | 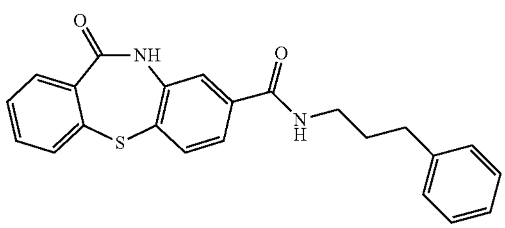 [SMILES: O=C(NCCCc1ccccc1)c1ccc2c(c1)NC(=O)c1ccccc1S2] | D, 6 | 71 | 389.1307 | 389.1324 for $C_{23}H_{21}N_2O_2S$ $(M + H)^+$ | $^1$H NMR (400 MHz, DMSO-$d_6$) δ 10.76 (s, 1H), 8.52 (t, J = 5.6 Hz, 1H), 7.71-7.60 (m, 3H), 7.60-7.42 (m, 4H), 7.30-7.13 (m, 5H), 3.23 (q, J = 6.6 Hz, 2H), 2.59 (t, J = 7.7 Hz, 2H), 1.83-1.74 (m, 2H). |
| 1109 | 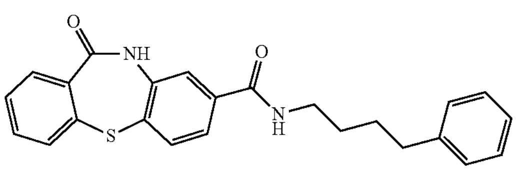 [SMILES: O=C(NCCCCc1ccccc1)c1ccc2c(c1)NC(=O)c1ccccc1S2] | D, 6 | 81 | 403.1496 | 403.1480 for $C_{24}H_{23}N_2O_2S$ $(M + H)^+$ | $^1$H NMR (400 MHz, DMSO-$d_6$) δ 10.75 (s, 1H), 8.48 (t, J = 5.6 Hz, 1H), 7.71-7.59 (m, 3H), 7.58-7.40 (m, 4H), 7.29-7.09 (m, 5H), 3.23 (q, J = 6.5 Hz, 2H), 2.57 (t, J = 7.4 Hz, 2H), 1.63-1.44 (m, 4H). |
| 1110 | 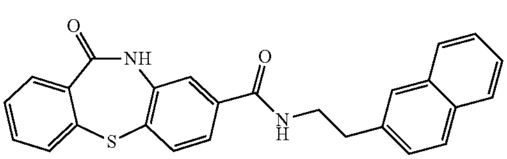 [SMILES: O=C(NCCc1ccc2ccccc2c1)c1ccc2c(c1)NC(=O)c1ccccc1S2] | D, 6 | 65 | 447.1162 | 447.1143 for $C_{26}H_{20}N_2O_2SNa$ $(M + Na)^+$ | $^1$H NMR (400 MHz, DMSO-$d_6$) δ 10.77 (s, 1H), 8.65 (t, J = 5.6 Hz, 1H), 7.83 (t, J = 8.5 Hz, 3H), 7.78-7.59 (m, 4H), 7.57-7.35 (m, 7H), 3.55 (q, J = 6.8 Hz, 2H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2.97 (t, J = 7.3 Hz, 2H). |
| 1111 | 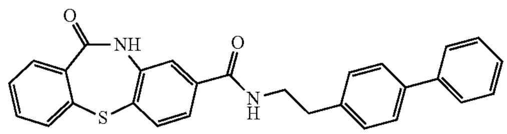 | D, 6 | 36 | 473.1319 | 473.1300 for $C_{28}H_{22}N_2O_2SNa$ $(M + Na)^+$ | $^1$H NMR (400 MHz, DMSO-$d_6$) δ 10.78 (s, 1H), 8.63 (t, J = 5.7 Hz, 1H), 7.71-7.39 (m, 13H), 7.32 (dd, J = 13.3, 7.5 Hz, 3H), 3.48 (q, J = 6.7 Hz, 2H), 2.85 (t, J = 7.2 Hz, 2H). |
| 1112 | 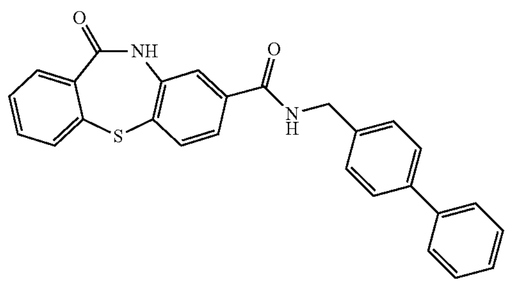 [SMILES: O=C(NCc1ccc(-c2ccccc2)cc1)c1ccc2c(c1)NC(=O)c1ccccc1S2] | D, 6 | 82 | 459.1154 | 459.1143 for $C_{27}H_{20}N_2O_2SNa$ $(M + Na)^+$ | $^1$H NMR (400 MHz, DMSO-$d_6$) δ 10.78 (s, 1H), 9.12 (t, J = 6.0 Hz, 1H), 7.76-7.29 (m, 16H), 4.48 (d, J = 5.9 Hz, 2H). |
| 1113 | 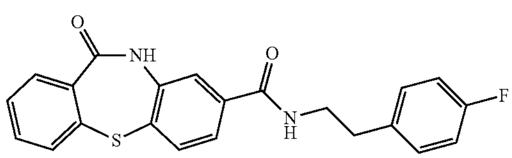 [SMILES: O=C(NCCc1ccc(F)cc1)c1ccc2c(c1)NC(=O)c1ccccc1S2] | D, 6 | 83 | 415.0894 | 415.0892 for $C_{22}H_{17}N_2O_2SFNa$ $(M + Na)^+$ | $^1$H NMR (400 MHz, DMSO-$d_6$) δ 10.78 (s, 1H), 8.57 (t, J = 5.7 Hz, 1H), 7.65 (ddd, J = 17.4, 6.5, 2.8 Hz, 3H), 7.57-7.40 (m, 4H), 7.23 (dd, J = 8.4, 5.6 Hz, 2H), 7.08 (t, J = 8.8 Hz, 2H), 3.43 (q, J = 6.8 Hz, 2H), 2.79 (t, J = 7.2 Hz, 2H). |
| 1114 | 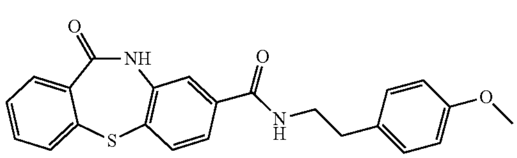 [SMILES: COc1ccc(CCNC(=O)c2ccc3c(c2)NC(=O)c2ccccc2S3)cc1] | D, 6 | 78 | 427.109 | 427.1092 for $C_{23}H_{20}N_2O_3SNa$ $(M + Na)+$ | $^1$H NMR (400 MHz, DMSO-$d_6$) δ 10.78 (s, 1H), 8.57 (t, J = 5.6 Hz, 1H), 7.72-7.60 (m, 3H), 7.57-7.40 (m, 4H), 7.15-7.08 (m, 2H), 6.87-6.79 (m, 2H), 3.70 (s, 3H), 3.45-3.35 (m, 2H), 2.73 (t, J = 7.4 Hz, 2H). |
| 1115 | 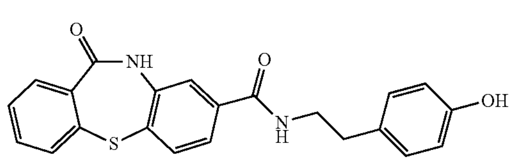 [SMILES: O=C(NCCc1ccc(O)cc1)c1ccc2c(c1)NC(=O)c1ccccc1S2] | D, 6 | 63 | 391.1121 | 391.1116 for $C_{22}H_{19}N_2O_3S$ $(M + H)^+$ | $^1$H NMR (400 MHz, DMSO-$d_6$) δ 10.78 (s, 1H), 9.14 (s, 1H), 8.55 (t, J = 5.6 Hz, 1H), 7.71-7.60 (m, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 3H), 7.58-7.40 (m, 4H), 6.99 (d, J = 8.2 Hz, 2H), 6.65 (d, J = 8.2 Hz, 2H), 3.37 (q, J = 6.8 Hz, 2H), 2.74-2.63 (m, 2H). |
| 1117 | [structure] | D, 6 | 81 | 455.1049 | 455.1041 for $C_{24}H_{20}N_2O_4SNa$ $(M + Na)^+$ | $^1$H NMR (400 MHz, DMSO-$d_6$) δ 10.78 (s, 1H), 8.60 (t, J = 5.7 Hz, 1H), 7.86 (d, J = 8.1 Hz, 2H), 7.71-7.60 (m, 3H), 7.57-7.40 (m, 4H), 7.36 (d, J = 8.0 Hz, 2H), 3.81 (s, 3H), 3.48 (q, J = 6.7 Hz, 2H), 2.88 (t, J = 7.1 Hz, 2H). |
| 1118 | [structure] | D, 6 | 76 | 413.0937 | 413.0936 for $C_{22}H_{18}N_2O_3SNa$ $(M + Na)^+$ | $^1$H NMR (400 MHz, DMSO-$d_6$) δ 10.78 (s, 1H), 9.23 (s, 1H), 8.59 (t, J = 5.6 Hz, 1H), 7.71-7.59 (m, 3H), 7.58-7.40 (m, 4H), 7.05 (t, J = 7.7 Hz, 1H), 6.59 (td, J = 9.0, 6.9 Hz, 3H), 3.40 (q, J = 6.8 Hz, 2H), 2.70 (t, J = 7.5 Hz, 2H). |
| 1120 | [structure] | D, 6 | 13 | 422.1 | 422.1 $(M + Na)^+$ | $^1$H NMR (400 MHz, DMSO-$d_6$) δ 10.78 (s, 1H), 8.59 (t, J = 5.6 Hz, 1H), 7.83-7.33 (m, 11H), 3.47 (dd, J = 7.8, 5.1 Hz, 2H), 2.90 (t, J = 7.0 Hz, 2H). |
| 1121 | [structure] | D, 6 | 32 | 458.2 | 458.2 $(M + H)^+$ | $^1$H NMR (400 MHz, DMSO-$d_6$) δ 10.78 (s, 1H), 8.57 (t, J = 5.6 Hz, 1H), 7.71-7.60 (m, 3H), 7.58-7.40 (m, 4H), 7.06-6.96 (m, 2H), 6.87-6.78 (m, 2H), 3.42-3.32 (m, 2H), 3.04 (t, J = 5.4 Hz, 4H), 2.68 (t, J = 7.5 Hz, 2H), 1.63-1.43 (m, 6H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1122 | 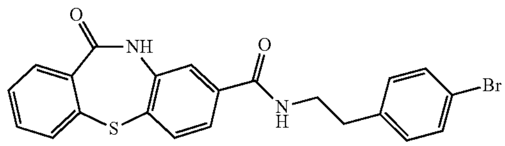 [SMILES: O=C(NCCc1ccc(Br)cc1)c1ccc2c(c1)NC(=O)c1ccccc1S2] | D, 6 | 49 | 486.9872 | 486.9883 for $C_{22}H_{17}N_2O_2SClBr$ $(M + Cl)^-$ | $^1$H NMR (400 MHz, DMSO-$d_6$) δ 10.78 (s, 1H), 8.58 (t, J = 5.6 Hz, 1H), 7.65 (ddd, J = 17.0, 5.8, 2.1 Hz, 3H), 7.57-7.40 (m, 6H), 7.17 (d, J = 8.3 Hz, 2H), 3.43 (q, J = 6.7 Hz, 2H), 2.77 (t, J = 7.1 Hz, 2H). |
| 1123 | 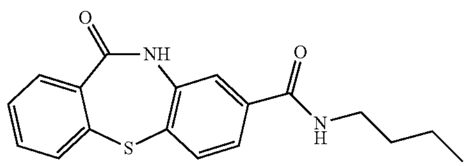 [SMILES: CCCCNC(=O)c1ccc2c(c1)NC(=O)c1ccccc1S2] | D, 6 | 37 | 361.078 | 361.0778 for $C_{18}H_{18}N_2O_2SCl$ $(M + Cl)^-$ | $^1$H NMR (400 MHz, DMSO-$d_6$) δ 10.75 (s, 1H), 8.45 (d, J = 5.7 Hz, 1H), 7.71-7.59 (m, 3H), 7.59-7.40 (m, 4H), 3.21 (q, J = 6.7 Hz, 2H), 1.45 (p, J = 7.5 Hz, 2H), 1.27 (dt, J = 20.8, 10.6 Hz, 2H), 0.86 (td, J = 7.2, 2.4 Hz, 3H). |
| 1124 | 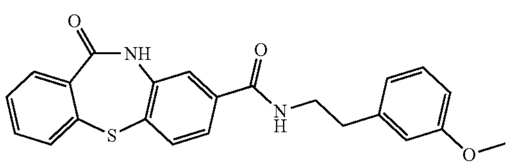 [SMILES: COc1cccc(CCNC(=O)c2ccc3c(c2)NC(=O)c2ccccc2S3)c1] | D, 6 | 48 | 439.2 | 439.2 $(M + Cl)^-$ | $^1$H NMR (400 MHz, DMSO-$d_6$) δ 10.78 (s, 1H), 8.59 (t, J = 5.6 Hz, 1H), 7.72-7.61 (m, 3H), 7.58-7.40 (m, 4H), 7.18 (t, J = 8.0 Hz, 1H), 6.81-6.71 (m, 3H), 3.70 (s, 3H), 3.44 (q, J = 7.1 Hz, 2H), 2.78 (t, J = 7.4 Hz, 2H). |
| 1125 | 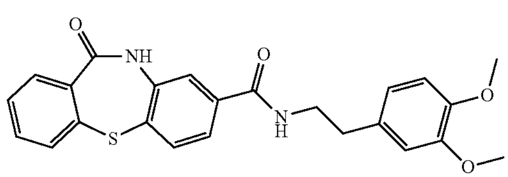 [SMILES: COc1ccc(CCNC(=O)c2ccc3c(c2)NC(=O)c2ccccc2S3)cc1OC] | D, 6 | 59 | 433.1206 | 433.1222 for $C_{24}H_{21}N_2O_4S$ | $^1$H NMR (400 MHz, DMSO-$d_6$) δ 10.78 (s, 1H), 8.56 (t, J = 5.6 Hz, 1H), 7.71-7.60 (m, 3H), 7.58-7.40 (m, 4H), 6.89-6.76 (m, 2H), 6.70 (dd, J = 8.2, 2.0 Hz, 1H), 3.68 (d, J = 2.0 Hz, 6H), 3.16 (d, J = 5.2 Hz, 2H), 2.73 (t, J = 7.3 Hz, 2H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1127 | 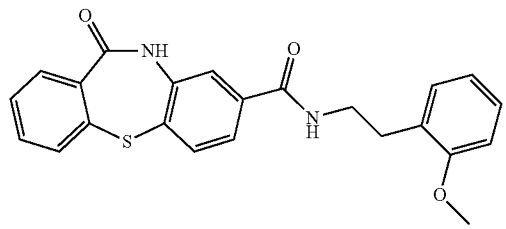 [SMILES: COc1ccccc1CCNC(=O)c1ccc2c(c1)NC(=O)c1ccccc1S2] | D, 6 | 49 | 405.1269 | 405.1273 for $C_{23}H_{21}N_2O_3S$ (M + H)$^+$ | $^1$H NMR (400 MHz, DMSO-$d_6$) δ 10.78 (s, 1H), 8.55 (d, J = 6.3 Hz, 1H), 7.71-7.59 (m, 3H), 7.57-7.40 (m, 4H), 7.22-7.07 (m, 2H), 6.94 (d, J = 8.3 Hz, 1H), 6.84 (t, J = 7.6 Hz, 1H), 3.76 (d, J = 2.1 Hz, 3H), 3.40 (q, J = 7.0 Hz, 2H), 2.82-2.74 (m, 2H). |
| 1130 | 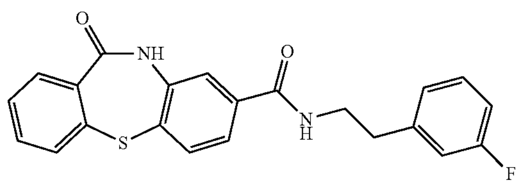 [SMILES: O=C(NCCc1cccc(F)c1)c1ccc2c(c1)NC(=O)c1ccccc1S2] | D, 6 | 41 | 391.091 | 391.0917 for $C_{22}H_{16}N_2O_2FS$ | $^1$H NMR (400 MHz, DMSO-$d_6$) δ 10.78 (s, 1H), 8.60 (t, J = 5.6 Hz, 1H), 7.75-7.57 (m, 3H), 7.57-7.39 (m, 4H), 7.30 (td, J = 8.0, 6.2 Hz, 1H), 7.09-6.95 (m, 3H), 3.46 (q, J = 6.7 Hz, 2H), 2.83 (t, J = 7.2 Hz, 2H). |
| 1149 | 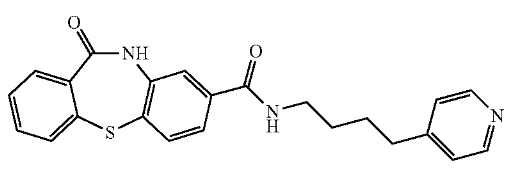 [SMILES: O=C(NCCCCc1ccncc1)c1ccc2c(c1)NC(=O)c1ccccc1S2] | D, 6 | 28 | 404.1438 | 404.1433 for $C_{23}H_{22}N_3O_2S$ | $^1$H NMR (400 MHz, DMSO-$d_6$) δ 10.75 (s, 1H), 8.49 (t, J = 5.7 Hz, 1H), 8.42 (d, J = 5.1 Hz, 2H), 7.71-7.40 (m, 7H), 7.20 (d, J = 5.4 Hz, 2H), 3.24 (q, J = 6.5 Hz, 2H), 2.49 (q, J = 2.8, 1.7 Hz, 2H), 1.54 (dp, J = 41.6, 7.1 Hz, 4H). |
| 1150 | 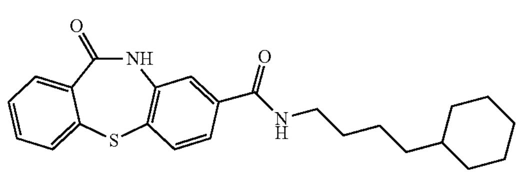 [SMILES: O=C(NCCCCC1CCCCC1)c1ccc2c(c1)NC(=O)c1ccccc1S2] | D, 6 | 75 | 409.1961 | 409.1950 for $C_{24}H_{29}N_2O_2S$ | $^1$H NMR (400 MHz, DMSO-$d_6$) δ 10.76 (s, 1H), 8.46 (t, J = 5.7 Hz, 1H), 7.71-7.40 (m, 7H), 3.19 (q, J = 6.6 Hz, 2H), 1.68-1.54 (m, 5H), 1.44 (p, J = 7.2 Hz, 2H), 1.33-1.03 (m, 8H), 0.83 (t, J = 11.1 Hz, 2H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1151 | 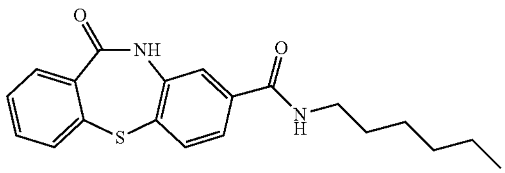 [SMILES: CCCCCCNC(=O)c1ccc2c(c1)NC(=O)c1ccccc1S2] | D, 6 | 74 | 355.1477 | 355.1480 for $C_{20}H_{23}N_2O_2S$ | $^1$H NMR (400 MHz, DMSO-$d_6$) δ 10.75 (s, 1H), 8.46 (t, J = 5.7 Hz, 1H), 7.71-7.40 (m, 7H), 3.20 (q, J = 6.6 Hz, 2H), 1.46 (p, J = 6.9 Hz, 2H), 1.32-1.20 (m, 6H), 0.88-0.80 (m, 3H). |
| 1152 | 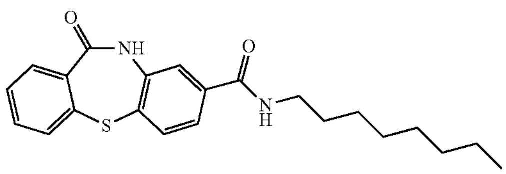 [SMILES: CCCCCCCCNC(=O)c1ccc2c(c1)NC(=O)c1ccccc1S2] | D, 6 | 59 | 383.1802 | 383.1793 for $C_{22}H_{27}N_2O_2S$ | $^1$H NMR (400 MHz, DMSO-$d_6$) δ 10.75 (s, 1H), 8.46 (t, J = 5.7 Hz, 1H), 7.71-7.40 (m, 7H), 3.19 (q, J = 6.6 Hz, 2H), 1.50-1.42 (m, 2H), 1.23 (q, J = 4.6, 4.0 Hz, 10H), 0.83 (t, J = 6.6 Hz, 3H). |
| 1154 | 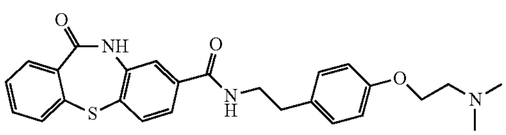 [SMILES: CN(C)CCOc1ccc(CCNC(=O)c2ccc3c(c2)NC(=O)c2ccccc2S3)cc1] | D, 6 | 38 | 462.186 | 462.1851 for $C_{26}H_{28}N_3O_3S$ | $^1$H NMR (400 MHz, DMSO-$d_6$) δ 10.78 (s, 1H), 8.57 (t, J = 5.6 Hz, 1H), 7.71-7.60 (m, 3H), 7.57-7.40 (m, 4H), 7.10 (d, J = 8.3 Hz, 2H), 6.83 (d, J = 8.2 Hz, 2H), 3.98 (t, J = 5.8 Hz, 2H), 3.44-3.34 (m, 2H), 2.72 (t, J = 7.4 Hz, 2H), 2.58 (t, J = 5.8 Hz, 2H), 2.19 (s, 6H). |
| 1155 | 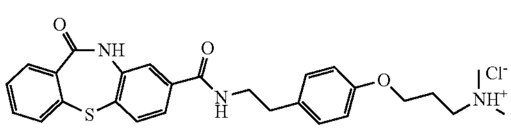 [SMILES: C[NH+](C)CCCOc1ccc(CCNC(=O)c2ccc3c(c2)NC(=O)c2ccccc2S3)cc1 ; [Cl-]] | D, 6 | 40 | 476.2007 | 476.2008 for $C_{27}H_{30}39N_3O_3S$ | $^1$H NMR (400 MHz, DMSO-$d_6$) δ 10.79 (s, 1H), 10.43 (s, 1H), 8.60 (t, J = 5.6 Hz, 1H), 7.71-7.40 (m, 7H), 7.13 (d, J = 8.2 Hz, 2H), 6.84 (d, J = 8.2 Hz, 2H), 3.99 (t, J = 6.1 Hz, 2H), 3.40 (q, J = 6.8 Hz, 2H), 3.16 (dt, J = 13.2, 5.4 Hz, 2H), 2.75 (d, J = 5.0 Hz, 8H), 2.10 (dq, J = 12.2, 6.1 Hz, 2H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1156 | 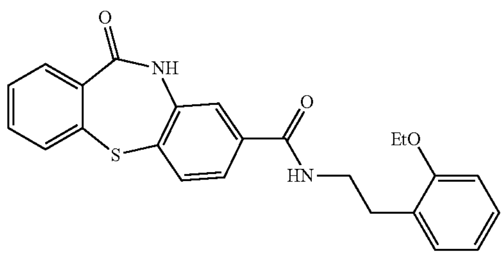 [SMILES: CCOc1ccccc1CCNC(=O)c1ccc2c(c1)NC(=O)c1ccccc1S2] | D, 6 | 59 | 419.2 (M + 1)⁺ | | (DMSO-d₆, 400 MHz): δ 10.76 (br s, 1H), 8.54 (br s, 1H), 7.69-7.62 (m, 3H), 7.55-7.45 (m, 4H), 7.17-7.10 (m, 2H), 6.93 (d, J = 8.4 Hz, 1H), 6.82 (t, J = 7.2 Hz, 1H), 4.03-3.99 (m, 2H), 3.43 (d, J = 6.8 Hz, 2H), 2.78 (t, J = 6.8 Hz, 2H), 1.32 (t, J = 6.8 Hz, 3H); |
| 1157 | 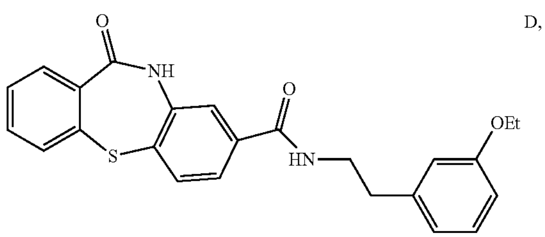 | D, 6 | 49 | 419.2 (M + 1)⁺; | | ¹H-NMR (DMSO-d₆, 400 MHz): δ 10.79 (br s, 1H), 8.59-8.58 (m, 1H), 7.69-7.63 (m, 3H), 7.55-7.44 (m, 4H), 7.16 (t, J = 8.0 Hz, 1H), 6.75 (t, J = 8.0 Hz, 3H), 3.95 (q, 2H), 3.46-3.43 (m, 2H), 2.76 (t, J = 7.6 Hz, 2H), 1.26 (t, J = 6.8 Hz, 3H) |
| 1158 | 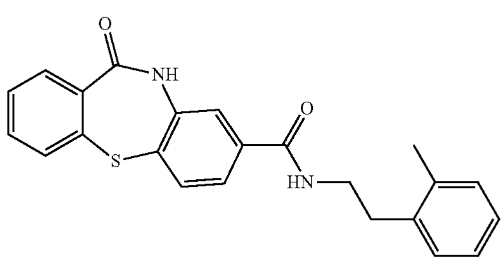 [SMILES: Cc1ccccc1CCNC(=O)c1ccc2c(c1)NC(=O)c1ccccc1S2] | D, 6 | 52 | 389.2 (M + 1)⁺; | | (DMSO-d₆, 500 MHz): δ 10.76 (s, 1H), 8.64 (t, J = 5.5 Hz, 1H), 7.67-7.62 (m, 3H), 7.55-7.42 (m, 4H), 7.12-7.06 (m, 4H), 3.40-3.36 (m, 2H), 2.77 (t, J = 8.0 Hz, 2H), 2.28 (s, 3H); |
| 1159 | 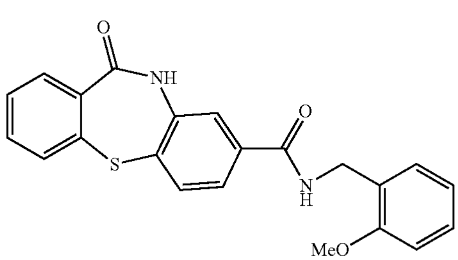 [SMILES: COc1ccccc1CNC(=O)c1ccc2c(c1)NC(=O)c1ccccc1S2] | D, 6 | 35 | 391.3 (M + 1)⁺; | | (DMSO-d₆, 400 MHz): δ 10.76 (s, 1H), 8.88-8.87 (m, 1H), 7.72-7.63 (m, 4H), 7.55-7.43 (m, 3H), 7.22 (t, J = 7.2 Hz, 1H), 7.13 (d, J = 7.6 Hz, 1H), 6.98 (d, J = 7.2 Hz, 1H), 6.87 (t, J = 7.2 Hz, 1H), 4.40 (d, J = 4.8 Hz, 2H), 3.80 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1161 | 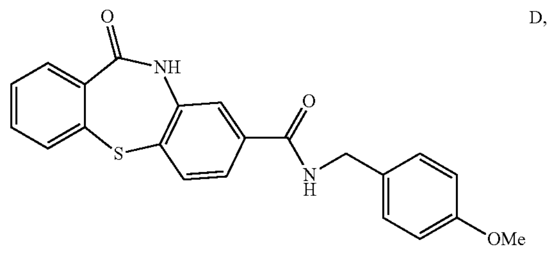 | D, 6 | 43 | 391.2 (M + 1)$^+$; | | (DMSO-d$_6$, 400 MHz): δ 10.76 (s, 1H), 8.99 (t, J = 4.4 Hz, 1H), 7.69-7.59 (m, 4H), 7.54-7.43 (m, 3H), 7.20 (d, J = 8.4 Hz, 2H), 6.86 (d, J = 8.4 Hz, 2H), 4.36 (d, J = 5.6 Hz, 2H), 3.71 (s, 3H); |
| 1163 | 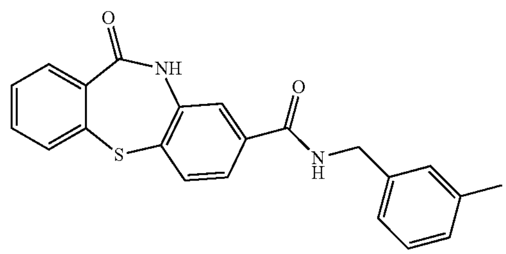 [SMILES: Cc1cccc(CNC(=O)c2ccc3c(c2)NC(=O)c2ccccc2S3)c1] | A, 6 | 36 | 375.0 (M + 1)$^+$; | | (DMSO-d$_6$, 400 MHz): δ 10.76 (s, 1H), 9.04 (t, J = 6.0 Hz, 1H), 7.71-7.61 (m, 4H), 7.55-7.43 (m, 3H), 7.18 (t, J = 7.2 Hz, 1H), 7.08-7.03 (m, 3H), 4.40 (d, J = 6.0 Hz, 2H), 2.26 (s, 3H) |
| 1164 | 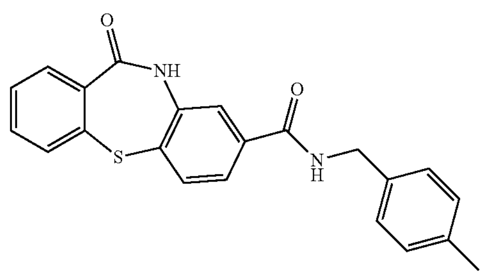 [SMILES: Cc1ccc(CNC(=O)c2ccc3c(c2)NC(=O)c2ccccc2S3)cc1] | D, 6 | 64 | 375.3 (M + 1)$^+$; | | (DMSO-d$_6$, 400 MHz): δ 10.77 (s, 1H), 9.03-9.02 (m, 1H), 7.70-7.60 (m, 4H), 7.55-7.45 (m, 3H), 7.16 (d, J = 8.0 Hz, 2H), 7.10 (d, J = 8.0 Hz, 2H), 4.38 (d, J = 6.0 Hz, 2H), 2.25 (s, 3H) |
| 1165 | 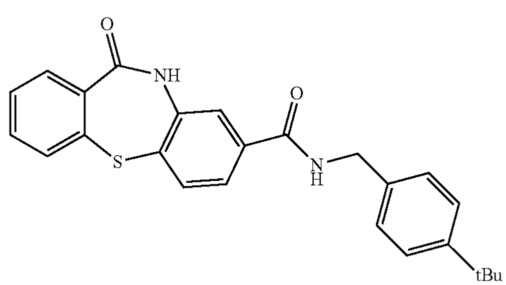 [SMILES: CC(C)(C)c1ccc(CNC(=O)c2ccc3c(c2)NC(=O)c2ccccc2S3)cc1] | A, 6 | 65 | 417.4 (M + 1)$^+$; | | (DMSO-d$_6$, 400 MHz): δ 10.76 (br s, 1H), 9.02 (t, J = 6.0 Hz, 1H), 7.71-7.60 (m, 4H), 7.55-7.43 (m, 3H), 7.32 (d, J = 8.4 Hz, 2H), 7.20 (d, J = 8.4 Hz, 2H), 4.39 (d, J = 6.0 Hz, 2H), 1.24 (s, 9H); |
| 1166 | 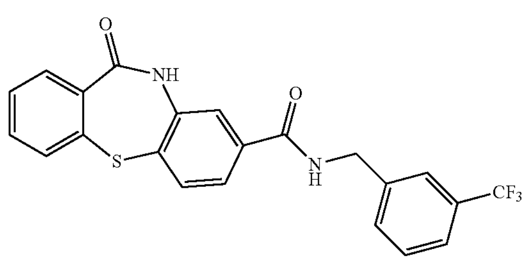 [SMILES: O=C(NCc1cccc(C(F)(F)F)c1)c1ccc2c(c1)NC(=O)c1ccccc1S2] | D, 6 | 48 | 429.4 (M + 1)$^+$; | | (DMSO-d$_6$, 400 MHz): δ 10.77 (s, 1H), 9.17 (t, J = 4.8 Hz, 1H), 7.72-7.67 (m, 3H), 7.64-7.59 (m, 6H), 7.57-7.43 (m, 2H), 4.52 (d, J = 4.8 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1168 | 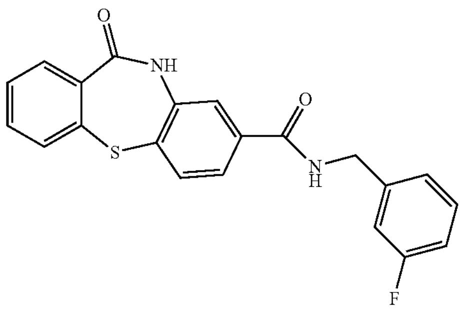 [SMILES: O=C(NCc1cccc(F)c1)c1ccc2c(c1)NC(=O)c1ccccc1S2] | A, 6 | 62 | 379.1 (M + 1)$^+$; | | (DMSO-d$_6$, 400 MHz): δ 10.77 (s, 1H), 9.11 (t, J = 6.0 Hz, 1H), 7.72-7.62 (m, 4H), 7.55-7.44 (m, 3H), 7.36 (t, J = 8.0 Hz, 1H), 7.13-7.04 (m, 3H), 4.45 (d, J = 6.0 Hz, 2H); |
| 1169 | 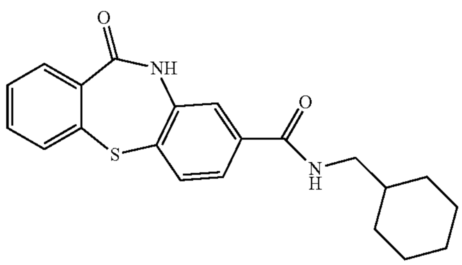 [SMILES: O=C(NCC1CCCCC1)c1ccc2c(c1)NC(=O)c1ccccc1S2] | D, 6 | 56 | 367.3 (M + 1)$^+$; | | (DMSO-d$_6$, 400 MHz): δ 10.75 (s, 1H), 8.46 (t, J = 6.0 Hz, 1H), 7.69-7.62 (m, 3H), 7.57-7.51 (m, 2H), 7.49-7.43 (m, 2H), 3.07-3.04 (m, 2H), 1.67-1.60 (m, 4H), 1.50-1.48 (m, 2H), 1.17-1.12 (m, 3H), 0.93-0.87 (m, 2H); |
| 1171 | 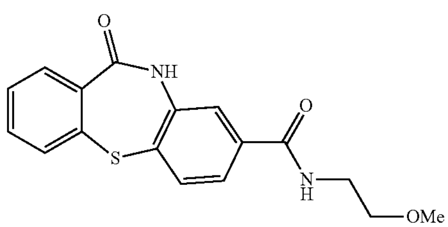 [SMILES: COCCNC(=O)c1ccc2c(c1)NC(=O)c1ccccc1S2] | A, 6 | 40 | 329.1 (M + 1)$^+$; | | (DMSO-d$_6$, 400 MHz): δ 10.76 (s, 1H), 8.58 (t, J = 6.8 Hz, 1H), 7.72-7.69 (m, 3H), 7.56-7.52 (m, 2H), 7.48-7.44 (m, 2H), 3.44-3.38 (m, 4H), 3.24 (s, 3H); |
| 1172 | 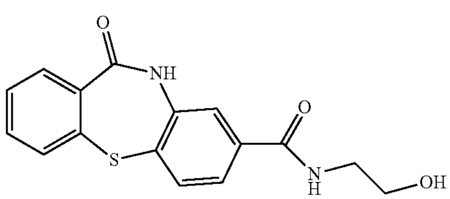 [SMILES: O=C(NCCO)c1ccc2c(c1)NC(=O)c1ccccc1S2] | D, 6 | 82 | 315 (M + 1)$^+$; | | (DMSO-d$_6$, 400 MHz): δ 10.73 (s, 1H), 8.43 (t, J = 4.8 Hz, 1H), 7.66-7.56 (m, 3H), 7.54-7.40 (m, 4H), 4.65 (t, J = 4.8 Hz, 1H), 3.46-3.41 (m, 2H), 3.25-3.23 (m, 2H); |
| 1173 | 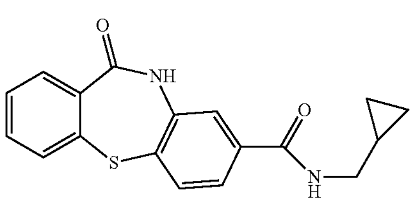 [SMILES: O=C(NCC1CC1)c1ccc2c(c1)NC(=O)c1ccccc1S2] | D, 6 | 52 | 325.2 (M + 1)$^+$; | | (DMSO-d$_6$, 400 MHz): δ 10.75 (s, 1H), 8.58 (t, J = 4.8 Hz, 1H), 7.69-7.59 (m, 4H), 7.57-7.55 (m, 3H), 7.53-7.43 (m, 2H), 3.10 (t, J = 6.4 Hz, 2H), 1.01-0.97 (m, 1H), 0.43-0.38 (m, 2H), 0.21-0.19 (m, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1174 | 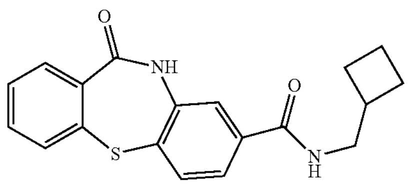 [SMILES: O=C(NCC1CCC1)c1ccc2c(c1)NC(=O)c1ccccc1S2] | A, 6 | 54 | 339.1 (M + 1)$^+$; | | (DMSO-d$_6$, 400 MHz): δ 10.75 (s, 1H), 8.48-8.46 (m, 1H), 7.69-7.63 (m, 3H), 7.57-7.43 (m, 4H), 3.26-3.23 (m, 2H), 2.50-2.49 (m, 1H), 1.97-1.91 (m, 2H), 1.82-1.76 (m, 2H), 1.71-1.65 (m, 2H); |
| 1176 | 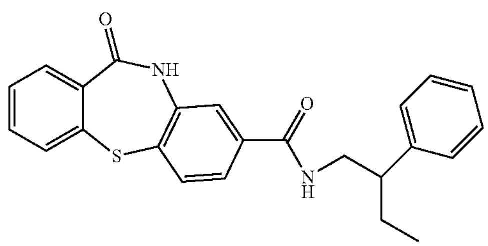 [SMILES: CCC(CNC(=O)c1ccc2c(c1)NC(=O)c1ccccc1S2)c1ccccc1] | D, 6 | 39 | 403.1 (M + 1)$^+$ | | $^1$H NMR (400 MHz, DMSO-d$_6$) δ 10.75 (s, 1H), 8.47 (t, J = 5.8 Hz, 1H), 7.64 (ddd, J = 24.5, 5.6, 1.9 Hz, 3H), 7.56-7.39 (m, 4H), 7.27 (t, J = 7.6 Hz, 2H), 7.18 (d, J = 7.3 Hz, 3H), 3.40 (ddt, J = 24.8, 13.3, 6.4 Hz, 2H), 2.76 (dt, J = 11.9, 5.8 Hz, 1H), 1.72 (ddd, J = 13.0, 7.1, 4.9 Hz, 1H), 1.52 (ddd, J = 16.5, 14.1, 7.7 Hz, 1H), 0.69 (t, J = 7.3 Hz, 3H). |
| 1177 | 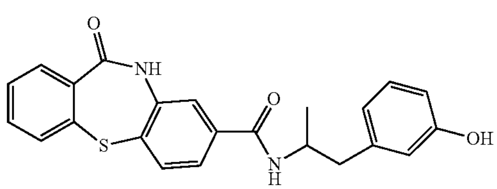 [SMILES: CC(Cc1cccc(O)c1)NC(=O)c1ccc2c(c1)NC(=O)c1ccccc1S2] | D, 6 | 92 | 405.0 | | $^1$H NMR (400 MHz, DMSO-d$_6$) δ 10.75 (s, 1H), 9.19 (s, 1H), 8.32 (d, J = 8.2 Hz, 1H), 7.65 (dd, J = 18.8, 7.5 Hz, 3H), 7.49 (dt, J = 23.9, 8.6 Hz, 4H), 7.02 (t, J = 7.9 Hz, 1H), 6.60 (d, J = 7.6 Hz, 2H), 4.17-4.07 (m, 1H), 2.76 (dd, J = 13.1, 7.3 Hz, 1H), 2.56 (dd, J = 12.9, 6.7 Hz, 1H), 1.08 (d, J = 6.5 Hz, 3H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1182 | 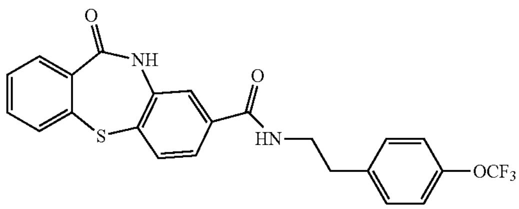 [SMILES: O=C(NCCc1ccc(OC(F)(F)F)cc1)c1ccc2c(c1)NC(=O)c1ccccc1S2] | A, 6 | 46 | 459.2 (M$^+$ + 1); | | (DMSO-d$_6$, 500 MHz): δ 10.76 (s, 1H), 8.59-8.58 (m, 1H), 7.66 (d, J = 7.0 Hz, 1H), 7.62 (d, J = 7.5 Hz, 2H), 7.51-7.42 (m, 4H), 7.32 (d, J = 8.0 Hz, 2H), 7.24 (d, J = 8.0 Hz, 2H), 3.43 (t, J = 6.5 Hz, 2H), 2.82 (t, J = 7.0 Hz, 2H); |
| 1183 | 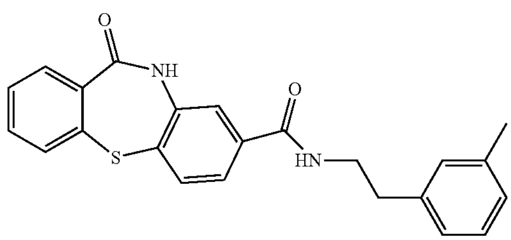 [SMILES: Cc1cccc(CCNC(=O)c2ccc3c(c2)NC(=O)c2ccccc2S3)c1] | A, 6 | 43 | 389.2 (M + 1)$^+$; | | (DMSO-d$_6$, 400 MHz): δ 10.76 (s, 1H), 9.04 (t, J = 6.0 Hz, 1H), 7.71-7.61 (m, 4H), 7.55-7.43 (m, 3H), 7.18 (t, J = 7.2 Hz, 1H), 7.08-7.03 (m, 3H), 4.40 (d, J = 6.0 Hz, 2H), 2.72 (t, J = 6.0 Hz, 2H), 2.26 (s, 3H); |
| 1184 | 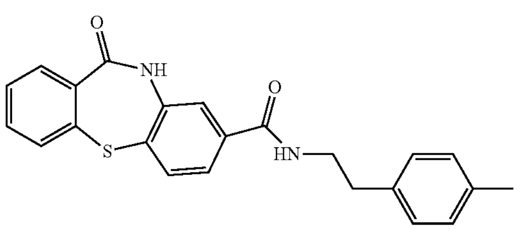 [SMILES: Cc1ccc(CCNC(=O)c2ccc3c(c2)NC(=O)c2ccccc2S3)cc1] | A, 6 | 43 | 389.2 (M + 1)$^+$; | | (DMSO-d$_6$, 400 MHz): δ 10.77 (s, 1H), 8.58-8.57 (m, 1H), 7.69-7.63 (m, 3H), 7.55-7.45 (m, 4H), 7.09-7.07 (m, 4H), 3.44-3.39 (m, 2H), 2.75 (t, J = 7.6 Hz, 2H), 2.24 (s, 3H); |
| 1185 | 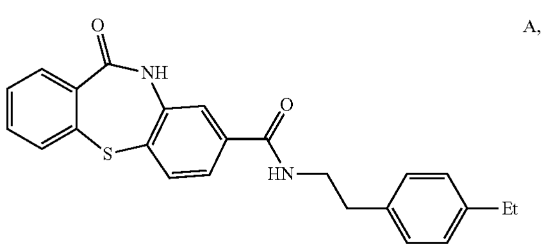 | A, 6 | 42 | 403.2 (M + 1)$^+$; | | (DMSO-d$_6$, 400 MHz): δ 10.76 (s, 1H), 8.58-8.57 (m, 1H), 7.67-7.61 (m, 3H), 7.53-7.41 (m, 4H), 7.10-7.08 (m, 4H), 3.42-3.37 (m, 2H), 2.74 (t, J = 7.2 Hz, 2H), 2.55-2.51 (m, 2H), 1.12 (t, J = 7.6 Hz, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1186 | 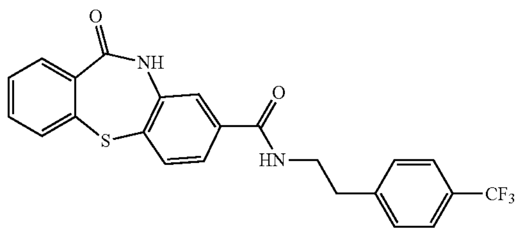 [SMILES: O=C(NCCc1ccc(C(F)(F)F)cc1)c1ccc2c(c1)NC(=O)c1ccccc1S2] | A, 6 | 28 | 443.2 $(M^+ + 1)$; | | (DMSO-$d_6$, 400 MHz): δ 10.78 (s, 1H), 8.59 (t, J = 5.6 Hz, 1H), 7.69-7.62 (m, 5H), 7.55-7.43 (m, 6H), 3.49 (q, 2H), 2.91 (t, J = 7.2 Hz, 2H); |
| 1187 | 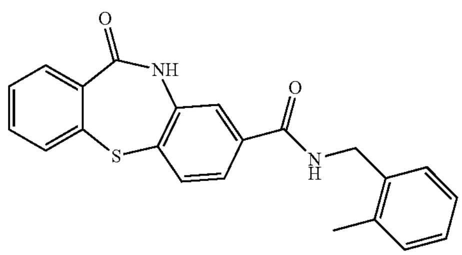 [SMILES: Cc1ccccc1CNC(=O)c1ccc2c(c1)NC(=O)c1ccccc1S2] | D, 6 | 36 | 375.2 $(M + 1)^+$; | | NMR (DMSO-$d_6$, 400 MHz): δ 10.75 (br s, 1H), 8.92 (br s, 1H), 7.72-7.65 (m, 4H), 7.53-7.45 (m, 3H), 7.19-7.14 (m, 4H), 4.42 (br s, 2H), 2.29 (s, 3H); |
| 1188 | 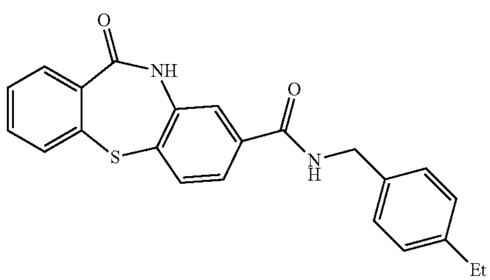 [SMILES: CCc1ccc(CNC(=O)c2ccc3c(c2)NC(=O)c2ccccc2S3)cc1] | A, 6 | 56 | 389.1 $(M + 1)^+$; | | (DMSO-$d_6$, 400 MHz): δ 10.76 (s, 1H), 9.02 (t, J = 6.0 Hz, 1H), 7.71-7.60 (m, 4H), 7.55-7.43 (m, 3H), 7.19 (d, J = 8.0 Hz, 2H), 7.13 (d, J = 8.0 Hz, 2H), 4.39 (d, J = 6.0 Hz, 2H), 2.58-2.54 (m, 2H), 1.14 (t, J = 7.6 Hz, 3H); |
| 1190 | 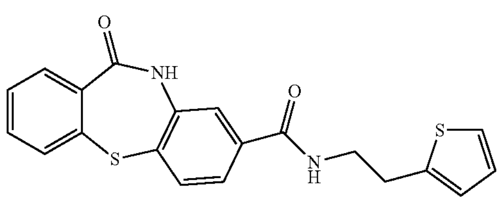 [SMILES: O=C(NCCc1cccs1)c1ccc2c(c1)NC(=O)c1ccccc1S2] | D, 6 | 52 | 381.1 $(M + 1)^+$; | | (CDCl$_3$, 400 MHz): δ 10.79 (s, 1H), 8.67-8.66 (m, 1H), 7.69-7.64 (m, 3H), 7.57-7.45 (m, 4H), 7.31 (d, J = 4.8 Hz, 1H), 6.94-6.89 (m, 2H), 3.48-3.46 (m, 2H), 3.04-3.01 (m, 2H); |
| 1191 | 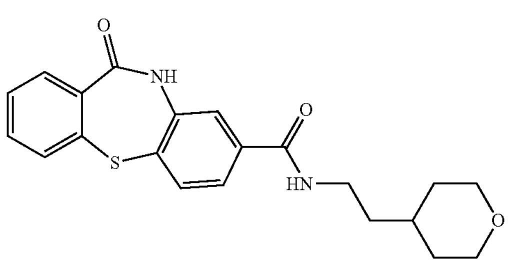 [SMILES: O=C(NCCC1CCOCC1)c1ccc2c(c1)NC(=O)c1ccccc1S2] | A, 6 | 46 | 383.2 $(M^+ + 1)$; | | (DMSO-$d_6$, 400 MHz): δ 10.77 (s, 1H), 8.48-8.47 (m, 1H), 7.69-7.63 (m, 3H), 7.57-7.43 (m, 4H), 3.82-3.78 (m, 2H), 3.26-3.20 (m, 4H), 1.57 (d, J = 9.6 Hz, 2H), 1.45-1.40 (m, 3H), 1.18-1.09 (m, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1193 | 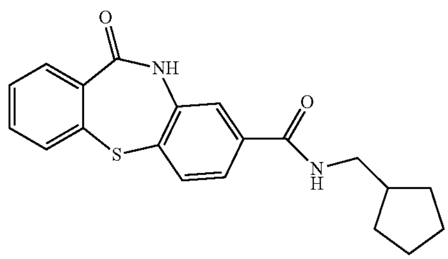 [SMILES: O=C(NCC1CCCC1)c1ccc2c(c1)NC(=O)c1ccccc1S2] | A, 6 | 52 | 353.1 (M$^+$ + 1); | | (CDCl$_3$, 400 MHz): δ 10.75 (s, 1H), 8.50-8.49 (m, 1H), 7.69-7.63 (m, 3H), 7.57-7.43 (m, 4H), 3.14 (t, J = 6.8 Hz, 2H), 2.13-2.06 (m, 1H), 1.66-1.60 (m, 2H), 1.56-1.45 (m, 4H), 1.25-1.17 (m, 2H); |
| 1194 | 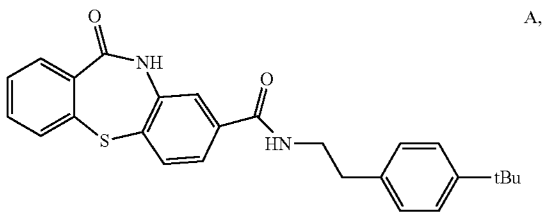 | A, 6 | 22 | 431.3 (M$^+$ + 1); | | (DMSO-d$_6$, 400 MHz): δ 10.78 (s, 1H), 8.61-8.60 (m, 1H), 7.69-7.63 (m, 3H), 7.56-7.53 (m, 2H), 7.51-7.45 (m, 2H), 7.29 (d, J = 8.0 Hz, 2H), 7.13 (d, J = 8.4 Hz, 2H), 3.45-3.41 (m, 2H), 2.78-2.74 (m, 2H), 1.24 (s, 9H); |
| 1195 | 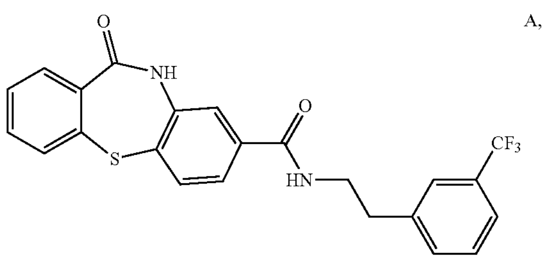 | A, 6 | 58 | 443.7 (M + 1)$^+$ | | (DMSO-d$_6$, 500 MHz): δ 10.77 (s, 1H), 8.59 (t, J = 6.0 Hz, 1H), 7.67 (d, J = 7.5 Hz, 1H), 7.62 (d, J = 8.0 Hz, 2H), 7.56-7.42 (m, 8H), 3.50-3.46 (m, 2H), 2.92-2.87 (m, 2H); |
| 1196 | 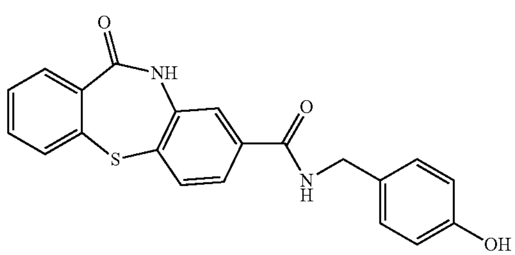 [SMILES: O=C(NCc1ccc(O)cc1)c1ccc2c(c1)NC(=O)c1ccccc1S2] | A, 6 | 43 | 377.0 (M + 1)$^+$; | | (DMSO-d$_6$, 500 MHz): δ 10.78 (s, 1H), 9.26 (br s, 1H), 8.96 (t, J = 6.0 Hz, 1H), 7.72-7.64 (m, 4H), 7.56-7.44 (m, 3H), 7.08 (d, J = 8.5 Hz, 2H), 6.66 (d, J = 8.5 Hz, 2H), 4.31-4.29 (m, 2H); |
| 1197 | 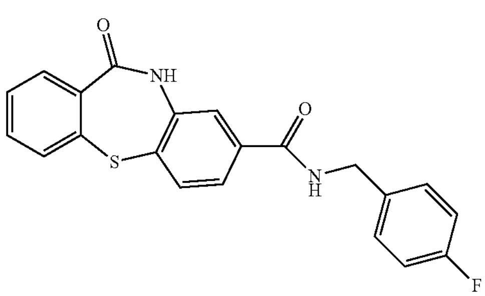 [SMILES: O=C(NCc1ccc(F)cc1)c1ccc2c(c1)NC(=O)c1ccccc1S2] | A, 6 | 36 | 379.2 (M + 1)$^+$; | | (DMSO-d$_6$, 400 MHz): δ 10.76 (s, 1H), 9.08 (t, J = 5.6 Hz, 1H), 7.71-7.61 (m, 4H), 7.55-7.43 (m, 3H), 7.32 (t, J = 6.0 Hz, 2H), 7.15-7.10 (m, 2H), 4.41 (d, J = 6.0 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1199 | 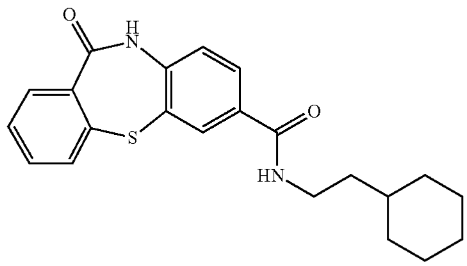 [SMILES: O=C(NCCC1CCCCC1)c1ccc2c(c1)Sc1ccccc1C(=O)N2] | A, 6 | 54 | 380.9 (M$^+$ + 1) | | (DMSO-d$_6$, 500 MHz): δ 10.85 (s, 1H), 8.43 (t, J = 5.5 Hz, 1H), 8.02 (s, 1H), 7.78 (d, J = 8.5 Hz, 1H), 7.67 (d, J = 7.5 Hz, 1H), 7.55-7.43 (m, 3H), 7.25 (d, J = 8.0 Hz, 1H), 3.25-3.21 (m, 2H), 1.69-1.57 (m, 5H), 1.40-1.36 (m, 2H), 1.18-1.09 (m, 4H), 0.90-0.83 (m, 2H); |
| 1201 | 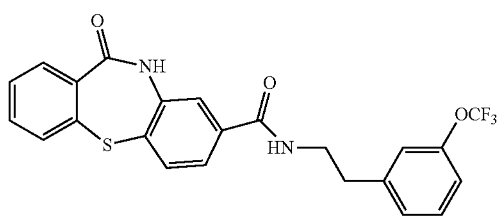 [SMILES: O=C(NCCc1cccc(OC(F)(F)F)c1)c1ccc2c(c1)NC(=O)c1ccccc1S2] | A, 6 | 60 | 459.2 (M$^+$ + 1); | | (DMSO-d$_6$, 400 MHz): δ 10.76 (s, 1H), 8.59-8.58 (m, 1H), 7.69-7.64 (m, 3H), 7.53-7.38 (m, 5H), 7.26-7.16 (m, 3H), 3.48-3.47 (m, 2H), 2.89-2.87 (m, 2H); |
| 1202 | 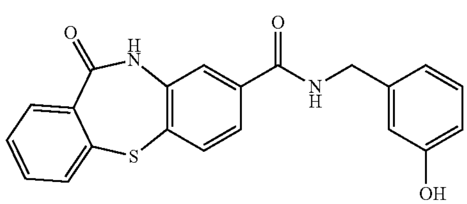 [SMILES: O=C(NCc1cccc(O)c1)c1ccc2c(c1)NC(=O)c1ccccc1S2] | A, 6 | 36 | 377.1 (M$^+$ + 1); | | (DMSO-d$_6$, 500 MHz): δ 10.79 (s, 1H), 9.29 (s, 1H), 9.03 (t, J = 5.5 Hz, 1H), 7.72-7.62 (m, 4H), 7.55-7.45 (m, 3H), 7.08 (t, J = 8.0 Hz, 1H), 6.68 (d, J = 12.0 Hz, 2H), 6.60 (d, J = 8.5 Hz, 1H), 4.35 (d, J = 6.0 Hz, 2H); |
| 1203 | 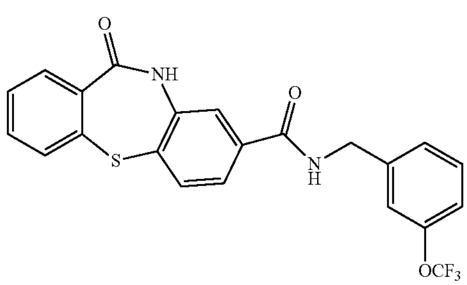 [SMILES: O=C(NCc1cccc(OC(F)(F)F)c1)c1ccc2c(c1)NC(=O)c1ccccc1S2] | A, 6 | 45 | 445.1 (M + 1)$^+$; | | (DMSO-d$_6$, 400 MHz): δ 10.77 (s, 1H), 9.15 (t, J = 4.8 Hz, 1H), 7.71-7.61 (m, 4H), 7.55-7.43 (m, 4H), 7.31 (d, J = 8.0 Hz, 1H), 7.23 (d, J = 8.4 Hz, 2H), 4.48 (d, J = 6.0 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1204 | 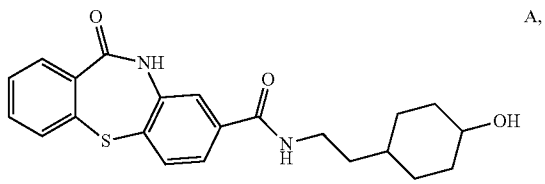 | A, 6 | 34 | 397.2 (M⁺ + 1); | | (DMSO-d₆, 400 MHz): δ 10.74 (s, 1H), 8.46 (t, J = 6.0 Hz, 1H), 7.74-7.64 (m, 3H), 7.54-7.42 (m, 4H), 4.40 (d, J = 5.2 Hz, 1H), 3.26-3.20 (m, 2H), 1.77 (d, J = 11.2 Hz, 2H), 1.68 (d, J = 11.2 Hz, 2H), 1.39-1.34 (m, 3H), 1.18-1.12 (m, 2H), 0.93-0.84 (m, 2H); |
| 1205 | 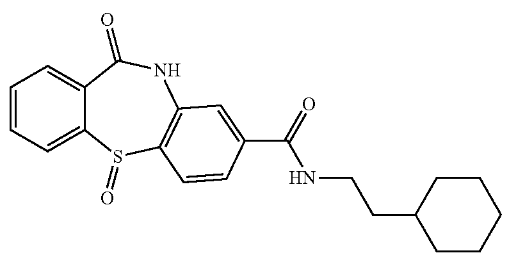 [SMILES: O=C(NCCC1CCCCC1)c1ccc2c(c1)NC(=O)c1ccccc1S2=O] | A, 156 | 50 | 459.2 (M⁺ + 1); | | (DMSO-d₆, 400 MHz): δ 11.05-11.04 (m, 1H), 8.54-8.53 (m, 1H), 7.81-7.73 (m, 3H), 7.68-7.60 (m, 4H), 3.26-3.25 (m, 3H), 1.70-1.62 (m, 6H), 1.39-1.37 (m, 2H), 1.23-1.14 (m, 2H), 0.88-0.85 (m, 2H); |
| 1209 | 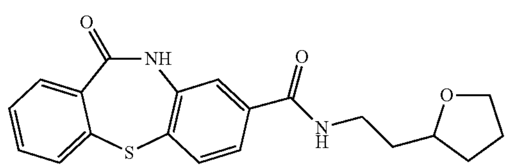 [SMILES: O=C(NCCC1CCCO1)c1ccc2c(c1)NC(=O)c1ccccc1S2] | A, 6 | 56 | 369.1 (M⁺ + 1); | | (DMSO-d₆, 400 MHz): δ 10.75 (s, 1H), 8.49 (t, J = 5.6 Hz, 1H), 7.69-7.63 (m, 3H), 7.56-7.45 (m, 4H), 3.77-3.70 (m, 2H), 3.59-3.54 (m, 1H), 3.26-3.24 (m, 2H), 1.98-1.90 (m, 1H), 1.83-1.76 (m, 2H), 1.69-1.63 (m, 2H), 1.43-1.34 (m, 1H); |
| 1210 | 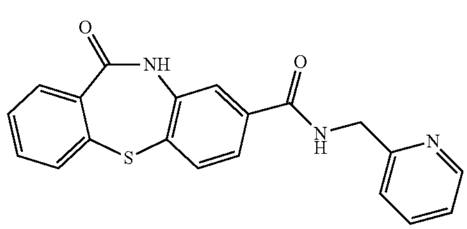 [SMILES: O=C(NCc1ccccn1)c1ccc2c(c1)NC(=O)c1ccccc1S2] | A, 6 | 56 | 362.4 (M⁺ + 1); | | (DMSO-d₆, 500 MHz): δ 10.78 (s, 1H), 9.14 (t, J = 6.0 Hz, 1H), 8.49 (s, 1H), 7.74-7.65 (m, 5H), 7.55-7.44 (m, 3H), 7.28-7.23 (m, 2H), 4.53 (d, J = 5.5 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1211 | 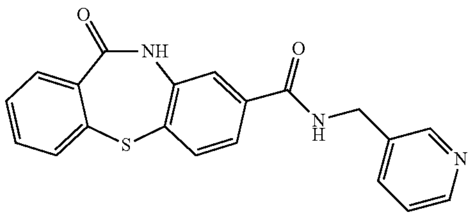 [SMILES: O=C(NCc1cccnc1)c1ccc2c(c1)NC(=O)c1ccccc1S2] | A, 6 | 66 | 362.1 (M$^+$ + 1); | | (DMSO-d$_6$, 500 MHz): δ 10.76 (s, 1H), 9.12 (t, J = 6.0 Hz, 1H), 8.52 (s, 1H), 8.45-8.44 (m, 1H), 7.70 (d, J = 10.0 Hz, 1H), 7.67-7.60 (m, 4H), 7.55-7.44 (m, 3H), 7.33 (t, J = 6.5 Hz, 1H), 4.46 (d, J = 5.5 Hz, 2H); |
| 1212 | 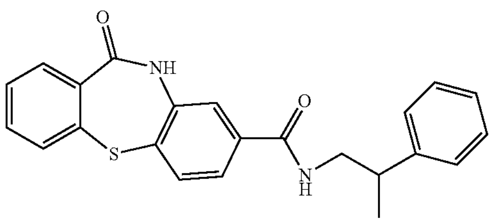 [SMILES: CC(CNC(=O)c1ccc2c(c1)NC(=O)c1ccccc1S2)c1ccccc1] | D, 6 | 44 | 389.1 (M + 1)$^+$ | | $^1$H NMR (400 MHz, DMSO-d$_6$) δ 10.76 (s, 1H), 8.54 (t, J = 5.8 Hz, 1H), 7.71-7.58 (m, 3H), 7.48 (tt, J = 15.3, 7.6 Hz, 4H), 7.23 (ddd, J = 25.3, 16.4, 7.3 Hz, 5H), 3.45-3.26 (m, 2H), 3.01 (q, J = 7.1 Hz, 1H), 1.19 (d, J = 6.9 Hz, 3H). |
| 1213 | 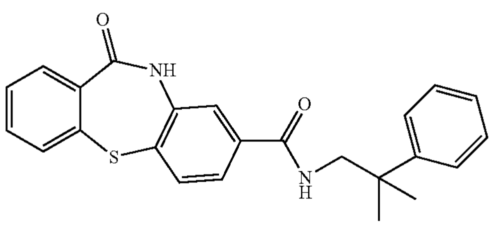 [SMILES: CC(C)(CNC(=O)c1ccc2c(c1)NC(=O)c1ccccc1S2)c1ccccc1] | D, 6 | 54 | 403.1 (M + 1)$^+$ | | $^1$H NMR (400 MHz, DMSO-d$_6$) δ 10.74 (s, 1H), 8.28 (t, J = 6.4 Hz, 1H), 7.71-7.58 (m, 3H), 7.57-7.35 (m, 6H), 7.29 (t, J = 7.6 Hz, 2H), 7.17 (t, J = 7.3 Hz, 1H), 3.41 (d, J = 6.3 Hz, 2H), 1.26 (s, 6H). |
| 1214 | 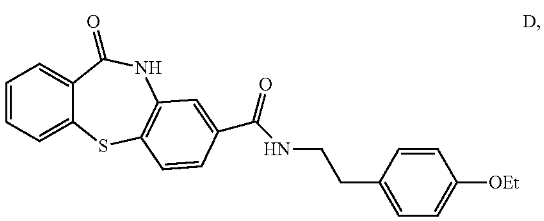 | D, 6 | 60 | 419.5 (M$^+$ + 1); | | NMR (DMSO-d$_6$, 400 MHz): δ 10.77 (s, 1H), 8.56 (t, J = 4.8 Hz, 1H), 7.69-7.63 (m, 3H), 7.55-7.43 (m, 4H), 7.10 (d, J = 8.8 Hz, 2H), 6.81 (d, J = 8.4 Hz, 2H), 3.96 (q, 2H), 3.42-3.37 (m, 2H), 2.72 (t, J = 7.2 Hz, 2H), 1.30-1.23 (m, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1216 | 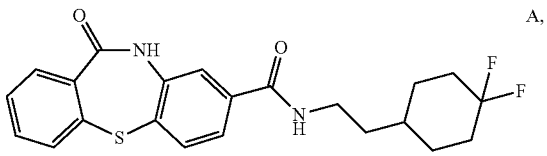 | A, 6 | 30 | 417.3 ($M^+ + 1$); | | (DMSO-$d_6$, 400 MHz): δ 10.76 (s, 1H), 8.47 (t, J = 5.6 Hz, 1H), 7.69-7.63 (m, 3H), 7.57-7.45 (m, 4H), 3.30-3.25 (m, 2H), 2.00-1.93 (m, 2H), 1.78-1.76 (m, 4H), 1.45-1.43 (m, 3H), 1.18-1.10 (m, 2H); |
| 1218 | 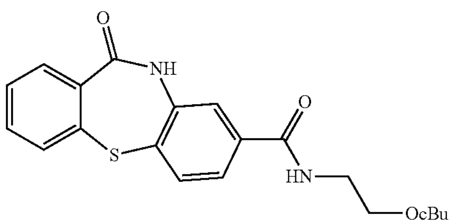 | A, 6 | 75 | 371.2 ($M^+ + 1$); | | (DMSO-$d_6$, 400 MHz): δ 10.77 (s, 1H), 8.50 (t, J = 5.6 Hz, 1H), 7.69-7.63 (m, 3H), 7.58-7.43 (m, 4H), 3.40-3.37 (m, 2H), 3.28 (s, 2H), 1.10 (s, 9H); |
| 1220 | 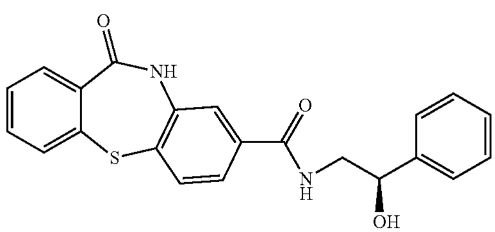 [SMILES: O=C(NC[C@H](O)c1ccccc1)c1ccc2c(c1)NC(=O)c1ccccc1S2] | A, 6 | 74 | 391.4 ($M^+ + 1$); | | (DMSO-$d_6$, 400 MHz): δ 10.77 (s, 1H), 8.53 (t, J = 6.8 Hz, 1H), 7.69-7.63 (m, 3H), 7.57-7.43 (m, 4H), 7.35-7.29 (m, 4H), 7.23 (t, J = 6.8 Hz, 1H), 5.46 (d, J = 4.8 Hz, 1H), 4.76-4.71 (m, 1H), 3.47-3.41 (m, 1H); |
| 1221 | 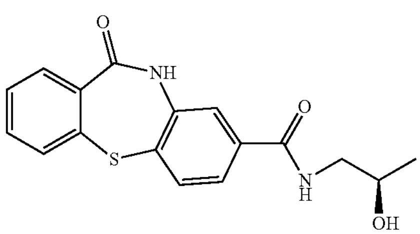 [SMILES: C[C@@H](O)CNC(=O)c1ccc2c(c1)NC(=O)c1ccccc1S2] | A, 6 | 62 | 329.1 ($M^+ + 1$); | | (DMSO-$d_6$, 400 MHz): δ 10.74 (s, 1H), 8.40 (t, J = 5.6 Hz, 1H), 7.69-7.43 (m, 7H), 4.68 (d, J = 4.8 Hz, 1H), 3.77-3.71 (m, 1H), 3.16 (t, J = 6.0 Hz, 2H), 1.03 (d, J = 6.4 Hz, 3H); |
| 1222 | 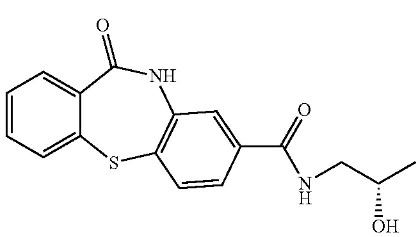 [SMILES: C[C@H](O)CNC(=O)c1ccc2c(c1)NC(=O)c1ccccc1S2] | A, 6 | 41 | 329.2 ($M^+ + 1$); | | (DMSO-$d_6$, 400 MHz): δ 10.74 (s, 1H), 8.40 (t, J = 5.6 Hz, 1H), 7.69-7.58 (m, 4H), 7.55-7.45 (m, 3H), 4.68 (d, J = 4.8 Hz, 1H), 3.77-3.71 (m, 1H), 3.16 (t, J = 6.0 Hz, 2H), 1.03 (d, J = 6.4 Hz, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1226 | 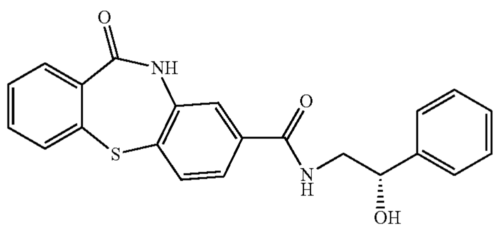 [SMILES: O=C(NC[C@@H](O)c1ccccc1)c1ccc2c(c1)NC(=O)c1ccccc1S2] | A, 6 | 75 | 391.6 (M$^+$ + 1); | | (DMSO-d$_6$, 400 MHz): δ 10.78 (s, 1H), 8.54 (t, J = 6.4 Hz, 1H), 7.69-7.63 (m, 3H), 7.57-7.43 (m, 4H), 7.35-7.29 (m, 4H), 7.23 (t, J = 7.2 Hz, 1H), 5.46 (d, J = 4.8 Hz, 1H), 4.75-4.71 (m, 1H), 3.47-3.41 (m, 1H); |
| 1227 | 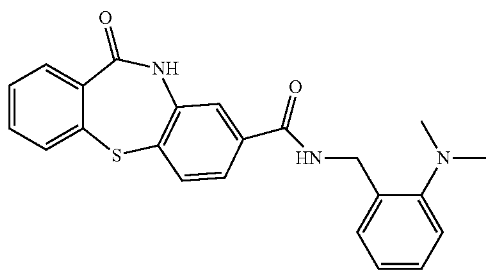 [SMILES: CN(C)c1ccccc1CNC(=O)c1ccc2c(c1)NC(=O)c1ccccc1S2] | A, 6 | 83 | 404.4 (M$^+$ + 1); | | (DMSO-d$_6$, 400 MHz): δ 10.77 (s, 1H), 8.97 (t, J = 6.0 Hz, 1H), 7.73 (s, 1H), 7.70-7.63 (m, 3H), 7.56-7.43 (m, 3H), 7.21-7.16 (m, 2H), 7.11 (d, J = 7.6 Hz, 1H), 6.97 (t, J = 7.2 Hz, 1H), 4.53 (d, J = 5.6 Hz, 2H), 2.64 (s, 6H); |
| 1228 | 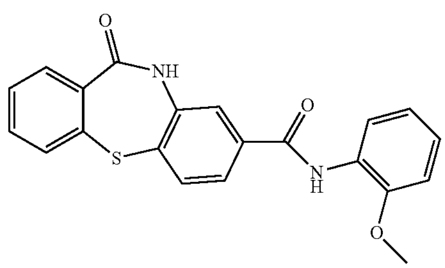 [SMILES: COc1ccccc1NC(=O)c1ccc2c(c1)NC(=O)c1ccccc1S2] | A, 6 | 27 | 376.4 (M$^+$ + 1); | | (DMSO-d$_6$, 400 MHz): δ 10.80 (s, 1H), 9.49 (s, 1H), 7.75 (s, 1H), 7.73-7.70 (m, 3H), 7.55-7.46 (m, 3H), 7.16 (t, J = 7.6 Hz, 1H), 7.08 (d, J = 7.2 Hz, 1H), 6.95 (t, J = 7.6 Hz, 1H), 3.81 (s, 3H); |
| 1232 | 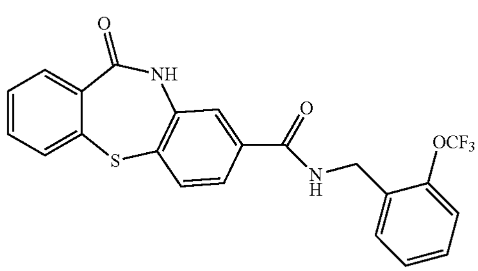 [SMILES: O=C(NCc1ccccc1OC(F)(F)F)c1ccc2c(c1)NC(=O)c1ccccc1S2] | D, 6 | 50 | 445.1 (M + 1)$^+$ | | $^1$H NMR (400 MHz, DMSO-d$_6$) δ 10.79 (s, 1H), 9.08 (t, J = 5.9 Hz, 1H), 7.74-7.59 (m, 4H), 7.58-7.25 (m, 7H), 4.50 (d, J = 5.7 Hz, 2H). |
| 1233 | 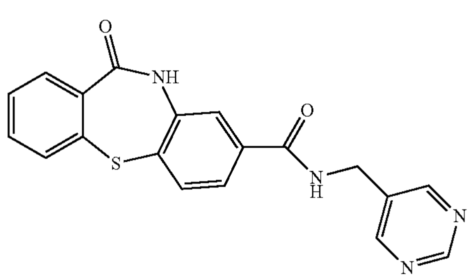 [SMILES: O=C(NCc1cncnc1)c1ccc2c(c1)NC(=O)c1ccccc1S2] | D, 6 | 83 | 363.1 (M + 1)$^+$ | | $^1$H NMR (400 MHz, DMSO-d$_6$) δ 10.77 (s, 1H), 9.15 (t, J = 5.9 Hz, 1H), 9.07 (s, 1H), 8.73 (s, 2H), 7.72-7.40 (m, 7H), 4.46 (d, J = 5.7 Hz, 2H). |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1234 | 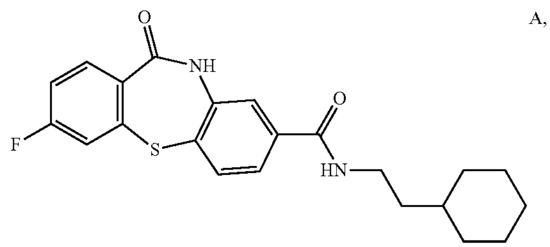 | A, 6 | 57 | 399.5 ($M^+$ + 1); | | (DMSO-$d_6$, 400 MHz): δ 10.79 (br s, 1H), 8.45 (t, J = 5.6 Hz, 1H), 7.67-7.73 (m, 1H), 7.66-7.63 (m, 2H), 7.58-7.56 (m, 1H), 7.46-7.43 (m, 1H), 7.35-7.30 (m, 1H), 3.27-3.22 (m, 2H), 1.70-1.58 (m, 5H), 1.41-1.35 (m, 2H), 1.27-1.09 (m, 4H), 0.95-0.83 (m, 2H); |
| 1237 | 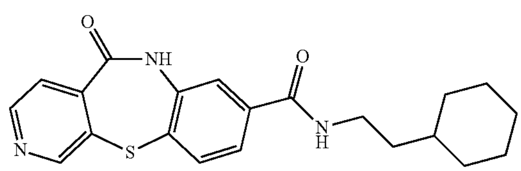 [SMILES: O=C(NCCC1CCCCC1)c1ccc2c(c1)NC(=O)c1ccncc1S2] | A, 6 | 71 | 382.3 ($M^+$ + 1); | | (DMSO-$d_6$, 400 MHz): δ 11.04 (br s, 1H), 8.72 (s, 1H), 8.65 (d, J = 4.8 Hz, 1H), 8.46 (t, J = 5.6 Hz, 1H), 7.69-7.67 (m, 2H), 7.63-7.58 (m, 2H), 3.27-3.22 (m, 2H), 1.70-1.58 (m, 4H), 1.41-1.35 (m, 2H), 1.27-1.14 (m, 4H), 0.93-0.83 (m, 3H); LC-MS: 93.50%; 382.3 ($M^+$ + 1); |
| 1240 | 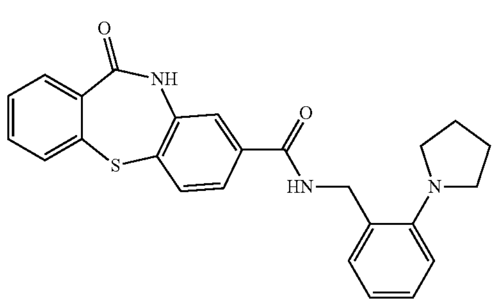 [SMILES: O=C(NCc1ccccc1N1CCCC1)c1ccc2c(c1)NC(=O)c1ccccc1S2] | A, 6 | 25 | 430.4 ($M^+$ + 1); | | (DMSO-$d_6$, 400 MHz): δ 10.77 (s, 1H), 8.92 (t, J = 5.2 Hz, 1H), 7.73 (s, 1H), 7.70-7.62 (m, 3H), 7.56-7.43 (m, 3H), 7.12 (t, J = 7.6 Hz, 2H), 6.96 (d, J = 8.0 Hz, 1H), 6.84 (t, J = 6.8 Hz, 1H), 4.46 (d, J = 5.6 Hz, 2H), 3.10 (t, J = 6.0 Hz, 4H), 1.87 (t, J = 6.0 Hz, 4H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1241 | 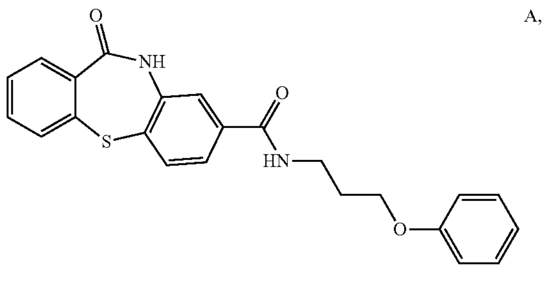 | A, 6 | 33 | 405.4 (M$^+$ + 1); | | (DMSO-d$_6$, 500 MHz): δ 10.75 (s, 1H), 8.58 (t, J = 6.0 Hz, 1H), 7.67-7.45 (m, 7H), 7.26 (t, J = 7.5 Hz, 2H), 6.91-6.89 (m, 3H), 3.99 (t, J = 6.0 Hz, 2H), 3.41-3.30 (m, 2H), 1.94 (t, J = 6.5 Hz, 2H); |
| 1245 | 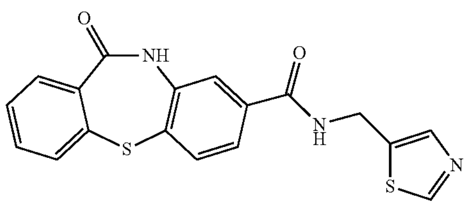 [SMILES: O=C(NCc1cncs1)c1ccc2c(c1)NC(=O)c1ccccc1S2] | D, 6 | 54 | 368.1 (M + 1)$^+$ | | $^1$H NMR (400 MHz, DMSO-d$_6$) δ 10.77 (s, 1H), 9.23 (t, J = 5.9 Hz, 1H), 8.95 (s, 1H), 7.79 (s, 1H), 7.71-7.40 (m, 7H), 4.64 (d, J = 5.8 Hz, 2H). |
| 1246 | 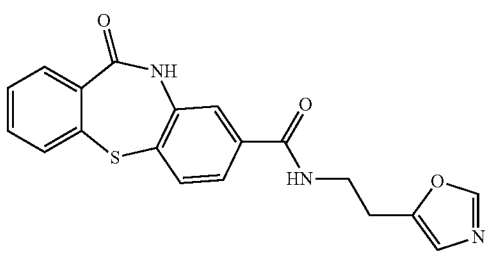 [SMILES: O=C(NCCc1cnco1)c1ccc2c(c1)NC(=O)c1ccccc1S2] | A, 6 | 75 | 366.2 (M$^+$ + 1); | | (DMSO-d$_6$, 400 MHz): δ 10.78 (s, 1H), 8.65 (t, J = 6.0 Hz, 1H), 8.21 (s, 1H), 7.69-7.64 (m, 3H), 7.54-7.43 (m, 4H), 6.91 (s, 1H), 3.48 (q, 2H), 2.90 (t, J = 6.8 Hz, 2H); |
| 1247 | 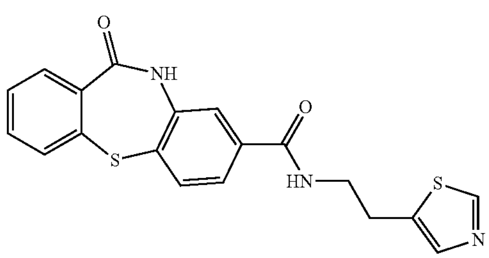 | A, 6 | 40 | 382.2 (M$^+$ + 1); | | (DMSO-d$_6$, 400 MHz): δ 10.79 (s, 1H), 8.90 (s, 1H), 8.69-8.68 (m, 1H), 7.68-7.65 (m, 4H), 7.56-7.45 (m, 4H), 3.47 (q, 2H), 3.09 (t, J = 6.8 Hz, 2H); |
| 1248 | 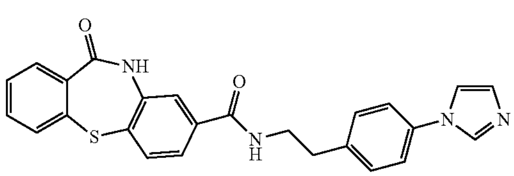 [SMILES: O=C(NCCc1ccc(-n2ccnc2)cc1)c1ccc2c(c1)NC(=O)c1ccccc1S2] | A, 6 | 28 | 441.4 (M$^+$ + 1); | | (DMSO-d$_6$, 400 MHz): δ 10.77 (s, 1H), 8.60 (t, J = 6.4 Hz, 1H), 8.19 (s, 1H), 7.69-7.65 (m, 4H), 7.55-7.43 (m, 6H), 7.34 (d, J = 7.6 Hz, 2H), 7.08 (s, 1H), 3.51-3.46 (m, 2H), 2.86 (t, J = 7.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1249 | 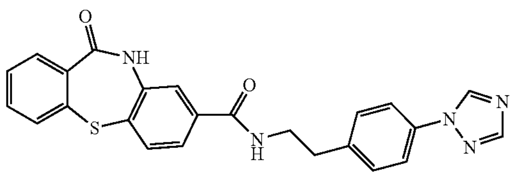 [SMILES: O=C(NCCc1ccc(-n2cncn2)cc1)c1ccc2c(c1)NC(=O)c1ccccc1S2] | A, 6 | 50 | 442.4 (M$^+$ + 1); | | (DMSO-d$_6$, 400 MHz): δ 10.78 (s, 1H), 9.22 (s, 1H), 8.62-8.61 (m, 1H), 8.20 (s, 1H), 7.75 (d, J = 8.4 Hz, 2H), 7.69-7.63 (m, 3H), 7.55-7.38 (m, 6H), 3.52-3.47 (m, 2H), 2.87 (t, J = 6.0 Hz, 2H); |
| 1251 | 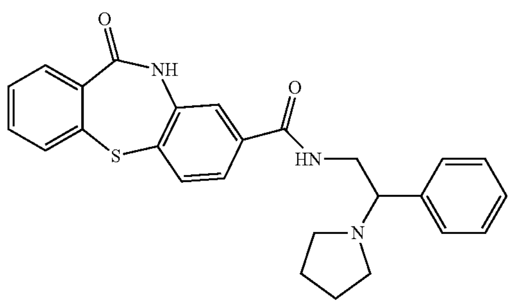 [SMILES: O=C(NCC(c1ccccc1)N1CCCC1)c1ccc2c(c1)NC(=O)c1ccccc1S2] | A, 6 | 33 | 444.4 (M$^+$ + 1); | | (CDCl$_3$ + CD$_3$OD, 400 MHz): δ 7.71 (d, J = 8.0 Hz, 1H), 7.56 (d, J = 8.0 Hz, 1H), 7.51-7.40 (m, 4H), 7.34-7.28 (m, 6H), 4.01 (dd, J = 13.2, 4.8 Hz, 1H), 3.70-3.66 (m, 1H), 3.60-3.55 (m, 1H), 2.85-2.78 (m, 2H), 2.63-2.50 (m, 2H), 1.83 (t, J = 6.4 Hz, 4H); |
| 1253 | 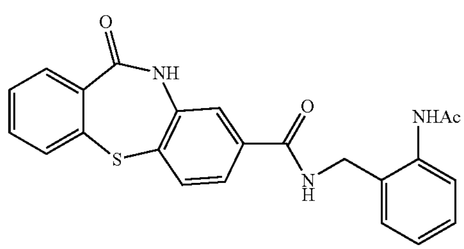 [SMILES: CC(=O)Nc1ccccc1CNC(=O)c1ccc2c(c1)NC(=O)c1ccccc1S2] | A, 6 | 34 | 418.3 (M$^+$ + 1); | | (DMSO-d$_6$, 400 MHz): δ 10.76 (s, 1H), 9.69 (s, 1H), 9.09 (t, J = 6.0 Hz, 1H), 7.72 (s, 1H), 7.68-7.66 (m, 2H), 7.62 (d, J = 8.0 Hz, 1H), 7.55-7.51 (m, 2H), 7.50-7.43 (m, 2H), 7.25-7.20 (m, 2H), 7.10 (t, J = 7.2 Hz, 1H), 4.41 (d, J = 5.6 Hz, 2H), 2.08 (s, 3H); |
| 1256 | 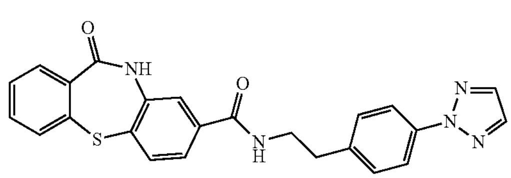 [SMILES: O=C(NCCc1ccc(-n2nccn2)cc1)c1ccc2c(c1)NC(=O)c1ccccc1S2] | A, 6 | 46 | 442.3 (M$^+$ + 1); | | (DMSO-d$_6$, 400 MHz): δ 10.78 (br s, 1H), 8.62 (br s, 1H), 8.08 (br s, 2H), 7.92 (d, J = 7.2 Hz, 2H), 7.69-7.65 (m, 3H), 7.54-7.40 (m, 6H), 3.50-3.49 (m, 2H), 2.88-2.87 (m, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1257 | 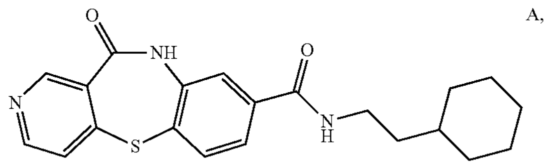 | A, 6 | 22 | 381.9 (M$^+$ + 1); | | (DMSO-d$_6$, 400 MHz): δ 10.96 (s, 1H), 8.77 (s, 1H), 8.61 (d, J = 5.2 Hz, 1H), 8.47 (t, J = 5.2 Hz, 1H), 7.70 (s, 1H), 7.66 (d, J = 8.0 Hz, 1H), 7.60-7.56 (m, 2H), 3.27-3.24 (m, 2H), 1.71-1.58 (m, 5H), 1.41-1.36 (m, 2H), 1.29-1.09 (m, 4H), 0.91-0.83 (m, 2H); |
| 1258 | 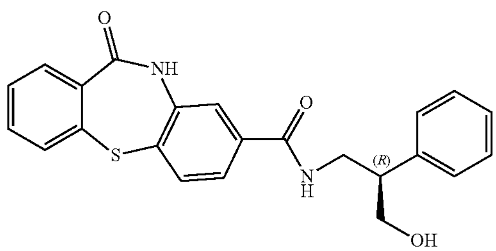 | A, 6 | 42 | 404.9 (M$^+$ + 1); | | (DMSO-d$_6$, 400 MHz): δ 10.75 (s, 1H), 8.45 (t, J = 5.6 Hz, 1H), 7.68 (d, J = 7.2 Hz, 1H), 7.61 (d, J = 8.0 Hz, 2H), 7.54-7.42 (m, 4H), 7.28-7.15 (m, 5H), 4.67 (t, J = 5.2 Hz, 1H), 3.61-3.57 (m, 2H), 3.55-3.48 (m, 2H), 3.10-2.98 (m, 1H); |
| 1259 | 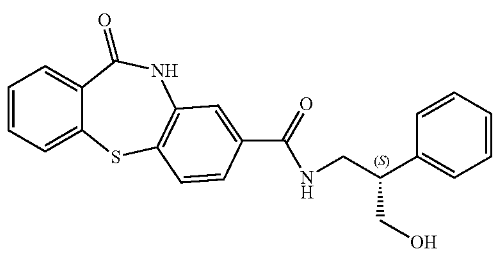 | A, 6 | 34 | 404.9 (M$^+$ + 1); | | (DMSO-d$_6$, 400 MHz): δ 10.74 (s, 1H), 8.43 (t, J = 5.6 Hz, 1H), 7.67 (d, J = 6.0 Hz, 1H), 7.61 (d, J = 8.0 Hz, 2H), 7.54-7.42 (m, 4H), 7.28-7.15 (m, 5H), 4.65 (t, J = 5.2 Hz, 1H), 3.62-3.57 (m, 2H), 3.55-3.45 (m, 2H), 3.06-2.99 (m, 1H); |
| 1260 | 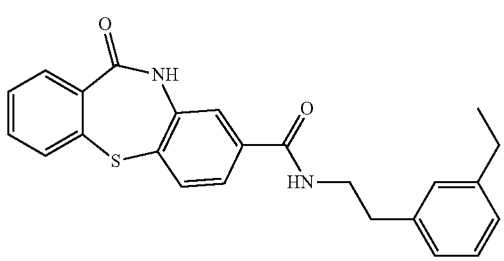 [SMILES: CCc1cccc(CCNC(=O)c2ccc3c(c2)NC(=O)c2ccccc2S3)c1] | A, 6 | 59 | 403.5 (M$^+$ + 1); | | (CD$_3$OD + CDCl$_3$, 400 MHz): δ 7.73 (d, J = 7.6 Hz, 1H), 7.62 (d, J = 8.0 Hz, 2H), 7.59-7.41 (m, 4H), 7.17 (t, J = 7.2 Hz, 1H), 7.03 (t, J = 7.6 Hz, 2H), 3.55 (t, J = 7.6 Hz, 2H), 2.86 (t, J = 7.6 Hz, 2H), 2.58 (q, 2H), 1.16 (t, J = 7.6 Hz, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1264 | 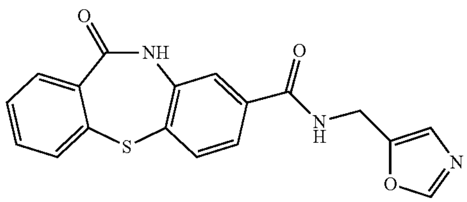 | D, 6 | 73 | 352.1 (M + 1)⁺ | | ¹H NMR (400 MHz, DMSO-d₆) δ 10.74 (s, 1H), 9.04 (t, J = 5.6 Hz, 1H), 8.24 (s, 1H), 7.68-7.59 (m, 3H), 7.56 (dd, J = 8.2, 1.9 Hz, 1H), 7.53-7.38 (m, 3H), 7.00 (s, 1H), 4.47 (d, J = 5.5 Hz, 2H). |
| 1266 | 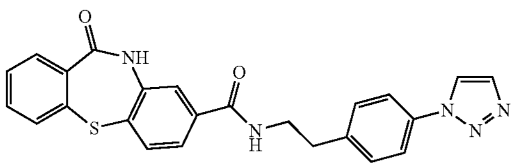 | A, 6 | 41 | 442.5 (M⁺ + 1); | | (DMSO-d₆, 400 MHz): δ 10.78 (s, 1H), 8.76 (s, 1H), 8.62 (t, J = 5.6 Hz, 1H), 7.94 (s, 1H), 7.80 (d, J = 8.0 Hz, 2H), 7.69-7.63 (m, 3H), 7.55-7.42 (m, 6H), 3.51 (q, 2H), 2.90 (t, J = 6.8 Hz, 2H); |
| 1267 | 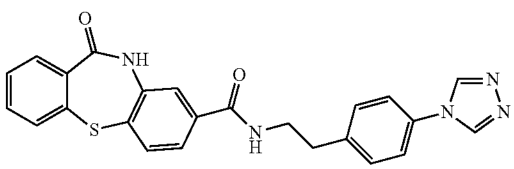 | A, 6 | 43 | 442.5 (M⁺ + 1); | | (DMSO-d₆, 400 MHz): δ 10.80 (s, 1H), 9.10 (s, 2H), 8.63-8.61 (m, 1H), 7.74-7.57 (m, 6H), 7.56-7.36 (m, 5H), 3.52-3.46 (m, 2H), 2.91-2.89 (m, 2H); |
| 1270 | 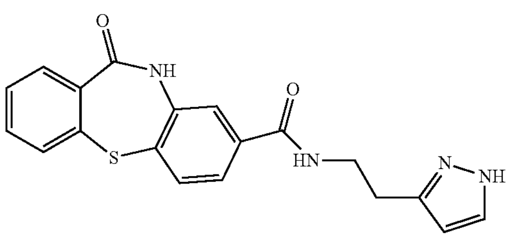 [SMILES: O=C(NCCc1cc[nH]n1)c1ccc2c(c1)NC(=O)c1ccccc1S2] | A, 6 | 41 | 365.3 (M⁺ + 1); | | (DMSO-d₆, 400 MHz): δ 12.50-12.36 (m, 1H), 10.77 (s, 1H), 8.60 (br s, 1H), 7.69-7.63 (m, 3H), 7.57-7.34 (m, 5H), 6.06 (br s, 1H), 3.49-3.44 (m, 2H), 2.82-2.78 (m, 2H); |
| 1271 | 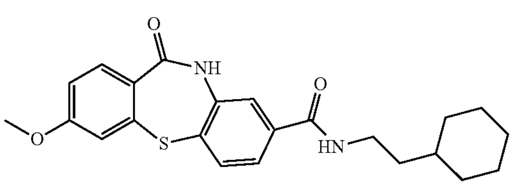 [SMILES: COc1ccc2c(c1)Sc1ccc(C(=O)NCCC3CCCCC3)cc1NC2=O] | A, P-42 | 28 | 411.8 (M⁺ + 1); | | (DMSO-d₆, 400 MHz): δ 10.59 (s, 1H), 8.43 (t, J = 5.6 Hz, 1H), 7.65-7.59 (m, 3H), 7.55 (d, J = 8.4 Hz, 1H), 7.06 (s, 1H), 7.01 (d, J = 8.8 Hz, 1H), 3.80 (s, 3H), 3.26-3.23 (m, 2H), 1.71-1.58 (m, 5H), 1.41-1.36 (m, 2H), 1.29-1.23 (m, 1H), 1.19-1.09 (m, 3H), 0.91-0.83 |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | (m, 2H); |
| 1273 | 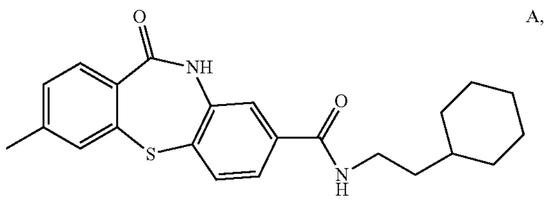 | A, P-8 | 29 | 395.9 (M$^+$ + 1); | | (DMSO-d$_6$, 400 MHz): δ 10.66 (br s, 1H), 8.43 (t, J = 5.6 Hz, 1H), 7.64-7.53 (m, 4H), 7.36 (s, 1H), 7.26 (d, J = 7.6 Hz, 1H), 3.26-3.21 (m, 2H), 2.30 (s, 3H), 1.70-1.58 (m, 5H), 1.41-1.35 (m, 2H), 1.28-1.14 (m, 4H), 0.91-0.83 (m, 2H); |
| 1274 | 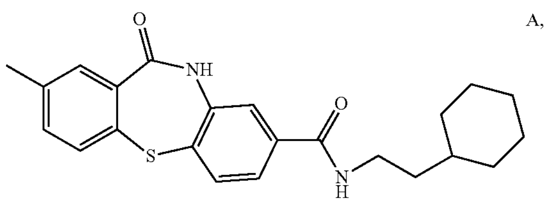 | A, P-51 | 55 | 395.5 (M$^+$ + 1); | | (DMSO-d$_6$, 400 MHz): δ 10.70 (br s, 1H), 8.42 (t, J = 5.2 Hz, 1H), 7.62 (t, J = 5.6 Hz, 2H), 7.54 (d, J = 7.2 Hz, 1H), 7.49 (s, 1H), 7.40 (d, J = 7.6 Hz, 1H), 7.29 (d, J = 7.6 Hz, 1H), 3.26-3.21 (m, 2H), 2.29 (s, 3H), 1.70-1.62 (m, 5H), 1.40-1.35 (m, 2H), 1.26-1.09 (m, 4H), 0.95-0.83 (m, 2H); |
| 1279 | 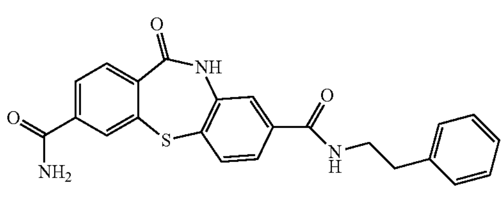 [SMILES: NC(=O)c1ccc2c(c1)Sc1ccc(C(=O)NCCc3ccccc3)cc1NC2=O] | A, 135 | 50 | 418.8 (M$^+$ + 1) | | (DMSO-d$_6$, 500 MHz): δ 10.89 (s, 1H), 8.62-8.61 (m, 1H), 8.14 (s, 1H), 8.00 (s, 1H), 7.89 (d, J = 8.0 Hz, 1H), 7.75 (d, J = 8.0 Hz, 1H), 7.66 (d, J = 7.0 Hz, 2H), 7.55 (d, J = 7.5 Hz, 2H), 7.29-7.26 (m, 2H), 7.22-7.17 (m, 3H), 3.47-3.43 (m, 2H), 2.80 (t, J = 7.5 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1283 | 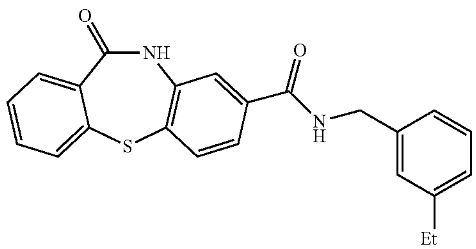 [SMILES: CCc1cccc(CNC(=O)c2ccc3c(c2)NC(=O)c2ccccc2S3)c1] | A, 6 | 35 | 389.5 ($M^+ + 1$); | | (DMSO-$d_6$, 400 MHz): δ 10.77 (s, 1H), 9.04 (t, J = 5.6 Hz, 1H), 7.71-7.61 (m, 4H), 7.55-7.43 (m, 3H), 7.21 (t, J = 7.6 Hz, 1H), 7.12-7.08 (m, 3H), 4.41 (d, J = 5.6 Hz, 2H), 2.59-2.55 (m, 2H), 1.15 (t, J = 7.6 Hz, 3H); |
| 1285 | 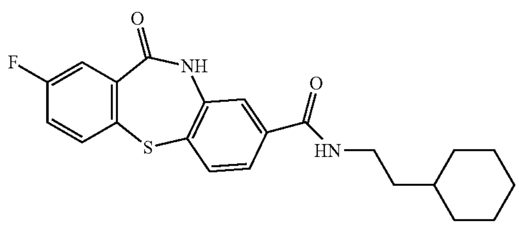 [SMILES: O=C(NCCC1CCCCC1)c1ccc2c(c1)NC(=O)c1cc(F)ccc1S2] | A, 35 | 55 | 399.7 ($M^+ + 1$); | | (DMSO-$d_6$, 400 MHz): δ 10.88 (s, 1H), 8.46 (t, J = 6.8 Hz, 1H), 7.66-7.62 (m, 2H), 7.58-7.55 (m, 2H), 7.46 (d, J = 7.2 Hz, 1H), 7.38 (t, J = 7.2 Hz, 1H), 3.28-3.24 (m, 2H), 1.74-1.56 (m, 5H), 1.42-1.38 (m, 2H), 1.28-1.26 (m, 1H), 1.22-1.08 (m, 3H), 0.94-0.85 (m, 2H); |
| 1290 | 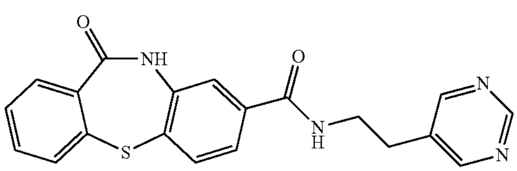 [SMILES: O=C(NCCc1cncnc1)c1ccc2c(c1)NC(=O)c1ccccc1S2] | A, 6 | 29 | 377.5 ($M^+ + 1$); | | (DMSO-$d_6$, 500 MHz): δ 10.77 (s, 1H), 9.01 (s, 1H), 8.66 (s, 2H), 7.69-7.62 (m, 4H), 7.55-7.44 (m, 4H), 3.54-3.51 (m, 2H), 2.85 (t, J = 5.6 Hz, 2H); |
| 1291 | 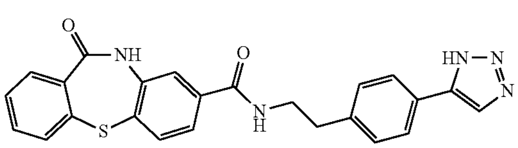 [SMILES: O=C(NCCc1ccc(-c2cnn[nH]2)cc1)c1ccc2c(c1)NC(=O)c1ccccc1S2] | A, 6 | 60 | 442.6 ($M^+ + 1$); | | (DMSO-$d_6$, 400 MHz): δ 15.01 (br s, 1H), 10.77 (s, 1H), 8.61 (t, J = 5.6 Hz, 1H), 8.25 (br s, 1H), 7.76 (d, J = 8.0 Hz, 2H), 7.69-7.63 (m, 3H), 7.55-7.43 (m, 4H), 7.30 (d, J = 8.4 Hz, 2H), 3.50-3.45 (m, 2H), 2.84 (t, J = 7.2 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1160 | 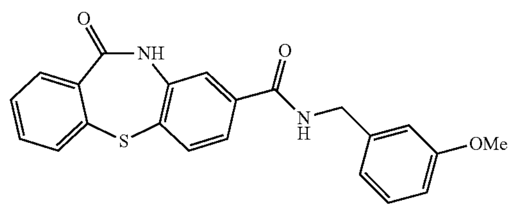 [SMILES: COc1cccc(CNC(=O)c2ccc3c(c2)NC(=O)c2ccccc2S3)c1] | A$^a$, 6, 171 (a = solvent DMF:CH$_2$Cl$_2$ 1:1) | 52 | 391.3 (M$^+$ + 1) | 390.10 for C$_{22}$H$_{18}$N$_2$O$_3$S | $^1$H-NMR DMSO-d$_6$, 400 MHz): δ 10.77 (s, 1H), 9.05 (t, J = 5.6 Hz, 1H), 7.71-7.61 (m, 4H), 7.55-7.45 (m, 3H), 7.21 (t, J = 8.0 Hz, 1H), 6.85-6.79 (m, 3H), 4.41 (d, J = 5.6 Hz, 2H), 3.71 (s, 3H); |
| 1162 | 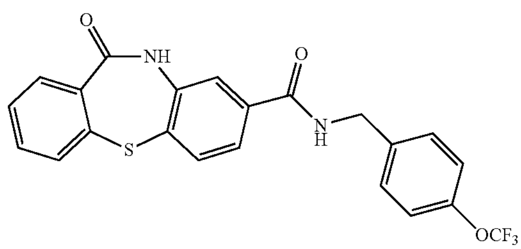 [SMILES: O=C(NCc1ccc(OC(F)(F)F)cc1)c1ccc2c(c1)NC(=O)c1ccccc1S2] | D, 6, 172 | 55 | 445.4 (M$^+$ + 1) | 444.08 for C$_{22}$H$_{15}$F$_3$N$_2$O$_3$ | $^1$H-NMR DMSO-d$_6$, 400 MHz): δ 10.78 (s, 1H), 9.13 (t, J = 6.0 Hz, 1H), 7.72-7.61 (m, 4H), 7.55-7.39 (m, 5H), 7.30 (d, J = 8.0 Hz, 2H), 4.46 (d, J = 6.0 Hz, 2H); |
| 1167 | 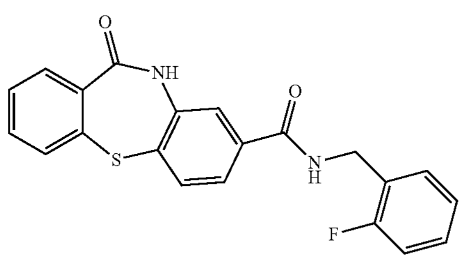 | A, 6, 173 | 54 | 379.3 (M$^+$ + 1) | 378.08 for C$_{21}$H$_{15}$FN$_2$O$_2$S | $^1$H-NMR DMSO-d$_6$, 400 MHz): δ 10.76 (s, 1H), 9.07-9.04 (m, 1H), 7.71-7.61 (m, 4H), 7.55-7.43 (m, 3H), 7.34-7.27 (m, 2H), 7.19-7.12 (m, 2H), 4.47 (d, J = 4.8 Hz, 2H); |
| 1170 | 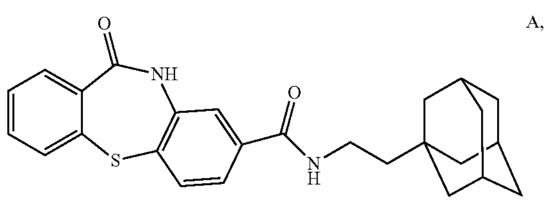 | A, 6, 174 | 63 | 433.3 (M$^+$ + 1) | 432.19 for C$_{26}$H$_{28}$N$_2$O$_2$S | $^1$H-NMR DMSO-d$_6$, 400 MHz): δ 10.77 (br s, 1H), 8.40 (t, J = 4.8 Hz, 1H), 7.69-7.62 (m, 3H), 7.55-7.43 (m, 4H), 3.25-3.20 (m, 2H), 1.91-1.90 (m, 3H), 1.67-1.58 (m, 6H), 1.49-1.47 (m, 6H), 1.30-1.26 (m, 2H); |
| 1189 | 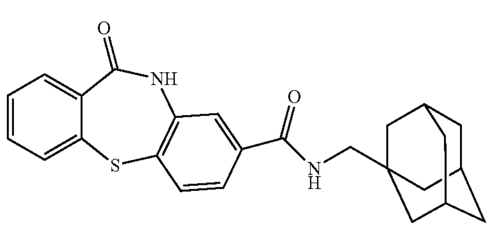 [SMILES: O=C(NCC12CC3CC(CC(C3)C1)C2)c1ccc2c(c1)NC(=O)c1ccccc1S2] | A, 6, 175 | 40 | 419.2 (M$^+$ + 1) | 418.17 for C$_{25}$H$_{26}$N$_2$O$_2$S | $^1$H-NMR DMSO-d$_6$, 400 MHz): δ 10.74 (s, 1H), 8.29 (t, J = 6.0 Hz, 1H), 7.69-7.63 (m, 3H), 7.59-7.43 (m, 4H), 2.94 (d, J = 6.4 Hz, 2H), 1.93-1.91 (m, 3H), 1.66-1.56 (m, 6H), 1.46 (s, 6H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1192 | 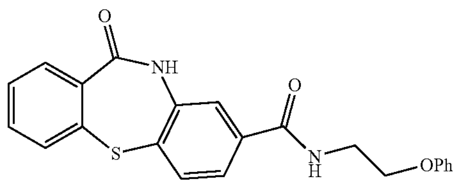 [SMILES: O=C(NCCOc1ccccc1)c1ccc2c(c1)NC(=O)c1ccccc1S2] | A, 6, 176 | 35 | 391.2 (M$^+$ + 1); | 390.10 for $C_{22}H_{18}N_2O_3S$ | $^1$H-NMR DMSO-d$_6$, 400 MHz): δ 10.77 (s, 1H), 8.74 (t, J = 6.0 Hz, 1H), 7.69-7.64 (m, 3H), 7.60-7.58 (m, 1H), 7.54-7.43 (m, 3H), 7.28 (t, J = 8.4 Hz, 2H), 6.92 (t, J = 8.4 Hz, 3H), 4.07 (t, J = 6.0 Hz, 2H), 3.59 (q, 2H); |
| 1175 | 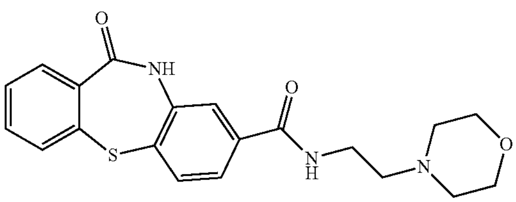 [SMILES: O=C(NCCN1CCOCC1)c1ccc2c(c1)NC(=O)c1ccccc1S2] | D, 6, 177 | 59 | 384.3 (M$^+$ + 1); | 383.13 for $C_{20}H_{21}N_3O_3S$ | $^1$H-NMR DMSO-d$_6$, 400 MHz): δ 10.77 (s, 1H), 8.43 (t, J = 4.8 Hz, 1H), 7.69-7.64 (m, 3H), 7.56-7.43 (m, 4H), 3.55-3.53 (m, 4H), 3.35-3.33 (m, 2H), 2.50 (s, 2H), 2.44-2.38 (m, 4H); |
| 1208 | 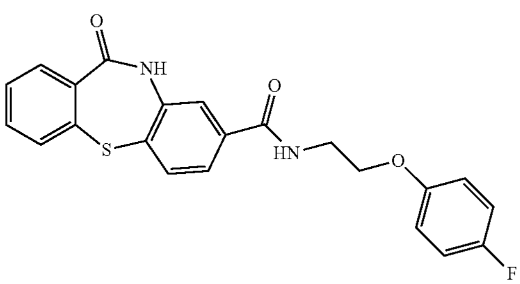 [SMILES: O=C(NCCOc1ccc(F)cc1)c1ccc2c(c1)NC(=O)c1ccccc1S2] | A, 6, 265 | 33 | 409.1 (M$^+$ + 1); | 408.09 for $C_{22}H_{17}FN_2O_3S$ | $^1$H-NMR DMSO-d$_6$, 400 MHz): δ 10.77 (s, 1H), 8.72 (t, J = 5.2 Hz, 1H), 7.69-7.58 (m, 3H), 7.55 (s, 1H), 7.53-7.45 (m, 3H), 7.09 (t, J = 8.8 Hz, 2H), 6.96-6.93 (m, 2H), 4.06 (t, J = 5.2 Hz, 2H), 3.58 (d, J = 5.6 Hz, 2H); |
| 1217 | 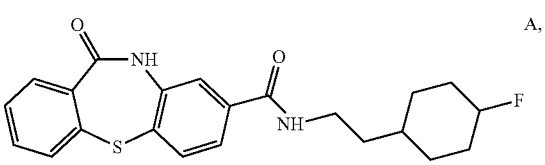 | A, 6, 269 | 28 | 399.3 (M$^+$ + 1); | 398.15 for $C_{22}H_{23}FN_2O_2S$ | $^1$H-NMR (DMSO-d$_6$, 400 MHz): δ 10.76 (s, 1H), 8.45 (t, J = 5.6 Hz, 1H), 7.65-7.63 (m, 3H), 7.56-7.45 (m, 4H), 4.84-4.72 (m, 1H), 3.30-3.29 (m, 2H), 1.87-1.78 (m, 3H), 1.54-1.51 (m, 2H), 1.42-1.41 (m, 4H), 1.21-1.18 (m, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1238 | 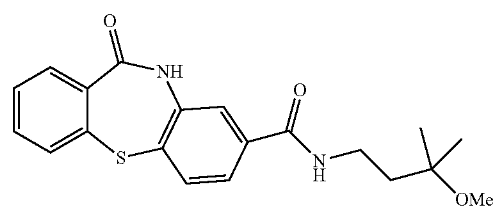 [SMILES: COC(C)(C)CCNC(=O)c1ccc2c(c1)NC(=O)c1ccccc1S2] | A, 6, 273 | 37 | 371.2 (M$^+$ + 1); | 370.14 for $C_{20}H_{22}N_2O_3S$ | $^1$H-NMR (DMSO-d$_6$, 400 MHz): δ 10.74 (s, 1H), 8.41 (t, J = 5.6 Hz, 1H), 7.69-7.63 (m, 3H), 7.55-7.41 (m, 4H), 3.28-3.22 (m, 2H), 3.10 (s, 3H), 1.66 (t, J = 8.4 Hz, 2H), 1.11 (s, 6H); |
| 1252 | 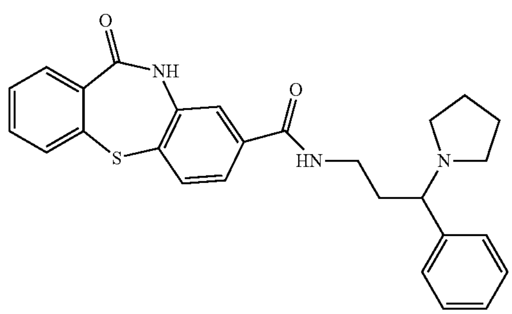 [SMILES: O=C(NCCC(c1ccccc1)N1CCCC1)c1ccc2c(c1)NC(=O)c1ccccc1S2] | A, 6, 277 | 22 | 458.4 (M$^+$ +1); | 457.18 for $C_{27}H_{27}N_3O_2S$ | $^1$H-NMR (CDCl$_3$ + CD$_3$OD, 400 MHz): δ 7.73 (d, J = 7.6 Hz, 1H), 7.61 (d, 8.0 Hz, 1H), 7.52 (d, J = 8.4 Hz, 2H), 7.48-7.46 (m, 3H), 7.45-7.31 (m, 4H), 7.26 (d, J = 6.8 Hz, 1H), 3.31-3.30 (m, 1H), 3.25-3.17 (m, 1H), 3.06-3.00 (m, 1H), 2.68-2.67 (m, 2H), 2.44-2.42 (m, 2H), 2.36-2.28 (m, 1H), 2.13-2.04 (m, 1H), 1.78 (t, J = 6.4 Hz, 4H); |
| 1219 | 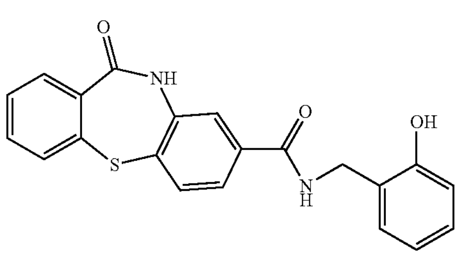 [SMILES: O=C(NCc1ccccc1O)c1ccc2c(c1)NC(=O)c1ccccc1S2] | A, 6, 178 | 59 | 376.9 (M$^+$ + 1) | $C_{21}H_{16}N_2O_3S$ 376.09 | $^1$H-NMR (DMSO-d$_6$, 400 MHz): δ 10.75 (s, 1H), 9.50 (s, 1H), 8.91(t, J = 6.0 Hz, 1H), 7.72-7.65 (m, 4H), 7.55-7.43 (m, 3H), 7.08-7.03 (m, 2H), 6.79 (d, J = 7.6 Hz, 1H), 6.72 (t, J = 7.2 Hz, 1H), 4.38 (d, J = 5.6 Hz, 2H); |
| 1223 | 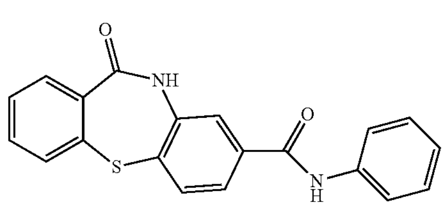 | A, 6, 179 | 59 | 347.2 (M$^+$ + 1); | $C_{20}H_{14}N_2O_2S$ 346.08 | $^1$H-NMR (DMSO-d$_6$, 400 MHz): δ 10.80 (s, 1H), 10.25 (s, 1H), 7.75-7.71 (m, 6H), 7.55 (br s, 1H), 7.49 (t, J = 8.8 Hz, 2H), 7.32 (t, J = 6.8 Hz, 2H), 7.10 (t, J = 7.2 Hz, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1229 | 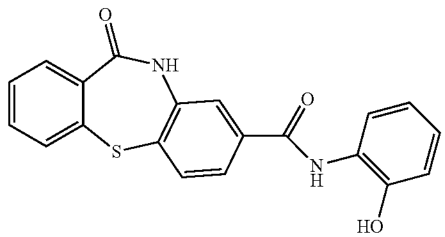 [SMILES: O=C(Nc1ccccc1O)c1ccc2c(c1)NC(=O)c1ccccc1S2] | D, 6, 180 | 34 | 363.5 ($M^+ + 1$) | $C_{20}H_{14}N_2O_3S$ 362.07 | $^1$H-NMR (DMSO-$d_6$, 400 MHz): δ 10.81 (s, 1H), 9.71 (br s, 1H), 9.51 (br s, 1H), 7.76 (s, 1H), 7.71 (s, 3H), 7.64 (d, J = 8.4 Hz, 1H), 7.57-7.45 (m, 3H), 7.02 (t, J = 6.8 Hz, 1H), 6.90 (d, J = 7.2 Hz, 1H), 6.81 (t, J = 8.0 Hz, 1H); |
| 1230 | 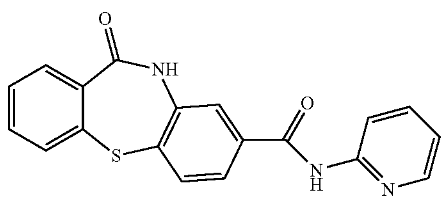 [SMILES: O=C(Nc1ccccn1)c1ccc2c(c1)NC(=O)c1ccccc1S2] | E, 6, 181 | 35 | 348.4 ($M^+ + 1$) | $C_{19}H_{13}N_3O_2S$ 347.07 | $^1$H-NMR (DMSO-$d_6$, 500 MHz): δ 10.85-10.82 (m, 2H), 8.38 (br s, 1H), 8.14 (d, J = 8.0 Hz, 1H), 7.83-7.67 (m, 5H), 7.57-7.47 (m, 3H), 7.16 (t, J = 7.5 Hz, 1H); |
| 1231 | 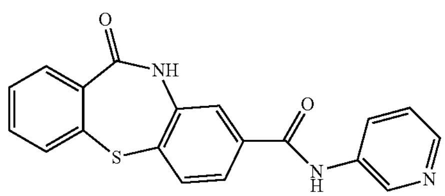 [SMILES: O=C(Nc1cccnc1)c1ccc2c(c1)NC(=O)c1ccccc1S2] | B, 6, 182 | 61 | 348.2 ($M^+ + 1$); | $C_{19}H_{13}N_3O_2S$ 347.07 | $^1$H-NMR (DMSO-$d_6$, 400 MHz): δ 10.85 (s, 1H), 10.48 (s, 1H), 8.88 (s, 1H), 8.31 (s, 1H), 8.15 (d, J = 8.4 Hz, 1H), 7.78-7.70 (m, 4H), 7.57-7.45 (m, 3H), 7.40-7.37 (m, 1H); |
| 1242 | 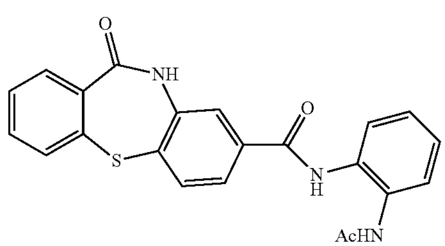 [SMILES: CC(=O)Nc1ccccc1NC(=O)c1ccc2c(c1)NC(=O)c1ccccc1S2] | A, 6, 183 | 28 | 404.2 ($M^+ + 1$); | $C_{22}H_{17}N_3O_3S$ 403.10 | $^1$H-NMR (DMSO-$d_6$, 400 MHz): δ 10.85 (s, 1H), 9.85 (s, 1H), 9.61 (s, 1H), 7.76-7.68 (m, 4H), 7.57 (t, J = 6.8 Hz, 2H), 7.53-7.47 (m, 3H), 7.19 (t, J = 4.4 Hz, 2H), 2.05 (s, 3H); |
| 1243 | 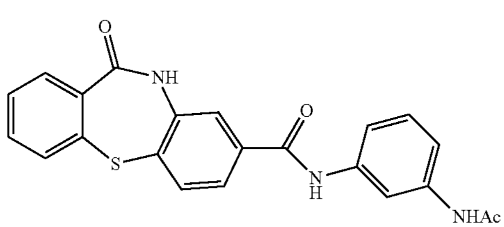 [SMILES: CC(=O)Nc1cccc(NC(=O)c2ccc3c(c2)NC(=O)c2ccccc2S3)c1] | A, 6, 184 | 51 | 404.3 ($M^+ + 1$); | $C_{22}H_{17}N_3O_3S$ 403.10 | $^1$H-NMR (DMSO-$d_6$, 400 MHz): δ 10.82 (br s, 1H), 10.29 (br s, 1H), 9.95 (br s, 1H), 8.06 (s, 1H), 7.75-7.70 (m, 4H), 7.57-7.47 (m, 3H), 7.37 (d, J = 7.6 Hz, 1H), 7.32 (d, J = 7.2 Hz, 1H), 7.23 (t, J = 7.6 Hz, 1H), 2.03 |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | (s, 3H); |
| 1444 | 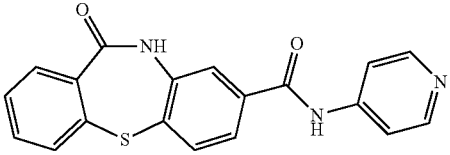 [SMILES: O=C(Nc1ccncc1)c1ccc2c(c1)NC(=O)c1ccccc1S2] | A, 6, 185 | 32 | 347.9 (M$^+$ + 1); | C$_{19}$H$_{13}$N$_3$O$_2$S 347.07 | $^1$H-NMR (DMSO-d$_6$, 400 MHz): δ 10.85 (s, 1H), 10.62 (s, 1H), 8.48 (d, J = 6.1 Hz, 2H), 7.79-7.69 (m, 6H), 7.60-7.45 (m, 3H); |
| 1445 | 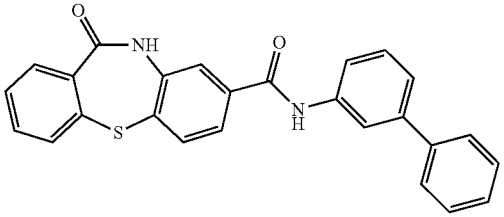 [SMILES: O=C(Nc1cccc(-c2ccccc2)c1)c1ccc2c(c1)NC(=O)c1ccccc1S2] | A, 6, 186 | 25 | 423.1 (M$^+$ + 1); | C$_{26}$H$_{18}$N$_2$O$_2$S 422.11 | $^1$H-NMR (DMSO-d$_6$, 400 MHz): δ 10.85 (s, 1H), 10.36 (s, 1H), 8.07-8.04 (m, 1H), 7.80-7.70 (m, 5H), 7.65-7.61 (m, 2H), 7.57 (dd, J = 7.7, 1.6 Hz, 1H), 7.54-7.35 (m, 7H); |
| 1567 | 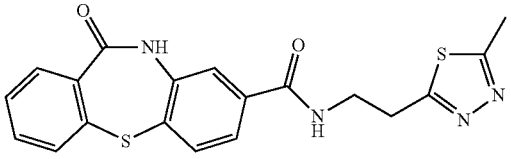 [SMILES: Cc1nnc(CCNC(=O)c2ccc3c(c2)NC(=O)c2ccccc2S3)s1] | A, 6, 187 | 44 | 396.9 (M$^+$ + 1); | C$_{19}$H$_{16}$N$_4$O$_2$S$_2$ 396.07 | $^1$H-NMR (DMSO-d$_6$, 400 MHz): δ 10.79 (s, 1H), 8.72 (t, J = 5.3 Hz, 1H), 7.71-7.63 (m, 3H), 7.59-7.41 (m, 4H), 3.59 (q, J = 6.3 Hz, 2H), 3.29-3.25 (m, 2H), 2.66 (s, 3H); |
| 1568 | 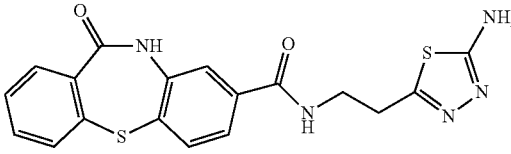 | A, 6, 188 | 55 | 398.0 (M$^+$ + 1) | C$_{18}$H$_{15}$N$_5$O$_2$S$_2$ 397.07 | $^1$H-NMR (DMSO-d$_6$, 400 MHz): δ 10.78 (s, 1H), 8.69 (t, J = 5.4 Hz, 1H), 7.74-7.63 (m, 3H), 7.60-7.43 (m, 4H), 6.97 (s, 2H), 3.51 (q, 3.03 (t, J = 6.7 Hz, 2H); |
| 1582 | 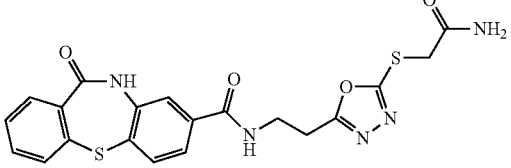 | B, 6, 189 | 63 | 456.1 (M$^+$ + 1); | C$_{20}$H$_{17}$N$_5$O$_4$S$_2$ 455.07 | $^1$H-NMR (DMSO-d$_6$, 400 MHz): δ 10.78 (s, 1H), 8.71 (t, J = 5.4 Hz, 1H), 7.74-7.62 (m, 4H), 7.56-7.41 (m, 4H), 7.32 (br s, 1H), 3.99 (s, 2H), 3.58 (q, J = 6.5 Hz, 2H), 3.06 (t, J = 6.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1569 | 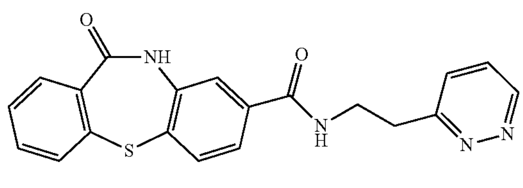 [SMILES: O=C(NCCc1cccnn1)c1ccc2c(c1)NC(=O)c1ccccc1S2] | A, 6, 190 | 75 | 377.1 (M⁺ + 1) | $C_{20}H_{16}N_4O_2S$ 376.10 | ¹H-NMR (DMSO-d₆, 400 MHz): δ 10.76 (s, 1H), 9.07 (dd, J = 4.4, 2.0 Hz, 1H), 8.64 (t, J = 5.5 Hz, 1H), 7.71-7.41 (m, 9H), 3.68-3.62 (m, 2H), 3.14 (t, J = 7.0 Hz, 2H); |
| 1551 | 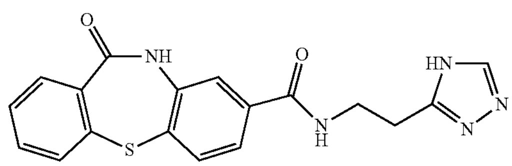 [SMILES: O=C(NCCc1nnc[nH]1)c1ccc2c(c1)NC(=O)c1ccccc1S2] | A, 6, 191 | 22 | 366.0 (M⁺ + 1); | $C_{18}H_{15}N_5O_2S$ 365.09 | ¹H-NMR (DMSO-d₆, 400 MHz): δ 13.67 (br s, 1H), 10.77 (s, 1H), 8.64 (br s, 1H), 8.42 (br s, 0.4H), 7.82 (br s, 0.6H), 7.71-7.62 (m, 3H), 7.58-7.42 (m, 4H), 3.55 (q, J = 6.7 Hz, 2H), 3.00-2.82 (m, 2H); |
| 1583 | 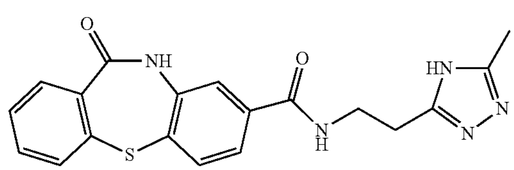 [SMILES: Cc1nnc(CCNC(=O)c2ccc3c(c2)NC(=O)c2ccccc2S3)[nH]1] | Bᵃ, 6, 192 (a = RT 8 h) | 51 | 380.1 (M⁺ + 1); | $C_{19}H_{17}N_5O_2S$ 379.11 | ¹H-NMR (DMSO-d₆, 500 MHz): δ 13.24 (d, J = 9.8 Hz, 1H), 10.77 (br s, 1H), 8.69-8.57 (m, 1H), 7.71-7.63 (m, 3H), 7.58-7.43 (m, 4H), 3.56-3.47 (m, 2H), 2.87 (t, J = 7.1 Hz, 1H), 2.76 (t, J = 7.5 Hz, 1H), 2.31-2.16 (s, 3H); |
| 1570 | 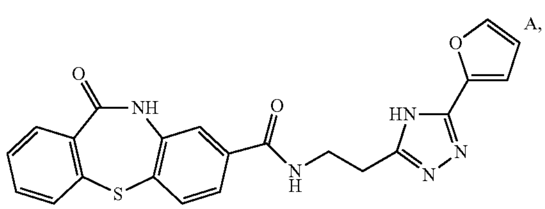 | A, 6, 193 | 46 | 432.0 (M⁺ + 1); | $C_{22}H_{17}N_5O_3S$ 431.11 | ¹H-NMR (DMSO-d₆, 400 MHz): δ 13.80 (br s, 1H), 10.77 (s, 1H), 8.69 (br s, 1H), 7.74 (br s, 1H), 7.70-7.65 (m, 2H), 7.64 (s, 1H), 7.58-7.43 (m, 4H), 6.84 (br s, 1H), 6.59 (br s, 1H), 3.62-3.55 (m, 2H), 3.00-2.91 (m, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1552 | 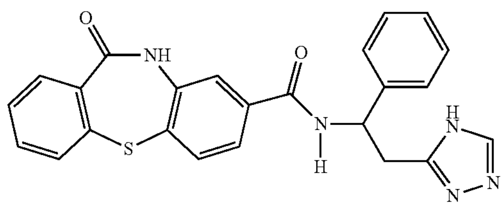 [SMILES: O=C(NC(Cc1nnc[nH]1)c1ccccc1)c1ccc2c(c1)NC(=O)c1ccccc1S2] | A, 6, 194 | 31 | 442.1 (M$^+$ + 1); | $C_{24}H_{19}N_5O_2S$ 441.13 | $^1$H-NMR (DMSO-d$_6$, 400 MHz): δ 13.62 (br, s, 1H), 10.75 (s, 1H), 9.01 (br s, 1H), 8.38 (br s, 0.5H), 7.77 (br s, 0.5H), 7.71-7.62 (m, 3H), 7.60-7.42 (m, 4H), 7.37-7.32 (m, 2H), 7.27 (t, J = 7.5 Hz, 2H), 7.22-7.17 (m, 1H), 5.47 (q, J = 7.7 Hz, 1H), 3.39-3.33 (m, 1H), 3.27-3.17 (m, 1H); |
| 1571 | 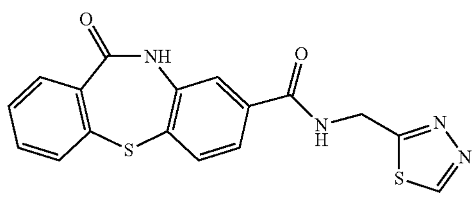 [SMILES: O=C(NCc1nncs1)c1ccc2c(c1)NC(=O)c1ccccc1S2] | A, 6, 195 | 86 | 369.0 (M$^+$ + 1); | $C_{17}H_{12}N_4O_2S_2$ 368.04 | $^1$H-NMR (DMSO-d$_6$, 400 MHz): δ 10.79 (s, 1H), 9.53-9.48 (m, 2H), 7.73-7.67 (m, 3H), 7.62 (dd, J = 8.0, 1.8 Hz, 1H), 7.57-7.43 (m, 3H), 4.86 (d, J = 5.9 Hz, 2H); |
| 1584 | 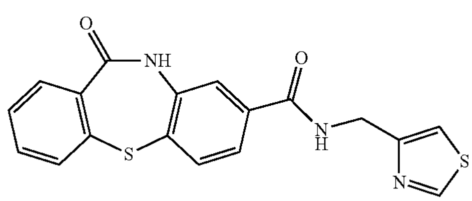 [SMILES: O=C(NCc1cscn1)c1ccc2c(c1)NC(=O)c1ccccc1S2] | A, 6, 196 | 54 | 367.9 (M$^+$ + 1); | $C_{18}H_{13}N_3O_2S_2$ 367.04 | $^1$H-NMR (DMSO-d$_6$, 400 MHz): δ 10.77 (s, 1H), 9.10 (t, J = 5.7 Hz, 1H), 9.04 (s, 1H), 7.74-7.62 (m, 4H), 7.57-7.42 (m, 4H), 4.58 (d, J = 5.6 Hz, 2H); |
| 1599 | 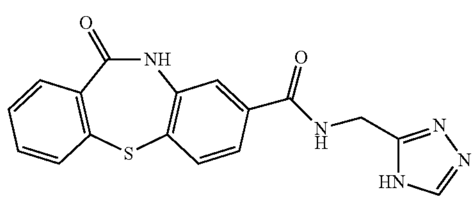 [SMILES: O=C(NCc1nnc[nH]1)c1ccc2c(c1)NC(=O)c1ccccc1S2] | A, 6, 197 | 23 | 352.1 (M$^+$ + 1); | $C_{17}H_{13}N_5O_2S$ 351.08 | $^1$H-NMR (DMSO-d$_6$, 400 MHz): δ 13.77 (br s, 1H), 10.79 (br s, 1H), 9.06 (br s, 1H), 8.33 (br s, 1H), 7.74-7.60 (m, 4H), 7.57-7.42 (m, 3H), 4.51 (d, J = 4.8 Hz, 2H); |
| 1572 | 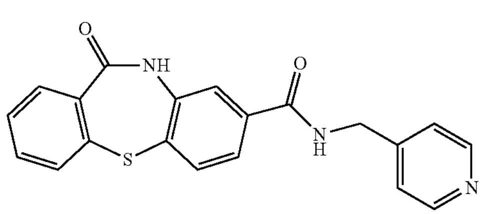 [SMILES: O=C(NCc1ccncc1)c1ccc2c(c1)NC(=O)c1ccccc1S2] | A, 6, 198 | 50 | 361.9 (M$^+$ + 1); | $C_{20}H_{15}N_3O_2S$ 361.09 | $^1$H-NMR (DMSO-d$_6$, 400 MHz): δ 10.78 (s, 1H), 9.16 (t, J = 5.9 Hz, 1H), 8.48 (d, J = 5.9 Hz, 2H), 7.76-7.63 (m, 4H), 7.57-7.42 (m, 3H), 7.27 (d, J = 5.5 Hz, 2H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 4.46 (d, J = 5.7 Hz, 2H); |
| 1585 | 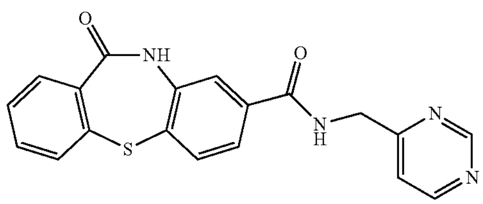 [SMILES: O=C(NCc1ccncn1)c1ccc2c(c1)NC(=O)c1ccccc1S2] | A, 6, 199 | 64 | 362.9 (M$^+$ + 1); | $C_{19}H_{14}N_4O_2S$ 362.08 | $^1$H-NMR (DMSO-d$_6$, 400 MHz): δ 10.79 (s, 1H), 9.22 (t, J = 5.3 Hz, 1H), 9.09 (s, 1H), 8.71 (d, J = 5.2 Hz, 1H), 7.74 (s, 1H), 7.72-7.65 (m, 3H), 7.57-7.44 (m, 3H), 7.39 (d, J = 4.9 Hz, 1H), 4.52 (d, J = 5.9 Hz, 2H); |
| 1586 | 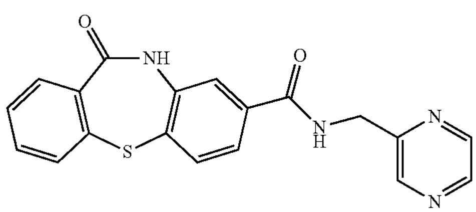 [SMILES: O=C(NCc1cnccn1)c1ccc2c(c1)NC(=O)c1ccccc1S2] | A, 6, 200 | 60 | 362.9 (M$^+$ + 1); | $C_{19}H_{14}N_4O_2S$ 362.08 | $^1$H-NMR (DMSO-d$_6$, 400 MHz): δ 10.78 (s, 1H), 9.22 (t, J = 5.7 Hz, 1H), 8.61 (s, 1H), 8.58-8.56 (m, 1H), 8.54-8.51 (m, 1H), 7.73 (s, 1H), 7.71-7.63 (m, 3H), 7.57-7.43 (m, 3H), 4.59 (d, J = 5.7 Hz, 2H); |
| 1587 | 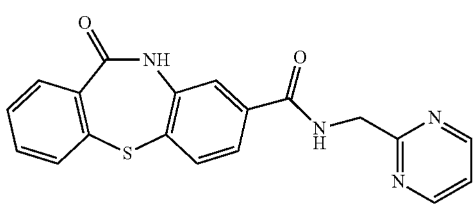 [SMILES: O=C(NCc1ncccn1)c1ccc2c(c1)NC(=O)c1ccccc1S2] | A, 6, 201 | 67 | 362.9 (M$^+$ + 1); | $C_{19}H_{14}N_4O_2S$ 362.08 | $^1$H-NMR (DMSO-d$_6$, 400 MHz): δ 10.80 (s, 1H), 9.10 (t, J = 5.8 Hz, 1H), 8.74 (d, J = 4.9 Hz, 2H), 7.73 (s, 1H), 7.71-7.65 (m, 3H), 7.57-7.43 (m, 3H), 7.38 (t, J = 4.9 Hz, 1H), 4.63 (d, J = 5.9 Hz, 2H); |
| 1588 | 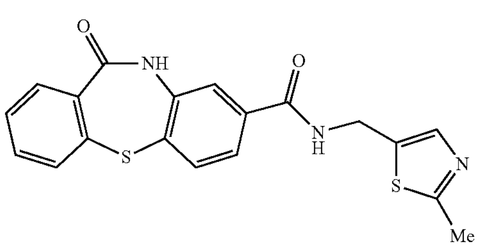 [SMILES: Cc1ncc(CNC(=O)c2ccc3c(c2)NC(=O)c2ccccc2S3)s1] | A, 6, 202 | 71 | 381.9 (M$^+$ + 1); | $C_{19}H_{15}N_3O_2S_2$ 381.06 | $^1$H-NMR (DMSO-d$_6$, 400 MHz): δ 10.77 (s, 1H), 9.17 (t, J = 5.7 Hz, 1H), 7.71-7.64 (m, 3H), 7.59-7.42 (m, 5H), 4.55 (d, J = 5.6 Hz, 2H), 2.57 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1589 | 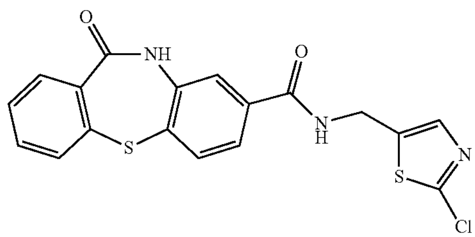 | A, 6, 203 | 72 | 401.9 (M$^+$ + 1); | $C_{18}H_{12}ClN_3O_2S_2$ 401.01 | $^1$H-NMR (DMSO-d$_6$, 400 MHz): δ 10.77 (s, 1H), 9.28 (t, J = 5.7 Hz, 1H), 7.72-7.64 (m, 3H), 7.61-7.42 (m, 5H), 4.55 (d, J = 5.4 Hz, 2H); |
| 1590 | 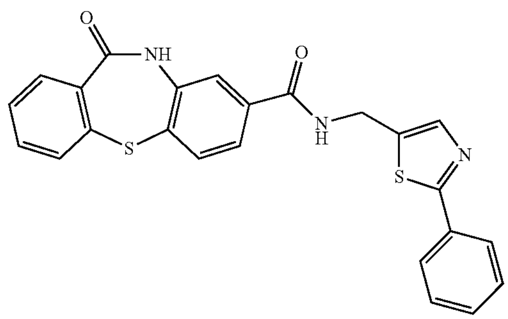 [SMILES: O=C(NCc1cnc(-c2ccccc2)s1)c1ccc2c(c1)NC(=O)c1ccccc1S2] | A, 6, 204 | 65 | 443.9 (M$^+$ + 1); | $C_{24}H_{17}N_3O_2S_2$ 443.08 | $^1$H-NMR (DMSO-d$_6$, 400 MHz): δ 10.78 (s, 1H), 9.28 (t, J = 5.7 Hz, 1H), 7.90-7.86 (m, 2H), 7.79 (s, 1H), 7.73-7.66 (m, 3H), 7.61 (dd, J = 8.2, 1.8 Hz, 1H), 7.56-7.42 (m, 6H), 4.66 (d, J = 5.6 Hz, 2H); |
| 1600 | 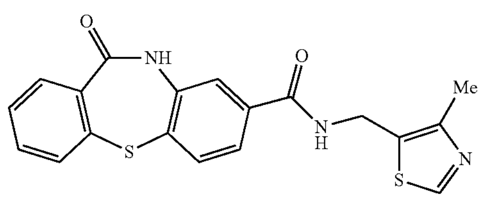 [SMILES: Cc1ncsc1CNC(=O)c1ccc2c(c1)NC(=O)c1ccccc1S2] | A, 6, 205 | 28 | 382.0 (M$^+$ + 1); | $C_{19}H_{15}N_3O_2S_2$ 381.06 | $^1$H-NMR (DMSO-d$_6$, 400 MHz): δ 10.76 (s, 1H), 9.15 (t, J = 5.7 Hz, 1H), 8.83 (s, 1H), 7.70-7.64 (m, 3H), 7.59-7.43 (m, 4H), 4.55 (d, J = 5.7 Hz, 2H), 2.39 (s, 3H); |
| 1605 | 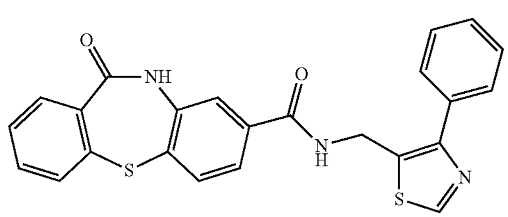 [SMILES: O=C(NCc1scnc1-c1ccccc1)c1ccc2c(c1)NC(=O)c1ccccc1S2] | A$^b$, 6, 206 b = 24 h RT | 32 | 443.9 (M$^+$ + 1); | $C_{24}H_{17}N_3O_2S_2$ 443.08 | $^1$H NMR (DMSO-d$_6$, 400 MHz): δ 10.78 (s, 1H), 9.34 (t, J = 5.5 Hz, 1H), 9.02 (s, 1H), 7.74-7.66 (m, 5H), 7.60 (dd, J = 8.1, 1.8 Hz, 1H), 7.56-7.39 (m, 6H), 4.74 (d, J = 5.5 Hz, 2H); |
| 1525 | 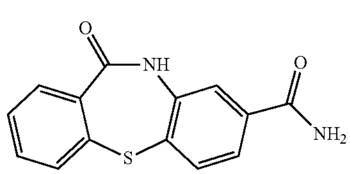 [SMILES: NC(=O)c1ccc2c(c1)NC(=O)c1ccccc1S2] | B, 6, 133 | 73 | 270.8 (M$^+$ + 1); | $C_{14}H_{10}N_2O_2S$ 270.05 | $^1$H-NMR (DMSO-d$_6$, 400 MHz): δ 10.77 (s, 1H), 7.99 (br s, 1H), 7.72-7.58 (m, 4H), 7.56-7.43 (m, 4H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1592 | 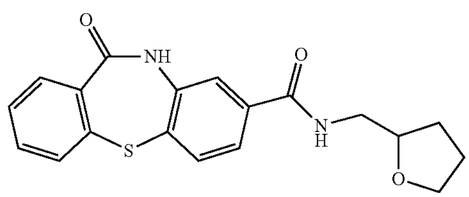 [SMILES: O=C(NCC1CCCO1)c1ccc2c(c1)NC(=O)c1ccccc1S2] | A, 6, 207 | 23 | 354.9 (M$^+$ + 1) | C$_{19}$H$_{18}$N$_2$O$_3$S 354.10 | $^1$H-NMR (DMSO-d$_6$, 400 MHz): δ 10.75 (br s, 1H), 8.55 (t, J = 5.4 Hz, 1H), 7.71-7.62 (m, 3H), 7.60-7.43 (m, 4H), 3.98-3.89 (m, 1H), 3.79-3.72 (m, 1H), 3.65-3.57 (m, 1H), 3.29-3.25 (m, 2H), 1.93-1.73 (m, 3H), 1.61-1.49 (m, 1H); |
| 1606 | 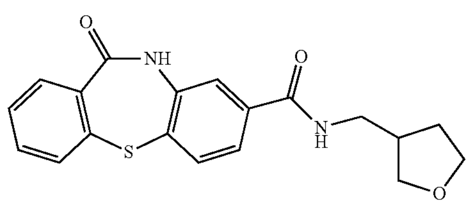 [SMILES: O=C(NCC1CCOC1)c1ccc2c(c1)NC(=O)c1ccccc1S2] | A, 6, 208 | 23 | 354.9 (M$^+$ + 1); | C$_{19}$H$_{18}$N$_2$O$_3$S 354.10 | $^1$H-NMR (DMSO-d$_6$, 400 MHz): δ 10.75 (br s, 1H), 8.60 (t, J = 5.5 Hz, 1H), 7.71-7.63 (m, 3H), 7.59-7.43 (m, 4H), 3.76-3.56 (m, 3H), 3.43 (dd, J = 8.5, 5.4 Hz, 1H), 3.26-3.14 (m, 2H), 2.47-2.38 (m, 1H), 1.96-1.86 (m, 1H), 1.63-1.51 (m, 1H); |
| 1607 | 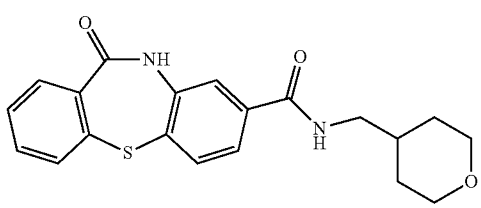 [SMILES: O=C(NCC1CCOCC1)c1ccc2c(c1)NC(=O)c1ccccc1S2] | A, 6, 209 | 22 | 354.9 (M$^+$ + 1); | C$_{20}$H$_{20}$N$_2$O$_3$S 368.12 | $^1$H-NMR (DMSO-d$_6$, 400 MHz): δ 10.75 (s, 1H), 8.51 (t, J = 5.6 Hz, 1H), 7.71-7.62 (m, 3H), 7.60-7.43 (m, 4H), 3.82 (dd, J = 11.2, 2.5 Hz, 2H), 3.27-3.20 (m, 2H), 3.12 (t, J = 6.3 Hz, 2H), 1.81-1.69 (m, 1H), 1.61-1.51 (m, 2H), 1.24-1.10 (m, 2H); |
| 1578 | 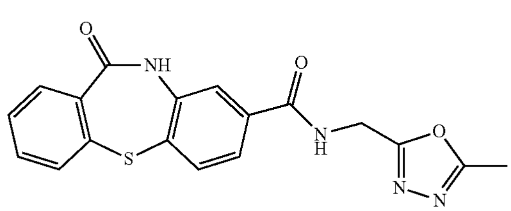 [SMILES: Cc1nnc(CNC(=O)c2ccc3c(c2)NC(=O)c2ccccc2S3)o1] | A, 6, 210 | 30 | 367.0 (M$^+$ + 1); | C$_{18}$H$_{14}$N$_4$O$_3$S 366.08 | $^1$H-NMR (DMSO-d$_6$, 400 MHz): δ 10.79 (s, 1H), 9.26 (t, J = 5.7 Hz, 1H), 7.72-7.67 (m, 3H), 7.62 (dd, J = 7.9, 1.8 Hz, 1H), 7.57-7.43 (m, 3H), 4.63 (d, J = 5.6 Hz, 2H), 2.45 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1603 | 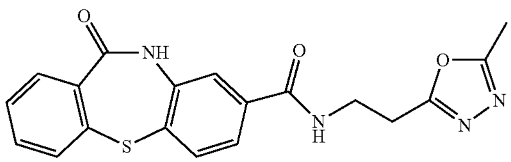 | A, 6, 283 | 70 | 381.0 (M$^+$ + 1); | $C_{19}H_{16}N_4O_3S$ 380.09 | $^1$H-NMR (DMSO-d$_6$, 400 MHz): δ 10.78 (s, 1H), 8.69 (t, J = 5.7 Hz, 1H), 7.70-7.62 (m, 3H), 7.56-7.42 (m, 4H), 3.58 (q, J = 6.6 Hz, 2H), 3.03 (t, J = 6.8 Hz, 2H), 2.43 (s, 3H); |
| 1604 | 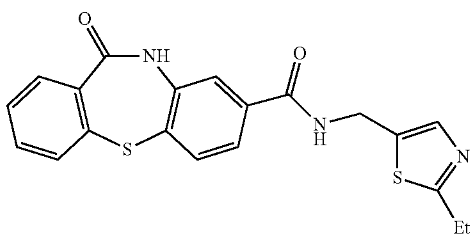 [SMILES: CCc1ncc(CNC(=O)c2ccc3c(c2)NC(=O)c2ccccc2S3)s1] | B, 6, 292 | 89 | 395.9 (M$^+$ + 1); | $C_{20}H_{17}N_3O_2S_2$ 395.08 | $^1$H-NMR (CDCl$_3$, 400 MHz): δ 10.77 (s, 1H), 9.18 (t, J = 5.7 Hz, 1H), 7.71-7.64 (m, 3H), 7.60-7.43 (m, 5H), 4.56 (d, J = 5.6 Hz, 2H), 2.90 (q, J = 7.5 Hz, 2H), 1.24 (t, J = 7.5 Hz, 3H); |
| 1611 | 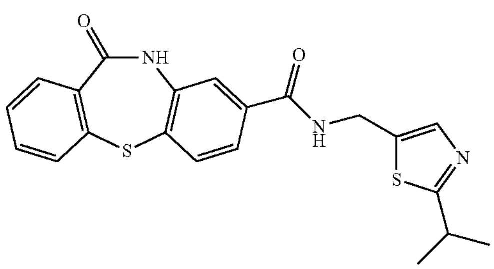 [SMILES: CC(C)c1ncc(CNC(=O)c2ccc3c(c2)NC(=O)c2ccccc2S3)s1] | B, 6, 298 | 73 | 410.0 (M$^+$ + 1); | $C_{21}H_{19}N_3O_2S_2$ 409.09 | $^1$H NMR (DMSO-d$_6$, 400 MHz): δ 10.77 (s, 1H), 9.18 (t, J = 5.7 Hz, 1H), 7.72-7.64 (m, 3H), 7.61-7.42 (m, 5H), 4.57 (d, J = 5.6 Hz, 2H), 3.22-3.15 (m, 1H), 1.27 (d, J = 6.9 Hz, 6H); |
| 1612 | 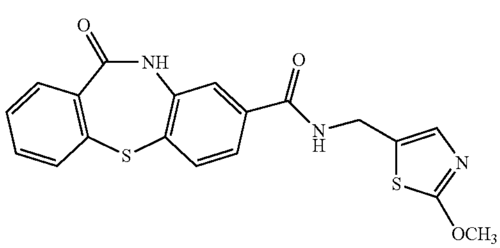 [SMILES: COc1ncc(CNC(=O)c2ccc3c(c2)NC(=O)c2ccccc2S3)s1] | B, 6, 300 | 59 | 397.9 (M$^+$ + 1); | $C_{19}H_{15}N_3O_3S_2$ 397.06 | $^1$H NMR (DMSO-d$_6$, 400 MHz): δ 10.76 (s, 1H), 9.15 (t, J = 5.6 Hz, 1H), 7.71-7.63 (m, 3H), 7.60-7.42 (m, 4H), 7.06 (s, 1H), 4.44 (d, J = 5.6 Hz, 2H), 3.95 (s, 3H); |
| 1613 | 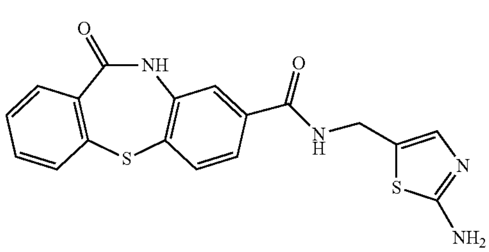 [SMILES: Nc1ncc(CNC(=O)c2ccc3c(c2)NC(=O)c2ccccc2S3)s1] | A, 6, 303 | 23 | 382.9 (M$^+$ + 1); | $C_{18}H_{14}N_4O_2S_2$ 382.06 | $^1$H NMR (DMSO-d$_6$, 400 MHz): δ 10.76 (s, 1H), 9.00 (t, J = 5.5 Hz, 1H), 7.72-7.42 (m, 7H), 6.88 (br s, 2H), 6.81 (s, 1H), 4.35 (d, J = 5.5 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1638 | 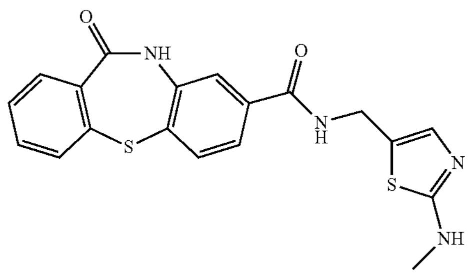 [SMILES: CNc1ncc(CNC(=O)c2ccc3c(c2)NC(=O)c2ccccc2S3)s1] | A, 6, 308 | 53 | 396.9 (M$^+$ + 1); | $C_{19}H_{16}N_4O_2S_2$ 396.07 | $^1$H NMR (DMSO-d$_6$, 500 MHz): δ 10.77 (s, 1H), 9.03 (t, J = 5.6 Hz, 1H), 7.69-7.62 (m, 3H), 7.59-7.42 (m, 4H), 7.34-7.30 (m, 1H), 6.87 (s, 1H), 4.36 (d, J = 5.8 Hz, 2H), 2.72 (d, J = 4.9 Hz, 3H); |
| 1639 | 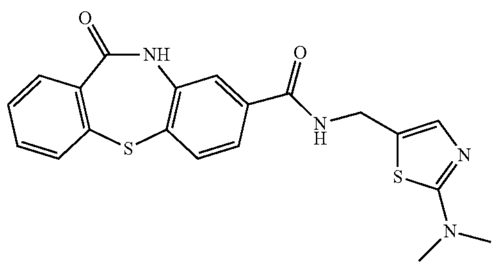 [SMILES: CN(C)c1ncc(CNC(=O)c2ccc3c(c2)NC(=O)c2ccccc2S3)s1] | A, 6, 311 | 61 | 411.0 (M$^+$ + 1); | $C_{20}H_{18}N_4O_2S_2$ 410.09 | $^1$H NMR (DMSO-d$_6$, 400 MHz): δ 10.75 (s, 1H), 9.05 (t, J = 5.7 Hz, 1H), 7.72-7.62 (m, 3H), 7.59-7.42 (m, 4H), 6.99 (s, 1H), 4.41 (d, J = 5.5 Hz, 2H), 2.95 (s, 6H); |
| 1631 | 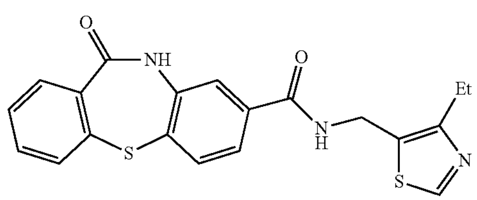 [SMILES: CCc1ncsc1CNC(=O)c1ccc2c(c1)NC(=O)c1ccccc1S2] | A, 6, 319 | 15 | 395.9 (M$^+$ + 1); | $C_{20}H_{17}N_3O_2S_2$ 395.08 | $^1$H-NMR (DMSO-d$_6$, 400 MHz): δ 10.78 (s, 1H), 8.69 (t, J = 5.7 Hz, 1H), 7.70-7.62 (m, 3H), 7.56-7.42 (m, 4H), 3.58 (q, J = 6.6 Hz, 2H), 3.03 (t, J = 6.8 Hz, 2H), 2.43 (s, 3H); |
| 1614 | 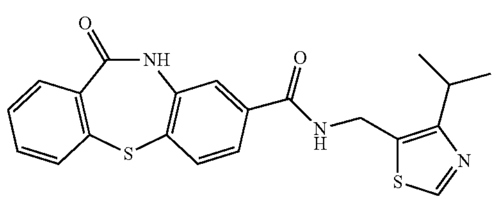 [SMILES: CC(C)c1ncsc1CNC(=O)c1ccc2c(c1)NC(=O)c1ccccc1S2] | A, 6, 327 (Reaction time 24 h) | 27 | 409.9 (M$^+$ + 1); | $C_{21}H_{19}N_3O_2S_2$ 409.09 | $^1$H NMR (DMSO-d$_6$, 400 MHz): δ 10.77 (s, 1H), 9.15 (t, J = 5.8 Hz, 1H), 8.84 (s, 1H), 7.70-7.64 (m, 3H), 7.59-7.42 (m, 4H), 4.58 (d, J = 5.9 Hz, 2H), 3.32-3.29 (m, 1H), 1.21 (d, J = 6.8 Hz, 6H); |
| 1632 | 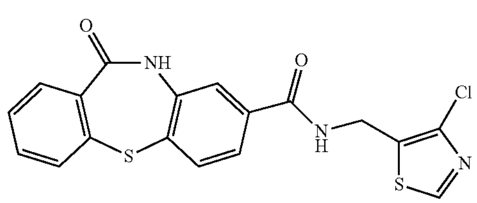 | A, 6, 337 | 33 | 401.9 (M$^+$ + 1); | $C_{18}H_{12}ClN_3O_2S_2$ 401.01 | $^1$H NMR (DMSO-d$_6$, 400 MHz): δ 10.77 (s, 1H), 9.31 (t, J = 5.5 Hz, 1H), 9.01 (s, 1H), 7.73-7.65 (m, 3H), 7.59 (dd, J = 7.9, 1.8 Hz, 1H), 7.56-7.42 (m, 3H), 4.57 (d, J = 5.7 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1640 | 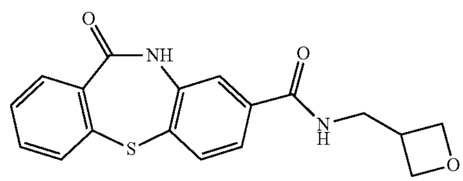 [SMILES: O=C(NCC1COC1)c1ccc2c(c1)NC(=O)c1ccccc1S2] | A, 6, 341 (Reaction time 12 h) | 16 | 341.0 (M$^+$ + 1); | $C_{18}H_{16}N_2O_3S$ 340.09 | $^1$H NMR (DMSO-d$_6$, 400 MHz): δ 10.75 (s, 1H), 8.62 (t, J = 5.5 Hz, 1H), 7.70-7.63 (m, 3H), 7.59-7.43 (m, 4H), 4.60 (dd, J = 7.8, 6.0 Hz, 2H), 4.31 (t, J = 6.0 Hz, 2H), 3.50 (dd, J = 7.8, 6.0 Hz, 2H), 3.17-3.09 (m, 1H). |
| 1235 | 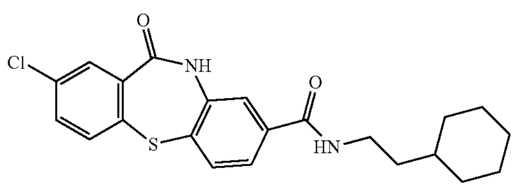 [SMILES: O=C(NCCC1CCCCC1)c1ccc2c(c1)NC(=O)c1cc(Cl)ccc1S2] | A, 14, 261 | 45 | 415.4 (M$^+$ + 1); | $C_{22}H_{23}ClN_2O_2S$ 414.12 | $^1$H-NMR (CDCl$_3$, 400 MHz): δ 8.16 (br s, 1H), 7.81 (s, 1H), 7.61 (d, J = 8.0 Hz, 1H), 7.57 (s, 1H), 7.45-7.42 (m, 2H), 7.39-7.36 (m, 1H), 5.99-5.98 (m, 1H), 3.48-3.43 (m, 2H), 1.75-1.67 (m, 5H), 1.57-1.46 (m, 2H), 1.34-1.31 (m, 1H), 1.27-1.16 (m, 3H), 0.98-0.92 (m, 2H); |
| 1250 | 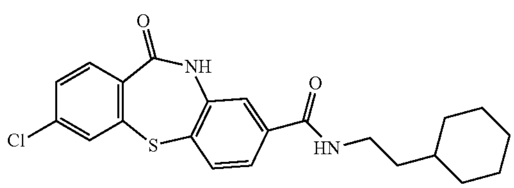 [SMILES: O=C(NCCC1CCCCC1)c1ccc2c(c1)NC(=O)c1ccc(Cl)cc1S2] | A, 21, 261 (285 mg) | 45 | 415.5 (M$^+$ + 1) | $C_{22}H_{23}ClN_2O_2S$ 414.12 | $^1$H-NMR (CDCl$_3$, 400 MHz): δ 8.70 (s, 1H), 7.77 (d, J = 8.4 Hz, 1H), 7.63-7.60 (m, 2H), 7.51 (s, 1H), 7.45 (d, J = 9.6 Hz, 1H), 7.35 (d, J = 10.0 Hz, 1H), 6.07 (t, J = 6.0 Hz, 1H), 3.48-3.43 (m, 2H), 1.73-1.45 (m, 8H), 1.30-1.14 (m, 3H), 1.00-0.91 (m, 2H); |
| 1540 | 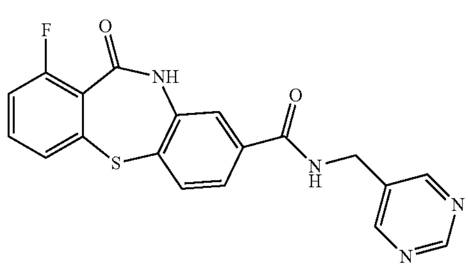 [SMILES: O=C(NCc1cncnc1)c1ccc2c(c1)NC(=O)c1c(F)cccc1S2] | A, 28, 212 (75 mg) | 15 | 381.0 (M$^+$ + 1); | $C_{19}H_{13}FN_4O_2S$ 380.07 | $^1$H NMR (DMSO-d$_6$, 400 MHz): δ 10.94 (br s, 1H), 9.20 (t, J = 5.7 Hz, 1H), 9.08 (s, 1H), 8.75 (s, 2H), 7.75-7.60 (m, 3H), 7.53-7.46 (m, 1H), 7.41 (dd, J = 7.8, 0.9 Hz, 1H), 7.32-7.28 (m, 1H), 4.47 |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| | | | | | | (d, J = 5.6 Hz, 2H); |
| 1541 | 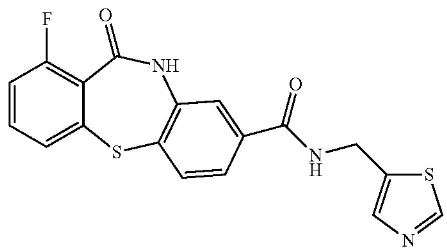 [SMILES: O=C(NCc1cncs1)c1ccc2c(c1)NC(=O)c1c(F)cccc1S2] | A, 28, 213 | 22 | 385.9 (M⁺ + 1); | $C_{18}H_{12}FN_3O_2S_2$ 385.04 | ¹H-NMR (DMSO-d₆, 400 MHz): δ 10.95 (s, 1H), 9.25 (t, J = 5.7 Hz, 1H), 8.96 (s, 1H), 7.80 (s, 1H), 7.71-7.65 (m, 2H), 7.60 (dd, J = 8.0, 2.0 Hz, 1H), 7.52-7.46 (m, 1H), 7.40 (d, J = 7.7 Hz, 1H), 7.34-7.28 (m, 1H), 4.65 (d, J = 5.7 Hz, 2H); |
| 1542 | 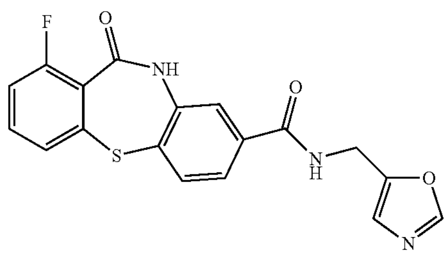 [SMILES: O=C(NCc1cnco1)c1ccc2c(c1)NC(=O)c1c(F)cccc1S2] | A, 28, 214 | 31 | 370.0 (M⁺ + 1); | $C_{18}H_{12}FN_3O_3S$ 369.06 | ¹H NMR (DMSO-d₆, 400 MHz): δ 10.95 (s, 1H), 9.09 (t, J = 5.4 Hz, 1H), 8.27 (s, 1H), 7.72-7.65 (m, 2H), 7.61 (dd, J = 8.0, 1.9 Hz, 1H), 7.53-7.46 (m, 1H), 7.40 (d, J = 7.2 Hz, 1H), 7.34-7.27 (m, 1H), 7.03 (s, 1H), 4.51 (d, J = 5.4 Hz, 2H); |
| 1543 | 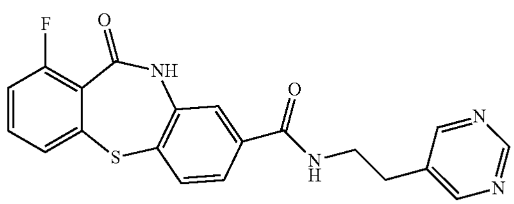 [SMILES: O=C(NCCc1cncnc1)c1ccc2c(c1)NC(=O)c1c(F)cccc1S2] | A, 28, 215 | 22 | 370.0 (M⁺ + 1); | $C_{20}H_{15}FN_4O_2S$ 394.09 | ¹H NMR (DMSO-d₆, 400 MHz): δ 10.96 (s, 1H), 9.01 (s, 1H), 8.69-8.60 (m, 3H), 7.66 (d, J = 8.0 Hz, 1H), 7.62 (s, 1H), 7.51 (dd, J = 8.2, 2.0 Hz, 1H), 7.49-7.46 (m, 1H), 7.40 (d, J = 7.8 Hz, 1H), 7.28-7.33 (m, 1H), 3.53 (q, J = 6.4 Hz, 2H), 2.84 (t, J = 6.6 Hz, 2H); |
| 1471 | 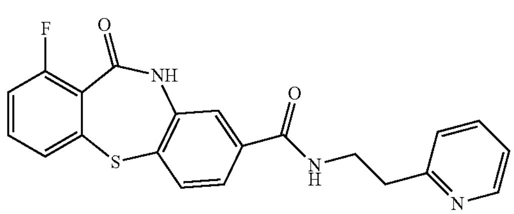 [SMILES: O=C(NCCc1ccccn1)c1ccc2c(c1)NC(=O)c1c(F)cccc1S2] | A, 28, 216 | 22 | 393.9 (M⁺ + 1) | $C_{21}H_{16}FN_3O_2S$ 393.09 | ¹H NMR (DMSO-d₆, 400 MHz): δ 10.96 (s, 1H), 8.63 (t, J = 5.5 Hz, 1H), 8.52-8.47 (m, 1H), 7.71-7.64 (m, 3H), 7.55 (dd, J = 8.2, 1.8 Hz, 1H), 7.51-7.49 (m, 1H), 7.40 (d, J = 7.4 Hz, 1H), 7.31- |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | (t, J = 9.2 Hz, 1H), 7.25 (d, J = 7.7 Hz, 1H), 7.23-7.19 (m, 1H), 3.59 (q, J = 6.8 Hz, 2H), 2.96 (t, J = 7.3 Hz, 2H); |
| 1555 | 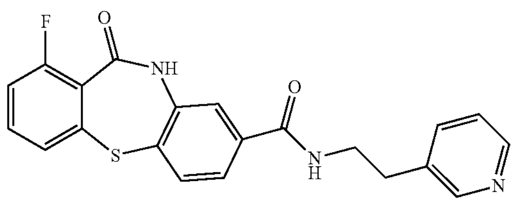 [SMILES: O=C(NCCc1cccnc1)c1ccc2c(c1)NC(=O)c1c(F)cccc1S2] | A, 28, 217 | 20 | 393.9 (M$^+$ + 1); | $C_{21}H_{16}FN_3O_2S$ 393.09 | $^1$H NMR (DMSO-d$_6$, 400 MHz): δ 10.97 (s, 1H), 8.64 (t, J = 5.5 Hz, 1H), 8.43 (s, 1H), 8.40 (dd, J = 4.8, 1.6 Hz, 1H), 7.68-7.61 (m, 3H), 7.53 (dd, J = 8.0, 2.0 Hz, 1H), 7.51-7.46 (m, 1H), 7.40 (d, J = 7.8, Hz, 1H), 7.34-7.27 (m, 2H), 3.49 (q, J = 7.0 Hz, 2H), 2.84 (t, J = 7.0 Hz, 2H); |
| 1490 | 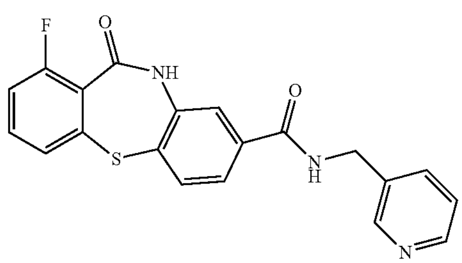 [SMILES: O=C(NCc1cccnc1)c1ccc2c(c1)NC(=O)c1c(F)cccc1S2] | A, 28, 218 | 27 | 393.9 (M$^+$ + 1); | $C_{20}H_{14}FN_3O_2S$ 379.08 | $^1$H NMR (DMSO-d$_6$, 400 MHz): δ 10.96 (s, 1H), 9.15 (t, J = 5.7 Hz, 1H), 8.52 (s, 1H), 8.45 (dd, J = 4.7, 1.4 Hz, 1H), 7.73-7.66 (m, 3H), 7.63 (dd, J = 8.2, 1.8 Hz, 1H), 7.54-7.44 (m, 1H), 7.40 (d, J = 7.3 Hz, 1H), 7.36-7.28 (m, 2H), 4.46 (d, J = 5.6 Hz, 2H); |
| 1463 | 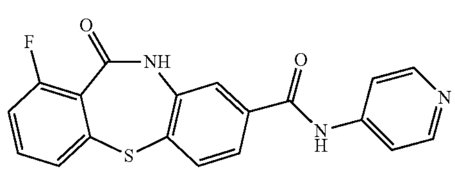 | A, 28, 185 | 39 | 365.9 (M$^+$ + 1); | $C_{19}H_{12}FN_3O_2S$ 365.06 | $^1$H NMR (DMSO-d$_6$, 400 MHz): δ 11.04 (s, 1H), 10.63 (s, 1H), 8.48 (d, J = 6.0 Hz, 2H), 7.80-7.69 (m, 5H), 7.43 (d, J = 7.6 Hz, 2H), 7.33 (t, J = 9.1 Hz, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1472 | 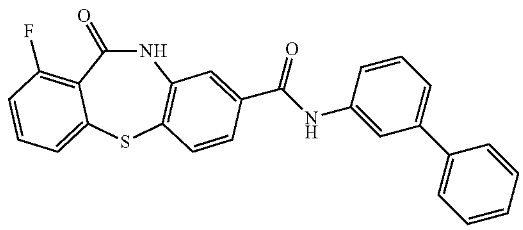 [SMILES: O=C(Nc1cccc(-c2ccccc2)c1)c1ccc2c(c1)NC(=O)c1c(F)cccc1S2] | A, 28, 186 | 13 | 440.9 (M$^+$ + 1); | $C_{26}H_{17}FN_2O_2S$ 440.10 | $^1$H NMR (DMSO-d$_6$, 400 MHz): δ 11.04 (s, 1H), 10.38 (s, 1H), 8.07-8.04 (m, 1H), 7.82-7.72 (m, 4H), 7.67-7.61 (m, 2H), 7.55-7.30 (m, 8H); |
| 1580 | 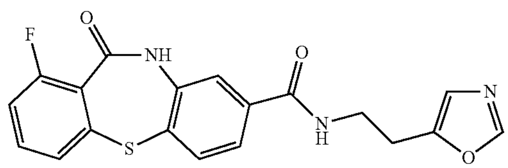 | A, 28, 347 | 9 | 384.0 (M$^+$ + 1); | $C_{19}H_{14}FN_3O_3S$ 383.07 | $^1$H NMR (DMSO-d$_6$, 400 MHz): δ 10.98 (s, 1H), 8.68 (t, J = 5.6 Hz, 1H), 8.22 (s, 1H), 7.69-7.64 (m, 2H), 7.55 (dd, J = 8.0, 1.9 Hz, 1H), 7.53-7.46 (m, 1H), 7.40 (dd, J = 7.6, 0.9 Hz, 1H), 7.36-7.28 (m, 1H), 6.92 (s, 1H), 3.49 (q, J = 6.2 Hz, 2H), 2.90 (t, J = 6.7 Hz, 2H); |
| 1598 | 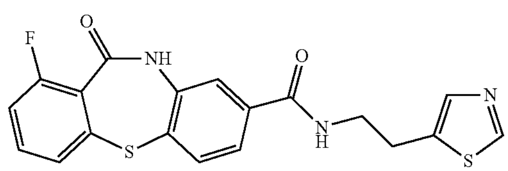 [SMILES: O=C(NCCc1cnco1)c1ccc2c(c1)NC(=O)c1c(F)cccc1S2] | A, 28, 352 | 29 | 399.9 (M$^+$ + 1); | $C_{19}H_{14}FN_3O_2S_2$ 399.05 | $^1$H NMR (DMSO-d$_6$, 400 MHz): δ 10.98 (br s, 1H), 8.91 (s, 1H), 8.70 (t, J = 5.6 Hz, 1H), 7.68 (d, J = 7.9 Hz, 3H), 7.57 (dd, J = 8.0, 1.9 Hz, 1H), 7.53-7.47 (m, 1H), 7.41 (d, J = 7.1 Hz, 1H), 7.35-7.29 (m, 1H), 3.48 (q, J = 5.9 Hz, 2H), 3.10 (t, J = 6.7 Hz, 2H); |
| 1465 | 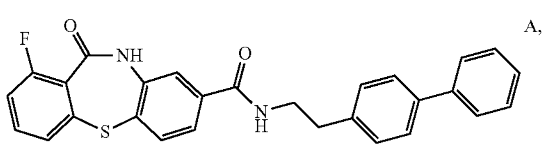 | A, 28, 219 | 30 | 469.0 (M$^+$ + 1); | $C_{28}H_{21}FN_2O_2S$ 468.13 | $^1$H NMR (DMSO-d$_6$, 400 MHz): δ 10.97 (s, 1H), 8.66 (t, J = 5.3 Hz, 1H), 7.77-7.24 (m, 15H), 3.50 (q, J = 7.0 Hz, 2H), 2.86 (t, J = 7.0 Hz, 2H); |
| 1477 | 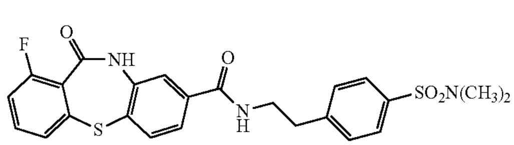 | A, 28, 406 | 12 | 500.1 (M$^+$ + 1); | $C_{24}H_{22}FN_3O_4S_2$ 499.10 | $^1$H NMR (DMSO-d$_6$, 400 MHz): δ 10.97 (s, 1H), 8.63 (t, J = 5.5 Hz, 1H), 7.69-7.61 (m, 4H), 7.54-7.46 (m, 4H), 7.40 (d, J = 7.0 Hz, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 1H), 7.34-7.28 (m, 1H), 3.56-3.46 (m, 2H), 2.93 (t, J = 7.0 Hz, 2H), 2.54 (s, 6H); |
| 1308 | 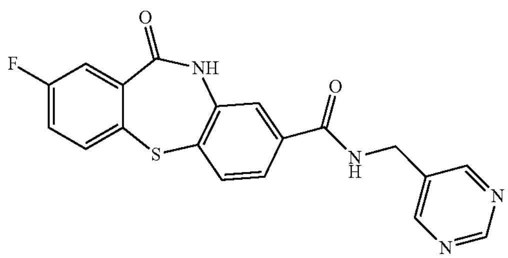 [SMILES: O=C(NCc1cncnc1)c1ccc2c(c1)NC(=O)c1cc(F)ccc1S2] | A, 35, 212 | 39 | 380.9 (M$^+$ + 1); | $C_{19}H_{13}FN_4O_2S$ 380.07 | $^1$H-NMR (DMSO-d$_6$, 400 MHz): δ 10.89 (s, 1H), 9.16 (t, J = 5.6 Hz, 1H), 9.07 (s, 1H), 8.74 (s, 2H), 7.71-7.66 (m, 2H), 7.64-7.58 (m, 2H), 7.47 (dd, J = 9.2, 2.8 Hz, 1H), 7.37 (dt, J = 11.6, 3.2 Hz, 1H), 4.47 (d J = 5.6 Hz, 2H); |
| 1309 | 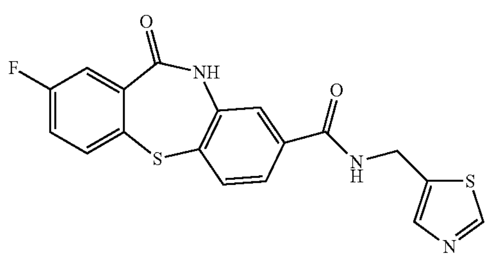 | B, 25, 213 | 21 | 385.9 (M$^+$ + 1); | $C_{18}H_{12}FN_3O_2S_2$ 385.04 | $^1$H-NMR (DMSO-d$_6$, 400 MHz): δ 10.89 (br s, 1H), 9.24 (t, J = 5.6 Hz, 1H), 8.95 (br s, 1H), 7.80 (br s, 1H), 7.70-7.65 (m, 2H), 7.61-7.57 (m, 2H), 7.47 (d, J = 6.4 Hz, 1H), 7.39-7.37 (m, 1H), 4.64 (d, J = 5.6 Hz, 2H); |
| 1310 | 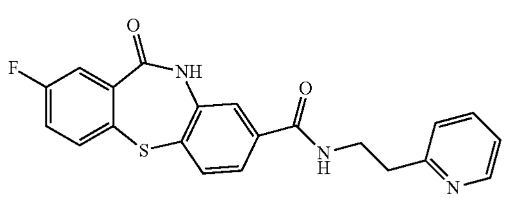 [SMILES: O=C(NCCc1ccccn1)c1ccc2c(c1)NC(=O)c1cc(F)ccc1S2] | A, 35, 216 | 44 | 393.9 (M$^+$ + 1); | $C_{21}H_{16}FN_3O_2S$ 393.09 | $^1$H-NMR (DMSO-d$_6$, 400 MHz): δ 10.89 (s, 1H), 8.62 (t, J = 5.6 Hz, 1H), 8.47 (d, J = 8.0 Hz, 1H), 7.70-7.61 (m, 3H), 7.59-7.54 (m, 2H), 7.48 (dd, J = 9.2, 2.8 Hz, 1H), 7.36 (dt, J = 11.6, 3.2 Hz, 1H), 7.24 (d, J = 8.0 Hz, 1H), 7.22-7.19 (m, 1H), 3.61-3.50 (m, 2H), 2.96 (t, J = 7.2 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1311 | 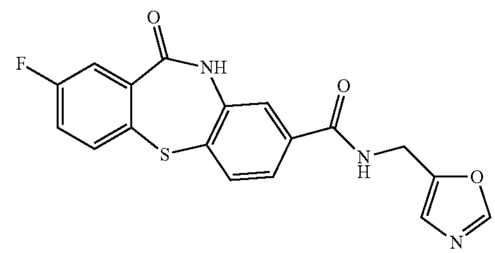 [SMILES: O=C(NCc1cnco1)c1ccc2c(c1)NC(=O)c1cc(F)ccc1S2] | A, 35, 214 | 35 | 369.9 (M$^+$ + 1); | $C_{18}H_{12}FN_3O_3S$ 369.06 | $^1$H-NMR (DMSO-d$_6$, 400 MHz): δ 10.89 (br s, 1H), 9.07 (t, J = 5.2 Hz, 1H), 8.27 (s, 1H), 7.70 (s, 1H), 7.66 (d, J = 8.0 Hz, 1H), 7.62-7.57 (m, 2H), 7.48 (dd, J = 9.2, 2.8 Hz, 1H), 7.37 (dt, J = 11.6, 3.2 Hz, 1H), 7.03 (s, 1H), 4.50 (d, J = 5.2 Hz, 2H); |
| 1312 | 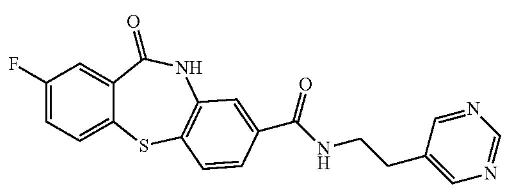 [SMILES: O=C(NCCc1cncnc1)c1ccc2c(c1)NC(=O)c1cc(F)ccc1S2] | A, 35, 215 | 11 | 395.2 (M$^+$ + 1); | $C_{20}H_{15}FN_4O_2S$ 394.09 | $^1$H-NMR (DMSO-d$_6$, 400 MHz): δ 10.89 (br s, 1H), 9.01 (s, 1H), 8.65-8.62 (m, 3H), 7.65-7.35 (m, 6H), 3.52 (t, J = 6.4 Hz, 2H), 2.84 (t, J = 6.4 Hz, 2H); |
| 1313 | 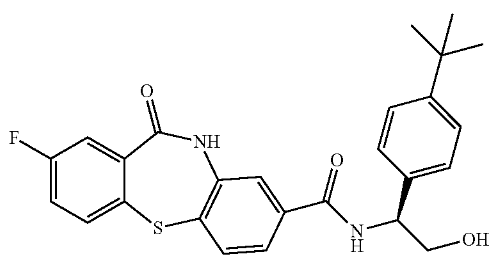 [SMILES: CC(C)(C)c1ccc([C@@H](CO)NC(=O)c2ccc3c(c2)NC(=O)c2cc(F)ccc2S3)cc1] | A, 35, 220 | 69 | 465.2 (M$^+$ + 1); | $C_{26}H_{25}FN_2O_3S$ 464.16 | $^1$H-NMR (DMSO-d$_6$, 400 MHz): δ 10.88 (s, 1H), 8.72 (d, J = 8.0 Hz, 1H), 7.70 (s, 1H), 7.66 (s, 2H), 7.62-7.58 (m, 1H), 7.47 (dd, J = 8.8, 2.8 Hz, 1H), 7.37 (dt, J = 11.6, 3.2 Hz, 1H), 7.32-7.25 (m, 4H), 5.01-4.95 (m, 1H), 4.86 (t, J = 6.0 Hz, 1H), 3.68-3.57 (m, 2H), 1.24 (s, 9H); |
| 1316 | 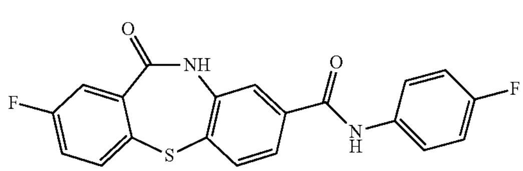 [SMILES: O=C(Nc1ccc(F)cc1)c1ccc2c(c1)NC(=O)c1cc(F)ccc1S2] | A, 35, 221 | 50 | 382.8 (M$^+$ + 1) | $C_{20}H_{12}F_2N_2O_2S$ 382.06 | $^1$H-NMR (DMSO-d$_6$, 400 MHz): δ 10.96 (s, 1H), 10.35 (s, 1H), 7.76-7.72 (m, 5H), 7.63-7.60 (m, 1H), 7.50 (dd, J = 9.2, 2.8 Hz, 1H), 7.41-7.36 (m, 1H), 7.19 (t, J = 8.8 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1321 | 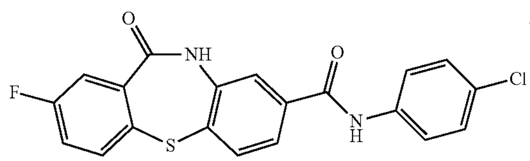 [SMILES: O=C(Nc1ccc(Cl)cc1)c1ccc2c(c1)NC(=O)c1cc(F)ccc1S2] | A, 35, 222 | 51 | 398.9 (M$^+$ + 1) | C$_{20}$H$_{12}$ClFN$_2$O$_2$S 398.03 | $^1$H-NMR (DMSO-d$_6$, 400 MHz): δ 10.94 (s, 1H), 10.40 (s, 1H), 7.78-7.70 (m, 5H), 7.63-7.60 (m, 1H), 7.50 (dd, J = 9.2, 3.2 Hz, 1H), 7.41-7.37 (m, 3H); |
| 1320 | 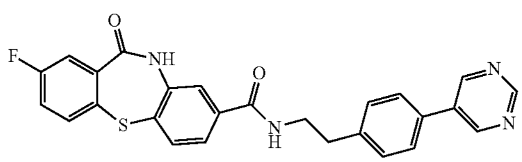 [SMILES: O=C(NCCc1ccc(-c2cncnc2)cc1)c1ccc2c(c1)NC(=O)c1cc(F)ccc1S2] | A, 35, 359 | 7 | 471.0 (M$^+$ + 1) | C$_{26}$H$_{19}$FN$_4$O$_2$S 470.12 | $^1$H-NMR (DMSO-d$_6$, 400 MHz): δ 10.90 (s, 1H), 9.15 (s, 1H), 9.11 (s, 1H), 8.64 (t, J = 5.2 Hz, 1H), 7.73 (d, J = 8.0 Hz, 2H), 7.67-7.61 (m, 2H), 7.59-7.55 (m, 2H), 7.48 (dd, J = 9.2, 2.8 Hz, 1H), 7.40-7.34 (m, 2H), 3.50 (q, 2H), 2.89 (t, J = 7.2 Hz, 2H); |
| 1343 | 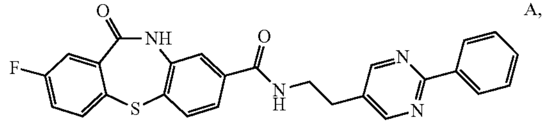 | A, 35, 367 | 49 | 471.4 (M$^+$ + 1); | C$_{26}$H$_{19}$FN$_4$O$_2$S 470.12 | $^1$H-NMR (DMSO-d$_6$, 400 MHz): δ 10.88 (s, 1H), 8.75 (s, 2H), 8.64 (t, J = 6.0 Hz, 1H), 8.36-8.34 (m, 2H), 7.65-7.63 (m, 2H), 7.60-7.57 (m, 2H), 7.55-7.45 (m, 4H), 7.39-7.34 (m, 1H), 3.56 (q, J = 6.4 Hz, 2H), 2.88 (t, J = 6.8 Hz, 2H); |
| 1314 | 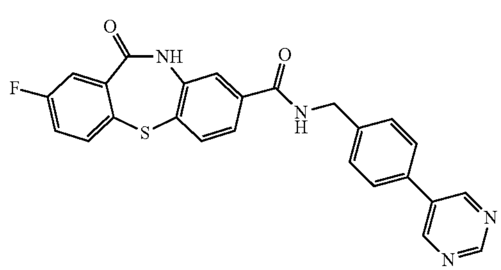 [SMILES: O=C(NCc1ccc(-c2cncnc2)cc1)c1ccc2c(c1)NC(=O)c1cc(F)ccc1S2] | A, 35, 372 | 13 | 457.0 (M$^+$ + 1) | C$_{25}$H$_{17}$FN$_4$O$_2$S 456.11 | $^1$H-NMR (DMSO-d$_6$, 400 MHz): δ 10.91 (s, 1H), 9.20 (t, J = 6.0 Hz, 1H), 9.17 (s, 1H), 9.11 (s, 2H), 7.77-7.74 (m, 3H), 7.67 (s, 2H), 7.62-7.58 (m, 1H), 7.50-7.40 (m, 3H), 7.38 (td, J = 11.6, 3.2 Hz, 1H), 4.50 (d, J = 6.0 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1315 | 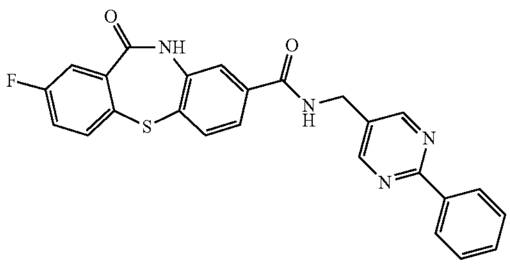 [SMILES: O=C(NCc1cnc(-c2ccccc2)nc1)c1ccc2c(c1)NC(=O)c1cc(F)ccc1S2] | A, 35, 377 | 32 | 456.9 ($M^+ + 1$); | $C_{25}H_{17}FN_4O_2S$ 456.11 | $^1$H-NMR (DMSO-$d_6$, 400 MHz): δ 10.89 (s, 1H), 9.17 (t, J = 5.6 Hz, 1H), 8.84 (s, 2H), 8.38-8.35 (m, 2H), 7.72 (s, 1H), 7.69-7.60 (m, 2H), 7.59-7.58 (m, 1H), 7.52-7.51 (m, 3H), 7.49-7.46 (m, 1H), 7.37 (td, J = 11.6, 2.8 Hz, 1H), 4.50 (d, J = 6.0 Hz, 2H); |
| 1317 | 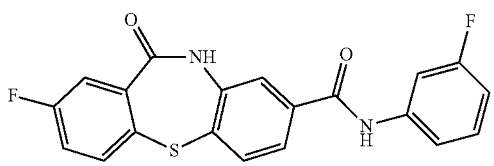 [SMILES: O=C(Nc1cccc(F)c1)c1ccc2c(c1)NC(=O)c1cc(F)ccc1S2] | A, 35, 223 | 30 | 382.9 ($M^+ + 1$); | $C_{20}H_{12}F_2N_2O_2S$ 382.06 | $^1$H-NMR (DMSO-$d_6$, 400 MHz): δ 10.96 (s, 1H), 10.46 (s, 1H), 7.76-7.68 (m, 4H), 7.64-7.60 (m, 1H), 7.52-7.49 (m, 2H), 7.41-7.35 (m, 2H), 6.93 (dt, J = 10.0, 1.6 Hz, 1H); |
| 1334 | 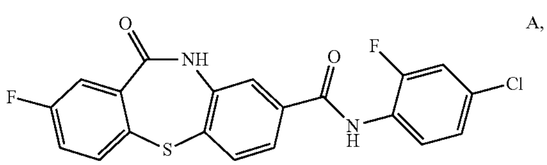 | A, 35, 224 | 14 | 417.6 ($M^+ + 1$); | $C_{20}H_{11}ClF_2N_2O_2S$ 416.02 | $^1$H-NMR (DMSO-$d_6$, 400 MHz): δ 10.94 (s, 1H), 10.26 (s, 1H), 7.78 (s, 1H), 7.75-7.70 (m, 2H), 7.64-7.60 (m, 2H), 7.54-7.51 (m, 2H), 7.39 (dt, J = 11.6, 3.2 Hz, 1H), 7.31 (dd, J = 8.8, 1.2 Hz, 1H); |
| 1322 | 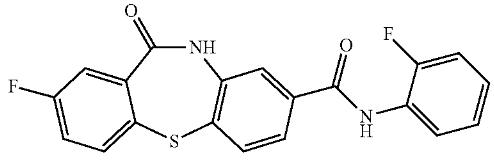 [SMILES: O=C(Nc1ccccc1F)c1ccc2c(c1)NC(=O)c1cc(F)ccc1S2] | A, 35, 225 | 15 | 382.9 ($M^+ + 1$) | $C_{20}H_{12}F_2N_2O_2S$ 382.06 | $^1$H-NMR (DMSO-$d_6$, 400 MHz): δ 10.94 (s, 1H), 10.18 (s, 1H), 7.78 (s, 1H), 7.75-7.74 (m, 2H), 7.64-7.55 (m, 2H), 7.50 (dd, J = 9.2, 2.8 Hz, 1H), 7.39 (dt, J = 8.8, 2.8 Hz, 1H), 7.31-7.26 (m, 2H), 7.24-7.19 (m, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1323 | 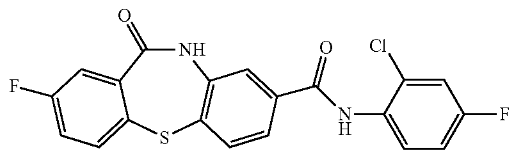 [SMILES: O=C(Nc1ccc(F)cc1Cl)c1ccc2c(c1)NC(=O)c1cc(F)ccc1S2] | C, 35, 226 | 21 | 417.7 (M$^+$ + 1) | C$_{20}$H$_{11}$ClF$_2$N$_2$O$_2$S 416.02 | $^1$H-NMR (DMSO-d$_6$, 400 MHz): δ 10.94 (s, 1H), 10.16 (s, 1H), 7.80 (s, 1H), 7.77-7.72 (m, 2H), 7.63-7.60 (m, 1H), 7.57-7.53 (m, 2H), 7.50 (dd, J = 9.2, 2.8 Hz, 1H), 7.39 (td, J = 11.2, 2.8 Hz, 1H), 7.27 (td, J = 11.2, 2.8 Hz, 1H); |
| 1324 | 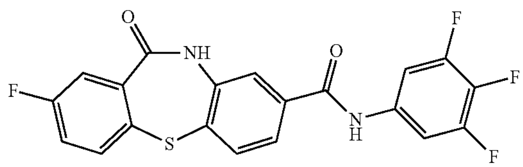 [SMILES: O=C(Nc1cc(F)c(F)c(F)c1)c1ccc2c(c1)NC(=O)c1cc(F)ccc1S2] | A, 35, 227 | 7 | 419.2 (M$^+$ + 1) | C$_{20}$H$_{10}$F$_4$N$_2$O$_2$S 418.04 | $^1$H-NMR (DMSO-d$_6$, 400 MHz): δ 10.98 (br s, 1H), 10.60 (br s, 1H), 7.77-7.66 (m, 5H), 7.63-7.60 (m, 1H), 7.51 (dd, J = 9.2, 2.8 Hz, 1H), 7.41-7.37 (m, 1H); |
| 1318 | 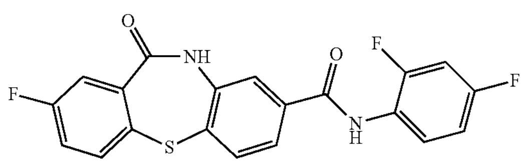 [SMILES: O=C(Nc1ccc(F)cc1F)c1ccc2c(c1)NC(=O)c1cc(F)ccc1S2] | A, 35, 228 | 67 | 401.2 (M$^+$ + 1), | C$_{20}$H$_{11}$F$_3$N$_2$O$_2$S 400.05 | $^1$H-NMR (DMSO-d$_6$, 400 MHz): δ 10.93 (s, 1H), 10.19 (s, 1H), 7.78 (s, 2H), 7.63-7.48 (m, 3H), 7.41-7.32 (m, 2H), 7.11 (t, J = 8.8 Hz, 1H); |
| 1319 | 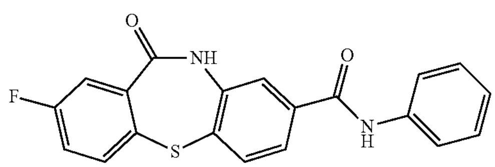 [SMILES: O=C(Nc1ccccc1)c1ccc2c(c1)NC(=O)c1cc(F)ccc1S2] | A, 35, 179 | 53 | 364.9 (M$^+$ + 1); | C$_{20}$H$_{13}$FN$_2$O$_2$S 364.07 | $^1$H-NMR (DMSO-d$_6$, 400 MHz): δ 10.95 (s, 1H), 10.29 (s, 1H), 7.76 (s, 1H), 7.73-7.72 (m, 4H), 7.64-7.60 (m, 1H), 7.51 (dd, J = 9.2, 2.8 Hz, 1H), 1H), 7.40 (dd, J = 8.4, 2.8 Hz, 1H), 7.37-7.32 (m, 2H), 7.10 (t, J = 7.6 Hz, 1H); |
| 1328 | 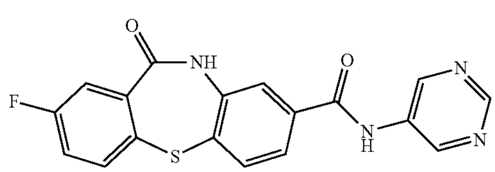 [SMILES: O=C(Nc1cncnc1)c1ccc2c(c1)NC(=O)c1cc(F)ccc1S2] | A, 35, 229 | 5 | 366.9 (M$^+$ + 1), | C$_{18}$H$_{11}$FN$_4$O$_2$S 366.06 | $^1$H-NMR (DMSO-d$_6$, 400 MHz): δ 10.99 (s, 1H), 10.69 (s, 1H), 9.13 (s, 2H), 8.93 (s, 1H), 7.80 (s, 1H), 7.77 (s, 2H), 7.64-7.60 (m, 1H), 7.51 (dd, J = 9.2, 3.2 Hz, 1H), 7.39 (dt, J = 11.2, 2.8 Hz, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1344 | 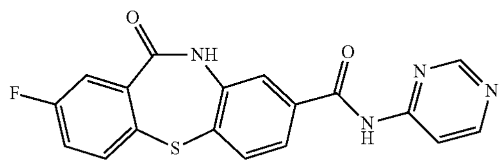 [SMILES: O=C(Nc1ccncn1)c1ccc2c(c1)NC(=O)c1cc(F)ccc1S2] | C, 35, 230 | 8 | 367.5 (M$^+$ + 1); | C$_{18}$H$_{11}$FN$_4$O$_2$S 366.06 | $^1$H NMR (DMSO-d$_6$, 400 MHz): δ 11.29 (s, 1H), 10.94 (s, 1H), 8.95 (s, 1H), 8.72 (d, J = 5.8 Hz, 1H), 8.17 (d, J = 5.7 Hz, 1H), 7.83-7.76 (m, 2H), 7.75-7.67 (m, 1H), 7.62 (dd, J = 8.5, 5.1 Hz, 1H), 7.51 (dd, J = 9.1, 2.8 Hz, 1H), 7.39 (t, J = 8.0 Hz, 1H); |
| 1329 | 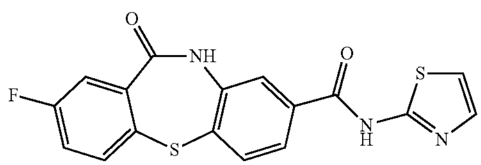 [SMILES: O=C(Nc1nccs1)c1ccc2c(c1)NC(=O)c1cc(F)ccc1S2] | A, 35, 231 | 28 | 371.9 (M$^+$ + 1) | C$_{17}$H$_{10}$FN$_3$O$_2$S$_2$ 371.02 | $^1$H-NMR (DMSO-d$_6$, 400 MHz): δ 12.70 (br s, 1H), 10.98 (s, 1H), 7.87-7.86 (m, 2H), 7.72 (d, J = 8.4 Hz, 1H), 7.63-7.60 (m, 1H), 7.51 (dt, J = 9.2, 2.8 Hz, 2H), 7.41-7.37 (m, 1H), 7.28-7.25 (m, 1H); |
| 1335 | 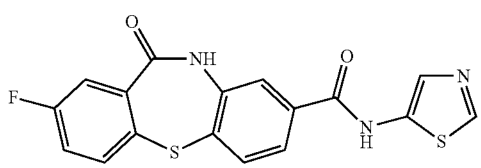 | A, 35, 380 | 17 | 371.8 (M$^+$ + 1); | C$_{17}$H$_{10}$FN$_3$O$_2$S$_2$ 371.02 | $^1$H-NMR (DMSO-d$_6$, 400 MHz): δ 11.79 (br s, 1H), 10.98 (s, 1H), 8.62 (s, 1H), 7.79-7.73 (m, 2H), 7.61-7.58 (m, 2H), 7.50-7.47 (m, 1H), 7.47 (d, J = 9.2, 2.8 Hz, 1H), 7.37 (td, J = 11.2, 3.2 Hz, 1H); |
| 1353 | 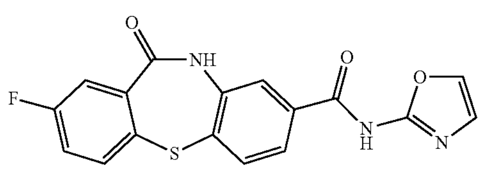 [SMILES: O=C(Nc1ncco1)c1ccc2c(c1)NC(=O)c1cc(F)ccc1S2] | A, 35, 232 | 4 | 355.8 (M$^+$ + 1), | C$_{17}$H$_{10}$FN$_3$O$_3$S 355.04 | $^1$H-NMR (DMSO-d$_6$, 400 MHz): δ 11.62 (br s, 1H), 10.94 (br s, 1H), 7.95-7.85 (m, 1H), 7.81-7.69 (m, 3H), 7.63-7.59 (m, 1H), 7.50 (d, J = 6.4 Hz, 1H), 7.40-7.37 (m, 1H), 7.20 (br s, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1330 | 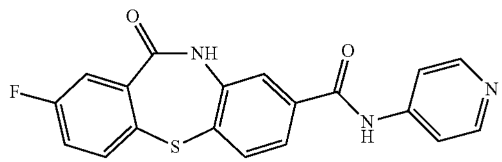 [SMILES: O=C(Nc1ccncc1)c1ccc2c(c1)NC(=O)c1cc(F)ccc1S2] | C, 35, 185 | 20 | 365.8 (M$^+$ + 1), | $C_{19}H_{12}FN_3O_2S$ 365.06 | $^1$H-NMR (DMSO-d$_6$, 400 MHz): δ 10.97 (s, 1H), 10.63 (s, 1H), 8.48-8.47 (m, 2H), 7.77-7.73 (m, 5H), 7.64-7.60 (m, 1H), 7.51 (dd, J = 9.2, 2.8 Hz, 1H), 7.39 (td, J = 11.2, 2.8 Hz, 1H); |
| 1336 | 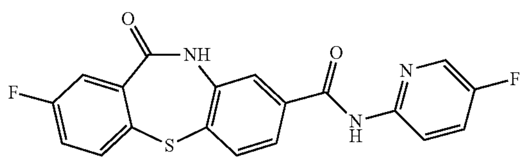 [SMILES: O=C(Nc1ccc(F)cn1)c1ccc2c(c1)NC(=O)c1cc(F)ccc1S2] | C, 35, 233 | 30 | 383.9 (M + 1)$^+$, | $C_{19}H_{11}F_2N_3O_2S$ 383.05 | $^1$H-NMR (DMSO-d$_6$, 400 MHz): δ 10.98 (s, 1H), 10.93 (s, 1H), 8.39-8.35 (m, 1H), 8.17 (dd, J = 9.2, 4.0 Hz, 1H), 7.82-7.77 (m, 3H), 7.69 (d, J = 8.0 Hz, 1H), 7.63-7.60 (m, 1H), 7.50 (dd, J = 9.2, 2.8 Hz, 1H), 7.38 (td, J = 11.6, 3.2 Hz, 1H); |
| 1337 | 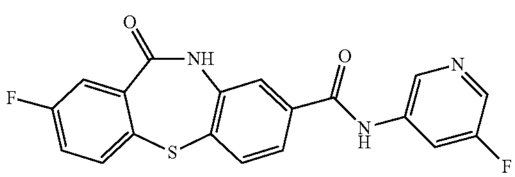 [SMILES: O=C(Nc1cncc(F)c1)c1ccc2c(c1)NC(=O)c1cc(F)ccc1S2] | B, 35, 234 | 14 | 383.9 (M$^+$ + 1), | $C_{19}H_{11}F_2N_3O_2S$ 383.05 | $^1$H-NMR (DMSO-d$_6$, 400 MHz): δ 10.98 (br s, 1H), 10.73 (br s, 1H), 8.74 (s, 1H), 8.34 (s, 1H), 8.16 (d, J = 9.2 Hz, 1H), 7.78 (s, 1H), 7.76 (s, 2H), 7.64-7.60 (m, 1H), 7.51 (dd, J = 9.2, 3.2 Hz, 1H), 7.39 (dt, J = 11.6, 3.2 Hz, 1H); |
| 1338 | 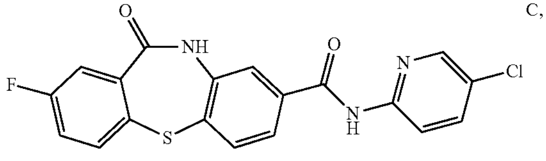 | C, 35, 235 | 12 | 400.5 (M + 1)$^+$, | $C_{19}H_{11}ClFN_3O_2S$ 399.02 | $^1$H-NMR (DMSO-d$_6$, 400 MHz): δ 11.01 (br s, 2H), 8.43 (br s, 1H), 8.18 (d, J = 8.8 Hz, 1H), 7.95 (d, J = 8.4 Hz, 1H), 7.80-7.77 (m, 2H), 7.69 (d, J = 7.6 Hz, 1H), 7.61-7.60 (m, 1H), 7.50 (d, J = 9.2 Hz, 1H), 7.38 (t, J = 8.0 Hz, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1345 | 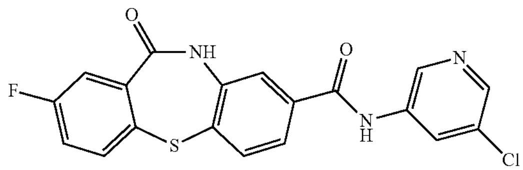 [SMILES: O=C(Nc1cncc(Cl)c1)c1ccc2c(c1)NC(=O)c1cc(F)ccc1S2] | C, 35, 236 | 6 | 400.5 (M⁺ + 1), | $C_{19}H_{11}ClFN_3O_2S$ 399.02 | ¹H-NMR (DMSO-d₆, 400 MHz): δ 10.97 (br s, 1H), 10.71 (br s, 1H), 8.82 (br s, 1H), 8.36 (d, J = 7.6 Hz, 2H), 7.78-7.76 (m, 3H), 7.62 (t, J = 7.6 Hz, 1H), 7.51 (d, J = 8.0 Hz, 1H), 7.39 (t, J = 7.2 Hz, 1H); |
| 1331 | 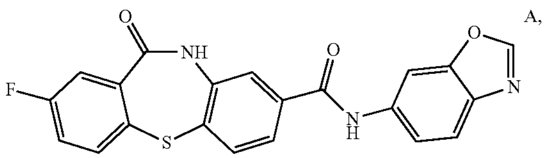 | A, 35, 237 | 21 | 406.6 (M⁺ + 1), | $C_{21}H_{12}FN_3O_3S$ 405.06 | ¹H-NMR (DMSO-d₆, 400 MHz): δ 10.97 (s, 1H), 10.55 (s, 1H), 8.68 (s, 1H), 8.31 (s, 1H), 7.79-7.75 (m, 4H), 7.60-7.61 (m, 2H), 7.51 (dd, J = 9.2, 2.8 Hz, 1H), 7.39 (dt, J = 11.6, 3.2 Hz, 1H); |
| 1354 | 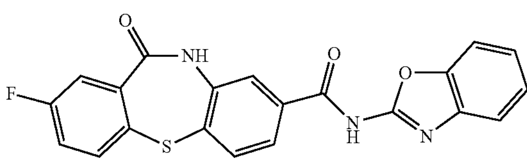 [SMILES: O=C(Nc1nc2ccccc2s1)c1ccc2c(c1)NC(=O)c1cc(F)ccc1S2] | Cᵃ, 35, 238 (a = Et₃N, DMAP | 14 | 405.9 (M⁺ + 1), | $C_{21}H_{12}FN_3O_3S$ 405.06 | ¹H-NMR (DMSO-d₆, 400 MHz): δ 12.44 (br s, 1H), 10.94 (s, 1H), 7.92 (br s, 1H), 7.86-7.84 (m, 1H), 7.72 (d, J = 8.0 Hz, 1H), 7.62-7.60 (m, 2H), 7.55-7.49 (m, 2H), 7.40-7.30 (m, 3H); |
| 1325 | 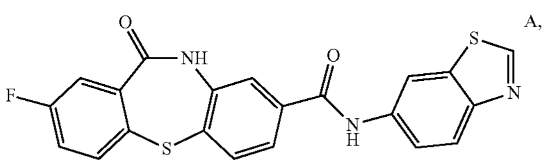 | A, 35, 239 | 25 | 422.0 (M⁺ + 1); | $C_{21}H_{12}FN_3O_2S_2$ 421.04 | ¹H-NMR (DMSO-d₆, 400 MHz): δ 10.97 (s, 1H), 10.56 (s, 1H), 9.30 (s, 1H), 8.65 (s, 1H), 8.05 (d, J = 8.8 Hz, 1H), 7.79-7.73 (m, 4H), 7.64-7.61 (m, 1H), 7.51 (dd, J = 9.2, 2.8 Hz, 1H), 7.39 (dt, J = 11.2, 2.8 Hz, 1H); |
| 1339 | 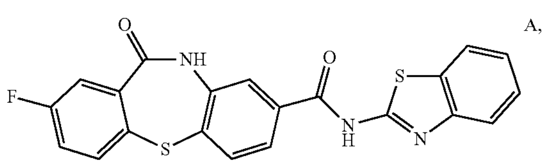 | A, 35, 240 | 28 | 422.3 (M⁺ + 1), | $C_{21}H_{12}FN_3O_2S_2$ 421.04 | ¹H-NMR (DMSO-d₆, 400 MHz): δ 12.09 (br s, 1H), 10.98 (s, 1H), 8.00 (d, J = 8.0 Hz, 1H), 7.93-7.91 (m, 2H), 7.79-7.74 (m, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2H), 7.64-7.60 (m, 1H), 7.53-7.44 (m, 2H), 7.41-7.32 (m, 2H); |
| 1332 | 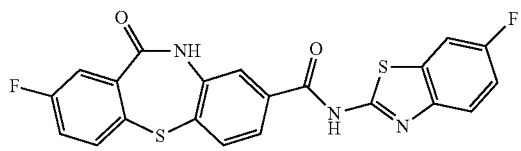 [SMILES: O=C(Nc1nc2ccc(F)cc2s1)c1ccc2c(c1)NC(=O)c1cc(F)ccc1S2] | C, 35, 241 | 13 | 439.9 (M + 1)$^+$, | $C_{21}H_{11}F_2N_3O_2S_2$ 439.03 | $^1$H-NMR (DMSO-d$_6$, 400 MHz): δ 12.91 (br s, 1H), 10.96 (s, 1H), 7.93-7.90 (m, 2H), 7.78 (d, J = 6.8 Hz, 1H), 7.68-7.59 (m, 3H), 7.50 (dd, J = 9.2, 2.8 Hz, 1H), 7.38 (td, J = 11.6, 3.2 Hz, 1H), 7.23-7.17 (m, 1H); |
| 1340 | 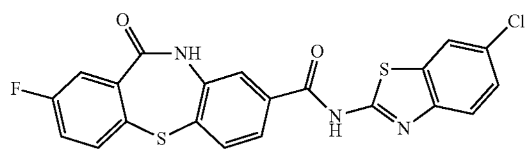 [SMILES: O=C(Nc1nc2ccc(Cl)cc2s1)c1ccc2c(c1)NC(=O)c1cc(F)ccc1S2] | C, 35, 242 | 5 | 455.9 (M$^+$ + 1) | $C_{21}H_{11}ClFN_3O_2S_2$ 455.00 | $^1$H-NMR (DMSO-d$_6$, 400 MHz): δ 13.01 (br s, 1H), 11.00 (s, 1H), 8.16 (s, 1H), 7.91 (d, J = 8.0 Hz, 2H), 7.79-7.70 (m, 2H), 7.64-7.60 (m, 1H), 7.53-7.47 (m, 2H), 7.39 (td, J = 8.4, 3.2 Hz, 1H); |
| 1326 | 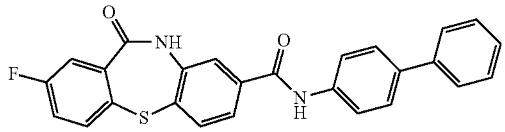 [SMILES: O=C(Nc1ccc(-c2ccccc2)cc1)c1ccc2c(c1)NC(=O)c1cc(F)ccc1S2] | A, 35, 243 | 46 | 441.5 (M$^+$ + 1); | $C_{26}H_{17}FN_2O_2S$ 440.10 | $^1$H-NMR (DMSO-d$_6$, 400 MHz): δ 10.96 (s, 1H), 10.39 (s, 1H), 7.84 (d, J = 8.8 Hz, 2H), 7.78 (s, 1H), 7.74 (s, 2H), 7.68-7.61 (m, 4H), 7.51 (dd, J = 9.2, 2.8 Hz, 1H), 7.47-7.45 (m, 1H), 7.43-7.32 (m, 4H); |
| 1333 | 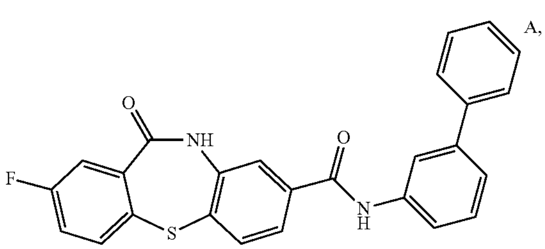 | A, 35, 186 | 46 | 441.4 (M$^+$ + 1): | $C_{26}H_{17}FN_2O_2S$ 440.10 | $^1$H NMR (400 MHz, DMSO-d$_6$) δ 10.97 (s, 1H), 10.38 (s, 1H), 8.05 (s, 1H), 7.83-7.73 (m, 4H), 7.68-7.61 (m, 3H), 7.52-7.37 (m, 7H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1376 | 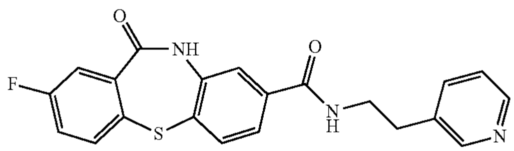 [SMILES: O=C(NCCc1cccnc1)c1ccc2c(c1)NC(=O)c1cc(F)ccc1S2] | A, 35, 217 | 59 | 393.9 (M$^+$ + 1); | C$_{21}$H$_{16}$FN$_3$O$_2$S 393.09 | $^1$H NMR (DMSO-d$_6$, 400 MHz): δ 10.91 (s, 1H), 8.62 (t, J = 5.5 Hz, 1H), 8.44-8.38 (m, 2H), 7.67-7.57 (m, 4H), 7.54 (dd, J = 8.2, 1.8 Hz, 1H), 7.48 (dd, J = 9.2, 2.9 Hz, 1H), 7.37 (dt, J = 8.5, 2.9 Hz, 1H), 7.29 (dd, J = 7.7, 4.8 Hz, 1H), 3.54-3.44 (m, 2H), 2.84 (t, J = 7.0 Hz, 2H); |
| 1417 | 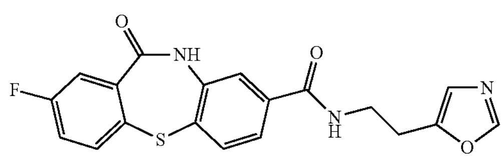 [SMILES: O=C(NCCc1cncs1)c1ccc2c(c1)NC(=O)c1cc(F)ccc1S2] | B, 35, 347 | 12 | 383.9 (M$^+$ +1); | C$_{19}$H$_{14}$FN$_3$O$_3$S 383.07 | $^1$H NMR (DMSO-d$_6$, 400 MHz): δ 10.90 (br s, 1H), 8.66 (t, J = 5.5 Hz, 1H), 8.21 (s, 1H), 7.68-7.63 (m, 2H), 7.60 (dd, J = 8.6, 5.3 Hz, 1H), 7.55 (dd, J = 8.2, 1.7 Hz, 1H), 7.48 (dd, J = 9.2, 2.9 Hz, 1H), 7.37 (dt, J = 8.5, 3.0 Hz, 1H), 6.92 (s, 1H), 3.49 (q, 2H), 2.90 (t, J = 6.7 Hz, 2H); |
| 1418 | 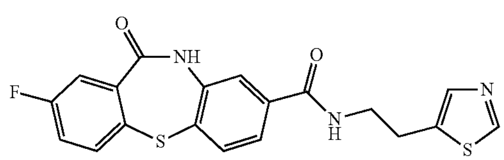 | B, 35, 352 | 36 | 399.9 (M$^+$ + 1); | C$_{19}$H$_{14}$FN$_3$O$_2$S$_2$ 399.05 | $^1$H NMR (DMSO-d$_6$, 400 MHz): δ 10.92 (br s, 1H), 8.91 (br s, 1H), 8.70 (br s, 1H), 7.73-7.54 (m, 5H), 7.49 (d, J = 7.2 Hz, 1H), 7.42-7.36 (m, 1H), 3.52-3.45 (m, 2H), 3.13-3.10 (m, 2H); |
| 1364 | 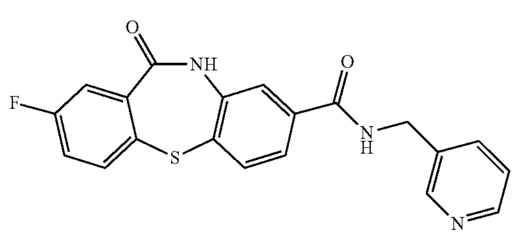 [SMILES: O=C(NCc1cccnc1)c1ccc2c(c1)NC(=O)c1cc(F)ccc1S2] | A, 35, 218 | 38 | 380.0 (M ++ 1); | C20H14FN3O2S 379.08 | 1H NMR (400 MHz, DMSO-d6): δ 10.89 (s, 1H), 9.15 (t, J = 5.4 Hz, 1H), 8.52 (s, 1H), 8.45 (dd, J = 4.8, 1.5 Hz, 1H), 7.73-7.57 (m, 5H), 7.48 (dd, J = 9.2, 2.9 Hz, 1H), 7.41-7.36 (m, 1H), 7.34 (dd, J = 7.9, 4.9 Hz, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 1H), 4.46 (d, J = 5.9 Hz, 2H); |
| 1370 | 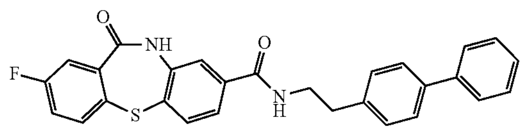 [SMILES: O=C(NCCc1ccc(-c2ccccc2)cc1)c1ccc2c(c1)NC(=O)c1cc(F)ccc1S2] | A, 35, 219 | 31 | 469.7 (M ++ 1); | C28H21FN2O2S 468.13 | 1H NMR (DMSO-d6, 400 MHz): δ 10.91 (s, 1H), 8.65 (t, J = 5.4 Hz, 1H), 7.69-7.53 (m, 8H), 7.50-7.41 (m, 3H), 7.40-7.28 (m, 4H), 3.50 (q, J = 6.7 Hz, 2H), 2.86 (t, J = 7.2 Hz, 2H); |
| 1384 | 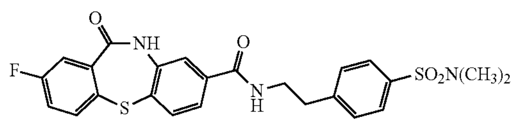 | A, 35, 406 | 29 | 499.9 (M ++ 1) | C24H22FN3O4S2 499.10 | 1H NMR (DMSO-d6, 400 MHz): δ 10.91 (br s, 1H), 8.62 (t, J = 5.6 Hz, 1H), 7.67-7.62 (m, 4H), 7.59 (dd, J = 8.6, 5.3 Hz, 1H), 7.53 (dd, J = 8.2, 1.7 Hz, 1H), 7.51-7.46 (m, 3H), 7.37 (td, J = 8.5, 3.0 Hz, 1H), 3.51 (q, J = 6.6 Hz, 2H), 2.93 (t, J = 7.0 Hz, 2H), 2.54 (s, 6H); |
| 1385 | 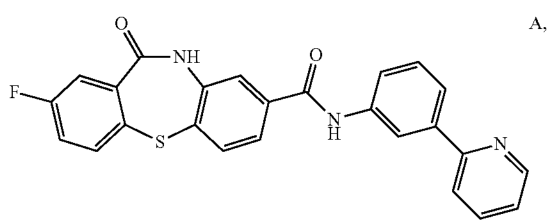 | A, 35, 244 | 40 | 441.9 (M ++ 1); | C25H16FN3O2S 441.09 | $^1$H NMR (400 MHz, DMSO-d$_6$): δ 10.98 (br s, 1H), 10.44 (s, 1H), 8.68 (d, J = 5.1 Hz, 1H), 8.50 (s, 1H), 7.94-7.89 (m, 2H), 7.87-7.84 (m, 1H), 7.83-7.77 (m, 3H), 7.76-7.72 (m, 1H), 7.63 (dd, J = 8.6, 5.3 Hz, 1H), 7.52 (dd, J = 9.1, 2.7 Hz, 1H), 7.47 (t, J = 7.9 Hz, 1H), 7.43-7.35 (m, 2H); |
| 1400 | 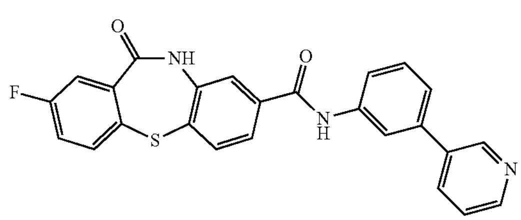 [SMILES: O=C(Nc1cccc(-c2cccnc2)c1)c1ccc2c(c1)NC(=O)c1cc(F)ccc1S2] | A, 35, 245 | 21 | 441.9 (M ++ 1); | C25H16FN3O2S 441.09 | $^1$H NMR (400 MHz, DMSO-d$_6$): δ 10.98 (s, 1H), 10.42 (s, 1H), 8.85 (br s, 1H), 8.59 (d, J = 3.7 Hz, 1H), 8.08 (s, 1H), 8.03 (d, J = 8.0 Hz, 1H), 7.85-7.72 (m, 4H), 7.63 (dd, J = |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 8.5, 5.2 Hz, 1H), 7.54-7.45 (m, 4H), 7.40 (td, J = 8.4, 2.9 Hz, 1H); |
| 1401 | 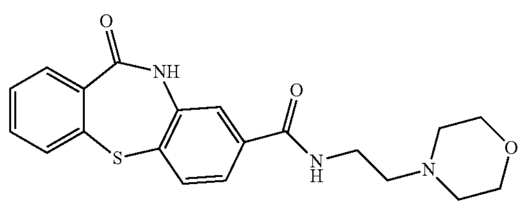 | A, 35, 246 | 33 | 442.0 (M ++ 1); | C25H16FN3O2S 441.09 | $^1$H NMR (400 MHz, DMSO-d$_6$, δ 10.99 (s, 1H), 10.46 (s, 1H), 8.66 (d, J = 6.0 Hz, 2H), 8.18-8.16 (m, 1H), 7.85 (dt, J = 7.6, 1.6 Hz, 1H), 7.81-7.78 (m, 1H), 7.77-7.74 (m, 2H), 7.68-7.61 (m, 3H), 7.56-7.49 (m, 3H), 7.40 (td, J = 8.5, 2.5 Hz, 1H); |
| 1386 | 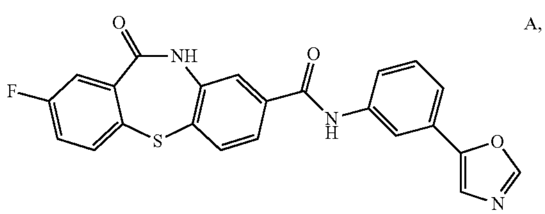 | A, 35, 247 | 34 | 431.9 (M$^+$ + 1); | C$_{23}$H$_{14}$FN$_3$O$_3$S 431.07 | $^1$H NMR (400 MHz, DMSO-d$_6$): δ 10.98 (s, 1H), 10.44 (s, 1H), 8.46 (s, 1H), 8.16 (s, 1H), 7.83-7.69 (m, 4H), 7.69-7.59 (m, 2H), 7.55-7.43 (m, 3H), 7.40 (td, J = 8.5, 3.0 Hz, 1H); |
| 1424 | 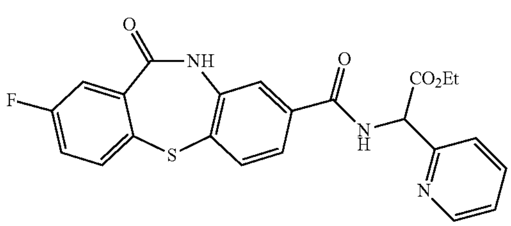 [SMILES: CCOC(=O)C(NC(=O)c1ccc2c(c1)NC(=O)c1cc(F)ccc1S2)c1ccccn1] | F, 35, 248 | 32 | 452.0 (M$^+$ + 1); | C$_{23}$H$_{18}$FN$_3$O$_4$S 451.10 | $^1$H NMR (400 MHz, DMSO-d$_6$): 10.89 (s, 1H), 9.20 (d, J = 7.3 Hz, 1H), 8.57-8.54 (m, 1H), 7.84 (td, J = 7.7, 1.8 Hz, 1H), 7.74 (s, 1H), 7.70-7.64 (m, 2H), 7.60 (dd, J = 8.6, 5.3 Hz, 1H), 7.53 (d, J = 7.9 Hz, 1H), 7.48 (dd, J = 9.2, 2.9 Hz, 1H), 7.43-7.33 (m, 2H), 5.77 (d, J = 7.3 Hz, 1H), 4.16-4.09 (m, 2H), 1.14 (t, J = 7.1 Hz, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1405 | 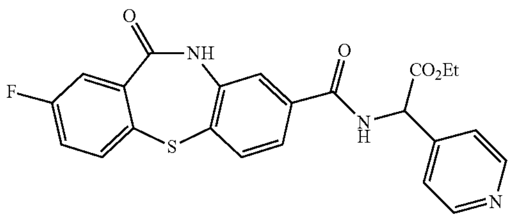 [SMILES: CCOC(=O)C(NC(=O)c1ccc2c(c1)NC(=O)c1cc(F)ccc1S2)c1ccncc1] | F, 35, 249 | 28 | 451.9 (M$^+$ + 1); | $C_{23}H_{18}FN_3O_4S$ 451.10 | $^1$H NMR (400 MHz, DMSO-d$_6$): δ 10.90 (s, 1H), 9.38 (d, J = 7.5 Hz, 1H), 8.58 (d, J = 5.0 Hz, 2H), 7.73 (s, 1H), 7.71-7.65 (m, 2H), 7.61 (dd, J = 8.6, 5.2 Hz, 1H), 7.52-7.44 (m, 3H), 7.38 (td, J = 8.4, 3.0 Hz, 1H), 5.71 (d, J = 7.4 Hz, 1H), 4.19-4.10 (m, 2H), 1.15 (t, J = 7.1 Hz, 3H); |
| 1442 | 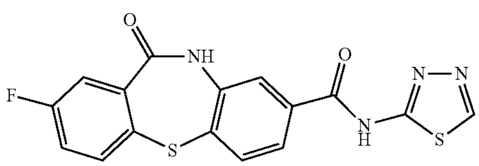 | F, 35, 250 | 31 | 372.8 (M$^+$ + 1); | $C_{16}H_9FN_4O_2S_2$ 372.02 | $^1$H NMR (400 MHz, DMSO-d$_6$): δ 10.91 (s, 1H), 8.87 (br s, 1H), 7.94 (s, 1H), 7.87 (dd, J = 8.0, 1.7 Hz, 1H), 7.61 (d, J = 9.0 Hz, 1H), 7.59-7.56 (m, 1H), 7.48 (dd, J = 9.2, 2.9 Hz, 1H), 7.35 (td, J = 8.5, 3.0 Hz, 1H); |
| 1537 | 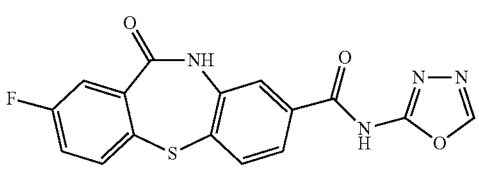 [SMILES: O=C(Nc1nncs1)c1ccc2c(c1)NC(=O)c1cc(F)ccc1S2] | F, 35, 251 | 16 | 357.0 (M$^+$ + 1); | $C_{16}H_9FN_4O_3S$ 356.04 | $^1$H NMR (400 MHz, DMSO-d$_6$) δ 12.26 (br s, 1H), 10.97 (br s, 1H), 9.02 (s, 1H), 7.84-7.71 (m, 3H), 7.62 (dd, J = 8.4, 5.3 Hz, 1H), 7.51 (dd, J = 9.2, 2.7 Hz, 1H), 7.39 (td, J = 8.4, 2.9 Hz, 1H); |
| 1503 | 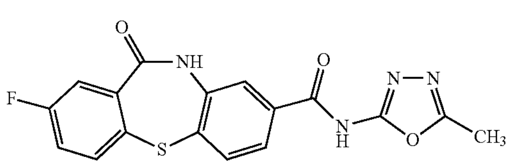 | F$^a$, 35, 252 (a = Microwave 100° C. temp, 1 h) | 39 | 371.0 (M$^+$ + 1); | $C_{17}H_{11}FN_4O_3S$ 370.05 | $^1$H NMR (400 MHz, DMSO-d$_6$): δ 11.95 (br s, 1H), 10.97 (br s, 1H), 7.85-7.70 (m, 3H), 7.62 (dd, J = 8.6, 5.2 Hz, 1H), 7.50 (dd, J = 9.2, 2.8 Hz, 1H), 7.39 (td, J = 8.5, 2.9 Hz, 1H), 2.45 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1443 | 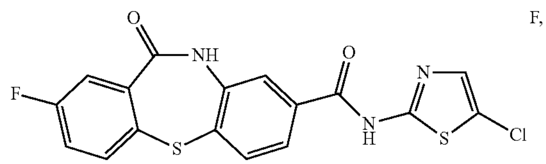 [SMILES: Cc1nnc(NC(=O)c2ccc3c(c2)NC(=O)c2cc(F)ccc2S3)o1] | F, 35, 253 | 17 | 405.9 (M⁺ + 1); | $C_{17}H_9ClFN_3O_2S_2$ 404.98 | ¹H NMR (400 MHz, DMSO-d₆): δ 12.97 (br s, 1H), 11.00 (br s, 1H), 7.86 (br s, 2H), 7.73 (d, J = 8.2 Hz, 1H), 7.60 (br s, 2H), 7.51 (d, J = 7.7 Hz, 1H), 7.43-7.35 (m, 1H); |
| 1440 | 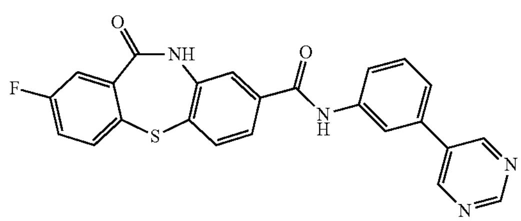 [SMILES: O=C(Nc1cccc(-c2cncnc2)c1)c1ccc2c(c1)NC(=O)c1cc(F)ccc1S2] | A, 35, 383 | 34 | 443.0 (M⁺ + 1); | $C_{24}H_{15}FN_4O_2S$ 442.09 | ¹H NMR (DMSO-d₆, 400 MHz): δ 10.99 (s, 1H), 10.47 (s, 1H), 9.21 (s, 1H), 9.09 (s, 2H), 8.13-8.11 (m, 1H), 7.88-7.85 (m, 1H), 7.80 (s, 1H), 7.77-7.75 (m, 2H), 7.63 (dd, J = 8.6, 5.3 Hz, 1H), 7.56-7.50 (m, 3H), 7.40 (td, J = 8.5, 3.0 Hz, 1H); |
| 1451 | 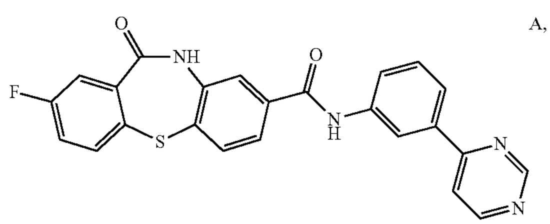 | A, 35, 386 | 26 | 443.0 (M⁺ + 1); | $C_{24}H_{15}FN_4O_2S$ 442.09 | ¹H NMR (400 MHz DMSO-d₆): δ 10.99 (s, 1H), 10.52 (s, 1H), 9.27 (s, 1H), 8.88 (d, J = 5.3 Hz, 1H), 8.66-8.63 (m, 1H), 8.04 (dd, J = 5.4, 1.3 Hz, 1H), 7.98-7.91 (m, 2H), 7.83-7.73 (m, 3H), 7.63 (dd, J = 8.6, 5.3 Hz, 1H), 7.58-7.49 (m, 2H), 7.40 (td, J = 8.5, 3.0 Hz, 1H); |
| 1441 | 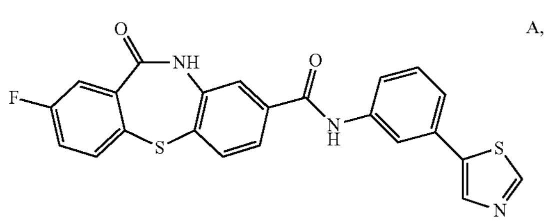 | A, 35, 389 | 32 | 448.0 (M⁺ + 1); | $C_{23}H_{14}FN_3O_2S_2$ 447.05 | ¹H NMR (400 MHz, DMSO-d₆): δ 10.99 (s, 1H), 9.10 (s, 1H), 8.27 (s, 1H), 8.06-8.04 (m, 1H), 7.82-7.71 (m, 4H), 7.63 (dd, J = 8.6, 5.2 Hz, 1H), 7.57-7.35 (m, 4H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1453 | (structure) | B, 35, 392 | 10 | 457.0 (M$^+$ + 1); | $C_{26}H_{17}FN_2O_3S$ 456.09 | $^1$H NMR (DMSO-d$_6$, 400 MHz): δ 10.99 (br s, 1H), 10.33 (s, 1H), 9.57 (s, 1H), 7.96 (s, 1H), 7.79 (s, 1H), 7.75-7.74 (m, 2H), 7.68 (d, J = 8.7 Hz, 1H), 7.63 (dd, J = 8.6, 5.3 Hz, 1H), 7.52 (dd, J = 9.2, 2.9 Hz, 1H), 7.45 (d, J = 8.7 Hz, 2H), 7.43-7.36 (m, 2H), 7.33-7.29 (m, 1H), 6.86 (d, J = 8.7 Hz, 2H); |
| 1480 | (structure) | F$^b$, 35, 396 (b = EDC solvent) | 32 | 432.4 (M$^+$ + 1) | $C_{23}H_{14}FN_3O_3S$ 431.07 | $^1$H NMR (400 MHz DMSO-d$_6$): δ 11.78 (br s, 1H), 10.96 (br s, 1H), 7.90-7.45 (m, 10H), 7.44-7.33 (m, 2H); |
| 1454 | (structure) | A, 35, 429 | 37 | 471.0 (M$^+$ + 1); | $C_{23}H_{14}FN_3O_3S$ 431.07 | $^1$H NMR (DMSO-d$_6$, 400 MHz): δ 10.98 (s, 1H), 10.37 (s, 1H), 8.02 (s, 1H), 7.83-7.70 (m, 4H), 7.63 (dd, J = 8.6, 5.3 Hz, 1H), 7.52 (dd, J = 9.2, 2.9 Hz, 1H), 7.47-7.36 (m, 4H), 7.20 (d, J = 7.8 Hz, 1H), 7.16-7.14 (m, 1H), 6.96 (dd, J = 8.0, 2.2 Hz, 1H), 3.82 (s, 3H); |
| 1481 | (structure) | F$^c$, 35, 397 (c = CH$_3$CH solvent, Mw, 100° C., 2 h | 43 | 448.4 (M$^+$ + 1) | $C_{23}H_{14}FN_3O_2S_2$ 447.05 | $^1$H NMR (400 MHz DMSO-d$_6$): δ 12.82 (br s, 1H), 11.01 (s, 1H), 7.97 (s, 1H), 7.93-7.85 (m, 2H), 7.76-7.71 (m, 1H), 7.68-7.60 (m, 3H), 7.52 (dd, J = 9.2, 2.9 Hz, 1H), 7.47-7.37 (m, 3H), 7.35-7.30 (m, 1H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1397 | 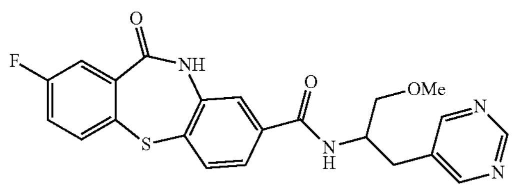 [SMILES: COCC(Cc1cncnc1)NC(=O)c1ccc2c(c1)NC(=O)c1cc(F)ccc1S2] | B, 35, 401 (Reaction time 5 h) | 31 | 439.0 (M$^+$ + 1) | $C_{22}H_{19}FN_4O_3S$ 438.12 | $^1$H NMR (DMSO-d$_6$, 400 MHz): δ 10.87 (s, 1H), 8.96 (s, 1H), 8.64 (s, 2H), 8.41 (d, J = 8.7 Hz, 1H), 7.64 (d, J = 8.0 Hz, 1H), 7.62-7.57 (m, 2H), 7.51 (dd, J = 8.1, 1.8 Hz, 1H), 7.47 (dd, J = 9.1, 3.0 Hz, 1H), 7.37 (dt, J = 8.5, 3.0 Hz, 1H), 4.42-4.29 (m, 1H), 3.43 (d, J = 6.1 Hz, 2H), 3.28 (s, 3H), 2.94 (dd, J = 14.0, 4.1 Hz, 1H), 2.74 (dd, J = 14.0, 10.1, Hz, 1H); |
| 1347 | 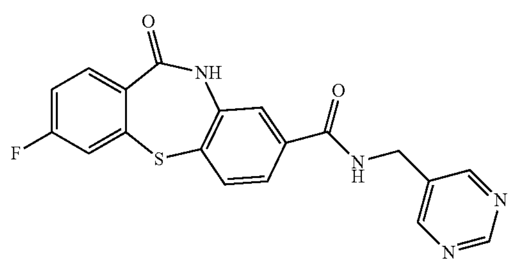 [SMILES: O=C(NCc1cncnc1)c1ccc2c(c1)NC(=O)c1ccc(F)cc1S2] | A, 42, 212 | 46 | 380.9 (M$^+$ + 1) | $C_{19}H_{13}FN_4O_2S$ 380.07 | $^1$H NMR (DMSO-d$_6$, 400 MHz): δ 10.81 (s, 1H), 9.17 (t, J = 5.6 Hz, 1H), 9.08 (s, 1H), 8.75 (s, 2H), 7.79-7.59 (m, 4H), 7.45 (dd, J = 8.5 Hz, 2.5 Hz, 1H), 7.32 (td, J = 8.6, 2.6 Hz, 1H), 4.48 (d, J = 5.6 Hz, 2H); |
| 1356 | 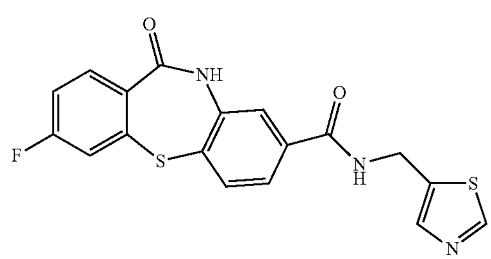 | F, 42, 213 | 13 | 385.8 (M$^+$ + 1) | $C_{18}H_{12}FN_3O_2S_2$ 385.04 | $^1$H NMR (DMSO-d$_6$, 400 MHz): δ 10.81 (s, 1H), 9.25 (t, J = 5.9 Hz, 1H), 8.96 (s, 1H), 7.80 (s, 1H), 7.75 (dd, J = 8.7, 5.9 Hz, 1H), 7.71-7.70 (m, 1H), 7.68-7.65 (m, 1H), 7.63-7.58 (m, 1H), 7.45 (dd, J = 8.5, 2.6 Hz, 1H), 7.32 (td, J = 8.5, 2.6 Hz, 1H), 7.32 (td, J = 8.5, 2.6 Hz, 1H), 4.65 (d, J = 5.7 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1348 | 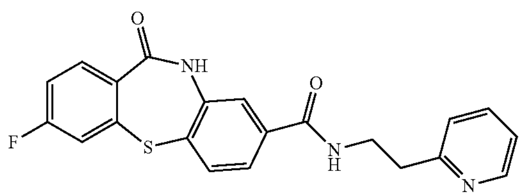 [SMILES: O=C(NCCc1ccccn1)c1ccc2c(c1)NC(=O)c1ccc(F)cc1S2] | A, 42, 216 | 41 | 394.6 (M$^+$ + 1) | C$_{21}$H$_{16}$FN$_3$O$_2$S 393.09 | $^1$H NMR (DMSO-d$_6$, 400 MHz): δ 10.81 (s, 1H), 8.62 (t, J = 5.5 Hz, 1H), 8.49 (dd, J = 0.8, 4.0 Hz, 1H), 7.75 (dd, J = 8.7, 6.0 Hz, 1H), 7.71-7.61 (m, 3H), 7.55 (dd, J = 1.8, 8.1 Hz, 1H), 7.45 (dd, J = 8.5 Hz, 2.6 Hz, 1H), 7.32 (dt, J = 8.5, 2.6 Hz, 1H), 7.25 (d, J = 7.8 Hz, 1H), 7.22-7.19 (m, 1H), 3.67-3.50 (m, 2H), 2.96 (t, J = 7.3 Hz, 2H); |
| 1349 | 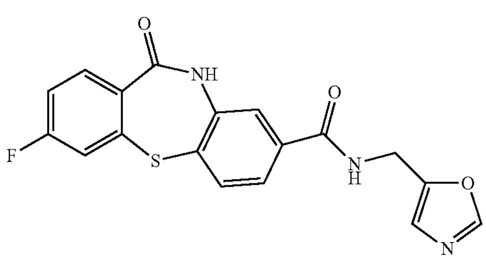 [SMILES: O=C(NCc1cnco1)c1ccc2c(c1)NC(=O)c1ccc(F)cc1S2] | A, 42, 214 | 47 | 369.9 (M$^+$ + 1) | C$_{18}$H$_{12}$FN$_3$O$_3$S 369.06 | $^1$H NMR (DMSO-d$_6$, 400 MHz): δ 10.79 (br s, 1H), 9.08 (t, J = 5.5 Hz, 1H), 8.27 (s, 1H), 7.91-7.89 (m, 1H), 7.75 (dd, J = 8.7, 6.0 Hz, 1H), 7.68-7.60 (m, 2H), 7.45 (dd, J = 8.5, 2.5 Hz, 1H), 7.32 (td, J = 8.5, 2.6 Hz, 1H), 7.03 (s, 1H), 4.51 (d, J = 5.4 Hz, 2H); |
| 1362 | 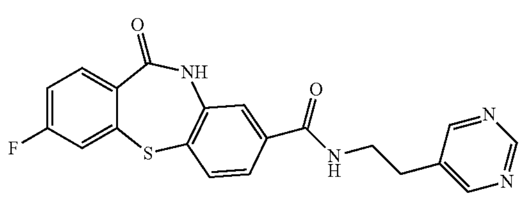 [SMILES: O=C(NCCc1cncnc1)c1ccc2c(c1)NC(=O)c1ccc(F)cc1S2] | A, 42, 215 | 26 | 395.0 (M$^+$ + 1) | C$_{20}$H$_{15}$FN$_4$O$_2$S 394.09 | $^1$H NMR (DMSO-d$_6$, 400 MHz): δ 10.81 (s, 1H), 9.01 (s, 1H), 8.68-8.60 (m, 3H), 7.75 (dd, J = 8.7, 6.0 Hz, 1H), 7.67-7.59 (m, 2H), 7.52 (dd, J = 8.0, 1.8 Hz, 1H), 7.44 (t, J = 6.4 Hz, 1H), 7.32 (dt, J = 8.5, 2.5 Hz, 1H), 3.52 (q, J = 6.4 Hz, 2H), 2.84 (t, J = 6.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1377 | 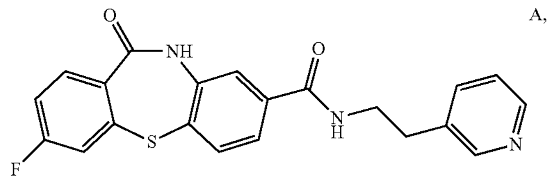 | A, 42, 217 | 34 | 393.9 (M$^+$ + 1) | C$_{21}$H$_{16}$FN$_3$O$_2$S 393.09 | $^1$H NMR (DMSO-d$_6$, 400 MHz): δ 10.82 (s, 1H), 8.62 (t, J = 5.5 Hz, 1H), 8.43-8.42 (m, 1H), 8.40 (d, J = 5.0 Hz, 1H), 7.75 (t, J = 6.7 Hz, 1H), 7.68-7.60 (m, 3H), 7.54 (dd, J = 8.0, 1.8 Hz, 1H), 7.45 (dd, J = 8.6, 2.6 Hz, 1H), 7.38-7.24 (m, 2H), 3.57-3.42 (m, 2H), 2.84 (t, J = 7.0 Hz, 2H); |
| 1402 | 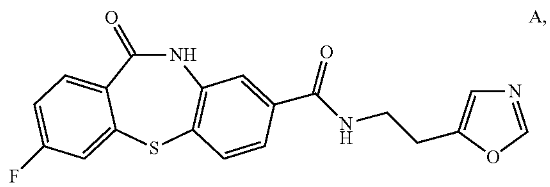 | A, 42, 347 | 23 | 383.9 (M$^+$ + 1) | C$_{19}$H$_{14}$FN$_3$O$_3$S 383.07 | $^1$H NMR (DMSO-d$_6$, 400 MHz): δ 10.82 (s, 1H), 8.66 (t, J = 5.6 Hz, 1H), 8.21 (s, 1H), 7.75 (dd, J = 8.7, 6.0 Hz, 1H), 7.69-7.62 (m, 2H), 7.55 (dd, J = 8.1, 1.7 Hz, 1H), 7.45 (dd, J = 8.5, 2.5 Hz, 1H), 7.32 (td, J = 8.5, 2.5 Hz, 1H), 6.92 (s, 1H), 3.58-3.42 (m, 2H), 2.91 (t, J = 6.7 Hz, 2H); |
| 1403 | 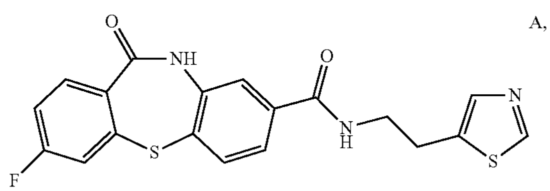 | A, 42, 352 | 14 | | C$_{19}$H$_{14}$FN$_3$O$_2$S$_2$ 399.05 | $^1$H NMR (DMSO-d$_6$, 400 MHz): δ 10.83 (s, 1H), 8.91 (s, 1H), 8.69 (t, J = 5.4 Hz, 1H), 7.76 (dd, J = 8.6, 5.9 Hz, 1H), 7.71-7.63 (m, 3H), 7.58 (d, J = 8.2 Hz, 1H), 7.45 (dd, J = 8.5, 2.5 Hz, 1H), 7.33 (td, J = 8.6, 2.5 Hz, 1H), 3.48 (q, J = 6.4 Hz, 2H), 3.10 (t, J = 6.7 Hz, 2H); |
| 1365 | 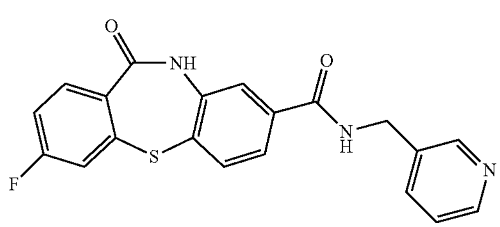 [SMILES: O=C(NCc1cccnc1)c1ccc2c(c1)NC(=O)c1ccc(F)cc1S2] | A, 42, 218 | 53 | 379.9 (M$^+$ + 1) | C$_{20}$H$_{14}$FN$_3$O$_2$S 379.08 | $^1$H NMR (DMSO-d$_6$, 400 MHz): δ 10.81 (s, 1H), 9.15 (t, J = 6.1 Hz, 1H), 8.56-8.49 (m, 1H), 8.45 (dd, J = 4.7, 1.4 Hz, 1H), 7.78-7.60 (m, 5H), 7.45 |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| | | | | | | (dd, J = 8.6, 2.5 Hz, 1H), 7.39-7.27 (m, 2H), 4.47 (d, J = 5.7 Hz, 2H); |
| 1371 | 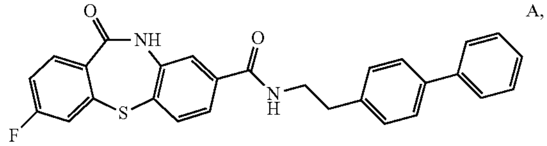 | A, 42, 219 | 25 | 469.8 (M⁺ + 1); | $C_{28}H_{21}FN_2O_2S$ 468.13 | ¹H NMR (DMSO-d₆, 400 MHz): δ 10.82 (s, 1H), 8.65 (t, J = 5.5 Hz, 1H), 7.76 (t, J = 6.9 Hz, 1H), 7.69-7.54 (m, 7H), 7.49-7.39 (m, 3H), 7.38-7.26 (m, 4H), 3.57-3.35 (m, 2H), 2.86 (t, J = 7.2 Hz, 2H); |
| 1387 | 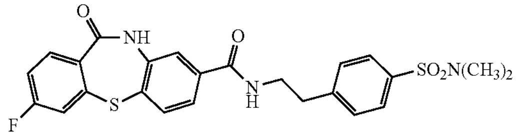 | A, 42, 406 | 23 | 499.9 (M⁺ + 1) | $C_{24}H_{22}FN_3O_4S_2$ 499.10 | ¹H-NMR (DMSO-d₆, 400 MHz): δ 10.82 (s, 1H), 8.62 (t, J = 5.6 Hz, 1H), 7.76 (dd, J = 8.7, 6.0 Hz, 1H), 7.66-7.62 (m, 4H), 7.55-7.43 (m, 4H), 7.33 (td, J = 8.6, 2.6 Hz, 1H), 3.54-3.48 (m, 2H), 2.93 (t, J = 7.1 Hz, 2H), 2.57-2.52 (m, 6H); |
| 1366 | 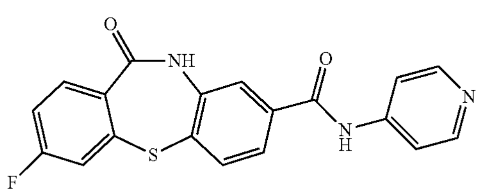 [SMILES: O=C(Nc1ccncc1)c1ccc2c(c1)NC(=O)c1ccc(F)cc1S2] | A, 42, 185 | 24 | 365.9 (M⁺ + 1); | $C_{19}H_{12}FN_3O_2S$ 365.06 | ¹H NMR (DMSO-d₆, 400 MHz): δ 10.89 (s, 1H), 10.64 (s, 1H), 8.48 (d, J = 5.2 Hz, 2H), 7.84-7.67 (m, 6H), 7.48 (dd, J = 8.5, 2.6 Hz, 1H), 7.34 (t, J = 8.3 Hz, 1H); |
| 1358 | 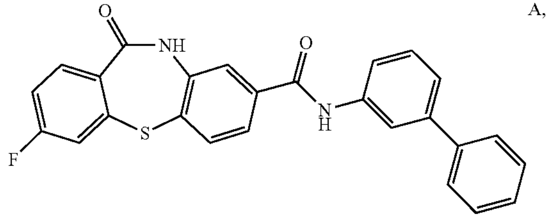 | A, 42, 186 | 46 | 441.6 (M⁺ + 1) | $C_{26}H_{17}FN_2O_2S$ 440.10 | ¹H NMR (DMSO-d₆, 400 MHz): δ 10.89 (s, 1H), 10.38 (s, 1H), 8.05 (s, 1H), 7.82-7.71 (m, 5H), 7.63 (d, J = 7.2 Hz, 2H), 7.54-7.31 (m, 7H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1398 | 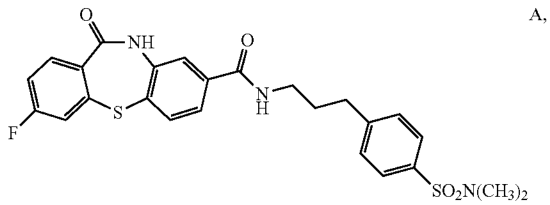 | A, 42, 410 | 20 | 514.0 (M$^+$ + 1); | C$_{24}$H$_{24}$FN$_3$O$_4$S$_2$ 513.12 | $^1$H NMR (DMSO-d$_6$, 400 MHz): δ 10.81 (s, 1H), 8.55 (t, J = 5.7 Hz, 1H), 7.76 (dd, J = 8.7, 6.0 Hz, 1H), 7.70-7.63 (m, 4H), 7.58 (dd, J = 8.0, 1.7 Hz, 1H), 7.53-7.42 (m, 3H), 7.33 (td, J = 8.6, 2.6 Hz, 1H), 3.28-3.23 (m, 2H), 2.72 (t, J = 7.6 Hz, 2H), 2.57 (s, 6H), 1.99-1.78 (m, 2H); |
| 1390 | 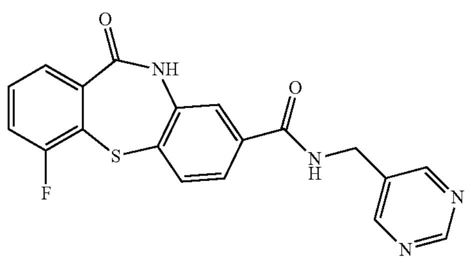 [SMILES: O=C(NCc1cncnc1)c1ccc2c(c1)NC(=O)c1cccc(F)c1S2] | A, 50, 212 | 61 | 380.9 (M$^+$ + 1) | C$_{19}$H$_{13}$FN$_4$O$_2$S 380.07 | $^1$H NMR (DMSO-d$_6$, 400 MHz): δ 10.88 (s, 1H), 9.17 (t, J = 5.7 Hz, 1H), 9.08 (s, 1H), 8.74 (s, 2H), 7.71 (dd, J = 4.9 Hz, 3.1 Hz, 2H), 7.67-7.59 (m, 1H), 7.54-7.43 (m, 3H), 4.47 (d, J = 5.7 Hz, 2H); |
| 1407 | 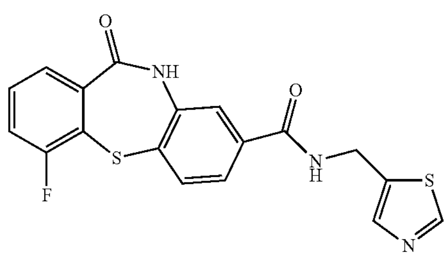 | A, 50, 213 | 30 | 385.9 (M$^+$ + 1) | C$_{18}$H$_{12}$FN$_3$O$_2$S$_2$ 385.04 | $^1$H NMR (DMSO-d$_6$, 400 MHz): δ 10.89 (s, 1H), 9.25 (t, J = 5.7 Hz, 1H), 8.96 (s, 1H), 7.80 (s, 1H), 7.71 (dd, J = 4.8, 3.1 Hz, 2H), 7.60 (dd, J = 8.1, 1.8 Hz, 1H), 7.54-7.45 (m, 3H), 4.65 (d, J = 5.6 Hz, 2H); |
| 1408 | 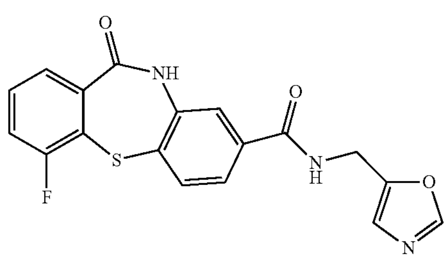 [SMILES: O=C(NCc1cncs1)c1ccc2c(c1)NC(=O)c1cccc(F)c1S2] | A, 50, 214 | 23 | 369.9 (M$^+$ + 1) | C$_{18}$H$_{12}$FN$_3$O$_3$S 369.06 | $^1$H NMR (DMSO-d$_6$, 400 MHz): δ 10.88 (s, 1H), 9.08 (t, J = 5.5 Hz, 1H), 8.27 (s, 1H), 7.75-7.66 (m, 2H), 7.61 (dd, J = 8.0, 1.5 Hz 1H), 7.54-7.44 (m, 3H), 7.03 (s, 1H), 4.51 (d, J = 5.3 Hz, 2H); |
| 1409 | 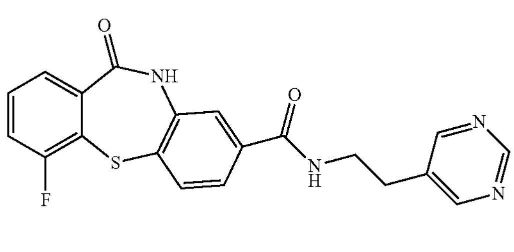 [SMILES: O=C(NCCc1cncnc1)c1ccc2c(c1)NC(=O)c1cccc(F)c1S2] | A, 50, 215 | 29 | 395.8 (M$^+$ + 1); | C$_{20}$H$_{15}$FN$_4$O$_2$S 394.09 | $^1$H NMR (DMSO-d$_6$, 400 MHz): δ 10.89 (s, 1H), 9.01 (s, 1H), 8.68-8.61 (m, 3H), 7.69 (d, J = 8.0 Hz, 1H), 7.63 (s, 1H), 7.55-7.45 (m, 4H), 3.55-3.49 (m, 2H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
|  |  |  |  |  |  | 2.84 (t, J = 6.6 Hz, 2H); |
| 1383 | 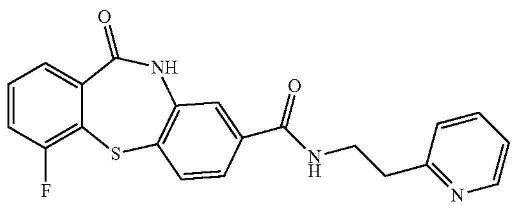 [SMILES: O=C(NCCc1ccccn1)c1ccc2c(c1)NC(=O)c1cccc(F)c1S2] | A, 50, 216 | 30 | 393.9 (M$^+$ + 1) | C$_{21}$H$_{16}$FN$_3$O$_2$S 393.09 | $^1$H NMR (DMSO-d$_6$, 400 MHz): δ 10.89 (s, 1H), 8.63 (t, J = 5.3 Hz, 1H), 8.50-8.47 (m, 1H), 7.72-7.63 (m, 3H), 7.55 (dd, J = 8.1, 1.8 Hz, 1H), 7.53-7.44 (m, 3H), 7.25 (d, J = 7.8 Hz, 1H), 7.23-7.18 (m, 1H), 3.62-3.55 (m, 2H), 2.96 (t, J = 7.3 Hz, 2H); |
| 1391 | 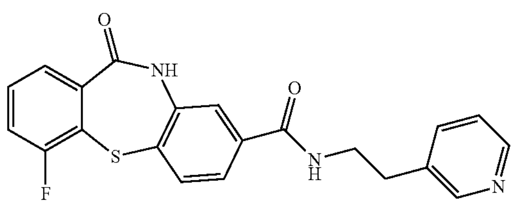 [SMILES: O=C(NCCc1cccnc1)c1ccc2c(c1)NC(=O)c1cccc(F)c1S2] | A, 50, 217 | 44 | 393.9 (M$^+$ + 1) | C$_{21}$H$_{16}$FN$_3$O$_2$S 393.09 | $^1$H NMR (DMSO-d$_6$, 500 MHz): δ 10.88 (s, 1H), 8.61 (t, J = 5.4 Hz, 1H), 8.44-8.36 (m, 2H), 7.67 (d, J = 8.1 Hz, 1H), 7.65-7.59 (m, 2H), 7.54-7.43 (m, 4H), 7.28 (dd, J = 7.4, 5.1 Hz, 1H), 3.47 (q, J = 6.7 Hz, 2H), 2.82 (t, J = 6.9 Hz, 2H); |
| 1392 | 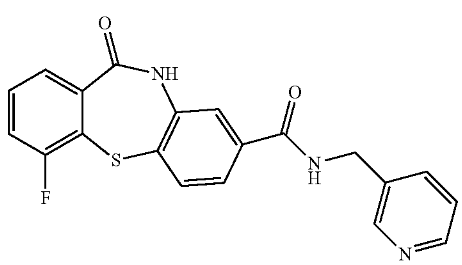 [SMILES: O=C(NCc1cccnc1)c1ccc2c(c1)NC(=O)c1cccc(F)c1S2] | A, 50, 218 | 22 | 379.9 (M$^+$ + 1); | C$_{20}$H$_{14}$FN$_3$O$_2$S 379.08 | $^1$H NMR (DMSO-d$_6$, 400 MHz): δ 10.88 (s, 1H), 9.15 (t, J = 5.8 Hz, 1H), 8.56-8.49 (m, 1H), 8.45 (d, J = 5.2 Hz, 1H), 7.74-7.67 (m, 3H), 7.65-7.62 (m, 1H), 7.54-7.43 (m, 3H), 7.34 (dd, J = 7.7, 4.9 Hz, 1H), 4.46 (d, J = 5.7 Hz, 2H); |
| 1393 | 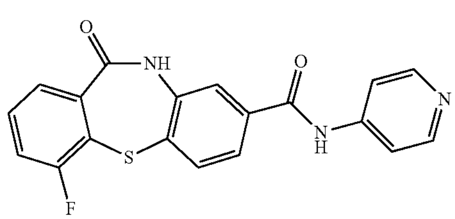 [SMILES: O=C(Nc1ccncc1)c1ccc2c(c1)NC(=O)c1cccc(F)c1S2] | A, 50, 185 | 12 | 365.9 (M$^+$ + 1) | C$_{19}$H$_{12}$FN$_3$O$_2$S 365.06 | $^1$H NMR (DMSO-d$_6$, 400 MHz): δ 10.97 (s, 1H), 10.63 (s, 1H), 8.48 (d, J = 5.3 Hz, 2H), 7.82-7.76 (m, 2H), 7.76-7.71 (m, 3H), 7.56-7.47 (m, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1410 | 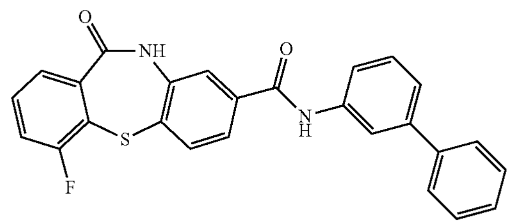 [SMILES: O=C(Nc1cccc(-c2ccccc2)c1)c1ccc2c(c1)NC(=O)c1cccc(F)c1S2] | A, 50, 186 | 19 | 440.9 (M$^+$ + 1) | C$_{26}$H$_{17}$FN$_2$O$_2$S 440.10 | $^1$H NMR (DMSO-d$_6$, 400 MHz): δ 10.97 (s, 1H), 10.38 (s, 1H), 8.05 (s, 1H), 7.85-7.70 (m, 4H), 7.63 (d, J = 7.2 Hz, 2H), 7.57-7.36 (m, 8H); |
| 1487 | 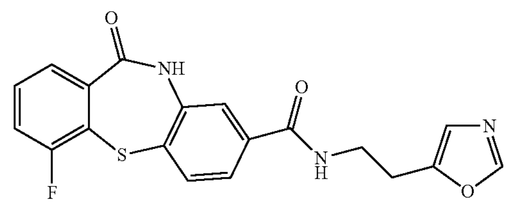 | A, 50, 347 | 22 | 383.9 (M$^+$ + 1) | C$_{19}$H$_{14}$FN$_3$O$_3$S 383.07 | $^1$H NMR (DMSO-d$_6$, 500 MHz): δ 10.88 (s, 1H), 8.65 (t, J = 5.5 Hz, 1H), 8.20 (s, 1H), 7.68 (d, J = 8.1 Hz, 1H), 7.64 (s, 1H), 7.57-7.43 (m, 4H), 6.90 (s, 1H), 3.47 (q, J = 6.7 Hz, 2H), 2.89 (t, J = 6.8 Hz, 2H); |
| 1528 | 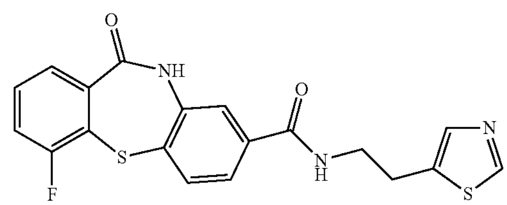 [SMILES: O=C(NCCc1cnco1)c1ccc2c(c1)NC(=O)c1cccc(F)c1S2] | A, 50, 352 | 43 | 399.8 (M$^+$ + 1) | C$_{19}$H$_{14}$FN$_3$O$_2$S$_2$ 399.05 | $^1$H NMR (DMSO-d$_6$, 400 MHz): δ 10.92 (br s, 1H), 8.91 (s, 1H), 8.71 (t, J = 5.4 Hz, 1H), 7.74-7.67 (m, 3H), 7.57 (dd, J = 8.1, 1.8 Hz, 1H), 7.54-7.44 (m, 3H), 3.48 (q, J = 6.5 Hz, 2H), 3.10 (t, J = 6.7 Hz, 2H); |
| 1466 | 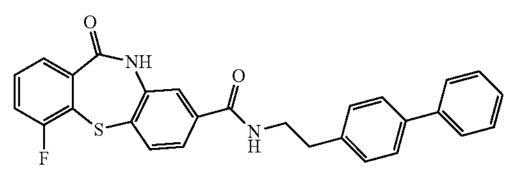 [SMILES: O=C(NCCc1ccc(-c2ccccc2)cc1)c1ccc2c(c1)NC(=O)c1cccc(F)c1S2] | A, 50, 219 | 50 | 469.0 (M$^+$ + 1) | C$_{28}$H$_{21}$FN$_2$O$_2$S 468.13 | $^1$H NMR (DMSO-d$_6$, 400 MHz): δ 10.90 (s, 1H), 8.66 (t, J = 5.6 Hz, 1H), 7.72-7.67 (m, 2H), 7.65-7.61 (m, 2H), 7.60-7.56 (m, 3H), 7.54-7.42 (m, 5H), 7.36-7.29 (m, 3H), 3.49 (q, J = 6.8 Hz, 2H), 2.86 (t, J = 7.3 Hz, 2H); |
| 1488 | 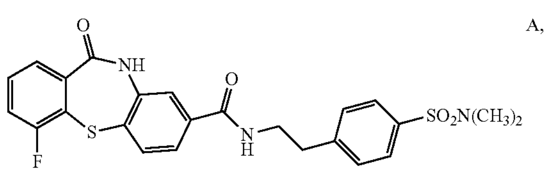 | A, 50, 406 | 34 | 500.0 (M$^+$ + 1) | C$_{24}$H$_{22}$FN$_3$O$_4$S$_2$ 499.10 | $^1$H NMR (DMSO-d$_6$, 400 MHz) δ 10.90 (s, 1H), 8.63 (t, J = 5.6 Hz, 1H), 7.71-7.61 (m, 4H), 7.56-7.44 (m, 6H), 3.58-3.45 (m, 2H), 2.92 (t, J = 7.0 Hz, 2H), 2.54 (s, 6H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1428 | 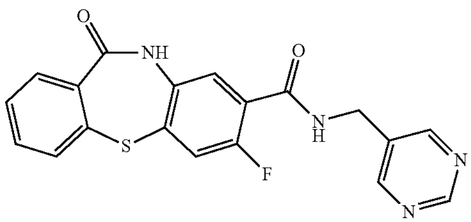 [SMILES: O=C(NCc1cncnc1)c1cc2c(cc1F)Sc1ccccc1C(=O)N2] | A, 55, 212 | 23 | 381.0 (M$^+$ + 1) | $C_{19}H_{13}FN_4O_2S$ 380.07 | $^1$H NMR (DMSO-d$_6$, 400 MHz): δ 10.70 (s, 1H), 9.09 (s, 1H), 8.99 (t, J = 5.1 Hz, 1H), 8.74 (s, 2H), 7.69 (d, J = 6.5 Hz, 1H), 7.59 (d, J = 9.5 Hz, 1H), 7.56-7.45 (m, 4H), 4.48 (d, J = 5.6 Hz, 2H); |
| 1429 | 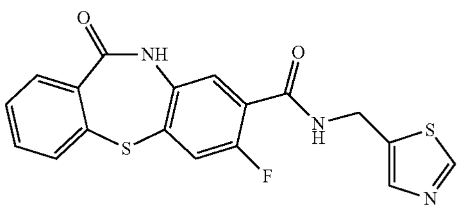 [SMILES: O=C(NCc1cncs1)c1cc2c(cc1F)Sc1ccccc1C(=O)N2] | A, 55, 213 | 30 | 385.8 (M$^+$ + 1); | $C_{18}H_{12}FN_3O_2S_2$ 385.04 | $^1$H NMR (DMSO-d$_6$, 400 MHz): δ 10.71 (s, 1H), 9.03 (t, J = 5.1 Hz, 1H), 8.98 (s, 1H), 7.79 (s, 1H), 7.69 (dd, J = 7.4, 1.4 Hz, 1H), 7.58 (d, J = 9.5 Hz, 1H), 7.56-7.47 (m, 3H), 7.46-7.42 (m, 1H), 4.64 (d, J = 5.7 Hz, 2H); |
| 1430 | 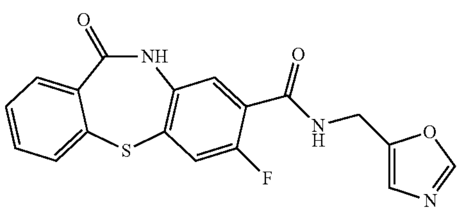 [SMILES: O=C(NCc1cnco1)c1cc2c(cc1F)Sc1ccccc1C(=O)N2] | A, 55, 214 | 24 | 369.9 (M$^+$ + 1); | $C_{18}H_{12}FN_3O_3S$ 369.06 | $^1$H NMR (DMSO-d$_6$, 400 MHz): δ 10.71 (s, 1H), 8.89 (t, J = 5.1 Hz, 1H), 8.29 (s, 1H), 7.69 (dd, J = 7.4, 1.5 Hz, 1H), 7.58 (d, J = 9.4 Hz, 1H), 7.56-7.45 (m, 3H), 7.43 (d, J = 6.5 Hz, 1H), 7.02 (s, 1H), 4.50 (d, J = 5.5 Hz, 2H); |
| 1411 | 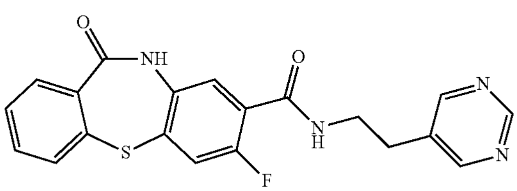 [SMILES: O=C(NCCc1cncnc1)c1cc2c(cc1F)Sc1ccccc1C(=O)N2] | A, 55, 215 | 37 | 394.9 (M$^+$ + 1); | $C_{20}H_{15}FN_4O_2S$ 394.09 | $^1$H NMR (DMSO-d$_6$, 400 MHz): δ 10.73 (s, 1H), 9.02 (s, 1H), 8.67 (s, 2H), 8.44 (t, J = 5.1 Hz, 1H), 7.69 (d, J = 6.9 Hz, 1H), 7.58-7.45 (m, 4H), 7.34 (d, J = 6.5 Hz, 1H), 3.52 (q, 2H), 2.82 (t, J = 6.6 Hz, 2H); |
| 1394 | 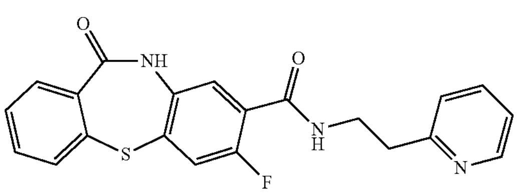 [SMILES: O=C(NCCc1ccccn1)c1cc2c(cc1F)Sc1ccccc1C(=O)N2] | A, 55, 216 | 44 | 393.9 (M$^+$ + 1) | $C_{21}H_{16}FN_3O_2S$ 393.09 | $^1$H NMR (DMSO-d$_6$, 400 MHz): δ 10.73 (br s, 1H), 8.53-8.46 (m, 1H), 8.45-8.39 (m, 1H), 7.72-7.67 (m, 2H), 7.57-7.45 (m, 4H), 7.40 (d, J = 6.6 Hz, 1H), 7.26 (d, J = 7.7 Hz, 1H), 7.24-7.22 (m, 1H), 3.58 (q, 2H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2.94 (t, J = 7.2 Hz, 2H); |
| 1395 | 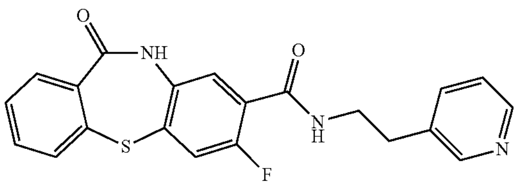 [SMILES: O=C(NCCc1cccnc1)c1cc2c(cc1F)Sc1ccccc1C(=O)N2] | A, 55, 217 | 51 | 393.9 (M$^+$ + 1) | C$_{21}$H$_{16}$FN$_3$O$_2$S 393.09 | $^1$H NMR (DMSO-d$_6$, 400 MHz): δ 10.74 (s, 1H), 8.42 (d, J = 8.7 Hz, 3H), 7.69 (d, J = 7.0 Hz, 1H), 7.64 (d, J = 7.8 Hz, 1H), 7.60-7.44 (m, 4H), 7.36 (d, J = 6.5 Hz, 1H), 7.30 (dd, J = 7.5, 4.9 Hz, 1H), 3.48 (q, 2H), 2.81 (t, J = 6.8 Hz, 2H); |
| 1396 | 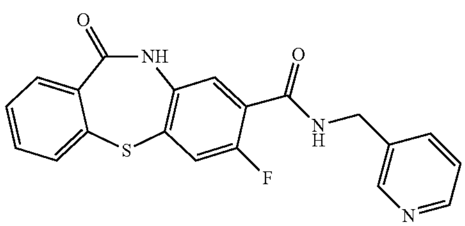 [SMILES: O=C(NCc1cccnc1)c1cc2c(cc1F)Sc1ccccc1C(=O)N2] | A, 55, 218 | 46 | 379.9 (M$^+$ + 1); | C$_{20}$H$_{14}$FN$_3$O$_2$S 379.08 | $^1$H NMR (DMSO-d$_6$, 400 MHz): δ 10.70 (br s, 1H), 8.95 (t, J = 5.1 Hz, 1H), 8.52 (s, 1H), 8.46 (d, J = 3.9 Hz, 1H), 7.75-7.64 (m, 2H), 7.59 (d, J = 9.5 Hz, 1H), 7.56-7.44 (m, 4H), 7.35 (dd, J = 7.7, 4.9 Hz, 1H), 4.46 (d, J = 6.0 Hz, 2H); |
| 1557 | 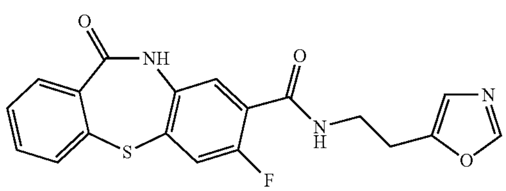 | A, 55, 347 | 38 | 383.9 (M$^+$ + 1) | C$_{19}$H$_{14}$FN$_3$O$_3$S 383.07 | $^1$H NMR (DMSO-d$_6$, 400 MHz): δ 10.73 (s, 1H), 8.46 (t, J = 4.9 Hz, 1H), 8.22 (s, 1H), 7.71-7.67 (m, 1H), 7.58-7.45 (m, 4H), 7.39 (d, J = 6.5 Hz, 1H), 6.92 (s, 1H), 3.48 (q, J = 6.6 Hz, 2H), 2.89 (t, J = 6.7 Hz, 2H); |
| 1558 | 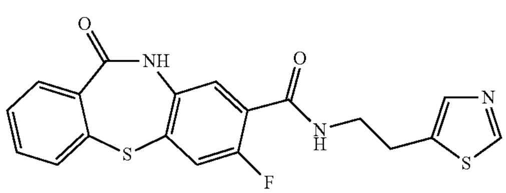 [SMILES: O=C(NCCc1cncs1)c1cc2c(cc1F)Sc1ccccc1C(=O)N2] | A, 55, 352 | 33 | 400.0 (M$^+$ + 1) | C$_{19}$H$_{14}$FN$_3$O$_2$S$_2$ 399.05 | $^1$H NMR (DMSO-d$_6$, 400 MHz): δ 10.75 (s, 1H), 8.93 (s, 1H), 8.49 (t, J = 4.5 Hz, 1H), 7.72-7.64 (br s, 2H), 7.59-7.44 (m, 4H), 7.41 (d, J = 6.5 Hz, 1H), 3.47 (q, J = 6.4 Hz, 2H), 3.08 (t, J = 6.6 Hz, 2H); |
| 1491 | 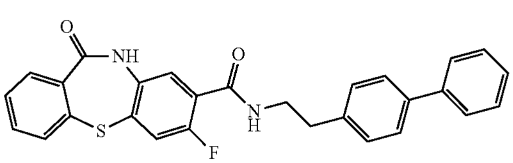 [SMILES: O=C(NCCc1ccc(-c2ccccc2)cc1)c1cc2c(cc1F)Sc1ccccc1C(=O)N2] | A, 55, 219 | 87 | 469.0 (M$^+$ + 1); | C$_{28}$H$_{21}$FN$_2$O$_2$S 468.13 | $^1$H NMR (DMSO-d$_6$, 400 MHz): δ 10.75 (s, 1H), 8.45 (t, J = 4.5 Hz, 1H), 7.69 (dd, J = 7.4, 1.3 Hz, 1H), 7.64 (d, J = 7.3 Hz, 2H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 7.61-7.42 (m, 8H), 7.40 (d, J = 6.5 Hz, 1H), 7.37-7.30 (m, 3H), 3.48 (q, J = 6.8 Hz, 2H), 2.84 (t, J = 7.2 Hz, 2H) |
| 1507 | 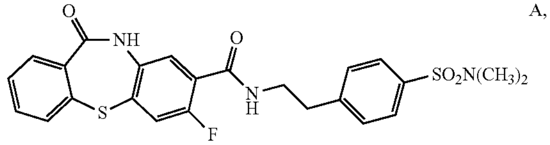 | A, 55, 406 | 47 | 499.9 (M$^+$ + 1); | C$_{24}$H$_{22}$FN$_3$O$_4$S$_2$ 499.10 | $^1$H NMR (DMSO-d$_6$, 400 MHz): δ 10.75 (s, 1H), 8.42 (t, J = 5.1 Hz, 1H), 7.71-7.63 (m, 3H), 7.57-7.45 (m, 6H), 7.35 (d, J = 6.5 Hz, 1H), 3.50 (q, J = 6.7 Hz, 2H), 2.91 (t, J = 6.9 Hz, 2H), 2.56 (s, 6H); |
| 1508 | 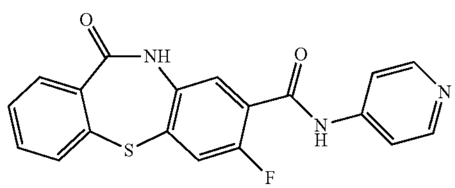 [SMILES: O=C(Nc1ccncc1)c1cc2c(cc1F)Sc1ccccc1C(=O)N2] | A, 55, 185 | 32 | 365.9 (M$^+$ + 1) | C$_{19}$H$_{12}$FN$_3$O$_2$S 365.06 | $^1$H NMR (DMSO-d$_6$, 400 MHz): δ 10.79 (s, 2H), 8.48 (d, J = 6.0 Hz, 2H), 7.73-7.66 (m, 2H), 7.62 (d, J = 6.3 Hz, 2H), 7.59-7.45 (m, 4H); |
| 1509 | 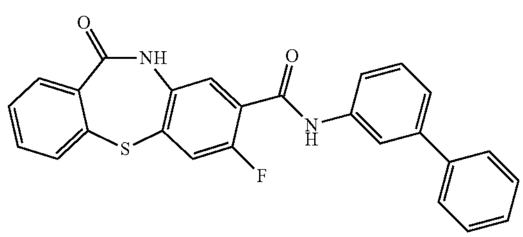 [SMILES: O=C(Nc1cccc(-c2ccccc2)c1)c1cc2c(cc1F)Sc1ccccc1C(=O)N2] | A, 55, 186 | 53 | 441.0 (M$^+$ + 1) | C$_{26}$H$_{17}$FN$_2$O$_2$S 440.10 | $^1$H NMR (DMSO-d$_6$, 400 MHz): δ 10.79 (s, 1H), 10.51 (s, 1H), 7.98 (s, 1H), 7.71 (dd, J = 7.4, 15 Hz, 1H), 7.68-7.59 (m, 4H), 7.58-7.44 (m, 6H), 7.43-7.35 (m, 3H); |
| 1518 | 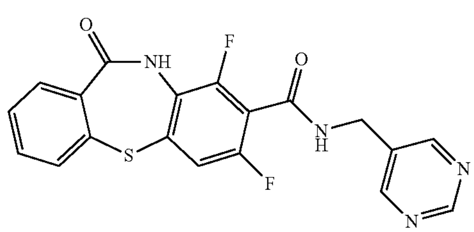 [SMILES: O=C1Nc2c(cc(F)c(C(=O)NCc3cncnc3)c2F)Sc2ccccc21] | B, 62, 212 | 39 | 398.9 (M$^+$ + 1) | C$_{19}$H$_{12}$F$_2$N$_4$O$_2$S 398.06 | $^1$H NMR (DMSO-d$_6$, 400 MHz): δ 10.68 (s, 1H), 9.38 (t, J = 6.0 Hz, 1H), 9.10 (s, 1H), 8.73 (s, 2H), 7.72-7.68 (m, 1H), 7.59-7.46 (m, 4H), 4.50 (d, J = 5.9 Hz, 2H); |
| 1545 | 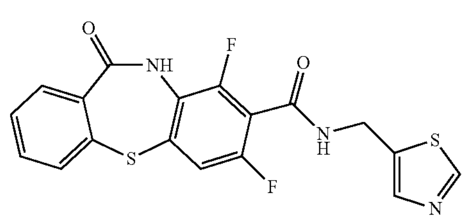 [SMILES: O=C1Nc2c(cc(F)c(C(=O)NCc3cncs3)c2F)Sc2ccccc21] | B, 62, 213 | 25 | 403.9 (M$^+$ + 1) | C$_{18}$H$_{11}$F$_2$N$_3$O$_2$S$_2$ 403.03 | $^1$H NMR (DMSO-d$_6$, 400 MHz): δ 10.66 (s, 1H), 9.39 (t, J = 5.9 Hz, 1H), 9.00 (s, 1H), 7.79 (s, 1H), 7.72-7.68 (m, 1H), 7.59-7.45 (m, 4H), 4.66 (d, J = 5.7 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1530 | 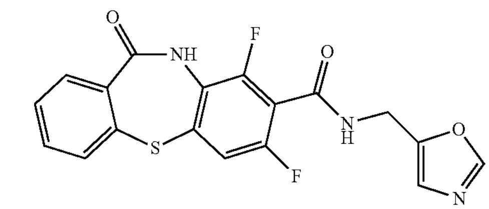 [SMILES: O=C1Nc2c(cc(F)c(C(=O)NCc3cnco3)c2F)Sc2ccccc21] | B, 62, 214 | 30 | 387.9 (M$^+$ + 1) | C$_{18}$H$_{11}$F$_2$N$_3$O$_3$S 387.05 | $^1$H NMR (DMSO-d$_6$, 400 MHz): δ 10.66 (s, 1H), 9.26 (t, J = 5.6 Hz, 1H), 8.31 (s, 1H), 7.73-7.66 (m, 1H), 7.58-7.46 (m, 4H), 7.02 (s, 1H), 4.51 (d, J = 5.5 Hz, 2H); |
| 1562 | 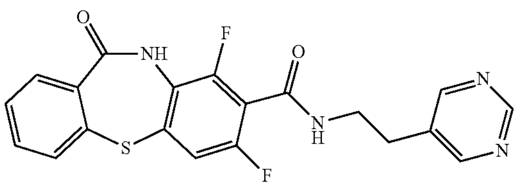 [SMILES: O=C1Nc2c(cc(F)c(C(=O)NCCc3cncnc3)c2F)Sc2ccccc21] | B, 62, 215 | 25 | 413.0 (M$^+$ + 1) | C$_{20}$H$_{14}$F$_2$N$_4$O$_2$S 412.08 | $^1$H NMR (DMSO-d$_6$, 400 MHz): δ 10.66 (s, 1H), 9.03 (s, 1H), 8.80 (t, J = 5.9 Hz, 1H), 8.67 (s, 2H), 7.78-7.62 (m, 1H), 7.58-7.43 (m, 4H), 3.53 (q, 2H), 2.81 (t, J = 6.5 Hz, 2H); |
| 1519 | 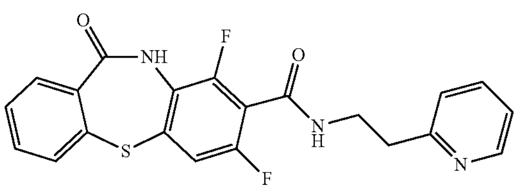 [SMILES: O=C1Nc2c(cc(F)c(C(=O)NCCc3ccccn3)c2F)Sc2ccccc21] | B, 62, 216 | 25 | 411.9 (M$^+$ + 1) | C$_{21}$H$_{15}$F$_2$N$_3$O$_2$S 411.09 | $^1$H NMR (DMSO-d$_6$, 400 MHz): δ 10.64 (s, 1H), 8.78 (t, J = 5.5 Hz, 1H), 8.49 (d, J = 4.2 Hz, 1H), 7.77-7.62 (m, 2H), 7.59-7.41 (m, 4H), 7.35-7.13 (m, 2H), 3.58 (q, 2H), 2.92 (t, J = 7.2 Hz, 2H); |
| 1531 | 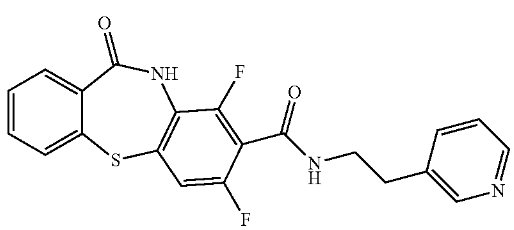 [SMILES: O=C1Nc2c(cc(F)c(C(=O)NCCc3cccnc3)c2F)Sc2ccccc21] | B, 62, 217 | 57 | 411.9 (M$^+$ + 1) | C$_{21}$H$_{15}$F$_2$N$_3$O$_2$S 411.09 | $^1$H NMR (DMSO-d$_6$, 400 MHz): δ 10.66 (s, 1H), 8.80 (t, J = 5.6 Hz, 1H), 8.51-8.34 (m, 2H), 7.72-7.68 (m, 1H), 7.65 (td, J = 1.9, 7.8 Hz, 1H), 7.57-7.45 (m, 4H), 7.31 (dd, J = 7.7, 4.8 Hz, 1H), 3.49 (q, 2H), 2.80 (t, J = 6.8 Hz, 2H); |
| 1563 | 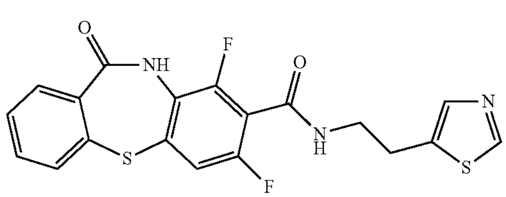 [SMILES: O=C1Nc2c(cc(F)c(C(=O)NCCc3cncs3)c2F)Sc2ccccc21] | B, 62, 352 | 28 | 418.0 (M$^+$ + 1) | C$_{19}$H$_{13}$F$_2$N$_3$O$_2$S$_2$ 417.04 | $^1$H NMR (DMSO-d$_6$, 400 MHz): δ 10.66 (s, 1H), 8.94 (s, 1H), 8.88 (t, J = 5.5 Hz, 1H), 7.72-7.69 (m, 1H), 7.68 (s, 1H), 7.58-7.46 (m, 4H), 3.48 (q, 2H), 3.06 (t, J = 6.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1546 | 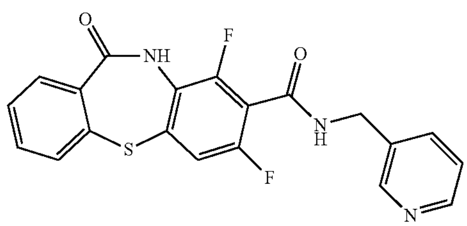 [SMILES: O=C1Nc2c(cc(F)c(C(=O)NCc3cccnc3)c2F)Sc2ccccc21] | B, 62, 218 | 46 | 398.0 (M$^+$ + 1) | C$_{20}$H$_{13}$F$_2$N$_3$O$_2$S 397.07 | $^1$H NMR (DMSO-d$_6$, 400 MHz): δ 10.67 (s, 1H), 9.31 (t, J = 6.0 Hz, 1H), 8.52 (s, 1H), 8.48 (dd, J = 4.8, 1.6 Hz, 1H), 7.74-7.64 (m, 2H), 7.58-7.46 (m, 4H), 7.39-7.36 (m, 1H), 4.48 (d, J = 5.9 Hz, 2H); |
| 1497 | 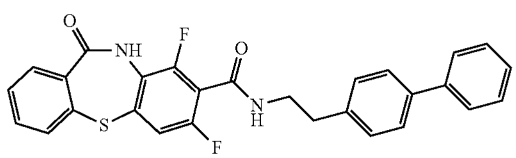 [SMILES: O=C1Nc2c(cc(F)c(C(=O)NCCc3ccc(-c4ccccc4)cc3)c2F)Sc2ccccc21] | B, 62, 219 | 15 | 487.0 (M$^+$ + 1); | C$_{28}$H$_{20}$F$_2$N$_2$O$_2$S 486.12 | $^1$H NMR (DMSO-d$_6$, 400 MHz): δ 10.63 (s, 1H), 8.81 (t, J = 5.9 Hz, 1H), 7.71-7.65 (m, 1H), 7.63-7.60 (m, 2H), 7.58-7.50 (m, 3H), 7.50-7.40 (m, 5H), 7.35-7.28 (m, 3H), 3.46 (q, 2H), 2.80 (t, J = 7.1 Hz, 2H); |
| 1272 | 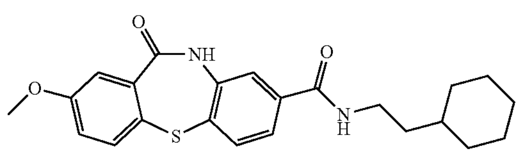 [SMILES: COc1ccc2c(c1)C(=O)Nc1cc(C(=O)NCCC3CCCCC3)ccc1S2] | A, 70, 261 | 55 | 412.8 (M$^+$ + 1); | C$_{23}$H$_{26}$N$_2$O$_3$S 410.17 | $^1$H-NMR (DMSO-d$_6$, 400 MHz): δ 10.74 (s, 1H), 8.42 (t, J = 6.4 Hz, 1H), 7.64-7.60 (m, 2H), 7.54 (s, 1H), 7.43 (d, J = 8.8 Hz, 1H), 7.18 (s, 1H), 7.05 (d, J = 8.8 Hz, 1H), 3.76 (s, 3H), 3.24-3.21 (m, 2H), 1.70-1.58 (m, 5H), 1.40-1.35 (m, 2H), 1.26-1.09 (m, 4H), 0.91-0.83 (m, 2H); |
| 1287 | 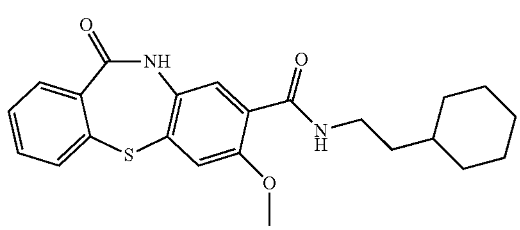 [SMILES: COc1cc2c(cc1C(=O)NCCC1CCCCC1)NC(=O)c1ccccc1S2] | A, 76, 261 | 46 | 411.9 (M$^+$ + 1); | C$_{23}$H$_{26}$N$_2$O$_3$S 410.17 | $^1$H-NMR (DMSO-d$_6$, 400 MHz): δ 10.55 (s, 1H), 8.08 (t, J = 5.6 Hz, 1H), 7.67 (t, J = 5.6 Hz, 1H), 7.54-7.43 (m, 4H), 7.27 (s, 1H), 3.85 (s, 3H), 3.26-3.21 (m, 2H), 1.70-1.59 (m, 5H), 1.39-1.33 (m, 2H), 1.29-1.12 (m, 4H), 0.93-0.85 (m, 2H); |
| 1286 | 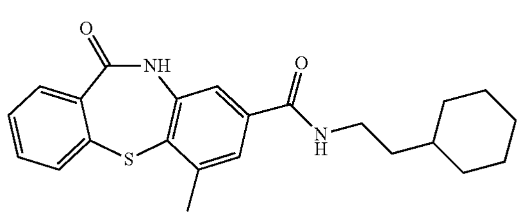 [SMILES: Cc1cc(C(=O)NCCC2CCCCC2)cc2c1Sc1ccccc1C(=O)N2] | A, 82, 261 | 20 | 395.6 (M$^+$ + 1) | C$_{23}$H$_{26}$N$_2$O$_2$S 394.17 | $^1$H-NMR (DMSO-d$_6$, 400 MHz): δ 10.69 (s, 1H), 8.37 (t, J = 5.6 Hz, 1H), 7.68-7.59 (m, 3H), 7.53-7.43 (m, 3H), 3.25-3.20 (m, 2H), 2.55 (s, 3H), 1.70-1.58 (m, 5H), 1.40-1.35 (m, 2H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 1.26-1.14 (m, 4H), 0.91-0.85 (m, 2H); |
| 1275 | 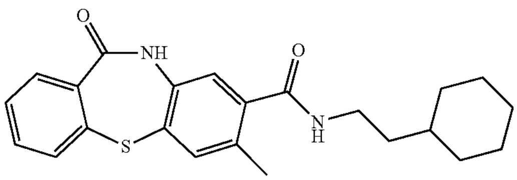 [SMILES: Cc1cc2c(cc1C(=O)NCCC1CCCCC1)NC(=O)c1ccccc1S2] | A, 88, 261 | 35 | 395.8 (M$^+$ + 1) | $C_{23}H_{26}N_2O_2S$ 394.17 | $^1$H-NMR (DMSO-d$_6$, 400 MHz): δ 10.66 (br s, 1H), 8.20 (br s, 1H), 7.66 (d, J = 7.2 Hz, 1H), 7.53-7.44 (m, 4H), 7.10 (s, 1H), 3.22-3.17 (m, 2H), 2.22 (s, 3H), 1.70-1.58 (m, 5H), 1.37-1.09 (m, 6H), 0.90-0.82 (m, 2H); |
| 1641 | 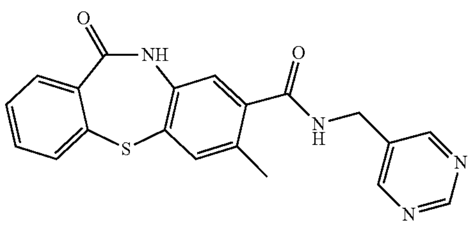 [SMILES: Cc1cc2c(cc1C(=O)NCc1cncnc1)NC(=O)c1ccccc1S2] | A, 88, 212 | 61 | 377.3 (M$^+$ + 1) | $C_{20}H_{16}N_4O_2S$ 376.10 | $^1$H NMR (DMSO-d$_6$, 400 MHz): δ 10.62 (s, 1H), 9.10 (s, 1H), 8.91 (t, J = 5.7 Hz, 1H), 8.75 (s, 2H), 7.67 (dd, J = 1.6, 7.4, 1.6 Hz, 1H), 7.57-7.42 (m, 4H), 7.23 (s, 1H), 4.44 (d, J = 5.9 Hz, 2H), 2.23 (s, 3H) |
| 1642 | 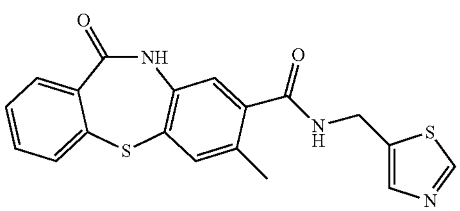 [SMILES: Cc1cc2c(cc1C(=O)NCc1cncs1)NC(=O)c1ccccc1S2] | A, 88, 213 | 34 | 381.9 (M$^+$ + 1) | $C_{19}H_{15}N_3O_2S_2$ 381.06 | $^1$H NMR (DMSO-d$_6$, 400 MHz): δ 10.63 (s, 1H), 9.00-8.95 (m, 2H), 7.79 (s, 1H), 7.66 (dd, J = 7.5, 1.5 Hz, 1H), 7.54-7.41 (m, 4H), 7.15 (s, 1H), 4.61 (d, J = 5.7 Hz, 2H), 2.23 (s, 3H); |
| 1643 | 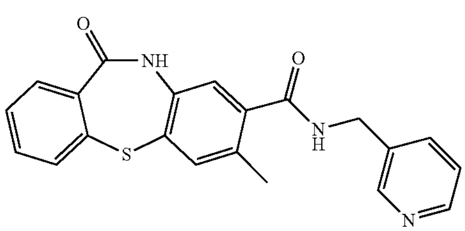 | A, 88, 218 | 75 | 376.0 (M$^+$ + 1) | $C_{21}H_{17}N_3O_2S$ 375.10 | $^1$H NMR (DMSO-d$_6$, 400 MHz): δ 10.63 (s, 1H), 8.87 (t, J = 5.9 Hz, 1H), 8.53 (s, 1H), 8.47 (dd, J = 4.8, 1.5 Hz, 1H), 7.74-7.65 (m, 2H), 7.56-7.41 (m, 4H), 7.36 (dd, J = 7.4, 5.1 Hz, 1H), 7.20 (s, 1H), 4.42 (d, J = 6.0 Hz, 2H), 2.23 (s, 3H) |
| 1478 | 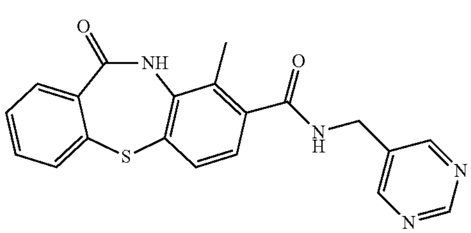 [SMILES: Cc1c(C(=O)NCc2cncnc2)ccc2c1NC(=O)c1ccccc1S2] | A, 97, 212 (Reaction time 18 h) | 45 | 376.9 (M$^+$ + 1) | $C_{20}H_{16}N_4O_2S$ 376.10 | $^1$H NMR (DMSO-d$_6$, 400 MHz): δ 10.24 (s, 1H), 9.09 (s, 1H), 8.93 (t, J = 5.9 Hz, 1H), 8.75 (s, 2H), 7.69-7.59 (m, 1H), 7.56-7.39 (m, 4H), 7.14 (d, J = 7.9 Hz, 1H), 4.44 (d, J = 5.7 Hz, 2H), 2.26 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1513 | 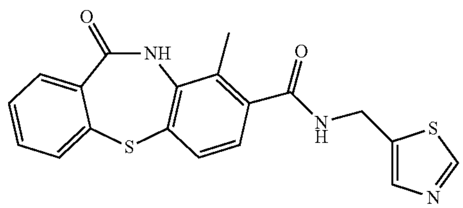 [SMILES: Cc1c(C(=O)NCc2cncs2)ccc2c1NC(=O)c1ccccc1S2] | A, 97, 213 | 28 | 382.2 (M$^+$ + 1) | $C_{19}H_{15}N_3O_2S_2$ 381.06 | $^1$H NMR (DMSO-d$_6$, 400 MHz): δ 10.23 (s, 1H), 9.01 (t, J = 5.9 Hz, 1H), 8.98 (s, 1H), 7.79 (s, 1H), 7.71-7.59 (m, 1H), 7.55-7.48 (m, 2H), 7.47-7.40 (m, 2H), 7.06 (d, J = 7.9 Hz, 1H), 4.61 (d, J = 5.7 Hz, 2H), 2.27 (s, 3H); |
| 1514 | 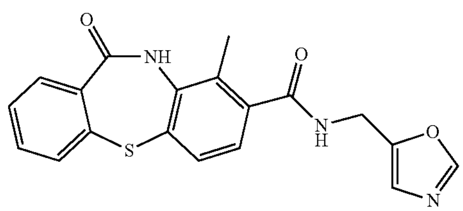 [SMILES: Cc1c(C(=O)NCc2cnco2)ccc2c1NC(=O)c1ccccc1S2] | B, 97, 214 | 55 | 365.8 (M$^+$ + 1) | $C_{19}H_{15}N_3O_3S$ 365.08 | $^1$H NMR (DMSO-d$_6$, 400 MHz): δ 10.21 (s, 1H), 8.83 (t, J = 5.7 Hz, 1H), 8.26 (s, 1H), 7.83-7.56 (m, 1H), 7.56-7.36 (m, 4H), 7.06 (d, J = 7.9 Hz, 1H), 7.01 (s, 1H), 4.44 (d, J = 5.6 Hz, 2H), 2.24 (s, 3H); |
| 1529 | 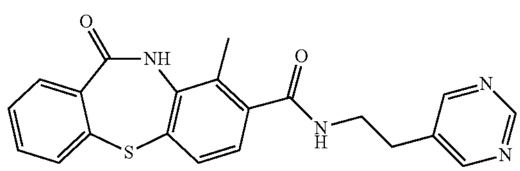 [SMILES: Cc1c(C(=O)NCCc2cncnc2)ccc2c1NC(=O)c1ccccc1S2] | A, 97, 215 | 25 | 390.9 (M$^+$ + 1) | $C_{21}H_{18}N_4O_2S$ 390.12 | $^1$H NMR (DMSO-d$_6$, 400 MHz): δ 10.20 (s, 1H), 9.03 (s, 1H), 8.68 (s, 2H), 8.38 (t, J = 5.3 Hz, 1H), 7.69-7.60 (m, 1H), 7.53-7.39 (m, 4H), 6.96 (d, J = 7.9 Hz, 1H), 3.51 (q, 2H), 2.81 (t, J = 6.6 Hz, 2H), 2.13 (s, 3H); |
| 1459 | 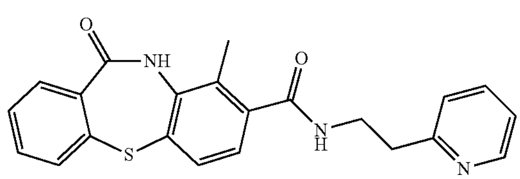 [SMILES: Cc1c(C(=O)NCCc2ccccn2)ccc2c1NC(=O)c1ccccc1S2] | A, 97, 216 | 58 | 390.0 (M$^+$ + 1) | $C_{22}H_{19}N_3O_2S$ 389.12 | $^1$H NMR (DMSO-d$_6$, 400 MHz): δ 10.20 (s, 1H), 8.48 (d, J = 4.0 Hz, 1H), 8.34 (br s, 1H), 7.76-7.58 (m, 2H), 7.55-7.35 (m, 4H), 7.26 (d, J = 7.8 Hz, 1H), 7.23-7.18 (m, 1H), 7.00 (d, J = 7.8 Hz, 1H), 3.55 (d, J = 5.5 Hz, 2H), 2.93 (t, J = 7.1 Hz, 2H), 2.19 (s, 3H); |
| 1467 | 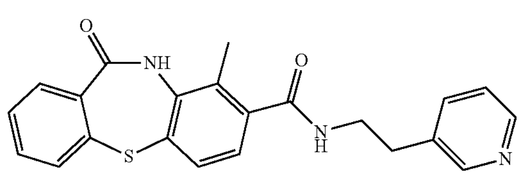 [SMILES: Cc1c(C(=O)NCCc2cccnc2)ccc2c1NC(=O)c1ccccc1S2] | A, 97, 217 | 29 | 390.0 (M$^+$ + 1) | $C_{22}H_{19}N_3O_2S$ 389.12 | $^1$H NMR (DMSO-d$_6$, 500 MHz): δ 10.20 (s, 1H), 8.46-8.39 (m, 2H), 8.36 (t, J = 5.4 Hz, 1H), 7.65 (td, J = 6.2, 3.0 Hz, 2H), 7.58-7.38 (m, 4H), 7.31 (dd, J = 7.7, 4.8 Hz, 1H), 6.96 (d, J = 8.1 Hz, 1H), 3.47 (d, J = 5.5 Hz, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2H), 2.80 (t, J = 6.8 Hz, 2H), 2.15 (s, 3H); |
| 1560 | 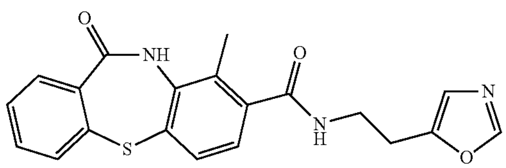 [SMILES: Cc1c(C(=O)NCCc2cnco2)ccc2c1NC(=O)c1ccccc1S2] | A, 97, 347 | 21 | 379.9 (M$^+$ + 1) | C$_{20}$H$_{17}$N$_3$O$_3$S 379.10 | $^1$H NMR (DMSO-d$_6$, 400 MHz): δ 10.22 (s, 1H), 8.41 (t, J = 5.7 Hz, 1H), 8.22 (s, 1H), 7.22-7.58 (m, 1H), 7.56-7.35 (m, 4H), 7.01 (d, J = 7.9 Hz, 1H), 6.92 (s, 1H), 3.45 (d, J = 6.2 Hz, 2H), 2.98-2.81 (m, 2H), 2.22 (s, 3H); |
| 1561 | 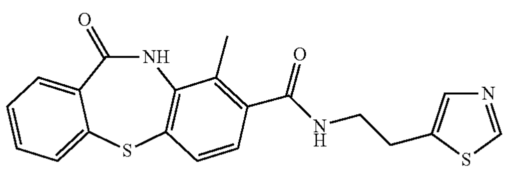 | A, 97, 352 | 34 | 396.0 (M$^+$ + 1) | C$_{20}$H$_{17}$N$_3$O$_2$S$_2$ 395.08 | $^1$H NMR (DMSO-d$_6$, 400 MHz): δ 10.22 (s, 1H), 8.93 (s, 1H), 8.44 (t, J = 5.9 Hz, 1H), 7.68 (s, 1H), 7.67-7.63 (m, 1H), 7.54-7.47 (m, 2H), 7.46-7.42 (m, 2H), 7.02 (d, J = 7.9 Hz, 1H), 3.45 (q, 2H), 3.07 (t, J = 6.6 Hz, 2H), 2.21 (s, 3H); |
| 1515 | 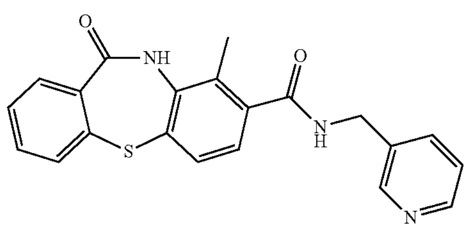 [SMILES: Cc1c(C(=O)NCc2cccnc2)ccc2c1NC(=O)c1ccccc1S2] | A, 97, 218 | 40 | 376.0 (M$^+$ + 1) | C$_{21}$H$_{17}$N$_3$O$_2$S 375.10 | $^1$H NMR (DMSO-d$_6$, 400 MHz): δ 10.24 (s, 1H), 8.90 (t, J = 6.1 Hz, 1H), 8.54-8.51 (m, 1H), 8.46 (d, J = 5.3 Hz, 1H), 7.70 (dt, J = 7.8, 1.9 Hz, 1H), 7.67-7.63 (m, 1H), 7.54-7.40 (m, 4H), 7.36 (dd, J = 7.5, 5.1 Hz, 1H), 7.12 (d, J = 7.9 Hz, 1H), 4.42 (d, J = 6.0 Hz, 2H), 2.27 (s, 3H); |
| 1495 | 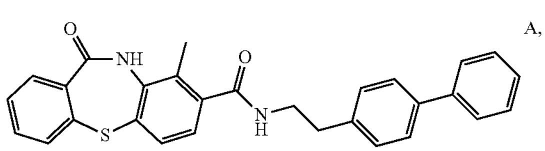 | A, 97, 219 | 41 | 465.0 (M$^+$ + 1) | C$_{29}$H$_{24}$N$_2$O$_2$S 464.16 | $^1$H NMR (DMSO-d$_6$, 400 MHz): δ 10.20 (s, 1H), 8.37 (t, J = 5.1 Hz, 1H), 7.64 (d, J = 7.2 Hz, 3H), 7.59 (d, J = 8.0 Hz, 2H), 7.53-7.40 (m, 6H), 7.39-7.26 (m, 3H), 7.00 (d, J = 7.9 Hz, 1H), 3.48 (q, 2H), 2.83 (t, J = 6.9 Hz, 2H), 2.19 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1516 | 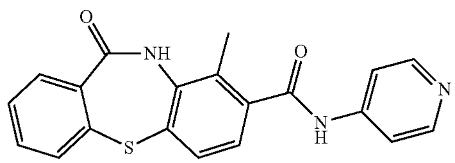 [SMILES: Cc1c(C(=O)Nc2ccncc2)ccc2c1NC(=O)c1ccccc1S2] | B, 97, 185 | 34 | 361.9 (M$^+$ + 1) | $C_{20}H_{15}N_3O_2S$ 361.09 | $^1$H NMR (DMSO-d$_6$, 400 MHz): δ 10.73 (br s, 1H), 10.34 (br s, 1H), 8.45 (d, J = 4.6 Hz, 2H), 7.71-7.53 (m, 5H), 7.50-7.44 (m, 2H), 7.26 (d, J = 7.9 Hz, 1H), 2.34 (s, 3H); |
| 1517 | 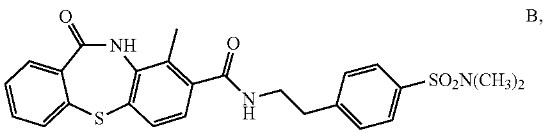 | B, 97, 406 | 50 | 496.0 (M$^+$ + 1) | $C_{25}H_{25}N_3O_4S_2$ 495.13 | $^1$H NMR (DMSO-d$_6$, 400 MHz): δ 10.21 (s, 1H), 8.36 (t, J = 5.6 Hz, 1H), 7.69-7.62 (m, 3H), 7.57-7.40 (m, 6H), 6.96 (d, J = 7.9 Hz, 1H), 3.50 (d, J = 5.3 Hz, 2H), 2.90 (t, J = 6.7 Hz, 2H), 2.58 (s, 6H), 2.14 (s, 3H); |
| 1496 | 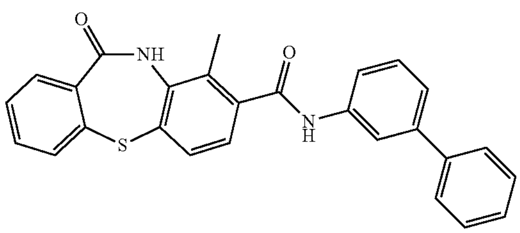 [SMILES: Cc1c(C(=O)Nc2cccc(-c3ccccc3)c2)ccc2c1NC(=O)c1ccccc1S2] | B, 97, 186 | 37 | 437.0 (M$^+$ + 1) | $C_{27}H_{20}N_2O_2S$ 436.12 | $^1$H NMR (DMSO-d$_6$, 400 MHz): δ 10.42 (s, 1H), 10.31 (s, 1H), 8.00 (s, 1H), 7.70-7.63 (m, 2H), 7.62-7.53 (m, 4H), 7.51-7.43 (m, 4H), 7.43-7.35 (m, 3H), 7.26 (d, J = 7.9 Hz, 1H), 2.37 (s, 3H); |
| 1276 | 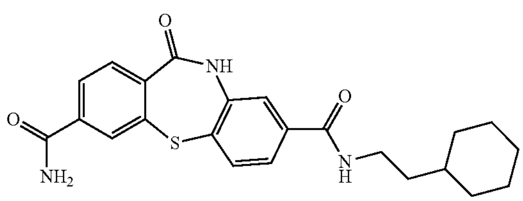 [SMILES: NC(=O)c1ccc2c(c1)Sc1ccc(C(=O)NCCC3CCCCC3)cc1NC2=O] | A, 135, 261 | 40 | 424.8 (M$^+$ + 1); | $C_{23}H_{25}N_3O_3S$ 423.16 | $^1$H-NMR (DMSO-d$_6$, 500 MHz): δ 10.86 (br s, 1H), 8.45-8.44 (m, 1H), 8.14 (s, 1H), 8.00 (s, 1H), 7.89 (d, J = 8.0 Hz, 1H), 7.75 (d, J = 8.0 Hz, 1H), 7.65 (d, J = 8.5 Hz, 2H), 3.24-3.23 (m, 2H), 1.70-1.58 (m, 5H), 1.37 (t, J = 6.5 Hz, 2H), 1.18-1.09 (m, 5H), 0.86 (t, J = 6.5 Hz, 2H); |
| 1200 | 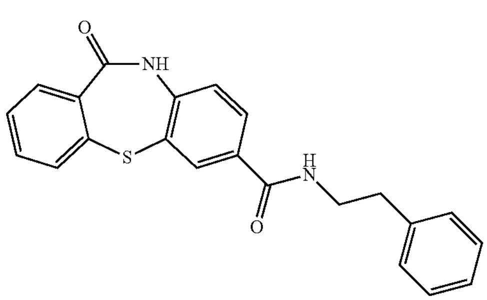 [SMILES: O=C(NCCc1ccccc1)c1ccc2c(c1)Sc1ccccc1C(=O)N2] | A, 140, 211 | 73 | 375.1 (M$^+$ + 1); | $C_{22}H_{18}N_2O_2S$ 374.11 | $^1$H-NMR (DMSO-d$_6$, 400 MHz): δ 10.85 (s, 1H), 8.60 (t, J = 4.8 Hz, 1H), 8.01 (s, 1H), 7.78 (d, J = 8.4 Hz, 1H), 7.69 (d, J = 8.4 Hz, 1H), 7.54-7.44 (m, 3H), 7.30-7.17 (m, 6H), 3.47-3.42 (m, 2H), 2.82 (t, J = 7.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1207 | 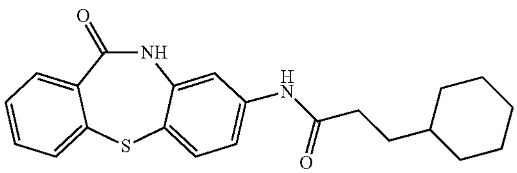 [SMILES: O=C(CCC1CCCCC1)Nc1ccc2c(c1)NC(=O)c1ccccc1S2] | A, 145, 3-cyclohexyl-propanoic acid | 35 | 381.1 (M$^+$ + 1) | $C_{22}H_{24}N_2O_2S$ 380.16 | $^1$H-NMR (DMSO-d$_6$, 400 MHz): δ 10.67 (s, 1H), 10.03 (s, 1H), 7.66 (d, J = 7.2 Hz, 1H), 7.60 (s, 1H), 7.50-7.40 (m, 4H), 7.31 (d, J = 8.4 Hz, 1H), 2.32-2.27 (m, 2H), 1.69-1.60 (m, 5H), 1.48-1.43 (m, 2H), 1.18-1.13 (m, 4H), 0.90-0.85 (m, 2H); |
| 1644 | 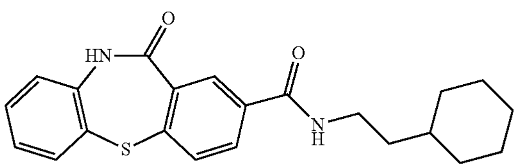 [SMILES: O=C(NCCC1CCCCC1)c1ccc2c(c1)C(=O)Nc1ccccc1S2] | A, 150, 261 | 54 | 381.4 (M$^+$ + 1) | $C_{22}H_{24}N_2O_2S$ 380.16 | $^1$H-NMR (DMSO-d$_6$, 400 MHz): δ 10.77 (br s, 1H), 8.58-8.54 (m, 1H), 8.12 (s, 1H), 7.90 (d, J = 8.0 Hz, 1H), 7.62-7.56 (m, 2H), 7.38-7.34 (m, 1H), 7.23 (d, J = 8.0 Hz, 1H), 7.16 (t, J = 6.8 Hz, 1H), 3.27-3.24 (m, 2H), 1.72-1.58 (m, 5H), 1.26-1.11 (m, 5H), 0.96-0.82 (m, 2H); |
| 1645 | 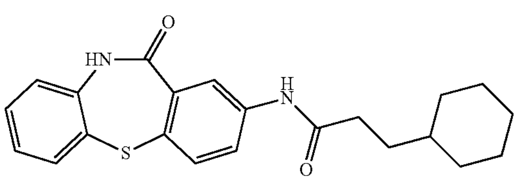 [SMILES: O=C(CCC1CCCCC1)Nc1ccc2c(c1)C(=O)Nc1ccccc1S2] | B, 155, 3-cyclohexyl-propanic acid | 6 | 381.2 (M$^+$ + 1); | $C_{22}H_{24}N_2O_2S$ 380.16 | $^1$H-NMR (DMSO-d$_6$, 400 MHz): δ 10.64 (s, 1H), 10.08 (s, 1H), 7.95 (s, 1H), 7.68-7.65 (m, 1H), 7.53 (d, J = 7.2 Hz, 1H), 7.43 (d, J = 8.4 Hz, 1H), 7.34 (t, J = 8.0 Hz, 1H), 7.22 (d, J = 7.2 Hz, 1H), 7.13 (t, J = 7.6 Hz, 1H), 2.32-2.27 (m, 2H), 1.69-1.60 (m, 4H), 1.49-1.41 (m, 2H), 1.28-1.13 (m, 4H), 0.90-0.85 (m, 3H); |
| 1373 | 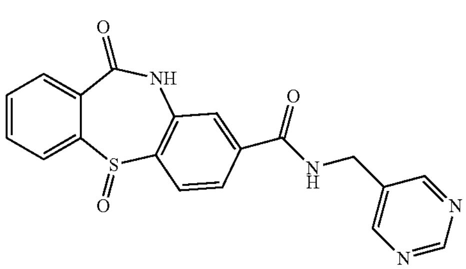 [SMILES: O=C(NCc1cncnc1)c1ccc2c(c1)NC(=O)c1ccccc1S2=O] | A, 156, 212 (Reaction time 24 h) | 21 | 378.9 (M$^+$ + 1) | $C_{19}H_{14}N_4O_3S$ 378.08 | $^1$H NMR (DMSO-d$_6$, 500 MHz): δ 11.03 (br s, 1H), 9.21 (t, J = 5.4 Hz, 1H), 9.06 (s, 1H), 8.73 (s, 2H), 7.88 (d, J = 8.1 Hz, 1H), 7.83-7.76 (m, 2H), 7.74-7.67 (m, 3H), 7.63-7.59 (m, 1H), 4.46 (d, J = 4.9 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1388 | 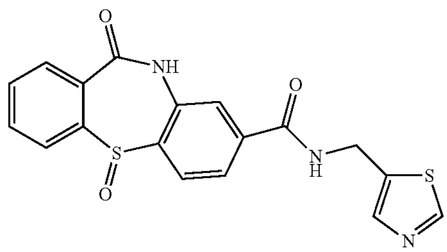 [SMILES: O=C(NCc1cncs1)c1ccc2c(c1)NC(=O)c1ccccc1S2=O] | A, 156, 213 | 21 | 383.9 (M$^+$ + 1) | $C_{18}H_{13}N_3O_3S_2$ 383.04 | $^1$H NMR (DMSO-d$_6$, 400 MHz): δ 11.05 (s, 1H), 9.31 (t, J = 6.3 Hz, 1H), 8.96 (s, 1H), 7.88-7.60 (m, 8H), 4.65 (d, J = 5.6 Hz, 2H); |
| 1381 | 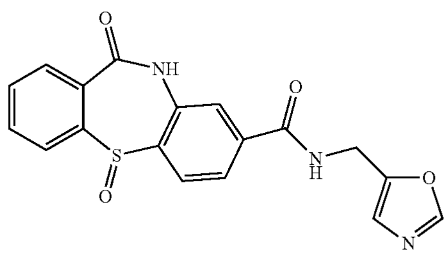 | A, 156, 214 | 23 | 367.9 (M$^+$ + 1) | $C_{18}H_{13}N_3O_4S$ 367.06 | $^1$H NMR (DMSO-d$_6$, 400 MHz): δ 11.05 (s, 1H), 9.14 (t, J = 5.6 Hz, 1H), 8.27 (s, 1H), 7.88 (dd, J = 8.2, 1.5 Hz, 1H), 7.84-7.78 (m, 2H), 7.76-7.67 (m, 3H), 7.63 (dd, J = 7.7, 1.0 Hz, 1H), 7.04 (s, 1H), 4.51 (d, J = 5.5 Hz, 2H); |
| 1423 | 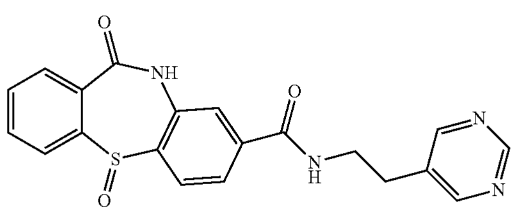 [SMILES: O=C(NCCc1cncnc1)c1ccc2c(c1)NC(=O)c1ccccc1S2=O] | B, 156, 215 | 32 | 393.0 (M$^+$ + 1) | $C_{20}H_{16}N_4O_3S$ 392.09 | $^1$H NMR (DMSO-d$_6$, 400 MHz): δ 11.06 (s, 1H), 9.01 (s, 1H), 8.69 (t, J = 5.6 Hz, 1H), 8.66 (s, 2H), 7.84-7.77 (m, 3H), 7.74 (d, J = 7.0 Hz, 1H), 7.67 (d, J = 8.2 Hz, 1H), 7.65-7.60 (m, 2H), 3.53 (q, J = 6.3 Hz, 2H), 2.84 (t, J = 6.6 Hz, 2H); |
| 1374 | 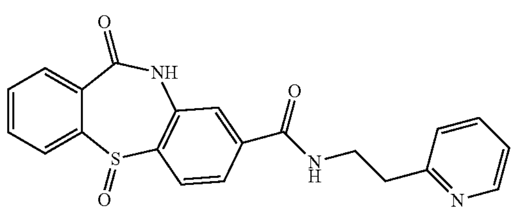 [SMILES: O=C(NCCc1ccccn1)c1ccc2c(c1)NC(=O)c1ccccc1S2=O] | A, 156, 216 | 44 | 391.9 (M$^+$ + 1) | $C_{21}H_{17}N_3O_3S$ 391.10 | $^1$H NMR (DMSO-d$_6$, 400 MHz): δ 11.06 (s, 1H), 8.69 (t, J = 5.6 Hz, 1H), 8.51-8.47 (m, 1H), 7.85-7.78 (m, 3H), 7.74 (d, J = 6.9 Hz, 1H), 7.71-7.60 (m, 4H), 7.25 (d, J = 7.7 Hz, 1H), 7.23-7.18 (m, 1H), 3.59 (q, J = 6.5 Hz, 2H), 2.96 (t, J = 7.3 Hz, 2H); |
| 1389 | 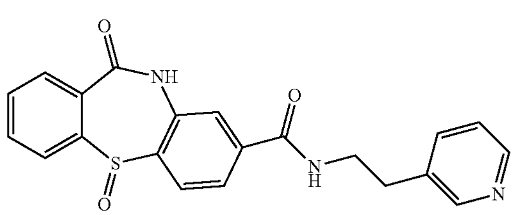 [SMILES: O=C(NCCc1cccnc1)c1ccc2c(c1)NC(=O)c1ccccc1S2=O] | A, 156, 217 | 21 | 391.9 (M$^+$ + 1) | $C_{21}H_{17}N_3O_3S$ 391.10 | $^1$H NMR (DMSO-d$_6$, 400 MHz): δ 11.06 (s, 1H), 8.69 (t, J = 5.2 Hz, 1H), 8.44-8.37 (m, 2H), 7.84-7.72 (m, 4H), 7.70-7.60 (m, 4H), 7.29 (dd, J = 7.5, 5.0 Hz, 1H), 3.49 (q, J = 6.5 Hz, 2H), 2.83 (t, J = 7.0 |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | Hz, 2H); |
| 1382 | 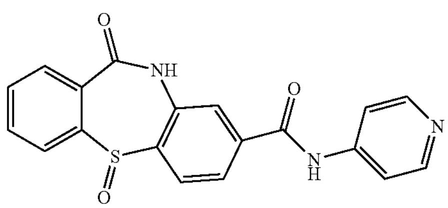 [SMILES: O=C(Nc1ccncc1)c1ccc2c(c1)NC(=O)c1ccccc1S2=O] | A, 156, 185 | 8 | 363.9 (M$^+$ + 1) | C$_{19}$H$_{13}$N$_3$O$_3$S 363.07 | $^1$H NMR (DMSO-d$_6$, 400 MHz): δ 11.13 (br s, 1H), 10.69 (s, 1H), 8.53-8.43 (m, 2H), 7.99 (dd, J = 8.1, 1.5 Hz, 1H), 7.86-7.75 (m, 5H), 7.75-7.70 (m, 2H), 7.67-7.62 (m, 1H); |
| 1375 | 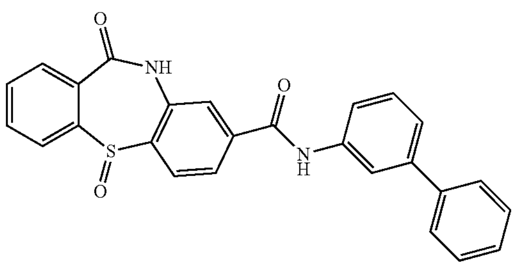 [SMILES: O=C(Nc1cccc(-c2ccccc2)c1)c1ccc2c(c1)NC(=O)c1ccccc1S2=O] | A, 156, 186 | 33 | 439.5 (M$^+$ + 1) | C$_{26}$H$_{18}$N$_2$O$_3$S 438.10 | $^1$H NMR (DMSO-d$_6$, 400 MHz): δ 11.13 (s, 1H), 10.44 (s, 1H), 8.07-7.98 (m, 2H), 7.87-7.72 (m, 6H), 7.68-7.60 (m, 3H), 7.52-7.35 (m, 5H); |
| 1427 | 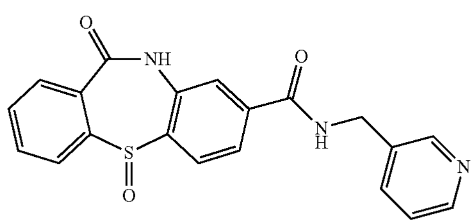 [SMILES: O=C(NCc1cccnc1)c1ccc2c(c1)NC(=O)c1ccccc1S2=O] | A, 156, 218 | 19 | 377.9 (M$^+$ + 1) | C$_{20}$H$_{15}$N$_3$O$_3$S 377.08 | $^1$H NMR (DMSO-d$_6$, 400 MHz): δ 11.05 (s, 1H), 9.21 (t, J = 5.9 Hz, 1H), 8.53 (s, 1H), 8.45 (dd, J = 4.7, 1.4 Hz, 1H), 7.90 (dd, J = 8.2, 1.5 Hz, 1H), 7.85-7.68 (m, 6H), 7.63 (td, J = 7.5, 1.3 Hz, 1H), 7.34 (dd, J = 7.8, 4.8 Hz, 1H), 4.47 (d, J = 5.2 Hz, 2H); |
| 1485 | 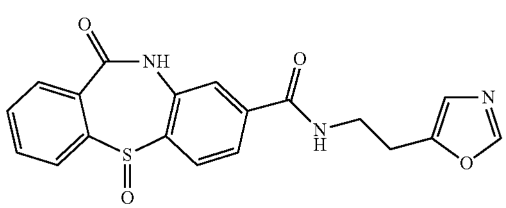 | A, 156, 347 | 18 | 381.9 (M$^+$ + 1) | C$_{19}$H$_{15}$N$_3$O$_4$S 381.08 | $^1$H NMR (DMSO-d$_6$, 400 MHz): δ 11.06 (s, 1H), 8.73 (t, J = 5.6 Hz, 1H), 8.21 (s, 1H), 7.85-7.78 (m, 3H), 7.74 (dd, J = 9.5, 2.7 Hz, 1H), 7.68 (d, J = 8.4 Hz, 2H), 7.63 (td, J = 10.1, 1.1 Hz, 1H), 6.92 (s, 1H), 3.53-3.46 (m, 2H), 2.90 (t, J = 6.7 Hz, 2H); |
| 1527 | 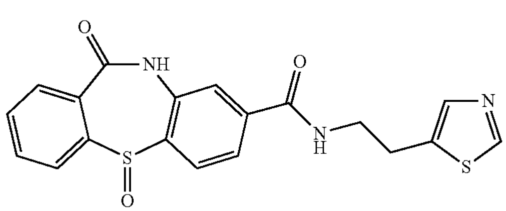 [SMILES: O=C(NCCc1cnco1)c1ccc2c(c1)NC(=O)c1ccccc1S2=O] | A, 156, 352 | 24 | 397.8 (M$^+$ + 1) | C$_{19}$H$_{15}$N$_3$O$_3$S$_2$ 397.06 | $^1$H NMR (DMSO-d$_6$, 400 MHz): δ 11.07 (br s, 1H), 8.90 (s, 1H), 8.76 (t, J = 5.5 Hz, 1H), 7.87-7.78 (m, 3H), 7.75 (d, J = 7.3 Hz, 1H), 7.71-7.67 (m, 3H), 7.66-7.60 (m, 1H), 3.52-3.45 (m, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2H), 3.10 (t, J = 6.7 Hz, 2H); |
| 1476 | 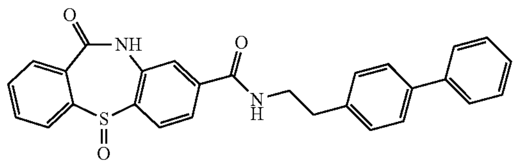 | A, 156, 219 | 29 | 467.0 (M$^+$ + 1) | $C_{28}H_{22}N_2O_3S$ 466.14 | $^1$H NMR (DMSO-d$_6$, 400 MHz): δ 11.07 (s, 1H), 8.72 (t, J = 5.4 Hz, 1H), 7.87-7.78 (m, 3H), 7.76-7.73 (m, 1H), 7.71-7.67 (m, 2H), 7.65-7.60 (m, 3H), 7.58 (d, J = 8.2 Hz, 2H), 7.47-7.41 (m, 2H), 2H), 7.36-7.29 (m, 3H), 3.50 (q, J = 6.7 Hz, 2H), 2.86 (t, J = 7.2 Hz, 2H); |
| 1486 | 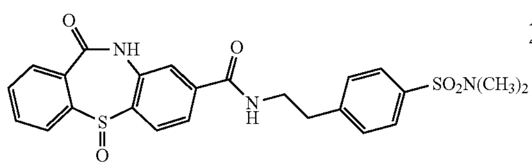 | A, 156, 406 | 17 | 498.0 (M$^+$ + 1) | $C_{24}H_{23}N_3O_5S_2$ 497.11 | $^1$H NMR (DMSO-d$_6$, 400 MHz): δ 11.06 (s, 1H), 8.68 (t, J = 5.5 Hz, 1H), 7.85-7.77 (m, 3H), 7.76-7.73 (m, 1H), 7.68-7.61 (m, 5H), 7.48 (d, J = 8.4 Hz, 2H), 3.61-3.45 (m, 2H), 2.92 (t, J = 7.0 Hz, 2H), 2.53 (s, 6H); |
| 1575 | 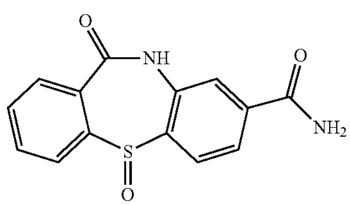 [SMILES: NC(=O)c1ccc2c(c1)NC(=O)c1ccccc1S2=O] | B, 156, 133 | 48 | 286.8 (M$^+$ + 1) | $C_{14}H_{10}N_2O_3S$ 286.04 | $^1$H-NMR (DMSO-d$_6$, 400 MHz): δ 11.05 (br s, 1H), 8.06 (br s, 1H), 7.93-7.58 (m, 7H), 7.52 (br s, 1H); |
| 1446 | 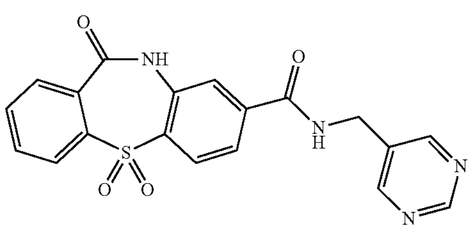 [SMILES: O=C(NCc1cncnc1)c1ccc2c(c1)NC(=O)c1ccccc1S2(=O)=O] | A, 159, 212 | 38 | 395.0 (M$^+$ + 1) | $C_{19}H_{14}N_4O_4S$ 394.07 | $^1$H NMR (DMSO-d$_6$, 400 MHz): δ 11.51 (s, 1H), 9.34 (t, J = 5.8 Hz, 1H), 9.08 (s, 1H), 8.76 (s, 2H), 8.06 (d, J = 8.2 Hz, 1H), 8.01-7.95 (m, 2H), 7.92-7.80 (m, 4H), 4.50 (d, J = 5.6 Hz, 2H); |
| 1455 | 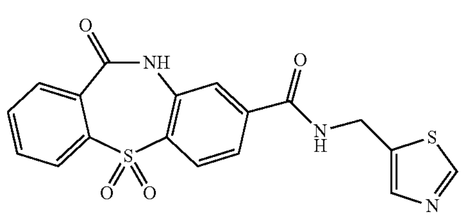 | A, 159, 213 | 27 | 399.9 (M$^+$ + 1) | $C_{18}H_{13}N_3O_4S_2$ 399.03 | $^1$H NMR (DMSO-d$_6$, 400 MHz): δ 11.50 (s, 1H), 9.42 (t, J = 5.9 Hz, 1H), 8.97 (s, 1H), 8.05 (d, J = 8.3 Hz, 1H), 7.98 (td, J = 7.4, 1.1 Hz, 2H), 7.90 (td, J = 7.5, 1.4 Hz, 1H), 7.87-7.77 (m, 4H), 4.67 (d, J = 5.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | ¹H-NMR |
|---|---|---|---|---|---|---|
| 1456 | 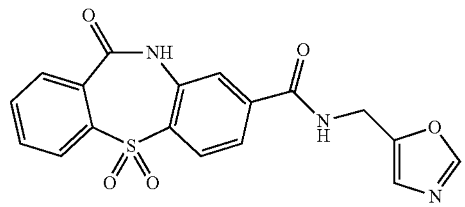 [SMILES: O=C(NCc1cncs1)c1ccc2c(c1)NC(=O)c1ccccc1S2(=O)=O] | A, 159, 214 | 23 | 384.0 (M⁺ + 1) | $C_{18}H_{13}N_3O_5S$ 383.06 | ¹H NMR (DMSO-d$_6$, 400 MHz): δ 11.51 (br s, 1H), 9.26 (t, J = 5.6 Hz, 1H), 8.29 (s, 1H), 8.05 (d, J = 8.3 Hz, 1H), 8.01-7.95 (m, 2H), 7.90 (td, J = 7.5, 1.5 Hz, 1H), 7.88-7.78 (m, 3H), 7.06 (s, 1H), 4.53 (d, J = 5.3 Hz 2H); |
| 1457 | 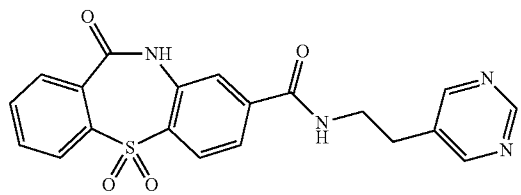 [SMILES: O=C(NCCc1cncnc1)c1ccc2c(c1)NC(=O)c1ccccc1S2(=O)=O] | A, 159, 215 | 32 | 409.0 (M⁺ + 1) | $C_{20}H_{16}N_4O_4S$ 408.09 | ¹H NMR (DMSO-d$_6$, 400 MHz): δ 11.51 (s, 1H), 9.01 (s, 1H), 8.80 (t, J = 5.7 Hz, 1H), 8.67 (s, 2H), 8.03 (d, J = 8.2 Hz, 1H), 8.01-7.96 (m, 2H), 7.94-7.82 (m, 2H), 7.76 (s, 1H), 7.71 (dd, J = 8.3, 1.6 Hz, 1H), 3.55 (q, J = 6.3 Hz, 2H), 2.86 (t, J = 6.6 Hz, 2H); |
| 1447 | 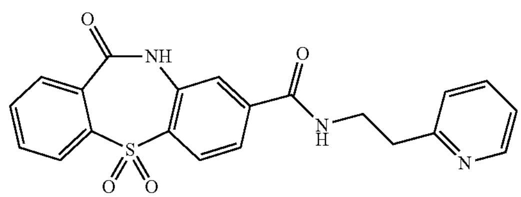 [SMILES: O=C(NCCc1ccccn1)c1ccc2c(c1)NC(=O)c1ccccc1S2(=O)=O] | A, 159, 216 | 30 | 408.0 (M⁺ + 1) | $C_{21}H_{17}N_3O_4S$ 407.09 | ¹H NMR (DMSO-d$_6$, 400 MHz): δ 11.51 (s, 1H), 8.80 (t, J = 5.5 Hz, 1H), 8.51-8.48 (m, 1H), 8.03 (d, J = 8.3 Hz, 1H), 8.00-7.96 (m, 2H), 7.93-7.83 (m, 2H), 7.79-7.78 (m, 1H), 7.74 (dd, J = 8.3, 1.6 Hz, 1H), 7.69 (td, J = 7.7, 1.8 Hz, 1H), 7.26 (d, J = 7.7 Hz, 1H), 7.23-7.19 (m, 1H), 3.64-3.57 (m, 2H), 2.97 (t, J = 7.3 Hz, 2H); |
| 1448 | 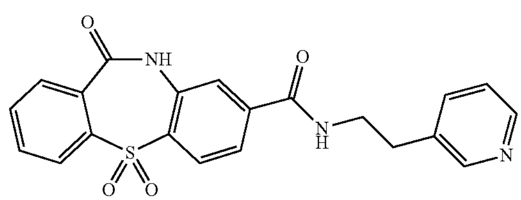 [SMILES: O=C(NCCc1cccnc1)c1ccc2c(c1)NC(=O)c1ccccc1S2(=O)=O] | A, 159, 217 | 22 | 407.9 (M⁺ + 1) | $C_{21}H_{17}N_3O_4S$ 407.09 | ¹H NMR (DMSO-d$_6$, 400 MHz): δ 11.52 (s, 1H), 8.81 (t, J = 5.6 Hz, 1H), 8.48-8.36 (m, 2H), 8.03 (d, J = 8.3 Hz, 1H), 8.01-7.95 (m, 2H), 7.93-7.83 (m, 2H), 7.79-7.78 (m, 1H), 7.73 (dd, J = 8.3, 1.5 Hz, 1H), 7.64 (d, J = 7.8 Hz, 1H), 7.29 (dd, J = 7.8, 4.7 Hz, 1H), 3.51 (q, J = 6.5 Hz, 2H), 2.85 (t, J = 7.0 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1449 | 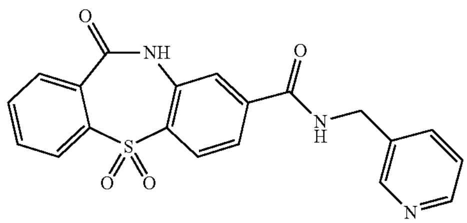 [SMILES: O=C(NCc1cccnc1)c1ccc2c(c1)NC(=O)c1ccccc1S2(=O)=O] | A, 159, 218 | 15 | 393.9 ($M^+ + 1$) | $C_{20}H_{15}N_3O_4S$ 393.08 | $^1$H NMR (DMSO-$d_6$, 400 MHz): δ 11.49 (br s, 1H), 9.33 (t, J = 5.5 Hz, 1H), 8.60-8.39 (m, 2H), 8.05 (d, J = 8.2 Hz, 1H), 8.02-7.94 (m, 2H), 7.93-7.81 (m, 4H), 7.70 (d, J = 7.7 Hz, 1H), 7.34 (dd, J = 7.6, 4.8 Hz, 1H), 4.49 (d, J = 5.5 Hz, 2H); |
| 1462 | 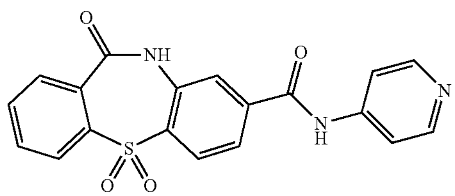 [SMILES: O=C(Nc1ccncc1)c1ccc2c(c1)NC(=O)c1ccccc1S2(=O)=O] | A, 159, 185 | 15 | 379.9 ($M^+ + 1$) | $C_{19}H_{13}N_3O_4S$ 379.06 | $^1$H NMR (DMSO-$d_6$, 400 MHz): δ 11.60 (s, 1H), 10.80 (s, 1H), 8.50 (d, J = 6.1 Hz, 2H), 8.13 (d, J = 8.2 Hz, 1H), 8.01 (td, J = 7.9, 1.0 Hz, 2H), 7.96-7.84 (m, 4H), 7.73 (d, J = 6.3 Hz, 2H); |
| 1458 | 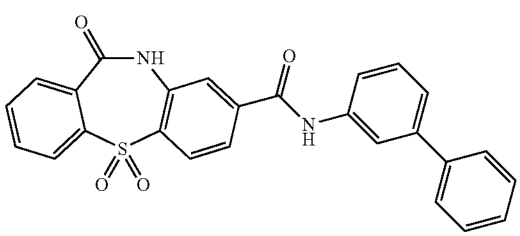 [SMILES: O=C(Nc1cccc(-c2ccccc2)c1)c1ccc2c(c1)NC(=O)c1ccccc1S2(=O)=O] | A, 159, 186 | 33 | 455.0 ($M^+ + 1$) | $C_{26}H_{18}N_2O_4S$ 454.10 | $^1$H NMR (DMSO-$d_6$, 400 MHz): δ 11.57 (s, 1H), 10.53 (s, 1H), 8.10 (d, J = 8.2 Hz, 1H), 8.04-7.96 (m, 3H), 7.95-7.82 (m, 4H), 7.73 (d, J = 7.6 Hz, 1H), 7.66-7.56 (m, 2H), 7.50-7.33 (m, 5H); |
| 1616 | 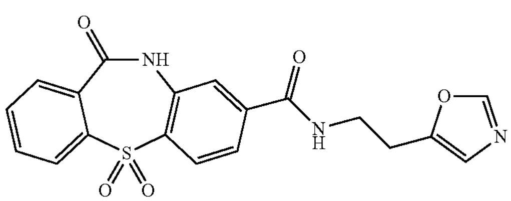 [SMILES: O=C(NCCc1cnco1)c1ccc2c(c1)NC(=O)c1ccccc1S2(=O)=O] | A, 159, 347 | 9 | 398.0 ($M^+ + 1$) | $C_{19}H_{15}N_3O_5S$ 397.07 | $^1$H NMR (DMSO-$d_6$, 400 MHz): δ 11.52 (s, 1H), 8.84 (t, J = 5.7 Hz, 1H), 8.22 (s, 1H), 8.04 (d, J = 8.2 Hz, 1H), 8.00-7.96 (m, 2H), 7.91 (dd, J = 7.4, 1.5 Hz, 1H), 7.89-7.79 (m, 2H), 7.74 (dd, J = 8.3, 1.5 Hz, 1H), 6.92 (s, 1H), 3.51 (q, J = 6.5 Hz, 2H), 2.92 (t, J = 6.8 Hz, 2H). |
| 1617 | 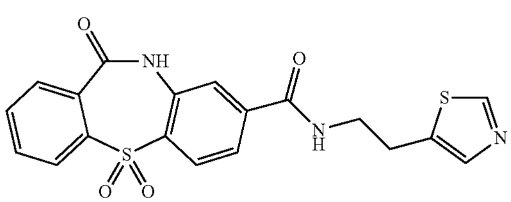 [SMILES: O=C(NCCc1cncs1)c1ccc2c(c1)NC(=O)c1ccccc1S2(=O)=O] | A, 159, 352 | 44 | 414.0 ($M^+ + 1$) | $C_{19}H_{15}N_3O_4S_2$ 413.05 | $^1$H NMR (DMSO-$d_6$, 400 MHz): δ 11.53 (s, 1H), 8.91 (s, 1H), 8.87 (t, J = 5.5 Hz, 1H), 8.05 (d, J = 8.3 Hz, 1H), 8.01-7.96 (m, 2H), 7.92-7.83 (m, 2H), 7.81 (s, 1H), 7.76 (dd, J = 8.3, 1.4 Hz, 1H), 7.69 (s, 1H), 3.50 (q, J = 6.0 Hz, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2H), 3.11 (t, J = 6.6 Hz, 2H); |
| 1618 | 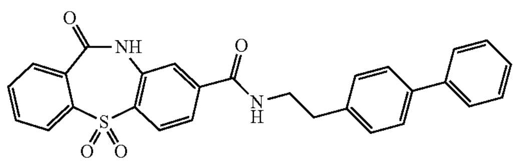 [SMILES: O=C(NCCc1ccc(-c2ccccc2)cc1)c1ccc2c(c1)NC(=O)c1ccccc1S2(=O)=O] | B, 159, 219 (Reaction time 24 h) | 50 | 481.1 (M$^+$ − 1) | $C_{28}H_{22}N_2O_4S$ 482.13 | $^1$H NMR (DMSO-d$_6$, 400 MHz): δ 11.49 (br s, 1H), 8.83 (t, J = 5.4 Hz, 1H), 8.04 (d, J = 8.3 Hz, 1H), 8.00-7.95 (m, 2H), 7.93-7.80 (m, 3H), 7.76 (dd, J = 8.3, 1.4 Hz, 1H), 7.64-7.61 (m, 2H), 7.58 (d, J = 8.3 Hz, 2H) 7.44 (t, J = 7.6 Hz, 2H), 7.36-7.30 (m, 3H), 3.52 (q, J = 6.5, 2H), 2.87 (t, J = 7.1 Hz, 2H); |
| 1619 | 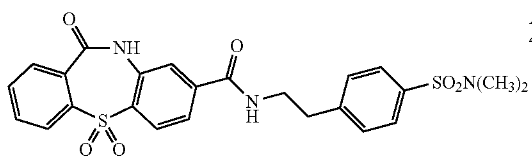 | A, 159, 406 | 25 | 514.0 (M$^+$ + 1) | $C_{24}H_{23}N_3O_6S_2$ 513.10 | $^1$H NMR (DMSO-d$_6$, 400 MHz): δ 11.52 (br s, 1H), 8.80 (t, J = 5.2 Hz, 1H), 8.03 (d, J = 8.2 Hz, 1H), 8.01-7.96 (m, 2H), 7.93-7.82 (m, 2H), 7.77 (s, 1H), 7.72 (d, J = 8.2 Hz, 1H), 7.65 (d, J = 8.2 Hz, 2H), 7.49 (d, J = 8.2 Hz, 2H), 3.59-3.49 (m, 2H), 2.94 (t, J = 6.8 Hz, 2H), 2.54 (s, 6H). |
| 1620 | 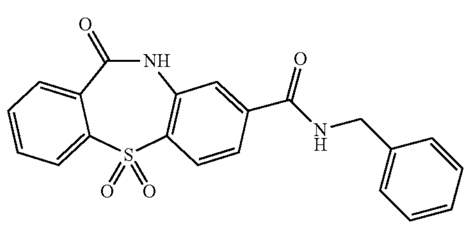 [SMILES: O=C(NCc1ccccc1)c1ccc2c(c1)NC(=O)c1ccccc1S2(=O)=O] | A, 159, 254 | 39 | 392.9 (M$^+$ + 1) | $C_{21}H_{16}N_2O_4S$ 392.08 | $^1$H NMR (DMSO-d$_6$, 400 MHz): δ 11.44 (br s, 1H), 9.27 (t, J = 5.9 Hz, 1H), 8.05 (d, J = 8.2 Hz, 1H), 7.98 (td, J = 7.7, 1.4, Hz, 2H), 7.93-7.82 (m, 4H), 7.35-7.28 (m, 4H), 7.27-7.21 (m, 1H), 4.47 (d, J = 6.1 Hz, 2H); |
| 1621 | 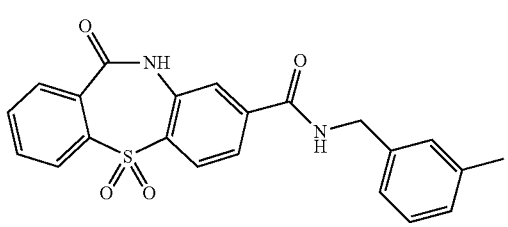 [SMILES: Cc1cccc(CNC(=O)c2ccc3c(c2)NC(=O)c2ccccc2S3(=O)=O)c1] | A, 159, 255 | 42 | 406.9 (M$^+$ + 1) | $C_{22}H_{18}N_2O_4S$ 406.10 | $^1$H NMR (DMSO-d$_6$, 400 MHz): δ 11.45 (br s, 1H), 9.24 (t, J = 5.9 Hz, 1H), 8.05 (d, J = 8.2 Hz, 1H), 7.98 (td, J = 7.7, 1.1 Hz, 2H), 7.93-7.81 (m, 4H), 7.22-7.18 (m, 1H), 7.13-7.04 (m, 3H), 4.43 (d, J = 5.6 Hz, 2H), 2.27 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1622 | 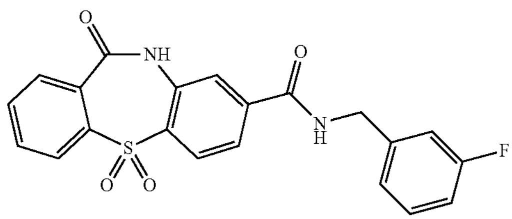 [SMILES: O=C(NCc1cccc(F)c1)c1ccc2c(c1)NC(=O)c1ccccc1S2(=O)=O] | A, 159, 256 | 29 | 411.0 ($M^+ + 1$) | $C_{21}H_{15}FN_2O_4S$ 410.07 | $^1$H NMR (DMSO-$d_6$, 400 MHz): δ 11.26 (br s, 1H), 9.31 (t, J = 6.0 Hz, 1H), 8.06 (d, J = 8.2 Hz, 1H), 7.98 (td, J = 7.8, 1.3 Hz, 2H), 7.93-7.83 (m, 4H), 7.36 (td, J = 7.8, 6.3 Hz, 1H), 7.16-7.04 (m, 3H), 4.48 (d, J = 6.0 Hz, 2H); |
| 1623 | 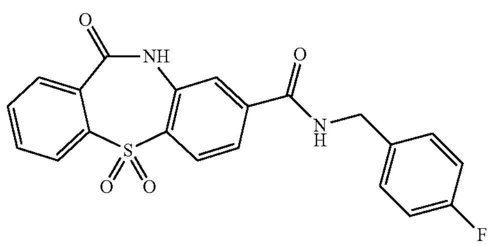 [SMILES: O=C(NCc1ccc(F)cc1)c1ccc2c(c1)NC(=O)c1ccccc1S2(=O)=O] | A, 159, 257 | 43 | 411.0 ($M^+ + 1$) | $C_{21}H_{15}FN_2O_4S$ 410.07 | $^1$H NMR (DMSO-$d_6$, 400 MHz): δ 11.49 (br s, 1H), 9.26 (t, J = 5.9 Hz, 1H), 8.04 (d, J = 8.3 Hz, 1H), 8.00-7.94 (m, 2H), 7.92-7.78 (m, 4H), 7.34 (dd, J = 8.7, 5.6 Hz, 2H), 7.18-7.10 (m, 2H), 4.44 (d, J = 5.9 Hz, 2H); |
| 1624 | 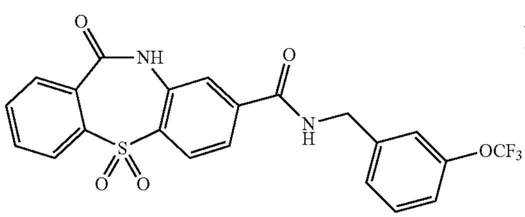 [SMILES: O=C(NCc1cccc(OC(F)(F)F)c1)c1ccc2c(c1)NC(=O)c1ccccc1S2(=O)=O] | A, 159, 258 | 21 | 476.9 ($M^+ + 1$) | $C_{22}H_{15}F_3N_2O_5S$ 476.07 | $^1$H NMR (DMSO-$d_6$, 400 MHz): δ 11.52 (s, 1H), 9.34 (t, J = 5.9 Hz, 1H), 8.07 (d, J = 8.2 Hz, 1H), 8.01-7.96 (m, 2H), 7.93-7.82 (m, 4H), 7.46 (t, J = 7.9 Hz, 1H), 7.33 (d, J = 7.7 Hz, 1H), 7.30-7.22 (m, 2H), 4.51 (d, J = 5.9 Hz, 2H) |
| 1634 | 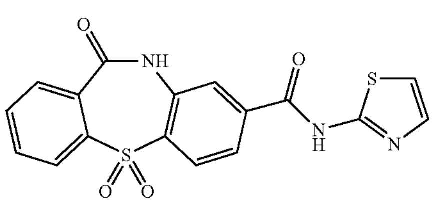 [SMILES: O=C(Nc1nccs1)c1ccc2c(c1)NC(=O)c1ccccc1S2(=O)=O] | G, 159, 231 | 11 | 385.8 ($M^+ + 1$) | $C_{17}H_{11}N_3O_4S_2$ 385.02 | $^1$H NMR (DMSO-$d_6$, 400 MHz): δ 12.90 (br s, 1H), 11.61 (s, 1H), 8.12-7.98 (m, 5H), 7.96-7.84 (m, 2H), 7.58 (d, J = 3.7 Hz, 1H), 7.31 (d, J = 3.0 Hz, 1H); |
| 1635 | 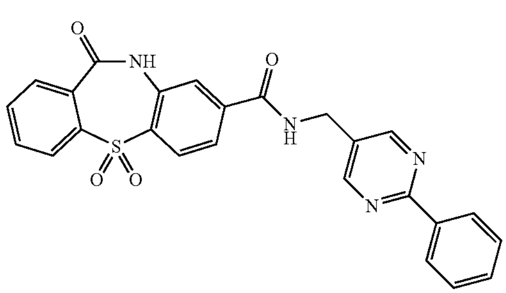 [SMILES: O=C(NCc1cnc(-c2ccccc2)nc1)c1ccc2c(c1)NC(=O)c1ccccc1S2(=O)=O] | A, 159, 377 | 32 | 471.0 ($M^+ + 1$) | $C_{25}H_{18}N_4O_4S$ 470.10 | $^1$H NMR (DMSO-$d_6$, 500 MHz): δ 11.51 (s, 1H), 9.35 (t, J = 5.7 Hz, 1H), 8.85 (s, 2H), 8.39-8.35 (m, 2H), 8.06 (d, J = 8.2 Hz, 1H), 8.01-7.95 (m, 2H), 7.92-7.81 (m, 4H), 7.54-7.49 (m, 3H), 4.53 (d, J = 5.5 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1646 | 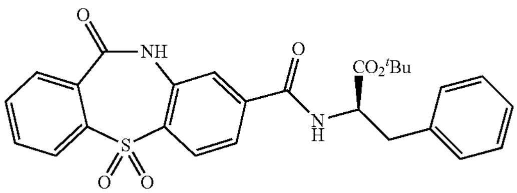 [SMILES: CC(C)(C)OC(=O)[C@@H](Cc1ccccc1)NC(=O)c1ccc2c(c1)NC(=O)c1ccccc1S2(=O)=O] | A, 159, 259 | 36 | 505.3 (M − 1)$^+$ | $C_{27}H_{26}N_2O_6S$ 506.15 | $^1$H NMR (DMSO-d$_6$, 400 MHz): δ 11.52 (s, 1H), 8.99 (br s, 1H), 8.05 (d, J = 8.5 Hz, 1H), 8.01-7.96 (m, 2H), 7.93-7.83 (m, 2H), 7.79-7.73 (m, 2H), 7.26 (d, J = 4.8 Hz, 4H), 7.21-7.16 (m, 1H), 4.54 (br s, 1H), 3.14-2.98 (m, 2H), 1.34 (s, 9H); |
| 1625 | 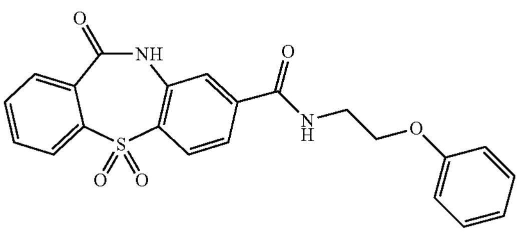 [SMILES: O=C(NCCOc1ccccc1)c1ccc2c(c1)NC(=O)c1ccccc1S2(=O)=O] | A, 159, 176 | 18 | 423.0 (M$^+$ + 1) | $C_{22}H_{18}N_2O_5S$ 422.09 | $^1$H NMR (DMSO-d$_6$, 400 MHz): δ 11.48 (br s, 1H), 8.94 (t, J = 5.4 Hz, 1H), 8.04 (d, J = 8.3 Hz, 1H), 8.01-7.95 (m, 2H), 7.93-7.78 (m, 4H), 7.31-7.24 (m, 2H), 6.97-6.89 (m, 3H), 4.10 (t, J = 5.7 Hz, 2H), 3.63 (q, J = 5.6 Hz, 2H); |
| 1647 | 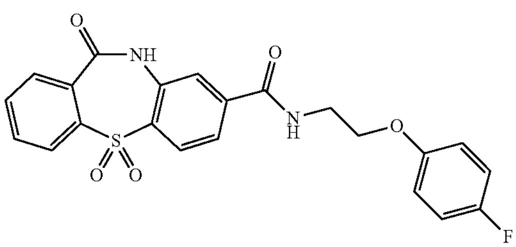 [SMILES: O=C(NCCOc1ccc(F)cc1)c1ccc2c(c1)NC(=O)c1ccccc1S2(=O)=O] | A, 159, 265 | 29 | 440.9 (M$^+$ + 1) | $C_{22}H_{17}FN_2O_5S$ 440.08 | $^1$H NMR (DMSO-d$_6$, 400 MHz): δ 11.51 (s, 1H), 8.92 (s, 1H), 8.04 (d, J = 8.2 Hz, 1H), 7.98 (td, J = 7.5, 0.9 Hz, 2H), 7.93-7.77 (m, 4H), 7.10 (t, J = 9.3 Hz, 2H), 7.00-6.91 (m, 2H), 4.08 (t, J = 5.5 Hz, 2H), 3.61 (q, J = 5.6 Hz, 2H); |
| 1648 | 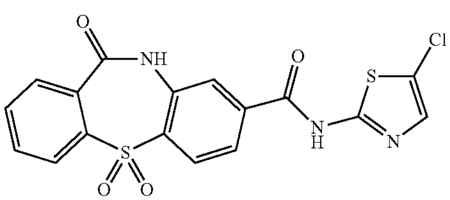 [SMILES: O=C(Nc1ncc(Cl)s1)c1ccc2c(c1)NC(=O)c1ccccc1S2(=O)=O] | A, 159, 253 | 18 | 419.8 (M$^+$ + 1) | $C_{17}H_{10}ClN_3O_4S_2$ 418.98 | $^1$H NMR (DMSO-d$_6$, 400 MHz): δ 13.19 (br s, 1H), 11.62 (s, 1H), 8.10 (d, J = 8.2 Hz, 1H), 8.07-7.97 (m, 4H), 7.95-7.85 (m, 2H), 7.63 (s, 1H); |
| 1627 | 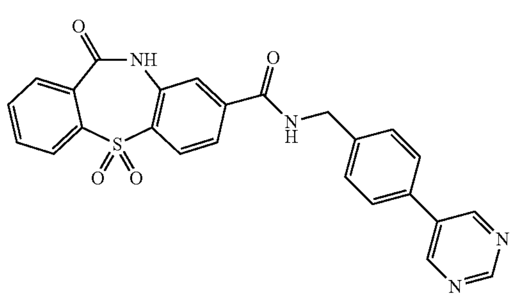 [SMILES: O=C(NCc1ccc(-c2cncnc2)cc1)c1ccc2c(c1)NC(=O)c1ccccc1S2(=O)=O] | A, 159, 372 | 16 | 471.0 (M$^+$ + 1) | $C_{25}H_{18}N_4O_4S$ 470.10 | $^1$H NMR (DMSO-d$_6$, 400 MHz): δ 11.52 (s, 1H), 9.34 (t, J = 5.9 Hz, 1H), 9.17 (s, 1H), 9.12 (s, 2H), 8.07 (d, J = 8.2 Hz, 1H), 7.99 (td, J = 7.8, 1.1 Hz, 2H), 7.94-7.83 (m, 4H), 7.77 (d, J = 8.3 Hz, 2H), 7.46 (d, J = 8.2 Hz, 2H), 4.53 (d, J = 5.7 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1637 | 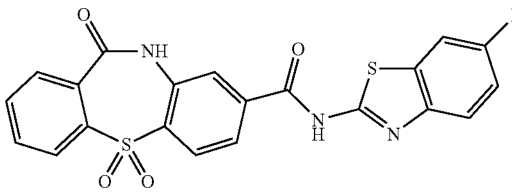 | H, 159, 241 | 47 | 453.9 (M$^+$ +1) | $C_{21}H_{12}FN_3O_4S_2$ 453.03 | $^1$H NMR (DMSO-d$_6$, 400 MHz): δ 13.22 (br s, 1H), 11.63 (s, 1H), 8.15-8.08 (m, 2H), 8.06-7.98 (m, 3H), 7.98-7.84 (m, 3H), 7.79 (dd, J = 7.9, 4.8 Hz, 1H), 7.33 (td, J = 8.9, 2.4 Hz, 1H); |
| 1649 | 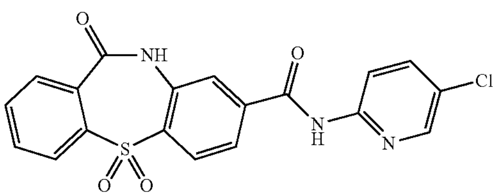 [SMILES: O=C(Nc1ccc(Cl)cn1)c1ccc2c(c1)NC(=O)c1ccccc1S2(=O)=O] | C, 159, 235 | 27 | 413.8 (M$^+$ + 1) | $C_{19}H_{12}ClN_3O_4S$ 413.02 | $^1$H NMR (DMSO-d$_6$, 400 MHz): δ 11.56 (br s, 1H), 11.26 (br s, 1H), 8.46 (br s, 1H), 8.20 (d, J = 8.7 Hz, 1H), 8.10-7.83 (m, 8H); |
| 1628 | 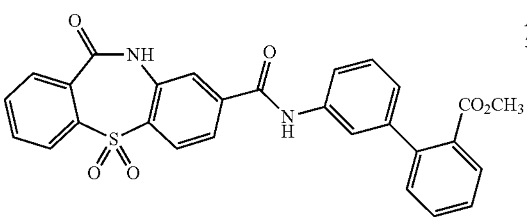 [SMILES: COC(=O)c1ccccc1-c1cccc(NC(=O)c2ccc3c(c2)NC(=O)c2ccccc2S3(=O)=O)c1] | A, 159, 519 | 32 | 513.0 (M$^+$ + 1) | $C_{28}H_{20}N_2O_6S$ 512.10 | $^1$H NMR (DMSO-d$_6$, 400 MHz): δ 11.57 (br s, 1H), 10.54 (s, 1H), 8.11 (d, J = 8.3 Hz, 1H), 8.00 (td, J = 9.0, 1.0 Hz, 2H), 7.95-7.84 (m, 4H), 7.76-7.72 (m, 3H), 7.64 (td, J = 9.1, 1.5 Hz, 1H), 7.50 (td, J = 7.6, 1.3 Hz, 1H), 7.46-7.39 (m, 2H), 7.08-7.03 (m, 1H), 3.61 (s, 3H); |
| 1629 | 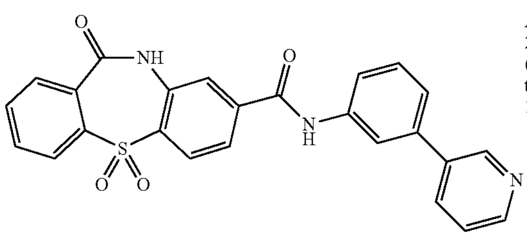 [SMILES: O=C(Nc1cccc(-c2cccnc2)c1)c1ccc2c(c1)NC(=O)c1ccccc1S2(=O)=O] | A, 159, 246 (Reaction time RT-18 h) | 31 | 455.9 (M$^+$ +1) | $C_{25}H_{17}N_3O_4S$ 455.09 | $^1$H NMR (DMSO-d$_6$, 400 MHz): δ 11.60 (s, 1H), 10.60 (s, 1H), 8.86 (br s, 1H), 8.60 (d, J = 3.7 Hz, 1H), 8.13 (d, J = 8.3 Hz, 1H), 8.08 (s, 1H), 8.06-7.98 (m, 3H), 7.97-7.85 (m, 4H), 7.81 (d, J = 6.7 Hz, 1H), 7.55-7.48 (m, 3H); |
| 1520 | 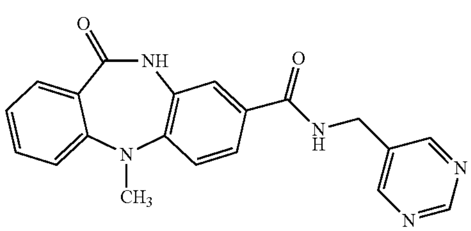 [SMILES: CN1c2ccc(C(=O)NCc3cncnc3)cc2NC(=O)c2ccccc21] | A, 164, 212 | 25 | 360.2 (M$^+$ + 1) | $C_{20}H_{17}N_5O_2$ 359.14 | $^1$H NMR (DMSO-d$_6$, 400 MHz): δ 10.28 (s, 1H), 9.07 (s, 1H), 9.01 (t, J = 5.7 Hz, 1H), 8.74 (s, 2H), 7.66-7.60 (m, 2H), 7.56 (s, 1H), 7.53-7.47 (m, 1H), 7.26 (d, J = 8.6 Hz, 1H), 7.20 (d, J = 8.0 Hz, 1H), 7.10 (t, J = 7.2 Hz, 1H), 4.47 (d, J = 5.6 Hz, 2H), 3.29 (s, 3H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1581 | 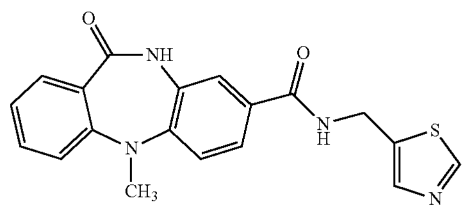 [SMILES: CN1c2ccc(C(=O)NCc3cncs3)cc2NC(=O)c2ccccc21] | A, 164, 213 | 10 | 365.0 (M$^+$ + 1) | $C_{19}H_{16}N_4O_2S$ 364.10 | $^1$H NMR (DMSO-d$_6$, 500 MHz): δ 10.26 (s, 1H), 9.05 (t, J = 5.7 Hz, 1H), 8.93 (s, 1H), 7.77 (s, 1H), 7.66-7.44 (m, 4H), 7.20 (dd, J = 18.1, 8.2 Hz, 2H), 7.08 (t, J = 7.4 Hz, 1H), 4.62 (d, J = 5.6 Hz, 2H), 3.28 (s, 3H); |
| 1547 | 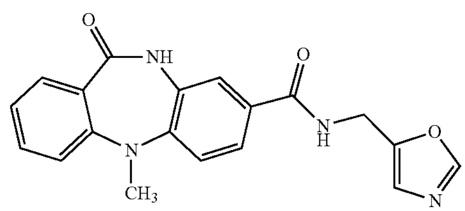 | A, 164, 214 | 25 | 348.9 (M$^+$ + 1) | $C_{19}H_{16}N_4O_3$ 348.12 | ); $^1$H NMR (DMSO-d$_6$, 400 MHz): δ 10.28 (s, 1H), 8.90 (t, J = 5.6 Hz, 1H), 8.27 (s, 1H), 7.66-7.59 (m, 2H), 7.55 (s, 1H), 7.52-7.47 (m, 1H), 7.24 (d, J = 8.5 Hz, 1H), 7.20 (d, J = 7.9 Hz, 1H), 7.10 (t, J = 7.5 Hz, 1H), 7.02 (s, 1H), 4.50 (d, J = 5.3 Hz, 2H), 3.30 (s, 3H); |
| 1548 | 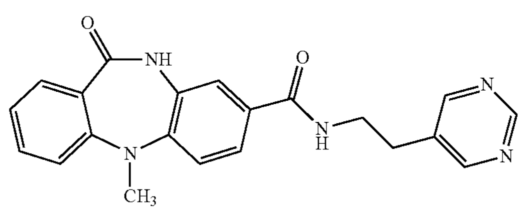 [SMILES: CN1c2ccc(C(=O)NCCc3cncnc3)cc2NC(=O)c2ccccc21] | A, 164, 215 | 29 | 374.0 (M$^+$ + 1) | $C_{21}H_{19}N_5O_2$ 373.15 | $^1$H NMR (DMSO-d$_6$, 400 MHz): δ 10.28 (s, 1H), 9.01 (s, 1H), 8.65 (s, 2H), 8.46 (t, J = 5.7 Hz, 1H), 7.63 (dd, J = 7.7, 1.6 Hz, 1H), 7.53-7.47 (m, 3H), 7.21 (dd, J = 11.2, 8.3 Hz, 2H), 7.10 (t, J = 7.5 Hz, 1H), 3.52 (q, J = 6.4 Hz, 2H), 3.29 (s, 3H), 2.85 (t, J = 6.6 Hz, 2H); |
| 1498 | 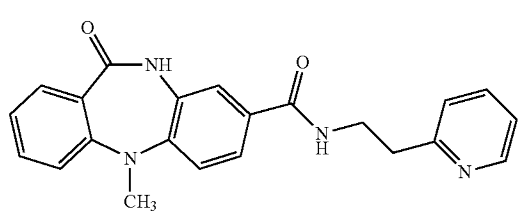 [SMILES: CN1c2ccc(C(=O)NCCc3ccccn3)cc2NC(=O)c2ccccc21] | A, 164, 216 | 21 | 373.0 (M$^+$ + 1) | $C_{22}H_{20}N_4O_2$ 372.16 | $^1$H NMR (DMSO-d$_6$, 400 MHz): δ 10.29 (s, 1H), 8.50 (d, J = 4.0 Hz, 1H), 8.46 (t, J = 5.4 Hz, 1H), 7.69 (td, J = 7.6, 1.9 Hz, 1H), 7.64 (dd, J = 7.7, 1.7 Hz, 1H), 7.57-7.47 (m, 3H), 7.27-7.18 (m, 4H), 7.10 (t, J = 7.2 Hz, 1H), 3.57 (q, J = 7.0 Hz, 2H), 3.30 (s, 3H), 2.96 (t, J = 7.3 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1549 | 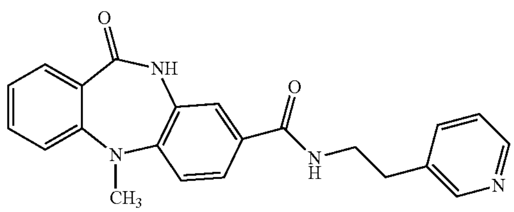 [SMILES: CN1c2ccc(C(=O)NCCc3cccnc3)cc2NC(=O)c2ccccc21] | A, 164, 217 | 27 | 373.0 (M$^+$ + 1) | C$_{22}$H$_{20}$N$_4$O$_2$ 372.16 | $^1$H NMR (DMSO-d$_6$, 400 MHz): δ 10.29 (s, 1H), 8.48-8.42 (m, 2H), 8.40 (dd, J = 4.7, 1.5 Hz, 1H), 7.63 (dd, J = 7.7, 1.6 Hz, 2H), 7.57-7.45 (m, 3H), 7.29 (dd, J = 7.7, 4.8 Hz, 1H), 7.21 (dd, J = 11.0, 8.4 Hz, 2H), 7.10 (t, J = 7.4 Hz, 1H), 3.48 (q, J = 7.1 Hz, 2H), 3.30 (s, 3H), 2.84 (t, J = 7.0 Hz, 2H); |
| 1532 | 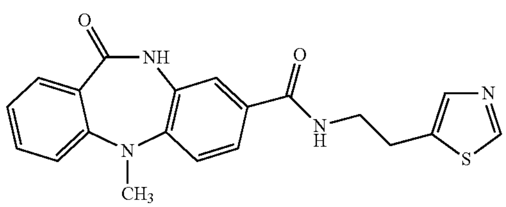 [SMILES: CN1c2ccc(C(=O)NCCc3cncs3)cc2NC(=O)c2ccccc21] | A, 164, 352 | 24 | 378.0 (M$^+$ + 1); | C$_{20}$H$_{18}$N$_4$O$_2$S 378.12 | $^1$H NMR (DMSO-d$_6$, 400 MHz): δ 10.30 (s, 1H), 8.91 (s, 1H), 8.53 (t, J = 5.7 Hz, 1H), 7.69 (s, 1H), 7.64 (dd, J = 7.7, 1.7 Hz, 1H), 7.57 (dd, J = 8.4, 2.0 Hz, 1H), 7.54-7.47 (m, 2H), 7.22 (dd, J = 16.5, 8.1 Hz, 2H), 7.10 (t, J = 7.1 Hz, 1H), 3.47 (q, J = 6.8 Hz, 2H), 3.31 (s, 3H), 3.10 (t, J = 6.7 Hz, 2H); |
| 1499 | 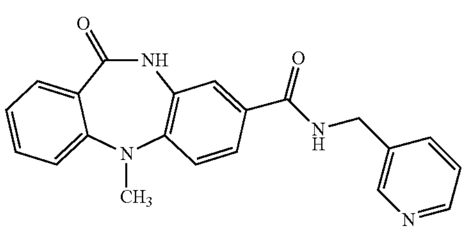 [SMILES: CN1c2ccc(C(=O)NCc3cccnc3)cc2NC(=O)c2ccccc21] | A, 164, 218 | 30 | 358.9 (M$^+$ + 1) | C$_{21}$H$_{18}$N$_4$O$_2$ 358.14 | $^1$H NMR (DMSO-d$_6$, 400 MHz): δ 10.29 (s, 1H), 8.98 (t, J = 5.8 Hz, 1H), 8.51 (s, 1H), 8.44 (dd, J = 4.8, 1.6 Hz, 1H), 7.68 (tt, J = 7.9, 1.9 Hz, 1H), 7.63 (tt, J = 8.0, 1.9 Hz, 2H), 7.57 (s, 1H), 7.53-7.47 (m, 1H), 7.34 (dd, J = 7.3, 4.8 Hz, 1H), 7.25 (d, J = 8.5 Hz, 1H), 7.20 (d, J = 8.0 Hz, 1H), 7.10 (t, J = 7.1 Hz, 1H), 4.46 (d, J = 5.9 Hz, 2H), 3.30 (s, 3H); |
| 1521 | 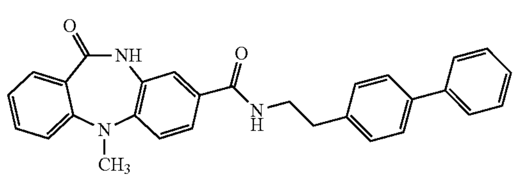 [SMILES: CN1c2ccc(C(=O)NCCc3ccc(-c4ccccc4)cc3)cc2NC(=O)c2ccccc21] | A, 164, 219 | 36 | 448.1 (M$^+$ + 1) | C$_{29}$H$_{25}$N$_3$O$_2$ 447.19 | $^1$H NMR (DMSO-d$_6$, 500 MHz): δ 10.28 (s, 1H), 8.47 (t, J = 5.4 Hz, 1H), 7.65-7.54 (m, 6H), 7.52 (s, 1H), 7.48 (t, J = 7.8 Hz, 1H), 7.43 (t, J = 7.7 Hz, 2H), 7.35-7.28 (m, 3H), 7.20 (dd, J = 16.8, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 8.4 Hz, 2H), 7.08 (t, J = 7.5 Hz, 1H), 3.47 (q, J = 6.4 Hz, 2H), 3.28 (s, 3H), 2.84 (t, J = 7.2 Hz, 2H); |
| 1533 | 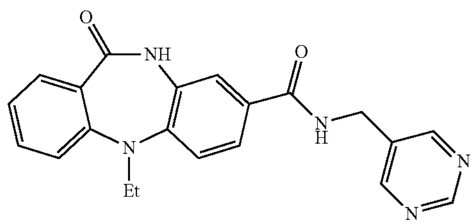 [SMILES: CCN1c2ccc(C(=O)NCc3cncnc3)cc2NC(=O)c2ccccc21] | A$^c$, 167, 212 (c = Reaction Time 12 h- RT) | 19 | 373.9 (M$^+$ + 1); | $C_{21}H_{19}N_5O_2$ 373.15 | $^1$H NMR (DMSO-d$_6$, 400 MHz): δ 10.29 (s, 1H), 9.07 (s, 1H), 9.02 (t, J = 5.7 Hz, 1H), 8.74 (s, 2H), 7.65-7.55 (m, 3H), 7.52-7.46 (m, 1H), 7.25 (d, J = 8.5 Hz, 1H), 7.20 (d, J = 8.2 Hz, 1H), 7.11 (t, J = 7.4 Hz, 1H), 4.46 (d, J = 5.6 Hz, 2H), 3.83-3.75 (m, 2H), 1.12 (t, J = 6.9 Hz, 3H); |
| 1534 | 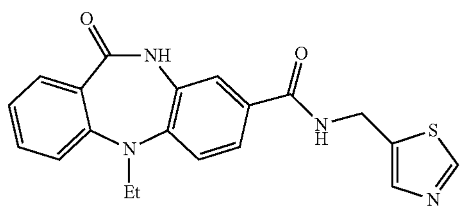 [SMILES: CCN1c2ccc(C(=O)NCc3cncs3)cc2NC(=O)c2ccccc21] | A$^c$, 167, 213 | 22 | 378.9 (M$^+$ + 1) | $C_{20}H_{18}N_4O_2S$ 378.12 | $^1$H NMR (DMSO-d$_6$, 400 MHz): δ 10.29 (s, 1H), 9.07 (t, J = 5.9 Hz, 1H), 8.95 (s, 1H), 7.79 (s, 1H), 7.63-7.54 (m, 3H), 7.52-7.46 (m, 1H), 7.24 (d, J = 8.5 Hz, 1H), 7.20 (d, J = 8.0 Hz, 1H), 7.10 (t, J = 7.2 Hz, 1H), 4.64 (d, J = 5.7 Hz, 2H), 3.84-3.75 (m, 2H), 1.12 (t, J = 7.0 Hz, 3H); |
| 1564 | 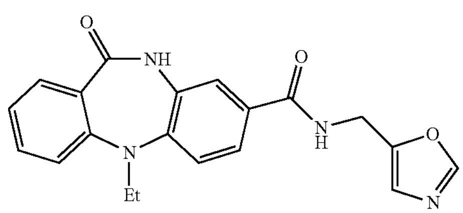 [SMILES: CCN1c2ccc(C(=O)NCc3cnco3)cc2NC(=O)c2ccccc21] | A$^c$, 167, 214 | 31 | 363.0 (M$^+$ + 1) | $C_{20}H_{18}N_4O_3$ 362.14 | $^1$H NMR (DMSO-d$_6$, 400 MHz): δ 10.29 (s, 1H), 8.90 (t, J = 5.6 Hz, 1H), 8.27 (s, 1H), 7.63-7.55 (m, 3H), 7.52-7.47 (m, 1H), 7.24 (d, J = 8.5 Hz, 1H), 7.20 (d, J = 8.2 Hz, 1H), 7.11 (t, J = 7.3 Hz, 1H), 7.01 (s, 1H), 4.50 (d, J = 5.4 Hz, 2H), 3.83-3.76 (m, 2H), 1.12 (t, J = 7.0 Hz, 3H); |
| 1565 | 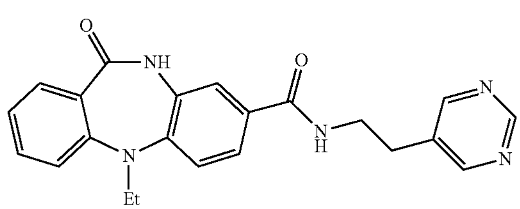 [SMILES: CCN1c2ccc(C(=O)NCCc3cncnc3)cc2NC(=O)c2ccccc21] | A$^c$, 167, 215 | 36 | 388.0 (M$^+$ + 1) | $C_{22}H_{21}N_5O_2$ 387.17 | $^1$H NMR (DMSO-d$_6$, 500 MHz): δ 10.27 (s, 1H), 8.99 (s, 1H), 8.64 (s, 2H), 8.44 (t, J = 5.4 Hz, 1H), 7.58 (d, J = 6.7 Hz, 1H), 7.52-7.45 (m, 3H), 7.19 (dd, J = 14.6, 8.2 Hz, 2H), 7.08 (t, J = 7.5 Hz, 1H), 3.81-3.72 (m, |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 2H), 3.50 (q, J = 6.1 Hz, 2H), 2.83 (t, J = 6.7 Hz, 2H), 1.10 (t, J = 6.9 Hz, 3H); |
| 1522 | 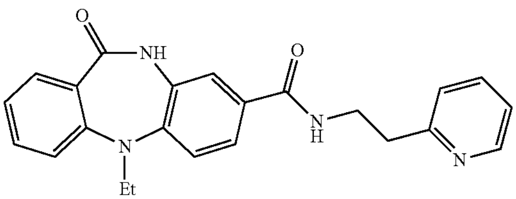 [SMILES: CCN1c2ccc(C(=O)NCCc3ccccn3)cc2NC(=O)c2ccccc21] | A$^c$, 167, 216 | 29 | 387.0 (M$^+$ + 1) | C$_{23}$H$_{22}$N$_4$O$_2$ 386.17 | $^1$H NMR (DMSO-d$_6$, 400 MHz): δ 10.29 (s, 1H), 8.49 (d, J = 4.1 Hz, 1H), 8.45 (t, J = 5.3 Hz, 1H), 7.69 (td, J = 7.7, 1.8 Hz, 1H), 7.60 (dd, J = 7.7, 1.6 Hz, 1H), 7.57-7.47 (m, 3H), 7.27-7.18 (m, 4H), 7.10 (t, J = 7.4 Hz, 1H), 3.83-3.74 (m, 2H), 3.57 (q, J = 6.9 Hz, 2H), 2.96 (t, J = 7.3 Hz, 2H), 1.12 (t, J = 6.9 Hz, 3H); |
| 1523 | 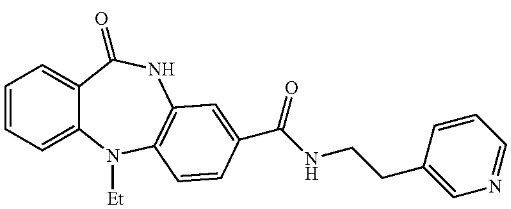 [SMILES: CCN1c2ccc(C(=O)NCCc3cccnc3)cc2NC(=O)c2ccccc21] | A$^c$, 167, 217 | 36 | 387.0 (M$^+$ + 1) | C$_{23}$H$_{22}$N$_4$O$_2$ 386.17 | $^1$H NMR (DMSO-d$_6$, 500 MHz): δ 10.28 (s, 1H), 8.47-8.34 (m, 3H), 7.65-7.56 (m, 2H), 7.54-7.45 (m, 3H), 7.28 (dd, J = 7.5, 4.9 Hz, 1H), 7.19 (dd, J = 13.7, 8.2 Hz, 2H), 7.09 (t, J = 7.2 Hz, 1H), 3.76 (br s, 2H), 3.46 (q, J = 6.7 Hz, 2H), 2.82 (t, J = 7.1 Hz, 2H), 1.10 (t, J = 6.9 Hz, 3H); |
| 1566 | 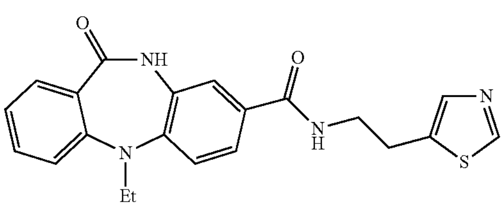 [SMILES: CCN1c2ccc(C(=O)NCCc3cncs3)cc2NC(=O)c2ccccc21] | A$^c$, 167, 352 | 36 | 393.1 (M$^+$ + 1) | C$_{21}$H$_{20}$N$_4$O$_2$S 392.13 | $^1$H NMR (DMSO-d$_6$, 500 MHz): δ 10.29 (s, 1H), 8.89 (s, 1H), 8.51 (t, J = 5.4 Hz, 1H), 7.67 (s, 1H), 7.61-7.43 (m, 4H), 7.22 (d, J = 8.4 Hz, 1H), 7.18 (d, J = 8.1 Hz, 1H), 7.09 (t, J = 7.4 Hz, 1H), 3.82-3.74 (m, 2H), 3.45 (q, J = 6.5 Hz, 2H), 3.08 (t, J = 6.7 Hz, 2H), 1.11 (t, J = 6.8 Hz, 3H); |
| 1550 | 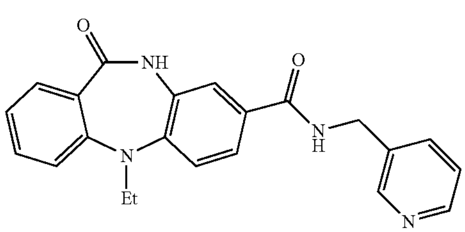 [SMILES: CCN1c2ccc(C(=O)NCc3cccnc3)cc2NC(=O)c2ccccc21] | A$^c$, 167, 218 | 30 | 373.1 (M$^+$ + 1) | C$_{22}$H$_{20}$N$_4$O$_2$ 372.16 | $^1$H NMR (DMSO-d$_6$, 400 MHz): δ 10.29 (s, 1H), 8.98 (t, J = 5.9 Hz, 1H), 8.52 (s, 1H), 8.44 (dd, J = 4.7, 1.6 Hz, 1H), 7.68 (dt, J = 7.9, 1.8 Hz, 1H), 7.65-7.56 (m, 3H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 7.49 (td, J = 7.7, 1.7 Hz, 1H), 7.36-7.32 (m, 1H), 7.25 (d, J = 8.5 Hz, 1H), 7.20 (d, J = 7.9 Hz, 1H), 7.10 (td, J = 7.5, 0.8 Hz, 1H), 4.46 (d, J = 5.7 Hz, 2H), 3.82-3.75 (m, 2H), 1.12 (t, J = 7.0 Hz, 3H); |
| 1524 | 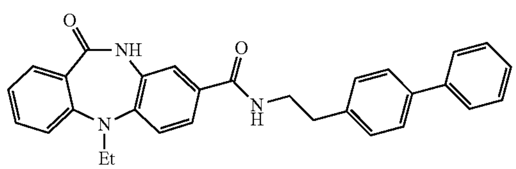 [SMILES: CCN1c2ccc(C(=O)NCCc3ccc(-c4ccccc4)cc3)cc2NC(=O)c2ccccc21] | A$^c$, 167, 219 | 15 | 462.1 (M$^+$ + 1) | C$_{30}$H$_{27}$N$_3$O$_2$ 461.21 | $^1$H NMR (DMSO-d$_6$, 400 MHz): δ 10.30 (s, 1H), 8.48 (t, J = 5.5 Hz, 1H), 7.68-7.41 (m, 10H), 7.36-7.29 (m, 3H), 7.21 (dd, J = 13.5, 8.3 Hz, 2H), 7.10 (t, J = 7.5 Hz, 1H), 3.82-3.75 (m, 2H), 3.48 (q, J = 6.9 Hz, 2H), 2.86 (t, J = 7.2 Hz, 2H), 1.12 (t, J = 6.9 Hz, 3H); |
| 1482 | 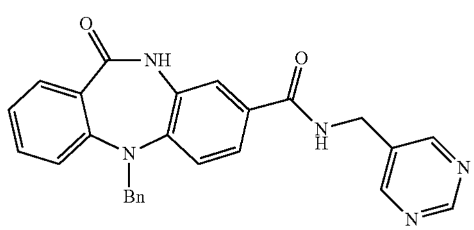 [SMILES: O=C(NCc1cncnc1)c1ccc2c(c1)NC(=O)c1ccccc1N2Cc1ccccc1] | A, 170, 212 | 36 | 436.1 (M$^+$ + 1) | C$_{26}$H$_{21}$N$_5$O$_2$ 435.17 | $^1$H NMR (DMSO-d$_6$, 500 MHz): δ 10.36 (s, 1H), 9.06 (s, 1H), 8.97 (t, J = 5.8 Hz, 1H), 8.72 (s, 2H), 7.61 (dd, J = 7.7, 1.3 Hz, 1H), 7.57-7.51 (m, 2H), 7.47-7.39 (m, 3H), 7.33 (d, J = 8.4 Hz, 1H), 7.30-7.23 (m, 3H), 7.15 (t, J = 7.8 Hz, 1H), 7.08 (t, J = 7.4 Hz, 1H), 5.03 (s, 2H), 4.44 (d, J = 5.5 Hz, 2H); |
| 1510 | 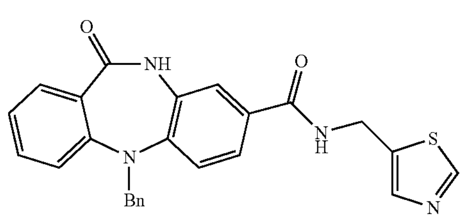 [SMILES: O=C(NCc1cncs1)c1ccc2c(c1)NC(=O)c1ccccc1N2Cc1ccccc1] | A, 170, 213 | 20 | 441.1 (M$^+$ + 1) | C$_{25}$H$_{20}$N$_4$O$_2$S 440.13 | $^1$H NMR (DMSO-d$_6$, 400 MHz): δ 10.37 (s, 1H), 9.04 (t, J = 5.8 Hz, 1H), 8.94 (s, 1H), 7.77 (s, 1H), 7.61 (dd, J = 7.7, 1.6 Hz, 1H), 7.56 (s, 1H), 7.50 (dd, J = 8.5, 1.9 Hz, 1H), 7.47-7.39 (m, 3H), 7.32 (d, J = 8.6 Hz, 1H), 7.29-7.22 (m, 3H), 7.14 (t, J = 7.2 Hz, 1H), 7.08 (t, J = 7.3 Hz, 1H), 5.03 (s, 2H), 4.61 (d, J = 5.6 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1492 | 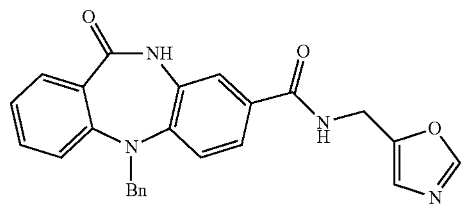 [SMILES: O=C(NCc1cnco1)c1ccc2c(c1)NC(=O)c1ccccc1N2Cc1ccccc1] | A, 170, 214 | 35 | 425.1 (M$^+$ + 1) | $C_{25}H_{20}N_4O_3$ 424.15 | $^1$H NMR (DMSO-d$_6$, 400 MHz): δ 10.37 (s, 1H), 8.87 (t, J = 5.6 Hz, 1H), 8.25 (s, 1H), 7.61 (dd, J = 7.7, 1.6 Hz, 1H), 7.51 (dd, J = 8.4, 2.0 Hz, 1H), 7.47-7.39 (m, 3H), 7.32 (d, J = 8.5 Hz, 1H), 7.30-7.23 (m, 3H), 7.17-7.12 (m, 1H), 7.08 (t, J = 7.2 Hz, 1H), 7.00 (s, 1H), 5.03 (s, 2H), 4.47 (d, J = 5.4 Hz, 2H); |
| 1464 | 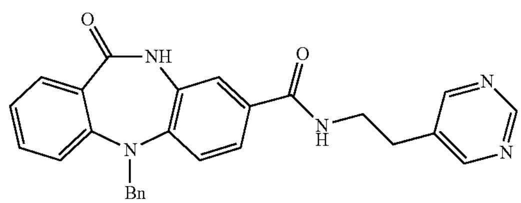 [SMILES: O=C(NCCc1cncnc1)c1ccc2c(c1)NC(=O)c1ccccc1N2Cc1ccccc1] | A, 170, 215 | 16 | 450.1 (M$^+$ + 1) | $C_{27}H_{23}N_5O_2$ 449.19 | $^1$H NMR (DMSO-d$_6$, 400 MHz): δ 10.36 (s, 1H), 9.01 (s, 1H), 8.64 (s, 2H), 8.42 (t, J = 5.5 Hz, 1H), 7.60 (dd, J = 7.7, 1.6 Hz, 1H), 7.49-7.38 (m, 5H), 7.33-7.21 (m, 4H), 7.15 (t, J = 7.1 Hz, 1H), 7.08 (t, J = 7.4 Hz, 1H), 5.02 (s, 2H), 3.49 (q, J = 6.4 Hz, 2H), 2.82 (t, J = 6.7 Hz, 2H); |
| 1474 | 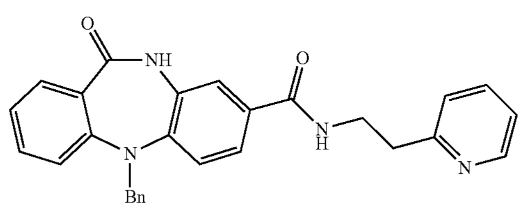 | A, 170, 216 | 38 | 449.1 (M$^+$ + 1) | $C_{28}H_{24}N_4O_2$ 448.19 | $^1$H NMR (DMSO-d$_6$, 500 MHz): δ 10.35 (s, 1H), 8.47 (d, J = 3.8 Hz, 1H), 8.41 (t, J = 5.4 Hz, 1H), 7.68-7.64 (m, 1H), 7.59 (d, J = 7.8 Hz, 1H), 7.52-7.49 (m, 1H), 7.47-7.37 (m, 4H), 7.31-7.17 (m, 6H), 7.16-7.11 (m, 1H), 7.07 (t, J = 7.2 Hz, 1H), 5.01 (s, 2H), 3.53 (q, J = 6.7 Hz, 2H), 2.92 (t, J = 7.2 Hz, 2H); |
| 1475 | 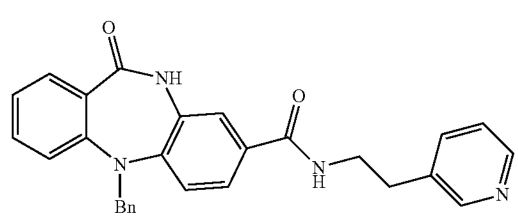 | A, 170, 217 | 38 | 449.1 (M$^+$ + 1) | $C_{28}H_{24}N_4O_2$ 448.19 | $^1$H NMR (DMSO-d$_6$, 500 MHz): δ 10.36 (s, 1H), 8.43-8.39 (m, 2H), 8.37 (dd, J = 4.6, 1.2 Hz, 1H), 7.75-7.54 (m, 2H), 7.49 (s, 1H), 7.46-7.36 (m, 4H), 7.33-7.21 (m, 5H), 7.18-7.10 (m, 1H), 7.06 (t, J = 7.4 Hz, 1H), 5.01 (s, 2H), 3.47-3.41 (m, 2H), 2.80 (t, J = 6.9 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1559 | 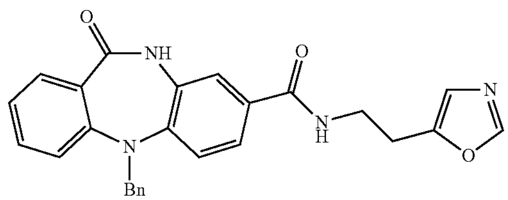 [SMILES: O=C(NCCc1cnco1)c1ccc2c(c1)NC(=O)c1ccccc1N2Cc1ccccc1] | A, 170, 347 | 20 | 439.1 (M$^+$ + 1) | $C_{26}H_{22}N_4O_3$ 438.17 | $^1$H NMR (DMSO-d$_6$, 400 MHz): δ 10.37 (s, 1H), 8.47 (t, J = 5.6 Hz, 1H), 8.20 (s, 1H), 7.61 (dd, J = 7.7, 1.6 Hz, 1H), 7.51 (s, 1H) 7.47-7.40 (m, 4H), 7.33-7.23 (m, 4H), 7.18-7.12 (m, 1H), 7.08 (t, J = 7.4 Hz, 1H), 6.90 (s, 1H), 3.46 (q, J = 6.6 Hz, 2H), 2.88 (t, J = 6.8 Hz, 2H); |
| 1511 | 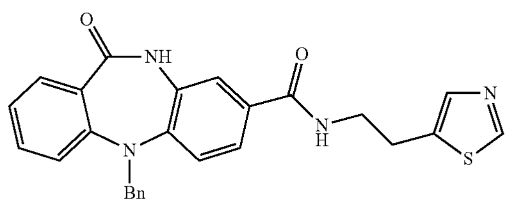 [SMILES: O=C(NCCc1cncs1)c1ccc2c(c1)NC(=O)c1ccccc1N2Cc1ccccc1] | A, 170, 352 | 32 | 455.0 (M$^+$ + 1) | $C_{26}H_{22}N_4O_2S$ 454.15 | $^1$H NMR (DMSO-d$_6$, 500 MHz): δ 10.37 (s, 1H), 8.89 (s, 1H), 8.49 (t, J = 5.5 Hz, 1H), 7.66 (s, 1H), 7.60 (dd, J = 7.7, 1.3 Hz, 1H), 7.52 (s, 1H), 7.49-7.38 (m, 4H), 7.31 (d, J = 8.7 Hz, 1H), 7.28-7.22 (m, 3H), 7.14 (t, J = 7.2 Hz, 1H), 7.07 (t, J = 7.4 Hz, 1H), 5.02 (s, 2H), 3.43 (q, J = 6.5 Hz, 2H), 3.06 (t, J = 6.7 Hz, 2H); |
| 1493 | 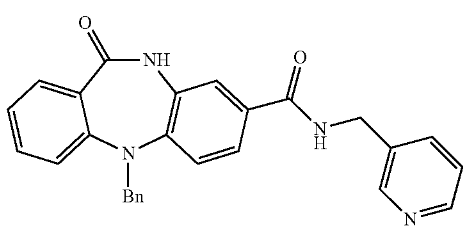 | A, 170, 218 | 16 | 434.1 (M$^+$ + 1) | $C_{27}H_{22}N_4O_2$ 434.17 | $^1$H NMR (DMSO-d$_6$, 400 MHz): δ 10.37 (s, 1H), 8.95 (t, J = 5.9 Hz, 1H), 8.51-8.49 (m, 1H), 8.43 (dd, J = 4.8, 1.6 Hz, 1H), 7.66 (td, J = 7.5, 1.7 Hz, 1H), 7.61 (dd, J = 7.7, 1.7 Hz, 1H), 7.58-7.52 (m, 2H), 7.47-7.38 (m, 3H), 7.35-7.22 (m, 5H), 7.18-7.12 (m, 1H), 7.08-(t, J = 7.1 Hz, 1H), 5.03 (s, 2H), 4.43 (d, J = 5.7 Hz, 2H); |
| 1483 | 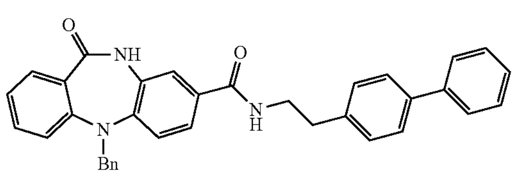 [SMILES: O=C(NCCc1ccc(-c2ccccc2)cc1)c1ccc2c(c1)NC(=O)c1ccccc1N2Cc1ccccc1] | A, 170, 219 | 20 | 524.3 (M$^+$ + 1) | $C_{35}H_{29}N_3O_2$ 523.23 | $^1$H NMR (DMSO-d$_6$, 500 MHz): δ 10.38 (s, 1H), 8.45 (t, J = 5.5 Hz, 1H), 7.66-7.52 (m, 6H), 7.51-7.39 (m, 6H), 7.37-7.23 (m, 7H), 7.18-7.13 (m, 1H), 7.08 (t, J = 7.4 Hz, 1H), 5.03 (s, 2H), 3.49-3.43 (m, 2H), 2.84 (t, J = 7.2 Hz, 2H); |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| 1494 | 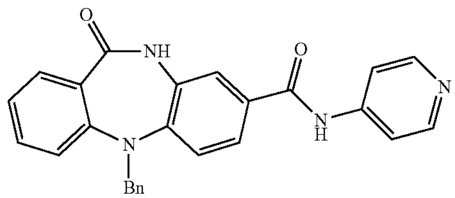 [SMILES: O=C(Nc1ccncc1)c1ccc2c(c1)NC(=O)c1ccccc1N2Cc1ccccc1] | A, 170, 185 | 16 | 421.1 (M$^+$ + 1) | $C_{26}H_{20}N_4O_2$ 420.16 | ); $^1$H NMR (DMSO-d$_6$, 400 MHz): δ 10.45 (d, J = 4.4 Hz, 2H), 8.53-8.38 (m, 2H), 7.74-7.70 (m, 2H), 7.67-7.62 (m, 3H), 7.50-7.39 (m, 4H), 7.31 (d, J = 8.0 Hz, 1H), 7.27 (t, J = 7.6 Hz, 2H), 7.20-7.08 (m, 2H), 5.07 (s, 2H); |
| 1512 | 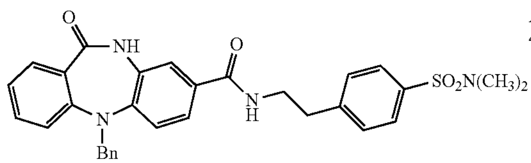 | A, 170, 406 | 18 | 555.1 (M$^+$ + 1) | $C_{31}H_{30}N_4O_4S$ 554.20 | $^1$H NMR (DMSO-d$_6$, 400 MHz): δ 10.35 (s, 1H), 8.40 (t, J = 5.6 Hz, 1H), 7.68-7.53 (m, 3H), 7.52-7.36 (m, 7H), 7.31-7.18 (m, 4H), 7.13 (t, J = 7.3 Hz, 1H), 7.06 (t, J = 7.4 Hz, 1H), 5.00 (s, 2H), 3.49-3.41 (m, 2H), 2.88 (t, J = 7.0 Hz, 2H), 2.51 (s, 6H); |
| 1484 | 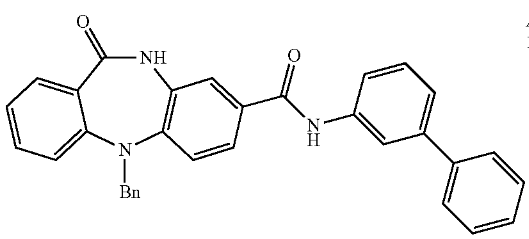 | A, 170, 186 | 7 | 496.2 (M$^+$ + 1) | $C_{33}H_{25}N_3O_2$ 495.19 | $^1$H NMR (DMSO-d$_6$, 400 MHz): δ 10.44 (s, 1H), 10.20 (s, 1H), 8.05-8.03 (m, 1H), 7.75 (d, J = 8.4 Hz, 1H), 7.69-7.58 (m, 5H), 7.51-7.35 (m, 9H), 7.34-7.24 (m, 3H), 7.17 (t, J = 7.7 Hz, 1H), 7.11 (t, J = 7.5 Hz, 1H), 5.07 (s, 2H); |
| 1468 | 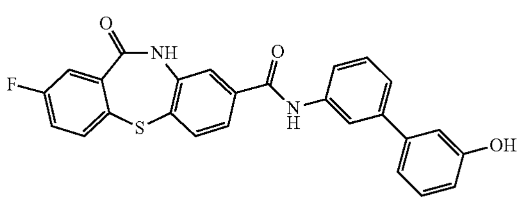 [SMILES: O=C(Nc1cccc(-c2cccc(O)c2)c1)c1ccc2c(c1)NC(=O)c1cc(F)ccc1S2] | A, 35, 413 | 15 | 456.9 (M$^+$ + 1) | $C_{26}H_{17}FN_2O_3S$ 456.09 | $^1$H NMR (400 MHz, DMSO-d$_6$), δ 10.97 (s, 1H), 10.36 (s, 1H), 9.53 (s, 1H), 8.03-8.01 (m, 1H), 7.81-7.71 (m, 4H), 7.63 (dd, J = 8.6, 5.3 Hz, 1H), 7.51 (dd, J = 9.2, 2.9 Hz, 1H), 7.45-7.36 (m, 2H), 7.35-7.32 (m, 1H), 7.26 (t, J = 7.8 Hz, 1H), 7.06-7.00 (m, 2H), 6.79-6.75 (m, 1H); |
| 1452 | 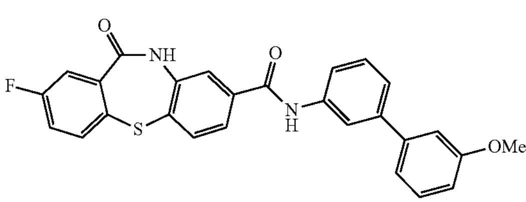 [SMILES: COc1cccc(-c2cccc(NC(=O)c3ccc4c(c3)NC(=O)c3cc(F)ccc3S4)c2)c1] | A, 35, 412 | 37 | 471.0 (M$^+$ + 1) | $C_{27}H_{19}FN_2O_3S$ 470.11 | $^1$H NMR (DMSO-d$_6$, 400 MHz): δ 10.98 (s, 1H), 10.37 (s, 1H), 8.02 (s, 1H), 7.83-7.70 (m, 4H), 7.63 (dd, J = 8.6, 5.3 Hz, 1H), 7.52 (dd, J = 9.2, 2.9 Hz, 1H), 7.47-7.36 (m, 4H), |

TABLE 1-continued

Synthesis of compounds from compounds 6, 14, 21, 28, 35, 42, 50, 55, 62, 70, 76, 82, 88, 97, 103, 112, 118, 124, 135, 140, 145, 150, 155, 156, 159, 164, 167, 170, P-42 and various amines

| No. | Structure | Procedure, Intermediate, Amine | Rx Yield (%) | Mass Spec. Found | Mass Spec. Calculated | $^1$H-NMR |
|---|---|---|---|---|---|---|
| | | | | | | 7.20 (d, J = 7.8 Hz, 1H), 7.16-7.14 (m, 1H), 6.96 (dd, J = 8.0, 2.2 Hz, 1H), 3.82 (s, 3H); |
| 1636 | 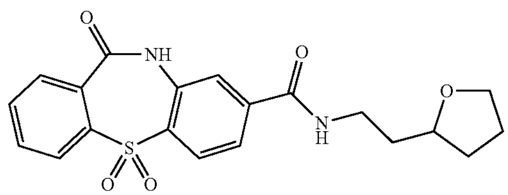 [SMILES: O=C(NCCC1CCCO1)c1ccc2c(c1)NC(=O)c1ccccc1S2(=O)=O] | A, 159, 415 | 50 | 400.9 (M$^+$ + 1) | C$_{20}$H$_{20}$N$_2$O$_5$S 400.11 | $^1$H NMR (DMSO-d$_6$, 400 MHz): δ 11.50 (s, 1H), 8.69 (t, J = 5.4 Hz, 1H), 8.03 (d, J = 8.3 Hz, 1H), 8.01-7.96 (m, 2H), 7.93-7.82 (m, 2H), 7.80-7.76 (m, 2H), 3.81-3.71 (m, 2H), 3.61-3.54 (m, 1H), 3.45-3.40 (m, 1H). 3.29-3.25 (m, 1H), 2.00-1.90 (m, 1H), 1.86-1.73 (m, 2H), 1.68 (q, J = 7.0 Hz, 2H), 1.46-1.35 (m, 1H); |
| 1626 | 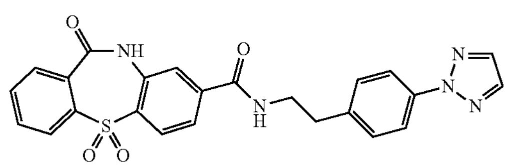 [SMILES: O=C(NCCc1ccc(-n2nccn2)cc1)c1ccc2c(c1)NC(=O)c1ccccc1S2(=O)=O] | A, 159, 421 | 14 | 474.0 (M$^+$ + 1) | C$_{24}$H$_{19}$N$_5$O$_4$S 473.12 | $^1$H NMR (DMSO-d$_6$, 400 MHz): δ 11.52 (s, 1H), 8.81 (t, J = 5.5 Hz, 1H), 8.09 (s, 2H), 8.04 (d, J = 8.3 Hz, 1H), 8.00-7.82 (m, 6H), 7.80-7.72 (m, 2H), 7.42 (d, J = 8.6 Hz, 2H), 3.57-3.49 (m, 2H), 2.90 (t, J = 7.0 Hz, 2H); |
| 1650 | 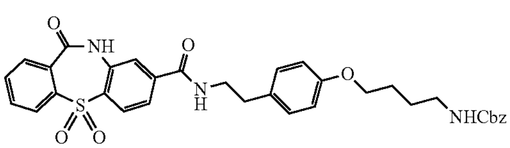 [SMILES: O=C(NCCCCOc1ccc(CCNC(=O)c2ccc3c(c2)NC(=O)c2ccccc2S3(=O)=O)cc1)OCc1ccccc1] | A, 159, 427 | 51 | 628.1 (M$^+$ + 1) | C$_{34}$H$_{33}$N$_3$O$_7$S 627.20 | $^1$H NMR (DMSO-d$_6$, 400 MHz): δ 11.52 (s, 1H), 8.76 (t, J = 5.5 Hz, 1H), 8.03 (d, J = 8.3 Hz, 1H), 8.00-7.96 (m, 2H), 7.92-7.83 (m, 2H), 7.79 (s, 1H), 7.75 (dd, J = 8.2, 1.4 Hz, 1H), 7.44-7.22 (m, 6H), 7.11 (d, J = 8.6 Hz, 2H), 6.82 (d, J = 8.5 Hz, 2H), 5.00 (s, 2H), 3.90 (t, J = 6.2 Hz, 2H), 3.43 (q, J = 6.7 Hz, 2H), 3.04 (q, J = 6.7 Hz, 2H), 2.74 (t, J = 7.3 Hz, 2H), 1.71-1.63 (m, 2H), 1.58-1.49 (m, 2H); |

Example 27: Synthesis of Compounds 1268 and 1269

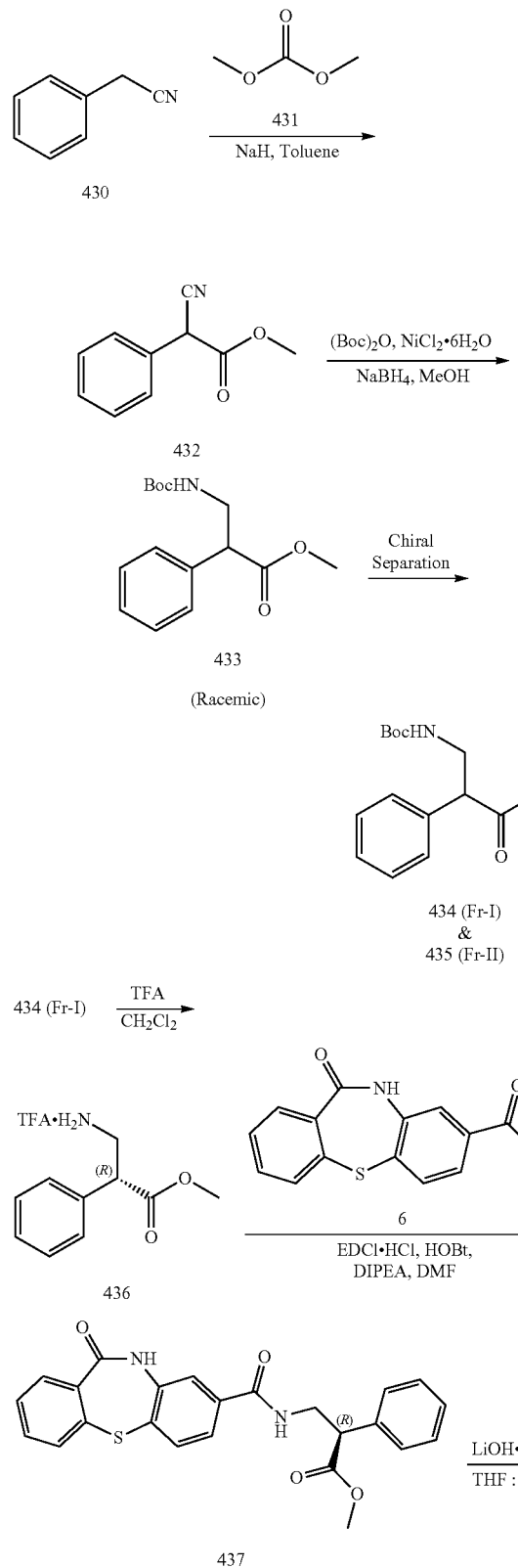

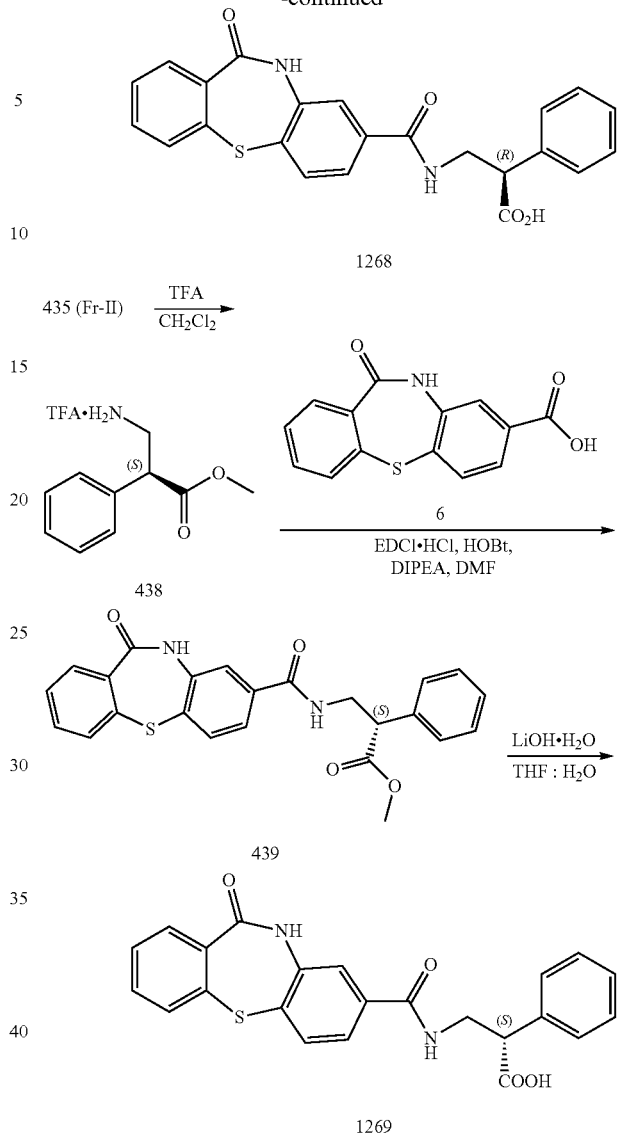

Synthesis of Methyl 2-cyano-2-phenylacetate (432)

To a stirred solution of sodium hydride (60%, 2.5 g, 63.82 mmol) in anhydrous toluene (50 mL) under argon atmosphere was added 2-phenyl acetonitrile 430 (5 g, 42.55 mmol) at 0° C. and stirred for 30 min. To this dimethyl carbonate 431 (5.74 g, 63.82 mmol) in anhydrous toluene (30 mL) was added drop wise for 10 min and stirred at 0° C. for 4 h. The reaction was monitored by TLC; after completion of the reaction, the reaction mixture was diluted with saturated ammonium chloride (20 mL) and extracted with EtOAc (2×50 mL). The combined organic extracts were washed with brine (50 mL), dried over sodium sulphate, filtered and concentrated in vacuo to obtain the crude. The crude compound was purified through silica gel column chromatography using 20% EtOAc/hexanes to afford compound 432 (4.8 g, 64%) as colorless syrup. TLC: 30% EtOAc/hexanes ($R_f$: 0.7); $^1$H-NMR (CDCl$_3$, 400 MHz): δ 7.47-7.39 (m, 5H), 4.74 (s, 1H), 3.81 (s, 3H).

Synthesis of Methyl 3-amino-2-phenylpropanoate (433)

To a stirred solution of compound 432 (1 g, 5.71 mmol) in MeOH (50 mL) under argon atmosphere were added Boc-anhydride (2.49 g, 11.42 mmol), nickel dichloride hexahydrate (135 mg, 0.57 mmol) and sodium borohydride (1.5 g, 39.99 mmol) at 0° C.; warmed to RT and stirred for 16 h. The reaction was monitored by TLC; after completion of the reaction, the reaction mixture was diluted with MeOH (30 mL), filtered through celite and the filtrate was concentrated in vacuo to obtain the crude. The crude was purified through silica gel column chromatography using 30% EtOAc/Hexanes to afford racemic compound 433 (550 mg, 36%) as an off white solid. TLC: 20% EtOAc/hexanes ($R_f$: 0.4); $^1$H-NMR (DMSO-$d_6$, 500 MHz): δ 7.34 (t, J=7.0 Hz, 2H), 7.30-7.25 (m, 3H), 6.93 (t, J=6.0 Hz, 1H), 3.85 (t, J=7.5 Hz, 1H), 3.60 (s, 3H), 3.28-3.23 (m, 1H), 1.34 (s, 9H). The racemic compound 433 was purified through chiral preparative HPLC to afford compound 434 Fr-I (120 mg) and compound 435 Fr-II (90 mg) as off-white solids.

Compound 434 Fr-I Analytical Data:
Chiral HPLC:
99.27%, $R_t$=9.58 min (Chiralcel AD-H, 250×4.6 mm, 5 μm); mobile phase (A) 0.1% DEA in n-Hexane (B) EtOH (A:B:98:2); Flow Rate: 1.0 mL/min).

Compound 435 Fr-II Analytical Data:
Chiral HPLC:
99.29%, $R_t$=10.87 min (Chiralcel AD-H, 250×4.6 mm, 5 μm); mobile phase (A) 0.1% DEA in n-Hexane (B) EtOH (A:B:98:2); Flow Rate: 1.0 mL/min).

Synthesis of Methyl (R)-2-phenyl-3-((2, 2, 2-trifluoroacetyl)-$\lambda^4$-azanyl) propanoate (436)

To a stirred solution of compound 434 (Fr-I) (50 mg, 0.17 mmol) in CH$_2$Cl$_2$ (2 mL) under inert atmosphere was added trifluoroacetic acid (0.026 mL, 0.35 mmol) at 0° C.; warmed to RT and stirred for 3 h. The reaction was monitored by TLC; after completion of the reaction, the volatiles were removed in vacuo to obtain the crude compound 436 (20 mg, TFA salt) as off-white solid. TLC: 70% EtOAc/hexanes ($R_f$: 0.2); $^1$H-NMR (DMSO-$d_6$, 400 MHz): δ 8.10 (br s, 2H), 7.41-7.28 (m, 5H), 4.03 (t, J=6.0 Hz, 1H), 3.63 (s, 3H), 3.48 (t, J=9.2 Hz, 1H), 3.12-3.08 (m, 1H).

Synthesis of Methyl (R)-3-(11-oxo-10, 11-dihydrodibenzo [b,f] [1,4] thiazepine-8-carboxamido)-2-phenylpropanoate (437)

To a stirred solution of compound 6 (70 mg, 0.25 mmol) in DMF (5 mL) under argon atmosphere were added EDCI-·HCl (73.9 mg, 0.38 mmol), HOBt (30 mg, 0.38 mmol), compound 436 (70 mg, 0.38 mmol), diisopropyl ethyl amine (0.09 mL, 0.51 mmol) at 0° C.; warmed to RT and stirred for 16 h. The reaction was monitored by TLC; after completion of the reaction, the reaction mixture was diluted with water (20 mL) and extracted with EtOAc (2×10 mL). The combined organic extracts were dried over sodium sulphate, filtered and concentrated in vacuo to obtain the crude. The crude was purified through silica gel column chromatography using 90% EtOAc/Hexanes to afford compound 437 (70 mg, 63%) as colorless syrup. TLC: 5% MeOH/CH$_2$Cl$_2$ ($R_f$: 0.5); $^1$H-NMR (DMSO-$d_6$, 400 MHz): δ 10.75 (s, 1H), 8.65 (t, J=5.6 Hz, 1H), 7.68 (d, J=7.2 Hz, 2H), 7.67-7.60 (m, 4H), 7.54-7.49 (m, 2H), 7.49-7.44 (m, 3H), 7.35-7.25 (m, 1H), 4.02 (t, J=7.2 Hz, 1H), 3.80-3.73 (m, 1H), 3.55 (t, J=6.4 Hz, 1H), 3.47 (s, 3H).

Synthesis of (R)-3-(11-oxo-10, 11-dihydrodibenzo [b,f] [1,4] thiazepine-8-carboxamido)-2-phenylpropanoic acid (1268)

To a stirred solution of compound 437 (40 mg, 0.092 mmol) in THF:H$_2$O (4:1, 2.5 mL) was added LiOH.H$_2$O (7.7 mg, 0.18 mmol) at 0° C.; warmed to RT and stirred for 2 h. The reaction was monitored by TLC; after completion of the reaction, diluted with water (5 mL), pH was adjusted to ~6 using 1 N HCl and extracted with EtOAc (2×10 mL). The combined organic extracts were dried over sodium sulphate, filtered and concentrated in vacuo to afford 1268 (25 mg, 65%) as white solid. TLC: 10% MeOH/CH$_2$Cl$_2$ ($R_f$: 0.5); $^1$H-NMR (DMSO-$d_6$, 400 MHz): δ 12.49 (br s, 1H), 10.76 (s, 1H), 8.62 (t, J=5.6 Hz, 1H), 7.68 (d, J=7.2 Hz, 1H), 7.66-7.61 (m, 2H), 7.54-7.42 (m, 4H), 7.34-7.23 (m, 5H), 3.92 (t, J=7.6 Hz, 1H), 3.77-3.72 (m, 1H), 3.57-3.50 (m, 1H); LC-MS: 90.53%; 419.4 (M$^+$+1); (column; X-bridge C-18, (50×3.0 mm, 3.5 μm); RT 3.76 min. 0.05% TFA (Aq): ACN; 0.8 mL/min); UPLC (purity): 93.78%; (column: Acquity BEH C-18 (50×2.1 mm, 1.7μ); RT 2.04 min. ACN: 0.025% TFA (Aq); 0.5 mL/min).

Synthesis of Methyl (S)-2-phenyl-3-((2, 2, 2-trifluoroacetyl)-$\lambda^4$-azanyl) propanoate (438)

To a stirred solution of compound 435 (Fr-II) (90 mg, 0.32 mmol) in CH$_2$Cl$_2$ (3 mL) under inert atmosphere was added trifluoroacetic acid (0.073 mL, 0.64 mmol) at 0° C.; warmed to RT and stirred for 3 h. The reaction was monitored by TLC; after completion of the reaction, the volatiles were removed in vacuo to obtain the crude compound 438 (90 mg, TFA salt) as an off-white solid. TLC: 70% EtOAc/Hexanes ($R_f$: 0.2); $^1$H-NMR (DMSO-$d_6$, 400 MHz): δ 8.10 (br s, 2H), 7.41-7.28 (m, 5H), 4.03 (t, J=6.0 Hz, 1H), 3.63 (s, 3H), 3.48 (t, J=9.2 Hz, 1H), 3.12-3.08 (m, 1H).

Synthesis of Methyl (S)-3-(11-oxo-10, 11-dihydrodibenzo [b,f] [1,4] thiazepine-8-carboxamido)-2-phenylpropanoate (439)

To a stirred solution of compound 6 (70 mg, 0.25 mmol) in DMF (5 mL) under argon atmosphere were added EDCI-·HCl (73.9 mg, 0.38 mmol), HOBt (52 mg, 0.38 mmol), compound 438 (70 mg, 0.38 mmol), diisopropyl ethyl amine (0.09 mL, 0.51 mmol) at 0° C.; warmed to RT and stirred for 16 h. The reaction was monitored by TLC; after completion of the reaction, the reaction mixture was diluted with water (20 mL) and extracted with EtOAc (2×10 mL). The combined organic extracts were dried over sodium sulphate, filtered and concentrated in vacuo to obtain the crude. The crude was purified through silica gel column chromatography using 80% EtOAc/hexanes to afford compound 439 (70 mg, 63%) as an off-white solid. TLC: 5% MeOH/CH$_2$Cl$_2$ ($R_f$: 0.5); $^1$H-NMR (DMSO-$d_6$, 400 MHz): δ 10.77 (s, 1H), 8.65 (t, J=5.6 Hz, 1H), 7.69 (d, J=7.2 Hz, 1H), 7.65-7.61 (m, 2H), 7.55-7.45 (m, 4H), 7.37-7.34 (m, 2H), 7.31-7.27 (m, 3H), 4.02 (t, J=7.2 Hz, 1H), 3.80-3.74 (m, 1H), 3.59 (s, 3H), 3.56-3.53 (m, 1H).

Synthesis of (S)-3-(11-oxo-10, 11-dihydrodibenzo [b,f] [1,4] thiazepine-8-carboxamido)-2-phenylpropanoic acid (1269)

To a stirred solution of compound 439 (40 mg, 0.09 mmol) in THF:H$_2$O (4:1, 2.5 mL) was added lithium hydroxide monohydrate (7.7 mg, 0.18 mmol) at 0° C.; warmed to RT and stirred for 2 h. The reaction was monitored by TLC; after completion of the reaction, diluted with water (5 mL), the pH was adjusted to ~6 using 1 N HCl and extracted with EtOAc (2×10 mL). The combined organic extracts were dried over sodium sulphate, filtered and concentrated in vacuo to afford 1269 (25 mg, 65%) as white solid. TLC: 10% MeOH/CH$_2$Cl$_2$ (R$_f$: 0.3); $^1$H-NMR (DMSO-d$_6$, 400 MHz): δ 12.51 (br s, 1H), 10.76 (s, 1H), 8.62 (t, J=5.6 Hz, 1H), 7.68 (d, J=7.2 Hz, 1H), 7.66-7.61 (m, 2H), 7.54-7.43 (m, 4H), 7.34-7.23 (m, 5H), 3.92 (t, J=7.6 Hz, 1H), 3.77-3.72 (m, 1H), 3.57-3.50 (m, 1H); LC-MS: 96.04%; 417.8 (M−1)$^+$; (column; X-select C-18, (50×3.0 mm, 3.5 μm); RT 2.38 min. 5.0 mM NH$_4$OAc: ACN; 0.8 mL/min); UPLC (purity): 96.12%; (column: Acquity BEH C-18 (50×2.1 mm, 1.7 g); RT 2.03 min. ACN: 0.025% TFA (Aq); 0.5 mL/min).

Example 28: Synthesis of Compound 1239

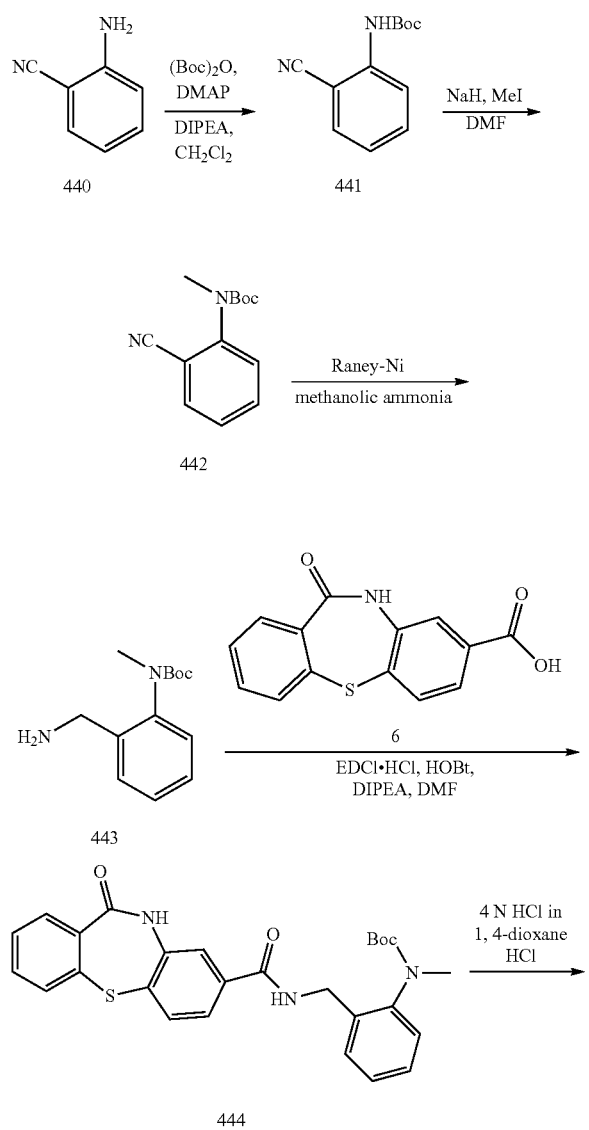

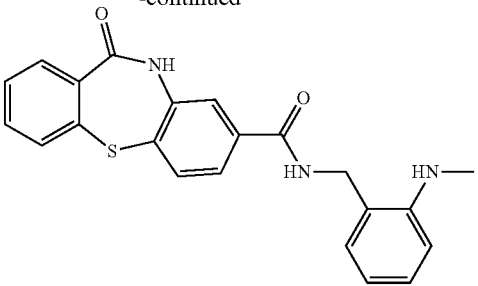

1239

Synthesis of Tert-Butyl (2-cyanophenyl) carbamate (441)

To a stirred solution of 2-aminobenzonitrile 440 (1 g, 8.47 mmol) in CH$_2$Cl$_2$ (15 mL) under argon atmosphere were added Boc-anhydride (1.84 g, 4.76 mmol) and triethyl amine (0.83 mL, 5.96 mmol), DMAP (0.1 mg, catalytic amount) at 0° C.; warmed to RT and stirred for 5 h. The reaction was monitored by TLC; after completion of the reaction, the volatiles were removed in vacuo to obtain the crude. The crude was purified through silica gel column chromatography using 30% EtOAc/hexanes to afford compound 441 (500 mg, 28%) as white solid. TLC: 30% EtOAc/hexanes (R$_f$: 0.8); $^1$H-NMR (DMSO-d$_6$, 400 MHz): δ 9.25 (br s, 1H), 7.85 (d, J=7.6 Hz, 1H), 7.73 (t, J=7.6 Hz, 1H), 7.53 (d, J=8.0 Hz, 1H), 7.45 (t, J=7.6 Hz, 1H), 1.35 (br s, 9H).

Synthesis of Tert-Butyl (2-cyanophenyl)(methyl) carbamate (442)

To a stirred solution of compound 441 (500 mg, 2.29 mmol) in DMF (10 mL) under argon atmosphere were added sodium hydride (60%, 55 mg, 2.29 mmol), methyl iodide (325 mg, 2.29 mmol) at 0° C.; warmed to RT and stirred for 5 h. The reaction was monitored by TLC; after completion of the reaction, the reaction mixture was quenched with ice cold water (10 mL), extracted with EtOAc (2×20 mL). The combined organic extracts were dried over sodium sulphate, filtered and concentrated in vacuo to obtain the crude. The crude was purified through silica gel column chromatography using 40% EtOAc/hexanes to afford compound 442 (480 mg, 88%) as white solid. TLC: 30% EtOAc/hexanes (R$_f$: 0.5); $^1$H-NMR (DMSO-d$_6$, 400 MHz): δ 7.85 (d, J=7.6 Hz, 1H), 7.73 (t, J=7.6 Hz, 1H), 7.53 (d, J=7.6 Hz, 1H), 7.45 (t, J=7.6 Hz, 1H), 3.18 (s, 3H), 1.35 (br s, 9H).

Synthesis of Tert-Butyl (2-(aminomethyl) phenyl)(methyl) carbamate (443)

To a stirred solution of compound 442 (50 mg, 0.21 mmol) in MeOH (3 mL) under argon atmosphere was added Raney Nickel (20 mg), methanolic ammonia (1.5 mL) at RT and stirred under hydrogen atmosphere (balloon pressure) for 6 h. The reaction was monitored by TLC; after completion of the reaction, the reaction mixture was filtered through celite, washed with MeOH (2×5 mL) and the filtrate was concentrated in vacuo to obtain the crude. The crude was washed with diethyl ether (2×10 mL) and dried in vacuo to afford compound 443 (40 mg, 80%) as white solid. TLC: 50% EtOAc/hexanes (R$_f$: 0.2); $^1$H-NMR (DMSO-d$_6$, 400

MHz): δ 7.52 (d, J=7.2 Hz, 1H), 7.28-7.20 (m, 2H), 7.12 (t, J=5.6 Hz, 1H), 3.60-3.57 (m, 2H), 3.14 (br s, 3H), 1.25 (s, 9H).

Synthesis of Tert-Butyl methyl (2-((11-oxo-10, 11-dihydrodibenzo [b,f] [1,4] thiazepine-8-carboxamido) methyl) phenyl) carbamate (444)

To a stirred solution of compound 6 (40 mg, 0.14 mmol) in DMF (3 mL) under argon atmosphere were added EDCI·HCl (42 mg, 0.22 mmol), HOBt (30 mg, 0.22 mmol), compound 443 (37.6 mg, 0.16 mmol), diisopropyl ethyl amine (0.05 mL, 0.29 mmol) at 0° C.; warmed to RT and stirred for 16 h. The reaction was monitored by TLC; after completion of the reaction, the reaction mixture was diluted with ice-cold water (20 mL). The precipitate was filtered and the obtained solid was dried in vacuo to afford compound 444 (40 mg, 55%) as white solid. TLC: 5% MeOH/CH$_2$Cl$_2$ (R$_f$: 0.5); LC-MS: 93.49%; 390.3 (M$^+$+1) (Des-Boc).

Synthesis of N-(2-(methylamino) benzyl)-11-oxo-10, 11-dihydrodibenzo [b,f] [1,4] thiazepine-8-carboxamide (1239)

A stirred solution of compound 444 (40 mg, 0.08 mmol) in 4 N HCl in 1, 4-dioxane (2 mL) under argon atmosphere at 0-5° C. was stirred for 1 h. The reaction was monitored by TLC; after completion of the reaction, the reaction mixture was diluted with saturated NaHCO$_3$ solution (20 mL) and extracted with EtOAc (2×20 mL). The combined organic extracts were washed with water (15 mL), dried over sodium sulphate, filtered and concentrated in vacuo to afford 1239 (10 mg, 32%) as white solid. TLC: 5% MeOH/CH$_2$Cl$_2$ (R$_f$: 0.4); $^1$H-NMR (DMSO-d$_6$, 400 MHz): δ 10.74 (s, 1H), 8.96 (t, J=6.0 Hz, 1H), 7.72-7.60 (m, 4H), 7.55-7.43 (m, 3H), 7.08 (t, J=7.6 Hz, 1H), 7.02 (d, J=7.2 Hz, 1H), 6.53 (t, J=7.2 Hz, 2H), 5.38-5.37 (m, 1H), 4.29 (d, J=7.2 Hz, 2H), 2.72 (d, J=4.8 Hz, 3H); LC-MS: 93.74%; 390.3 (M$^+$+1); (column; X-select CSH C-18, (50×3.0 mm, 3.5 μm); RT 3.44 min. 0.05% TFA (Aq): ACN; 0.8 mL/min); UPLC (purity): 94.35%; (column: Acquity UPLC BEH C-18 (2.1×50 mm, 1.7μ); RT 1.87 min. ACN: 0.025% TFA (Aq); 0.5 mL/min).

Example 29: Synthesis of Compound 1244

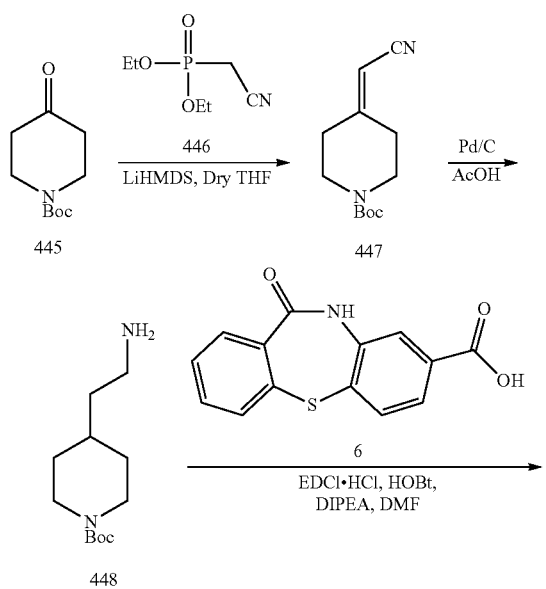

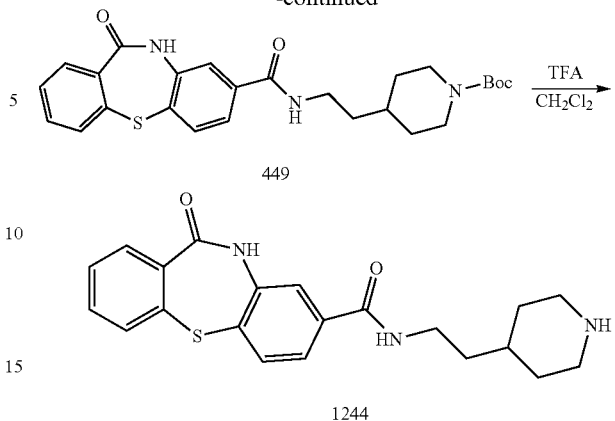

1244

Synthesis of Tert-Butyl 4-(cyanomethylene) piperidine-1-carboxylate (447)

To a stirred solution of diethyl (cyanomethyl) phosphonate 445 (978 mg, 5.52 mmol) in anhydrous THF (10 mL) under argon atmosphere was added LiHMDS (1 mL, 5.52 mmol, 1M in THF) was added drop wise for 10 min at −78° C. To this was added tert-butyl 4-oxopiperidine-1-carboxylate 446 (1 g, 5.01 mmol) in THF (2 mL) dropwise for 10 min and stirred for 3 h at the same temperature. The reaction was monitored by TLC; after completion of the reaction, the reaction mixture was quenched with saturated ammonium chloride solution (30 mL) and extracted with EtOAc (2×50 mL). The combined organic extracts were washed with brine (30 mL), dried over sodium sulfate, filtered and concentrated in vacuo to obtain the crude. The crude was purified through silica gel column chromatography using 15% EtOAc/hexanes to afford compound 447 (900 mg, 82%) as white solid. TLC: 30% EtOAc/hexanes (R$_f$: 0.5); $^1$H NMR (CDCl$_3$, 400 MHz) δ 5.19 (s, 1H), 3.54-3.49 (m, 4H), 2.56 (t, J=5.8 Hz, 2H), 2.33 (t, J=5.6 Hz, 2H), 1.48 (s, 9H);

Synthesis of Tert-Butyl 4-(2-aminoethyl) piperidine-1-carboxylate (448)

To a stirred solution of 447 (100 mg, 0.45 mmol) in AcOH (5 mL) under argon atmosphere was added 10% Pd/C (50 mg) at RT and stirred under hydrogen atmosphere (balloon pressure) for 16 h. The reaction was monitored by TLC; after completion of the reaction, the reaction mass was filtered through celite and washed with EtOAc (3×15 mL) and the volatiles were removed in vacuo to afford compound 448 (70 mg, mixture of isomers) as pale brown syrup. TLC: 6% MeOH/CH$_2$Cl$_2$ (R$_f$: 0.2); $^1$H-NMR (DMSO-d$_6$, 400 MHz): δ 3.89 (d, J=12.4 Hz, 2H), 2.70-2.68 (m, 2H), 1.68-1.65 (m, 2H), 1.59 (d, J=12.0 Hz, 1H), 1.38 (s, 9H), 1.33-1.28 (m, 4H), 0.99-0.89 (m, 2H).

Synthesis of Tert-Butyl 4-(2-(11-oxo-10, 11-dihydrodibenzo [b,f] [1,4] thiazepine-8-carboxamido) ethyl) piperidine-1-carboxylate (449)

To a stirred solution of compound 6 (40 mg, 0.14 mmol) in DMF (3 mL) under argon atmosphere were added EDCI·HCl (42 mg, 0.22 mmol), HOBt (30 mg, 0.22 mmol), compound 448 (40 mg, 0.17 mmol), diisopropyl ethyl amine (0.05 mL, 0.29 mmol) at 0° C.; warmed to RT and stirred for 16 h. The reaction was monitored by TLC; after completion of the reaction, the volatiles were removed in vacuo to obtain the crude. The crude was triturated with EtOAc: H₂O (1:5, 12 mL), filtered and the precipitate was dried in vacuo to afford compound 449 (36 mg, 51%) as white solid. TLC: 7% MeOH/CH₂Cl₂ (R_f: 0.7); ¹H-NMR (DMSO-d₆, 400 MHz): δ 10.76 (s, 1H), 8.47 (br s, 1H), 7.69-7.63 (m, 3H), 7.57-7.53 (m, 2H), 7.47 (t, J=8.8 Hz, 2H), 3.89 (d, J=10.8 Hz, 2H), 3.26-3.25 (m, 2H), 2.67 (s, 3H), 1.64 (d, J=10.8 Hz, 2H), 1.42-1.41 (m, 2H), 1.37 (s, 9H), 0.97-0.95 (m, 2H).

Synthesis of 11-oxo-N-(2-(piperidin-4-yl) ethyl)-10, 11-dihydrodibenzo [b,f] [1,4] thiazepine-8-carboxamide (1244)

To a stirred solution of compound 449 (36 mg, 0.07 mmol) in CH₂Cl₂ (3 mL) under argon atmosphere was added trifluoro acetic acid (0.03 mL, 0.37 mmol) at 0° C.; warmed to RT and stirred for 4 h. The reaction was monitored by TLC; after completion of the reaction, the volatiles were removed in vacuo to obtain the crude. The crude was neutralized with 10% NaHCO₃ solution (15 mL) and extracted with EtOAc (3×15 mL). The combined organic extracts were dried over sodium sulfate, filtered and concentrated in vacuo to afford 1244 (15 mg, 53%) as an off-white solid. TLC: 7% MeOH/CH₂Cl₂ (R_f: 0.2); ¹H-NMR (DMSO-d₆, 400 MHz): δ 10.77 (br s, 1H), 8.48 (t, J=5.6 Hz, 1H), 7.69-7.64 (m, 3H), 7.57-7.43 (m, 4H), 3.26-3.25 (m, 3H), 3.16-3.12 (m, 2H), 2.68 (t, J=10.0 Hz, 2H), 1.77-1.74 (m, 2H), 1.44 (t, J=6.8 Hz, 3H); 1.23-1.13 (m, 2H); LC-MS: 90.01%; 382.4 (M⁺+1); (column; X-select CSH C-18, (50× 3.0 mm, 3.5 µm); RT 2.97 min. 0.05% TFA (Aq): ACN; 0.8 mL/min); UPLC (purity): 92.90%; (column: Acquity UPLC BEH C-18 (2.1×50 mm, 1.7 g); RT 1.60 min. ACN: 0.025% TFA (Aq); 0.5 mL/min).

Example 30: Synthesis of Compounds 1651 and 1652

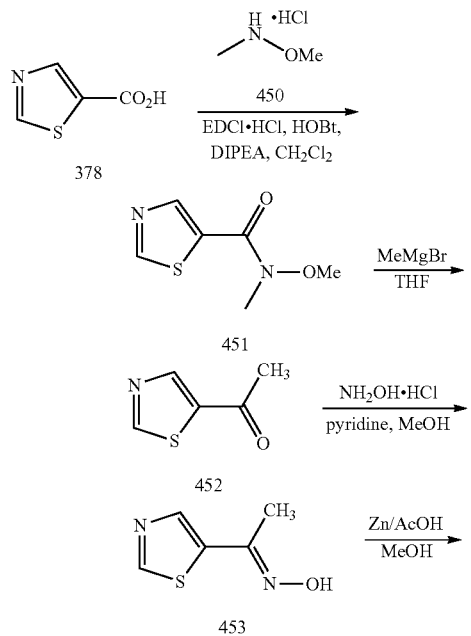

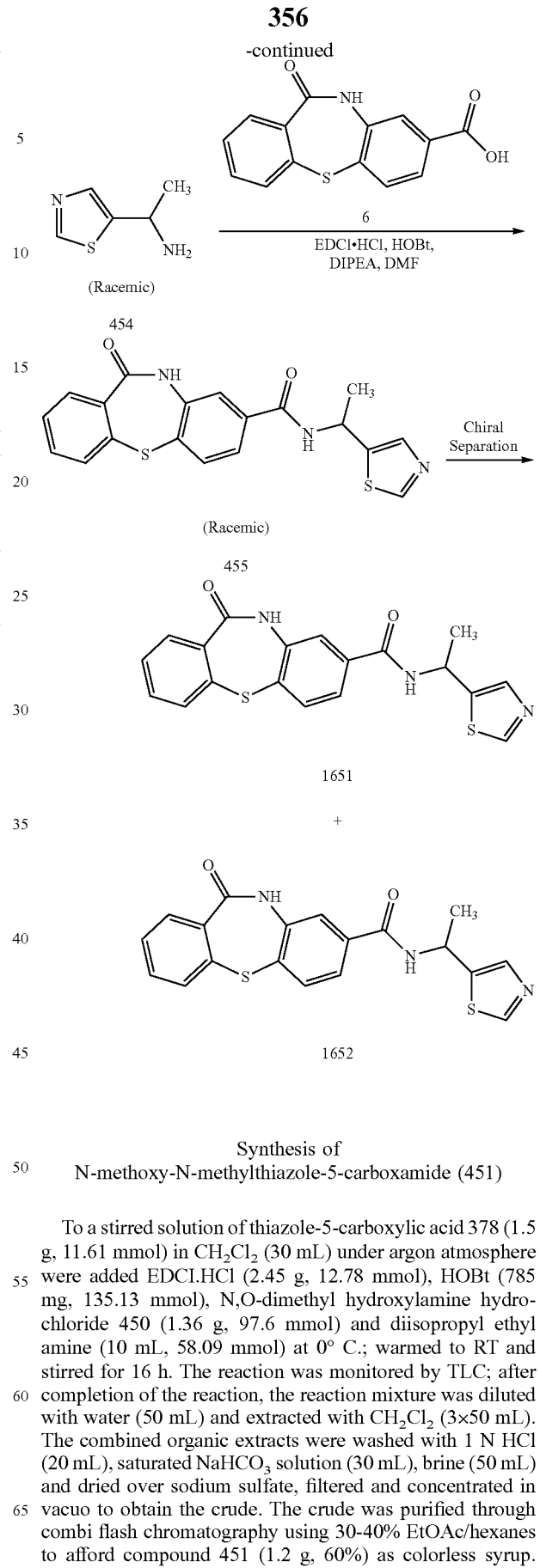

Synthesis of N-methoxy-N-methylthiazole-5-carboxamide (451)

To a stirred solution of thiazole-5-carboxylic acid 378 (1.5 g, 11.61 mmol) in CH₂Cl₂ (30 mL) under argon atmosphere were added EDCI.HCl (2.45 g, 12.78 mmol), HOBt (785 mg, 135.13 mmol), N,O-dimethyl hydroxylamine hydrochloride 450 (1.36 g, 97.6 mmol) and diisopropyl ethyl amine (10 mL, 58.09 mmol) at 0° C.; warmed to RT and stirred for 16 h. The reaction was monitored by TLC; after completion of the reaction, the reaction mixture was diluted with water (50 mL) and extracted with CH₂Cl₂ (3×50 mL). The combined organic extracts were washed with 1 N HCl (20 mL), saturated NaHCO₃ solution (30 mL), brine (50 mL) and dried over sodium sulfate, filtered and concentrated in vacuo to obtain the crude. The crude was purified through combi flash chromatography using 30-40% EtOAc/hexanes to afford compound 451 (1.2 g, 60%) as colorless syrup.

TLC: 5% MeOH/CH₂Cl₂ (R_f: 0.6); 1H NMR (DMSO-d₆, 400 MHz): 9.32 (s, 1H), 8.52 (s, 1H), 3.77 (s, 3H), 3.30 (s, 3H).

Synthesis of 1-(thiazol-5-yl) ethan-1-one (452)

To a stirred solution of compound 451 (1.2 g, 6.97 mmol) in THF (20 mL) under argon atmosphere was added methyl magnesium bromide (3.2 mL, 10.46 mmol, 3 M solution in Et₂O) dropwise for 10 min at −10° C.; warmed to RT and stirred for 16 h. The reaction was monitored by TLC; after completion of the reaction, the reaction mixture was quenched with saturated ammonium chloride (30 mL) and extracted with EtOAc (2×50 mL). The combined organic extracts were dried over sodium sulfate, filtered and concentrated in vacuo to obtain the crude. The crude was purified through combi flash chromatography using 25-30% EtOAc/hexanes to afford compound 452 (800 mg, 90%) as white solid. TLC: 50% EtOAc/hexanes (R_f: 0.6); 1H NMR (DMSO-d₆, 400 MHz): δ 9.40 (s, 1H), 8.71 (s, 1H), 2.60 (s, 3H).

Synthesis of 1-(thiazol-5-yl) ethan-1-one oxime (453)

To a stirred solution of compound 452 (800 mg, 6.29 mmol) in MeOH (20 mL) under inert atmosphere was added hydroxyl amine hydrochloride (875 mg, 12.59 mmol) and pyridine (2 mL) dropwise for 5 min at 0° C. warmed to RT and stirred for 16 h. The reaction was monitored by TLC; after completion of the reaction, the volatiles were removed in vacuo diluted with water (50 mL) and stirred for 30 min. The precipitated solid was filtered dried in vacuo to afford compound 453 (800 mg, 90%) as white solid. TLC: 40% EtOAc/hexanes (R_f: 0.4, 0.6); 1H NMR (DMSO-d₆, 400 MHz) (Mixture of E/Z isomers): δ 11.86 (s, 1H), 11.41 (s, 0.6H), 9.19 (s, 1H), 9.01 (s, 0.56H), 8.35 (s, 1H), 8.15 (s, 0.65H), 2.31 (s, 3H), 2.21 (s, 2H).

Synthesis of 1-(thiazol-5-yl) ethan-1-amine (454)

To a stirred solution of compound 453 (800 mg, 5.63 mmol) in MeOH: acetic acid (1:1, 20 mL) under inert atmosphere were zinc powder (2.2 g, 33.80 mmol) at RT; heated at 50° C. and stirred for 4 h. The reaction was monitored by TLC; after completion of the reaction, the reaction mixture was filtered through celite washed with MeOH (3×10 mL). The filtrate were removed in vacuo, the residue was diluted with water (20 mL), basified with aqueous ammonia (15 mL) and extracted with EtOAc (3×50 mL). The combined organic extracts were dried over sodium sulfate, filtered and concentrated in vacuo to obtain the crude compound 454 (racemic) (700 mg, 92%) as brown syrup. TLC: 5% MeOH/CH₂Cl₂ (R_f: 0.4, 0.6); 1H NMR (DMSO-d₆, 400 MHz): δ 8.90 (s, 1H), 7.71 (s, 1H), 4.33-4.28 (m, 1H), 3.38 (t, J=6.4 Hz, 1H), 1.87 (s, 3H).

Synthesis of 11-oxo-N-(1-(thiazol-5-yl) ethyl)-10,11-dihydrodibenzo [b,f] [1,4] thiazepine-8-carboxamide (455 Racemic)

Using Procedure A the title compound was prepared with DBT-Acid (150 mg, 0.55 mmol) and compound 454 racemic (109 mg, 0.66) to afford compound 455 (Racemic) (100 mg, 48%); TLC: 5% MeOH/CH₂Cl₂ (R_f: 0.5); 1H NMR (DMSO-d₆, 400 MHz): δ 10.87 (br s, 1H), 9.14 (d, J=8.0 Hz, 1H), 8.95 (s, 1H), 7.79 (d, J=3.6 Hz, 2H), 7.70-7.58 (m, 3H), 7.56-7.42 (m, 3H), 5.48-5.41 (m, 1H), 1.60 (s, 3H); LC-MS: 98.31%; 381.9 (M⁺+1); (column; Ascentis Express C18, (50×3.0 mm, 2.7 μm); RT 2.03 min. 0.025% Aq. TFA+5% ACN: ACN+5% 0.025% Aq. TFA, 1.2 mL/min); HPLC (purity): 97.68%; (column; Eclipse XDB C-18 (150×4.6 mm, 5.0 μm); RT 7.58 min. ACN: 0.05% TFA (Aq); 1.0 mL/min) (IP14012554); Chiral HPLC: 35.10%, R_t=9.01 min (Chiralpak-IA, 250×4.6 mm, 5 μm); mobile phase (A) 0.1% DEA in n-Hexane (B) CH₂Cl₂: MeOH (50:50) (A:B::63:35); Flow Rate: 1.0 mL/min).

The racemic compound 455 (100 mg) was separated by preparative HPLC using a CHIRALPAK-IC column (250× 20 mm×5 μm) (10 mg loading; mobile phase (A) 0.1% DEA in n-Hexane (B) CH₂Cl₂: MeOH: DMF (65:35:05) (A:B:: 75:25) to afford 1651 (10 mg) and 1652 (15 mg) as an off-white solids.

Analytical Data of 1651:

TLC: 5% MeOH/CH₂Cl₂ (R_f: 0.5); 1H NMR (DMSO-d₆, 400 MHz): δ 10.75 (s, 1H), 9.02 (d, J=7.8 Hz, 1H), 8.95 (s, 1H), 7.79 (s, 1H), 7.72-7.64 (m, 3H), 7.62-7.58 (m, 1H), 7.56-7.41 (m, 3H), 5.45 (t, J=7.0 Hz, 1H), 1.57 (d, J=6.8 Hz, 3H); LC-MS: 96.06%; 381.8 (M⁺+1); (column; Ascentis Express C18, (50×3.0 mm, 2.7 μm); RT 2.03 min. 0.025% Aq. TFA+5% ACN: ACN+5% 0.025% Aq. TFA, 1.2 mL/min); HPLC (purity): 95.02%; (column; Zorbax SB C-18 (150×4.6 mm, 3.5 μm); RT 7.79 min. ACN: 0.05% TFA (Aq); 1.0 mL/min) (IP15010530); Chiral HPLC: 96.24%, R_t=14.33 min (Chiralpak-IA, 250×4.6 mm, 5 μm); mobile phase (A) 0.1% DEA in n-Hexane (B) CH₂Cl₂: MeOH: DMF (65:35:05) (A:B::75:25); Flow Rate: 1.0 mL/min). Note: Alternatively the racemic compound 454 was resolved and one fraction had led to 1651.

Analytical Data of 1652:

TLC: 5% MeOH/CH₂Cl₂ (R_f: 0.5); 1H NMR (DMSO-d₆, 400 MHz): δ 10.75 (s, 1H), 9.03 (d, J=8.3 Hz, 1H), 8.95 (s, 1H), 7.79 (s, 1H), 7.71-7.63 (m, 3H), 7.62-7.58 (m, 1H), 7.56-7.42 (m, 3H), 5.48-5.47 (m, 1H), 1.57 (d, J=6.9 Hz, 3H); LC-MS: 96.65%; 381.9 (M⁺+1); (column; Ascentis Express C18, (50×3.0 mm, 2.7 μm); RT 2.68 min. 0.025% Aq. TFA+5% ACN: ACN+5% 0.025% Aq. TFA, 1.2 mL/min); HPLC (purity): 98.53%; (column; Zorbax SB C-18 (150×4.6 mm, 3.5 μm); RT 7.76 min. ACN: 0.05% TFA (Aq); 1.0 mL/min) (IP15010229). Chiral HPLC: 99.87%, R_t=16.90 min (Chiralpak-IA, 250×4.6 mm, 5 μm); mobile phase (A) 0.1% DEA in n-Hexane (B) CH₂Cl₂: MeOH: DMF (65:35:05) (A:B::75:25); Flow Rate: 1.0 mL/min).

Example 31: Synthesis of Compounds 1653 and 1633

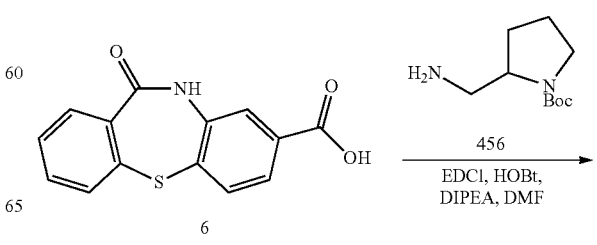

359
-continued

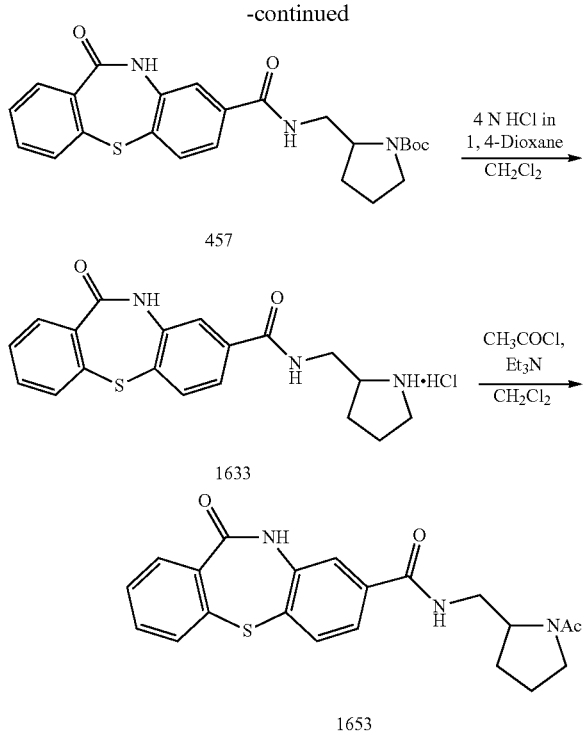

457

1633

1653

Synthesis of Tert-Butyl 2-((11-oxo-10, 11-dihydrodibenzo [b,f] [1,4] thiazepine-8-carboxamido) methyl) pyrrolidine-1-carboxylate (457)

Using Procedure A the title compound was prepared with compound 6 (300 mg, 1.10 mmol), tert-butyl 2-(aminomethyl) pyrrolidine-1-carboxylate 456 (0.24 mL, 1.21 mmol) and was obtained in 50% yield as an off-white solid; TLC: 10% MeOH/CH$_2$Cl$_2$ (R$_f$: 0.7); 1H NMR (DMSO-d$_6$, 400 MHz): δ 10.76 (br s, 1H), 8.53 (t, J=5.5 Hz, 1H), 7.71-7.63 (m, 3H), 7.56-7.43 (m, 4H), 3.95-3.79 (m, 1H), 3.52-3.35 (m, 1H), 3.26-3.19 (m, 3H), 1.86-1.71 (m, 4H), 1.38 (s, 9H).

Synthesis of 11-oxo-N-(pyrrolidin-2-ylmethyl)-10, 11-dihydrodibenzo [b,f] [1,4] thiazepine-8-carboxamide hydrochloride (1633)

To a stirred solution of compound 457 (250 mg, 0.55 mmol) in CH$_2$Cl$_2$ (5 mL) under argon atmosphere was added 4 N HCl in 1, 4-dioxane (1 mL) at 0° C.; warmed to RT and stirred for 5 h. The reaction was monitored by TLC; after completion of the reaction, the volatiles were removed in vacuo to afford compound 1633 (150 mg, 77%; HCl salt) as an off-white solid. TLC: 10% MeOH/CH$_2$Cl$_2$ (R$_f$: 0.1); 1H NMR (DMSO-d$_6$, 400 MHz): δ 10.82 (br s, 1H), 8.88 (br s, 3H), 7.74-7.62 (m, 4H), 7.56-7.43 (m, 3H), 3.67-3.57 (m, 1H), 3.56-3.46 (m, 2H), 3.24-3.07 (m, 2H), 2.07-1.95 (m, 1H), 1.95-1.78 (m, 2H), 1.68-1.59 (m, 1H); LC-MS: 96.49%; 354.0 (M$^+$+1) (—HCl); (column; Ascentis Express C18, (50×3.0 mm, 2.7 μm); RT 1.64 min. 0.025% Aq. TFA+5% ACN: ACN+5% 0.025% Aq. TFA, 1.2 mL/min); HPLC (purity): 96.28%; (column; Zorbax SB C-18 (150×4.6 mm, 3.5 μm); RT 6.64 min. ACN: 0.05% TFA (Aq); 1.0 mL/min).

360

Synthesis of N-((1-acetylpyrrolidin-2-yl) methyl)-11-oxo-10, 11-dihydrodibenzo [b,f] [1,4] thiazepine-8-carboxamide (1653)

To a stirred solution of compound 1633 (100 mg, 0.25 mmol) in CH$_2$Cl$_2$ (5 mL) under argon atmosphere were added triethylamine (0.12 mL, 0.77 mmol), acetyl chloride (0.02 mL, 0.30 mmol) at 0° C.; warmed to RT, stirred for 12 h. The reaction was monitored by TLC; after completion the reaction, the reaction the volatiles were removed in vacuo; the residue was basified with saturated NaHCO$_3$ solution and extracted with CH$_2$Cl$_2$ (2×50 mL). The combined organic extracts were dried over sodium sulfate, filtered and concentrated in vacuo to obtain the crude. The crude was purified through silica gel column chromatography using 5% MeOH/CH$_2$Cl$_2$ to afford 1653 (20 mg, 20%) as an off-white solid. TLC: 10% MeOH/CH$_2$Cl$_2$ (R$_f$: 0.6); $^1$H NMR (DMSO-d$_6$, 400 MHz): δ 10.84-10.73 (m, 1H), 8.87-8.55 (m, 1H), 7.72-7.63 (m, 3H), 7.60-7.43 (m, 4H), 4.17-3.94 (m, 1H), 3.53-3.33 (m, 3H), 3.32-3.30 (m, 0.5H), 3.20-3.09 (m, 0.5H), 2.08-1.92 (m, 3H), 1.88-1.70 (m, 4H); LC-MS: 99.36%; 396.4 (M$^+$+1); (column; X-Select C-18, (50×3.0 mm, 3.5 μm); RT 3.34 min, 0.77 min. 5 mM Aq.NH$_4$OAc: ACN 0.8 mL/min). HPLC (purity): 98.67%; (column; Eclipse XDB C-18 (150×4.6 mm, 5.0 μm); RT 7.28 min. ACN: 5 mM Aq. NH$_4$OAc; 1.0 mL/min).

Example 32: Synthesis of Compounds 1615 and 1608

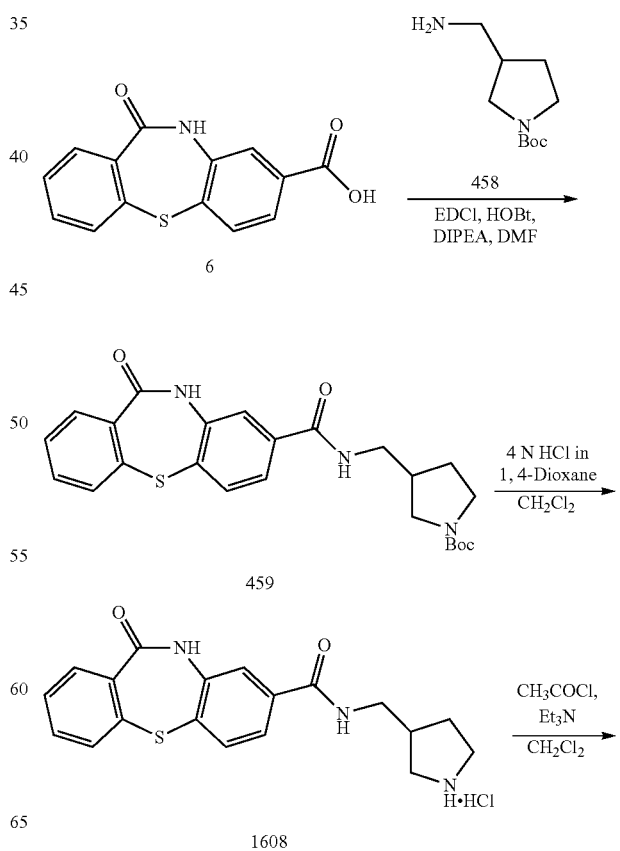

6

458

459

1608

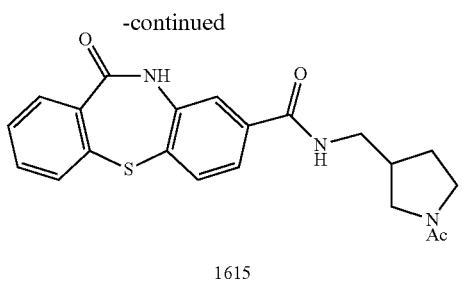

1615

Synthesis of Tert-Butyl 3-((11-oxo-10, 11-dihydrodibenzo [b,f] [1,4] thiazepine-8-carboxamido) methyl) pyrrolidine-1-carboxylate (459)

Using Procedure A the title compound was prepared with 6 (300 mg, 1.10 mmol), tert-butyl 3-(aminomethyl) pyrrolidine-1-carboxylate 458 (0.24 mL, 1.21 mmol) and was obtained in 60% yield as an off-white solid; TLC: 10% MeOH/$CH_2Cl_2$ ($R_f$: 0.5); 1H NMR (DMSO-$d_6$, 400 MHz): δ 10.76 (s, 1H), 8.61 (t, J=5.0 Hz, 1H), 7.72-7.63 (m, 3H), 7.60-7.42 (m, 4H), 3.34-3.18 (m, 1H), 3.28-3.13 (m, 4H), 2.99-2.92 (m, 1H), 2.42-2.34 (m, 1H), 1.94-1.82 (m, 1H), 1.64-1.50 (m, 1H), 1.37 (s, 9H).

Synthesis of 11-oxo-N-(pyrrolidin-3-ylmethyl)-10, 11-dihydrodibenz[b,f] [1,4] thiazepine-8-carboxamide hydrochloride (1608)

To a stirred solution of compound 459 (300 mg, 0.66 mmol) in $CH_2Cl_2$ (5 mL) under argon atmosphere was added 4 N HCl in 1, 4-dioxane (1 mL) at 0° C.; warmed to RT and stirred for 5 h. The reaction was monitored by TLC; after completion of the reaction, the volatiles were removed in vacuo to afford compound 1608 (200 mg, 78%; HCl salt) as an off-white solid. TLC: 10% MeOH/$CH_2Cl_2$ ($R_f$: 0.1); $^1$H-NMR (DMSO-$d_6$, 400 MHz): δ 10.78 (s, 1H), 8.88 (br s, 2H), 8.70 (t, J=5.7 Hz, 1H), 7.71-7.65 (m, 3H), 7.59 (dd, J=8.2, 2.0 Hz, 1H), 7.56-7.43 (m, 3H), 3.27-3.15 (m, 5H), 3.15-3.04 (m, 1H), 2.94-2.80 (m, 1H), 2.04-1.92 (m, 1H), 1.69-1.56 (m, 1H); LC-MS: 98.04%; 353.9 ($M^+$+1) (—HCl); (column; Ascentis Express C18, (50×3.0 mm, 2.7 μm); RT 1.64 min. 0.025% Aq. TFA+5% ACN: ACN+5% 0.025% Aq. TFA, 1.2 mL/min); UPLC (purity): 97.21%; (column; Acquity UPLC BEH C-18 (50×2.1 mm, 1.7μ); RT 1.55 min. ACN: 0.025% TFA (Aq); 0.5 mL/min) (IP14120205).

Synthesis of N-((1-acetylpyrrolidin-3-yl) methyl)-11-oxo-10, 11-dihydrodibenzo [b,f] [1,4] thiazepine-8-carboxamide (1615)

To a stirred solution of compound 1608 (100 mg, 0.28 mmol) in $CH_2Cl_2$ (5 mL) under argon atmosphere were added triethylamine (0.12 mL, 0.84 mmol), acetyl chloride (0.02 mL, 0.33 mmol) at 0° C.; warmed to RT, stirred for 12 h. The reaction was monitored by TLC; after completion the reaction, the reaction the volatiles were removed in vacuo; the residue was basified with saturated $NaHCO_3$ solution and extracted with $CH_2Cl_2$ (2×30 mL). The combined organic extracts were dried over sodium sulfate, filtered and concentrated in vacuo to obtain the crude. The crude was purified through silica gel column chromatography using 5% MeOH/$CH_2Cl_2$ to afford 1615 (30 mg, 26%) as an off-white solid. TLC: 10% MeOH/$CH_2Cl_2$ ($R_f$: 0.6); 1H NMR (DMSO-$d_6$, 400 MHz): δ 10.71 (m, 1H), 8.69-8.58 (m, 1H), 7.72-7.63 (m, 3H), 7.61-7.41 (m, 4H), 3.55-3.34 (m, 3H), 3.29-3.19 (m, 2H), 3.17-3.13 (m, 0.5H), 3.00 (dd, J=11.8, 7.3 Hz, 0.5H), 2.41-2.34 (m, 1H), 2.02-1.84 (m, 4H), 1.73-1.49 (m, 1H); LC-MS: 95.89%; 396.0 ($M^+$+1); (column; Ascentis Express C18, (50×3.0 mm, 2.7 μm); RT 1.87 min. 0.025% Aq. TFA+5% ACN: ACN+5% 0.025% Aq. TFA, 1.2 mL/min); HPLC (purity): 97.29%; (column; Eclipse XDB C-18 (150×4.6 mm, 5.0 μm); RT 7.05 min. ACN: 5 mM Aq. $NH_4OAc$; 1.0 mL/min).

Example 33: Synthesis of Compound 1654

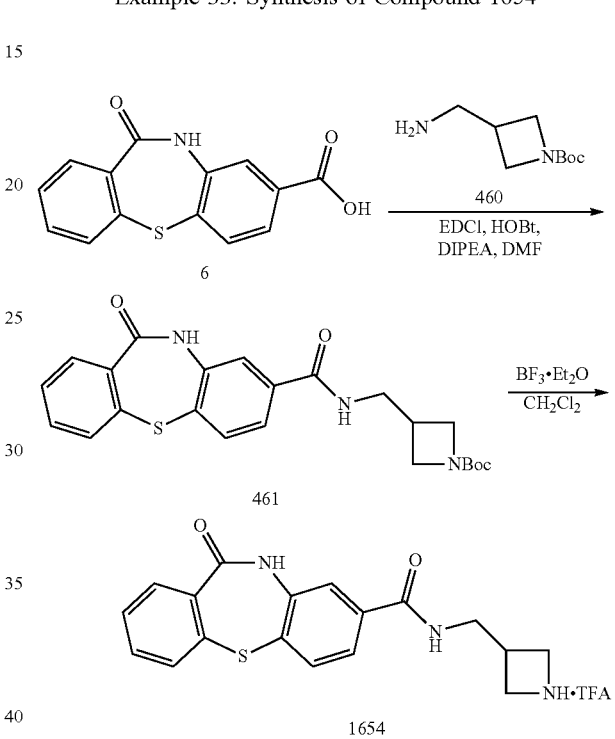

Synthesis of Tert-Butyl 3-((11-oxo-10, 11-dihydrodibenzo [b,f] [1,4] thiazepine-8-carboxamido) methyl) azetidine-1-carboxylate (461)

To a stirred solution of compound 6 (600 mg, 2.21 mmol) in DMF (5 mL) under argon atmosphere were added EDCI·HCl (634 mg, 3.32 mmol), HOBt (435 mg, 3.32 mmol), tert-butyl 3-(aminomethyl) azetidine-1-carboxylate 460 (453 mg, 2.43 mmol) and diisopropyl ethyl amine (1.14 mL, 6.64 mmol) at RT and stirred for 12 h. The reaction was monitored by TLC; after completion of the reaction, the reaction mixture was diluted with water (25 mL) and extracted with EtOAc (2×50 mL). The combined organic extracts were dried over sodium sulfate, filtered and concentrated in vacuo to obtain the crude. The crude was purified through silica gel column chromatography using 5% MeOH/$CH_2Cl_2$ to afford compound 461 (600 mg, 61%) as an off-white solid. TLC: 10% MeOH/$CH_2Cl_2$ ($R_f$: 0.6); 1H NMR (DMSO-$d_6$, 400 MHz): δ 10.76 (s, 1H), 8.64 (t, J=5.6 Hz, 1H), 7.71-7.64 (m, 3H), 7.59-7.43 (m, 4H), 3.84 (t, J=7.0 Hz, 2H), 3.66-3.50 (m, 2H), 3.41 (t, J=6.3 Hz, 2H), 2.72-2.64 (m, 1H), 1.33 (s, 9H).

363

Synthesis of 11-oxo-N-((1-(2, 2, 2-trifluoroacetyl)-114-azetidin-3-yl) methyl)-10, 11-dihydrodibenzo [b,f] [1,4] thiazepine-8-carboxamide (1654)

To a stirred solution of 461 (350 mg, 0.79 mmol) in CH$_2$Cl$_2$ (10 mL) under argon atmosphere were added BF$_3$.Et$_2$O (0.18 mL, 1.59 mmol), molecular sieves (20 mg) at 0° C.; warmed to RT and stirred for 1 h. The reaction was monitored by TLC; after completion of the reaction, the reaction mixture was diluted with water (25 mL) and extracted with CH$_2$Cl$_2$ (2×25 mL). The combined organic extracts were dried over sodium sulfate, filtered and concentrated in vacuo to obtain the crude. The crude was purified using preparative HPLC purification to afford compound 1654 (20 mg, 7%) as an off-white solid. TLC: 10% MeOH/CH$_2$Cl$_2$ (R$_f$: 0.6); 1H NMR (DMSO-d$_6$, 400 MHz): δ 10.79 (s, 1H), 8.70 (t, J=5.6 Hz, 1H), 8.62-8.39 (m, 1H), 7.73-7.66 (m, 3H), 7.59 (dd, J=8.1, 1.7 Hz, 1H), 7.57-7.43 (m, 3H), 3.99-3.88 (m, 2H), 3.80-3.69 (m, 2H), 3.45 (t, J=6.1 Hz, 2H), 3.04-2.94 (m, 1H); LC-MS: 99.41%; 339.9 (M*+ 1); (column; Ascentis Express C18, (50×3.0 mm, 2.7 μm); RT 1.70 min. 0.025% Aq. TFA+5% ACN: ACN+5% 0.025% Aq. TFA, 1.2 mL/min); HPLC (purity): 98.60%; (column; Zorbax SB C-18 (150×4.6 mm, 3.5 μm); RT 6.54 min. ACN: 0.05% TFA (Aq); 1.0 mL/min).

Example 34: Synthesis of Compounds 1601 and 1609

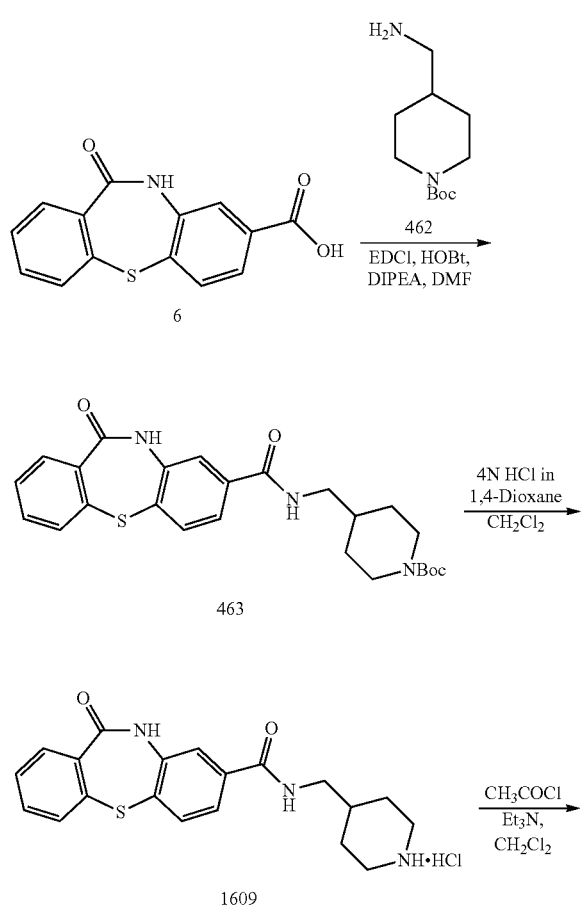

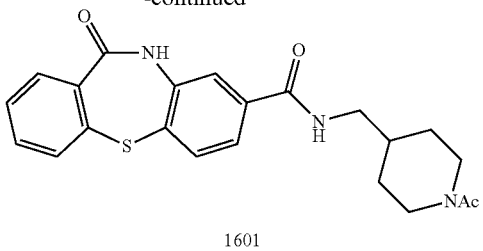

1601

Synthesis of Tert-Butyl 4-((11-oxo-10, 11-dihydrodibenzo [b,f] [1,4] thiazepine-8-carboxamido) methyl) piperidine-1-carboxylate (463)

Using Procedure A the title compound was prepared with compound 6 (200 mg, 0.73 mmol), tert-butyl 4-(aminomethyl) piperidine-1-carboxylate 462 (0.17 mL, 0.81 mmol) and was obtained in 86% yield as pale brown solid; TLC: 5% MeOH/CH$_2$Cl$_2$ (R$_f$: 0.5); $^1$H NMR (DMSO-d$_6$, 400 MHz): δ 10.75 (br s, 1H), 8.52 (t, J=5.6 Hz, 1H), 7.72-7.61 (m, 3H), 7.60-7.42 (m, 4H), 3.93-3.88 (m, 2H), 3.12 (t, J=6.0 Hz, 2H), 2.71-2.59 (m, 2H), 1.74-1.57 (m, 3H), 1.38 (s, 9H), 1.06-0.92 (m, 2H)

Synthesis of 11-oxo-N-(piperidin-4-ylmethyl)-10, 11-dihydrodibenzo [b,f] [1,4] thiazepine-8-carboxamide hydrochloride (1609)

To a stirred solution of compound 463 (300 mg, 0.64 mmol) in CH$_2$Cl$_2$ (5 mL) under argon atmosphere was added 4 N HCl in 1, 4-dioxane (1 mL) at 0° C.; warmed to RT and stirred for 5 h. The reaction was monitored by TLC; after completion of the reaction, the volatiles were removed in vacuo to afford compound 1609 (200 mg, 85%; HCl salt) as pale brown solid. TLC: 5% MeOH/CH$_2$Cl$_2$ (R$_f$: 0.2); $^1$H-NMR (DMSO-d$_6$, 400 MHz): δ 10.77 (s, 1H), 8.67-8.58 (m, 2H), 8.32 (br s, 1H), 7.71-7.64 (m, 3H), 7.61-7.43 (m, 4H), 3.27-3.20 (m, 2H), 3.18-3.12 (m, 2H), 2.89-2.76 (m, 2H), 1.82-1.72 (m, 3H), 1.38-1.23 (m, 2H); LC-MS: 98.23%; 368.0 (M$^+$+1) (—HCl); (column; Ascentis Express C18, (50×3.0 mm, 2.7 μm); RT 1.67 min. 0.025% Aq. TFA+5% ACN: ACN+5% 0.025% Aq. TFA, 1.2 mL/min); UPLC (purity): 97.67%; (column; Acquity UPLC BEH C-18 (50×2.1 mm, 1.7 g); RT 1.59 min. ACN: 0.025% TFA (Aq); 0.5 mL/min).

Synthesis of N-((1-acetylpiperidin-4-yl) methyl)-11-oxo-10, 11-dihydrodibenzo [b,f] [1,4] thiazepine-8-carboxamide (1601)

To a stirred solution of compound 1609 (100 mg, 0.24 mmol) in CH$_2$Cl$_2$ (5 mL) under argon atmosphere were added triethylamine (0.1 mL, 0.74 mmol), acetyl chloride (0.02 mL, 0.29 mmol) at 0° C.; warmed to RT, stirred for 12 h. The reaction was monitored by TLC; after completion the reaction, the reaction the volatiles were removed in vacuo; the residue was basified with saturated NaHCO$_3$ solution and extracted with CH$_2$Cl$_2$ (2×15 mL). The combined organic extracts were dried over sodium sulfate, filtered and concentrated in vacuo to obtain the crude. The crude was purified through silica gel column chromatography using 1% MeOH/CH$_2$Cl$_2$ to afford 1601 (20 mg, 20%) as an off-white solid. TLC: 10% MeOH/CH$_2$Cl$_2$ (R$_f$: 0.5); $^1$H-NMR (DMSO-d$_6$, 400 MHz): δ 10.75 (s, 1H), 8.53 (t, J=5.5 Hz, 1H), 7.71-7.63 (m, 3H), 7.61-7.43 (m, 4H), 4.36-4.29 (m, 1H), 3.81-3.73 (m, 1H), 3.19-3.06 (m, 2H), 3.00-2.91 (m, 1H), 2.53-2.46 (m, 1H), 1.96 (s, 3H), 1.82-1.58 (m, 3H), 1.14-0.89 (m, 2H); LC-MS: 99.33%; 410.0 (M⁺+1); (column; Ascentis Express C18, (50×3.0 mm, 2.7 μm); RT 1.99 min. 0.025% Aq. TFA+5% ACN: ACN+5% 0.025% Aq. TFA, 1.2 mL/min); UPLC (purity): 99.57%; (column; Acquity UPLC BEH C-18 (50×2.1 mm, 1.7 g); RT 1.79 min. ACN: 0.025% TFA (Aq); 0.5 mL/min).

Example 35: Synthesis of Compounds 1357, 1655, and 1367

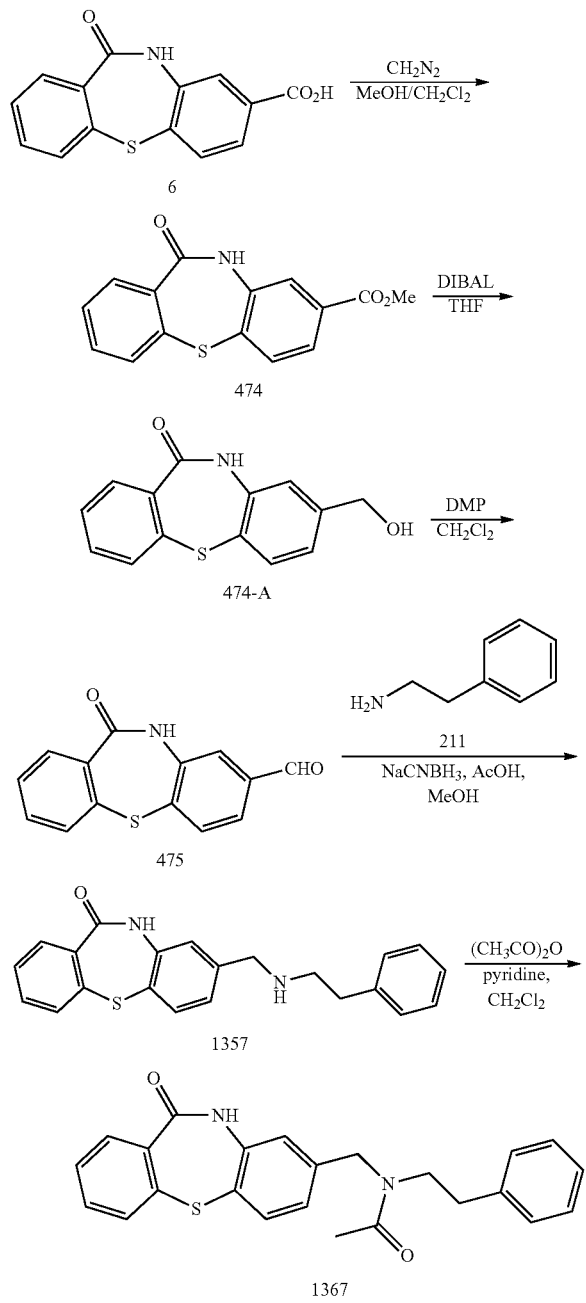

Synthesis of Methyl 11-oxo-10, 11-dihydrodibenzo [b,f] [1,4] thiazepine-8-carboxylate (474)

To a stirred solution of compound 6 (500 mg, 1.84 mmol) in MeOH: $CH_2Cl_2$ (1:1, 20 mL) under argon atmosphere was added $CH_2N_2$ (insitu prepared using N-nitrosomethyl urea (0.95 g, 9.2 mmol)+KOH (0.51 g, 9.22 mmol)) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 474 (450 mg, 86%) as white solid. TLC: 30% EtOAc/hexanes ($R_f$: 0.5); $^1$H-NMR (DMSO-$d_6$, 500 MHz): δ 10.82 (s, 1H), 7.82 (s, 1H), 7.75-7.69 (m, 3H), 7.58-7.63 (m, 3H), 3.82 (s, 3H).

Synthesis of 8-(hydroxymethyl) dibenzo [b,f] [1,4] thiazepin-11(10H)-one (474-A)

To a stirred solution of compound 474 (500 mg, 1.75 mmol) in dry THF (3 mL) under argon atmosphere was added diisobutylaluminium hydride (1 M sol. in Toluene, 5 mL, 5.26 mmol) dropwise for 5 min at −25° C.; warmed to RT and stirred for 3 h. The reaction was monitored by TLC; after completion of the reaction, the reaction mixture was cooled to 0° C., quenched with saturated sodium potassium tartrate solution (10 mL) and extracted with EtOAc (2×20 mL). The combined organic extracts were dried over sodium sulfate, filtered and concentrated in vacuo to obtain the crude, which was titurated with MeOH: diethyl ether (1:4, 5 mL) to afford 474-A (300 mg, 66%) as an off-white solid. TLC: 70% EtOAc/hexanes ($R_f$: 0.4); $^1$H NMR (DMSO-$d_6$, 400 MHz): δ 10.66 (s, 1H), 7.67 (dd, J=7.5, 1.6 Hz, 1H), 7.55-7.38 (m, 4H), 7.19 (s, 1H), 7.07 (dd, J=7.9, 1.7 Hz, 1H), 5.26 (t, J=5.7 Hz, 1H), 4.44 (d, J=5.6 Hz, 2H); LC-MS: 97.26%; 257.8 (M⁺+1); (column; Ascentis Express C18, (50×3.0 mm, 2.7 μm); RT 1.94 min. 0.025% Aq. TFA+5% ACN: ACN+; 5% 0.025% Aq. TFA, 1.2 mL/min); UPLC (purity): 96.65%; (column; Acquity BEH C-18 (50×2.1 mm, 1.7μ); RT 1.80 min. ACN: 0.025% TFA (Aq); 0.5 mL/min).

Synthesis of 11-oxo-10, 11-dihydrodibenzo [b,f] [1,4] thiazepine-8-carbaldehyde (475)

To a stirred solution of compound 474-A (60 mg, 0.23 mmol) in $CH_2Cl_2$ (5 mL) under argon atmosphere was added Dess-Martin periodinane (300 mg, 0.70 mmol) at 0° C.; warmed to RT and stirred for 2 h. The reaction was monitored by TLC; after completion of the reaction, the reaction mixture was diluted with $CH_2Cl_2$ (50 mL) and washed with saturated hypo solution (20 mL). The organic extract was dried over sodium sulfate, filtered and concentrated in vacuo to obtain the crude. The crude was purified using silicagel column chromatography using 30% EtOAc/hexanes to afford compound 475 (41 mg, 68%) as an off-white solid. TLC: 70% EtOAc/hexanes ($R_f$: 0.8); $^1$H NMR (DMSO-$d_6$, 400 MHz): δ 10.89 (s, 1H), 9.96 (s, 1H), 7.81 (d, J=7.6 Hz, 1H), 7.73-7.66 (m, 3H), 7.59-7.45 (m, 3H).

Synthesis of 8-((phenethylamino) methyl) dibenzo [b,f] [1,4] thiazepin-11(10H)-one (1357)

To a stirred solution of compound 475 (100 mg, 0.39 mmol) in MeOH (4 mL) under argon atmosphere were added 2-phenylethan-1-amine 211 (57 mg, 0.47 mmol) and acetic acid (1 mL) at RT and stirred for 1 h. To this was added sodium cyanoborohydride (72 mg, 1.16 mmol) at 0°

C.; warmed to RT and stirred for 16 h. The reaction was monitored by TLC; after completion of the reaction, the volatiles were removed in vacuo. The residue was diluted with water with EtOAc (100 mL), washed with saturated sodium bicarbonate solution (20 mL) and water (20 mL). The organic extract was dried over sodium sulfate, filtered and concentrated in vacuo to obtain the crude. The crude was purified using silicagel column chromatography using 2% MeOH/CH$_2$Cl$_2$ to afford compound 1357 (25 mg, 18%) as an off-white solid. TLC: 100% EtOAc (R$_f$: 0.3); $^1$H NMR (DMSO-d$_6$, 400 MHz): δ 10.65 (s, 1H), 7.67 (dd, J=7.4, 1.6 Hz, 1H), 7.54-7.39 (m, 4H), 7.28-7.23 (m, 2H), 7.21-7.14 (m, 4H), 7.10 (d, J=7.2 Hz, 1H), 3.70 (br s, 2H), 2.72 (br s, 4H); LC-MS: 95.70%; 361.0 (M$^+$+1); (column; X-select CSH C18, (50×3.0 mm, 3.5 μm); RT 2.65 min. 0.05% Aq. TFA: ACN; 0.8 mL/min); UPLC (purity): 95.01%; (column; Acquity BEH C-18 (50×2.1 mm, 1.7μ); RT 1.87 min. ACN: 0.025% TFA (Aq); 0.5 mL/min).

Synthesis of N-((11-oxo-10, 11-dihydrodibenzo [b,f] [1,4] thiazepin-8-yl) methyl)-N-phenethyl acetamide (1367)

To a stirred solution of compound 1357 (40 mg, 0.11 mmol) in CH$_2$Cl$_2$ (2 mL) under argon atmosphere were added pyridine (0.013 mL, 0.16 mmol), acetic anhydride (0.011 mL, 0.12 mmol) at 0-5° C.; warmed to RT and stirred for 2 h. The reaction was monitored by TLC; after completion the reaction, the reaction mixture was diluted with CH$_2$Cl$_2$ (20 mL) washed with 1 N HCl (5 mL) and brine (10 mL). The organic extract was dried over sodium sulfate, filtered and concentrated in vacuo to obtain the crude. The crude was purified through silica gel column chromatography using 5% EtOAc/hexanes to afford 1367 (25 mg, 57%) as an off-white solid. TLC: 70% EtOAc/hexanes (R$_f$: 0.8); $^1$H NMR (DMSO-d$_6$, 500 MHz): δ 10.62-10.60 (m, 1H), 7.67-7.64 (m, 1H), 7.57-7.38 (m, 4H), 7.29-6.94 (m, 7H), 4.45 (d, J=9.8 Hz, 2H), 3.41-3.35 (m, 2H), 2.82-2.66 (m, 2H), 1.97-1.87 (m, 3H); LC-MS: 92.67%; 403.5 (M$^+$+1); (column; X-select CSH C18, (50×3.0 mm, 3.5 μm); RT 4.37 min. 5 mM Aq.NH$_4$OAc: ACN; 0.8 mL/min); UPLC (purity): 93.63%; (column; Acquity BEH C-18 (50×2.1 mm, 1.7μ); RT 2.41 min. ACN: 0.025% TFA (Aq); 0.5 mL/min).

Example 36: Synthesis of Compound 1501

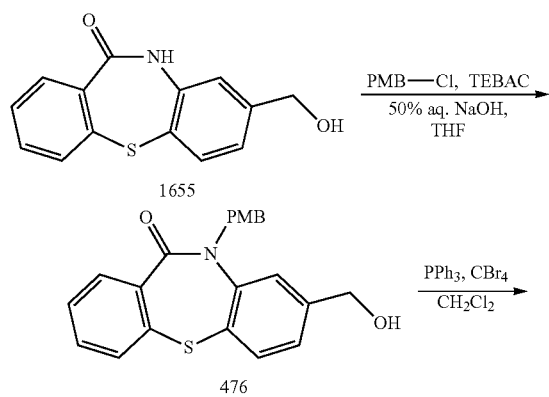

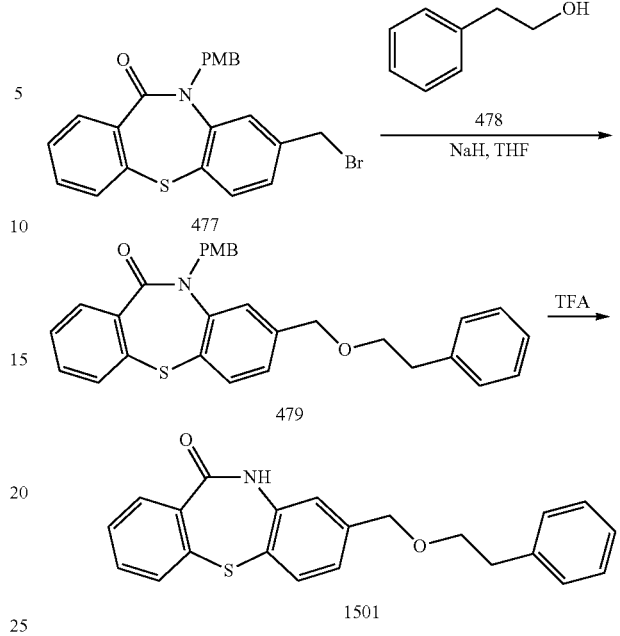

Synthesis of 8-(hydroxymethyl)-10-(4-methoxybenzyl) dibenzo [b,f] [1,4] thiazepin-11(10H)-one (476)

To a stirred solution of 1655 (1 g, 3.89 mmol) in THF (50 mL) were added Benzyltriethylammonium chloride (88 mg, 0.38 mmol), 50% aqueous sodium hydroxide solution (4 mL) at 0-5° C. and stirred for 20 min. To this was added 4-methoxybenzy chloride (0.52 mL, 3.89 mmol) at 0-5° C. and heated to reflux for 16 h. The reaction was monitored by TLC; after completion of the reaction, the reaction mixture was diluted with ice water (40 mL) and extracted with EtOAc (2×100 mL). The combined organic extracts was dried over sodium sulfate, filtered and concentrated in vacuo to obtain the crude. The crude was purified using silicagel column chromatography using 2% MeOH/CH$_2$Cl$_2$ to afford compound 476 (800 mg, 57%) as white solid. TLC: 5% MeOH/CH$_2$Cl$_2$ (R$_f$: 0.6); $^1$H NMR (DMSO-d$_6$, 500 MHz): δ 7.64-7.59 (m, 1H), 7.53 (s, 1H), 7.51-7.44 (m, 2H), 7.41-7.35 (m, 2H), 7.22 (d, J=8.7 Hz, 2H), 7.06 (d, J=7.8 Hz, 1H), 6.81 (d, J=8.7 Hz, 2H), 5.67 (d, J=15.3 Hz, 1H), 5.21 (br s, 1H), 4.85 (d, J=15.3 Hz, 1H), 4.41 (s, 2H), 3.68 (s, 3H).

Synthesis of 8-(bromomethyl)-10-(4-methoxybenzyl) dibenzo [b,f] [1,4] thiazepin-11(10H)-one (477)

To a stirred solution of compound 476 (800 mg, 2.12 mmol) in CH$_2$Cl$_2$ (20 mL) under argon atmosphere were added triphenyl phosphine (1.1 g, 4.24 mmol), CBr$_4$ (0.3 mL, 3.18 mmol) at 0° C.; warmed to RT and stirred for 2 h. The reaction was monitored by TLC; after completion of the reaction, the volatiles were removed in vacuo to obtain the crude. The crude was purified through silica gel column chromatography using 50% EtOAc/hexanes to afford compound 477 (600 mg, 66%) as an off-white solid. TLC: 5% MeOH/CH$_2$Cl$_2$ (R$_f$: 0.8); 1H NMR (DMSO-d$_6$, 500 MHz): δ 7.73 (s, 1H), 7.63 (dd, J=7.1, 1.9 Hz, 1H), 7.53-7.44 (m, 2H), 7.43-7.36 (m, 2H), 7.22-7.15 (m, 3H), 6.79 (d, J=8.7 Hz, 2H), 5.77-5.71 (m, 1H), 4.80 (d, J=15.0 Hz, 1H), 4.60 (s, 2H), 3.67 (s, 3H).

Synthesis of 10-(4-methoxybenzyl)-8-(phenethoxymethyl)dibenzo [b,f] [1,4] thiazepin-11 (10H)-one (479)

To a stirred solution of 2-phenylethan-1-ol 477 (100 mg, 0.81 mmol) in THF (10 mL) inert atmosphere was added was added sodium hydride (60%, 49 mg, 2.5 mmol) under portion wise for 5 min at 0° C.; warmed to RT and stirred for 2 h. To this was added compound 478 (359 mg, 0.81 mmol) at RT; heated to 65° C. and stirred for 16 h. The reaction was monitored by TLC; after completion of the reaction, the reaction mixture was diluted with ice-cold water (20 mL) and extracted with EtOAc (2×50 mL). The combined organic extracts were dried over sodium sulfate, filtered and concentrated in vacuo to obtain the crude compound 479 (150 mg) as yellow solid. TLC: 70% EtOAc/hexanes ($R_f$: 0.5); LC-MS: 58.75%; 482.0 ($M^+$+1); (column; Ascentis Express C18, (50×3.0 mm, 2.7 μm); RT 3.25 min. 0.025% Aq. TFA+5% ACN: ACN+; 5% 0.025% Aq. TFA, 1.2 mL/min).

Synthesis of 8-(phenethoxymethyl) dibenzo [b,f] [1,4] thiazepin-11(10H)-one (1501)

A mixture of compound 479 (140 mg, crude) and trifluoro acetic acid (2 mL) under inert atmosphere at RT was heated to 80° C. and stirred for 6 h in a sealed tube. The reaction was monitored by TLC; after completion of the reaction, the volatiles were removed in vacuo, the residue was quenched with 20% aqueous sodium bicarbonate solution (10 mL) and extracted with EtOAc (2×20 mL). The combined organic extracts was dried over sodium sulfate, filtered and concentrated in vacuo to obtain the crude. The crude was purified using silicagel column chromatography using 70% EtOAc/hexanes to afford compound 1501 (35 mg, 33%) as white solid. TLC: 70% EtOAc/hexanes ($R_f$: 0.4); $^1$H NMR (DMSO-$d_6$, 400 MHz): δ 10.65 (s, 1H), 7.67 (dd, J=7.5, 1.6 Hz, 1H), 7.54-7.40 (m, 4H), 7.29-7.13 (m, 6H), 7.04 (dd, J=7.9, 1.7 Hz, 1H), 4.44 (s, 2H), 3.63 (t, J=6.9 Hz, 2H), 2.84 (t, J=6.9 Hz, 2H); LC-MS: 96.49%; 361.9 ($M^+$+1); (column; Ascentis Express C18, (50×3.0 mm, 2.7 μm); RT 2.79 min. 0.025% Aq. TFA+5% ACN: ACN+; 5% 0.025% Aq. TFA, 1.2 mL/min); HPLC (purity): 96.59%; (column; Eclipse XDB-C-18 (150×4.6 mm, 5.0 μm); RT 10.25 min. ACN: 0.025% TFA (Aq); 1.0 mL/min).

Example 37: Synthesis of 10-methyl-11-oxo-10, 11-dihydrodibenzo [b,f] [1,4] thiazepine-8-carboxylic acid (486)—a Common Intermediate

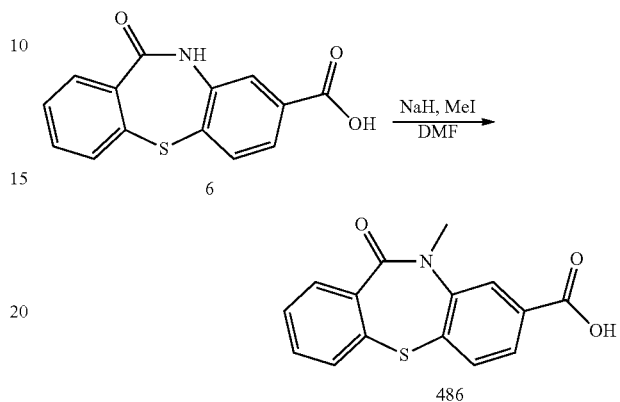

To a stirred solution of compound 6 (500 mg, 1.84 mmol) in DMF (10 mL) was added sodium hydride (60%, 442 mg, 18.45 mmol) under inert atmosphere at 0° C. and stirred for 1 h. To this was methyl iodide (1.14 mL, 18.45 mmol) at 0-5° C., warmed to RT and stirred for 1.5 h. The reaction was monitored by TLC; after completion of the reaction, the reaction mixture was diluted with water (20 mL) and washed with EtOAc (2×20 mL). The aqueous layer was separated and the pH was adjusted to ~2 with 4 N HCl. The precipitated solid was filtered, washed with n-hexane (10 mL) and dried in vacuo to obtain the compound 486 (400 mg, 76%) a white solid. TLC: 10% MeOH/$CH_2Cl_2$ ($R_f$: 0.2); $^1$H-NMR (DMSO-$d_6$, 500 MHz): δ 13.31 (br s, 1H), 7.99 (s, 1H), 7.75-7.68 (m, 2H), 7.65-7.61 (m, 1H), 7.54-7.49 (m, 1H), 7.44-7.39 (m, 2H), 3.53 (s, 3H).

Example 38: Synthesis of Compounds from Compound 486 and Various Commercially Available Amines Compound 486 was converted to final products using commercially available amines or by employing Procedure A and the results are captured in the Table 2:

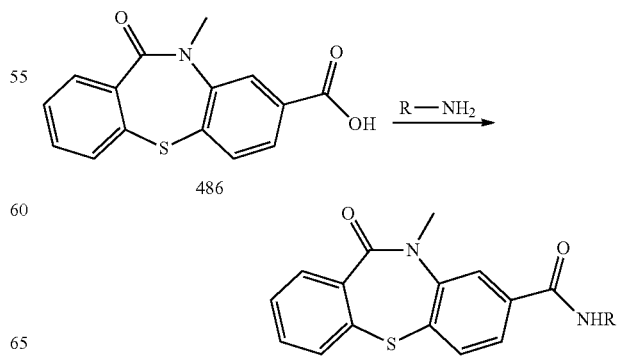

TABLE 2

Synthesis of compounds from compound 486 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| 1573 | 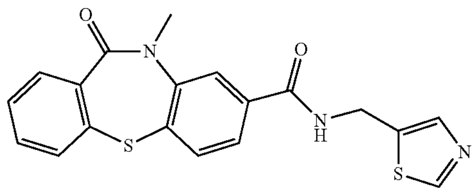 [SMILES: CN1C(=O)c2ccccc2Sc2ccc(C(=O)NCc3cncs3)cc21] | A, 486, 213 | 36 | 382.0 (M$^+$ + 1) | 381.06 for $C_{19}H_{15}N_3O_2S_2$ | $^1$H-NMR (DMSO-d$_6$, 400 MHz): δ 9.27 (t, J = 5.7 Hz, 1H), 8.96 (s, 1H), 7.96 (s, 1H), 7.82 (s, 1H), 7.74-7.70 (m, 1H), 7.68-7.61 (m, 2H), 7.54-7.49 (m, 1H), 7.45-7.38 (m, 2H), 4.67 (t, J = 5.4 Hz, 2H), 3.54 (s, 3H); |
| 1553 | 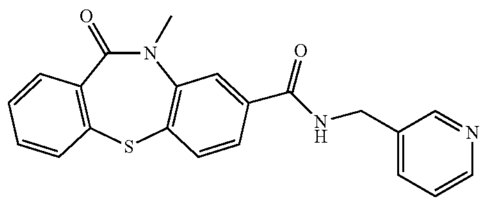 [SMILES: CN1C(=O)c2ccccc2Sc2ccc(C(=O)NCc3cccnc3)cc21] | A, 486, 218 | 30 | 376.1 (M$^+$ + 1) | 375.10 for $C_{21}H_{17}N_3O_2S$ | $^1$H-NMR (DMSO-d$_6$, 400 MHz): δ 9.16 (t, J = 5.7 Hz, 1H), 8.54 (s, 1H), 8.45 (dd, J = 4.6, 1.3 Hz, 1H), 7.98 (s, 1H), 7.75-7.61 (m, 4H), 7.55-7.49 (m, 1H), 7.46-7.38 (m, 2H), 7.33 (dd, J = 7.3, 4.8 Hz, 1H), 4.55-4.41 (m, 2H), 3.55 (s, 3H); |
| 1574 | 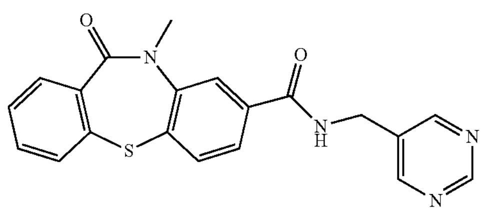 [SMILES: CN1C(=O)c2ccccc2Sc2ccc(C(=O)NCc3cncnc3)cc21] | A, 486, 212 | 36 | 376.9 (M$^+$ + 1); | 376.10 for $C_{20}H_{16}N_4O_2S$ | $^1$H-NMR (DMSO-d$_6$, 400 MHz): δ 9.19 (t, J = 5.7 Hz, 1H), 9.08 (s, 1H), 8.76 (s, 2H), 7.98 (s, 1H), 7.73 (d, J = 8.4 Hz, 1H), 7.68-7.60 (m, 2H), 7.55-7.49 (m, 1H), 7.46-7.38 (m, 2H), 4.57-4.39 (m, 2H), 3.55 (s, 3H); |
| 1133 | 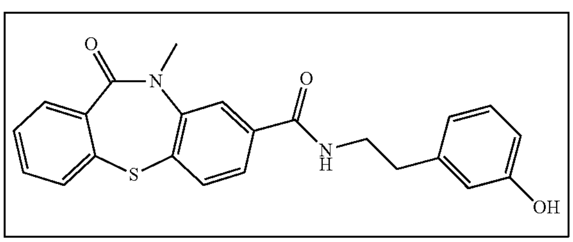 [SMILES: CN1C(=O)c2ccccc2Sc2ccc(C(=O)NCCc3cccc(O)c3)cc21] | D, 486 | 70 | 405.1272 | 405.1273 for $C_{23}H_{21}N_2O_3S$ | $^1$H NMR (400 MHz, DMSO-d$_6$) δ 9.25 (s, 1H), 8.63 (t, J = 5.6 Hz, 1H), 7.88 (d, J = 1.8 Hz, 1H), 7.73-7.56 (m, 3H), 7.55-7.47 (m, 1H), 7.47-7.36 (m, 2H), 7.05 (t, J = 7.7 Hz, 1H), 6.60 (td, J = 9.2, 7.1 Hz, 3H), 3.53 (s, 3H), 3.46-3.38 (m, 2H), 2.71 (t, J = 7.4 Hz, 2H). |

Example 39: Synthesis of Compounds 1342 and 1361

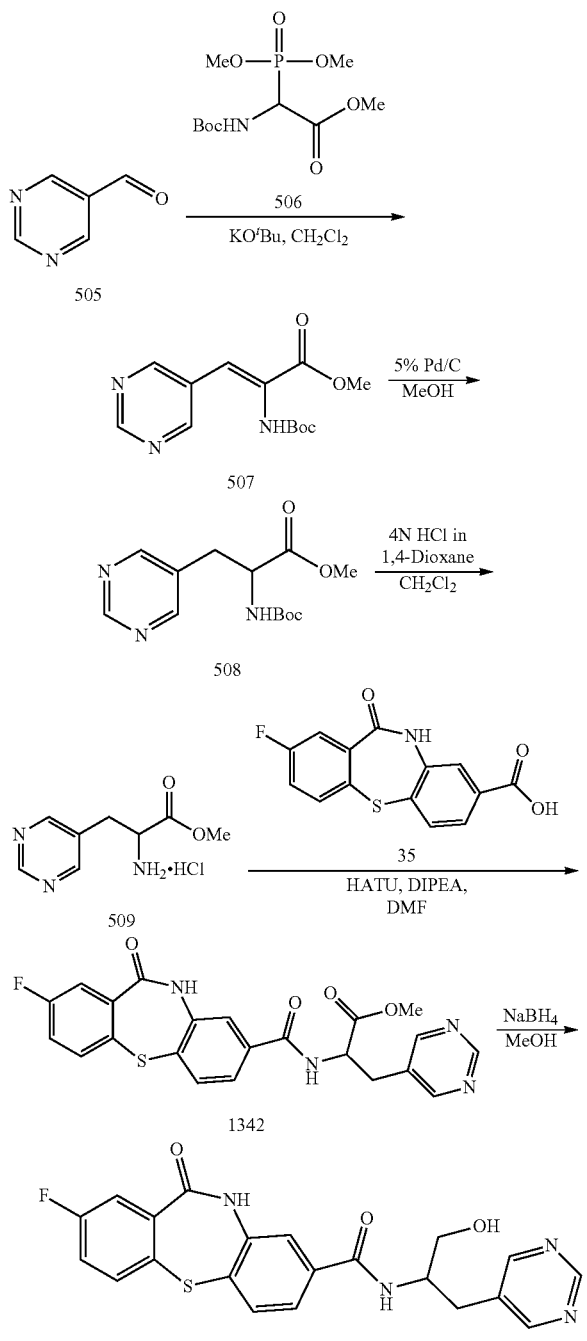

Synthesis of Methyl (Z)-2-((tert-butoxycarbonyl) amino)-3-(pyrimidin-5-yl) acrylate (507)

To a stirred solution of methyl 2-((tert-butoxycarbonyl) amino)-2-(dimethoxyphosphoryl) acetate 506 (3.3 g, 11.11 mmol) in CH$_2$Cl$_2$ (15 mL) under inert atmosphere was added potassium t-butoxide (13.8 mL, 13.88 mmol, 1M solution in THF), portion wise for 15 min at −30° C. To this was added pyrimidine-5-carbaldehyde 505 (1 g, 9.25 mmol) in CH$_2$Cl$_2$ (5 mL) drop wise for 10 min at −30° C., stirred for 2 h; warmed to 0° C. and stirred for 2 h. The reaction was monitored by TLC; after completion of the reaction, the reaction mixture was diluted with water (50 mL) and extracted with CH$_2$Cl$_2$ (2×100 mL). The combined organic extracts were washed with water (100 mL), dried over sodium sulfate, filtered and concentrated in vacuo to obtain the crude. The crude was purified through silica gel column chromatography using 50% EtOAc/hexanes to afford compound 507 (1.8 g, 72%) as an off-white solid. TLC: 70% EtOAc/hexanes (R$_f$: 0.8); 1H NMR (500 MHz, DMSO-d$_6$): δ 9.11 (s, 1H), 9.02 (brs, 1H), 8.98 (s, 2H), 6.46 (s, 1H), 3.76 (s, 3H), 1.42-1.38 (m, 9H).

Synthesis of Methyl 2-((tert-butoxycarbonyl) amino)-3-(pyrimidin-5-yl) propanoate (508)

To a stirred solution of compound 507 (1.8 g, 6.45 mmol) in MeOH (25 mL) under inert atmosphere was added 5% Pd/C (500 mg) at RT and stirred under hydrogen atmosphere (at 100 psi) for 16 h in a steel bomb. The reaction was monitored by TLC; after completion of the reaction, the reaction mixture was filtered through celite and washed with 10% MeOH/CH$_2$Cl$_2$ (2×50 mL). The filtrate was concentrated in vacuo to obtain the crude compound 508 (1.3 g, 72%) as colorless syrup. TLC: 5% MeOH/CH$_2$Cl$_2$ (R$_f$: 0.5); $^1$H NMR (DMSO-d$_6$, 500 MHz): δ 9.03 (s, 1H), 8.68 (s, 2H), 7.40 (d, J=7.8 Hz, 1H), 4.33-4.25 (m, 1H), 3.65 (s, 3H), 3.09 (dd, J=14.4, 4.4 Hz, 1H), 2.89-2.81 (m, 1H), 1.33-1.22 (m, 9H).

Synthesis of Methyl 2-amino-3-(pyrimidin-5-yl) propanoate hydrochloride (509)

To a stirred solution of compound 508 (1.3 g, 4.62 mmol) in CH$_2$Cl$_2$ (5 mL) under argon atmosphere was added 4 N HCl in 1, 4-dioxane (5 mL) at 0° C.; warmed to RT and stirred for 3.5 h. The reaction was monitored by TLC; after completion of the reaction, the volatiles were removed in vacuo to afford compound 509 (850 mg) as an off-white solid. TLC: 5% MeOH/CH$_2$Cl$_2$ (R$_f$: 0.2); $^1$H NMR (DMSO-d$_6$, 400 MHz): δ 9.15-9.08 (m, 1H), 8.75 (s, 4H), 4.45-4.44 (m, 1H), 3.73 (s, 3H), 3.22 (dd, J=6.6, 2.4 Hz, 2H).

Synthesis of Methyl 2-(2-fluoro-11-oxo-10, 11-dihydrodibenzo [b,f] [1,4] thiazepine-8-carboxamido)-3-(pyrimidin-5-yl) propanoate (1342)

Using Procedure B the title compound was prepared with compound 35 (200 mg, 0.69 mmol), compound 509 (165 mg, 0.76 mmol) and was obtained in 67% yield as an off-white solid; TLC: 5% MeOH/CH$_2$Cl$_2$ (R$_f$: 0.5); 1H NMR (DMSO-d$_6$, 500 MHz): δ 10.89 (s, 1H), 8.99 (t, J=4.0 Hz, 2H), 8.69 (s, 2H), 7.66 (d, J=8.1 Hz, 1H), 7.61-7.56 (m, 2H), 7.52 (dd, J=8.1, 1.4 Hz, 1H), 7.46 (dd, J=9.1, 2.7 Hz, 1H), 7.36 (td, J=8.4, 2.9 Hz, 1H), 4.81-4.70 (m, 1H), 3.64 (s, 3H), 3.22 (dd, J=14.2, 4.9 Hz, 1H), 3.05 (dd, J=14.0, 10.6 Hz, 1H); LC-MS: 98.59%; 453.4 (M$^+$+1); (column; X-select CSH C18, (50×3.0 mm, 3.5 μm); RT 3.45 min. 0.05% Aq. TFA: ACN; 0.8 mL/min); UPLC (purity): 99.40%; (column; Acquity BEH C-18 (50×2.1 mm, 1.7μ); RT 1.89 min. ACN: 0.025% TFA (Aq); 0.5 mL/min).

Synthesis of 2-fluoro-N-(1-hydroxy-3-(pyrimidin-5-yl) propan-2-yl)-11-oxo-10, 11-dihydrodibenzo [b,f] [1,4] thiazepine-8-carboxamide (1361)

To a stirred solution of 1342 (200 mg, 0.44 mmol) in MeOH (5 mL) under inert atmosphere was added sodium borohydride (65 mg, 1.76 mmol) at 0° C.; warmed to RT and stirred for 6 h. The reaction was monitored by TLC; after completion of the reaction, the reaction mixture was quenched with ice cold water (25 mL) and extracted with 5% MeOH/CH$_2$Cl$_2$ (5×25 mL). The combined organic extracts were dried over sodium sulfate, filtered and concentrated in vacuo to obtain the crude. The crude was purified through silica gel column chromatography using 8% MeOH/CH$_2$Cl$_2$ to afford compound 1361 (140 mg, 75%) as an off-white solid. TLC: 10% MeOH/CH$_2$Cl$_2$ (R$_f$: 0.4); $^1$H NMR (DMSO-d$_6$, 400 MHz): δ 10.87 (s, 1H), 8.96 (s, 1H), 8.64 (s, 2H), 8.30 (d, J=8.7 Hz, 1H), 7.66-7.63 (m, 1H), 7.61-7.57 (m, 2H), 7.53 (dd, J=8.1, 1.8 Hz, 1H), 7.47 (dd, J=9.2, 2.9 Hz, 1H), 7.37 (td, J=8.5, 3.0 Hz, 1H), 4.93 (t, J=5.6 Hz, 1H), 4.22-4.11 (m, 1H), 3.53-3.40 (m, 2H), 2.98 (dd, J=13.9, 4.2 Hz, 1H), 2.73 (dd, J=14.0, 10.1 Hz, 1H); LC-MS: 99.82%; 425.4 (M$^+$+1); (column; X-select CSH C18, (50×3.0 mm, 3.5 µm); RT 3.68 min. 0.05% Aq. TFA: ACN; 0.8 mL/min); UPLC (purity): 99.77%; (column; Acquity BEH C-18 (50× 2.1 mm, 1.7 g); RT 1.65 min. ACN: 0.025% TFA (Aq.); 0.5 mL/min).

Example 40: Synthesis of Compound 1346

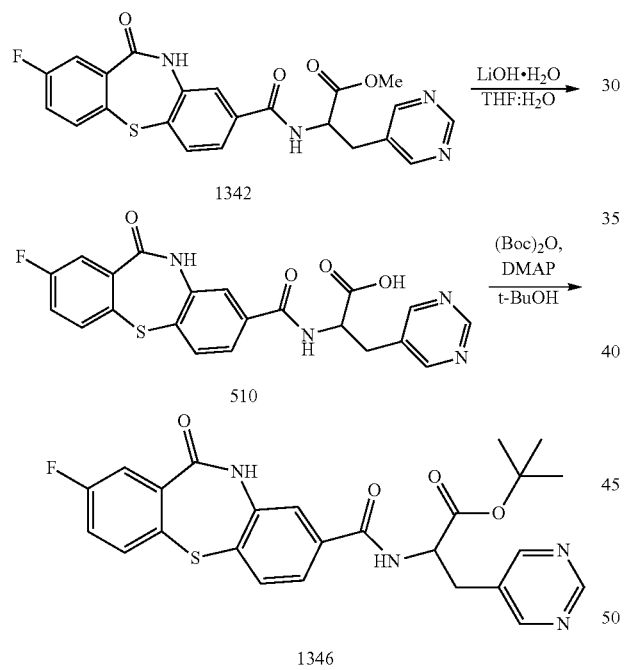

Synthesis of 2-(2-fluoro-11-oxo-10, 11-dihydrodibenzo [b,f] [1,4] thiazepine-8-carboxamido)-3-(pyrimidin-5-yl) propanoic acid (510)

To a stirred solution of compound 1342 (150 mg, 0.33 mmol) in a mixture of THF:H$_2$O (4:1, 5 mL) was added lithium hydroxide monohydrate (35 mg, 0.82 mmol) at RT and stirred for 16 h. The reaction was monitored by TLC; after completion of the reaction, the volatiles were removed in vacuo. The residue was diluted with water (3 mL) and the pH was adjusted to ~5 with 1 N HCl. The precipitated solid was filtered and dried in vacuo to afford compound 510 (75 mg, 52%) as white solid. TLC: 10% MeOH/CH$_2$Cl$_2$ (R$_f$: 0.2); 1H NMR (DMSO d$_6$, 400 MHz): δ 10.90 (s, 1H), 8.98 (s, 1H), 8.78 (d, J=7.6 Hz, 1H), 8.68 (s, 2H), 7.66 (d, J=8.0 Hz, 1H), 7.62-7.57 (m, 2H), 7.53 (dd, J=8.1, 1.7 Hz, 1H), 7.47 (dd, J=9.2, 2.9 Hz, 1H), 7.37 (dt, J=8.5, 2.9 Hz, 1H), 7.40-7.34 (m, 1H), 4.69-4.58 (m, 1H), 3.23 (dd, J=14.1, 4.6 Hz, 1H), 3.03 (dd, J=14.0, 10.3 Hz, 1H).

Synthesis of Tert-Butyl 2-(2-fluoro-11-oxo-10, 11-dihydrodibenzo [b,f] [1,4] thiazepine-8-carboxamido)-3-(pyrimidin-5-yl) propanoate (1346)

To a stirred solution of compound 510 (70 mg, 0.15 mmol) in t-butanol (4 mL) under inert atmosphere were added Boc-anhydride (0.11 mL, 0.47 mmol) and DMAP (30 mg, 0.03 mmol) at 5° C.; warmed to RT and stirred for 16 h. The reaction was monitored by TLC; after completion of the reaction, the reaction mixture was diluted with water (10 mL) and extracted with CH$_2$Cl$_2$ (2×25 mL). The combined organic extracts were dried over sodium sulfate, filtered and concentrated in vacuo to obtain the crude. The crude was purified through preparative TLC (50% EtOAc/hexanes) to afford 1346 (25 mg, 32%) as an off-white solid. TLC: 70% EtOAc/hexanes (R$_f$: 0.4); $^1$H NMR (DMSO-d$_6$, 400 MHz): δ 10.91 (s, 1H), 9.01 (s, 1H), 8.89 (d, J=7.8 Hz, 1H), 8.71 (s, 2H), 7.67 (d, J=8.0 Hz, 1H), 7.64-7.58 (m, 2H), 7.55 (dd, J=8.0, 1.9 Hz, 1H), 7.48 (dd, J=9.2, 2.9 Hz, 1H), 7.38 (td, J=8.5, 2.9 Hz, 1H), 4.65-4.59 (m, 1H), 3.21-3.13 (m, 1H), 3.09-2.99 (m, 1H), 1.39-1.31 (m, 9H); LC-MS: 98.60%; 495.6 (M$^+$+1); (column; X-select CSH C18, (50×3.0 mm, 3.5 µm); RT 3.91 min. 0.05% Aq. TFA: CAN; 0.8 mL/min); UPLC (purity): 98.29%; (column; Acquity BEH C-18 (50× 2.1 mm, 1.7µ); RT 2.15 min. CAN: 0.025% TFA (Aq); 0.5 mL/min).

Example 41: Synthesis of Compounds 1420 and 1419

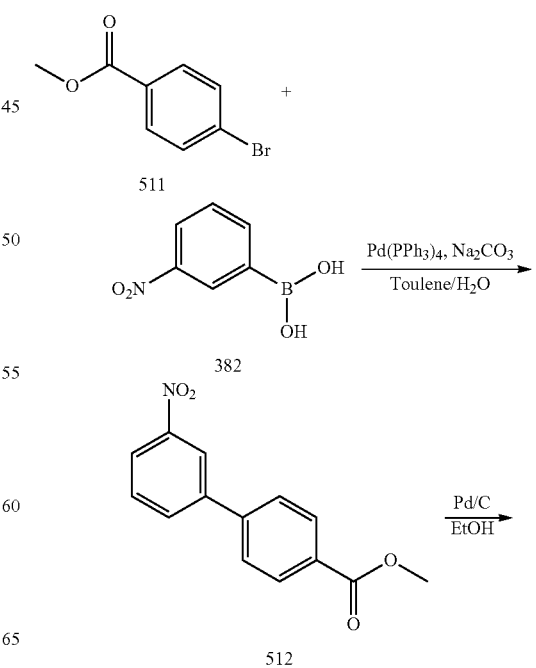

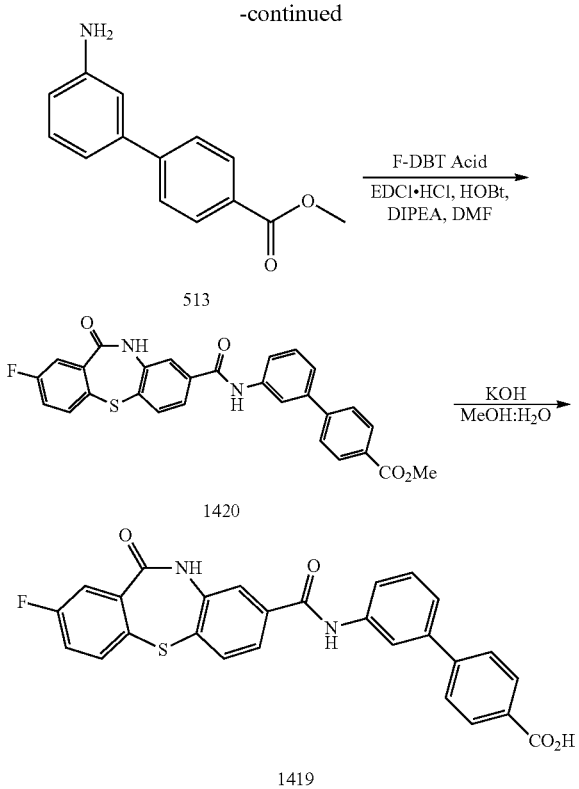

Synthesis of Methyl 3'-nitro-[1,1'-biphenyl]-4-carboxylate (512)

To a stirred solution of methyl 4-bromobenzoate 511 (2.5 g, 14.97 mmol) and (3-nitrophenyl) boronic acid 382 (3.8 g, 17.96 mmol) in Toluene (20 mL) under inert atmosphere were added sodium carbonate (3.17 g, 29.96 mmol in 25 mL of $H_2O$) at RT and purged under argon atmosphere for 20 min. To this was added $Pd(PPh_3)_4$ (691 mg, 0.59 mmol) and heated to 80° C. for 5 h. The reaction was monitored by TLC; after completion of the reaction, the reaction mixture was diluted with EtOAc (200 mL). The organic extract was dried over sodium sulfate, filtered and concentrated in vacuo to obtain the crude. The crude was purified through silica gel column chromatography using 10% EtOAc/hexanes to afford compound 512 (800 mg, 21%) as yellow liquid. TLC: 15% EtOAc/hexanes ($R_f$: 0.5); $^1H$ NMR (400 MHz, $CD_3OD$): δ 8.54-8.52 (m, 1H), 8.29-8.26 (m, 1H), 8.15 (d, J=8.7 Hz, 2H), 8.12-8.09 (m, 1H), 7.84 (d, J=8.6 Hz, 2H), 7.74 (t, J=8.0 Hz, 1H), 3.94 (s, 3H).

Synthesis of Methyl 3'-amino-[1, 1'-biphenyl]-4-carboxylate (513)

To a stirred solution of compound 512 (800 mg, 3.11 mmol) in EtOH (50 mL) under inert atmosphere was added 10% Pd/C (500 mg, wet) under argon atmosphere and stirred under $H_2$ atmosphere (balloon pressure) for 5 h. After completion of the reaction, the reaction mixture was filtered through celite, washed with 50% $MeOH/CH_2Cl_2$ (150 mL). The filtrate was concentrated in vacuo to obtain the crude which was purified through silicagel column chromatography in 5% $MeOH/CH_2Cl_2$ to afford compound 513 (600 mg, 67%) as an off-white solid. The crude was carried for next step without further purification. TLC: 5% $MeOH/CH_2Cl_2$ ($R_f$: 0.4).

Synthesis of Methyl 3'-(2-fluoro-11-oxo-10, 11-dihydrodibenzo [b,f] [1,4] thiazepine-8-carboxamido)-[1,1'-biphenyl]-4-carboxylate (1420)

Using Procedure A the title compound was prepared with 35 (50 mg, 0.17 mmol), compound 513 (43 mg, 0.19 mmol) and was obtained in 58% yield as white solid; TLC: 5% $MeOH/CH_2Cl_2$ ($R_f$: 0.5); 1H NMR (DMSO-$d_6$, 400 MHz): δ 10.99 (s, 1H), 10.43 (s, 1H), 8.14 (s, 1H), 8.07 (d, J=7.9 Hz, 2H), 7.85-7.72 (m, 6H), 7.63 (dd, J=8.6, 5.3 Hz, 1H), 7.54-7.45 (m, 3H), 7.40 (td, J=8.5, 3.0 Hz, 1H), 3.88 (s, 3H); LC-MS: 98.86%; 498.1 ($M^++1$); (column; X-select CSH C18, (50×3.0 mm, 3.5 μm); RT 4.15 min. 0.05% Aq. TFA: ACN; 0.8 mL/min); UPLC (purity): 95.09%; (column; Acquity BEH C-18 (50×2.1 mm, 1.7μ); RT 2.75 min. ACN: 0.025% TFA (Aq); 0.5 mL/min).

Synthesis of 3'-(2-fluoro-11-oxo-10, 11-dihydrodibenzo [b,f] [1,4] thiazepine-8-carboxamido)-[1, 1'-biphenyl]-4-carboxylic acid (1419)

To a stirred solution of 1420 (50 mg, 0.10 mmol) in MeOH: $H_2O$ (3:1, 8 mL) was added potassium hydroxide (56 mg, 1.00 mmol) at RT in a sealed tube and heated to 90° C. and stirred for 5 h. The reaction was monitored by TLC; after completion of the reaction, the pH of the reaction mixture was acidified with 4 N HCl to pH~2. The obtained solid was filtered, triturated with 10% EtOAc/hexanes (10 mL) and dried in vacuo and to afford compound 1419 (20 mg, 41%) as an off-white solid. TLC: 70% EtOAc/hexanes ($R_f$: 0.2); $^1H$ NMR (400 MHz, DMSO-$d_6$): δ 12.98 (br s, 1H), 11.00 (s, 1H), 10.51 (s, 1H), 8.15 (s, 1H), 8.04 (d, J=8.4 Hz, 2H), 7.87-7.70 (m, 6H), 7.63 (dd, J=8.6, 5.3 Hz, 1H), 7.54-7.46 (m, 3H), 7.40 (td, J=8.5, 2.9 Hz, 1H); LC-MS: 91.15%; 485.0 ($M^++1$); (column; Ascentis Express C18, (50×3.0 mm, 2.7 μm); RT 2.48 min. 0.025% Aq. TFA+5% ACN: ACN+5% 0.025% Aq. TFA, 1.2 mL/min); UPLC (purity): 93.75%; (column; Acquity BEH C-18 (50×2.1 mm, 1.7μ); RT 2.43 min. ACN: 0.025% TFA (Aq); 0.5 mL/min).

Example 42: Synthesis of Compounds 1422 and 1421

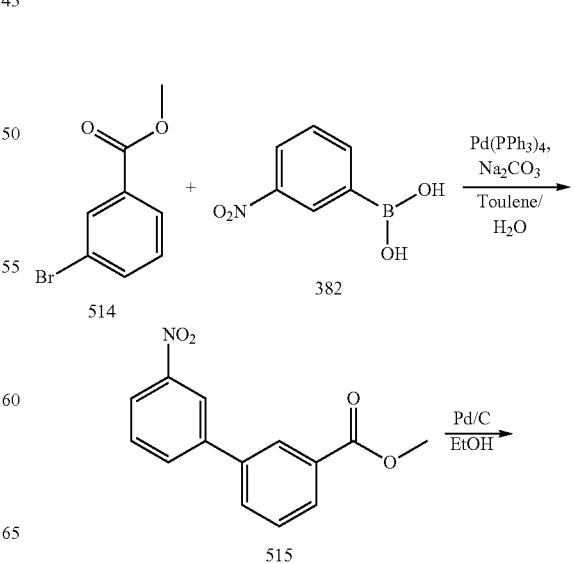

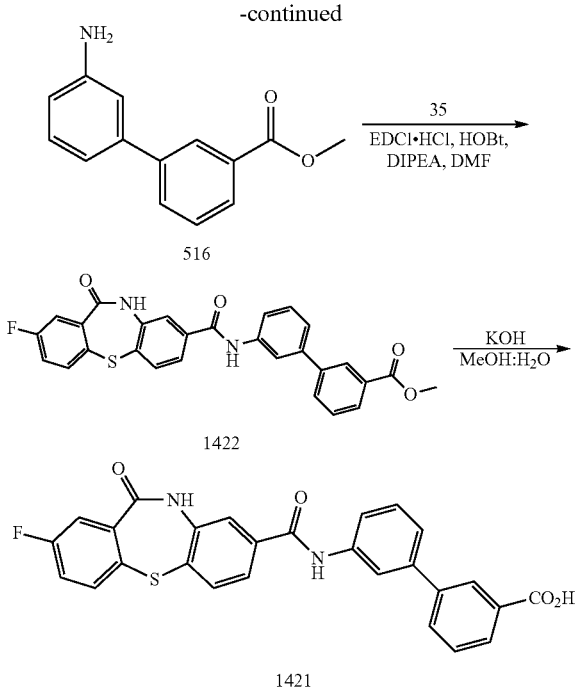

Synthesis of Methyl 3'-nitro-[1, 1'-biphenyl]-3-carboxylate (515)

To a stirred solution of methyl 3-bromobenzoate 514 (2.5 g, 14.99 mmol) and (3-nitrophenyl) boronic acid 382 (3.8 g, 17.99 mmol) in toluene (20 mL) under inert atmosphere were added sodium carbonate (3.17 g, 29.99 mmol in 20 mL of $H_2O$) at RT and purged under argon atmosphere for 20 min. To this was added $Pd(PPh_3)_4$ (693 mg, 0.59 mmol) and heated to 80° C. for 5 h. The reaction was monitored by TLC; after completion of the reaction, the reaction mixture was diluted with EtOAc (200 mL). The organic extract was dried over sodium sulfate, filtered and concentrated in vacuo to obtain the crude. The crude was purified through silica gel column chromatography using 10% EtOAc/hexanes to afford compound 515 (1 g, 26%) as yellow liquid. TLC: 15% EtOAc/hexanes ($R_f$: 0.5); $^1H$ NMR (400 MHz, DMSO-$d_6$): δ 8.48-8.46 (m, 1H), 8.30-8.25 (m, 2H), 8.22-8.18 (m, 1H), 8.11-8.07 (m, 1H), 8.04 (dt, J=7.8, 1.3 Hz, 1H), 7.80 (t, J=8.0 Hz, 1H), 7.69 (t, J=7.8 Hz, 1H), 3.91 (s, 3H).

Synthesis of Methyl 3'-amino-[1, 1'-biphenyl]-3-carboxylate (516)

To a stirred solution of compound 515 (1 g, 3.89 mmol) in EtOH (100 mL) under inert atmosphere was added 10% Pd/C (600 mg, wet) under argon atmosphere and stirred under $H_2$ atmosphere (balloon pressure) for 16 h. After completion of the reaction, the reaction mixture was filtered through celite and the celite pad was washed with 50% MeOH/$CH_2Cl_2$ (150 mL). The filtrate was evaporated in vacuo to obtain the crude which was purified through silicagel column chromatography in 20% EtOAc/hexanes to afford compound 516 (600 mg, 67%) as an off-white solid. TLC: 40% EtOAc/hexanes ($R_f$: 0.3); $^1H$ NMR (400 MHz, DMSO-$d_6$): δ 8.15-8.08 (m, 1H), 7.92 (d, J=7.7 Hz, 1H), 7.84 (d, J=8.2 Hz, 1H), 7.59 (t, J=7.7 Hz, 1H), 7.13 (t, J=7.8 Hz, 1H), 6.90-6.87 (m, 1H), 6.81 (d, J=7.6 Hz, 1H), 6.60 (dd, J=8.0, 1.4 Hz, 1H), 5.22 (s, 2H), 3.32 (s, 3H).

Synthesis of Methyl 3'-(2-fluoro-11-oxo-10, 11-dihydrodibenzo [b,f] [1,4] thiazepine-8-carboxamido)-[1, 1'-biphenyl]-3-carboxylate (1422)

Using Procedure A the title compound was prepared with compound 35 (70 mg, 0.24 mmol), compound 516 (55 mg, 0.24 mmol) and was obtained in 41% yield as white solid; TLC: 5% MeOH/$CH_2Cl_2$ ($R_f$: 0.5); $^1H$ NMR (400 MHz, DMSO-$d_6$): δ 10.99 (s, 1H), 10.43 (s, 1H), 8.12-8.19 (m, 1H), 8.10-8.08 (m, 1H), 7.96 (dd, J=12.8, 7.9 Hz, 2H), 7.85 (dt, J=7.1, 1.8 Hz, 1H), 7.81-7.73 (m, 3H), 7.69-7.59 (m, 2H), 7.54-7.45 (m, 3H), 7.40 (td, J=8.5, 2.9 Hz, 1H), 3.90 (s, 3H); LC-MS: 99.82%; 499.0 ($M^+$+1); (column; X-select CSH C18, (50×3.0 mm, 3.5 μm); RT 4.10 min. 0.05% Aq. TFA: ACN; 0.8 mL/min); UPLC (purity): 98.72%; (column; Acquity BEH C-18 (50×2.1 mm, 1.7 g); RT 2.78 min. ACN: 0.025% TFA (Aq); 0.5 mL/min).

Synthesis of 3'-(2-fluoro-11-oxo-10, 11-dihydrodibenzo [b,f] [1,4] thiazepine-8-carboxamido)-[1, 1'-biphenyl]-3-carboxylic acid (1421)

To a stirred solution of 1422 (35 mg, 0.07 mmol) in MeOH: $H_2O$ (3:1, 5 mL) under inert atmosphere was added potassium hydroxide (40 mg, 0.70 mmol) at RT in a sealed tube and heated to 80° C. and stirred for 3 h. The reaction was monitored by TLC; after completion of the reaction, the pH of the reaction mixture was acidified with 4 N HCl to pH~2 and extracted with EtOAc (2×10 mL). The combined organic extracts were dried over sodium sulfate, filtered and concentrated in vacuo to obtain the crude. The obtained solid was filtered, dried in vacuo and triturated with 10% EtOAc/hexanes (10 mL) to afford compound 1421 (20 mg, 58%) as white solid. TLC: 70% EtOAc/hexanes ($R_f$: 0.2); 1H NMR (400 MHz, DMSO-$d_6$): δ 12.99 (br s, 1H), 10.98 (s, 1H), 10.43 (s, 1H), 8.21-8.19 (m, 1H), 8.11-8.09 (m, 1H), 7.96 (d, J=7.7 Hz, 1H), 7.87 (dd, J=19.5, 7.3 Hz, 2H), 7.82-7.73 (m, 3H), 7.66-7.58 (m, 2H), 7.54-7.44 (m, 3H), 7.40 (td, J=8.5, 2.9 Hz, 1H); LC-MS: 99.07%; 484.9 ($M^+$+1); (column; X-select CSH C18, (50×3.0 mm, 3.5 μm); RT 3.73 min. 0.05% Aq. TFA: ACN; 0.8 mL/min); UPLC (purity): 96.90%; (column; Acquity BEH C-18 (50×2.1 mm, 1.7μ); RT 2.46 min. ACN: 0.025% TFA (Aq); 0.5 mL/min).

Example 43: Synthesis of Compounds 1436 and 1435

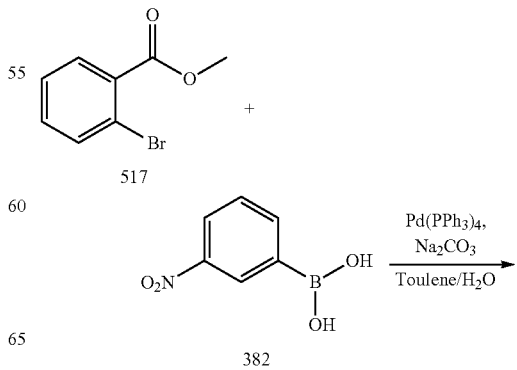

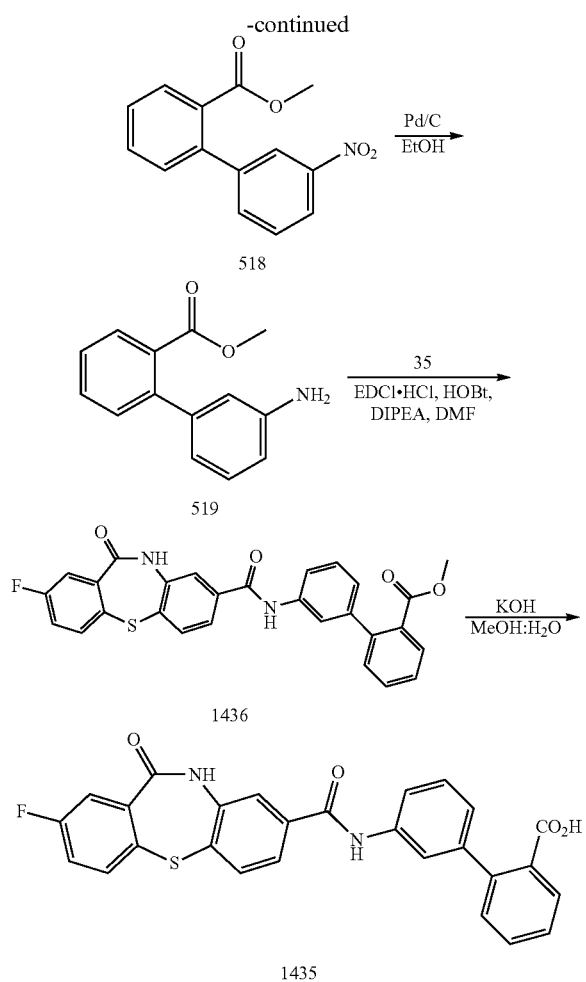

Synthesis of Methyl 3'-nitro-[1,1'-biphenyl]-2-carboxylate (518)

To a stirred solution of methyl 2-bromobenzoate 517 (2.5 g, 14.97 mmol) and (3-nitrophenyl) boronic acid 382 (3.8 g, 17.96 mmol) in toluene (20 mL) under inert atmosphere were added sodium carbonate (3.17 g, 29.94 mmol in 20 mL of $H_2O$) at RT and purged under argon atmosphere for 20 min. To this was added $Pd(PPh_3)_4$ (691 mg, 0.59 mmol) and heated to 80° C. for 6 h. The reaction was monitored by TLC; after completion of the reaction, the reaction mixture was diluted with EtOAc (200 mL). The organic extract was dried over sodium sulfate, filtered and concentrated in vacuo to obtain the crude. The crude was purified through silica gel column chromatography using 15% EtOAc/hexanes to afford compound 518 (600 mg, 17%) as yellow solid. TLC: 30% EtOAc/hexanes ($R_f$: 0.6); $^1$H NMR (400 MHz, DMSO-$d_6$): δ 8.27-8.23 (m, 1H), 8.11-8.09 (m, 1H), 7.89 (dd, J=7.7, 1.3 Hz, 1H), 7.79-7.67 (m, 3H), 7.59 (td, J=7.6, 1.1 Hz, 1H), 7.52 (dd, J=7.6, 0.6 Hz, 1H), 3.31 (s, 3H).

Synthesis of Methyl 3'-amino-[1, 1'-biphenyl]-2-carboxylate (519)

To a stirred solution of compound 518 (600 mg, 2.33 mmol) in EtOH (50 mL) under inert atmosphere was added 10% Pd/C (300 mg, wet) under argon atmosphere and stirred under $H_2$ atmosphere (balloon pressure) for 16 h. After completion of the reaction, the reaction mixture was filtered through celite and the celite pad was washed with 50% MeOH/$CH_2Cl_2$ (100 mL). The filtrate was evaporated in vacuo to afford compound 519 (500 mg, 87%) as an off-white solid. TLC: 30% EtOAc/hexanes ($R_f$: 0.6); 1H NMR (400 MHz, DMSO-$d_6$): δ 7.63 (dd, J=7.7, 1.0 Hz, 1H), 7.56 (td, J=9.0, 1.8 Hz, 1H), 7.43 (td, J=7.6, 1.1 Hz, 1H), 7.37 (dd, J=7.7, 0.8 Hz, 1H), 7.03 (t, J=7.7 Hz, 1H), 6.57-6.52 (m, 1H), 6.52-6.49 (m, 1H), 6.39 (d, J=7.5 Hz, 1H), 5.14 (br s, 2H), 3.59 (s, 3H).

Synthesis of Methyl 3'-(2-fluoro-11-oxo-10, 11-dihydrodibenzo [b,f] [1,4] thiazepine-8-carboxamido)-[1, 1'-biphenyl]-2-carboxylate (1436)

Using Procedure A the title compound was prepared with compound 35 (100 mg, 0.34 mmol), compound 519 (78 mg, 0.34 mmol) and was obtained in 35% yield as white solid; TLC: 5% MeOH/$CH_2Cl_2$ ($R_f$: 0.5); 1H NMR (400 MHz, DMSO-$d_6$): δ 10.97 (s, 1H), 10.37 (s, 1H), 7.78-7.72 (m, 6H), 7.66-7.60 (m, 2H), 7.54-7.48 (m, 2H), 7.46-7.36 (m, 3H), 7.04 (d, J=7.3 Hz, 1H), 3.61 (s, 3H); LC-MS: 93.05%; 499.0 ($M^+$+1); (column; Ascentis Express C18, (50×3.0 mm, 2.7 μm); RT 2.74 min. 0.025% Aq. TFA+5% ACN: ACN+ 5% 0.025% Aq. TFA, 1.2 mL/min); UPLC (purity): 91.54%; (column; Acquity BEH C-18 (50×2.1 mm, 1.7μ); RT 2.72 min. ACN: 0.025% TFA (Aq); 0.5 mL/min).

Synthesis of 3'-(2-fluoro-11-oxo-10, 11-dihydrodibenzo [b,f] [1,4] thiazepine-8-carboxamido)-[1, 1'-biphenyl]-2-carboxylic acid (1435)

To a stirred solution of 1436 (35 mg, 0.07 mmol) in MeOH: $H_2O$ (3:1, 8 mL) was added potassium hydroxide (40 mg, 0.70 mmol) at RT in a sealed tube and heated to 80° C. and stirred for 3 h. The reaction was monitored by TLC; after completion of the reaction, the pH of the reaction mixture was acidified with 4 N HCl to pH~2 and extracted with EtOAc (2×10 mL). The combined organic extracts were dried over sodium sulfate, filtered and concentrated in vacuo to obtain the crude. The obtained solid was filtered, triturated with 10% EtOAc/hexanes (5 mL) and dried in vacuo to afford compound 1435 (20 mg, 58%) as white solid. TLC: 70% EtOAc/hexanes ($R_f$: 0.2); $^1$H NMR (400 MHz, DMSO-$d_6$): δ 11.00 (br s, 1H), 10.36 (s, 1H), 7.81-7.69 (m, 5H), 7.67-7.59 (m, 2H), 7.54-7.48 (m, 2H), 7.44-7.31 (m, 4H), 7.07 (d, J=7.8 Hz, 1H); LC-MS: 91.40%; 484.9 ($M^+$+1); (column; Ascentis Express C18, (50×3.0 mm, 2.7 μm); RT 2.49 min. 0.025% Aq. TFA+5% ACN: ACN+ 5% 0.025% Aq. TFA, 1.2 mL/min); UPLC (purity): 92.47%; (column; Acquity BEH C-18 (50×2.1 mm, 1.7μ); RT 2.36 min. ACN: 0.025% TFA (Aq); 0.5 mL/min).

Example 44: Synthesis of 11-oxo-10, 11-dihydrodibenzo [b,f] [1,4] thiazepine-8-sulfonamide compounds

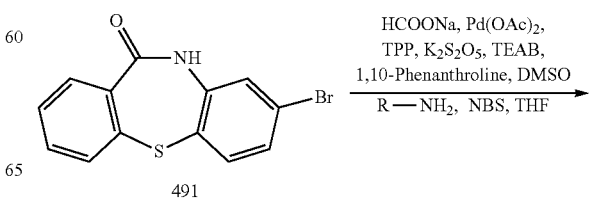

-continued

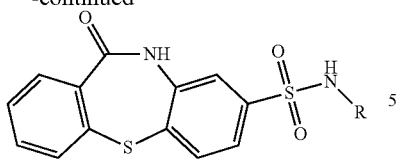

To a stirred solution of compound 491 (80 mg, 0.26 mmol) in DMSO (1.5 mL) under inert atmosphere were added potassium metabisulfate (116 mg, 0.52 mmol), tetra-ethyl ammonium bromide (60 mg, 0.28 mmol), sodium formate (40 mg, 0.57 mmol), palladium acetate (18 mg, 0.026 mmol) and 1, 10-phenanthroline (14 mg, 0.078 mmol) at RT in a microwave vial and purged under argon atmosphere for 10 min; heated to 90° C. for 4 h. The reaction was monitored by TLC; after completion of the reaction, the crude compound was carried forward to next step. TLC: 30% EtOAc/hexanes ($R_f$: 0.4).

The above crude compound and commercially available amines were converted to corresponding sulfonamide employing the Procedure L and the results are captured in the Table 3.

Procedure L:
To a stirred solution of above crude compound (100 mg, crude) in THF (2 mL) under argon atmosphere were added piperidine 521 (0.05 mL, 0.54 mmol) in THF (1 mL), N-bromosuccinimide (96 mg, 0.54 mmol) in THF (1 mL) at 0° C.; warmed to RT and stirred for 12 h. The reaction was monitored by TLC; after completion of the reaction, the reaction mixture was diluted with brine (20 mL) and extracted with EtOAc (2×50 mL). The combined organic extracts were dried over sodium sulfate, filtered and concentrated in vacuo to obtain the crude. The crude was purified through silica gel column chromatography to afford the desired compound.

Commercially Available Amines Used for the Preparation of Compounds:

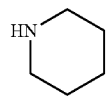 521

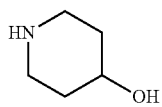 522

-continued

 275

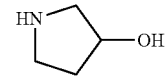 523

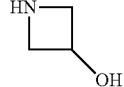 524

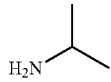 525

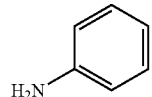 179

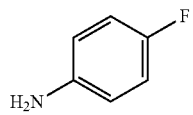 221

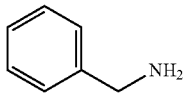 254

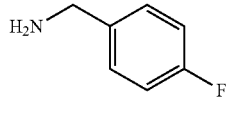 257

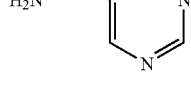 212

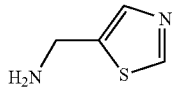 213

TABLE 3

Synthesis of compounds from compound 520 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| 1399 | (structure) | L, 521 (RT 18 h) | 15 | 374.9 ($M^+$ + 1) | 374.08 for $C_{18}H_{18}N_2O_3S_2$ | $^1$H NMR (DMSO-$d_6$, 400 MHz): δ 10.86 (s, 1H), 7.80 (d, J = 8.0 Hz, 1H), 7.72 (dd, J = 7.6, 1.4 Hz, 1H), 7.59-7.55 (m, 2H), 7.54-7.43 (m, |

TABLE 3-continued

Synthesis of compounds from compound 520 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| | | | | | | 3H), 2.93-2.84 (m, 4H), 1.57-1.48 (m, 4H), 1.42-1.31 (m, 2H); |
| 1431 | 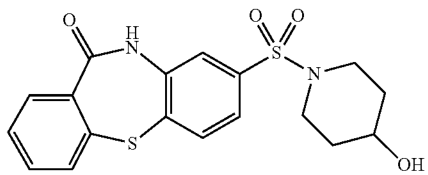 [SMILES: O=C1Nc2cc(S(=O)(=O)N3CCC(O)CC3)ccc2Sc2ccccc21] | L, 522 | 19 | 390.9 (M$^+$ + 1) | 390.07 for $C_{18}H_{18}N_2O_4S_2$ | $^1$H NMR (DMSO-d$_6$, 400 MHz): δ 10.87 (s, 1H), 7.81 (d, J = 8.2 Hz, 1H), 7.72 (dd, J = 7.4, 1.4 Hz, 1H), 7.60-7.53 (m, 3H), 7.52-7.45 (m, 2H), 4.66 (d, J = 4.0 Hz, 1H), 3.53- 3.49 (m, 1H), 3.19-3.12 (m, 2H), 2.76-2.69 (m, 2H), 1.77-1.68 (m, 2H), 1.49-1.35 (m, 2H); |
| 1432 | 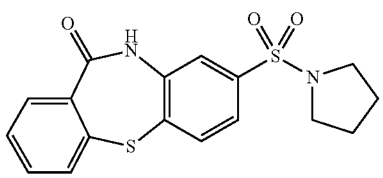 [SMILES: O=C1Nc2cc(S(=O)(=O)N3CCCC3)ccc2Sc2ccccc21] | L, 275 | 20 | 360.8 (M$^+$ + 1) | 360.06 for $C_{17}H_{16}N_2O_3S_2$ | $^1$H NMR (DMSO-d$_6$, 400 MHz): δ 10.85 (s, 1H), 7.79 (d, J = 8.0 Hz, 1H), 7.74-7.70 (m, 1H), 7.63 (s, 1H), 7.60-7.45 (m, 4H), 3.16-3.11 (m, 4H), 1.75-1.56 (m, 4H); |
| 1433 | 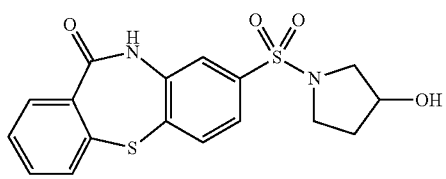 [SMILES: O=C1Nc2cc(S(=O)(=O)N3CCC(O)C3)ccc2Sc2ccccc21] | L, 523 | 19 | 376.9 (M$^+$ + 1) | 376.06 for $C_{17}H_{16}N_2O_4S_2$ | $^1$H NMR (DMSO-d$_6$, 400 MHz): δ 10.83 (s, 1H), 7.78 (d, J = 8.0 Hz, 1H), 7.74-7.68 (m, 1H), 7.63 (s, 1H), 7.59-7.45 (m, 4H), 4.86 (d, J = 3.4 Hz, 1H), 4.17-4.14 (m, 1H), 3.27-3.18 (m, 3H), 3.10-2.93 (m, 1H), 1.81-1.69 (m, 1H), 1.68-1.58 (m, 1H); |
| 1434 | 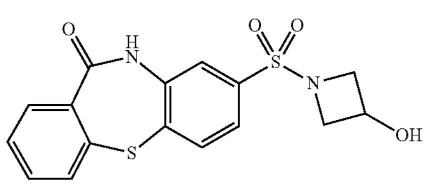 [SMILES: O=C1Nc2cc(S(=O)(=O)N3CC(O)C3)ccc2Sc2ccccc21] | L, 524 | 20 | 362.8 (M$^+$ + 1) | 362.04 for $C_{16}H_{14}N_2O_4S_2$ | $^1$H NMR (DMSO-d$_6$, 400 MHz): δ 10.90 (s, 1H), 7.86 (d, J = 8.2 Hz, 1H), 7.73 (dd, J = 7.5, 1.5 Hz, 1H), 7.64-7.62 (m, 1H), 7.60-7.47 (m, 4H), 5.71 (d, J = 6.3 Hz, 1H), 4.30-4.22 (m, 1H), 3.89 (dd, J = 8.5, 6.8 Hz, |

TABLE 3-continued

Synthesis of compounds from compound 520 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| | | | | | | 2H), 3.40-3.34 (m, 2H); |
| 1450 | 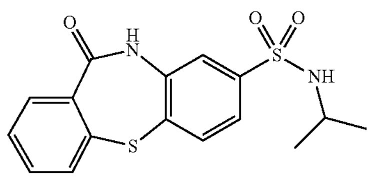 [SMILES: CC(C)NS(=O)(=O)c1ccc2c(c1)NC(=O)c1ccccc1S2] | L, 525 | 16 | 348.9 (M$^+$ + 1) | 348.06 for C$_{16}$H$_{16}$N$_2$O$_3$S$_2$ | $^1$H NMR (DMSO-d$_6$, 400 MHz): δ 10.89 (s, 1H), 7.77 (d, J = 8.2 Hz, 1H), 7.73-7.68 (m, 2H), 7.65-7.63 (m, 1H), 7.57-7.44 (m, 4H), 3.27-3.16 (m, 1H), 0.94 (d, J = 6.5 Hz, 6H); |
| 1412 | 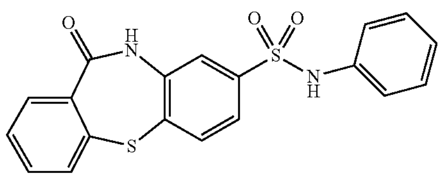 [SMILES: O=C1Nc2cc(S(=O)(=O)Nc3ccccc3)ccc2Sc2ccccc21] | L, 179 | 15 | 382.9 (M$^+$ + 1) | 382.04 for C$_{19}$H$_{14}$N$_2$O$_3$S$_2$ | $^1$H NMR (DMSO-d$_6$, 400 MHz): δ 10.90 (s, 1H), 10.42 (s, 1H), 7.73 (d, J = 8.2 Hz, 1H), 7.68 (dd, J = 6.9, 15. Hz, 1H), 7.65-7.63 (m, 1H), 7.55-7.43 (m, 4H), 7.24-7.18 (m, 2H), 7.08-7.04 (m, 2H), 7.01 (t, J = 7.7 Hz, 1H); |
| 1413 | 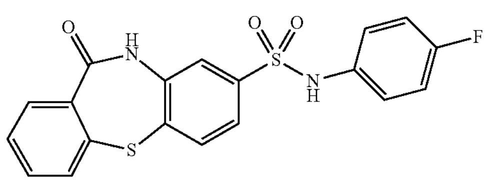 [SMILES: O=C1Nc2cc(S(=O)(=O)Nc3ccc(F)cc3)ccc2Sc2ccccc21] | L, 221 | 23 | 400.9 (M$^+$ + 1) | 400.04 for C$_{19}$H$_{13}$FN$_2$O$_3$S$_2$ | $^1$H NMR (DMSO-d$_6$, 400 MHz): 10.90 (s, 1H), 10.37 (s, 1H), 7.74 (d, J = 8.3 Hz, 1H), 7.69 (dd, J = 6.9, 1.5 Hz, 1H), 7.60-7.56 (m, 1H), 7.55-7.45 (m, 3H), 7.43 (dd, J = 8.2, 2.0 Hz, 1H), 7.09-7.04 (m, 4H); |
| 1414 | 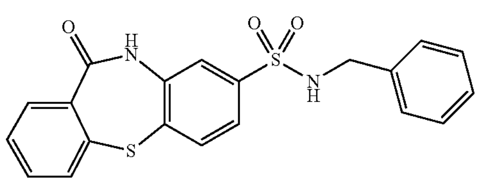 | L, 254 | 23 | 396.9 (M$^+$ + 1) | 396.06 for C$_{20}$H$_{16}$N$_2$O$_3$S$_2$ | $^1$H NMR (DMSO-d$_6$, 400 MHz): δ 10.83 (s, 1H), 8.28 (t, J = 6.3 Hz, 1H), 7.74 (dd, J = 6.8, 1.5 Hz, 1H), 7.69 (d, J = 8.2 Hz, 1H), 7.59-7.49 (m, 4H), 7.47 (dd, J = 8.2, 2.0 Hz, 1H), 7.15-7.10 (m, 2H), 7.06 (t, J = 7.4 Hz, 2H), 7.02-6.96 (m, 1H), 3.99 (d, J = 6.3 Hz, 2H); |

TABLE 3-continued

Synthesis of compounds from compound 520 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| 1415 | 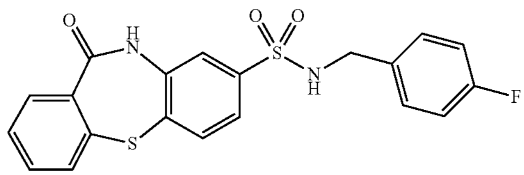 [SMILES: O=C1Nc2cc(S(=O)(=O)NCc3ccc(F)cc3)ccc2Sc2ccccc21] | L, 257 | 22 | 414.9 (M$^+$ + 1) | 414.05 for $C_{20}H_{15}FN_2O_3S_2$ | $^1$H NMR (DMSO-d$_6$, 400 MHz): δ 10.86 (s, 1H), 8.28 (t, J = 6.2 Hz, 1H), 7.76-7.67 (m, 2H), 7.63-7.60 (m, 1H), 7.58-7.44 (m, 4H), 7.18 (dd, J = 8.6, 5.6 Hz, 2H), 6.92 (t, J = 8.9 Hz, 2H), 4.04-3.92 (m, 2H); |
| 1473 | 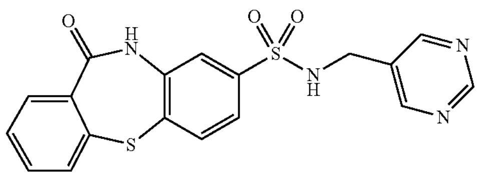 [SMILES: O=C1Nc2cc(S(=O)(=O)NCc3cncnc3)ccc2Sc2ccccc21] | L, 212 | 19 | 399.0 (M$^+$ + 1) | 398.05 for $C_{18}H_{14}N_4O_3S_2$ | $^1$H NMR (DMSO-d$_6$, 400 MHz): δ 10.86 (s, 1H), 8.76 (s, 1H), 8.59 (s, 2H), 8.43 (br s, 1H), 7.78-7.70 (m, 2H), 7.60-7.54 (m, 3H), 7.54-7.48 (m, 2H), 4.07 (s, 2H); |

Synthesis of 11-oxo-10, 11-dihydrodibenzo [b,f] [1,4] thiazepine-8-sulfonyl chloride (520)

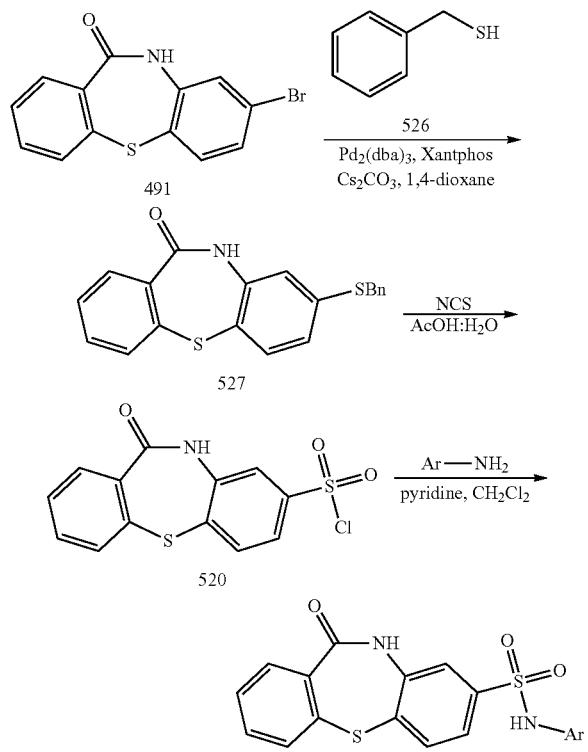

Synthesis of 8-(benzylthio) dibenzo [b,f] [1,4] thiazepin-11(10H)-one (527)

To a stirred solution of compound 491 (1 g, 3.26 mmol) in 1, 4-dioxane (20 mL) under argon atmosphere were added phenylmethanethiol 526 (0.4 mL, 3.59 mmol), CS$_2$CO$_3$ (921 mg, 3.92 mmol) at RT, purged under argon atmosphere for 20 min. To this were added Pd$_2$(dba)$_3$ (75 mg, 0.081 mmol), Xantphos (94 mg, 1.06 mmol) at RT and heated to 110-120° C. and stirred for 12 h. The reaction was monitored by TLC; after completion of the reaction, the reaction mixture was filtered and the filtrate was removed in vacuo to obtain the crude. The crude was purified through silica gel column chromatography using 5-40% EtOAc/hexanes to afford compound 527 (700 mg, 61%) as pale yellow solid. TLC: 30% EtOAc/hexanes (R$_f$: 0.4); $^1$H NMR (DMSO-d$_6$, 400 MHz): δ 10.63 (s, 1H), 7.68-7.65 (m, 1H), 7.53-7.41 (m, 4H), 7.39-7.34 (m, 2H), 7.32-7.20 (m, 3H), 7.17 (s, 1H), 7.10 (dd, J=8.2, 2.1 Hz, 1H), 4.24 (s, 2H).

Synthesis of 11-oxo-10, 11-dihydrodibenzo [b,f] [1,4] thiazepine-8-sulfonyl chloride (520)

To a stirred solution of 527 (700 mg, 2.00 mmol) in acetic acid: H$_2$O (3:1, 16 mL) under was added N-chlorosuccinimide (668 mg, 5.61 mmol) at 0° C.; warmed to RT and stirred for 3 h. The reaction was monitored by TLC; after completion of the reaction, the reaction mixture was diluted with water (100 mL) and extracted with diethyl ether (2×100 mL). The combined organic extracts were dried over sodium sulfate, filtered and concentrated in vacuo to afford crude compound 520 (700 mg) as yellow solid. The crude compound was carried forward for next step without further purification. TLC: 20% EtOAc/hexanes (R$_f$: 0.6); LC-MS: 68.55%; 325.9 (M$^+$+1); column; Ascentis Express C18, (50×3.0 mm, 2.7 μm); RT 2.51 min. 0.025% Aq. TFA+5% ACN: ACN+; 5% 0.025% Aq. TFA, 1.2 mL/min).

Example 45: Synthesis of Compounds from Compound 520 and Various Commercially Available Amines

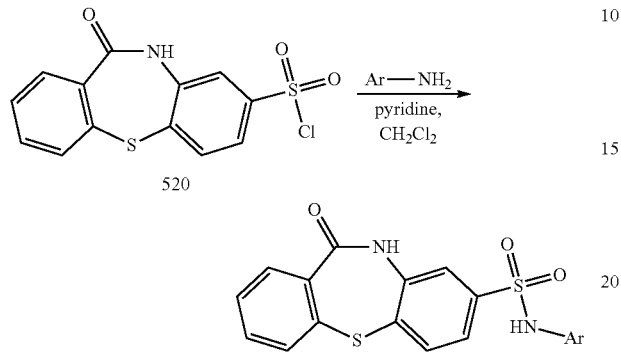

Compound 520 and commercially available amines were converted to corresponding sulfonamides employing Procedure M and the results are captured in Table 4.

Procedure M:

To a stirred solution of 2, 4-difluoroaniline 228 (100 mg, 0.77 mmol) in CH$_2$Cl$_2$ (5 mL) under argon atmosphere were added compound 520 (252 mg, crude), pyridine (3.87 mL, 5.26 mmol) at 0° C.; warmed to RT and stirred for 12 h. The reaction was monitored by TLC; after completion of the reaction, the reaction mixture was diluted with water (20 mL) and extracted with CH$_2$Cl$_2$ (2×50 mL). The combined organic extracts were dried over sodium sulfate, filtered and concentrated in vacuo to obtain the crude. The crude was purified through silica gel column chromatography to afford the desired compound.

Commercially Available Amines Used for the Synthesis of Compounds

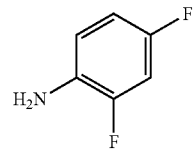
228

224

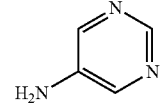
229

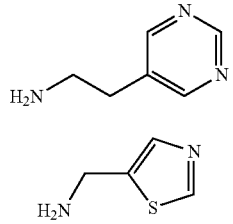
215

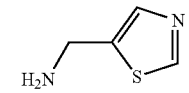
213

TABLE 4

Synthesis of compounds from compound 520 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| 1526 | 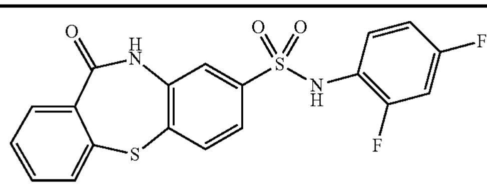 | M, 520, 228 | 8 | 418.8 (M$^+$ + 1) | 418.03 for C$_{19}$H$_{12}$F$_2$N$_2$O$_3$S$_2$ | $^1$H NMR (DMSO-d$_6$, 400 MHz): δ 10.89 (s, 1H), 10.25 (s, 1H), 7.77 (d, J = 8.2 Hz, 1H), 7.70 (dd, J = 7.5, 1.2 Hz, 1H), 7.58-7.45 (m, 4H), 7.43 (dd, J = 8.2, 2.0 Hz, 1H), 7.25-7.17 (m, 2H), 7.06-6.98 (m, 1H) |
| 1544 | 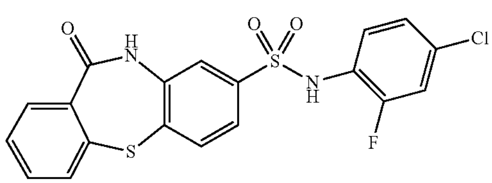 [SMILES: O=C1Nc2cc(S(=O)(=O)Nc3ccc(Cl)cc3F)ccc2Sc2ccccc21] | M, 520, 224 | 10 | 435.1 (M$^+$ + 1) | 434.00 for C$_{19}$H$_{12}$ClFN$_2$O$_3$S$_2$ | $^1$H NMR (DMSO-d$_6$, 400 MHz): δ 10.90 (s, 1H), 10.43 (s, 1H), 7.77 (d, J = 8.2 Hz, 1H), 7.70 (d, J = 7.0 Hz, 1H), 7.61-7.43 (m, 5H), 7.42-7.37 (m, 1H), |

TABLE 4-continued

Synthesis of compounds from compound 520 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| | | | | | | 7.26-7.18 (m, 2H); |
| 1505 | 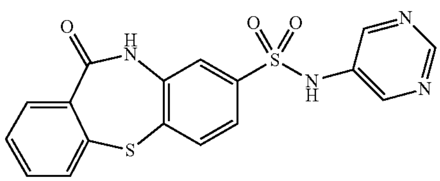 [SMILES: O=C1Nc2cc(S(=O)(=O)Nc3cncnc3)ccc2Sc2ccccc21] | M, 520, 229 | 6 | 385.1 (M$^+$ + 1) | 384.04 for $C_{17}H_{12}N_4O_3S_2$ | $^1$H NMR (DMSO-d$_6$, 400 MHz): δ 11.02 (br s, 1H), 10.90 (s, 1H), 8.90 (s, 1H), 8.52 (s, 2H), 7.78 (d, J = 8.2 Hz, 1H), 7.71-7.64 (m, 2H), 7.57-7.44 (m, 4H); |
| 1506 | 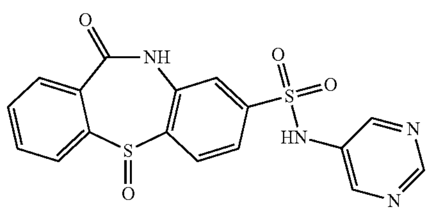 [SMILES: O=C1Nc2cc(S(=O)(=O)Nc3cncnc3)ccc2S(=O)c2ccccc21] | M, 520, 229 (excess equiv. of NCS) | 6 | 400.8 (M$^+$ + 1) | 400.03 for $C_{17}H_{12}N_4O_4S_2$ | $^1$H NMR (DMSO-d$_6$, 400 MHz): δ 11.15 (s, 1H), 11.08 (br s, 1H), 8.91 (s, 1H), 8.52 (s, 2H), 7.86-7.77 (m, 4H), 7.73 (d, J = 7.0 Hz, 1H), 7.68 (s, 1H), 7.66-7.61 (m, 1H); |
| 1556 | 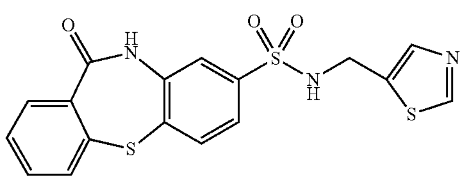 [SMILES: O=C1Nc2cc(S(=O)(=O)NCc3cncs3)ccc2Sc2ccccc21] | M, 520, 213 | 9 | 403.9 (M$^+$ + 1) | 403.01 for $C_{17}H_{13}N_3O_3S_3$ | $^1$H NMR (DMSO-d$_6$, 400 MHz): δ 10.86 (s, 1H), 8.76 (s, 1H), 8.44 (t, J = 6.0 Hz, 1H), 7.76 (d, J = 8.2 Hz, 1H), 7.74-7.71 (m, 1H), 7.66 (s, 1H), 7.62 (s, 1H), 7.59-7.47 (m, 4H), 4.25 (d, J = 5.9 Hz, 2H); |
| 1597 | 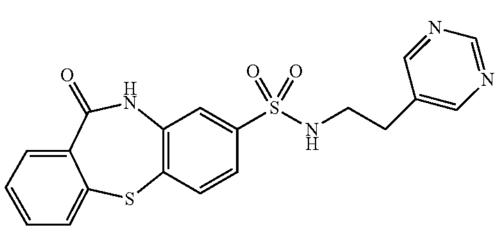 [SMILES: O=C1Nc2cc(S(=O)(=O)NCCc3cncnc3)ccc2Sc2ccccc21] | M, 520, 215 | 5 | 412.9 (M$^+$ + 1) | 412.07 for $C_{19}H_{16}N_4O_3S_2$ | $^1$H NMR (DMSO-d$_6$, 400 MHz): δ 10.87 (br s, 1H), 8.91 (s, 1H), 8.59 (s, 2H), 7.90-7.85 (m, 1H), 7.78-7.70 (m, 2H), 7.61-7.44 (m, 5H), 3.10-3.03 (m, 2H), 2.76-2.63 (m, 2H); |

Example 46: Synthesis of Compound 1228

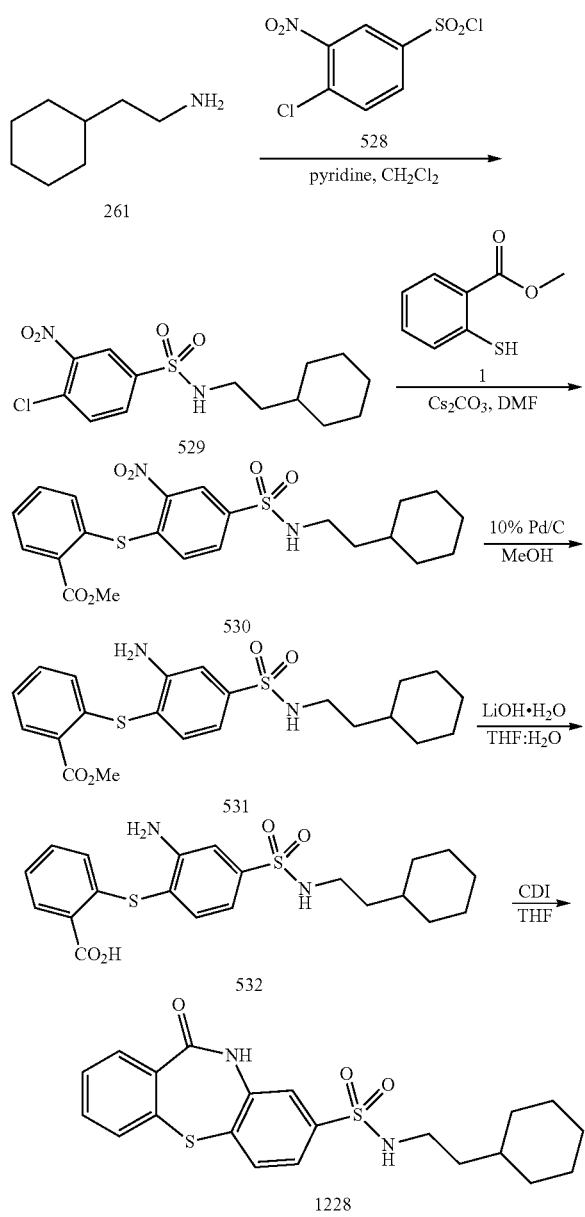

Synthesis of 4-chloro-N-(2-cyclohexylethyl)-3-nitrobenzenesulfonamide (529)

To a stirred solution of 2-cyclohexylethan-1-amine 261 (500 mg, 3.93 mmol) in $CH_2Cl_2$ (10 mL) under inert atmosphere were added pyridine (0.9 mL), 4-chloro-3-nitrobenzenesulfonyl chloride 528 (1 g, 3.93 mmol) at 0° C.; warmed to RT and stirred for 2 h. The reaction was monitored by TLC; after completion of the reaction, the reaction mixture was diluted with water (20 mL) and extracted with $CH_2Cl_2$ (2×30 mL). The combined organic extracts were dried over sodium sulfate, filtered and concentrated in vacuo to obtain the crude. The crude was purified through silica gel column chromatography using 15% EtOAc/hexanes to afford compound 529 (1.36 g, 52%) as yellow solid. TLC: 30% EtOAc/hexanes ($R_f$: 0.6); $^1$H-NMR (CDCl$_3$, 400 MHz): δ 8.33 (s, 1H), 7.97 (d, J=8.4 Hz, 1H), 7.71 (d, J=8.4 Hz, 1H), 4.52 (t, J=5.6 Hz, 1H), 3.03 (q, 2H), 1.69-1.56 (m, 4H), 1.40-1.35 (m, 2H), 1.28-1.08 (m, 5H), 0.89-0.83 (m, 2H).

Synthesis of Methyl 2-((4-(N-(2-cyclohexylethyl)sulfamoyl)-2-nitrophenyl) thio) benzoate (530)

To a stirred solution of compound 529 (200 mg, 0.57 mmol) in DMF (4 mL) under inert atmosphere was added cesium carbonate (281 mg, 0.86 mmol) at RT; heated to 40° C., then added methyl thio salicylate (106 mg, 0.63 mmol) and stirred for 2 h. The reaction was monitored by TLC; after completion of the reaction, the reaction mixture was diluted with water (20 mL) and extracted with EtOAc (2×30 mL). The combined organic extracts were washed with water (20 mL), dried over sodium sulfate, filtered and concentrated in vacuo to obtain the crude. The crude was purified through silica gel column chromatography using 20% EtOAc/hexanes to afford compound 530 (210 mg, 76%) as yellow syrup. TLC: 30% EtOAc/hexanes ($R_f$: 0.4); $^1$H-NMR (CDCl$_3$, 400 MHz): δ 8.67 (s, 1H), 7.99-7.97 (m, 1H), 7.73 (d, J=8.4 Hz, 1H), 7.65-7.59 (m, 3H), 6.97 (d, J=8.8 Hz, 1H), 4.44 (t, J=6.0 Hz, 1H), 3.81 (s, 3H), 3.03-2.98 (m, 2H), 1.67-1.58 (m, 5H), 1.42-1.33 (m, 3H), 1.29-1.09 (m, 3H), 0.91-0.87 (m, 2H).

Synthesis of Methyl 2-((2-amino-4-(N-(2-cyclohexylethyl) sulfamoyl) phenyl) thio) benzoate (531)

To a stirred solution of compound 530 (200 mg, 0.41 mmol) in MeOH (10 mL) under inert atmosphere was added 10% Pd/C (60 mg) at RT and stirred under hydrogen atmosphere (balloon pressure) for 16 h. The reaction was monitored by TLC; after completion of the reaction, the reaction mixture was filtered through celite and the filtrate was concentrated in vacuo to obtain the crude. The crude was purified through silica gel column chromatography using 10% EtOAc/Hexanes to afford compound 531 (120 mg, 64%) as an off-white solid. TLC: 30% EtOAc/Hexanes ($R_f$: 0.3); $^1$H-NMR (CDCl$_3$, 400 MHz): δ 8.03 (d, J=7.6 Hz, 1H), 7.59 (d, J=8.4 Hz, 1H), 7.30-7.29 (m, 2H), 7.21-7.16 (m, 2H), 6.71 (d, J=8.0 Hz, 1H), 4.36 (br s, 1H), 3.97 (s, 3H), 3.04 (t, J=6.4 Hz, 2H), 1.68-1.61 (m, 5H), 1.39-1.35 (m, 2H), 1.29-1.13 (m, 4H), 0.90-0.84 (m, 2H).

Synthesis of 2-((2-amino-4-(N-(2-cyclohexylethyl) sulfamoyl) phenyl) thio) benzoic acid (532)

To a stirred solution of compound 531 (110 mg, 0.24 mmol) in THF:H$_2$O (2:1, 6 mL) was added lithium hydroxide monohydrate (20 mg, 0.49 mmol) at RT and stirred for 16 h. The reaction was monitored by TLC; after completion of the reaction, the volatiles were removed in vacuo. The residue was diluted with water (15 mL), acidified with dil. HCl. The obtained precipitate was filtered, washed with ether (2×5 mL) and dried in vacuo to afford compound 532 (85 mg, 80%) as white solid. TLC: 30% EtOAc/hexanes ($R_f$: 0.2); $^1$H-NMR (DMSO-d$_6$, 400 MHz): δ 13.19 (br s, 1H), 7.94 (d, J=7.6 Hz, 1H), 7.50-7.47 (m, 2H), 7.34 (t, J=7.2 Hz, 1H), 7.24-7.18 (m, 2H), 6.94 (d, J=8.0 Hz, 1H), 6.61 (d, J=8.0 Hz, 1H), 5.82 (br s, 2H), 2.85-2.80 (m, 2H), 1.59-1.52 (m, 5H), 1.27-1.23 (m, 3H), 1.16-1.11 (m, 3H), 0.83-0.78 (m, 2H).

Synthesis of N-(2-cyclohexylethyl)-11-oxo-10,11-dihydrodibenzo [b,f] [1,4] thiazepine-8-sulfonamide (1228)

To a stirred solution of compound 532 (80 mg, 0.18 mmol) in THF (5 mL) under inert atmosphere was added CDI (89 mg, 0.55 mmol) at 0° C.; warmed to RT and stirred for 16 h. The reaction was monitored by TLC; after completion of the reaction, the volatiles were removed in vacuo. The residue was diluted with water (20 mL), acidified with dil. HCl. The obtained precipitate was filtered, washed with ether (2×5 mL) and dried in vacuo to afford 1228 (35 mg, 46%) as white solid. TLC: 5% MeOH/CH$_2$Cl$_2$ (R$_f$: 0.6); $^1$H-NMR (DMSO-d$_6$, 400 MHz): δ 10.89 (s, 1H), 7.77 (d, J=8.0 Hz, 1H), 7.71-7.69 (m, 1H), 7.64-7.62 (m, 2H), 7.56-7.45 (m, 4H), 2.78-2.73 (m, 2H), 1.48-1.42 (m, 5H), 1.19-1.07 (m, 6H), 0.71-0.66 (m, 2H); LC-MS: 98.00%; 417.6 (M$^+$+1); (column; X-Select CSH C-18, (50×3.0 mm, 3.5 μm); RT 4.76 min. 0.05% TFA (Aq): ACN; 0.8 mL/min); UPLC (purity): 95.34%; (column: Acquity BEH C-18 (50× 2.1 mm, 1.7μ); RT 2.74 min. ACN: 0.025% TFA (Aq.); 0.5 mL/min).

Example 47: Synthesis of Compound 1289

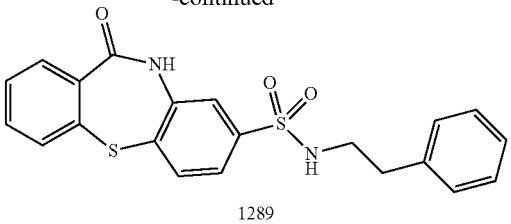

Synthesis of 4-chloro-3-nitro-N-phenethylbenzenesulfonamide (533)

To a stirred solution of 2-phenylethan-1-amine 211 (250 mg, 2.06 mmol) in CH$_2$Cl$_2$ (5 mL) under inert atmosphere were added 4-chloro-3-nitrobenzenesulfonyl chloride 528 (528 mg, 2.06 mmol), pyridine (0.5 mL) at 0° C.; warmed to RT and stirred for 2 h. The reaction was monitored by TLC; after completion of the reaction, the reaction mixture was diluted with water (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 15% EtOAc/hexanes to afford compound 533 (410 mg, 58%) as colorless syrup. TLC: 30% EtOAc/hexanes (R$_f$: 0.6); $^1$H-NMR (CDCl$_3$, 400 MHz): δ 8.21 (s, 1H), 7.85 (d, J=8.4 Hz, 1H), 7.64 (d, J=8.4 Hz, 1H), 7.27 (s, 1H), 7.25-7.22 (m, 2H), 7.08 (d, J=8.0 Hz, 2H), 4.59 (t, J=6.0 Hz, 1H), 3.32 (q, 2H), 2.81 (t, J=6.8 Hz, 2H).

Synthesis of Methyl 2-((2-nitro-4-(N-phenethylsulfamoyl) phenyl) thio) benzoate (534)

To a stirred solution of compound 533 (100 mg, 0.29 mmol) in DMF (3 mL) under inert atmosphere were added methyl thio salicylate (54 mg, 0.32 mmol), cesium carbonate (143 mg, 0.44 mmol) at RT; heated to 40° C. and stirred for 2 h. The reaction was monitored by TLC; after completion of the reaction, the reaction mixture was diluted with water (15 mL) and extracted with EtOAc (2×20 mL). The combined organic extracts were washed with water (20 mL), dried over sodium sulfate, filtered and concentrated in vacuo to obtain the crude. The crude was purified through silica gel column chromatography using 20% EtOAc/hexanes to afford compound 534 (90 mg, 65%) as yellow solid. TLC: 30% EtOAc/hexanes (R$_f$: 0.4); $^1$H-NMR (CDCl$_3$, 400 MHz): δ 8.56 (s, 1H), 7.98 (t, J=6.8 Hz, 1H), 7.64-7.60 (m, 4H), 7.23-7.20 (m, 3H), 7.07 (d, J=8.4 Hz, 2H), 6.91 (d, J=8.4 Hz, 1H), 4.50 (t, J=6.0 Hz, 1H), 3.80 (s, 3H), 3.28 (q, 2H), 2.79 (t, J=6.8 Hz, 2H).

Synthesis of Methyl 2-((2-amino-4-(N-phenethylsulfamoyl) phenyl) thio) benzoate (535)

To a stirred solution of compound 534 (330 mg, 0.69 mmol) in MeOH (15 mL) under inert atmosphere was added 10% Pd/C (100 mg) at RT and stirred under hydrogen atmosphere (balloon pressure) for 12 h. The reaction was monitored by TLC; after completion of the reaction, the reaction mixture was filtered through celite, washed with CH$_2$Cl$_2$ (2×5 mL) and the filtrate was concentrated in vacuo to obtain the crude. The crude was purified through silica gel column chromatography using 15% EtOAc/hexanes to afford compound 535 (210 mg, 68%) as an off-white solid.

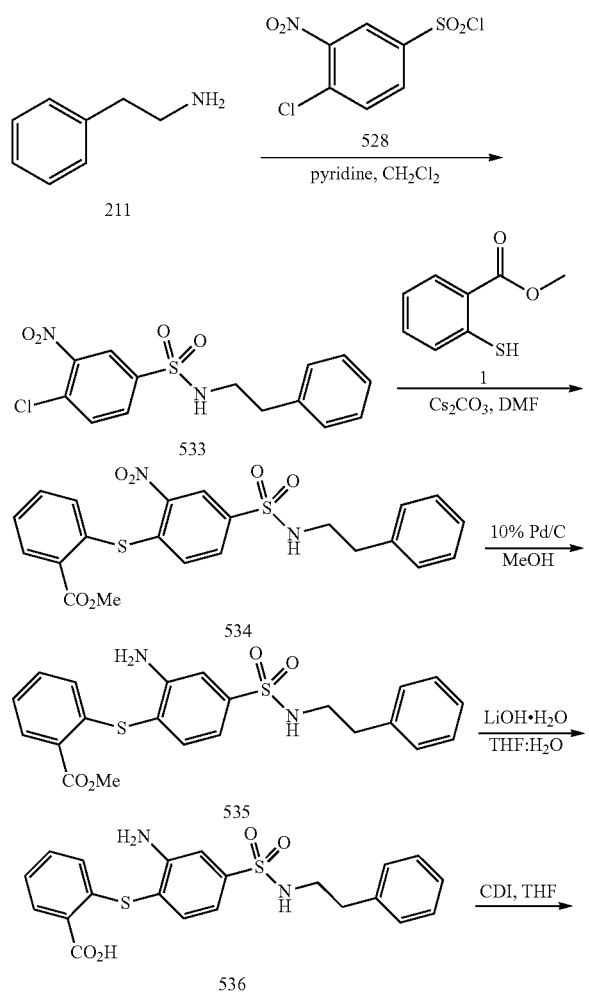

TLC: 30% EtOAc/hexanes ($R_f$: 0.3); $^1$H-NMR (CDCl$_3$, 400 MHz): δ 8.03 (d, J=8.0 Hz, 1H), 7.56 (d, J=8.0 Hz, 1H), 7.28 (d, J=8.0 Hz, 3H), 7.25-7.23 (m, 1H), 7.19-7.11 (m, 5H), 6.69 (d, J=8.0 Hz, 1H), 4.37 (t, J=6.4 Hz, 1H), 4.12 (q, 1H), 3.97 (s, 3H), 3.31 (q, 2H), 2.81 (t, J=6.8 Hz, 2H), 2.04 (s, 1H).

Synthesis of 2-((2-amino-4-(N-phenethylsulfamoyl) phenyl) thio) benzoic acid (536)

To a stirred solution of compound 535 (200 mg, 0.45 mmol) in THF:H$_2$O (2:1, 6 mL) was added lithium hydroxide monohydrate (38 mg, 0.90 mmol) at RT and stirred for 16 h; heated to 40° C. and stirred for 3 h. The reaction was monitored by TLC; after completion of the reaction, the volatiles were removed in vacuo. The residue was diluted with water (15 mL), acidified with dil. HCl. The obtained precipitate was filtered, washed with ether (2×5 mL) and dried in vacuo to afford compound 536 (130 mg, 67%) as white solid. TLC: 40% EtOAc/hexanes ($R_f$: 0.2); $^1$H-NMR (DMSO-d$_6$, 400 MHz): δ 7.93 (d, J=7.6 Hz, 1H), 7.68 (t, J=6.0 Hz, 1H), 7.47 (d, J=8.0 Hz, 1H), 7.32-7.25 (m, 4H), 7.21-7.16 (m, 4H), 6.95 (d, J=8.0 Hz, 1H), 6.60 (d, J=8.4 Hz, 1H), 5.81 (br s, 2H), 3.03 (q, 2H), 2.70 (t, J=8.0 Hz, 2H).

Synthesis of 11-oxo-N-phenethyl-10, 11-dihydrodibenzo [b,f] [1,4] thiazepine-8-sulfonamide (1289)

To a stirred solution of compound 536 (100 mg, 0.23 mmol) in THF (5 mL) under inert atmosphere was added CDI (113 mg, 0.70 mmol) at 0° C.; warmed to RT and stirred for 16 h. The reaction was monitored by TLC; after completion of the reaction, the volatiles were removed in vacuo. The residue was diluted with water (20 mL), acidified with 1N HCl. The obtained precipitate was filtered, washed with ether (2×5 mL) and dried in vacuo to obtain the crude. The crude was purified through silica gel column chromatography using 3-5% MeOH/CH$_2$Cl$_2$ to afford 1289 (35 mg, 37%) as white solid. TLC: 5% MeOH/CH$_2$Cl$_2$ ($R_f$: 0.6); $^1$H-NMR (DMSO-d$_6$, 400 MHz): δ 10.86 (s, 1H), 7.81 (br s, 1H), 7.73 (d, J=8.0 Hz, 2H), 7.71 (s, 1H), 7.59-7.45 (m, 4H), 7.18-7.14 (m, 2H), 7.11-7.07 (m, 3H), 2.97 (q, 2H), 2.64 (t, J=7.6 Hz, 2H); LC-MS: 97.83%; 411.5 (M$^+$+1); (column; X-Select CSH C-18, (50×3.0 mm, 3.5 μm); RT 4.33 min. 0.05% TFA (Aq): ACN; 0.8 mL/min); UPLC (purity): 98.00%; (column: Acquity BEH C-18 (50×2.1 mm, 1.7μ); RT 2.43 min. ACN: 0.025% TFA (Aq); 0.5 mL/min).

Example 48: Synthesis of Compounds 1277 and 1282

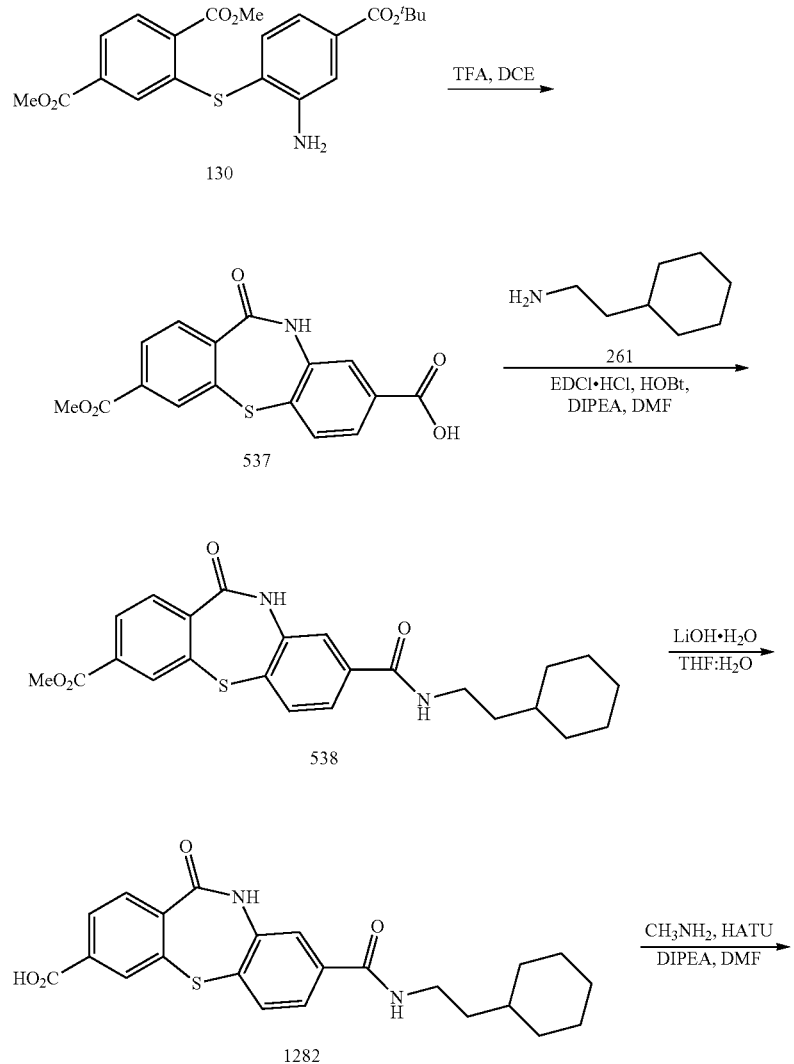

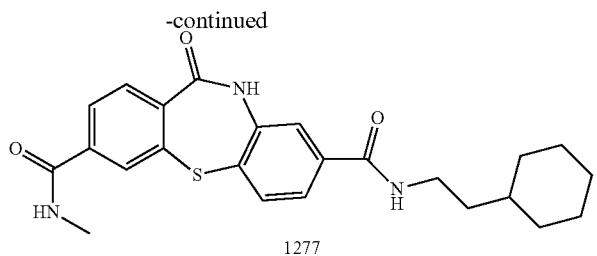

1277

Synthesis of 3-(methoxycarbonyl)-11-oxo-10, 11-dihydrodibenzo [b,f] [1,4] thiazepine-8-carboxylic acid (537)

To a stirred solution of dimethyl 2-((2-amino-4-(tert-butoxycarbonyl) phenyl) thio) terephthalate 130 (200 mg, 0.47 mmol) in 1, 2-dichloro ethane (10 mL) under inert atmosphere was added trifluoro acetic acid (1.09 g, 9.59 mmol) at RT; heated to 80° C. and stirred for 24 h. The reaction was monitored by TLC; after completion of the reaction, the volatiles were removed in vacuo to obtain the crude. The crude was purified through silica gel column chromatography using 6% MeOH/$CH_2Cl_2$ to afford compound 537 (60 mg, 38%) as an off-white solid. TLC: 10% MeOH/$CH_2Cl_2$ ($R_f$: 0.3); $^1$H-NMR (DMSO-$d_6$, 400 MHz): δ 13.17 (br s, 1H), 10.99 (s, 1H), 8.02 (s, 1H), 7.97 (d, J=8.0 Hz, 1H), 7.82 (d, J=8.0 Hz, 1H), 7.79 (s, 1H), 7.70-7.65 (m, 2H), 3.86 (s, 3H).

Synthesis of Methyl 8-((2-cyclohexylethyl) carbamoyl)-11-oxo-10, 11-dihydrodibenzo [b,f] [1,4] thiazepine-3-carboxylate (538)

To a stirred solution of compound 537 (60 mg, 0.18 mmol) in DMF (2.4 mL) under inert atmosphere were added 2-cyclohexylethan-1-amine 261 (28 mg, 0.21 mmol), HOBt (37 mg, 0.27 mmol), EDCI. HCl (52 mg, 0.27 mmol), diisopropyl ethyl amine (0.08 mL, 0.36 mmol) at RT and stirred for 16 h. The reaction was monitored by TLC; after completion of the reaction, the reaction mixture was diluted with water (20 mL). The obtained solid was filtered and dried in vacuo to afford compound 538 (45 mg, 56%) as an off-white solid. TLC: 10% MeOH/$CH_2Cl_2$ ($R_f$: 0.6); $^1$H-NMR (DMSO-$d_6$, 400 MHz): δ 10.94 (s, 1H), 8.46-8.45 (m, 1H), 8.02 (s, 1H), 7.97 (d, J=8.0 Hz, 1H), 7.81 (d, J=8.0 Hz, 1H), 7.68 (d, J=7.6 Hz, 2H), 7.57 (d, J=8.4 Hz, 1H), 3.87 (s, 3H), 3.26-3.21 (m, 2H), 1.70-1.62 (m, 5H), 1.40-1.35 (m, 2H), 1.26-1.09 (m, 4H), 0.91-0.83 (m, 2H).

Synthesis of 8-((2-cyclohexylethyl) carbamoyl)-11-oxo-10, 11-dihydrodibenzo [b, f] [1,4] thiazepine-3-carboxylic acid (1282)

To a stirred solution of compound 538 (125 mg, 0.28 mmol) in THF:$H_2O$ (4:1, 5 mL) was added lithium hydroxide monohydrate (59.9 mg, 1.42 mmol) at RT and stirred for 5 h. The reaction was monitored by TLC; after completion of the reaction, the volatiles were removed in vacuo to obtain the crude. The crude was diluted with water (20 mL), neutralized with HCl, the obtained solid was filtered and dried in vacuo to afford 1282 (90 mg, 74%) as white solid. TLC: 10% MeOH/$CH_2Cl_2$ ($R_f$: 0.3); $^1$H-NMR (DMSO-$d_6$, 400 MHz): δ 13.44 (br s, 1H), 10.92 (s, 1H), 8.45 (t, J=5.6 Hz, 1H), 8.00 (s, 1H), 7.95 (d, J=8.0 Hz, 1H), 7.79 (d, J=8.0 Hz, 1H), 7.68-7.66 (m, 2H), 7.58-7.56 (m, 1H), 3.26-3.21 (m, 2H), 1.70-1.58 (m, 5H), 1.40-1.35 (m, 2H), 1.30-1.22 (m, 4H), 0.91-0.83 (m, 2H). LC-MS: 99.29%; 425.9 (M$^+$+1); (column; X-Select CSH C-18, (50×3.0 mm, 3.5 μm); RT 4.40 min. 0.05% TFA (Aq): ACN; 0.8 mL/min); UPLC (purity): 98.94%; (column: Acquity BEH C-18 (50×2.1 mm, 1.7μ); RT 2.32 min. ACN: 0.025% TFA (Aq); 0.5 mL/min).

Synthesis of N-(2-cyclohexylethyl)-N$^3$-methyl-11-oxo-10, 11-dihydrodibenzo [b, f] [1,4] thiazepine-3, 8-dicarboxamide (1277)

To a stirred solution of 1282 (30 mg, 0.07 mmol) in DMF (1.2 mL) under inert atmosphere were added methyl amine 306 (2 M in THF, 0.07 mL, 0.14 mmol), HATU (54.7 mg, 0.14 mmol), diisopropyl ethyl amine (0.05 mL, 0.28 mmol) at 0° C.; warmed to RT and stirred for 16 h. The reaction was monitored by TLC; after completion of the reaction, the reaction mixture was diluted with ice water (10 mL). The obtained solid was filtered, washed with EtOAc (2×5 mL) and dried in vacuo to afford 1277 (11 mg, 35%) as white solid. TLC: 7% MeOH/$CH_2Cl_2$ ($R_f$: 0.8); $^1$H-NMR (DMSO-$d_6$, 400 MHz): δ 10.86 (s, 1H), 8.63-8.62 (m, 1H), 8.44 (t, J=5.2 Hz, 1H), 7.95 (s, 1H), 7.85 (d, J=8.0 Hz, 1H), 7.75 (d, J=8.4 Hz, 1H), 7.65 (d, J=8.4 Hz, 2H), 7.58-7.55 (m, 1H), 3.26-3.21 (m, 2H), 2.77 (s, 3H), 1.70-1.58 (m, 5H), 1.40-1.35 (m, 2H), 1.26-1.14 (m, 4H), 0.91-0.83 (m, 2H); LC-MS: 94.12%; 438.8 (M$^+$+1); (column: X-Select CSH C-18, (50×3.0 mm, 3.5 μm); RT 4.05 min. 0.05% TFA (Aq): ACN; 0.8 mL/min); UPLC (purity): 98.69%; (column: Acquity BEH C-18 (50×2.1 mm, 1.7μ); RT 2.28 min. ACN: 0.025% TFA (Aq); 0.5 mL/min).

Example 49: Synthesis of Compound 1278

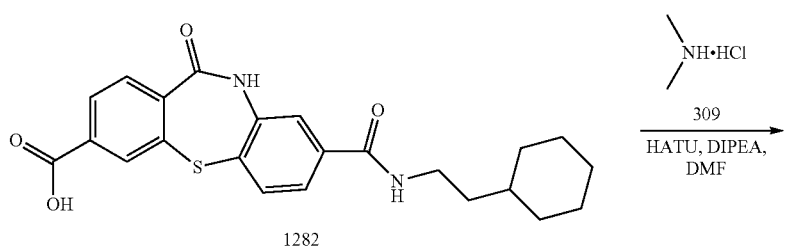

1282

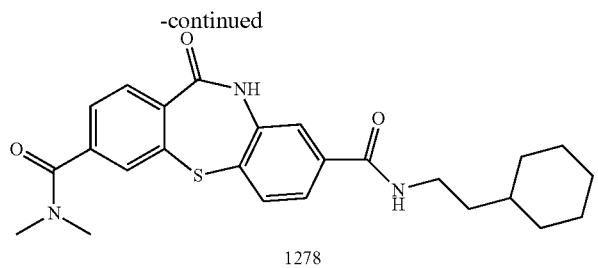

1278

Synthesis of N-(2-cyclohexylethyl)-N³,N³-dimethyl-11-oxo-10, 11-dihydrodibenzo [b,f] [1,4] thiazepine-3, 8-dicarboxamide (1278)

To a stirred solution of 1282 (40 mg, 0.09 mmol) in DMF (2 mL) under inert atmosphere were added dimethylamine hydrochloride (23 mg, 0.28 mmol), HATU (73 mg, 0.18 mmol), diisopropyl ethyl amine (0.09 mL, 0.47 mmol) at 0° C.; warmed to RT and stirred for 16 h. The reaction was monitored by TLC; after completion of the reaction, the reaction mixture was diluted with water (15 mL). The obtained solid was filtered, triturated with EtOAc (2×5 mL) and dried in vacuo to afford 1278 (19 mg, 48%) as an off-white solid. TLC: 5% MeOH/CH$_2$Cl$_2$ (R$_f$: 0.6); $^1$H-NMR (DMSO-d$_6$, 400 MHz): δ 10.84 (s, 1H), 8.44 (t, J=5.2 Hz, 1H), 7.72 (d, J=8.0 Hz, 1H), 7.67-7.63 (m, 2H), 7.58-7.47 (m, 2H), 7.45 (d, J=8.0 Hz, 1H), 3.27-3.22 (m, 2H), 2.96 (s, 3H), 2.88 (s, 3H), 1.70-1.58 (m, 5H), 1.41-1.35 (m, 2H), 1.28-1.26 (m, 1H), 1.25-1.14 (m, 3H), 0.91-0.83 (m, 2H); LC-MS: 98.41%; 452.7 (M$^+$+1); (column; X-Select CSH C-18, (50×3.0 mm, 3.5 μm); RT 4.11 min. 0.05% TFA (Aq): ACN; 0.8 mL/min); UPLC (purity): 99.60%; (column: Acquity BEH C-18 (50×2.1 mm, 1.7μ); RT 2.33 min. ACN: 0.025% TFA (Aq); 0.5 mL/min).

Example 50: Synthesis of Compounds 1280 and 1281

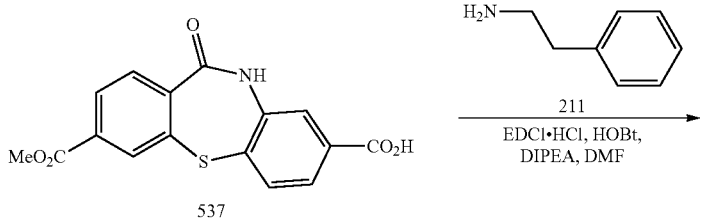

537

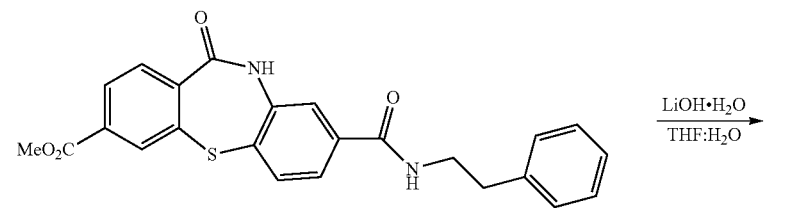

539

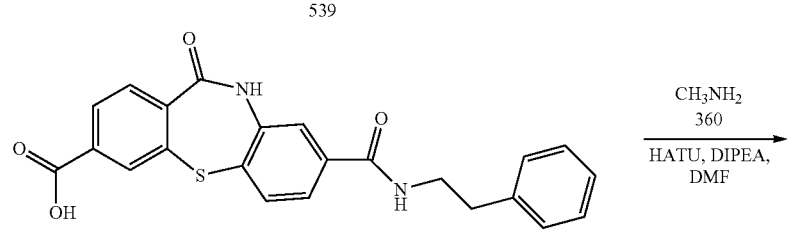

540

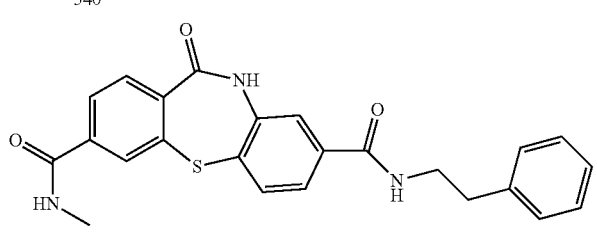

1280

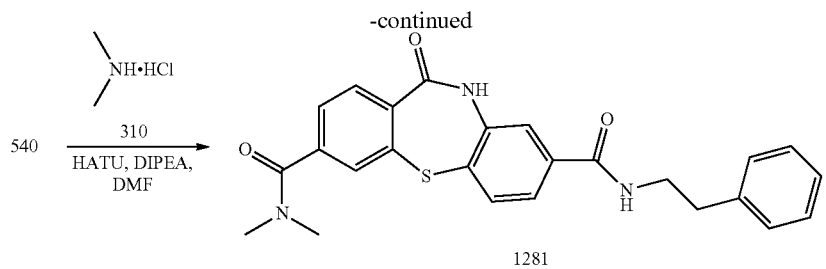

Synthesis of Methyl 11-oxo-8-(phenethylcarbamoyl)-10, 11-dihydrodibenzo [b,f] [1,4] thiazepine-3-carboxylate (539)

To a stirred solution of compound 537 (75 mg, 0.22 mmol) in DMF (3 mL) under inert atmosphere were added 2-phenylethan-1-amine 211 (30 mg, 0.25 mmol), HOBt (46 mg, 0.34 mmol), EDCI. HCl (65 mg, 0.34 mmol), diisopropyl ethyl amine (0.08 mL, 0.45 mmol) at 0° C.; warmed to RT and stirred for 16 h. The reaction was monitored by TLC; after completion of the reaction, the reaction mixture was diluted with ice water (20 mL). The obtained solid was filtered, washed with 20% EtOAc/Hexanes (2×5 mL) and dried in vacuo to afford compound 539 (80 mg, 81%) as white solid. TLC: 7% MeOH/CH$_2$Cl$_2$ (R$_f$: 0.8); $^1$H-NMR (DMSO-d$_6$, 400 MHz): δ 10.96 (s, 1H), 8.61 (t, J=5.6 Hz, 1H), 8.02 (s, 1H), 7.97 (d, J=8.0 Hz, 1H), 7.82 (d, J=8.4 Hz, 1H), 7.68 (d, J=8.0 Hz, 2H), 7.57-7.54 (m, 1H), 7.29-7.25 (m, 2H), 7.22-7.16 (m, 3H), 3.87 (s, 3H), 3.47-3.42 (m, 2H), 2.80 (t, J=7.2 Hz, 2H).

Synthesis of 11-oxo-8-(phenethylcarbamoyl)-10, 11-dihydrodibenzo [b,f] [1,4] thiazepine-3-carboxylic acid (540)

To a stirred solution of compound 539 (80 mg, 0.18 mmol) in THF:H$_2$O (4:1, 3 mL) was added lithium hydroxide monohydrate (39 mg, 0.92 mmol) at RT and stirred for 5 h. The reaction was monitored by TLC; after completion of the reaction, the volatiles were removed in vacuo. The residue was diluted with water (15 mL), acidified with HCl, the obtained solid was filtered, washed with 20% EtOAc/hexanes (2×5 mL) and dried in vacuo to afford compound 540 (65 mg, 84%) as white solid. TLC: 10% MeOH/CH$_2$Cl$_2$ (R$_f$: 0.2); $^1$H-NMR (DMSO-d$_6$, 400 MHz): δ 13.44 (br s, 1H), 10.94 (s, 1H), 8.62 (t, J=5.6 Hz, 1H), 8.00 (s, 1H), 7.95 (d, J=8.0 Hz, 1H), 7.79 (d, J=8.0 Hz, 1H), 7.68 (d, J=8.0 Hz, 2H), 7.57-7.54 (m, 1H), 7.29-7.25 (m, 2H), 7.22-7.16 (m, 3H), 3.47-3.42 (m, 2H), 2.80 (t, J=7.2 Hz, 2H).

Synthesis of N$^3$-methyl-11-oxo-N$^8$-phenethyl-10, 11-dihydrodibenzo [b,f] [1,4] thiazepine-3, 8-dicarboxamide (1280)

To a stirred solution of compound 540 (35 mg, 0.08 mmol) in DMF (2 mL) under inert atmosphere were added methyl amine (2 M in THF, 0.24 mL, 0.50 mmol), HATU (130 mg, 0.32 mmol), diisopropyl ethyl amine (0.10 mL, 0.50 mmol) at 0° C.; warmed to RT and stirred for 44 h. The reaction was monitored by TLC; after completion of the reaction, the reaction mixture was diluted with ice water (15 mL). The obtained solid was filtered, washed with EtOAc (2×5 mL) and dried in vacuo to afford 1280 (12 mg, 28%) as white solid. TLC: 10% MeOH/CH$_2$Cl$_2$ (R$_f$: 0.4); $^1$H-NMR (DMSO-d$_6$, 400 MHz): δ 10.89 (s, 1H), 8.63-8.60 (m, 2H), 7.96 (s, 1H), 7.85 (d, J=8.0 Hz, 1H), 7.76 (d, J=8.0 Hz, 1H), 7.66-7.65 (m, 2H), 7.56-7.54 (m, 1H), 7.29-7.26 (m, 2H), 7.22-7.16 (m, 3H), 3.47-3.42 (m, 2H), 2.88-2.73 (m, 5H); LC-MS: 95.22%; 432.6 (M$^+$+1); (column; X-Select CSH C-18, (50×3.0 mm, 3.5 μm); RT 3.61 min. 0.05% TFA (Aq): ACN; 0.8 mL/min); UPLC (purity): 94.66%; (column: Acquity BEH C-18 (50×2.1 mm, 1.7 μm); RT 1.97 min. ACN: 0.025% TFA (Aq); 0.5 mL/min).

Synthesis of N$^3$,N$^3$-dimethyl-11-oxo-N$^8$-phenethyl-10, 11-dihydrodibenzo [b,f] [1,4] thiazepine-3, 8-dicarboxamide (1281)

To a stirred solution of 540 (30 mg, 0.07 mmol) in DMF (2 mL) under inert atmosphere were added dimethyl amine hydrochloride 310 (17.5 mg, 0.21 mmol), HATU (55.5 mg, 0.14 mmol), diisopropyl ethyl amine (0.07 mL, 0.35 mmol) at 0° C.; warmed to RT and stirred for 16 h. The reaction was monitored by TLC; after completion of the reaction, the reaction mixture was diluted with water (10 mL). The obtained solid was filtered, washed with EtOAc (2×5 mL) and dried in vacuo to afford 1281 (17 mg, 53%) as an off-white solid. TLC: 5% MeOH/CH$_2$Cl$_2$ (R$_f$: 0.6); $^1$H-NMR (DMSO-d$_6$, 400 MHz): δ 10.86 (s, 1H), 8.61 (t, J=5.2 Hz, 1H), 7.72 (d, J=8.0 Hz, 1H), 7.67-7.64 (m, 2H), 7.57-7.53 (m, 2H), 7.46 (d, J=8.0 Hz, 1H), 7.29-7.26 (m, 2H), 7.20-7.16 (m, 3H), 3.48-3.43 (m, 2H), 2.96 (s, 3H), 2.86 (s, 3H), 2.82-2.79 (m, 2H); LC-MS: 97.11%; 446.7 (M$^+$+1); (column; X-Select CSH C-18, (50×3.0 mm, 3.5 μm); RT 3.68 min. 0.05% TFA (Aq): ACN; 0.8 mL/min); UPLC (purity): 98.02%; (column: Acquity BEH C-18 (50×2.1 mm, 1.7μ); RT 2.03 min. ACN: 0.025% TFA (Aq); 0.5 mL/min).

Example 51: Synthesis of Compounds 1225 and 1224

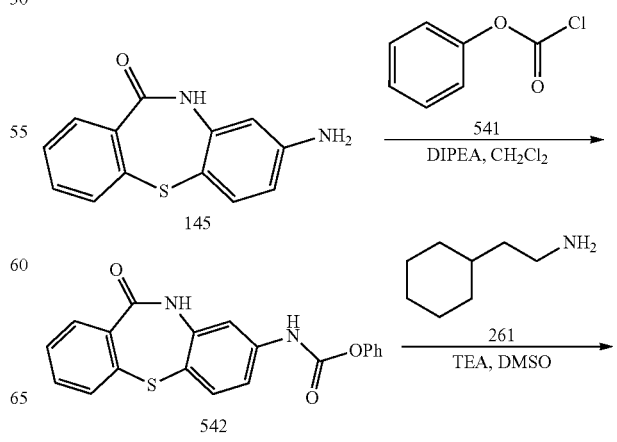

-continued

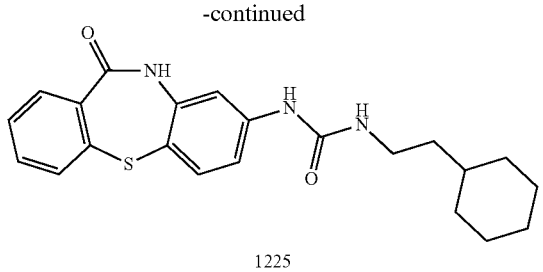

1225

Synthesis of Phenyl (11-oxo-10, 11-dihydrodibenzo [b,f] [1,4] thiazepin-8-yl) carbamate (542)

To a stirred solution of compound 145 (40 mg, 0.16 mmol) in CH$_2$Cl$_2$ (3 mL) under inert atmosphere were added diisopropyl ethyl amine (0.06 mL, 0.33 mmol), phenyl carbonochloridate 541 (28 mg, 0.18 mmol) at 0° C.; warmed to RT and stirred for 16 h. The reaction was monitored by TLC; after completion of the reaction, the reaction mixture was diluted with water (15 mL) and extracted with CH$_2$Cl$_2$ (2×25 mL). The combined organic extracts were dried over sodium sulfate, filtered and concentrated in vacuo to obtain the crude. The crude was triturated with 15% EtOAc/hexanes to afford compound 542 (50 mg, 83%) as an off-white solid. TLC: 70% EtOAc/Hexanes (R$_f$: 0.8); $^1$H-NMR (DMSO-d$_6$, 400 MHz): δ 10.73 (s, 1H), 10.45 (s, 1H), 7.68-7.65 (m, 1H), 7.52-7.40 (m, 7H), 7.28-7.24 (m, 2H), 7.21 (d, J=7.6 Hz, 2H).

Synthesis of 1-(2-cyclohexylethyl)-3-(11-oxo-10, 11-dihydrodibenzo [b,f] [1,4] thiazepin-8-yl) urea (1225)

To a stirred solution of compound 542 (50 mg, 0.13 mmol) in DMSO (3 mL) under inert atmosphere were added 2-cyclohexylethan-1-amine 161 (21 mg, 0.16 mmol), triethyl amine (0.04 mL, 0.27 mmol) at 0° C.; warmed to RT and stirred for 5 h. The reaction was monitored by TLC; after completion of the reaction, the reaction mixture was diluted with water (15 mL). The obtained solid was filtered, washed with EtOAc (2×5 mL) and dried in vacuo to afford 1225 (17 mg, 31%) as white solid. TLC: 5% MeOH/CH$_2$Cl$_2$ (R$_f$: 0.5); $^1$H-NMR (DMSO-d$_6$, 500 MHz): δ 10.58 (s, 1H), 8.58 (s, 1H), 7.64 (d, J=7.5 Hz, 1H), 7.48-7.40 (m, 3H), 7.34 (d, J=7.5 Hz, 2H), 7.13-7.11 (m, 1H), 6.10-6.07 (m, 1H), 3.08-3.04 (m, 2H), 1.67-1.57 (m, 5H), 1.31-1.11 (m, 6H), 0.86-0.84 (m, 2H); LC-MS: 95.28%; 396.4 (M$^+$+1); (column; X-Bridge C-18, (50×3.0 mm, 3.5 µm); RT 3.76 min. 0.05% TFA (Aq): ACN; 0.8 mL/min); UPLC (purity): 96.65%; (column: Acquity UPLC BEH C-18 (2.1×50 mm, 1.7 g); RT 2.65 min. ACN: 0.025% TFA (Aq); 0.5 mL/min).

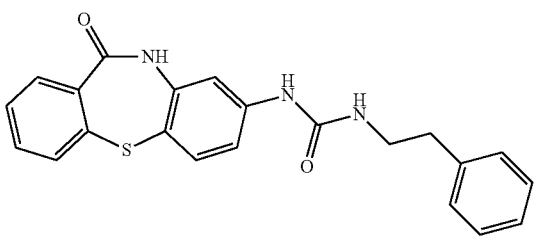

1224

In a similar manner 1224 (1-(11-oxo-10, 11-dihydrodibenzo [b,f] [1,4] thiazepin-8-yl)-3-phenethylurea) was prepared. Yield: 27% LC-MS: 390.3 (M$^+$+1); $^1$H-NMR (DMSO-d$_6$, 400 MHz): δ 10.59 (s, 1H), 8.69 (s, 1H), 7.65 (d, J=7.2 Hz, 1H), 7.49-7.41 (m, 3H), 7.35 (d, J=7.6 Hz, 2H), 7.29 (d, J=7.2 Hz, 2H), 7.22-7.13 (m, 4H), 6.14 (t, J=6.0 Hz, 1H), 3.30 (s, 2H), 2.73 (t, J=6.8 Hz, 2H).

Example 52: Synthesis of Compounds 1535 and 1536

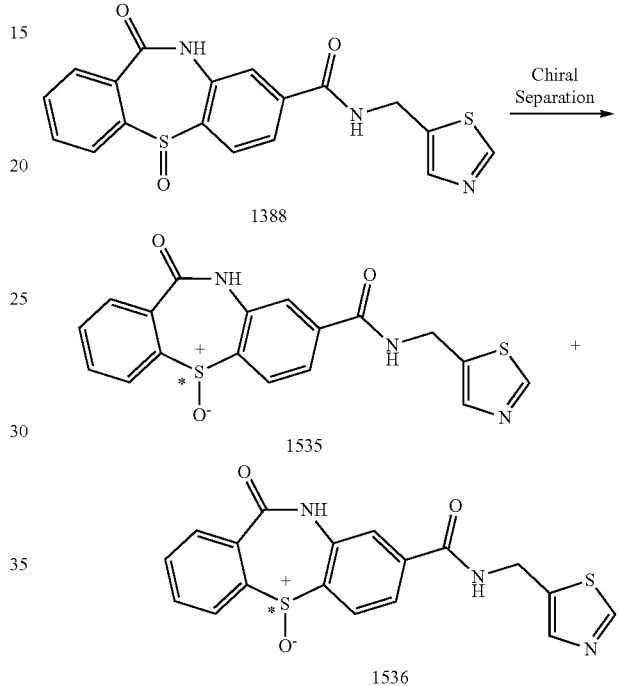

The racemic compound of 1388 (18 mg) was separated using a CHIRALPAK-IC column (250×20 mm×5 µm) (10 mg loading; 0.1% DEA in n-hexane: CH$_2$Cl$_2$: MeOH (50: 50) (A: B=25:75) as mobile phase) HPLC to afford 1535 (2.5 mg) and 1536 (2.5 mg) as off-white solids.

Compound 1535 Analytical Data (Fr-I):

LC-MS: 99.81%; 383.9 (M$^+$+1); (column; Ascentis Express C-18, (50×3.0 mm, 2.7 µm); RT 1.69 min. 0.025% Aq. TFA+5% ACN: ACN+5% 0.025% Aq. TFA, 1.2 mL/min). UPLC (purity): 96.76%; (column; Acquity UPLC BEH C-18 (50×2.1 mm, 1.7µ); RT 1.49 min. ACN: 0.025% TFA (Aq); 0.5 mL/min). Chiral HPLC: 99.16%, R$_t$=99.16 min (Chiralpak-IC, 250×4.6 mm, 5 µm); mobile phase (A) 0.1% DEA in n-Hexane (B) CH$_2$Cl$_2$: MeOH (50:50) (A:B:: 25:75); Flow Rate: 1.0 mL/min).

Compound 1536 Analytical Data (Fr-II):

LC-MS: 99.39%; 383.9 (M$^+$+1); (column; Ascentis Express C-18, (50×3.0 mm, 2.7 µm); RT 1.70 min. 0.025% Aq. TFA+5% ACN: ACN+5% 0.025% Aq. TFA, 1.2 mL/min). UPLC (purity): 99.56%; (column; Acquity UPLC BEH C-18 (50×2.1 mm, 1.7µ); RT 1.49 min. ACN: 0.025% TFA (Aq); 0.5 mL/min). Chiral HPLC: 98.30%, R$_t$=13.33 min (Chiralpak-IC, 250×4.6 mm, 5 µm); mobile phase (A) 0.1% DEA in n-Hexane (B) CH$_2$Cl$_2$: MeOH (50:50) (A:B:: 25:75); Flow Rate: 1.0 mL/min).

Example 53: Synthesis of Compound 1206

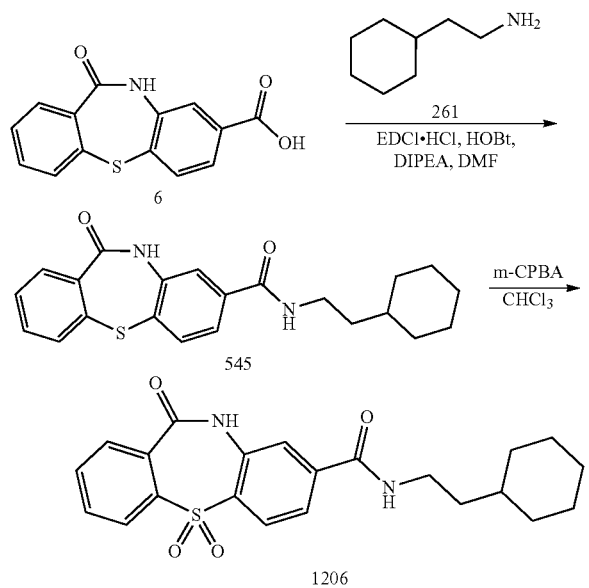

Synthesis of N-(2-cyclohexylethyl)-11-oxo-10,11-dihydrodibenzo [b,1] [1,4] thiazepine-8-carboxamide (545)

To a stirred solution of 6 (100 mg, 0.36 mmol) in DMF (6 mL) under argon atmosphere were added EDCI.HCl (105 mg, 0.54 mmol), HOBt (74 mg, 0.54 mmol), 2-cyclohexylethan-1-amine 261 (56 mg, 0.44 mmol), and diisopropyl ethyl amine (95 mg, 0.73 mmol) at 0-5° C.; warmed to RT and stirred for 16 h. The reaction was monitored by TLC; after completion of the reaction, the volatiles were removed in vacuo. The residue was diluted with water (20 mL), filtered and washed with water (2×5 mL) to obtain the crude. The crude was triturated with EtOAc (2×5 mL) to afford 545 (70 mg, 50%) as white solid. TLC: 5% MeOH/CH$_2$Cl$_2$ (R$_f$: 0.5); $^1$H-NMR (DMSO-d$_6$, 400 MHz): δ 10.75 (s, 1H), 8.43 (t, J=5.6 Hz, 1H), 7.69-7.62 (m, 3H), 7.56-7.43 (m, 4H), 3.26-3.21 (m, 2H), 1.70-1.58 (m, 5H), 1.40-1.35 (m, 2H), 1.28-1.09 (m, 4H), 0.91-0.83 (m, 2H).

Synthesis of N-(2-cyclohexylethyl)-11-oxo-10,11-dihydrodibenzo [b,f] [1,4] thiazepine-8-carboxamide 5, 5-dioxide (1206)

To a stirred solution of 545 (40 mg, 0.10 mmol) in chloroform (20 mL) under inert atmosphere was added m-chloro perbenzoic acid (36.3 mg, 0.21 mmol) at RT and stirred for 16 h. The reaction was monitored by TLC; after completion of the reaction, the reaction mixture was diluted with saturated sodium bicarbonate solution (15 mL) and extracted with CH$_2$Cl$_2$ (2×20 mL). The combined organic extracts were washed with water (20 mL), dried over sodium sulfate, filtered and concentrated in vacuo to obtain the crude. The crude was purified through silica gel column chromatography using 30% EtOAc/hexanes to afford 1206 (16 mg, 37%) as white solid. TLC: 5% MeOH/CH$_2$Cl$_2$ (R$_f$: 0.4); $^1$H-NMR (DMSO-d$_6$, 400 MHz): δ 11.49 (s, 1H), 8.63 (t, J=4.8 Hz, 1H), 8.04-7.96 (m, 3H), 7.91-7.83 (m, 2H), 7.77 (t, J=6.4 Hz, 2H), 3.25-3.24 (m, 2H), 1.71-1.58 (m, 5H), 1.42-1.37 (m, 2H), 1.28-1.14 (m, 4H), 0.92-0.84 (m, 2H); LC-MS: 97.31%; 413.2 (M$^+$+1); (column; X-bridge C-18, (50×3.0 mm, 3.5 µm); RT 3.78 min. 0.05% TFA in water: ACN; 0.8 mL/min); UPLC (purity): 96.73%; (column: Acquity UPLC BEH C-18 (2.1×50 mm, 1.7µ); RT 2.52 min. ACN: 0.025% TFA (Aq); 0.5 mL/min).

Example 54: Synthesis of Compound 1656

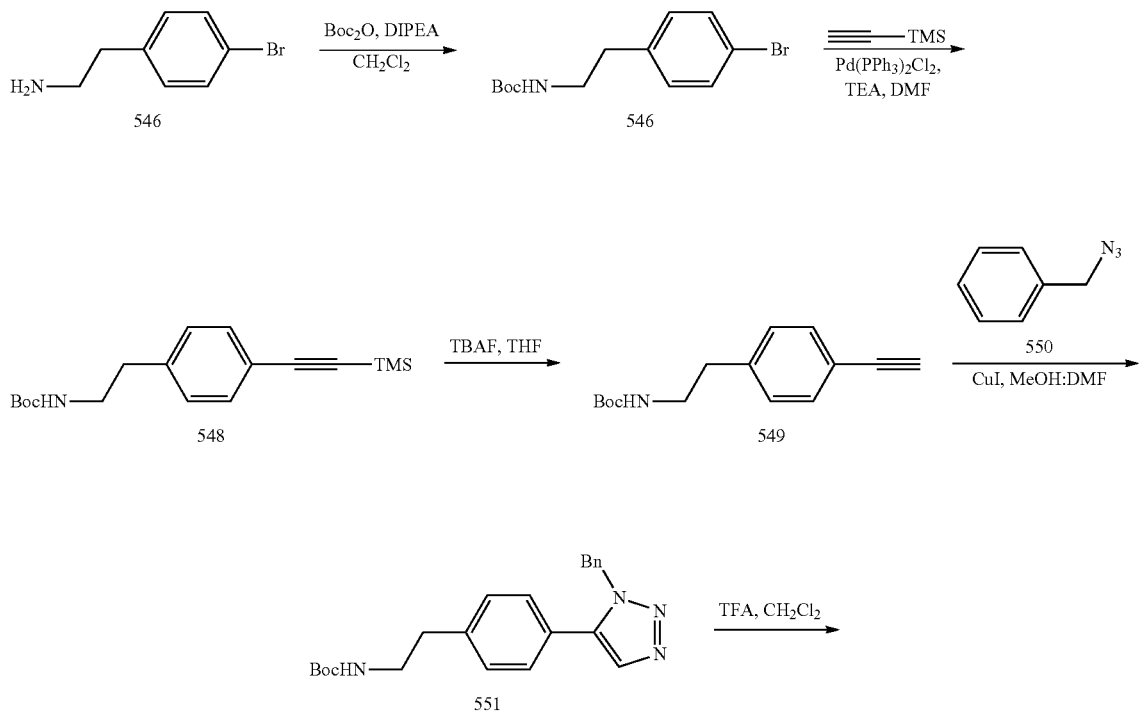

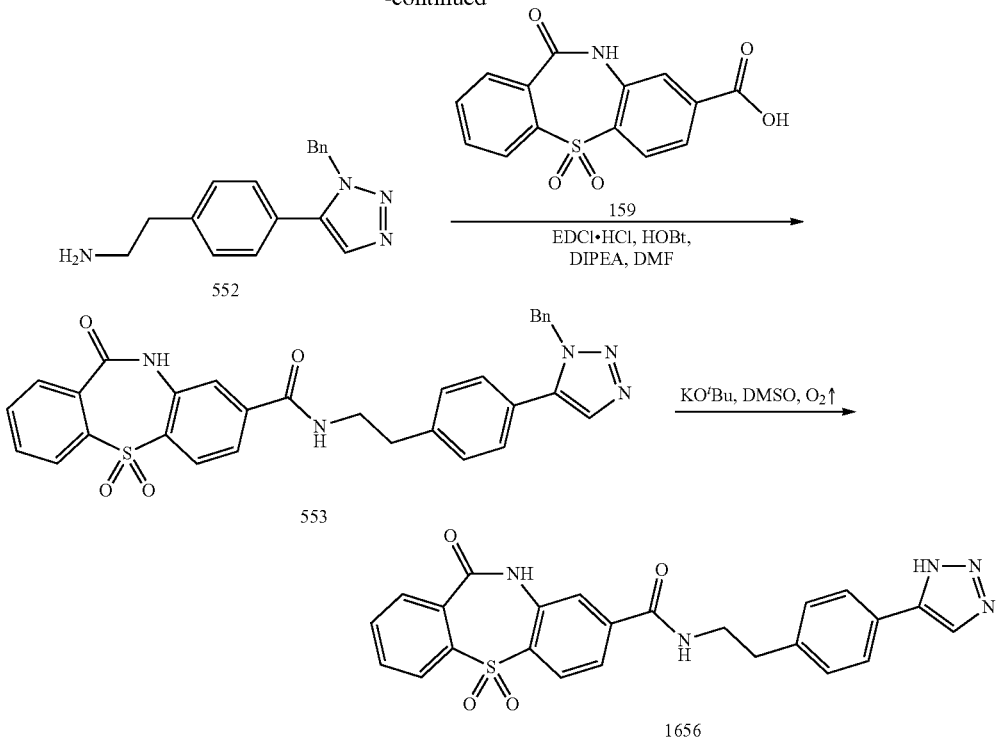

Synthesis of Tert-Butyl (4-bromophenethyl) carbamate (547)

To a stirred solution of 2-(4-bromophenyl) ethan-1-amine 546 (500 mg, 2.50 mmol) in $CH_2Cl_2$ (5 mL) under argon atmosphere were added Boc-anhydride (594 mg, 2.75 mmol), diisopropyl ethyl amine (1 mL, 7.50 mmol) at RT and stirred for 4 h. The reaction was monitored by TLC; after completion of the reaction, the reaction mixture was diluted with water (25 mL) and extracted with $CH_2Cl_2$ (2×35 mL). The combined organic extracts were washed with water (25 mL), dried over sodium sulfate, filtered and concentrated in vacuo to obtain the crude. The crude was purified through silica gel column chromatography using 5-8% EtOAc/hexanes to afford compound 547 (500 mg, 65%) as white solid. TLC: 10% EtOAc/hexanes ($R_f$: 0.5); $^1$H-NMR (DMSO-$d_6$, 400 MHz): δ 7.46 (d, J=8.0 Hz, 2H), 7.12 (d, J=8.0 Hz, 2H), 6.86-6.82 (m, 1H), 3.12-3.08 (m, 2H), 2.68-2.64 (m, 2H), 1.32 (s, 9H).

Synthesis of Tert-Butyl (4-((trimethylsilyl) ethynyl) phenethyl) carbamate (548)

To a stirred solution of compound 547 (500 mg, 1.66 mmol) in DMF (10 mL) under argon atmosphere were added ethynyltrimethylsilane (1.8 mL, 16.66 mmol), triethyl amine (2.32 mL, 16.66 mmol) and purged under argon for 15 min. To this were added Pd(PPh$_3$)$_2$Cl$_2$ (118 mg, 0.16 mmol), copper iodide (33 mg, 0.16 mmol) and purged under argon for 15 min; heated to 70° C. and stirred for 48 h. The reaction was monitored by TLC; after completion of the reaction, the volatiles were removed in vacuo to obtain the crude which was purified through silica gel column chromatography using 10% EtOAc/hexanes to afford compound 548 (500 mg, 95%) as brown syrup. TLC: 10% EtOAc/hexanes ($R_f$: 0.6); $^1$H-NMR (DMSO-$d_6$, 400 MHz): δ 7.38 (d, J=8.0 Hz, 2H), 7.18 (d, J=8.0 Hz, 2H), 6.85 (t, J=7.2 Hz, 1H), 3.16-3.11 (m, 2H), 2.70-2.66 (m, 2H), 1.34 (s, 9H), 0.23 (s, 9H).

Synthesis of Tert-Butyl (4-ethynylphenethyl) carbamate (549)

To a stirred solution of compound 548 (500 mg, 1.70 mmol) in THF (5 mL) under argon atmosphere was added TBAF (2.08 mL, 2.08 mmol) in THF (3 mL) at RT and stirred for 4 h. The reaction was monitored by TLC; after completion of the reaction, the volatiles were removed in vacuo to obtain the crude which was purified through silica gel column chromatography using 5-10% EtOAc/hexanes to afford compound 549 (450 mg, 95%) as brown syrup. TLC: 10% EtOAc/hexanes ($R_f$: 0.4); $^1$H-NMR (DMSO-$d_6$, 500 MHz): δ 7.39 (d, J=7.5 Hz, 2H), 7.20 (d, J=7.5 Hz, 2H), 6.87-6.85 (m, 1H), 4.10 (s, 1H), 3.15-3.12 (m, 2H), 2.71-2.69 (m, 2H), 1.30 (s, 9H).

Synthesis of Tert-Butyl (4-(1-benzyl-1H-1, 2, 3-triazol-5-yl) phenethyl) carbamate (551)

To a stirred solution of compound 549 (200 mg, 0.82 mmol) in MeOH: DMF (1:1, 20 mL) under argon atmosphere were added (azidomethyl) benzene 550 (410 mg, 3.06 mmol), copper iodide (202 mg, 1.02 mmol) at RT; heated to reflux and stirred for 18 h. The reaction was monitored by TLC; after completion of the reaction, the volatiles were removed in vacuo to obtain the crude which was purified through silica gel column chromatography using 30% EtOAc/hexanes to afford compound 551 (200 mg, 68%) as white solid. TLC: 30% EtOAc/hexanes ($R_f$: 0.3); $^1$H-NMR (DMSO-$d_6$, 500 MHz): δ 8.59 (s, 1H), 7.75 (d, J=8.5 Hz, 2H), 7.41-7.34 (m, 5H), 7.25 (d, J=8.0 Hz, 2H), 6.90-6.88 (m, 1H), 5.64 (s, 2H), 3.17-3.13 (m, 2H), 2.70 (t, J=7.5 Hz, 2H), 1.36 (s, 9H).

Synthesis of 2-(4-(1-benzyl-1H-1, 2, 3-triazol-5-yl) phenyl) ethan-1-amine (552)

To a stirred solution of compound 551 (190 mg, 0.50 mmol) in CH$_2$Cl$_2$ (4 mL) under argon atmosphere was added trifluoro acetic acid (1 mL) at RT and stirred for 3 h. The reaction was monitored by TLC; after completion of the reaction, the volatiles were removed in vacuo to obtain the crude to obtain compound 552 (180 mg, crude) as dark brown syrup which was carried to the next step without any purification. TLC: 100% EtOAc (R$_f$: 0.2); $^1$H-NMR (DMSO-d$_6$, 400 MHz): δ 8.61 (s, 1H), 7.81 (d, J=8.0 Hz, 2H), 7.78-7.76 (m, 3H), 7.39-7.32 (m, 6H), 5.64 (s, 2H), 3.09-3.04 (m, 2H), 2.87 (t, J=7.6 Hz, 2H).

Synthesis of N-(4-(1-benzyl-1H-1, 2, 3-triazol-5-yl) phenethyl)-11-oxo-10, 11-dihydrodibenzo [b,f] [1,4] thiazepine-8-carboxamide 5, 5-dioxide (553)

To a stirred solution compound 552 (200 mg, 0.66 mmol) in DMF (10 mL) under argon atmosphere were added EDCI.HCl (189 mg, 0.98 mmol), HOBt (189 mg, 0.98 mmol), compound 6 (297 mg, 0.79 mmol), diisopropyl ethyl amine (0.35 mL, 1.98 mmol) at 0° C.; warmed to RT and stirred for 16 h. The reaction was monitored by TLC; after completion of the reaction, the reaction mixture was diluted with EtOAc (2×50 mL) washed with water (50 mL), brine, dried over sodium sulfate, filtered and concentrated in vacuo to obtain the crude. The crude compound was purified through column chromatography using 2% MeOH/CH$_2$Cl$_2$ to afford compound 553 (180 mg, 49%) as an off-white solid. TLC: 5% MeOH/CH$_2$Cl$_2$ (R$_f$: 0.5); $^1$H NMR (DMSO-d$_6$, 400 MHz): δ 11.46 (br s, 1H), 8.80 (t, J=5.5 Hz, 1H), 8.56 (s, 1H), 8.03 (d, J=8.3 Hz, 1H), 8.00-7.95 (m, 2H), 7.92-7.83 (m, 2H), 7.79 (s, 1H), 7.75 (d, J=8.2 Hz, 3H), 7.42-7.31 (m, 5H), 7.29 (d, J=8.3 Hz, 2H), 5.63 (s, 2H), 3.50 (q, J=6.8 Hz, 2H), 2.85 (t, J=7.2 Hz, 2H).

Synthesis of N-(4-(1H-1, 2, 3-triazol-5-yl) phenethyl)-11-oxo-10, 11-dihydrodibenzo [b,f] [1,4] thiazepine-8-carboxamide 5, 5-dioxide (1656)

To a stirred solution of compound 553 (180 mg, 0.31 mmol) in DMSO (10 mL) under argon atmosphere was added potassium tertiary butoxide (1 M in THF, 2.5 mL, 2.55 mmol) at RT. The reaction mixture was stirred under oxygen atmosphere (balloon pressure) for 24 h. The reaction was monitored by TLC; after completion of the reaction, the reaction mixture was diluted with water (5 mL) and extracted with EtOAc (3×50 mL). The combined organic extracts were dried over sodium sulfate, filtered and concentrated in vacuo to obtain the crude. The crude compound was purified through column chromatography using 2% MeOH/CH$_2$Cl$_2$, lyophilized and washed EtOAc (5 mL), filtered, washed with n-pentane (5 mL) and dried in vacuo to afford 1656 (20 mg, 13%) as white solid. TLC: 5% MeOH/CH$_2$Cl$_2$ (R$_f$: 0.3); 1H NMR (DMSO-d$_6$, 400 MHz): δ 14.91 (br s, 1H), 11.52 (br s, 1H), 8.81 (t, J=5.5 Hz, 1H), 8.21 (br s, 1H), 8.04 (d, J=8.3 Hz, 1H), 8.01-7.95 (m, 2H), 7.92-7.85 (m, 2H), 7.82-7.73 (m, 4H), 7.31 (d, J=7.9 Hz, 2H), 3.51 (q, J=6.6 Hz, 2H), 2.86 (t, J=7.1 Hz, 2H); LC-MS: 96.04%; 473.9 (M$^+$+1); (column; Ascentis Express C-18, (50×3.0 mm, 2.7 μm); RT 2.01 min. 0.025% Aq. TFA+5% ACN: ACN+5% 0.025% Aq. TFA, 1.2 mL/min). HPLC (purity): 95.54%; (column; Zorbax SB C-18 (150×4.6 mm, 3.5 μm); RT 7.59 min. ACN: 0.05% TFA (Aq); 1.0 mL/min).

Example 55: Synthesis of Compounds from Compound 575 Using Various Commercially Available Amines Readily available acids similar to 575, 576 and 577 were converted to the desired compounds using commercially available amines employing Procedures A and B and the results are captured in Tables 5 and 6.

Carbon Bridged Compounds:

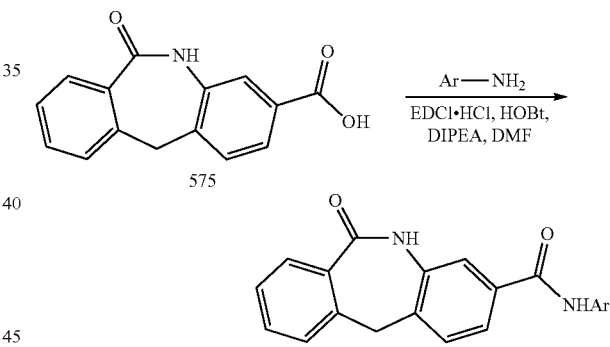

TABLE 5

Synthesis of compounds from compound 575 using various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| 1591 | 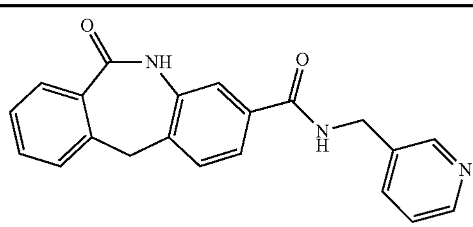 | A, 575, 218 (RT 12 h) | 44 | 343.9 (M$^+$ + 1) | 343.13 for C$_{21}$H$_{17}$N$_3$O$_2$ | $^1$H-NMR (DMSO-d$_6$, 400 MHz): δ 9.27 (t, J = 5.1 Hz, 1H), 8.96 (s, 1H), 7.96 (s, 1H), 7.82 (s, 1H), 7.74-7.70 (m, 1H), 7.68-7.61 (m, 2H), 7.54-7.49 (m, 1H), 7.45-7.38 (m, 2H), 4.67 (t, J = 5.4 Hz, |

TABLE 5-continued

Synthesis of compounds from compound 575 using various commercially available amines

| No. | Structure | Procedure, Intermediate, Amine | Rx. Yield (%) | Mass Spec. Found | Mass Spec. Calculated | ¹H-NMR |
|---|---|---|---|---|---|---|
| | | | | | | 2H), 3.54 (s, 3H); |
| 1198 | 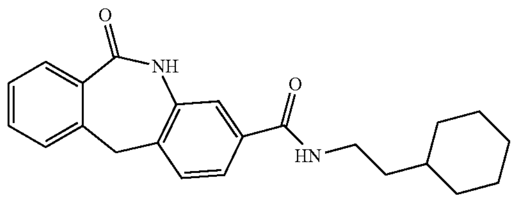 [SMILES: O=C(NCCC1CCCCC1)c1ccc2c(c1)NC(=O)c1ccccc1C2] | A, 575 | 64 | 363.2 (M⁺ + 1); | | (DMSO-d$_6$, 400 MHz): δ 10.51 (s, 1H), 8.30-8.29 (m, 1H), 7.70 (d, J = 8.0 Hz, 1H), 7.56 (s, 1H), 7.51-7.46 (m, 2H), 7.41-7.31 (m, 3H), 3.94 (s, 2H), 3.23 (d, J = 6.4 Hz, 2H), 1.70-1.62 (m, 5H), 1.39-1.37 (m, 2H), 1.26-1.14 (m, 4H), 0.91-0.86 (m, 2H); |
| 1576 | | A, 575, 212 (RT 12 h) | 44 | 344.9 (M⁺ + 1) | 344.13 for C$_{20}$H$_{16}$N$_4$O$_2$ | ¹H-NMR (DMSO-d$_6$, 400 MHz): δ 10.52 (s, 1H), 9.10-9.01 (m, 2H), 8.74 (s, 2H), 7.70 (d, J = 7.5 Hz, 1H), 7.62 (s, 1H), 7.57 (d, J = 7.9 Hz, 1H), 7.51-7.43 (m, 2H), 7.38 (d, J = 7.3 Hz, 1H), 7.33 (t, J = 7.5 Hz, 1H), 4.46 (d, J = 5.5 Hz, 2H), 3.96 (s, 2H); |
| 1577 | | A, 575, 213 | 26 | 350.0 (M⁺ + 1) | 349.09 for C$_{19}$H$_{15}$N$_3$O$_2$S | ¹H-NMR (DMSO-d$_6$, 400 MHz): δ 10.52 (s, 1H), 9.10 (t, J = 5.8 Hz, 1H), 8.95 (s, 1H), 7.79 (s, 1H), 7.70 (dd, J = 7.7, 1.1 Hz, 1H), 7.61 (s, 1H), 7.54 (dd, J = 7.9, 1.6 Hz, 1H), 7.48 (td, J = 8.8, 1.8 Hz, 1H), 7.43 (d, J = 7.9 Hz, 1H), 7.38 (d, J = 6.9 Hz, 1H), 7.33 (td, J = 7.6, 1.6 Hz, 1H), 4.64 (d, J = 5.7 Hz, 2H), 3.96 (s, 2H); |

Oxygen-Bridged Compounds:

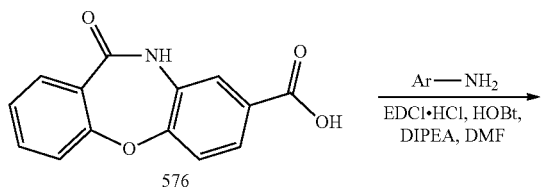

576

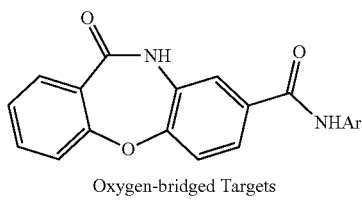

Oxygen-bridged Targets

TABLE 6

Synthesis of compounds from compound 576 and various commercially available amines

| No. | Structure | Procedure, Intermediate, Amine | Rx. Yield (%) | Mass Spec. Found | Mass Spec. Calculated | $^1$H-NMR |
|---|---|---|---|---|---|---|
| 1593 | 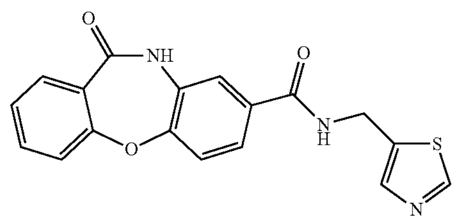 [SMILES: O=C(NCc1cncs1)c1ccc2c(c1)NC(=O)c1ccccc1O2] | B, 576, 213 | 38 | 351.9 ($M^+ + 1$) | 351.07 for $C_{18}H_{13}N_3O_3S$ | $^1$H-NMR (DMSO-$d_6$, 400 MHz): δ 10.63 (s, 1H), 9.17 (t, J = 5.8 Hz, 1H), 8.96 (s, 1H), 7.82-7.76 (m, 2H), 7.68 (s, 1H), 7.66-7.59 (m, 2H), 7.42 (d, J = 8.4 Hz, 1H), 7.38-7.31 (m, 2H), 4.65 (d, J = 5.6 Hz, 2H) |
| 1594 | 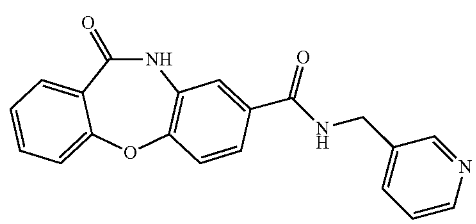 | A, 576, 218 | 55 | 345.9 ($M^+ + 1$) | 345.11 for $C_{20}H_{15}N_3O_3$ | $^1$H-NMR (DMSO-$d_6$, 400 MHz): δ 10.62 (s, 1H), 9.07 (t, J = 5.8 Hz, 1H), 8.53 (s, 1H), 8.45 (d, J = 4.1 Hz, 1H), 7.78 (dd, J = 7.7, 1.6 Hz, 1H), 7.72-7.60 (m, 4H), 7.43 (d, J = 8.4 Hz, 1H), 7.39-7.31 (m, 3H), 4.47 (d, J = 5.1 Hz, 2H) |
| 1595 | 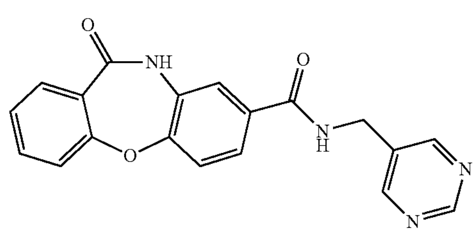 [SMILES: O=C(NCc1cncnc1)c1ccc2c(c1)NC(=O)c1ccccc1O2] | A, 576, 212 | 66 | 346.9 ($M^+ + 1$) | 346.11 for $C_{19}H_{14}N_4O_3$ | $^1$H-NMR (DMSO-$d_6$, 400 MHz): δ 10.62 (s, 1H), 9.13-9.05 (m, 2H), 8.75 (s, 2H), 7.78 (dd, J = 7.7, 1.6 Hz, 1H), 7.68 (s, 1H), 7.66-7.60 (m, 2H), 7.43 (d, J = 8.4 Hz, 1H), 7.39-7.30 (m, 2H), 4.48 (d, J = 5.6 Hz, 2H) |

Nitrogen-Bridged Compounds:

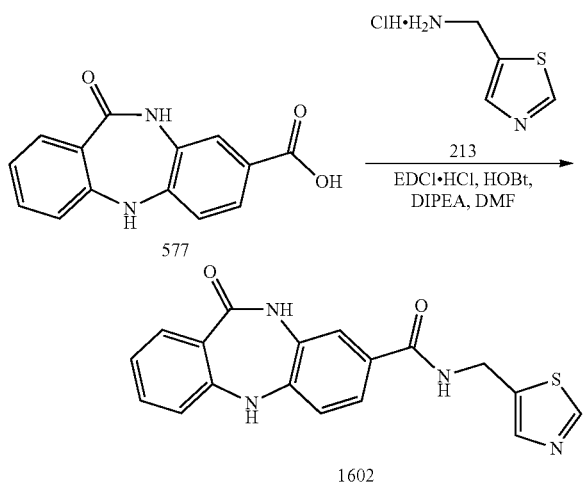

Synthesis of 11-oxo-N-(thiazol-5-ylmethyl)-10,11-dihydro-5H-dibenzo [b,e] [1,4] diazepine-8-carboxamide (1602)

Using Procedure A the title compound was prepared using compound 577 (35 mg, 0.13 mmol) and thiazol-5-ylmethanamine hydrochloride 213 (20 mg, 0.13 mmol) and diisopropyl ethyl amine (0.05 mL, 0.27 mmol) and was obtained in 31% yield as an off-white solid; TLC: 5% MeOH/CH$_2$Cl$_2$ (R$_f$: 0.5); $^1$H-NMR (DMSO-d$_6$, 400 MHz): δ 9.89 (s, 1H), 8.99-8.94 (m, 2H), 8.15 (s, 1H), 7.79 (s, 1H), 7.69 (dd, J=7.8, 1.3 Hz, 1H), 7.50-7.42 (m, 2H), 7.38-7.32 (m, 1H), 7.00 (dd, J=10.9, 8.3 Hz, 2H), 6.91 (t, J=7.4 Hz, 1H), 4.63 (d, J=5.6 Hz, 2H); LC-MS: 93.15%; 351.0 (M$^+$+1); column; Ascentis Express C18, (50×3.0 mm, 2.7 µm); RT 1.76 min. 0.025% Aq. TFA+5% ACN: ACN+5% 0.025% Aq. TFA, 1.2 mL/min); UPLC (purity): 93.21%; (column; Acquity BEH C-18 (50×2.1 mm, 1.7µ); RT 1.57 min. ACN: 0.025% TFA (Aq); 0.5 mL/min).

Example 56: Assay Measuring Activity of Compounds on Viral Production in and on Viability of AD38 Cells AD38 cells grown in a 175 cm flask with "Growth Medium" (DMEM/F12 (1:1) (cat#SH30023.01, Hyclone, 1×Pen/step (cat#: 30-002-CL, Mediatech, Inc), 10% FBS (cat#: 101, Tissue Culture Biologics), 250 µg/mL G418 (cat#: 30-234-CR, Mediatech, Inc), 1 µg/mL Tetracycline (cat#: T3325, Teknova)) were detached with 0.25% trypsin. Tetracycline-free "treatment medium" (15 mL DMEM/F12 (1:1) (cat# SH30023.01, Hyclone, lx Pen/step (cat#: 30-002-CL, Mediatech, Inc), with 2% FBS, Tet-system approved (cat#: 631106, Clontech) were then added to mix and spun at 1300 rpm for 5 min. Pelleted cells were then re-suspended/washed with 50 mL of 1×PBS 2 times and 10 mL Treatment Medium one time. AD38 cells were then re-suspended with 10 mL of Treatment Medium and counted. Wells of a collagen coated 96-well NUNC microtiter plate were seeded at 50,000/well in 180 µL of Treatment Medium, and 20 µL of in treatment media with either 10% DMSO (Control) or a 10× solution of compound in 10% DMSO was added. Plates were incubated for 6 days at 37° C.

Viral load production was assayed by quantitative PCR of the core sequence. Briefly, 5 µL of clarified supernatant was added to a PCR reaction mixture that contained forward primers HBV-f 5'-CTGTGCCTTGGGTGGCTTT-3', Reverse primers HBV-r 5'-AAGGAAAGAAGTCA-GAAGGCAAAA-3' and Fluorescent TaqMan™ Probes HBV-probe 5'-FAM/AGCTCCAAA/ZEN/TTCTT-TATAAGGGTCGATGTCCATG/3IABkFQ-3' in Quanta Biosciences PerfeCTa® qPCR Toughmix®, and was subsequently on an Applied Biosystems VIIA7 in a final volume of 20 µL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate).

At the end of compound treatment period cell viability was assessed using a Promega CellTiter-Glo protocol. All supernatant was removed the previously treated 96-well microtiter plate, and 50 µL Tetracycline-free treatment medium (DMEM/F12 (1:1), lx Pen/step (cat#: 30-002-CL, Mediatech, Inc), with 2% FBS, Tet-system approved (cat#: 631106, Clontech), and 1% DMSO was added back to each well. Another 50 µL of CellTiter-Glo reagent solution (Promega, G7573) was then added at room temperature and the contents mixed for 2 minutes on an orbital shaker to induce cell lysis. This was followed by incubation at room temperature for 10 minutes to stabilize the luminescent signal. The luminescence was recorded for 0.2 seconds per well on a Tecan multimode platereader (Infinite M1000 pro). The luminescent signal from each well was normalized against that of untreated (DMSO) control wells. All results were reported percent viability (with controls being 100%).

TABLE 7

| Compound No. | AD38 Viral Load (CpAM/DMSO %) at 10 µM | AD38 Viability Normalized Result (CPAM/DMSO %) at 10 µM |
| --- | --- | --- |
| 1101 | 15 | 107 |
| 1102 | 1 | 100 |
| 1103 | 2 | 87 |
| 1104 | 1 | 85 |
| 1105 | 1 | 101 |
| 1107 | 2 | 106 |
| 1108 | 1 | 105 |
| 1109 | 6 | 99 |
| 1110 | 2 | 119 |
| 1111 | 2 | 89 |
| 1112 | 4 | 73 |
| 1113 | 1 | 99 |
| 1114 | 1 | 104 |
| 1115 | 1 | 106 |
| 1117 | 67 | 108 |
| 1118 | 61 | 95 |
| 1120 | 7 | 94 |
| 1121 | 6 | 109 |
| 1122 | 21 | 86 |
| 1123 | 62 | 95 |
| 1124 | 80 | 99 |
| 1125 | 20 | 108 |
| 1127 | 22 | 94 |
| 1130 | 2 | 101 |
| 1133 | 94 | 99 |
| 1149 | 5 | 118 |
| 1150 | 1 | 22 |
| 1151 | 1 | 50 |
| 1152 | 1 | 45 |
| 1154 | 90 | 50 |
| 1155 | 18 | 103 |
| 1156 | 16 | 106 |

TABLE 7-continued

| Compound No. | AD38 Viral Load (CpAM/DMSO %) at 10 μM | AD38 Viability Normalized Result (CPAM/DMSO %) at 10 μM |
|---|---|---|
| 1157 | 1 | 48 |
| 1158 | 37 | 120 |
| 1159 | 8 | 92 |
| 1160 | 2 | 105 |
| 1161 | 1 | 99 |
| 1162 | 61 | 99 |
| 1163 | 3 | 104 |
| 1164 | 27 | 103 |
| 1165 | 5 | 82 |
| 1166 | 10 | 119 |
| 1167 | 57 | 124 |
| 1168 | 10 | 117 |
| 1169 | 39 | 107 |
| 1170 | 1 | 95 |
| 1171 | 49 | 103 |
| 1172 | 51 | 107 |
| 1173 | 39 | 105 |
| 1174 | 35 | 109 |
| 1175 | 30 | 123 |
| 1176 | 2 | 104 |
| 1177 | 47 | 118 |
| 1182 | 13 | 55 |
| 1183 | 2 | 36 |
| 1184 | 1 | 0 |
| 1185 | 1 | 0 |
| 1186 | 1 | 39 |
| 1187 | 1 | 73 |
| 1188 | 4 | 83 |
| 1189 | 1 | 85 |
| 1190 | 1 | 70 |
| 1191 | 14 | 121 |
| 1192 | 3 | 81 |
| 1193 | 4 | 90 |
| 1194 | 1 | 45 |
| 1195 | 0 | 48 |
| 1196 | 2 | 95 |
| 1197 | 1 | 88 |
| 1198 | 3 | 60 |
| 1199 | 19 | 109 |
| 1200 | 18 | 125 |
| 1201 | 1 | 50 |
| 1202 | 7 | 107 |
| 1203 | 3 | 89 |
| 1204 | 2 | 97 |
| 1205 | 2 | 89 |
| 1206 | 10 | 106 |
| 1207 | 24 | 99 |
| 1208 | 11 | 103 |
| 1209 | 1 | 102 |
| 1210 | 25 | 116 |
| 1211 | 1 | 106 |
| 1212 | 1 | 72 |
| 1213 | 2 | 55 |
| 1214 | 2 | 94 |
| 1216 | 1 | 125 |
| 1217 | 1 | 37 |
| 1218 | 12 | 104 |
| 1219 | 5 | 100 |
| 1220 | 2 | 94 |
| 1221 | 19 | 106 |
| 1222 | 32 | 100 |
| 1223 | 2 | 28 |
| 1224 | 3 | 65 |
| 1225 | 10 | 87 |
| 1226 | 1 | 80 |
| 1227 | 10 | 92 |
| 1228 | 22 | 101 |
| 1229 | 45 | 76 |
| 1230 | 46 | 102 |
| 1231 | 12 | 93 |
| 1232 | 42 | 94 |
| 1233 | 1 | 93 |
| 1234 | 3 | 79 |
| 1235 | 6 | 61 |
| 1237 | 4 | 66 |
| 1238 | 26 | 104 |
| 1239 | 33 | 106 |
| 1240 | 26 | 92 |
| 1241 | 12 | 86 |
| 1242 | 91 | 78 |
| 1243 | 20 | 118 |
| 1244 | 14 | 103 |
| 1245 | 1 | 101 |
| 1246 | 6 | 96 |
| 1247 | 8 | 103 |
| 1248 | 3 | 106 |
| 1249 | 34 | 108 |
| 1250 | 14 | 113 |
| 1251 | 8 | 99 |
| 1252 | 14 | 94 |
| 1253 | 15 | 103 |
| 1256 | 1 | 102 |
| 1257 | 26 | 113 |
| 1258 | 12 | 105 |
| 1259 | 11 | 84 |
| 1260 | 8 | 100 |
| 1264 | 8 | 104 |
| 1266 | 1 | 74 |
| 1267 | 77 | 93 |
| 1268 | 77 | 106 |
| 1269 | 63 | 107 |
| 1270 | 1 | 94 |
| 1271 | 6 | 100 |
| 1272 | 24 | 102 |
| 1273 | 6 | 96 |
| 1274 | 11 | 88 |
| 1275 | 3 | 93 |
| 1276 | 24 | 89 |
| 1277 | 43 | 89 |
| 1278 | 3 | 88 |
| 1279 | 55 | 84 |
| 1280 | 74 | 94 |
| 1281 | 29 | 86 |
| 1282 | 102 | 105 |
| 1283 | 1 | 97 |
| 1285 | 3 | 108 |
| 1286 | 36 | 114 |
| 1287 | 11 | 96 |
| 1288 | 5 | 49 |
| 1289 | 40 | 96 |
| 1290 | 33 | 94 |
| 1291 | 1 | 102 |
| 1293 | 95 | 97 |
| 1308 | 1 | 99 |
| 1309 | 1 | 107 |
| 1310 | 1 | 89 |
| 1311 | 8 | 95 |
| 1312 | 5 | 83 |
| 1313 | 17 | 108 |
| 1314 | 69 | 101 |
| 1315 | 4 | 103 |
| 1316 | 32 | 89 |
| 1317 | 50 | 95 |
| 1318 | 14 | 70 |
| 1319 | 16 | 83 |
| 1320 | 43 | 93 |
| 1321 | 15 | 74 |
| 1322 | 28 | 94 |
| 1323 | 96 | 60 |
| 1324 | 10 | 24 |
| 1325 | 26 | 90 |
| 1326 | 23 | 95 |
| 1328 | 54 | 105 |
| 1329 | 62 | 109 |
| 1330 | 41 | 109 |
| 1331 | 43 | 88 |
| 1332 | 70 | 103 |
| 1333 | 20 | 73 |
| 1334 | 33 | 83 |
| 1335 | 87 | 104 |
| 1336 | 70 | 90 |
| 1337 | 77 | 91 |

TABLE 7-continued

| Compound No. | AD38 Viral Load (CpAM/DMSO %) at 10 μM | AD38 Viability Normalized Result (CPAM/DMSO %) at 10 μM |
|---|---|---|
| 1338 | 70 | 118 |
| 1339 | 113 | 70 |
| 1340 | 64 | 116 |
| 1342 | 113 | 95 |
| 1343 | 8 | 91 |
| 1344 | 96 | 102 |
| 1345 | 115 | 93 |
| 1346 | 105 | 97 |
| 1347 | 3 | 94 |
| 1348 | 0 | 107 |
| 1349 | 12 | 102 |
| 1353 | 50 | 97 |
| 1354 | 98 | 70 |
| 1356 | 3 | 101 |
| 1357 | 39 | 115 |
| 1358 | 15 | 72 |
| 1361 | 79 | 113 |
| 1362 | 19 | 98 |
| 1364 | 1 | 102 |
| 1365 | 2 | 105 |
| 1366 | 12 | 93 |
| 1367 | 33 | 88 |
| 1370 | 5 | 94 |
| 1371 | 6 | 94 |
| 1372 | 60 | 103 |
| 1373 | 10 | 100 |
| 1374 | 1 | 98 |
| 1375 | 11 | 89 |
| 1376 | 3 | 63 |
| 1377 | 5 | 65 |
| 1381 | 40 | 93 |
| 1382 | 47 | 117 |
| 1383 | 1 | 87 |
| 1384 | 4 | 79 |
| 1385 | 26 | 51 |
| 1386 | 61 | 95 |
| 1387 | 2 | 78 |
| 1388 | 5 | 71 |
| 1389 | 15 | 89 |
| 1390 | 2 | 92 |
| 1391 | 2 | 71 |
| 1392 | 2 | 85 |
| 1393 | 41 | 87 |
| 1394 | 55 | 94 |
| 1395 | 64 | 79 |
| 1396 | 63 | 95 |
| 1397 | 73 | 95 |
| 1398 | 5 | 60 |
| 1399 | 105 | 92 |
| 1400 | 34 | 105 |
| 1401 | 31 | 79 |
| 1402 | 12 | 81 |
| 1403 | 15 | 82 |
| 1405 | 14 | 94 |
| 1407 | 3 | 103 |
| 1408 | 17 | 94 |
| 1409 | 4 | 83 |
| 1410 | 35 | 50 |
| 1411 | 66 | 91 |
| 1412 | 48 | 87 |
| 1413 | 92 | 78 |
| 1414 | 39 | 89 |
| 1415 | 27 | 77 |
| 1417 | 11 | 75 |
| 1418 | 12 | 73 |
| 1419 | 113 | 89 |
| 1420 | 29 | 86 |
| 1421 | 78 | 95 |
| 1422 | 64 | 95 |
| 1423 | 37 | 91 |
| 1424 | 65 | 96 |
| 1427 | 7 | 85 |
| 1428 | 28 | 93 |
| 1429 | 38 | 90 |
| 1430 | 56 | 92 |
| 1431 | 115 | 92 |
| 1432 | 79 | 91 |
| 1433 | 82 | 94 |
| 1434 | 85 | 96 |
| 1435 | 77 | 99 |
| 1436 | 10 | 104 |
| 1440 | 71 | 91 |
| 1441 | 28 | 90 |
| 1442 | 65 | 99 |
| 1443 | 64 | 95 |
| 1444 | 6 | 65 |
| 1445 | 24 | 38 |
| 1446 | 3 | 84 |
| 1447 | 1 | 85 |
| 1448 | 3 | 85 |
| 1449 | 2 | 86 |
| 1450 | 73 | 94 |
| 1451 | 30 | 92 |
| 1452 | 15 | 62 |
| 1453 | 48 | 97 |
| 1454 | 27 | 95 |
| 1455 | 3 | 89 |
| 1456 | 15 | 101 |
| 1457 | 28 | 92 |
| 1458 | 12 | 49 |
| 1459 | 4 | 92 |
| 1462 | 35 | 99 |
| 1463 | 31 | 97 |
| 1464 | 49 | 98 |
| 1465 | 39 | 106 |
| 1466 | 7 | 88 |
| 1467 | 1 | 92 |
| 1468 | 76 | 97 |
| 1471 | 16 | 97 |
| 1472 | 37 | 95 |
| 1473 | 81 | 97 |
| 1474 | 51 | 101 |
| 1475 | 47 | 107 |
| 1476 | 1 | 86 |
| 1477 | 67 | 16 |
| 1478 | 2 | 94 |
| 1480 | 72 | 95 |
| 1481 | 46 | 100 |
| 1482 | 46 | 98 |
| 1483 | 65 | 98 |
| 1484 | 26 | 100 |
| 1485 | 30 | 96 |
| 1486 | 53 | 94 |
| 1487 | 15 | 96 |
| 1488 | 84 | 97 |
| 1490 | 7 | 79 |
| 1491 | 39 | 80 |
| 1492 | 39 | 79 |
| 1493 | 51 | 80 |
| 1494 | 115 | 60 |
| 1495 | 9 | 77 |
| 1496 | 2 | 18 |
| 1497 | 9 | 49 |
| 1498 | 1 | 82 |
| 1499 | 2 | 84 |
| 1501 | 37 | 71 |
| 1503 | 40 | 87 |
| 1505 | 81 | 85 |
| 1506 | 72 | 85 |
| 1507 | 11 | 96 |
| 1508 | 31 | 81 |
| 1509 | 15 | 29 |
| 1510 | 62 | 82 |
| 1511 | 38 | 85 |
| 1512 | 27 | 99 |
| 1513 | 2 | 82 |
| 1514 | 13 | 84 |
| 1515 | 2 | 82 |
| 1516 | 30 | 82 |
| 1517 | 2 | 78 |
| 1518 | 67 | 85 |
| 1519 | 73 | 81 |

TABLE 7-continued

| Compound No. | AD38 Viral Load (CpAM/DMSO %) at 10 μM | AD38 Viability Normalized Result (CPAM/DMSO %) at 10 μM |
|---|---|---|
| 1520 | 1 | 81 |
| 1521 | 1 | 22 |
| 1522 | 1 | 82 |
| 1523 | 1 | 70 |
| 1524 | 2 | 18 |
| 1525 | 78 | 85 |
| 1526 | 57 | 92 |
| 1527 | 19 | 116 |
| 1528 | 4 | 85 |
| 1529 | 12 | 111 |
| 1530 | 70 | 93 |
| 1531 | 53 | 96 |
| 1532 | 17 | 112 |
| 1533 | 2 | 105 |
| 1534 | 5 | 109 |
| 1535 | 108 | 85 |
| 1536 | 2 | 120 |
| 1537 | 36 | 98 |
| 1540 | 12 | 87 |
| 1541 | 11 | 117 |
| 1542 | 34 | 95 |
| 1543 | 72 | 90 |
| 1544 | 40 | 97 |
| 1545 | 59 | 88 |
| 1546 | 65 | 89 |
| 1547 | 16 | 90 |
| 1548 | 28 | 85 |
| 1549 | 7 | 109 |
| 1550 | 1 | 87 |
| 1551 | 51 | 91 |
| 1552 | 64 | 93 |
| 1553 | 86 | 93 |
| 1555 | 36 | 81 |
| 1556 | 67 | 86 |
| 1557 | 54 | 86 |
| 1558 | 51 | 88 |
| 1559 | 68 | 92 |
| 1560 | 13 | 92 |
| 1561 | 8 | 118 |
| 1562 | 25 | 89 |
| 1563 | 41 | 93 |
| 1564 | 10 | 119 |
| 1565 | 4 | 103 |
| 1566 | 31 | 91 |
| 1567 | 1 | 109 |
| 1568 | 1 | 100 |
| 1569 | 1 | 114 |
| 1570 | 2 | 115 |
| 1571 | 35 | 117 |
| 1572 | 5 | 116 |
| 1573 | 46 | 126 |
| 1574 | 78 | 109 |
| 1575 | 90 | 108 |
| 1576 | 8 | 108 |
| 1577 | 6 | 120 |
| 1578 | 33 | 100 |
| 1580 | 59 | 89 |
| 1581 | 3 | 97 |
| 1582 | 8 | 112 |
| 1583 | 41 | 121 |
| 1584 | 52 | 95 |
| 1585 | 66 | 87 |
| 1586 | 23 | 112 |
| 1587 | 78 | 92 |
| 1588 | 0 | 98 |
| 1589 | 1 | 85 |
| 1590 | 1 | 96 |
| 1591 | 13 | 111 |
| 1592 | 50 | 102 |
| 1593 | 3 | 133 |
| 1594 | 4 | 109 |
| 1595 | 3 | 108 |
| 1597 | 64 | 87 |
| 1598 | 61 | 93 |
| 1599 | 72 | 101 |
| 1600 | 12 | 108 |
| 1601 | 62 | 106 |
| 1602 | 38 | 116 |
| 1603 | 6 | 91 |
| 1604 | 0 | 105 |
| 1605 | 25 | 106 |
| 1606 | 7 | 104 |
| 1607 | 14 | 93 |
| 1608 | 63 | 103 |
| 1609 | 68 | 99 |
| 1611 | 0 | 130 |
| 1612 | 0 | 112 |
| 1613 | 0 | 122 |
| 1614 | 2 | 45 |
| 1615 | 32 | 123 |
| 1616 | 5 | 115 |
| 1617 | 1 | 118 |
| 1618 | 0 | 44 |
| 1619 | 12 | 122 |
| 1620 | 3 | 111 |
| 1621 | 1 | 117 |
| 1622 | 0 | 120 |
| 1623 | 1 | 128 |
| 1624 | 1 | 136 |
| 1625 | 2 | 111 |
| 1626 | 0 | 118 |
| 1627 | 5 | 115 |
| 1628 | 17 | 138 |
| 1629 | 3 | 95 |
| 1631 | 9 | 112 |
| 1632 | 2 | 122 |
| 1633 | 66 | 124 |
| 1634 | 45 | 125 |
| 1635 | 1 | 93 |
| 1636 | 0 | 111 |
| 1637 | 32 | 123 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The invention claimed is:

1. A compound represented by:

[structural formula]

wherein
Y is $S(O)_y$, wherein y is 2;
$R^{m'}$ and $R^m$ are each independently selected from the group consisting of H, halogen, $C_{1-6}$ alkyl (optionally substituted by one, two or three substituents each independently selected from halogen and hydroxyl), $C_{2-6}$ alkenyl (optionally substituted by one, two or three substituents each independently selected from halogen and hydroxyl), NR'R", and hydroxyl;

$R^c$ is H;

$R^{78}$ is selected from the group consisting of H, halogen, hydroxyl, nitro, cyano, carboxy, $C_{1-6}$ alkyl, $C_{2-6}$ alkenyl, $C_{2-6}$ alkynyl, $C_{1-6}$ alkoxy, NR'R", —C(O)—$C_{1-6}$ alkyl, —C(O)—$C_{1-6}$ alkoxy, phenyl, heteroaryl, $C_{3-6}$ cycloalkyl, —$S(O)_w$—$C_{1-6}$ alkyl (where w is 1, 2 or 3), —$S(O)_w$—NR'R" (where w is 1, 2 or 3), and —NR'—$S(O)_w$, (where w is 1, 2 or 3));

$R^{79}$ is selected from the group consisting of H, halogen, hydroxyl, nitro, cyano, carboxy, $C_{1-6}$ alkyl, $C_{2-6}$ alkenyl, $C_{2-6}$ alkynyl, $C_{1-6}$ alkoxy, NR'R", —C(O)—$C_{1-6}$ alkyl, —C(O)—$C_{1-6}$ alkoxy, phenyl, heteroaryl, $C_{3-6}$ cycloalkyl, —$S(O)_w$—$C_{1-6}$ alkyl (where w is 1, 2 or 3), —$S(O)_w$—NR'R" (where w is 1, 2 or 3), and —NR'—$S(O)_w$, (where w is 1, 2 or 3));

R' is selected, independently for each occurrence, from H, methyl, ethyl, and propyl;

R" is selected, independently for each occurrence, from H, methyl, ethyl, propyl, butyl, C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$ alkyl, $C_{2-6}$ alkynyl, $C_{2-6}$ alkenyl, halogen, hydroxyl, nitro, cyano, and NR'R";

wherein for each occurrence, $C_{1-6}$ alkyl may be optionally substituted with one, two, three or more substituents selected from the group consisting of halogen, hydroxyl, nitro, cyano, carboxy, $C_{2-6}$ alkenyl, $C_{2-6}$ alkynyl, $C_{1-6}$ alkoxy, NR'R", —NR'—S(O)$_w$, and S(O)$_w$—NR'R"; $C_{1-6}$ alkoxy may be optionally substituted with one, two, three or more substituents selected from the group consisting of halogen, hydroxyl, nitro, cyano, carboxy, $C_{1-6}$ alkyl, NR'R", —NR'—S(O)$_w$, and S(O)$_w$—NR'R"; $C_{3-6}$ cycloalkyl may be optionally substituted with one, two, three or more substituents selected from the group consisting of halogen, hydroxyl, nitro, cyano, carboxy, $C_{1-6}$ alkyl, $C_{1-6}$ alkoxy, —C(O)—$C_{1-6}$ alkyl, —C(O)—$C_{1-6}$ alkoxy, and NR'R"; phenyl may be optionally substituted by one, two or three substituents each independently selected from the group consisting of halogen, hydroxyl, $C_{1-6}$ alkyl, $C_{2-6}$ alkenyl, $C_{2-6}$ alkynyl, $C_{1-6}$ alkoxy, NR'R", C(O)—NR'R", —C(O)—$C_{1-6}$ alkyl, —C(O)—$C_{1-6}$ alkoxy, —S(O)$_w$—$C_{1-6}$ alkyl (where w is 1, 2 or 3), NR'—S(O)$_w$, and —S(O)$_w$—NR'R" (where w is 1, 2 or 3), and heteroaryl may be optionally substituted by one, two or three substituents each independently selected from the group consisting of halogen, hydroxyl, $C_{1-6}$ alkyl, $C_{2-6}$ alkenyl, $C_{2-6}$ alkynyl, $C_{3-6}$ cycloalkyl, $C_{1-6}$ alkoxy, NR'R", C(O)—NR'R'—C(O)—$C_{1-6}$ alkyl, —C(O)—$C_{1-6}$ alkoxy, —S(O)$_w$—$C_{1-6}$ alkyl (where w is 1, 2 or 3), NR'—S(O)$_w$, and —S(O)$_w$—NR'R"(where w is 1, 2 or 3), and pharmaceutically acceptable salts thereof.

2. The compound of claim 1, wherein $R^7$ is selected from H and F.

3. The compound of claim 1, wherein $R^6$ is selected from H and F.

4. The compound of claim 1, wherein $R^5$ is selected from H and F.

5. The compound of claim 1, wherein $R^{10}$ is selected from the group consisting of H, methyl and F.

6. The compound of claim 1 wherein each of $R^4$, $R^5$, $R^6$, $R^7$, $R^8$, $R^9$, and $R^{10}$, and R are H.

7. A pharmaceutically acceptable composition comprising a compound of claim 1, and a pharmaceutically acceptable excipient.

8. A method of treating a hepatitis B infection in a patient in need thereof, comprising administering an effective amount of a compound of claim 1.

9. A method of treating a hepatitis B infection in a patient in need thereof, comprising administering a first compound of claim 1, and optionally administering one or more additional compounds of claim 1.

10. A method of treating a hepatitis B infection in a patient in need thereof, comprising administering an amount of a compound of claim 1, and administering another HBV capsid assembly promoter.

11. A method of treating a hepatitis B infection in a patient in need thereof, comprising administering a first compound of claim 1, and one or more other HBV agent each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists.

* * * * *